US009567302B2

(12) United States Patent
Cisar et al.

(10) Patent No.: US 9,567,302 B2
(45) Date of Patent: Feb. 14, 2017

(54) CARBAMATE COMPOUNDS AND OF MAKING AND USING SAME

(71) Applicants: Abide Therapeutics, Inc., San Diego, CA (US); The Scripps Research Institute, La Jolla, CA (US)

(72) Inventors: Justin S. Cisar, San Diego, CA (US); Cheryl A. Grice, Encinitas, CA (US); Todd K. Jones, Solana Beach, CA (US); Dong-Hui Wang, San Diego, CA (US); Olivia Weber, San Diego, CA (US); Benjamin F. Cravatt, La Jolla, CA (US); Micah J. Niphakis, San Diego, CA (US); Armand Cognetta, San Diego, CA (US); Jae Won Chang, San Diego, CA (US)

(73) Assignees: Abide Therapeutics, Inc., San Diego, CA (US); The Scripps Research Institute, La Jolla, CA (US)

( * ) Notice: Subject to any disclaimer, the term of this patent is extended or adjusted under 35 U.S.C. 154(b) by 0 days.

(21) Appl. No.: 14/383,076

(22) PCT Filed: Mar. 15, 2013

(86) PCT No.: PCT/US2013/031907
§ 371 (c)(1),
(2) Date: Sep. 4, 2014

(87) PCT Pub. No.: WO2013/142307
PCT Pub. Date: Sep. 26, 2013

(65) Prior Publication Data
US 2015/0080364 A1 Mar. 19, 2015

Related U.S. Application Data

(60) Provisional application No. 61/685,511, filed on Mar. 19, 2012.

(51) Int. Cl.
| | |
|---|---|
| *C07D 207/46* | (2006.01) |
| *C07D 401/12* | (2006.01) |
| *C07D 405/14* | (2006.01) |
| *C07D 413/12* | (2006.01) |
| *C07D 413/14* | (2006.01) |
| *A61K 31/496* | (2006.01) |
| *A61K 31/454* | (2006.01) |
| *C07D 403/12* | (2006.01) |
| *C07D 401/14* | (2006.01) |
| *C07D 491/08* | (2006.01) |
| *C07D 233/80* | (2006.01) |
| *C07D 403/14* | (2006.01) |
| *C07D 417/12* | (2006.01) |
| *C07D 471/04* | (2006.01) |
| *C07D 471/10* | (2006.01) |
| *C07D 487/04* | (2006.01) |
| *C07D 491/107* | (2006.01) |
| *C07D 498/08* | (2006.01) |
| *C07D 209/48* | (2006.01) |

(52) U.S. Cl.
CPC ......... *C07D 207/46* (2013.01); *C07D 209/48* (2013.01); *C07D 233/80* (2013.01); *C07D 401/12* (2013.01); *C07D 401/14* (2013.01); *C07D 403/12* (2013.01); *C07D 403/14* (2013.01); *C07D 405/14* (2013.01); *C07D 413/12* (2013.01); *C07D 413/14* (2013.01); *C07D 417/12* (2013.01); *C07D 471/04* (2013.01); *C07D 471/10* (2013.01); *C07D 487/04* (2013.01); *C07D 491/08* (2013.01); *C07D 491/107* (2013.01); *C07D 498/08* (2013.01)

(58) Field of Classification Search
None
See application file for complete search history.

(56) References Cited

U.S. PATENT DOCUMENTS 4,003,912 A 1/1977 Franz

FOREIGN PATENT DOCUMENTS

| JP | 2004177416 | 6/2004 |
|---|---|---|
| WO | WO2009/071638 | 6/2009 |
| WO | WO2009/100155 | 8/2009 |
| WO | WO2010/045401 | 4/2010 |
| WO | WO2010/056309 | 5/2010 |
| WO | WO2013/142307 | 9/2013 |

OTHER PUBLICATIONS

Chang et al. ACS Chem. Biol. 8, 1590-1599, May 2013.*
Vasilevich et al. vol. 137 No. 279162 (Abstract for Tetrahedron Letters 4(18), pp. 3443-3445 2002) (2002).*
Batz et al. Pharmakologisch active Polymere. Die Makromolekulare Chemie. 172:27-47 (1973) (w/English Abstract).
Blizzard et al. Side chain SAR of bicyclic <2>-lactamase inhibitors (BLIs). 1. Discovery of a class C BLI for combination with imipinem. Bioorganic & Medicinal Chemistry Letters. 20(3): 918-921 (2010).
Chen et al. Monoacylglycerol lipase is a therapeutic target for Alzheimer's disease. Cell Rep. 2(5):1329-39 (2012).
Iriepa et al. Synthesis, Structural and conformational study of some ureas derived from 3-methyl-2,4-diphenyl-3-azabicyclo[3.3.1]nonan-9beta-amine. Journal of Molecular Structure. 482-483:431-436 (1999).
Jaouadi et al. Novel Preparation of N-Protected Amino Acid Active Esters Using 1.2.2.2-Tetrachloroethyl Carbonates. Journal of Organic Chemistry 52(12):2364-2367 (1987).
Long et al. Selective blockade of 2-arachidonoylglycerol hydrolysis produces cannabinoid behavioral effects. Nat Chem Biol. 5(1):37-44 (2009).

(Continued)

*Primary Examiner* — Emily Bernhardt
(74) *Attorney, Agent, or Firm* — Wilson, Sonsini, Goodrich & Rosati

(57) ABSTRACT

Provided herein are carbamate compounds which may be useful in the treatment of for example, pain, solid tumors and/or obesity.

10 Claims, No Drawings

(56) References Cited

OTHER PUBLICATIONS

Nimura et al. Activated Carbamate Reagent as Derivatizing Agent for Amino Compounds in High-Performance Liquid Chromatography. Analytical Chemistry. 58(12): 2372-2375 (1986).

Nomura et al. Activation of the endocannabinoid system by organophosphorus nerve agents. Nat Chem Biol. 4(6):373-8 (2008).

Nomura et al. Endocannabinoid hydrolysis generates brain prostaglandins that promote neuroinflammation. Science. 334(6057):809-13 (2011).

Nomura et al. Monoacylglycerol lipase regulates 2-arachidonoylglycerol action and arachidonic acid levels, Bioorg Med Chem Lett. 18(22):5875-8 (2008).

PCT/US2013/031907 International Preliminary Report on Patentability dated Sep. 23, 2014.

PCT/US2013/031907 International Search Report dated Jun. 25, 2013.

Piro et al. A dysregulated endocannabinoid-eicosanoid network supports pathogenesis in a mouse model of Alzheimer's disease. Cell Rep. 1(6):617-23 (2012).

Qiao et al. 5'-O-[( N-Acyl)sulfamoyl]adenosines as Antitubercular Agents that Inhibit MbtA: An Adenylation Enzyme Required for Siderophore Biosynthesis of the Mycobactins. Journal of Medicinal Chemistry. 50(24):6080-6094 (2007).

Schmidt et al. Chroman and tetrahydroquinoline ureas as potent TRPV1 antagonists. Bioorganic & Medicinal Chemistry Letters. 21(5):1338-1341 (2011).

Vasilevich et al. Conversion of O-succinimidyl carbamates to N-(O-carbamoyl)-succinmonoamides and ureas: effects of N-substituents and reaction conditions on the reaction pathway. Tetrahedron Letters. 43(37):6649-6652 (2002).

Vasilevich et al. Selective conversion of O-succinimidyl carbamates to N-(O-carbamoyl)-succinmonoamides and Ureas. Tetrahedron Letters. 43(18):3443-3445 (2002).

\* cited by examiner

CARBAMATE COMPOUNDS AND OF MAKING AND USING SAME

CROSS REFERENCE TO RELATED APPLICATIONS

This application is a U.S. National Stage Entry of PCT/US2013/031907, filed Mar. 15, 2013; which claims the benefit of U.S. Provisional Application Ser. No. 61/685,511, filed Mar. 19, 2012, all of which are incorporated by reference in their entirety.

This invention was made with government support under DA025285 and DA017259 awarded by the National Institutes of Health. The government has certain rights in the invention.

BACKGROUND

Monoacylglycerol lipase (MAGL) is a primary enzyme responsible for hydrolyzing endocannabinoids such as 2-AG (2-arachidonoylglycerol), an arachidonate based lipid, in the nervous system. The endocannabinoid system regulates a range of physiological processes, including for example, appetite, pain sensation, inflammation, and memory. Further, disorders such as obesity, chronic pain, anxiety and depression have been linked to regulation of endocannabinoid system signaling activities.

For example, MAGL modulating compounds may be useful in stimulating 2-AG mediated signaling activities, and disorders associated with such signaling activities, including pain, inflammation, metabolic disorders and the like.

However, MAGL modulating compounds to date have typically lacked the selectivity required for general use as in vivo pharmaceutically acceptable agents, particularly, agents that are selective over fatty acid amide hydrolase (FAAH), a primary N-arachidonoyl ethanolamide (AEA) hydrolyzing enzyme. Genetic or pharmacological disruption of FAAH may result in one or more cannabinoid dependent behavioral effects, for example, inflammation, anxiety, depression, or reduction in pain sensation.

MAGL also serves as a source of arachidonic acid in the nervous system (Nomura Nat Chem Bio 2008; Nomura Bioorg Med Chem Lett 2008; Long Nat Chem Bio 2009) and controls brain levels of pro-inflammatory arachidonic acid derivatives such as prostaglandins (Nomura Science 2011). Blockade of MAGL reduces molecular and cellular signs of neuroinflammation and is protective in models of neurodegeneration (Nomura Science 2011; Chen Cell Rep 2012; Piro Cell Rep 2012).

Further, it has recently been discovered that MAGL and its free fatty acid products are upregulated in aggressive cancer cells and in primary tumors, where it regulates a fatty acid network that promotes cancer cell migration and tumor growth. Therefore, new, selective inhibitors of MAGL may be useful in the treatment of cancers.

The serine hydrolase α-β-hydrolase domain 6 (ABHD6) is another lipid mediator and also may control accumulation and efficacy of 2-AG at cannabinoid receptors. ABHD6 may be a rate-limiting step of 2-AG signaling and thus is a member of the endocannabinoid signaling system. Therefore, ABHD6 may also be a useful target for cannabinoid dependent disorders, alone or in conjunction with MAGL and/or another serine hydrolase.

SUMMARY

This disclosure provides, for example, compounds and compositions which may be modulators of MAGL and/or ABHD6, and their use as medicinal agents, processes for their preparation, and pharmaceutical compositions that include disclosed compounds as at least one active ingredient. The disclosure also provided for the use of disclosed compounds as medicaments and/or in the manufacture of medicaments for the inhibition of MAGL and/or ABHD6 activity in warm-blooded animals such as humans.

In an embodiment, provided herein are compounds represented by formula I:

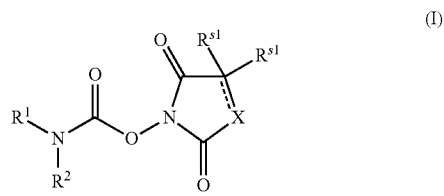

or pharmaceutically acceptable salts, stereoisomers, esters or prodrugs thereof, where $R^1$, $R^2$, X, and $R^{s1}$ are as defined herein.

The disclosure also provides for methods of treating indications such as pain, solid tumor cancer, obesity, Downs syndrome or Alzheimer's disease via administration of a disclosed compound. Also provided are pharmaceutical compositions comprising at least one disclosed compound and a pharmaceutically acceptable carrier.

DETAILED DESCRIPTION

This disclosure is directed, at least in part, to MAGL and/or ABHD6 modulators or inhibitors. For example, provided herein are compounds capable of inhibiting MAGL and/or ABHD6.

The features and other details of the disclosure will now be more particularly described. Before further description, certain terms employed in the specification, examples and appended claims are collected here. These definitions should be read in light of the remainder of the disclosure and as understood by a person of skill in the art. Unless defined otherwise, all technical and scientific terms used herein have the same meaning as commonly understood by a person of ordinary skill in the art.

Definitions

"Treating" includes any effect, e.g., lessening, reducing, modulating, or eliminating, that results in the improvement of the condition, disease, disorder and the like.

The term "alkenyl" as used herein refers to an unsaturated straight or branched hydrocarbon having at least one carbon-carbon double bond. Exemplary alkenyl groups include, but are not limited to, a straight or branched group of 2-6 or 3-4 carbon atoms, referred to herein as $C_{2-6}$alkenyl, and $C_{3-4}$alkenyl, respectively. Exemplary alkenyl groups include, but are not limited to, vinyl, allyl, butenyl, pentenyl, etc.

The term "alkoxy" as used herein refers to a straight or branched alkyl group attached to oxygen (alkyl-O—). Exemplary alkoxy groups include, but are not limited to, alkoxy groups of 1-6 or 2-6 carbon atoms, referred to herein as $C_{1-6}$alkoxy, and $C_{2-6}$alkoxy, respectively. Exemplary alkoxy groups include, but are not limited to methoxy, ethoxy, isopropoxy, etc.

The term "alkoxyalkyl" as used herein refers to a straight or branched alkyl group attached to oxygen, attached to a second straight or branched alkyl group (alkyl-O-alkyl-). Exemplary alkoxyalkyl groups include, but are not limited to, alkoxyalkyl groups in which each of the alkyl groups independently contains 1-6 carbon atoms, referred to herein as $C_{1-6}$alkoxy-$C_{1-6}$alkyl. Exemplary alkoxyalkyl groups include, but are not limited to methoxymethyl, 2-methoxyethyl, 1-methoxyethyl, 2-methoxypropyl, ethoxymethyl, 2-isopropoxyethyl etc.

The term "alkyoxycarbonyl" as used herein refers to a straight or branched alkyl group attached to oxygen, attached to a carbonyl group (alkyl-O—C(O)—). Exemplary alkoxycarbonyl groups include, but are not limited to, alkoxycarbonyl groups of 1-6 carbon atoms, referred to herein as $C_{1-6}$alkoxycarbonyl. Exemplary alkoxycarbonyl groups include, but are not limited to, methoxycarbonyl, ethoxycarbonyl, t-butoxycarbonyl, etc.

The term "alkenyloxy" used herein refers to a straight or branched alkenyl group attached to oxygen (alkenyl-O—). Exemplary alkenyloxy groups include, but are not limited to, groups with an alkenyl group of 3-6 carbon atoms, referred to herein as $C_{3-6}$alkenyloxy. Exemplary "alkenyloxy" groups include, but are not limited to allyloxy, butenyloxy, etc.

The term "alkynyloxy" used herein refers to a straight or branched alkynyl group attached to oxygen (alkynyl-O). Exemplary alkynyloxy groups include, but are not limited to, groups with an alkynyl group of 3-6 carbon atoms, referred to herein as $C_{3-6}$alkynyloxy. Exemplary alkynyloxy groups include, but are not limited to, propynyloxy, butynyloxy, etc.

The term "alkyl" as used herein refers to a saturated straight or branched hydrocarbon. Exemplary alkyl groups include, but are not limited to, straight or branched hydrocarbons of 1-6, 1-4, or 1-3 carbon atoms, referred to herein as $C_{1-6}$alkyl, $C_{1-4}$alkyl, and $C_{1-3}$alkyl, respectively. Exemplary alkyl groups include, but are not limited to, methyl, ethyl, propyl, isopropyl, 2-methyl-1-butyl, 3-methyl-2-butyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, etc.

The term "alkylcarbonyl" as used herein refers to a straight or branched alkyl group attached to a carbonyl group (alkyl-C(O)—). Exemplary alkylcarbonyl groups include, but are not limited to, alkylcarbonyl groups of 1-6 atoms, referred to herein as $C_{1-6}$alkylcarbonyl groups. Exemplary alkylcarbonyl groups include, but are not limited to, acetyl, propanoyl, isopropanoyl, butanoyl, etc.

The term "alkynyl" as used herein refers to an unsaturated straight or branched hydrocarbon having at least one carbon-carbon triple bond. Exemplary alkynyl groups include, but are not limited to, straight or branched groups of 2-6, or 3-6 carbon atoms, referred to herein as $C_{2-6}$alkynyl, and $C_{3-6}$alkynyl, respectively. Exemplary alkynyl groups include, but are not limited to, ethynyl, propynyl, butynyl, pentynyl, hexynyl, methylpropynyl, etc.

The term "aryl" as used herein refers to a mono- or bicyclic carbocyclic ring system with 3-14 carbon atoms having one or two aromatic rings including, but not limited to, phenyl, naphthyl, tetrahydronaphthyl, indanyl, indenyl, and the like.

The term "carbonyl" as used herein refers to the radical —C(O)—.

The term "cyano" as used herein refers to the radical —CN.

The term "cycloalkoxy" as used herein refers to a cycloalkyl group attached to oxygen (cycloalkyl-O—). Exemplary cycloalkoxy groups include, but are not limited to, cycloalkoxy groups of 3-6 carbon atoms, referred to herein as $C_{3-6}$cycloalkoxy groups. Exemplary cycloalkoxy groups include, but are not limited to, cyclopropoxy, cyclobutoxy, cyclohexyloxy, etc The terms "cycloalkyl" or a "carbocyclic group" as used herein refers to a saturated or partially unsaturated hydrocarbon group of, for example, 3-6, or 4-6 carbons, referred to herein as $C_{3-6}$cycloalkyl or $C_{4-6}$cycloalkyl, respectively. Exemplary cycloalkyl groups include, but are not limited to, cyclohexyl, cyclopentyl, cyclopentenyl, cyclobutyl or cyclopropyl.

The terms "halo" or "halogen" as used herein refer to F, Cl, Br, or I.

The terms "heteroaryl" or "heteroaromatic group" as used herein refers to a monocyclic aromatic 5-6 membered or bicyclic 9-10 membered ring system containing one or more heteroatoms, for example one to three heteroatoms, such as nitrogen, oxygen, and sulfur. Where possible, said heteroaryl ring may be linked to the adjacent radical though carbon or nitrogen. Examples of heteroaryl rings include but are not limited to benzoimidazole, benzothiazole, furan, imidazole, imidazo[1,2-a]pyridine, indazole, indole, isoquinoline, isothiazole, isoxazole, oxadiazole, oxadiazole, oxazole, pyrazole, pyridine, pyrimidine, pyrrole, quinoline, thiazole, thiophene, triazole, etc.

The terms "heterocyclyl" or "heterocyclic group" are art-recognized and refer to saturated or partially unsaturated 4-7 membered, or 7-10 membered bicyclic, spirocyclic, or bridged ring structures, whose ring structures include one to three heteroatoms, such as nitrogen, oxygen, and sulfur, and may be bridged rings as well as fused rings. Where possible, heterocyclyl rings may be linked to the adjacent radical through carbon or nitrogen. A heterocycle may be fused to one or more aryl, or partially unsaturated, or saturated rings. Where appropriate, the saturated rings may contain oxo groups, for example 2H-benzo[b][1,4]oxazin-3(4H)-one. Examples of heterocyclyl groups include, but are not limited to azetidine, benzodioxole, 2,8-diazaspiro[4.5]decan-1-one, 3,4-dihydro-2H-benzo[b][1,4]oxazine, dihydrobenzofuran, dihydrofuran, dihydroisobenzofuran, 6,7-dihydro-5H-pyrrolo[3,4-b]pyridine, indoline, isoindoline, 4-methyloctahydrocyclopenta[b][1,4]oxazine, 3-methyl-8-oxa-3-azabicyclo[3.2.1]octane, 7-methyl-5,6,7,8-tetrahydro-[1,2,4]triazolo[1,5-a]pyrazine, morpholine, octahydropyrrolo[1,2-a]pyrazine, 8-oxa-2-azaspiro[4.5]decane, oxetane, 2,3-dihydrobenzofuran, piperazine, piperidine, pyrrolidine, tetrahydrofuran, tetrahydropyran, thiomorpholine, etc.

The term "heterocyclyloxy" as used herein refers to a heterocyclyl group attached to oxygen (heterocyclyl-O—).

The term "heteroaryloxy" as used herein refers to a heteroaryl group attached to oxygen (heteroaryl-O—).

The terms "hydroxy" and "hydroxyl" as used herein refers to the radical —OH.

The term "oxo" as used herein refers to the radical =O.

"Pharmaceutically or pharmacologically acceptable" include molecular entities and compositions that do not produce an adverse, allergic or other untoward reaction when administered to an animal, or a human, as appropriate. For human administration, preparations should meet sterility, pyrogenicity, and general safety and purity standards as required by FDA Office of Biologics standards.

The term "pharmaceutically acceptable carrier" or "pharmaceutically acceptable excipient" as used herein refers to any and all solvents, dispersion media, coatings, isotonic and absorption delaying agents, and the like, that are compatible with pharmaceutical administration. The use of such media and agents for pharmaceutically active substances is well known in the art. The compositions may also contain other active compounds providing supplemental, additional, or enhanced therapeutic functions.

The term "pharmaceutical composition" as used herein refers to a composition comprising at least one compound as disclosed herein formulated together with one or more pharmaceutically acceptable carriers.

"Individual," "patient," or "subject" are used interchangeably and include any animal, including mammals, preferably mice, rats, other rodents, rabbits, dogs, cats, swine, cattle, sheep, horses, or primates, and most preferably humans. Disclosed compounds may be administered to a mammal, such as a human, but may also be administered to other mammals such as an animal in need of veterinary treatment, e.g., domestic animals (e.g., dogs, cats, and the like), farm animals (e.g., cows, sheep, pigs, horses, and the like) and laboratory animals (e.g., rats, mice, guinea pigs, and the like). "Modulation" includes antagonism (e.g., inhibition), agonism, partial antagonism and/or partial agonism.

In the present specification, the term "therapeutically effective amount" means the amount of the subject compound that will elicit the biological or medical response of a tissue, system or animal, (e.g. mammal or human) that is being sought by the researcher, veterinarian, medical doctor or other clinician. The compounds of the invention are administered in therapeutically effective amounts to treat a disease. Alternatively, a therapeutically effective amount of a compound is the quantity required to achieve a desired therapeutic and/or prophylactic effect.

The term "pharmaceutically acceptable salt(s)" as used herein refers to salts of acidic or basic groups that may be present in compounds used in the compositions. Compounds included in the present compositions that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, including, but not limited to, malate, oxalate, chloride, bromide, iodide, nitrate, sulfate, bisulfate, phosphate, acid phosphate, isonicotinate, acetate, lactate, salicylate, citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds included in the present compositions that are acidic in nature are capable of forming base salts with various pharmacologically acceptable cations. Examples of such salts include alkali metal or alkaline earth metal salts, particularly calcium, magnesium, sodium, lithium, zinc, potassium, and iron salts. Compounds included in the present compositions that include a basic or acidic moiety may also form pharmaceutically acceptable salts with various amino acids. The compounds of the disclosure may contain both acidic and basic groups; for example, one amino and one carboxylic acid group. In such a case, the compound can exist as an acid addition salt, a zwitterion, or a base salt.

The compounds of the disclosure may contain one or more chiral centers and, therefore, exist as stereoisomers. The term "stereoisomers" when used herein consist of all enantiomers or diastereomers. These compounds may be designated by the symbols "(+)," "(−)," "R" or "S," depending on the configuration of substituents around the stereogenic carbon atom, but the skilled artisan will recognize that a structure may denote a chiral center implicitly. The present invention encompasses various stereoisomers of these compounds and mixtures thereof. Mixtures of enantiomers or diastereomers may be designated "(±)" in nomenclature, but the skilled artisan will recognize that a structure may denote a chiral center implicitly.

The compounds of the disclosure may contain one or more double bonds and, therefore, exist as geometric isomers resulting from the arrangement of substituents around a carbon-carbon double bond. The symbol = denotes a bond that may be a single, double or triple bond as described herein. Substituents around a carbon-carbon double bond are designated as being in the "Z" or "E" configuration wherein the terms "Z" and "E" are used in accordance with IUPAC standards. Unless otherwise specified, structures depicting double bonds encompass both the "E" and "Z" isomers. Substituents around a carbon-carbon double bond alternatively can be referred to as "cis" or "trans," where "cis" represents substituents on the same side of the double bond and "trans" represents substituents on opposite sides of the double bond.

Compounds of the disclosure may contain a carbocyclic or heterocyclic ring and therefore, exist as geometric isomers resulting from the arrangement of substituents around the ring. The arrangement of substituents around a carbocyclic or heterocyclic ring are designated as being in the "Z" or "E" configuration wherein the terms "Z" and "E" are used in accordance with IUPAC standards. Unless otherwise specified, structures depicting carbocyclic or heterocyclic rings encompass both "Z" and "E" isomers. Substituents around a carbocyclic or heterocyclic rings may also be referred to as "cis" or "trans", where the term "cis" represents substituents on the same side of the plane of the ring and the term "trans" represents substituents on opposite sides of the plane of the ring. Mixtures of compounds wherein the substituents are disposed on both the same and opposite sides of plane of the ring are designated "cis/trans."

Individual enantiomers and diastereomers of contemplated compounds can be prepared synthetically from commercially available starting materials that contain asymmetric or stereogenic centers, or by preparation of racemic mixtures followed by resolution methods well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary, (2) salt formation employing an optically active resolving agent, (3) direct separation of the mixture of optical enantiomers on chiral liquid chromatographic columns or (4) kinetic resolution using stereoselective chemical or enzymatic reagents. Racemic mixtures can also be resolved into their component enantiomers by well known methods, such as chiral-phase liquid chromatography or crystallizing the compound in a chiral solvent. Stereoselective syntheses, a chemical or enzymatic reaction in which a single reactant forms an unequal mixture of stereoisomers during the creation of a new stereocenter or during the transformation of a pre-existing one, are well known in the art. Stereoselective syntheses encompass both enantio- and diastereoselective transformations, and may involve the use of chiral auxiliaries. For examples, see Carreira and Kvaerno, *Classics in Stereoselective Synthesis*, Wiley-VCH: Weinheim, 2009.

The compounds disclosed herein can exist in solvated as well as unsolvated forms with pharmaceutically acceptable solvents such as water, ethanol, and the like, and it is intended that the invention embrace both solvated and unsolvated forms. In one embodiment, the compound is amorphous. In one embodiment, the compound is a single polymorph. In another embodiment, the compound is a mixture of polymorphs. In another embodiment, the compound is in a crystalline form.

The invention also embraces isotopically labeled compounds as disclosed herein which are identical to those recited herein, except that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, sulfur, fluorine and chlorine, such as $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. For example, a compound of the invention may have one or more H atoms replaced with deuterium.

Certain isotopically-labeled disclosed compounds (e.g., those labeled with $^3$H and $^{14}$C) are useful in compound and/or substrate tissue distribution assays. Tritiated (i.e., $^3$H) and carbon-14 (i.e., $^{14}$C) isotopes are particularly preferred for their ease of preparation and detectability. Further, substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Isotopically labeled compounds of the invention can generally be prepared by following procedures analogous to those disclosed in the examples herein by substituting an isotopically labeled reagent for a non-isotopically labeled reagent.

The term "prodrug" refers to compounds that are transformed in vivo to yield a disclosed compound or a pharmaceutically acceptable salt, hydrate or solvate of the compound. The transformation may occur by various mechanisms (such as by esterase, amidase, phosphatase, oxidative and or reductive metabolism) in various locations (such as in the intestinal lumen or upon transit of the intestine, blood or liver). Prodrugs are well known in the art (for example, see Rautio, Kumpulainen, et al, Nature Reviews Drug Discovery 2008, 7, 255). For example, if a compound of the invention or a pharmaceutically acceptable salt, hydrate or solvate of the compound contains a carboxylic acid functional group, a prodrug can comprise an ester formed by the replacement of the hydrogen atom of the acid group with a group such as ($C_{1-8}$)alkyl, ($C_{2-12}$)alkylcarbonyloxymethyl, 1-(alkylcarbonyloxy)ethyl having from 4 to 9 carbon atoms, 1-methyl-1-(alkylcarbonyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—($C_{1-2}$)alkylamino($C_{2-3}$)alkyl (such as (3-dimethylaminoethyl), carbamoyl-($C_{1-2}$)alkyl, N,N-di($C_{1-2}$)alkylcarbamoyl-($C_{1-2}$)alkyl and piperidino-, pyrrolidino- or morpholino($C_{2-3}$)alkyl.

Similarly, if a compound of this disclosure contains an alcohol functional group, a prodrug can be formed by the replacement of the hydrogen atom of the alcohol group with a group such as ($C_{1-6}$)alkylcarbonyloxymethyl, 1-(($C_{1-6}$)alkylcarbonyloxy)ethyl, 1-methyl-1-(($C_{1-6}$)alkylcarbonyloxy)ethyl ($C_{1-6}$)alkoxycarbonyloxymethyl, N—($C_{1-6}$)alkoxycarbonylaminomethyl, succinoyl, ($C_{1-6}$)alkylcarbonyl, α-amino($C_{1-4}$)alkylcarbonyl, arylalkylcarbonyl and α-aminoalkylcarbonyl, or α-amino-alkylcarbonyl-α-aminoalkylcarbonyl, where each α-aminoalkylcarbonyl group is independently selected from the naturally occurring L-amino acids, P(O)(OH)$_2$, —P(O)(O($C_{1-6}$)alkyl)$_2$ or glycosyl (the radical resulting from the removal of a hydroxyl group of the hemiacetal form of a carbohydrate).

I. Carbamate Compounds

In certain embodiments, the present disclosure provides compounds such as those represented by formula I:

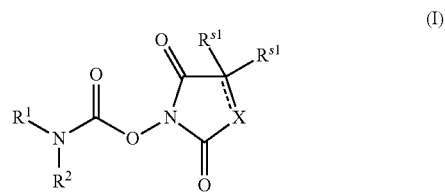

wherein

X is $CR^{s1}$, $—CR^{s1}—CR^{s1}—CR^{s1}R^{s1}$, or $NR^a$;

⚡ is a double or single bond;

$R^{s1}$ is independently selected for each occurrence from the group consisting of H, halogen, cyano, hydroxyl, nitro, phenyl (optionally substituted by one, two, or three substituents each independently selected from $R^c$), $C_{1-6}$alkyl (optionally substituted by one, two, or three halogens, cyano, phenyl, or hydroxyl), $C_{1-6}$alkoxy (optionally substituted by one, two, or three halogens, cyano, or hydroxyl), $C_{1-6}$alkenyl and $C_{1-6}$alkynyl; or two $R^{s1}$ moieties on separate carbons, taken together, form a fused ring selected from the group consisting of a phenyl and a 5-6 membered bridged or unbridged cycloalkyl or heterocycle, wherein the fused ring is optionally substituted by one or two substituents selected from $R^c$, and wherein a) $R_1$ and $R_2$ taken together with the nitrogen to which they are attached form a moiety selected from:

a monocyclic 5-7 membered heterocyclic ring B having one additional heteroatom independently selected from N, O, or S; or a monocyclic 4-7 membered heterocyclic ring A;

wherein one carbon of ring A has an optional substituent selected from the group consisting of:

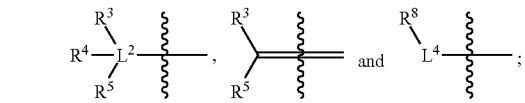

$L^2$ is $C_1$-$C_6$alkylene or $C_1$-$C_6$alkylene-NR$^a$—;

$R^3$ and $R^5$ are each independently selected from phenyl, naphthyl, or a mono or bicyclic heterocycle or heteroaryl having 1, 2 or 3 heteroatoms independently selected from O, S, or N; and wherein $R^3$ and $R^5$ may be independently and optionally substituted by one, two or three moieties each independently selected from $R^g$;

$R^4$ is selected from the group consisting of H, halogen, hydroxyl, cyano, or $C_1$-$C_5$ alkoxy;

$L^4$ is selected from the group consisting of: a bond, $C_1$-$C_6$alkylene, $—C_2$-$C_6$alkenylene-, $—O—$, $—O—C_1$-$C_6$alkylene-, $—NR^b—$, $—C(O)—$, $C_1$-$C_6$alkylene-C(O)—, $—C_0$-$C_6$alkylene-NR$^b$—C (O)—, —C$_0$-C$_6$alkylene-NR$^b$—S(O)$_w$—, —NR$^b$—C(O)—NR$^b$—C$_0$-C$_6$alkylene-, —C$_0$-C$_6$alkylene-O—C(O)—, —S(O)$_w$—, and C$_1$-C$_6$alkylene-S(O)$_w$—, wherein w is 0, 1, or 2, and wherein C$_1$-C$_6$alkylene is optionally substituted by one or two substituents selected from the group consisting of: halogen, hydroxyl, cyano, C$_{3-6}$cycloalkyl, and R$^8$, or L$^4$ is absent;

R$^8$ is selected from the group consisting of: H, hydroxyl, halogen, R$^a$R$^b$N—, C$_1$-C$_6$alkyl, phenyl, naphthyl, heterocycle, or mono or bicyclic heteroaryl having 1, 2 or 3 heteroatoms independently selected from O, S, or N; wherein R$^8$ is optionally substituted by one, two or three moieties independently selected from the group consisting of halogen, phenyl (optionally substituted by one, two, or three moieties each independently selected from R$^c$), phenyloxy (optionally substituted by one, two, or three moieties each independently selected from R$^c$), hydroxyl, cyano, C$_{1-6}$alkyl (optionally substituted by one, two or three halogens, cyano, or hydroxyl), C$_{2-6}$alkenyl (optionally substituted by one, two or three halogens, cyano, or hydroxyl), C$_{1-6}$alkoxy (optionally substituted by one, two or three halogens, cyano, or hydroxyl), R$^a$R$^b$N—, R$^a$—C(O)NR$^a$—, R$^a$R$^b$N—SO$_2$—, R$^a$R$^b$N-carbonyl-, R$^a$—S(O)$_w$— (wherein w is 0, 1 or 2), R$^a$—S(O)$_w$—NR$^b$— (wherein w is 0, 1 or 2), oxo, heterocycle (optionally substituted by one, two or three moieties each independently selected from R$^c$), heteroaryl (optionally substituted by one, two or three moieties each independently selected from R$^c$) or heteroaryloxy (optionally substituted by one, two, or three moieties each independently selected from R$^c$);

the additional heteroatom of ring B, when N, has an optional substituent represented by:

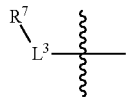

L$^3$ is selected from the group consisting of: a bond, C$_1$-C$_6$alkylene, C$_2$-C$_6$alkenylene, —C(O)—, —C(O)—O, C$_1$-C$_6$alkylene-C(O)—, C(O)—C$_1$-C$_6$alkylene-, C$_1$-C$_6$alkylene-O—C(O)—, —C$_0$-C$_6$alkylene-C(O)—NR$^a$, C$_0$-C$_6$alkylene-NR$^b$—S(O)$_w$—, —S(O)$_w$—, and C$_1$-C$_6$alkylene-S(O)$_w$—, wherein w is 0, 1, or 2, and wherein C$_1$-C$_6$alkylene is optionally substituted by one or two substituents selected from the group consisting of: halogen, hydroxyl, cyano, and an additional R$^7$, wherein when L$^3$ is —S(O)$_w$—, then R$^7$ is not H;

R$^7$ is selected from the group consisting of: H, hydroxyl, halogen, C$_1$-C$_{10}$alkyl, C$_2$-C$_{10}$alkynyl, C$_2$-C$_{10}$alkenyl, C$_3$-C$_{10}$cycloalkyl, phenyl, naphthyl, mono or bicyclic heterocyclyl, and mono or bicyclic heteroaryl, wherein the heteroaryl or the heterocyclyl has 1, 2 or 3 heteroatoms independently selected from O, S, or N; wherein R$^7$ is optionally substituted by one, two, three moieties or four moieties independently selected from R$^h$;

B is optionally substituted on one or more carbons by one, two, three or four moieties each independently selected from R$^d$; or b)
R$^1$ is L$^1$-R$^6$;
R$^2$ is H or C$_1$-C$_6$alkyl;
L$^1$ is C$_1$-C$_{10}$alkylene or a bond;
R$^6$ is selected from the group consisting of: H, C$_2$-C$_{10}$alkynyl, C$_2$-C$_{10}$alkenyl, phenyl, naphthyl, tetrahydronaphthalenyl, mono or bicyclic heterocycle or mono or bicyclic heteroaryl, wherein the heteroaryl or heterocycle has 1, 2 or 3 heteroatoms independently selected from O, S, or N; and wherein R$^6$ is optionally substituted by one, two, three or four moieties independently selected from the group consisting of: halogen, phenyl (optionally substituted by one, two or three moieties independently selected from R$^c$), phenyloxy (optionally substituted by one, two or three moieties independently selected from R$^c$), anilinyl (optionally substituted on a carbon by one, two or three moieties independently selected from R$^c$), hydroxyl, cyano, C$_{1-6}$alkyl (optionally substituted by one, two or three halogens, cyano, or hydroxyl), C$_{1-6}$alkoxy (optionally substituted by one, two or three halogens, cyano, or hydroxyl), R$^a$R$^b$N—, R$^a$R$^b$N—SO$_2$—, R$^a$R$^b$N-carbonyl-, —COOH, C$_{0-6}$alkyl-C(O)NR$^a$—, R$^a$—S(O)$_w$—, R$^a$—S(O)$_w$—NR$^b$— (wherein w is 0, 1 or 2), heteroaryl (optionally substituted by one, two or three moieties independently selected from R$^c$), heteroaryloxy (optionally substituted by one, two or three moieties independently selected from R$^c$), or a 4-7 membered heterocyclic ring (optionally substituted by one, two or three moieties independently selected from R$^c$);

R$^a$ and R$^b$ may be independently selected, for each occurrence, from the group consisting of hydrogen, C$_{1-3}$alkyl, and phenyl; wherein C$_{1-3}$alkyl may optionally be substituted by one or more substituents selected from halogen, cyano, oxo, phenyl, heterocycle and hydroxyl, and wherein phenyl or heterocycle is optionally substituted by one, two or three moieties each independently selected from R$^c$;

or R$^a$ and R$^b$, when they occur together with the nitrogen to which they are attached, form a 4-6 membered heterocyclic ring, a 9-10 membered bicyclic heterocycle or spirocyclic ring, or a 7-9 membered bridged ring, which may have an additional heteroatom selected from O, S, or N; wherein the 4-6 membered heterocyclic ring, 9-10 membered bicyclic heterocycle or spirocycle, or the 7-9 membered bridged ring may optionally be substituted by one or more substituents selected from the group consisting of halogen, cyano, oxo, C$_{1-6}$alkyl, —S(O)$_w$—C$_{1-6}$alkyl (where w is 0, 1 or 2), hydroxyl, —C(O)—C$_{1-6}$alkyl, —NH$_2$, NH—C$_{1-6}$alkyl, —NH—C(O)—C$_{1-6}$alkyl, NH—S(O)$_w$—C$_{1-6}$alkyl (where w is 0, 1 or 2) and —C(O)-heterocycle;

R$^c$ is selected from the group consisting of halogen, cyano, hydroxyl, nitro, C$_{1-6}$alkyl (optionally substituted by one, two, or three halogens, cyano, or hydroxyl), C$_{2-6}$alkenyl (optionally substituted by one, two, or three halogens), C$_{3-6}$cycloalkyl, C$_{1-6}$alkoxy (optionally substituted by one, two, or three halogens), oxo, R$^a$R$^b$N—, R$^a$R$^b$N—SO$_w$— (wherein w is 0, 1, or 2), R$^a$R$^b$N-carbonyl-, C$_{1-6}$alkyl-C(O)—, C$_{1-6}$alkyl-O—C(O)—, R$^a$—S(O)$_w$—NR$^b$— (wherein w is 0, 1 or 2), and R$^a$—S(O)$_w$— (wherein w is 0, 1 or 2);

R$^d$ is selected from the group consisting of consisting of: H, C$_{1-6}$alkyl (optionally substituted by one, two or three halogens, or hydroxyl) or R$^a$R$^b$N—C(O)—;

R$^g$ is selected from the group consisting of: halogen, phenyl, phenyloxy, anilinyl, hydroxyl, cyano, C$_{1-6}$alkyl (optionally substituted by one, two or three halogens, cyano, or hydroxyl), C$_{3-6}$cycloalkyl (optionally substituted by one, two or three halogens, cyano, or hydroxyl), C$_{2-6}$alkenyl (optionally substituted by one, two or three halogens, cyano, or hydroxyl), C$_{2-6}$alkynyl (optionally substituted by one, two or three halogens, cyano, or hydroxyl) C$_{1-6}$alkoxy (optionally substituted by one, two or three halogens, cyano, or hydroxyl), R$^a$—C(O)NR$^a$—, oxo, R$^a$R$^b$N—, R$^a$R$^b$N—SO$_2$—, R$^a$—S(O)$_w$— (wherein w is 0, 1 or 2), R$^a$—SO$_2$—NR$^b$—, R$^a$R$^b$N—C(O)—, heterocycle (optionally substituted by one, two or three moieties each independently selected from R$^c$, and connected to R$^3$ or R$^5$ through a carbon or heteroatom) or heteroaryl (optionally substituted by one, two or three moieties each independently selected from R$^c$, and connected to R$^3$ or R$^5$ through a carbon or heteroatom), or two adjacent R$^g$ groups along with the carbons to which they are attached can be taken together to form a 5- or 6-member mono or bicyclic heterocyclic or mono or bicyclic heteroaryl ring optionally substituted with 0, 1 or 2 halogens selected from F or Cl and which may have one or two additional heteroatoms selected from O, S, or N;

R$^h$ is selected from the group consisting of: halogen, phenyl (optionally substituted by one, two, or three moieties each independently selected from R$^c$), phenyloxy (optionally substituted by one, two, or three moieties each independently selected from R$^c$), hydroxyl, cyano, C$_{1-6}$alkyl (optionally substituted by one, two or three halogens, cyano, or hydroxyl), C$_{2-6}$alkenyl (optionally substituted by one, two or three halogens, cyano, or hydroxyl), C$_{2-6}$alkynyl (optionally substituted by one, two or three halogens, cyano, or hydroxyl), C$_{1-6}$alkoxy (optionally substituted by one, two or three halogens, cyano, or hydroxyl), oxo, R$^a$R$^b$N—, R$^a$—C(O)NR$^a$—, R$^a$R$^b$N—S(O)$_w$— (wherein w is 0, 1 or 2), R$^a$R$^b$N—C(O)—, R$^a$—S(O)$_w$— (wherein w is 0, 1 or 2), R$^a$—SO$_w$—NR$^h$— (wherein w is 0, 1 or 2), C$_{1-6}$alkyl-O—C(O)—, C$_{1-6}$alkyl-C(O)—, R$^a$—S(O)$_w$— (wherein w is 0, 1 or 2), heteroaryl (optionally substituted by one, two or three moieties each independently selected from R$^c$, and connected to R$^7$ through a carbon or heteroatom), heterocycle (optionally substituted by one, two or three moieties each independently selected from R$^c$, and connected to R$^7$ through a carbon or heteroatom) or heteroaryloxy (optionally substituted by one, two, or three moieties each independently selected from R$^c$), or two adjacent R$^h$ groups along with the carbons to which they are attached can be taken together to form a 5- or 6-member mono or bicyclic heterocyclic or mono or bicyclic heteroaryl ring optionally substituted with 0, 1 or 2 halogens selected from F or Cl and which may have one or two additional heteroatoms selected from O, S, or N;

and pharmaceutically acceptably salts or stereoisomers thereof.

In certain embodiments, the additional heteroatom of heterocyclic ring B is N.

In other embodiments, provided herein are compounds represented by:

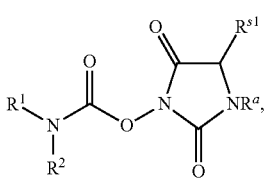

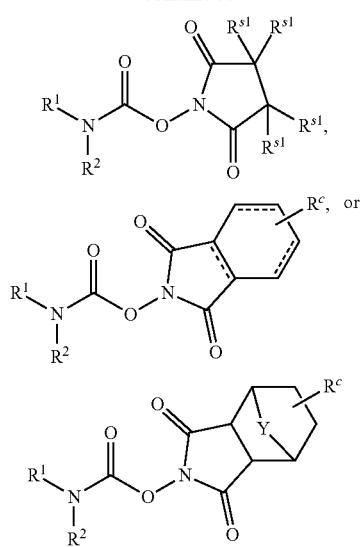

wherein Y is —CH$_2$— or CH$_2$—CH$_2$—, and R$^c$, R$^1$, and R$^2$ are provided above, e.g., a compound represented by:

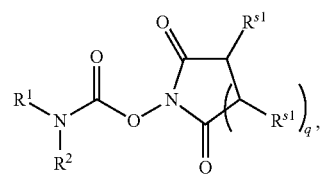

where q is 0, 1 or 2. An exemplary compound may be:

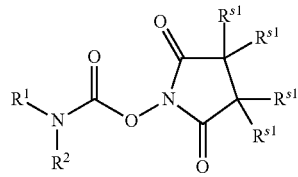

wherein R$^{s1}$ is independently selected from the group consisting of H, methyl, propyl, and phenyl, and R$^1$ and R$^2$ are provided above, and/or may be represented by, for example:

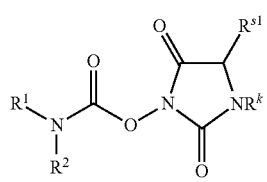

wherein R$^k$ is selected from the group consisting of H, methyl, ethyl, propyl, isopropyl, and benzyl.

For example compounds are provided herein, represented by:

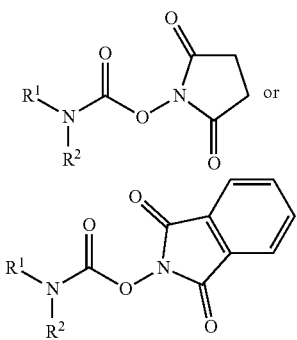

(with $R^1$ and $R^2$ described above) are contemplated herein.

In an embodiment, provided herein is a compound represented by:

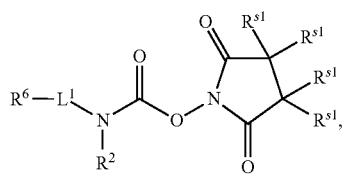

wherein $R^2$ is H or $C_1$-$C_3$alkyl; $L^1$ is a bond, $CH_2$— or $CH_2$—$CH_2$—; $R^{s1}$ is a moiety as described above, and for example, $R^6$ is selected from the group consisting of phenyl, naphthyl, 1,2,3,4-tetrahydronaphthalene, indanyl, benzodioxole, benzoxazole, benzoisoxazole, benzimidazole, benzotriazole, oxadiazole, indazole, isooxazole, quinoline, isoquinoline, pyridine, pyrazine, pyrimidine, theinyl, thiazole, benzothiopene, indole, benzothiadiazole, pyrazole, or dihydrobenzoxazine, wherein $R^6$ may be optionally substituted by one, two or three moieties each independently selected from the group consisting of halogen, phenyl (optionally substituted by halogen, cyano, methyl or $CF_3$), phenyloxy, hydroxyl, cyano, $C_{1-6}$alkyl (optionally substituted by one, two or three halogens, or hydroxyl), $C_{1-6}$alkoxy (optionally substituted by one, two or three halogens, or hydroxyl), $R^aR^bN$—, $R^aR^bN$—$SO_2$—, $R^a$—$S(O)_w$— (wherein w is 0, 1 or 2), $R^a$—$S(O)_w$—$NR^b$— (wherein w is 0, 1 or 2), $R^aR^bN$-carbonyl-, $C_{1-6}$alkyl-C(O)NR$^a$—, 4-6 membered heterocyclic ring (optionally substituted by $C_{1-6}$alkyl), heteroaryl (optionally substituted by $C_{1-6}$alkyl), or heteroaryloxy.

Provided here, for example, is a compound represented by:

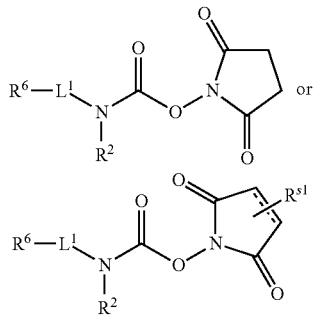

wherein:

$R^{s1}$ is H, $C_{1-6}$ alkyl or $C_{2-6}$alkenyl;

$R^2$ is H or $C_1$-$C_3$alkyl;

$L^1$ is $CH_2$— or $CH_2$—$CH_2$—; and $R^6$ is selected from the group consisting of phenyl, naphthyl, indanyl, benzodioxole, benzoxazole, benzoisoxazole, benzimidazole, benzotriazole, oxadiazole, indazole, isooxazole, quinoline, isoquinoline, pyridine, pyrazine, pyrimidine, theinyl, thiazole, benzothiopene, indole, benzothiadiazole, pyrazole, or dihydrobenzoxazine, wherein $R^6$ may be optionally substituted by one, two or three moieties each independently selected from the group consisting of halogen, phenyl (optionally substituted by halogen, cyano, methyl or $CF_3$), phenyloxy, hydroxyl, cyano, $C_{1-6}$alkyl (optionally substituted by one, two or three halogens, or hydroxyl), $C_{1-6}$alkoxy (optionally substituted by one, two or three halogens, or hydroxyl), $R^aR^bN$—, $R^aR^bN$—, $R^aR^bN$—$SO_2$—, $R^a$—$S(O)_w$— (wherein w is 0, 1 or 2), $R^a$—$S(O)_w$—$NR^b$— (wherein w is 0, 1 or 2), $R^aR^bN$-carbonyl-, $C_{1-6}$alkyl-C(O)NR$^a$—, 4-6 membered heterocyclic ring (optionally substituted by $C_{1-6}$alkyl), heteroaryl (optionally substituted by $C_{1-6}$alkyl), or heteroaryloxy. In certain embodiments, $R^6$ is phenyl, optionally substituted by halogen, cyano, hydroxyl, methoxy, oxadiazole (optionally substituted by methyl), pyridine (optionally substituted by methyl), phenyl (optionally substituted by halo), or phenyloxy.

$L^1$ may be, in certain embodiments, e.g. $(CH_2$—$)_q$. wherein q is 0, 1, 2, 3, 4, 5, 6, 7, 8, 9 or 10. For example, $L^1$ may be $CH_2$—. $R^6$ may be, for example, the following structures:

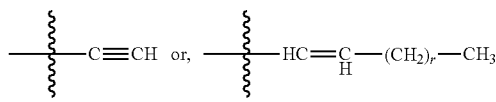

wherein r is 0, 1, 2, 3, 4, 5, 6, 7, 8, 9 or 10.

In certain embodiments, $R^2$ is methyl, ethyl or propyl, or branched or straight $C_1$-$C_{10}$ alkyl.

In other embodiments, $R^6$ may be selected from the group consisting of:

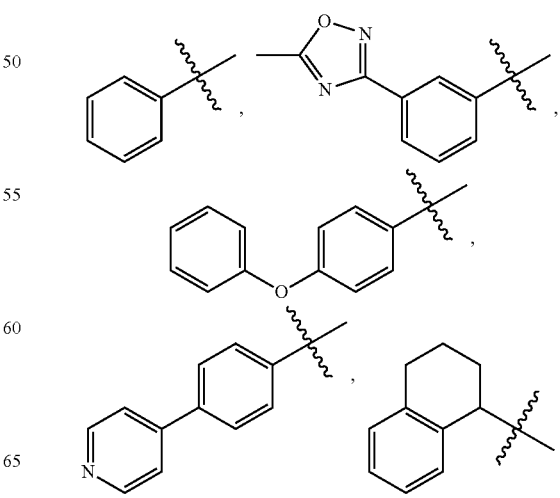

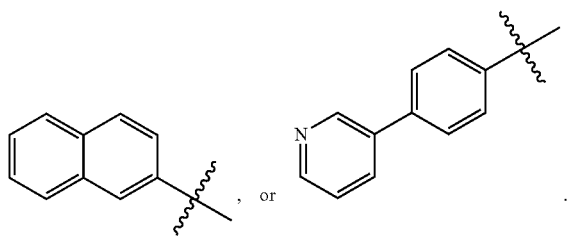

$R^1$ and $R^2$, in certain embodiments, may be taken together with the nitrogen to which they are attached form a 4-7 membered heterocyclic ring A. For example, a provided compound may be represented by:

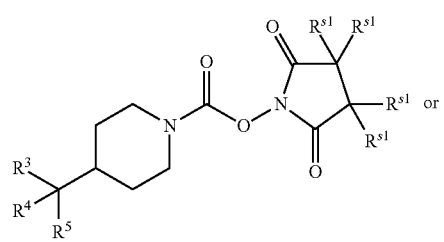

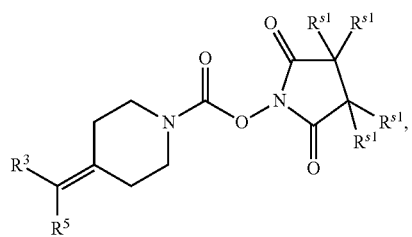

wherein $R^3$, $R^4$, $R^5$ and $R^{s1}$ are described above.

For example, provided herein are compounds represented by a formula such as:

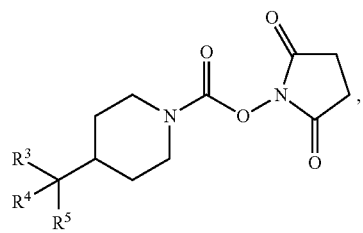

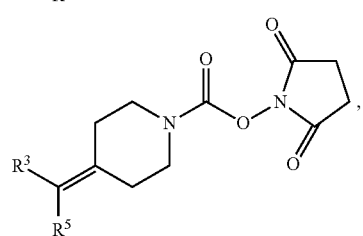

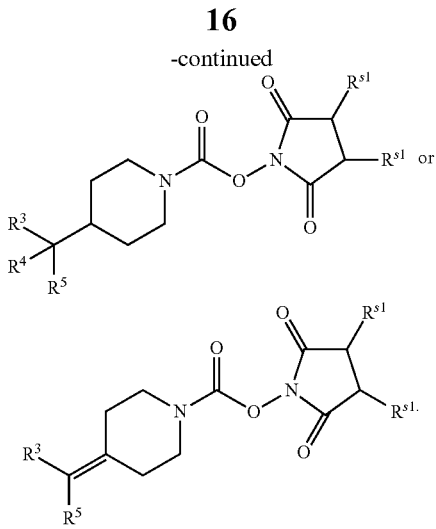

For example, in certain embodiments, $R^3$ and $R^5$ are each independently selected from the group consisting of:

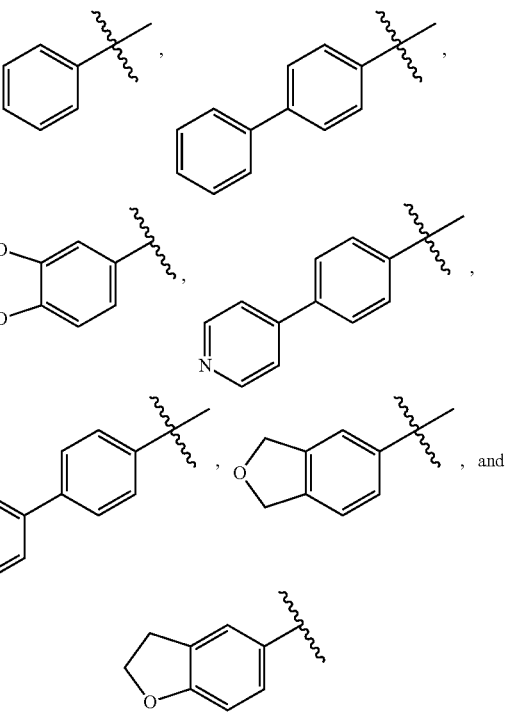

$R^4$, may be selected, for example, from the group consisting of H, hydroxyl and methoxy.

In another embodiment, provided herein is a compound represented by:

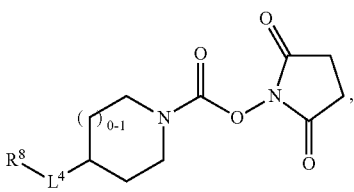

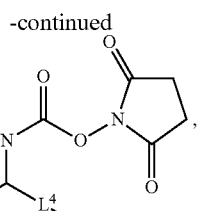

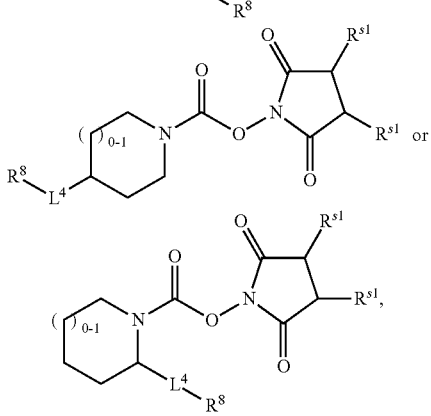

where $R^{s1}$, $L^4$ and $R^8$ are described above.

$L^4$ may be, certain embodiments, selected from the group consisting of C(O)—, —CH$_2$—, —CH$_2$—CH$_2$—, and a bond. $R^8$, for example, may be phenyl, or in a different embodiment, $R^8$ is H and $L^4$ is absent. In some embodiments, $R^8$ is selected from group consisting of piperidine, pyrrolidine, morpholine, or azetidine, wherein $R^8$ is optionally substituted by one or two substituents selected independently from the group consisting of halogen, C$_{1-6}$alkyl, and oxo.

In another embodiment, $R^1$ and $R^2$ taken together with the nitrogen to which they are attached form a 5-6 membered heterocyclic ring B, e.g., where B has an additional nitrogen. In an embodiment, provided herein is a compound represented by:

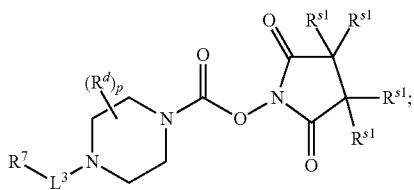

wherein p is 0, 1 or 2; and/or $R^d$ is independently selected for each occurrence from the group consisting of H or methyl, and wherein $L^3$, $R^2$, and $R^{s1}$ are described above. For example, in some embodiments, $L^3$ is selected from the group consisting of a bond, C$_1$-C$_2$alkylene, —C(O)—, —CH$_2$—C(O)—, and C(O)—CH$_2$—, wherein C$_1$-C$_2$alkylene is optionally substituted by a substituent selected from the group consisting of: phenyl (optionally substituted by one, two or three substituents selected independently from $R^h$), mono or bicyclic heteroaryl having 1, 2 or 3 heteroatoms independently selected from O, S, or N (optionally substituted by one, two or three substituents selected independently from $R^h$) and mono or bicyclic heterocycle having 1, 2 or 3 heteroatoms independently selected from O, S, or N (optionally substituted by one, two or three substituents selected independently from $R^h$, as described above); and $R^7$ is selected from the group consisting of phenyl, mono or bicyclic heteroaryl and mono or bicyclic heterocycle, wherein the heteroaryl or heterocycle has 1, 2 or 3 heteroatoms independently selected from O, S, or N, and $R^7$ is optionally substituted by one, two, three or four substituents each independently selected from $R^h$, where $R^h$ is described above.

In other embodiments, $R^7$ may be selected from the group consisting of phenyl, naphthyl, indanyl, benzodioxole, benzoxazole, benzoisoxazole, benzimidazole, benzotriazole, oxadiazole, indazole, oxazole, isooxazole, quinoline, isoquinoline, pyridine, pyrazine, pyrimidine, thienyl, thiazole, benzothiopene, indole, benzothiadiazole, pyrazole, imidazo (1,2-a)pyridine, dihydroisobenzofuran, and 3,4-dihydro-2H-benzo[b][1,4]oxazine. For example, $R^7$ may be selected from the group consisting of

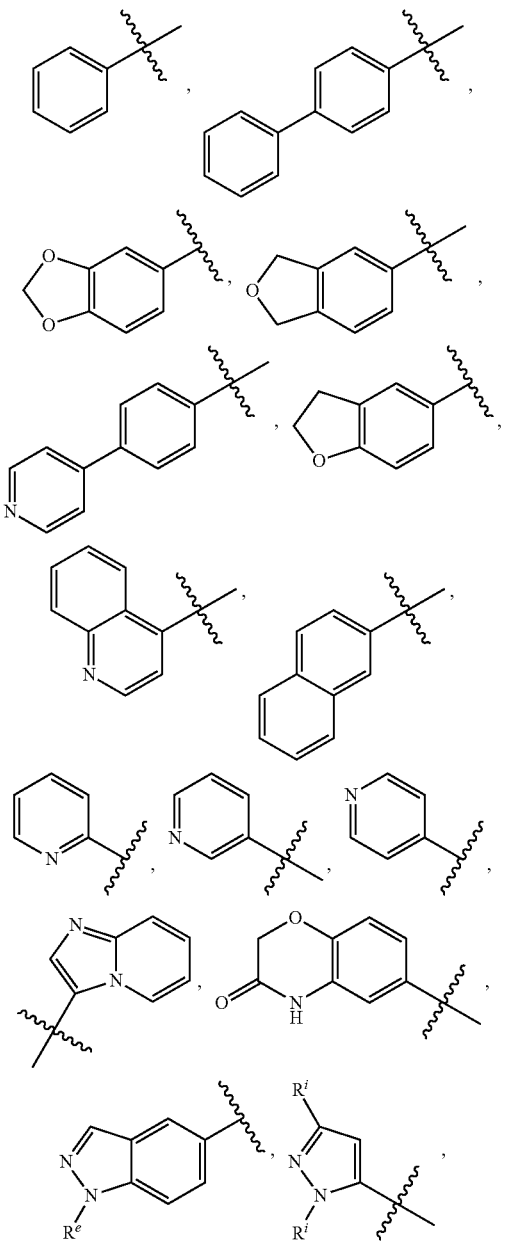

-continued

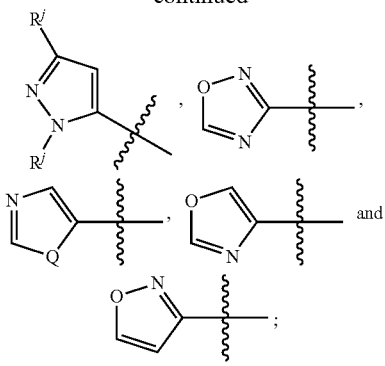

wherein Q is O or S; $R^e$ is selected from the group consisting of H, methyl, phenyl (optionally substituted by one, two or three substituents each independently selected from halogen, $C_{1-6}$alkyl (optionally substituted by one, two or three halogens), and $C_{1-6}$alkoxy (optionally substituted by one, two or three halogens)), and $C_{2-6}$alkyl (optionally substituted by one, two or three halogens); and $R^i$ and $R^j$ may be independently selected from the group consisting of: H, $CH_3$, $C_{2-6}$alkyl (optionally substituted by one, two or three halogens), phenyl (optionally substituted by one, two or three moieties independently selected from $R^c$), and $C_{3-6}$cycloalkyl (optionally substituted by one, two or three moieties independently selected from $R^c$) where $R^e$ is described above.

In certain embodiments, $R^7$ may be substituted by one or two substituents each selected from the group consisting of: halogen, $C_{1-6}$alkoxy (optionally substituted by one, two or three halogens), phenyl (optionally substituted by one, two, or three substituents independently selected from halogen, methyl and methoxy), phenyloxy, pyridinyl (optionally substituted by one, two, or three halogens or methyl), pyrazole (optionally substituted by one, two, or three halogens or methyl), $C_{1-6}$alkyl (optionally substituted by one, two or three halogens), $R^aR^bN$—, and $R^aR^bN$—C(O)—, wherein $R^a$ and $R^b$ are each independently selected from H or methyl, or $R^a$ and $R^b$ taken together with the nitrogen to which they are attached form a heterocycle selected from the group consisting of azetidinyl, pyrrolidinyl, piperdinyl, piperazinyl, morpholinyl, 8-oxa-2-azaspiro[4.5]decane, 6,7-dihydro-5H-pyrrolo[3,4-b]pyridine, 5,6,7,8-tetrahydro-[1,2,4]triazolo[1,5-a]pyrazine, octahydropyrrolo[1,2-a]pyrazine, octahydrocyclopenta[b][1,4]oxazine, and 8-oxa-3-azabicyclo[3.2.1]octane, wherein the heterocycle formed from $R^a$ and $R^b$ may be optionally substituted by one or two substituents each selected from (halogen, —NH—C(O)—$C_{1-6}$alkyl, oxo, $R^a$—S(O)$_w$— (wherein w is 0, 1 or 2), $R^a$—SO$_w$—NR$^b$— (wherein w is 0, 1 or 2), $C_{1-6}$alkyl-O—C(O)—, and $C_{1-6}$alkyl-C(O)—.

For example, provided herein is a compound represented by:

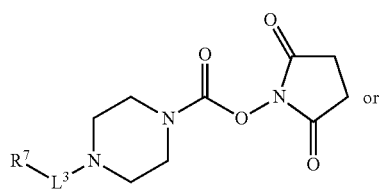 or

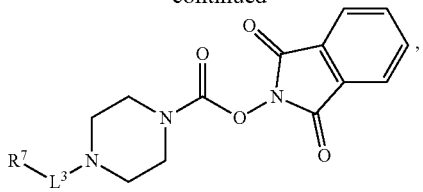

wherein $L^3$ and $R^7$ are described above.

In an embodiment, $L^3$ is $CH_2$(phenyl)-, —CH(phenyl)$_2$-, or $CH_2$(heteroaryl)-, or alternatively, $L^3$ may be selected from the group consisting of $CH_2$—, —$CH_2$—$CH_2$—, or $NR^a$—C(O)—$CH_2$—. $R^7$ may be selected from the group consisting of phenyl, biphenyl, oxydibenzene, wherein $R^7$ is optionally substituted by one, two or three substituents selected from the group consisting of halogen, cyano, $C_{1-6}$alkyl (optionally substituted by one, two or three halogens, or hydroxyl), or mono or bicyclic heteroaryl having 1, 2 or 3 heteroatoms independently selected from O, S, or N.

For example, $L^3$ may be CH—$R^{10}$, wherein $R^{10}$ selected from the group consisting of phenyl, naphthyl, indanyl, benzodioxole, benzoxazole, benzoisoxazole, benzimidazole, benzotriazole, oxadiazole, indazole, isooxazole, quinoline, isoquinoline, pyridine, pyrazine, pyrimidine, theinyl, thiazole, benzothiopene, indole, benzothiadiazole, pyrazole, or dihydrobenzoxazine, wherein $R^{10}$ may be optionally substituted by one, two or three moieties each independently selected from the group consisting of halogen, phenyl (optionally substituted by halogen, cyano, methyl or $CF_3$), phenyloxy (optionally substituted by halogen, cyano, methyl or $CF_3$), hydroxyl, cyano, $C_{1-6}$alkyl (optionally substituted by one, two or three halogens, or hydroxyl), $C_{1-6}$alkoxy (optionally substituted by one, two or three halogens, cyano or hydroxyl), $R^aR^bN$—, $R^aR^bN$—SO$_2$—, $R^a$—S(O)$_w$—NR$^b$— (wherein w is 0, 1 or 2), $R^aR^bN$-carbonyl-, $C_{1-6}$alkyl-C(O)NR$^a$—, heteroaryl (optionally substituted by $C_{1-6}$alkyl), or heteroaryloxy. $R^7$ may be, for example, selected from the group consisting of phenyl, naphthyl, indanyl, benzodioxole, benzoxazole, benzoisoxazole, benzimidazole, benzotriazole, oxadiazole, indazole, isooxazole, quinoline, isoquinoline, pyridine, pyrazine, pyrimidine, theinyl, thiazole, benzothiopene, indole, benzothiadiazole, pyrazole, or dihydrobenzoxazine, where $R^7$ is optionally substituted by one, two or three substituents selected from the group consisting of halogen, phenyl (optionally substituted by one, two, or three substituents selected from the group consisting of: halogen, methyl, ethyl, propyl, t-butyl, cyano or $CF_3$), phenyloxy, hydroxyl, cyano, $C_{1-6}$alkyl (optionally substituted by one, two or three halogens, or hydroxyl), $C_{1-6}$alkoxy, $R^aR^bN$—, $R^aR^bN$—SO$_2$—, $R^a$—S(O)$_w$—NR$^b$— (wherein w is 0, 1 or 2), $R^aR^bN$-carbonyl-, $C_{1-6}$alkyl-C(O)NR$^a$—, heteroaryl (optionally substituted by $C_{1-6}$alkyl), or heteroaryloxy.

In an embodiment, provided herein is a formula selected from the group consisting of:

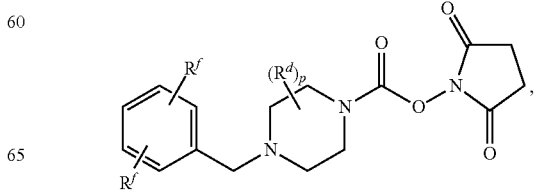

-continued

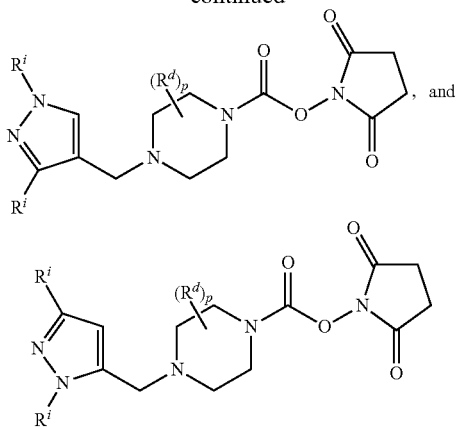

wherein R$^f$ is independently selected for each occurrence from H, R$^a$R$^b$N—, R$^a$R$^b$N—C(O)—, phenyoxy, halogen, C$_{1-6}$alkyl (optionally substituted by one, two or three halogens) and C$_{1-6}$alkoxy (optionally substituted by one, two or three halogens) wherein R$^a$ and R$^b$ together with the nitrogen to which they are attached, form a 4-6 membered heterocyclic ring, a 9-10 membered bicyclic heterocycle or spirocyclic ring, or a 7-9 membered bridged ring, which may have an additional heteroatom selected from O, S, or N; wherein the 4-6 membered heterocyclic ring, 9-10 membered bicyclic heterocycle or spirocycle, or the 7-9 membered bridged ring may optionally be substituted by one or more substituents selected from the group consisting of halogen, cyano, oxo, C$_{1-6}$alkyl, hydroxyl, —NH$_2$, —S(O)$_w$— C$_{1-6}$alkyl (wherein w is 0, 1 or 2), NH—C(O)—C$_{1-6}$alkyl and NH—S(O)$_w$— C$_{1-6}$alkyl. For example, R$_f$ may be a heterocyclic ring selected from piperidinyl, pyrrolidinyl, morpholinyl, pyrazole, azetidine, and piperazine. In certain embodiments, R$^7$ may be selected from group consisting of piperidine, pyrrolidine, morpholine, or azetidine, wherein R$^7$ is optionally substituted by one or two substituents selected independently from the group consisting of halogen, C$_{1-6}$alkyl, and oxo, or for example, R$^7$ may be morpholine, optionally substituted by one or two substituents selected independently from the group consisting of C$_{1-6}$alkyl, and oxo.

Provided herein is a compound represented by:

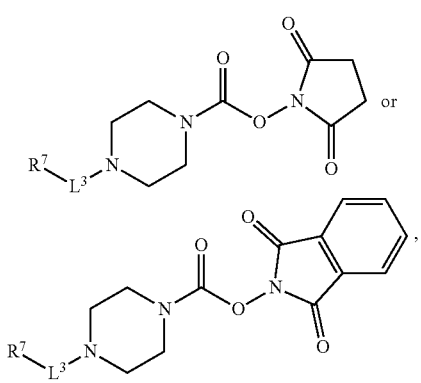

wherein:
L$^3$ is selected from the group consisting of: a bond, C$_1$-C$_6$alkylene, —C$_2$-C$_0$alkenylene-, —C(O)—, —O—C(O)—, C$_1$-C$_6$alkylene-C(O)—, C$_1$-C$_6$alkylene-O—C(O)—, C$_0$-C$_6$alkylene-C(O)— NR$^a$—, —S(O)$_w$—, and C$_1$-C$_6$alkylene-S(O)$_w$—, wherein w is 0, 1, or 2, and wherein C$_1$-C$_6$alkylene is optionally substituted by one or two substituents selected from the group consisting of: halogen, hydroxyl, cyano, and R$^7$;

R$^7$ is selected from the group consisting of: H, hydroxyl, halogen, C$_{1-10}$alkyl, C$_2$-C$_{10}$alkynyl, C$_2$-C$_{10}$alkenyl, phenyl, naphthyl, heterocycle, or mono or bicyclic heteroaryl having 1, 2 or 3 heteroatoms independently selected from O, S, or N; wherein R$^7$ is optionally substituted by one, two or three moieties independently selected from the group consisting of halogen, hydroxyl, phenyl (optionally substituted by one, two, or three moieties each independently selected from R$^c$), phenyloxy (optionally substituted by one, two, or three moieties each independently selected from R$^c$), hydroxyl, cyano, C$_{1-6}$alkyl (optionally substituted by one, two or three halogens, cyano, or hydroxyl), C$_{2-6}$alkenyl (optionally substituted by one, two or three halogens, cyano, or hydroxyl), C$_{1-6}$alkoxy (optionally substituted by one, two, or three halogens, cyano, or hydroxyl), R$^a$R$^b$N—, R$^a$—C(O)NR$^a$—, R$^a$R$^b$N—SO$_2$—, R$^a$R$^b$N-carbonyl-, R$^a$—S(O)$_w$— (wherein w is 0, 1 or 2), R$^a$—S(O)$_w$—NR$^b$— (wherein w is 0, 1 or 2), heteroaryl (optionally substituted by one, two or three moieties each independently selected from R$^c$) or heteroaryloxy (optionally substituted by one, two, or three moieties each independently selected from R$^c$);

R$^a$ and R$^b$ may be independently selected, for each occurrence, from the group consisting of hydrogen and C$_{1-3}$alkyl; wherein C$_{1-3}$alkyl may optionally be substituted by one or more substituents selected from fluorine, cyano, oxo and hydroxyl;

or R$^a$ and R$^b$, when they occur together with the nitrogen to which they are attached, may form a 4-6 membered heterocyclic ring, which may have an additional heteroatom selected from O, S, or N; wherein the 4-6 membered heterocyclic ring may optionally be substituted by one or more substituents selected from the group consisting of fluorine, cyano, oxo or hydroxyl;

R$^c$ is selected from the group consisting of halogen, cyano, hydroxyl, nitro, C$_{1-6}$alkyl (optionally substituted by one, two, or three halogens, cyano, or hydroxyl), C$_{2-6}$alkenyl (optionally substituted by one, two, or three halogens), C$_{3-6}$cycloalkyl, C$_{1-6}$alkoxy (optionally substituted by one, two, or three halogens), R$^a$R$^b$N—, R$^a$R$^b$N—SO$_2$—, R$^a$R$^b$N-carbonyl-, R$^a$—S(O)$_w$—NR$^b$— (wherein w is 0, 1 or 2), or R$^a$—S(O)$_w$— (wherein w is 0, 1 or 2);

or pharmaceutically acceptably salts or stereoisomers thereof.

In an embodiment, provided herein is a compound represented by:

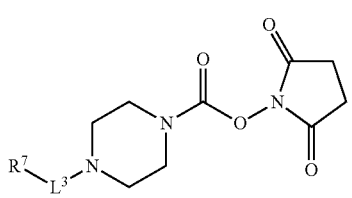

wherein:
L$^3$ is selected from the group consisting of: a bond, C$_1$-C$_6$alkylene, —C(O)—, —C(O)—O—, and —C$_1$-C$_6$alkylene-C(O), wherein w is 0, 1, or 2, and wherein $C_1$-$C_6$alkylene is optionally substituted by one or two substituents selected from the group consisting of: halogen, hydroxyl, cyano, and an additional $R^7$;

$R^7$ is selected from the group consisting of: phenyl, heterocycle having 1, 2 or 3 heteroatoms independently selected from O, S, or N, and heteroaryl having 1, 2 or 3 heteroatoms independently selected from O, S, or N; wherein $R^7$ is optionally substituted by one, two or three moieties each independently selected from $R^h$;

$R^a$ and $R^b$ may be independently selected, for each occurrence, from the group consisting of hydrogen, $C_{1-3}$alkyl, and phenyl; wherein $C_{1-3}$alkyl may optionally be substituted by one or more substituents selected from halogen, cyano, oxo, phenyl, heterocycle and hydroxyl, and wherein phenyl or heterocycle is optionally substituted by one, two or three moieties each independently selected from $R^c$;

or $R^a$ and $R^b$, when they occur together with the nitrogen to which they are attached, form a 4-6 membered heterocyclic ring, a 9-10 membered bicyclic heterocycle or spirocyclic ring, or a 7-9 membered bridged ring, which may have an additional heteroatom selected from O, S, or N; wherein the 4-6 membered heterocyclic ring, 9-10 membered bicyclic heterocycle or spirocycle, or the 7-9 membered bridged ring may optionally be substituted by one or more substituents selected from the group consisting of halogen, cyano, oxo, $C_{1-6}$alkyl, —S(O)$_w$—$C_{1-6}$alkyl (where w is 0, 1 or 2), hydroxyl, —C(O)—$C_{1-6}$alkyl, —NH$_2$, —NH—$C_{1-6}$alkyl, —NH—C(O)—$C_{1-6}$alkyl, —NH—S(O)$_w$—$C_{1-6}$alkyl (where w is 0, 1 or 2) and —C(O)-heterocycle;

$R^c$ is selected from the group consisting of halogen, cyano, hydroxyl, nitro, $C_{1-6}$alkyl (optionally substituted by one, two, or three halogens, cyano, or hydroxyl), $C_{2-6}$alkenyl (optionally substituted by one, two, or three halogens), $C_{3-6}$cycloalkyl, $C_{1-6}$alkoxy (optionally substituted by one, two, or three halogens), oxo, $R^aR^bN$—, $R^aR^bN$—SO$_w$— (wherein w is 0, 1, or 2), $R^aR^bN$-carbonyl-, $C_{1-6}$alkyl-C(O)—, $C_{1-6}$alkyl-O—C(O)—, $R^a$—S(O)$_w$—NR$^h$— (wherein w is 0, 1 or 2), and $R^a$—S(O)$_w$— (wherein w is 0, 1 or 2);

$R^d$ is selected from the group consisting of consisting of: H, $C_{1-6}$alkyl (optionally substituted by one, two or three halogens, or hydroxyl) or $R^aR^bN$—C(O)—;

$R^h$ is selected from the group consisting of: halogen, phenyl (optionally substituted by one, two, or three moieties each independently selected from $R^c$), phenyloxy (optionally substituted by one, two, or three moieties each independently selected from $R^c$), hydroxyl, cyano, $C_{1-6}$alkyl (optionally substituted by one, two or three halogens, cyano, or hydroxyl), $C_{2-6}$alkenyl (optionally substituted by one, two or three halogens, cyano, or hydroxyl), $C_{2-6}$alkynyl (optionally substituted by one, two or three halogens, cyano, or hydroxyl), $C_{1-6}$alkoxy (optionally substituted by one, two or three halogens, cyano, or hydroxyl), oxo, $R^aR^bN$—, $R^a$—C(O)NR$^a$—, $R^aR^bN$—S(O)$_w$— (wherein w is 0, 1 or 2), $R^aR^bN$—C(O)—, $R^a$—S(O)$_w$— (wherein w is 0, 1 or 2), $R^a$—SO$_w$—NR$^b$— (wherein w is 0, 1 or 2), $C_{1-6}$alkyl-O—C(O)—, $C_{1-6}$alkyl-C(O)—, $R^a$—S(O)$_w$— (wherein w is 0, 1 or 2), heteroaryl (optionally substituted by one, two or three moieties each independently selected from $R^c$, and connected to $R^7$ through a carbon or heteroatom), heterocycle (optionally substituted by one, two or three moieties each independently selected from $R^c$, and connected to $R^7$ through a carbon or heteroatom) or heteroaryloxy (optionally substituted by one, two, or three moieties each independently selected from $R^c$), or two adjacent $R^h$ groups along with the carbons to which they are attached can be taken together to form a 5- or 6-member mono or bicyclic heterocyclic or mono or bicyclic heteroaryl ring optionally substituted with 0, 1 or 2 halogens selected from F or Cl and which may have one or two additional heteroatoms selected from O, S, or N; and pharmaceutically acceptably salts or stereoisomers thereof Also provided herein is a compound represented by:

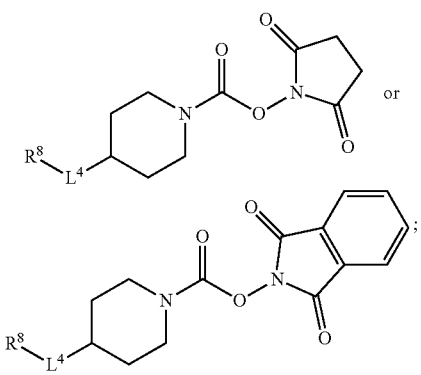

wherein $L^4$ is selected from the group consisting of: a bond, $C_1$-$C_6$alkylene, —$C_2$-$C_6$alkenylene-, —O—, —O—$C_1$-$C_6$alkylene-, —NR$^b$—, —C(O)—, $C_1$-$C_6$alkylene-C(O)—, —$C_0$-$C_6$alkylene-NR$^b$—C(O)—, —$C_0$-$C_6$alkylene-NR$^b$—S(O)$_w$—, —NR$^b$—C(O)—NR$^b$—$C_0$-$C_6$alkylene-, —$C_0$-$C_6$alkylene-O—C(O)—, —S(O)$_w$—, and $C_1$-$C_6$alkylene-S(O)$_w$—, wherein w is 0, 1, or 2, and wherein $C_1$-$C_6$alkylene is optionally substituted by one or two substituents selected from the group consisting of: halogen, hydroxyl, cyano, $C_{3-6}$cycloalkyl, and $R^8$, or $L^4$ is absent;

$R^8$ is selected from the group consisting of: H, hydroxyl, halogen, $C_{1-6}$alkyl, $R^aR^bN$—, phenyl, naphthyl, heterocycle, or mono or bicyclic heteroaryl having 1, 2 or 3 heteroatoms independently selected from O, S, or N; wherein $R^8$ is optionally substituted by one, two or three moieties independently selected from the group consisting of halogen, phenyl (optionally substituted by one, two, or three moieties each independently selected from $R^c$), phenyloxy (optionally substituted by one, two, or three moieties each independently selected from $R^c$), hydroxyl, cyano, $C_{1-6}$alkyl (optionally substituted by one, two or three halogens, cyano, or hydroxyl), $C_{2-6}$alkenyl (optionally substituted by one, two or three halogens, cyano, or hydroxyl), $C_{1-6}$alkoxy (optionally substituted by one, two or three halogens, cyano, or hydroxyl), $R^aR^bN$—, $R^a$—C(O)NR$^a$—, $R^aR^bN$—SO$_2$—, $R^aR^bN$-carbonyl-, $R^a$—S(O)$_w$— (wherein w is 0, 1 or 2), $R^a$—S(O)$_w$—NR$^b$— (wherein w is 0, 1 or 2), heterocycle (optionally substituted by one, two or three moieties each independently selected from $R^c$), heteroaryl (optionally substituted by one, two or three moieties each independently selected from $R^c$) or heteroaryloxy (optionally substituted by one, two, or three moieties each independently selected from $R^c$);

$R^a$ and $R^b$ may be independently selected, for each occurrence, from the group consisting of hydrogen and $C_{1-3}$alkyl; wherein $C_{1-3}$alkyl may optionally be substituted by one or more substituents selected from fluorine, cyano, oxo and hydroxyl;

or $R^a$ and $R^b$, when they occur together with the nitrogen to which they are attached, may form a 4-6 membered heterocyclic ring, which may have an additional heteroatom selected from O, S, or N; wherein the 4-6 membered heterocyclic ring may optionally be substituted by one or more substituents selected from the group consisting of fluorine, cyano, oxo or hydroxyl;

$R^c$ is selected from the group consisting of halogen, cyano, hydroxyl, nitro, $C_{1-6}$alkyl (optionally substituted by one, two, or three halogens, cyano, or hydroxyl), $C_{2-6}$alkenyl (optionally substituted by one, two, or three halogens), $C_{3-6}$cycloalkyl, $C_{1-6}$alkoxy (optionally substituted by one, two, or three halogens), $R^aR^bN-$, $R^aR^bN-SO_2-$, $R^aR^bN$-carbonyl-, $R^a-S(O)_w-NR^b-$ (wherein w is 0, 1 or 2), or $R^a-S(O)_w-$ (wherein w is 0, 1 or 2).

or pharmaceutically acceptably salts or stereoisomers thereof.

Procedures for making compounds described herein are provided below with exemplary reference to Scheme 1. In the reactions described below, it may be necessary to protect reactive functional groups (such as hydroxyl, amino, thio or carboxyl groups) to avoid their unwanted participation in the reactions. The incorporation of such groups, and the methods required to introduce and remove them are known to those skilled in the art [for example, see Greene, Wuts, Protective Groups in Organic Synthesis. 2nd Ed. (1999)]. Starting materials used in the following schemes can be purchased or prepared by methods described in the chemical literature, or by adaptations thereof, using methods known by those skilled in the art. The order in which the steps are performed can vary depending on the groups introduced and the reagents used, but would be apparent to those skilled in the art.

A general synthetic strategy that may be used to prepare carbamate compounds of Formula I is depicted in Scheme 1, where N,N'-disuccinimidyl carbonate and N-methylmorpholine are added with 1° or 2° amines.

A general synthetic strategy used to prepare the carbamate compounds of Formula I is depicted in SCHEME 1. The desired carbamate can be prepared using an amine A (where $R^1$ and $R^2$ are described above) and bis(2,5-dioxopyrrolidin-1-yl) carbonate (N,N'-disuccinimidyl carbonate, DSC) in the presence of a base such as N-methylmorpoholine (NMM), diisopropylethyl amine (Hunig's base, DIEA) or triethyl amine in a solvent such as acetonitrile or dichloromethane. The specific $R^1$ and $R^2$ groups are selected based on the desired groups in the final carbamate product C. Alternatively, compounds of the general structure C can be prepared by treating the amines, A, with triphosgene in the presence of pyridine to prepare, in-situ, the corresponding carbamoyl chloride followed by addition of N-hydroxysuccinimides, B, including those containing substitution with $R^{s1}$ (or hydantoins). $R^{s1}$ is described above. Compounds C, can also be prepared by treating the N-hydroxysuccinimide intermediates, B, including N-hydroxyphthalimide, with triphosgene in the presence of DIEA. Compounds, C can then be prepared by subsequent addition of the desired amine A to the in-situ prepared acyl chloride.

SCHEME 1

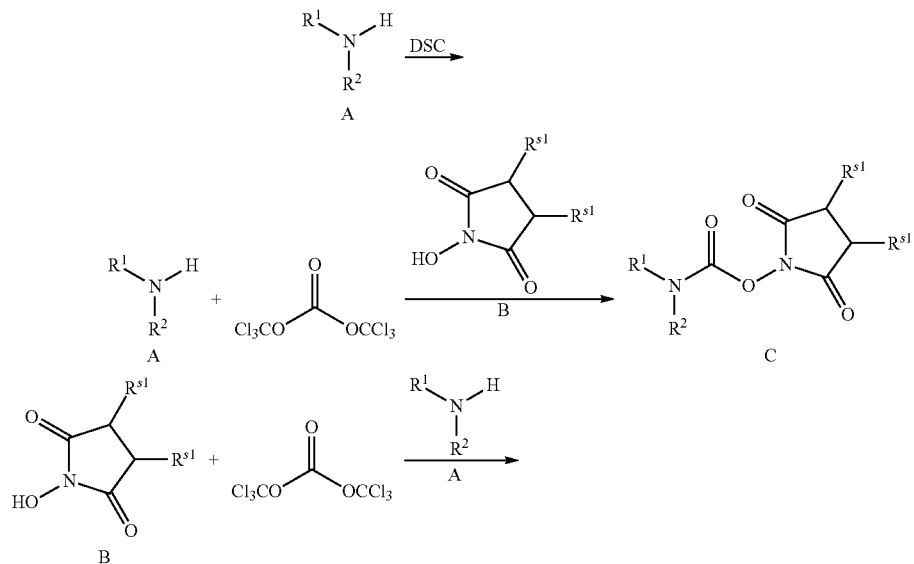

SCHEME 2 provides an exemplary synthetic procedure for making the amine starting material utilized in SCHEME 1. The desired amine, A, can be derived from the Boc-protected variant C. Removal of the Boc-group can be achieved by reaction of the Boc-protected amine with NMM and iodotrimethylsilane or alternatively, by treatment with a 4N solution of HCl in dioxane in a solvent such as $CH_2Cl_2$ at temperatures ranging from 0 to 25° C. or by treatment with trifluoroacetic acid in a solvent such as $CH_2Cl_2$.

SCHEME 2

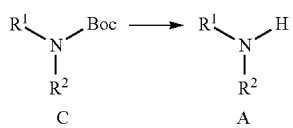

SCHEME 3 provides a detailed exemplary synthetic procedure for making carbamate derivatives having a optionally substituted succinimide group of the general structure C. $R^{s1}$ is described above. Anhydride E, appropriately substituted as needed with $R^{s1}$, can be obtained from commercial sources and converted to imide F by treatment with O-benzylhydroxylamine hydrochloride in the presence of NMM at elevated temperatures with azeotropic removal of water. The cyclization can be facilitated by the addition of acid, such as acetic acid. Removal the benzyl group, to obtain B, can be achieved through hydrogenolysis using catalytic Pd/C under a positive pressure of gaseous $H_2$ in a solvent such as a 1:1 mixture of EtOAc:MeOH. Compounds C can be prepared by reaction of intermediates B with an appropriately substituted amine, A, according to the representative protocols described above for SCHEME 1.

SCHEME 3

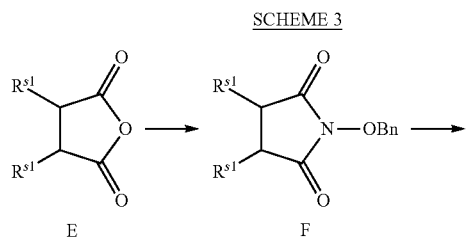

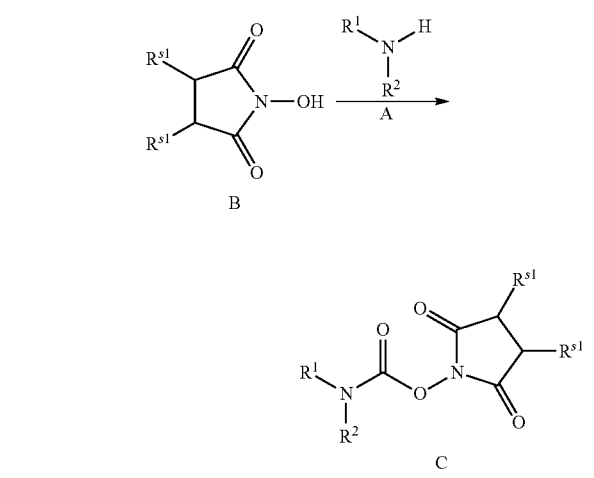

SCHEME 4 provides a detailed exemplary synthetic procedure for making carbamate derivatives having a hydantoin group of the general structures M or N. Commercially available protected amino acids, H, are coupled with O-benzylhydroxylamine hydrochloride in the presence of NMM and 1-ethyl-3-(3-dimethylaminopropyl)carbodiimide (EDCI) to yield intermediates I. Removal of the Boc protecting group can be achieved using 4N HCl in dioxane to yield intermediates J. Cyclization of J to yield hydantoin K can be achieved using carbonyldiimidazole (CDI) in the presence of NMM in a solvent such as $CH_2Cl_2$. Removal of the benzyl group, to obtain, L, can be achieved through hydrogenolysis using catalytic Pd/C under a positive pressure of gaseous $H_2$ in a solvent such as a 1:1 mixture of EtOAc:MeOH or EtOAc:EtOH. Compounds M can be prepared by reaction of intermediates L, or commercially available hydantoins, with an appropriately substituted amine, A, according to the representative protocol described above for SCHEME 1. Alternatively, M can be converted to N by alkylation with an alkyl halide in the presence of a base such as $Cs_2CO_3$ in a solvent such as acetonitrile.

SCHEME 4

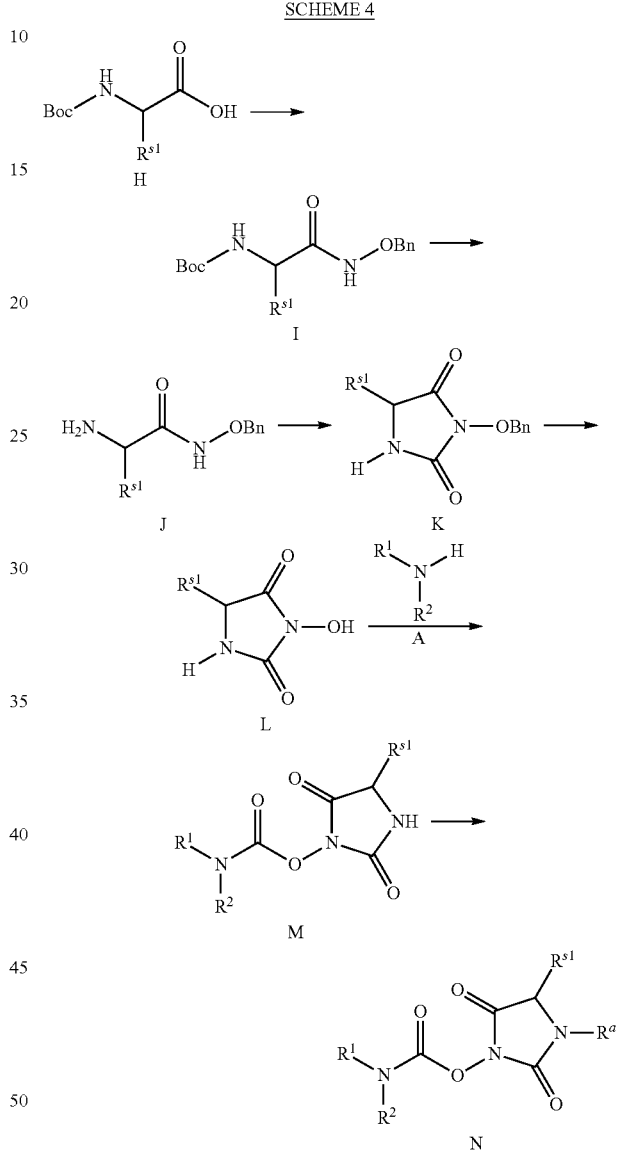

SCHEME 5 provides a detailed exemplary synthetic procedure for making carbamate derivatives having a piperidine group of the general structure S. $R^g$ is described above. Arylbromide O can be obtained from commercial sources and converted to aryllithium using an alkyl lithium, for example, tert-butyllithium at reduced temperatures. Reacting the aryllithium with ester P provides alcohol Q. The alcohol Q can be converted to intermediate R according to the representative protocol described in SCHEME 2. Compounds of the general structure S can be prepared according to the representative protocol described above for SCHEME 1. Similar chemistry can be executed using heteroarylbromides.

SCHEME 5

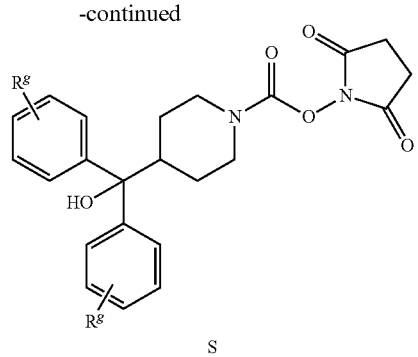

SCHEME 6 provides a detailed exemplary synthetic procedure for making carbamates of the general structure U, W, and Y. R$^g$ is, for example, described above. Intermediate Q can be converted to the methyl ether by treatment with NaH or similar base and methyl iodide in a solvent such as THF to produce intermediate T. Intermediate T may be converted to product U according to the representative protocols described in SCHEME 1 and SCHEME 2 above. Alternatively, intermediate Q can be converted to V by treatment with Et$_3$SiH followed by trifluoroacetic acid. Intermediate V may be converted to product W according to the representative protocols described in SCHEME 1 above. Additionally, intermediate Q can be converted to X using trifluoroacetic acid or 4N HCl in a solvent such as CH$_2$Cl$_2$. Conversion of X to the desired products Y can be achieved according to the representative protocols described in SCHEME 1. Similar chemistry can be executed using heteroarylbromides.

SCHEME 6

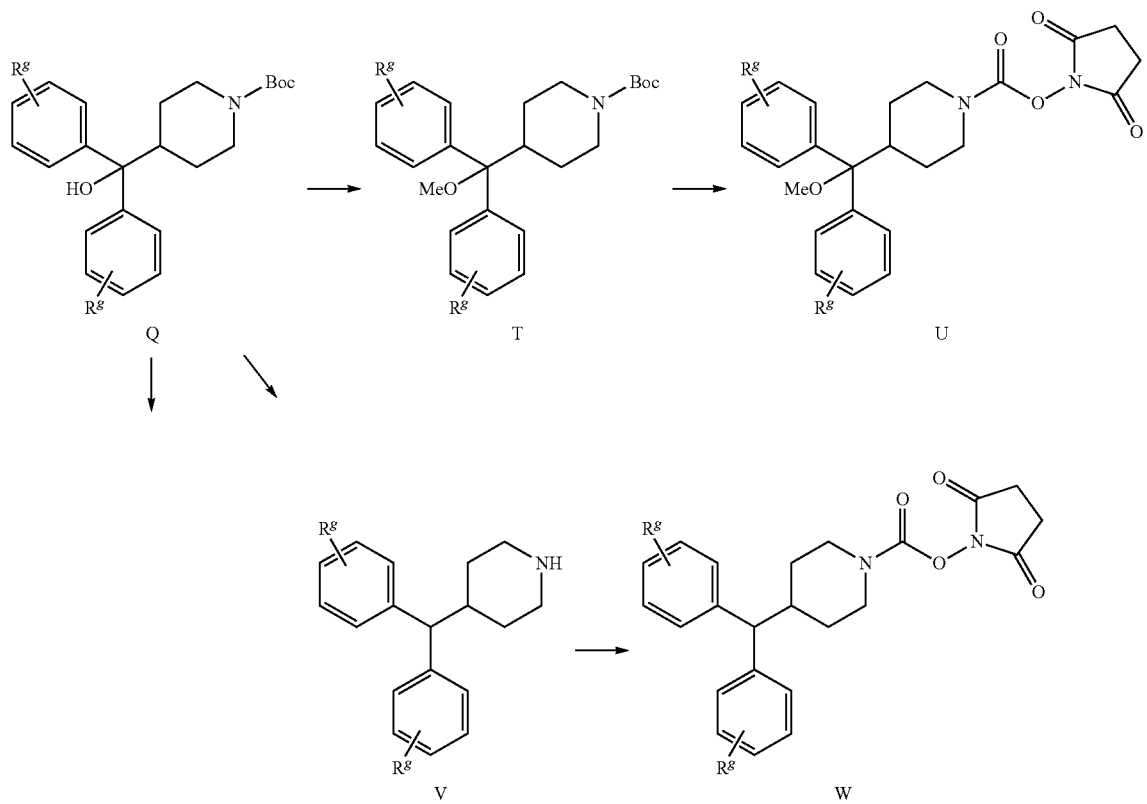

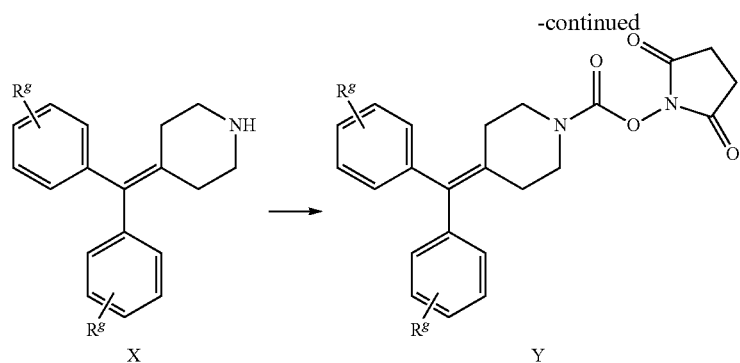

SCHEME 7 provides a detailed exemplary synthetic procedure for making carbamate derivatives having a piperazine group of the general structure AE. $R^h$ is, for example, described above and can be for example, independently selected from the recited moieties. Arylbromide P can be obtained from commercial sources and converted to an aryllithium using either tert-butyllithium or n-butyllithium at reduced temperatures or to the Grignard reagent using standard conditions to those skilled in the art. Alternatively, the aryllithiums or Grignard reagents can be purchased from commercial sources. Reacting the aryllithium or the Grignard reagent with ethyl formate or an appropriate aldehyde Z provides alcohol AA, which can be symmetrical (utilizing ethyl formate, where $R^h$ are equivalent) or unsymmetrical (utilizing aldehyde Z, where $R^h$ are not equivalent). Alcohol AA made according to the procedures above or purchased commercially can be converted to the chloro variant AB using thionyl chloride. Installation of the desired piperazine can be accomplished by treating AB with a Boc-protected piperazine in a solvent, such as acetonitrile, with or without added base, such as potassium carbonate, to give the diarylmethylpiperazine product AC. Alternatively, alcohol AA can be obtained from a commercially available ketone after reduction with $NaBH_4$ or similar reagent in solvents such as MeOH or $CH_2Cl_2$. The protected diarylmethylpiperazine AC can be converted to the intermediate AD followed by formation of the desired carbamate product AE according to the representative protocols described above in SCHEME 1 and SCHEME 2. Similar chemistry can be executed using heteroarylbromides.

SCHEME 7

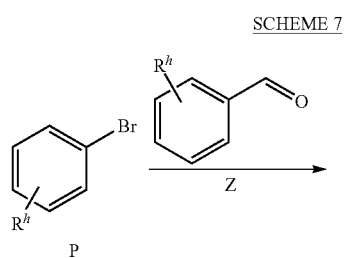

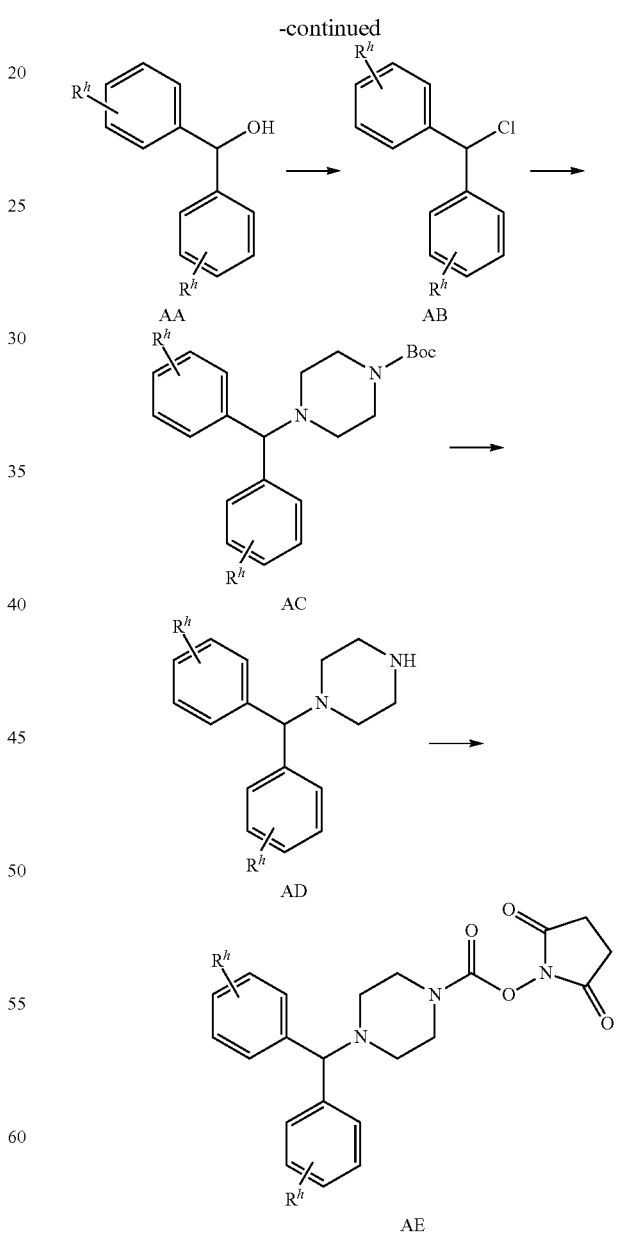

Additionally, compounds of the general Formula I can be obtained from metalation of commercially available aromatic heterocycles, AF, such as oxazole using an alkyllithium such as n-butyllithium as shown in SCHEME 8. The aryllithium can be allowed to react with an appropriate aldehyde AG to provide alcohol AH. Alcohol AH can be converted to the chloro variant, AI, using methansulfonyl chloride. The desired piperazine can be installed by treating AI with a Boc-protected piperazine to give the product AJ. AJ can be deprotected (to give AK) and converted to the desired carbamate product AL according to the representative protocols described above for SCHEME 1 and SCHEME 2.

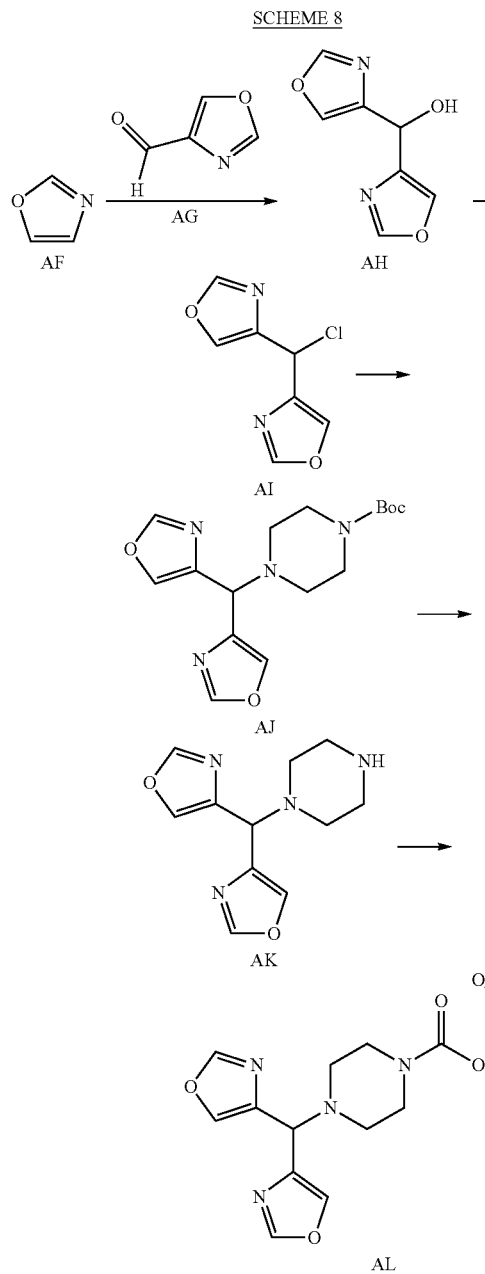

SCHEME 8 izine, for example, using EDCI in the presence of NMM or similar base to yield intermediates AN. Deprotection and formation of products AO can be accomplished according to the representative protocols described above for SCHEME 1 and SCHEME 2.

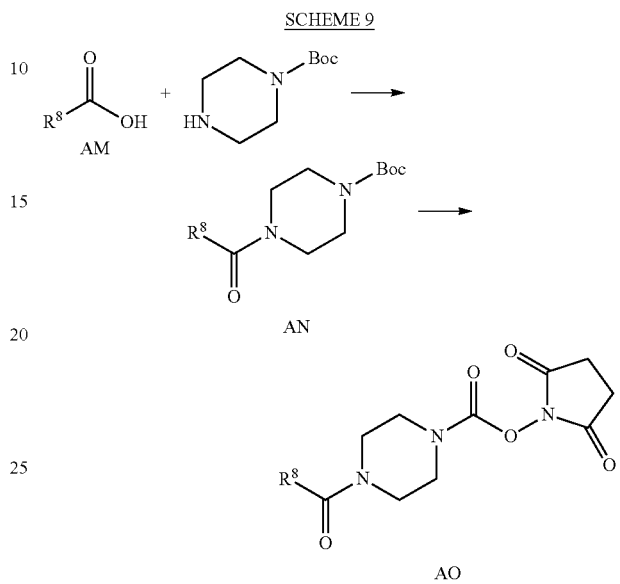

SCHEME 9

Substituted fluorobenzaldehydes AP may be subjected to nucleophilic aromatic substitution conditions according to the exemplary synthetic procedure described in SCHEME 10 using the appropriately substituted fluorobenzaldehyde and the desired amine or phenol in the presence of a base such as potassium carbonate in DMSO or dimethylacetamide at elevated temperature to provide aldehydes AQ or AR. $R^h$ is described above, for example, and can be independently selected for example from the described moieties. These aldehydes can be used as variants of aldehydes AU in SCHEME 12, below.

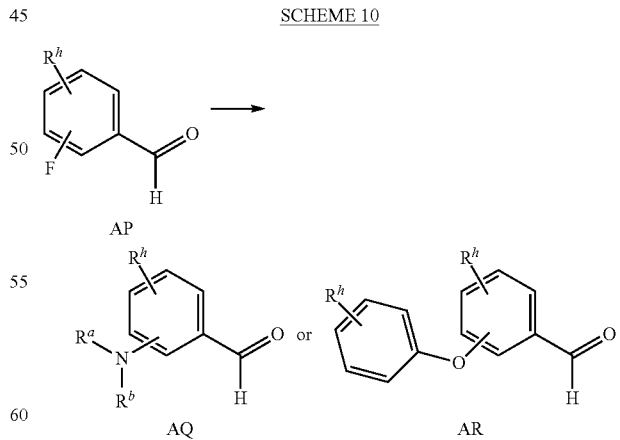

SCHEME 10

SCHEME 9 provides a detailed exemplary synthetic procedure for making carbamate derivatives having a piperazine or substituted piperazine group with e.g., a carbonyl linker, $L^3$. Acid AM, substituted with $R^8$ groups (as described above) can be coupled with Boc-protected piper- Substituted aldehydes AQ may be prepared under palladium cross coupling conditions according to the exemplary synthetic procedure described in SCHEME 11 using the appropriately substituted bromobenzaldehyde, AS, and the desired amine in the presence of a Pd catalyst such as Pd$_2$(dba)$_3$, a ligand such as BINAP, and a base such as sodium tert-butoxide, and in a solvent such as toluene at elevated temperature. R$^a$, R$^b$, and R$^h$ are described above. These aldehydes can be used as variants of aldehydes AU in SCHEME 12 below. Similar chemistry can be executed using heteroaryl aldehydes and heteroaryl boronic acids.

SCHEME 11

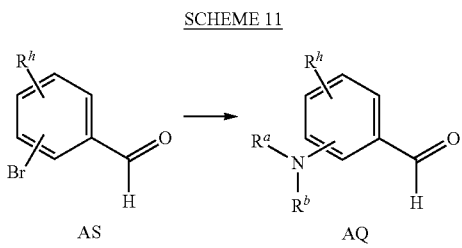

SCHEME 12 provides a detailed exemplary synthetic procedure for making carbamate derivatives containing a piperazine or substituted piperazine group. Aldehyde AU, optionally substituted with 1-3 R$^h$ groups (as described above) commercially available or prepared according to the general methods described in SCHEME 10 and SCHEME 11 can be allowed to react with amines using a reducing agent such as NaBH(OAc)$_3$, in dichloromethane, dichloroethane, N,N-dimethylformamide or the like in the presence or absence of molecular sieves to yield intermediates AV. Removal of the Boc protecting group can be achieved as described in SCHEME 2 to furnish AW. Conversion to the desired carbamate product AX can be achieved according to the representative protocols described above for SCHEME 1. Similar chemistry can be executed using heteroaryl aldehydes.

SCHEME 12

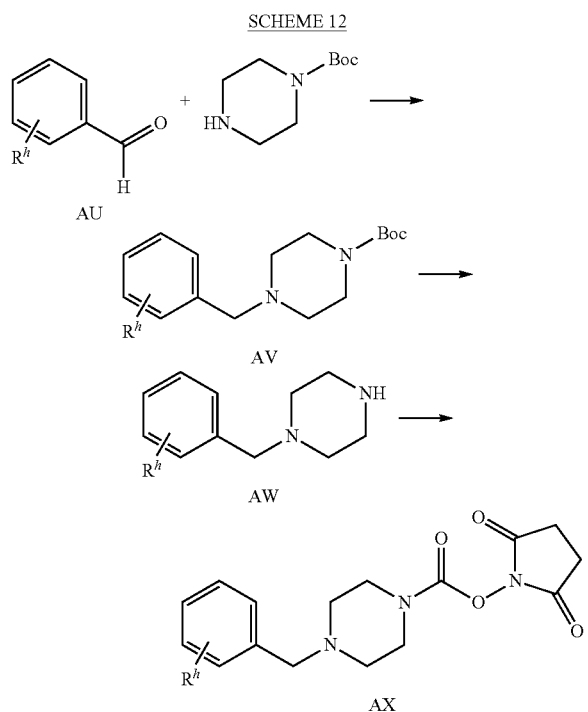

Alternatively, a palladium catalyzed cross coupling can be performed on a substituted aryl bromide after reductive amination with Boc-piperazine as described in SCHEME 13. R$^a$, R$^b$, and R$^h$ are described above. An appropriately substituted arylhalide or aryltriflate carboxaldehyde, for example bromide AY, can be allowed to react with Boc-piperazine as described in SCHEME 13 to provide AZ. Arylbromide AZ can be treated with a desired amine in the presence of a Pd catalyst such as Pd$_2$(dba)$_3$ or Pd(OAc)$_2$, a ligand such as BINAP, and a base such as sodium tert-butoxide, and in a solvent such as toluene at elevated temperature to provide intermediate BA. Intermediate AZ can also be treated with an appropriately substituted arylboronic acid optionally substituted with R$^h$ under palladium cross coupling conditions in the presence of a Pd catalyst such as Pd(PPh$_3$)$_4$ or PdCl$_2$(dppf) CH$_2$Cl$_2$ in the presence of a base such as potassium carbonate and a solvent such as dioxane or THF/water mixtures at elevated temperatures to generate BB. Intermediates BA and BB can then be converted to variants of AX as shown in SCHEME 12 according to the representative protocols described above for SCHEME 1 and SCHEME 2. Similar chemistry can be executed using heteroaryl aldehydes.

SCHEME 13

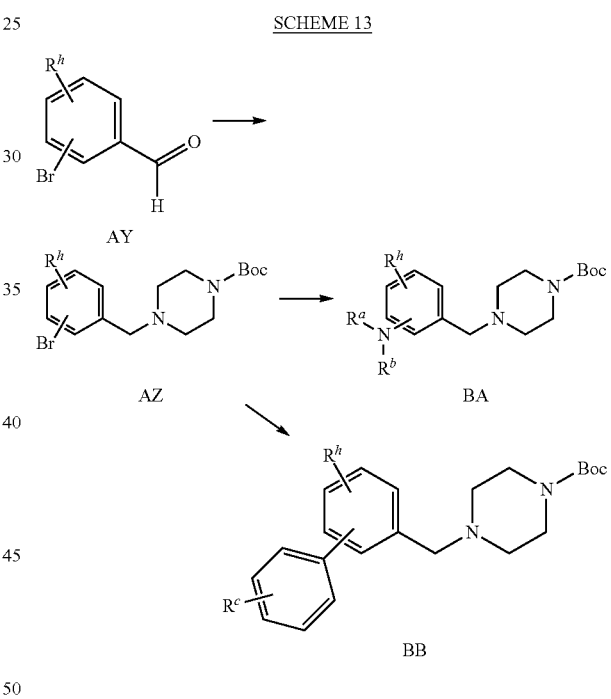

Alternatively, aldehydes of the general structure BC can be allowed to react with amines using a reducing agent such as NaBH(OAc)$_3$, in dichloromethane, dichloroethane, N,N-dimethylformamide or the like in the presence or absence of molecular sieves to yield intermediates BD, as shown in SCHEME 14. R$^a$, R$^b$, and R$^h$ are described above. Intermediates BD may be allowed to react with a base such as lithium hydroxide or sodium hydroxide and in a solvent such as MeOH/water to provide compounds of the general structure BE. Treatment of BE with amines under standard amide coupling conditions using EDCI or similar reagent and hydroxybenzotriazole in a solvent such as CH$_2$Cl$_2$ can yield intermediates BF. Conversion to products of Formula I can be achieved according to the protocols described in SCHEME 1 and SCHEME 2. Similar chemistry can be executed using heteroaryl aldehydes.

SCHEME 14

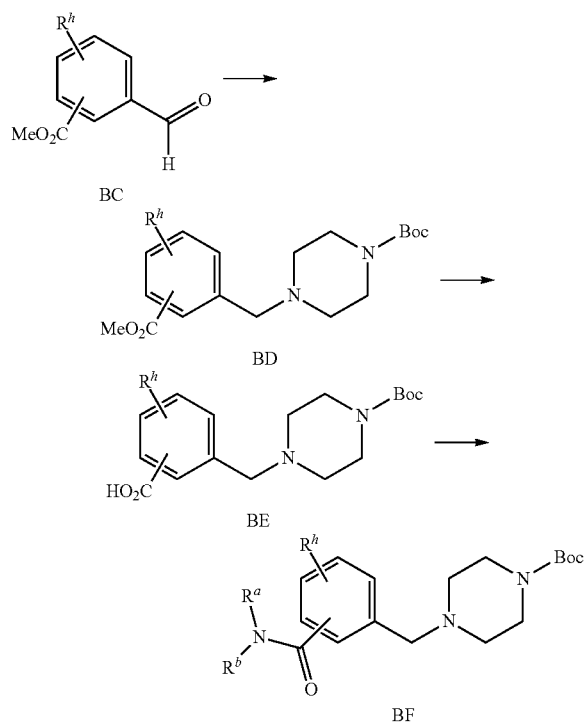

Substituted heteroaryl aldehydes of the general formula BJ can be prepared as shown in SCHEME 15 and used as shown in SCHEME 12 to prepare heteroaryl analogues of AX. $R^i$ and $R^j$ may be independently selected, and are as described above. Commercially available methyl ketones BG can be condensed with commercially available hydrazines or hydrazine salts BH in an alcoholic solvent at room temperature to reflux for hours to overnight to provide hydrazones BI. The hydrazones can then be treated with N-(chloromethylene)-N-methyl-methanaminium chloride in a solvent such as N,N-dimethylformamide and stirred at room temperature to 100° C. overnight. After an aqueous workup, aldehydes BJ are generated.

SCHEME 15

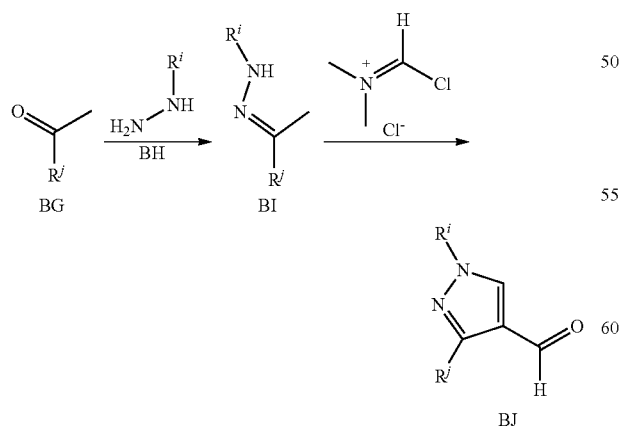

Substituted heteroaryl aldehydes of the general formula BN can be prepared as shown in SCHEME 16 and used as shown in SCHEME 12 to prepare heteroaryl analogues of AX. $R^i$ and $R^j$ may be independently selected, and are as described above. Commercially available 2,4-dioxo-pentanoic acid esters BK can be condensed with commercially available O-methylhydroxylamine or its salts in an alcoholic solvent at room temperature to reflux for hours to overnight in the presence of molecular sieves to provide oximes BL. The oximes can then be treated with commercially available hydrazines or hydrazine salts in an alcoholic solvent such as ethanol and stirred at room temperature to reflux overnight to provide esters BM. The esters can be converted to aldehydes BN through various routes known to those skilled in the art, including direct reduction with di-isobutylaluminum hydride in a solvent such as toluene or dichloromethane at −78° C. to 0° C. followed by aqueous workup, or by reducing to the alcohol with a reducing agent such as lithium borohydride or lithium aluminum hydride in a solvent such as tetrahydrofuran or diethyl ether at −78° C. to room temperature followed by an aqueous workup and oxidizing to the aldehyde with a reagent such as pyridinium chlorochromate or pyridinium dichromate in a solvent such as dichloromethane at 0° C. to reflux Other appropriate oxidants include dimethylsulfoxide with an appropriate activating agent, such as oxalyl chloride at −78° C. to 0° C. in a solvent such as dichloromethane or Dess-Martin periodinane in a solvent such as dichloromethane at room temperature.

SCHEME 16

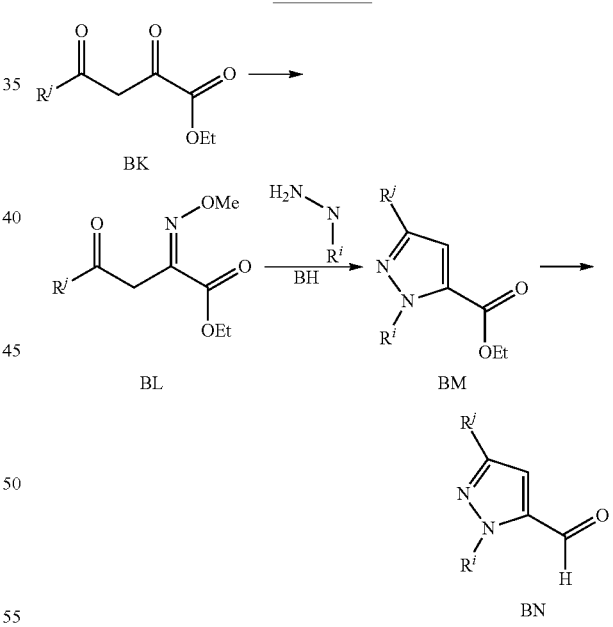

SCHEME 17 provides a detailed exemplary synthetic procedure for the preparation of intermediates BQ. Suitably substituted anilines (or amino heterocycles) can be allowed to react with chloroacetyl chloride (or similar haloalkylacyl chloride) to yield compounds BP. Treatment of BP with a mono-protected diamine such as Boc-piperizine, optionally in the presence of a base such as triethylamine, DIEA, $K_2CO_3$ and the like, yields intermediates BQ. Conversion to compounds of Formula I can be achieved according to the protocols described in SCHEME 1 and SCHEME 2.

SCHEME 17

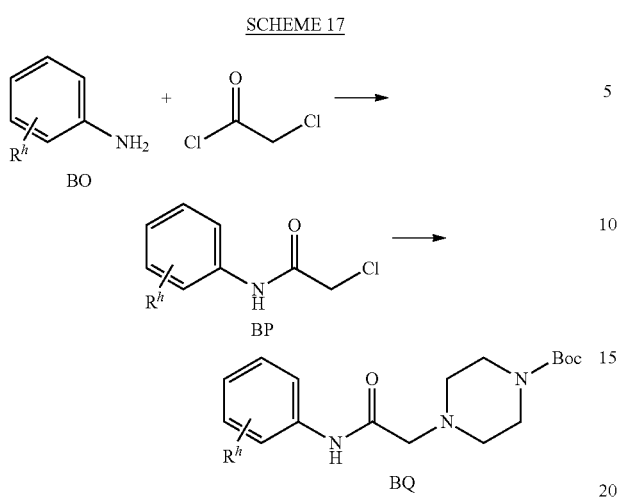

SCHEME 18 provides a detailed exemplary synthetic procedure for the preparation of intermediates BR. A mono-protected diamine, such as Boc-piperizine, can be allowed to react with chloroacetyl chloride (or similar haloalkylacyl chloride) to yield tert-butyl 4-(2-chloroacetyl)piperazine-1-carboxylate (or analogs). Treatment of tert-butyl 4-(2-chloroacetyl)piperazine-1-carboxylate (or analogs) with heterocycles containing a primary or secondary amine (such as azeditine or the like) in the presence of a base such as $K_2CO_3$ in a solvent such as DMF can yield intermediates BR. Conversion to compounds of Formula I can be achieved according to the protocols described in SCHEME 1 and SCHEME 2.

SCHEME 18

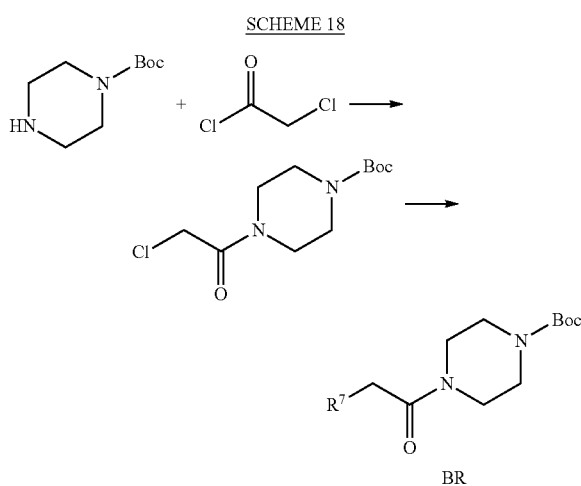

Alternatively, BR can be prepared from commercially available substituted acetic acids and a mono-protected diamine such as Boc-piperizine using EDCI or similar reagent and hydroxybenzotriazole in a solvent such as $CH_2Cl_2$ as shown in SCHEME 19. Conversion to compounds of Formula I can be achieved according to the protocols described in SCHEME 1 and SCHEME 2.

SCHEME 19

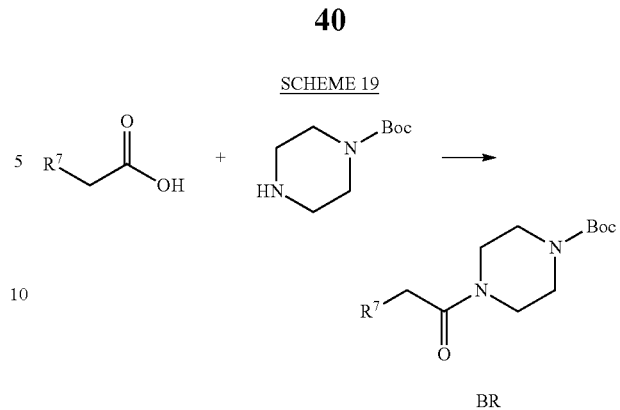

Representative contemplated compounds, including salts and/or stereoisomers, are listed below:

2,5-dioxopyrrolidin-1-yl 4-(bis(benzo[d][1,3]dioxol-5-yl) (hydroxy)methyl)piperidine-1-carboxylate; 2,5-dioxopyrrolidin-1-yl 4-[bis(4-chlorophenyl)methyl]piperazine-1-carboxylate; 2,5-dioxopyrrolidin-1-yl 4-[bis(4-bromophenyl) methyl]piperazine-1-carboxylate; 1-tert-butyl 4-(2,5-dioxopyrrolidin-1-yl) piperazine-1,4-dicarboxylate; 2,5-dioxopyrrolidin-1-yl 4-(4-methoxyphenyl)piperazine-1-carboxylate; 2,5-dioxopyrrolidin-1-yl N-[2-(4-phenoxyphenyl)ethyl]carbamate; 2,5-dioxopyrrolidin-1-yl 4-[(3-phenoxyphenyl)methyl]piperazine-1-carboxylate; 2,5-dioxopyrrolidin-1-yl 4-[2-(4-chlorophenyl)ethyl]piperidine-1-carboxylate; 2,5-dioxopyrrolidin-1-yl N-benzyl-N-ethylcarbamate; 2,5-dioxopyrrolidin-1-yl 2-methylpiperidine-1-carboxylate; 2,5-dioxopyrrolidin-1-yl 2-(hydroxymethyl) piperidine-1-carboxylate; 2,5-dioxopyrrolidin-1-yl N-methyl-N-{[3-(pyridin-4-yl)phenyl]methyl}carbamate; 2,5-dioxopyrrolidin-1-yl N-methyl-N-{[3-(pyridin-3-yl) phenyl]methyl}carbamate; 2,5-dioxopyrrolidin-1-yl N-methyl-N-{[3-(5-methyl-1,2,4-oxadiazol-3-yl)phenyl] methyl}carbamate; 2,5-dioxopyrrolidin-1-yl N-methyl-N-(2-phenylethyl)carbamate; 2,5-dioxopyrrolidin-1-yl 2-(morpholine-4-carbonyl)piperidine-1-carboxylate; 2,5-dioxopyrrolidin-1-yl piperidine-1-carboxylate; 2,5-dioxopyrrolidin-1-yl 4-(2-methylquinolin-4-yl)piperazine-1-carboxylate; 2,5-dioxopyrrolidin-1-yl N-{[4-(piperidin-1-yl)phenyl]methyl}-N-propylcarbamate; 2,5-dioxopyrrolidin-1-yl N-(1,2,3,4-tetrahydronaphthalen-1-yl) carbamate; 2,5-dioxopyrrolidin-1-yl 4-benzylpiperidine-1-carboxylate; 2,5-dioxopyrrolidin-1-yl 2-benzylpiperidine-1-carboxylate; 2,5-dioxopyrrolidin-1-yl 2-phenylpiperidine-1-carboxylate; 2,5-dioxopyrrolidin-1-yl 2-(trifluoromethyl) piperidine-1-carboxylate; 2,5-dioxopyrrolidin-1-yl 2-(2-phenylethyl)piperidine-1-carboxylate; 2,5-dioxopyrrolidin-1-yl 4-(pent-4-ynoyl)piperazine-1-carboxylate; 2,5-dioxopyrrolidin-1-yl N-[2-(naphthalen-2-yl)ethyl] carbamate; 2,5-dioxopyrrolidin-1-yl N-(hex-5-yn-1-yl) carbamate; 2,5-dioxopyrrolidin-1-yl pyrrolidine-1-carboxylate; 2,5-dioxopyrrolidin-1-yl azetidine-1-carboxylate; 2,5-dioxopyrrolidin-1-yl N-[(9Z)-octadec-9-en-1-yl]carbamate; 1,3-dioxo-2,3-dihydro-1H-isoindol-2-yl 4-[2-(4-chlorophenyl)ethyl]piperidine-1-carboxylate; 1,3-dioxo-2,3-dihydro-1H-isoindol-2-yl 4-[bis(4-chlorophenyl) methyl]piperazine-1-carboxylate; 1,3-dioxo-2,3-dihydro-1H-isoindol-2-yl 4-(4-methoxyphenyl)piperazine-1-carboxylate; 2,5-dioxopyrrolidin-1-yl 4-[(2-phenoxyphenyl) methyl]piperazine-1-carboxylate; 2,5-dioxopyrrolidin-1-yl 4-(2-(((2-chloro-5-(trifluoromethyl)phenyl)amino)-2-oxo ethyl)piperazine-1-carboxylate; 2,5-dioxopyrrolidin-1-yl 4-[(4-bromo-2-phenoxyphenyl)methyl]piperazine-1-carboxylate; 2,5-dioxopyrrolidin-1-yl morpholine-4-carboxylate; 2,5-dioxopyrrolidin-1-yl (3R)-3-(benzyloxy)pyrrolidine-1-carboxylate; 2,5-dioxopyrrolidin-1-yl (3S)-3-(benzyloxy)pyrrolidine-1-carboxylate; 3-methyl-2,5-dioxopyrrolidin-1-yl 4-(bis(4-chlorophenyl)methyl)piperazine-1-carboxylate; 3,3-dimethyl-2,5-dioxopyrrolidin-1-yl 4-(bis(4-chlorophenyl)methyl)piperazine-1-carboxylate; 2,5-dioxo-3-propylpyrrolidin-1-yl 4-(bis(4-chlorophenyl)methyl)piperazine-1-carboxylate; 2,5-dioxo-3-phenylpyrrolidin-1-yl 4-(bis(4-chlorophenyl)methyl)piperazine-1-carboxylate; 1,3-dioxohexahydro-1H-isoindol-2(3H)-yl 4-(bis(4-chlorophenyl)methyl)piperazine-1-carboxylate; 2,5-dioxoimidazolidin-1-yl 4-(bis(4-chlorophenyl)methyl)piperazine-1-carboxylate; 4-isopropyl-2,5-dioxoimidazolidin-1-yl 4-(bis(4-chlorophenyl)methyl)piperazine-1-carboxylate; 2,5-dioxoimidazolidin-1-yl 4-(4-chlorophenethyl)piperidine-1-carboxylate; 3-methyl-2,5-dioxoimidazolidin-1-yl 4-(4-chlorophenethyl)piperidine-1-carboxylate; 3-benzyl-2,5-dioxoimidazolidin-1-yl 4-(4-chlorophenethyl)piperidine-1-carboxylate; 2,5-dioxopyrrolidin-1-yl 4-acetylpiperazine-1-carboxylate; 3,3-dimethyl-2,5-dioxopyrrolidin-1-yl 4-(4-methoxyphenyl)piperazine-1-carboxylate; 1,3-dioxohexahydro-1H-isoindol-2 (3H)-yl 4-(4-methoxyphenyl)piperazine-1-carboxylate; 2,5-dioxo-3-phenylpyrrolidin-1-yl 4-(4-methoxyphenyl)piperazine-1-carboxylate; 4-isopropyl-2,5-dioxoimidazolidin-1-yl 4-(4-methoxyphenyl)piperazine-1-carboxylate; 3-methyl-2,5-dioxoimidazolidin-1-yl 4-(bis(4-chlorophenyl)methyl)piperazine-1-carboxylate; 2,5-dioxopyrrolidin-1-yl dimethylcarbamate; 2,5-dioxoimidazolidin-1-yl dimethylcarbamate; 2,5-dioxo-3-phenylpyrrolidin-1-yl dimethylcarbamate; 2,5-dioxo-3-phenylpyrrolidin-1-yl piperidine-1-carboxylate; 2,5-dioxoimidazolidin-1-yl piperidine-1-carboxylate; 2,5-dioxopyrrolidin-1-yl 4-(2-fluoro-4-morpholinobenzyl)piperazine-1-carboxylate; 2,5-dioxopyrrolidin-1-yl 4-(2-methyl-4-morpholinobenzyl)piperazine-1-carboxylate; 2,5-dioxopyrrolidin-1-yl 4-(4-chlorobenzyl)piperazine-1-carboxylate; 2,5-dioxopyrrolidin-1-yl 4-(4-bromo-2-(piperidin-1-yl)benzyl)piperazine-1-carboxylate; 2,5-dioxopyrrolidin-1-yl 4-(4-bromo-2-morpholinobenzyl)piperazine-1-carboxylate; 2,5-dioxopyrrolidin-1-yl 4-(2-methoxy-4-morpholinobenzyl)piperazine-1-carboxylate; 2,5-dioxopyrrolidin-1-yl 4-(2-methyl-4-(pyrrolidin-1-yl)benzyl)piperazine-1-carboxylate; 2,5-dioxopyrrolidin-1-yl 4-(4-chloro-2-morpholinobenzyl)piperazine-1-carboxylate; 2,5-dioxopyrrolidin-1-yl 4-(4-methoxybenzyl)piperazine-1-carboxylate; 2,5-dioxopyrrolidin-1-yl 4-(4-methylbenzyl)piperazine-1-carboxylate; 2,5-dioxopyrrolidin-1-yl 4-(4-bromo-2-(pyrrolidin-1-yl)benzyl)piperazine-1-carboxylate; 2,5-dioxopyrrolidin-1-yl 4-(2-morpholinobenzyl)piperazine-1-carboxylate; 2,5-dioxopyrrolidin-1-yl 4-(4-chloro-2-(pyrrolidin-1-yl)benzyl)piperazine-1-carboxylate; 2,5-dioxopyrrolidin-1-yl 4-(3-fluoro-4-(pyrrolidin-1-yl)benzyl)piperazine-1-carboxylate; 2,5-dioxopyrrolidin-1-yl 4-{[4-(morpholin-4-yl)-2-(trifluoromethyl)phenyl]methyl}piperazine-1-carboxylate; 2,5-dioxopyrrolidin-1-yl (2S)-2-methyl-4-{[4-(morpholin-4-yl)-2-(trifluoromethyl)phenyl]methyl}piperazine-1-carboxylate; 2,5-dioxopyrrolidin-1-yl 4-(2-chloro-4-(pyrrolidin-1-yl)benzyl)piperazine-1-carboxylate; 2,5-dioxopyrrolidin-1-yl (2R)-4-{[2-fluoro-4-(morpholin-4-yl)phenyl]methyl}-2-methylpiperazine-1-carboxylate; 2,5-dioxopyrrolidin-1-yl (2R)-2-methyl-4-{[4-(morpholin-4-yl)-2-(trifluoromethyl)phenyl]methyl}piperazine-1-carboxylate; 2,5-dioxopyrrolidin-1-yl 4-{[2-chloro-6-(morpholin-4-yl)phenyl]methyl}piperazine-1-carboxylate; 2,5-dioxopyrrolidin-1-yl 4-{[3-chloro-2-(morpholin-4-yl)phenyl]methyl}piperazine-1-carboxylate; 2,5-dioxopyrrolidin-1-yl 4-(3-morpholinobenzyl)piperazine-1-carboxylate; 2,5-dioxopyrrolidin-1-yl 4-(4-chloro-2-(1H-pyrazol-1-yl)benzyl)piperazine-1-carboxylate; 2,5-dioxopyrrolidin-1-yl 4-(2-(3-acetamidopyrrolidin-1-yl)-4-chlorobenzyl)piperazine-1-carboxylate; 2,5-dioxopyrrolidin-1-yl 2,2-dimethyl-4-{[4-(morpholin-4-yl)-2-(trifluoromethyl)phenyl]methyl}piperazine-1-carboxylate; 2,5-dioxopyrrolidin-1-yl 2,2-dimethyl-4-{[4-(morpholin-4-yl)-2-(trifluoromethoxy)phenyl]methyl}piperazine-1-carboxylate; 2,5-dioxopyrrolidin-1-yl (2S)-4-{[2-fluoro-4-(morpholin-4-yl)phenyl]methyl}-2-methylpiperazine-1-carboxylate; 2,5-dioxopyrrolidin-1-yl (2S)-4-{[2-chloro-4-(morpholin-4-yl)phenyl]methyl}-2-methylpiperazine-1-carboxylate; 2,5-dioxopyrrolidin-1-yl (2S)-2-methyl-4-{[4-(morpholin-4-yl)-2-(trifluoromethoxy)phenyl]methyl}piperazine-1-carboxylate; 2,5-dioxopyrrolidin-1-yl 4-{[2-(morpholin-4-yl)-4-(trifluoromethyl)phenyl]methyl}piperazine-1-carboxylate; 2,5-dioxopyrrolidin-1-yl 4-{[5-chloro-2-(morpholin-4-yl)phenyl]methyl}piperazine-1-carboxylate; 2,5-dioxopyrrolidin-1-yl 4-{[3-fluoro-2-(morpholin-4-yl)phenyl]methyl}piperazine-1-carboxylate; 2,5-dioxopyrrolidin-1-yl 4-(2-chloro-4-morpholinobenzyl)piperazine-1-carboxylate; 2,5-dioxopyrrolidin-1-yl 4-(4-chloro-2-(4-chloro-1H-pyrazol-1-yl)benzyl)piperazine-1-carboxylate; 2,5-dioxopyrrolidin-1-yl (2R)-4-{[2-chloro-4-(morpholin-4-yl)phenyl]methyl}-2-methylpiperazine-1-carboxylate; 2,5-dioxopyrrolidin-1-yl 4-{[2-chloro-6-(pyrrolidin-1-yl)phenyl]methyl}piperazine-1-carboxylate; 2,5-dioxopyrrolidin-1-yl 4-{[5-chloro-2-(pyrrolidin-1-yl)phenyl]methyl}piperazine-1-carboxylate; 2,5-dioxopyrrolidin-1-yl 4-(4-(pyrrolidin-1-yl)benzyl)piperazine-1-carboxylate; 2,5-dioxopyrrolidin-1-yl 4-(4-morpholinobenzyl)piperazine-1-carboxylate; 2,5-dioxopyrrolidin-1-yl 4-(3-chloro-4-morpholinobenzyl)piperazine-1-carboxylate; 2,5-dioxopyrrolidin-1-yl 4-{[4-(morpholin-4-yl)-2-(trifluoromethoxy)phenyl]methyl}piperazine-1-carboxylate; 2,5-dioxopyrrolidin-1-yl (2R)-2-methyl-4-{[4-(morpholin-4-yl)-2-(trifluoromethoxy)phenyl]methyl}piperazine-1-carboxylate; 2,5-dioxopyrrolidin-1-yl 4-{[4-(pyrrolidin-1-yl)-2-(trifluoromethoxy)phenyl]methyl}piperazine-1-carboxylate; 2,5-dioxopyrrolidin-1-yl 4-{[2-(pyrrolidin-1-yl)-4-(trifluoromethyl)phenyl]methyl}piperazine-1-carboxylate; 2,5-dioxopyrrolidin-1-yl 4-{[3-chloro-2-(pyrrolidin-1-yl)phenyl]methyl}piperazine-1-carboxylate; 2,5-dioxopyrrolidin-1-yl 4-{[3-fluoro-2-(pyrrolidin-1-yl)phenyl]methyl}piperazine-1-carboxylate; 2,5-dioxopyrrolidin-1-yl 4-(3-fluoro-4-(1H-pyrazol-1-yl)benzyl)piperazine-1-carboxylate; 2,5-dioxopyrrolidin-1-yl 4-[(4-chloro-2-{8-oxa-2-azaspiro[4.5]decan-2-yl}phenyl)methyl]piperazine-1-carboxylate; 2,5-dioxopyrrolidin-1-yl 4-{[4-chloro-2-(4-methanesulfonylpiperazin-1-yl)phenyl]methyl}piperazine-1-carboxylate; 2,5-dioxopyrrolidin-1-yl 4-[(4-chloro-2-{1-oxo-2,8-diazaspiro[4.5]decan-8-yl}phenyl)methyl]piperazine-1-carboxylate; 2,5-dioxopyrrolidin-1-yl 4-{[2-(azetidin-1-yl)-4-chlorophenyl]methyl}piperazine-1-carboxylate; 2,5-dioxopyrrolidin-1-yl 4-{[4-(2,6-dimethylpyridin-4-yl)-2-methylphenyl]methyl}piperazine-1-carboxylate; 2,5-dioxopyrrolidin-1-yl 4-[(4-chloro-2-{5H,6H,7H-pyrrolo[3,4-b]pyridin-6-yl}phenyl)methyl]piperazine-1-carboxylate; 2,5-dioxopyrrolidin-1-yl 4-{[2-(4-acetylpiperazin-1-yl)-4-chlorophenyl]methyl}piperazine-1-carboxylate; 2,5-dioxopyrrolidin-1-yl 4-({4-chloro-2-[4-(pyrrolidine-1-carbonyl)piperidin-1-yl]phenyl}methyl)piperazine-1-carboxylate; 2,5-dioxopyrrolidin-1-yl 4-[(4-chloro-2-{5H,6H,7H,8H-[1,2,4]triazolo[1,5- a]pyrazin-7-yl)phenyl]methyl}piperazine-1-carboxylate; 2,5-dioxopyrrolidin-1-yl 4-(3-(methoxycarbonyl)-4-morpholinobenzyl)piperazine-1-carboxylate; 2,5-dioxopyrrolidin-1-yl 4-{[2-(morpholin-4-yl)-5-(trifluoromethyl)phenyl]methyl}piperazine-1-carboxylate; 2,5-dioxopyrrolidin-1-yl 4-{[2-(pyrrolidin-1-yl)-5-(trifluoromethyl)phenyl]methyl}piperazine-1-carboxylate; 2,5-dioxopyrrolidin-1-yl 4-(2-methyl-3-morpholinobenzyl)piperazine-1-carboxylate; 2,5-dioxopyrrolidin-1-yl 4-(2-methyl-3-(piperidin-1-yl)benzyl)piperazine-1-carboxylate; 2,5-dioxopyrrolidin-1-yl 4-(2-methyl-3-(pyrrolidin-1-yl)benzyl)piperazine-1-carboxylate; 2,5-dioxopyrrolidin-1-yl 4-(4-fluoro-3-(pyrrolidin-1-yl)benzyl)piperazine-1-carboxylate; 2,5-dioxopyrrolidin-1-yl 4-({2-[(8aR)-octahydropyrrolo[1,2-a]piperazin-2-yl]-4-chlorophenyl}methyl)piperazine-1-carboxylate; 2,5-dioxopyrrolidin-1-yl 4-methanesulfonylpiperazine-1-carboxylate; 2,5-dioxopyrrolidin-1-yl 4-{[5-methyl-2-(morpholin-4-yl)phenyl]methyl}piperazine-1-carboxylate; 2,5-dioxopyrrolidin-1-yl 4-{[5-methyl-2-(pyrrolidin-1-yl)phenyl]methyl}piperazine-1-carboxylate; 2,5-dioxopyrrolidin-1-yl 4-(4-chloro-2-(piperidin-1-yl)benzyl)piperazine-1-carboxylate; 2,5-dioxopyrrolidin-1-yl 4-(2-(8-oxa-3-azabicyclo[3.2.1]octan-3-yl)-4-chlorobenzyl)piperazine-1-carboxylate; 2,5-dioxopyrrolidin-1-yl 4-(4-chloro-2-(hexahydrocyclopenta[b][1,4]oxazin-4(4aH)-yl)benzyl)piperazine-1-carboxylate; 2,5-dioxopyrrolidin-1-yl 4-(3-chloro-5-(piperidin-1-yl)benzyl)piperazine-1-carboxylate; 2,5-dioxopyrrolidin-1-yl 4-(3-(piperidin-1-yl)benzyl)piperazine-1-carboxylate; 2,5-dioxopyrrolidin-1-yl 4-((3-oxo-3,4-dihydro-2H-benzo[b][1,4]oxazin-6-yl)methyl)piperazine-1-carboxylate; 2,5-dioxopyrrolidin-1-yl 4-((4-bromo-1-methyl-1H-pyrazol-5-yl)methyl)piperazine-1-carboxylate; 2,5-dioxopyrrolidin-1-yl 4-((5-(4-methoxyphenyl)isoxazol-3-yl)methyl)piperazine-1-carboxylate; 2,5-dioxopyrrolidin-1-yl 4-((5-phenylisoxazol-3-yl)methyl)piperazine-1-carboxylate; 2,5-dioxopyrrolidin-1-yl 4-((3-methyl-1-phenyl-1H-pyrazol-4-yl)methyl)piperazine-1-carboxylate; 2,5-dioxopyrrolidin-1-yl 4-((1-methyl-3-phenyl-1H-pyrazol-5-yl)methyl)piperazine-1-carboxylate; 2,5-dioxopyrrolidin-1-yl 4-{[3-(2-chlorophenyl)-1-methyl-1H-pyrazol-4-yl]methyl}piperazine-1-carboxylate; 2,5-dioxopyrrolidin-1-yl 4-{[3-phenyl-1-(propan-2-yl)-1H-pyrazol-4-yl]methyl}piperazine-1-carboxylate; 2,5-dioxopyrrolidin-1-yl 4-{[3-(2-chlorophenyl)-1-(propan-2-yl)-1H-pyrazol-4-yl]methyl}piperazine-1-carboxylate; 2,5-dioxopyrrolidin-1-yl 4-((4-methyl-2-phenyloxazol-5-yl)methyl)piperazine-1-carboxylate; 2,5-dioxopyrrolidin-1-yl 4-((6-chloro-2-methylimidazo[1,2-a]pyridin-3-yl)methyl)piperazine-1-carboxylate; 2,5-dioxopyrrolidin-1-yl 4-((6-chloroimidazo[1,2-a]pyridin-3-yl)methyl)piperazine-1-carboxylate; 2,5-dioxopyrrolidin-1-yl 4-{[3-methyl-1-(propan-2-yl)-1H-pyrazol-5-yl]methyl}piperazine-1-carboxylate; 2,5-dioxopyrrolidin-1-yl 4-(imidazo[1,2-a]pyridin-3-ylmethyl)piperazine-1-carboxylate; 2,5-dioxopyrrolidin-1-yl 4-((4-methyl-2-(piperidin-1-yl)thiazol-5-yl)methyl)piperazine-1-carboxylate; 2,5-dioxopyrrolidin-1-yl 4-((1-methyl-3-phenyl-1H-pyrazol-4-yl)methyl)piperazine-1-carboxylate; 2,5-dioxopyrrolidin-1-yl 4-[bis(2,2-difluoro-2H-1,3-benzodioxol-5-yl)methyl]piperazine-1-carboxylate; 2,5-dioxopyrrolidin-1-yl 4-[bis(4-chlorophenyl)methyl]-3-methylpiperazine-1-carboxylate; 2,5-dioxopyrrolidin-1-yl 4-(bis(oxazol-4-yl)methyl)piperazine-1-carboxylate; 2,5-dioxopyrrolidin-1-yl 4-(bis(4-chloro-2-phenyl)methyl)piperazine-1-carboxylate; 2,5-dioxopyrrolidin-1-yl 4-(bis(1-methyl-1H-indazol-5-yl)methyl)piperazine-1-carboxylate; 2,5-dioxopyrrolidin-1-yl 4-(di(pyridin-3-yl)methyl)piperazine-1-carboxylate; 2,5-dioxopyrrolidin-1-yl 4-[bis(2H-1,3-benzodioxol-5-yl)methyl]piperazine-1-carboxylate; 2,5-dioxopyrrolidin-1-yl 4-[bis(1,3-dihydro-2-benzofuran-5-yl)methyl]piperazine-1-carboxylate; 2,5-dioxopyrrolidin-1-yl 4-[bis(1,3-dihydro-2-benzofuran-5-yl)(hydroxy)methyl]piperidine-1-carboxylate; 2,5-dioxopyrrolidin-1-yl 4-{[2-methyl-4-(2-methylpyridin-4-yl)phenyl]methyl}piperazine-1-carboxylate; 2,5-dioxopyrrolidin-1-yl 3-methyl-4-[(4-phenylphenyl)methyl]piperazine-1-carboxylate; 2,5-dioxopyrrolidin-1-yl 4-((3-morpholino-[1,1'-biphenyl]-4-yl)methyl)piperazine-1-carboxylate; 2,5-dioxopyrrolidin-1-yl 4-{[2-fluoro-4-(3-fluorophenyl)phenyl]methyl}piperazine-1-carboxylate; 2,5-dioxopyrrolidin-1-yl 4-{[2-methyl-4-(3-methylphenyl)phenyl]methyl}piperazine-1-carboxylate; 2,5-dioxopyrrolidin-1-yl 4-[(2-fluoro-4-phenylphenyl)methyl]piperazine-1-carboxylate; 2,5-dioxopyrrolidin-1-yl 4-[(2-methyl-4-phenylphenyl)methyl]piperazine-1-carboxylate; 2,5-dioxopyrrolidin-1-yl 4-{[2-fluoro-4-(2-methylpyridin-4-yl)phenyl]methyl}piperazine-1-carboxylate; 2,5-dioxopyrrolidin-1-yl 4-[(2-methoxy-4-phenylphenyl)methyl]piperazine-1-carboxylate; 2,5-dioxopyrrolidin-1-yl 4-{[5-(3-fluorophenyl)pyridin-2-yl]methyl}piperazine-1-carboxylate; 2,5-dioxopyrrolidin-1-yl 4-{[4-(3-methylphenyl)-2-phenoxyphenyl]methyl}piperazine-1-carboxylate; 2,5-dioxopyrrolidin-1-yl 4-{[2-methyl-4-(2-methylpyridin-3-yl)phenyl]methyl}piperazine-1-carboxylate; 2,5-dioxopyrrolidin-1-yl 4-{[2-methyl-4-(3-methylpyridin-4-yl)phenyl]methyl}piperazine-1-carboxylate; 2,5-dioxopyrrolidin-1-yl 4-{[2-methyl-4-(pyridin-3-yl)phenyl]methyl}piperazine-1-carboxylate; 2,5-dioxopyrrolidin-1-yl 4-{[2-methyl-4-(6-methylpyridin-2-yl)phenyl]methyl}piperazine-1-carboxylate; 2,5-dioxopyrrolidin-1-yl 4-{[2-fluoro-4-(2-methylpyridin-3-yl)phenyl]methyl}piperazine-1-carboxylate; 2,5-dioxopyrrolidin-1-yl 4-{[2-fluoro-4-(6-methylpyridin-2-yl)phenyl]methyl}piperazine-1-carboxylate; 2,5-dioxopyrrolidin-1-yl 4-{[4-(2,6-dimethylpyridin-4-yl)-2-fluorophenyl]methyl}piperazine-1-carboxylate; 2,5-dioxopyrrolidin-1-yl 4-{[2-fluoro-4-(3-methylpyridin-4-yl)phenyl]methyl}piperazine-1-carboxylate; 2,5-dioxopyrrolidin-1-yl 4-{[5-(2-fluorophenyl)-6-methylpyridin-2-yl]methyl}piperazine-1-carboxylate; 2,5-dioxopyrrolidin-1-yl 4-{[6-methyl-5-(2-methylphenyl)pyridin-2-yl]methyl}piperazine-1-carboxylate; 2,5-dioxopyrrolidin-1-yl 4-{[6-methyl-5-(3-methylphenyl)pyridin-2-yl]methyl}piperazine-1-carboxylate; 2,5-dioxopyrrolidin-1-yl 4-{[5-(3-fluorophenyl)-6-methylpyridin-2-yl]methyl}piperazine-1-carboxylate; 2,5-dioxopyrrolidin-1-yl 4-{[2-methyl-6-(2-methylphenyl)pyridin-3-yl]methyl}piperazine-1-carboxylate; 2,5-dioxopyrrolidin-1-yl 4-{[6-(2-fluorophenyl)-2-methylpyridin-3-yl]methyl}piperazine-1-carboxylate; 2,5-dioxopyrrolidin-1-yl 4-{[2-methyl-6-(3-methylphenyl)pyridin-3-yl]methyl}piperazine-1-carboxylate; 2,5-dioxopyrrolidin-1-yl 4-{[6-(3-fluorophenyl)-2-methylpyridin-3-yl]methyl}piperazine-1-carboxylate; 2,5-dioxopyrrolidin-1-yl 4-{[2-(propan-2-yl)-4-(pyrrolidin-1-yl)phenyl]methyl}piperazine-1-carboxylate; 2,5-dioxopyrrolidin-1-yl 4-{[4-(morpholin-4-yl)-2-(propan-2-yl)phenyl]methyl}piperazine-1-carboxylate; 2,5-dioxopyrrolidin-1-yl 4-{[4-phenyl-2-(propan-2-yl)phenyl]methyl}piperazine-1-carboxylate; 2,5-dioxopyrrolidin-1-yl 4-{[2-(dimethylcarbamoyl)-4-phenylphenyl]methyl}piperazine-1-carboxylate; 2,5-dioxopyrrolidin-1-yl 4-{[3-chloro-2-(pyrrolidine-1-carbonyl)phenyl]methyl}piperazine-1-carboxylate; 2,5-dioxopyrrolidin-1-yl 4-{[4-phenyl-2-(pyrrolidine-1-carbonyl)phenyl]methyl}piperazine-1-carboxylate; 2,5- dioxopyrrolidin-1-yl 4-{[2-chloro-4-(morpholine-4-carbonyl)phenyl]methyl}piperazine-1-carboxylate; 2,5-dioxopyrrolidin-1-yl 4-{[2-chloro-4-(pyrrolidine-1-carbonyl)phenyl]methyl}piperazine-1-carboxylate; 2,5-dioxopyrrolidin-1-yl 4-{[4-(azetidine-1-carbonyl)-2-chlorophenyl]methyl}piperazine-1-carboxylate; 2,5-dioxopyrrolidin-1-yl 4-{[4-chloro-2-(morpholine-4-carbonyl)phenyl]methyl}piperazine-1-carboxylate; 2,5-dioxopyrrolidin-1-yl 4-{[4-chloro-2-(pyrrolidine-1-carbonyl)phenyl]methyl}piperazine-1-carboxylate; 2,5-dioxopyrrolidin-1-yl 4-{[2-(azetidine-1-carbonyl)-4-chlorophenyl]methyl}piperazine-1-carboxylate; 2,5-dioxopyrrolidin-1-yl 4-{[3-chloro-2-(morpholine-4-carbonyl)phenyl]methyl}piperazine-1-carboxylate; 2,5-dioxopyrrolidin-1-yl 4-{[5-chloro-2-(morpholine-4-carbonyl)phenyl]methyl}piperazine-1-carboxylate; 2,5-dioxopyrrolidin-1-yl 4-{[5-chloro-2-(pyrrolidine-1-carbonyl)phenyl]methyl}piperazine-1-carboxylate; 2,5-dioxopyrrolidin-1-yl 4-{[5-methyl-2-(morpholine-4-carbonyl)phenyl]methyl}piperazine-1-carboxylate; 2,5-dioxopyrrolidin-1-yl 4-{[5-methyl-2-(pyrrolidine-1-carbonyl)phenyl]methyl}piperazine-1-carboxylate; 2,5-dioxopyrrolidin-1-yl 4-{[2-(morpholine-4-carbonyl)-5-(trifluoromethyl)phenyl]methyl}piperazine-1-carboxylate; 2,5-dioxopyrrolidin-1-yl 4-{[2-(pyrrolidine-1-carbonyl)-5-(trifluoromethyl)phenyl]methyl}piperazine-1-carboxylate; 2,5-dioxopyrrolidin-1-yl 4-{[2-methyl-3-(morpholine-4-carbonyl)phenyl]methyl}piperazine-1-carboxylate; 2,5-dioxopyrrolidin-1-yl 4-{[2-methyl-3-(pyrrolidine-1-carbonyl)phenyl]methyl}piperazine-1-carboxylate; 2,5-dioxopyrrolidin-1-yl 4-{[3-(azetidine-1-carbonyl)-2-methylphenyl]methyl}piperazine-1-carboxylate; 2,5-dioxopyrrolidin-1-yl 4-{[3-methyl-5-(morpholine-4-carbonyl)phenyl]methyl}piperazine-1-carboxylate; 2,5-dioxopyrrolidin-1-yl 4-{[4-chloro-3-(morpholine-4-carbonyl)phenyl]methyl}piperazine-1-carboxylate; 2,5-dioxopyrrolidin-1-yl 4-{[3-(azetidine-1-carbonyl)-4-chlorophenyl]methyl}piperazine-1-carboxylate; 2,5-dioxopyrrolidin-1-yl 4-(3-chlorobenzoyl)piperazine-1-carboxylate; 2,5-dioxopyrrolidin-1-yl 4-benzoylpiperazine-1-carboxylate; 2,5-dioxopyrrolidin-1-yl 4-[2-(piperidin-1-yl)acetyl]piperazine-1-carboxylate; 2,5-dioxopyrrolidin-1-yl 4-[2-(pyrrolidin-1-yl)acetyl]piperazine-1-carboxylate; 2,5-dioxopyrrolidin-1-yl 4-[2-(morpholin-4-yl)acetyl]piperazine-1-carboxylate; 2,5-dioxopyrrolidin-1-yl 4-[2-(azetidin-1-yl)acetyl]piperazine-1-carboxylate; 2,5-dioxopyrrolidin-1-yl 4-(pyrrolidin-1-yl)piperidine-1-carboxylate; 2,5-dioxopyrrolidin-1-yl 4-(piperidin-1-yl)piperidine-1-carboxylate; 2,5-dioxopyrrolidin-1-yl 4-(2-oxopyrrolidin-1-yl)piperidine-1-carboxylate; 2,5-dioxopyrrolidin-1-yl 4-(2-oxopiperidin-1-yl)piperidine-1-carboxylate.

II. Methods

Another aspect of the disclosure provides methods of modulating the activity of MAGL and/or ABHD6. Contemplated methods, for example, comprise exposing said enzyme to a compound described herein. In some embodiments, the compound utilized by one or more of the foregoing methods is one of the generic, subgeneric, or specific compounds described herein, such as a compound of Formula I. The ability of compounds described herein to modulate or inhibit MAGL and/or ABHD6 can be evaluated by procedures known in the art and/or described herein. Another aspect of this disclosure provides methods of treating a disease associated with expression or activity of MAGL and/or ABHD6 in a patient. For example, provided herein are compounds that may be selective in inhibiting MAGL or ABHD6, or both, as compared to inhibition of other serine hydrolases e.g., FAAH, e.g. 10, 100, 1000 or more fold inhibition of MAGL over FAAH. In other embodiments, disclosed compounds may be more selective in inhibition of MAGL as compared to ABHD6.

Also contemplated herein are methods of treating and/or preventing in a patient in need thereof a disorder such as one or more of acute or chronic pain, obesity, metabolic disorders (such as syndrome X), vomiting or nausea, eating disorders such as anorexia and/or bulimia; dislipidaemia, neuropathy such as diabetic neuropathy, pellagric neuropathy, alcoholic neuropathy, Beriberi neuropathy, burning feet syndrome, neurodegenerative disorders such as multiple sclerosis, Parkinson's disease, Huntington's chorea, Alzheimer's disease, amyotrophic lateral sclerosis, epilepsy, sleep disorders, cardiovascular diseases, hypertension, dyslipidemia, atherosclerosis, osteoporosis, osteoarthritis, emesis, epilepsy, mental disorders such as schizophrenia and depression, glaucoma, cachexia, insomnia, traumatic brain injury, spinal cord injury, seizures, excitotoxin exposure, ischemia, AIDS wasting syndrome, renal ischaemia, cancers (e.g., solid tumor cancers such as breast, lung, head and neck, ovarian, sarcoma, melanoma, and/or prostate cancer); cancers such as melanoma, metastatic tumors, kidney or bladder cancers, brain, gastrointestinal cancers (e.g., colon cancer), leukemia or blood cancers (e.g. myeloid, lymphoid or monocytic cancers), inflammatory disorders (e.g. bladder inflammation), including inflammatory pain, and/or psychological disorders including anxiety disorders (e.g., panic disorder, acute stress disorder, post-traumatic stress disorder, substance-induced anxiety disorders, obsessive-compulsive disorder, agoraphobia, specific phobia, social phobia. Contemplated methods include administering a pharmaceutically effective amount of a disclosed compound.

For example, provide herein is a method for treating chronic pain such as inflammatory pain, visceral pain, post operative pain, pain related to migraine, osteoarthritis, or rheumatoid arthritis, back pain, lower back pain, joint pain, abdominal pain, chest pain, labor, musculoskeletal diseases, skin diseases, toothache, pyresis, burn, sunburn, snake bite, venomous snake bite, spider bite, insect sting, neurogenic bladder, interstitial cystitis, urinary tract infection, rhinitis, contact dermatitis/hypersensitivity, itch, eczema, pharyngitis, mucositis, enteritis, irritable bowel syndrome, cholecystitis, pancreatitis, postmastectomy pain syndrome, menstrual pain, endometriosis, pain, pain due to physical trauma, headache, sinus headache, tension headache, or arachnoiditis.

For example, contemplated herein are methods for treating neuropathic pain (e.g., neuropathic low back pain, complex regional pain syndrome, post trigeminal neuralgia, causalgia, toxic neuropathy, reflex sympathetic dystrophy, diabetic neuropathy, chronic neuropathy caused by chemotherapeutic agents) in a patient in need thereof, comprising administering a pharmaceutically effective amount of a disclosed compound.

Also contemplated herein are methods for ameliorating cognitive function in a patient suffering from Down's syndrome or Alzheimer's disease, comprising administering an effective amount of a disclosed compound. Exemplary patients suffering from Down's syndrome may be a pediatric patient (e.g., a patient of age 0-11 years, 0-18 years, 0-6 years, or e.g., 12 to 18 years), an adult patient (e.g., 18 years or older), or e.g., an older patient e.g., 18-40 years, 20-50 years). Such patients may also suffer from further cognitive impairment and/or dementia, and/or seizures which may or may not be due to production of prostaglandins and/or amyloid beta. For example, such patients may also be suffering from, or may have one or more of the following symptoms associated with early-mid or late stage cognitive impairment: loss of language, impairment of social skills, progressive loss of activities of daily living, and may include psychotic behavior. Provided herein, for example, is a method for treating a patient having Down's syndrome or Alzheimer's disease with cognitive impairment, comprising administering an effective amount of a disclosed compound. Such disclosed methods may result in cognitive improvement, for example, measured by IQ or the Arizona Cognitive Test Battery (e.g., measured with a cognitive test battery designed for use in individuals with Down's syndrome). For example, a treated patient using a disclosed method may have at least one of: increased memory, improved memory or improved speech. In some embodiments, such disclosed methods may result in a patient having an increased quality of life as measured by an adaptive behavior scale after said administration.

In other embodiments, a method for at least partially providing a Down's syndrome patient a neuroprotective (such as a disclosed compounds), that may result in delayed onset of neurodegeneration or may substantially prevent neurodegeneration, is provided. Administration to a patient may be initiated before onset of neurodegeneration and/or onset of neurodegeneration symptoms. Contemplated herein are methods for treating and/or ameliorating cognitive decline, improving sleep duration and/or quality, and/or treating PANDAS (pediatric autoimmune neuropsychiatric disorders associated with streptococcal infections) in a patient in need thereof, comprising administering a disclosed compound.

In certain embodiments, a disclosed compound utilized by one or more of the foregoing methods is one of the generic, subgeneric, or specific compounds described herein, such as a compound of Formula I.

Disclosed compounds may be administered to patients (animals and humans) in need of such treatment in dosages that will provide optimal pharmaceutical efficacy. It will be appreciated that the dose required for use in any particular application will vary from patient to patient, not only with the particular compound or composition selected, but also with the route of administration, the nature of the condition being treated, the age and condition of the patient, concurrent medication or special diets then being followed by the patient, and other factors which those skilled in the art will recognize, with the appropriate dosage ultimately being at the discretion of the attendant physician. For treating clinical conditions and diseases noted above, a contemplated compound disclosed herein may be administered orally, subcutaneously, topically, parenterally, by inhalation spray or rectally in dosage unit formulations containing conventional non-toxic pharmaceutically acceptable carriers, adjuvants and vehicles. Parenteral administration may include subcutaneous injections, intravenous or intramuscular injections or infusion techniques.

Also contemplated herein are combination therapies, for example, co-administering a disclosed compound and an additional active agent, as part of a specific treatment regimen intended to provide the beneficial effect from the co-action of these therapeutic agents. The beneficial effect of the combination includes, but is not limited to, pharmacokinetic or pharmacodynamic co-action resulting from the combination of therapeutic agents. Administration of these therapeutic agents in combination typically is carried out over a defined time period (usually weeks, months or years depending upon the combination selected). Combination therapy is intended to embrace administration of multiple therapeutic agents in a sequential manner, that is, wherein each therapeutic agent is administered at a different time, as well as administration of these therapeutic agents, or at least two of the therapeutic agents, in a substantially simultaneous manner.

Substantially simultaneous administration can be accomplished, for example, by administering to the subject a single formulation or composition, (e.g., a tablet or capsule having a fixed ratio of each therapeutic agent or in multiple, single formuluations (e.g., capsules) for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection.

Combination therapy also can embrace the administration of the therapeutic agents as described above in further combination with other biologically active ingredients and non-drug therapies. Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

The components of the combination may be administered to a patient simultaneously or sequentially. It will be appreciated that the components may be present in the same pharmaceutically acceptable carrier and, therefore, are administered simultaneously. Alternatively, the active ingredients may be present in separate pharmaceutical carriers, such as, conventional oral dosage forms, that can be administered either simultaneously or sequentially.

For example, e.g., for contemplated treatment of pain or other contemplated indications (e.g., Alzheimer' or Down's syndrome), a disclosed compound can be co-administered with another therapeutic for pain such as an opioid, a cannabinoid receptor (CB-1 or CB-2) modulator, a COX-2 inhibitor, acetaminophen, and/or a non-steroidal anti-inflammatory agent. Additional therapeutics e.g., for the treatment of pain that may be co-administered include morphine, codeine, hydromorphone, hydrocodone, oxymorphone, fentanyl, tramadol, and levorphanol.

Other contemplated therapeutics for co-administration include aspirin, naproxen, ibuprofen, salsalate, diflunisal, dexibuprofen, fenoprofen, ketoprofen, oxaprozin, loxoprofen, indomethacin, tolmetin, sulindac, etodolac, ketorolac, piroxicam, meloxicam, tenoxicam, droxicam, lornoxicam, celecoxib, parecoxib, rimonabant, and/or etoricoxic.

III. Pharmaceutical Compositions

This disclosure provides pharmaceutical compositions comprising compounds as disclosed herein formulated together with a pharmaceutically acceptable carrier. In particular, the present disclosure provides pharmaceutical compositions comprising compounds as disclosed herein formulated together with one or more pharmaceutically acceptable carriers. These formulations include those suitable for oral, rectal, topical, buccal, parenteral (e.g., subcutaneous, intramuscular, intradermal, or intravenous) rectal, vaginal, or aerosol administration, although the most suitable form of administration in any given case will depend on the degree and severity of the condition being treated and on the nature of the particular compound being used. For example, disclosed compositions may be formulated as a unit dose, and/or may be formulated for oral or subcutaneous administration.

Exemplary pharmaceutical compositions may be used in the form of a pharmaceutical preparation, for example, in solid, semisolid or liquid form, which includes one or more of a disclosed compound, as an active ingredient, in admixture with an organic or inorganic carrier or excipient suitable for external, enteral or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The active object compound is included in the pharmaceutical composition in an amount sufficient to produce the desired effect upon the process or condition of the disease.

For preparing solid compositions such as tablets, the principal active ingredient may be mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a disclosed compound or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules.

In solid dosage forms for oral administration (capsules, tablets, pills, dragees, powders, granules and the like), the subject composition is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the subject composition moistened with an inert liquid diluent. Tablets, and other solid dosage forms, such as dragees, capsules, pills and granules, may optionally be scored or prepared with coatings and shells, such as enteric coatings and other coatings well known in the pharmaceutical-formulating art.

Compositions for inhalation or insufflation include solutions and suspensions in pharmaceutically acceptable, aqueous or organic solvents, or mixtures thereof, and powders. Liquid dosage forms for oral administration include pharmaceutically acceptable emulsions, microemulsions, solutions, suspensions, syrups and elixirs. In addition to the subject composition, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, cyclodextrins and mixtures thereof.

Suspensions, in addition to the subject composition, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing a subject composition with one or more suitable non-irritating excipients or carriers comprising, for example, cocoa butter, polyethylene glycol, a suppository wax or a salicylate, and which is solid at room temperature, but liquid at body temperature and, therefore, will melt in the body cavity and release the active agent.

Dosage forms for transdermal administration of a subject composition include powders, sprays, ointments, pastes, creams, lotions, gels, solutions, patches and inhalants. The active component may be mixed under sterile conditions with a pharmaceutically acceptable carrier, and with any preservatives, buffers, or propellants which may be required.

The ointments, pastes, creams and gels may contain, in addition to a subject composition, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays may contain, in addition to a subject composition, excipients such as lactose, talc, silicic acid, aluminum hydroxide, calcium silicates and polyamide powder, or mixtures of these substances. Sprays may additionally contain customary propellants, such as chlorofluorohydrocarbons and volatile unsubstituted hydrocarbons, such as butane and propane.

Compositions and compounds disclosed herein may alternatively be administered by aerosol. This is accomplished by preparing an aqueous aerosol, liposomal preparation or solid particles containing the compound. A non-aqueous (e.g., fluorocarbon propellant) suspension could be used. Sonic nebulizers may be used because they minimize exposing the agent to shear, which may result in degradation of the compounds contained in the subject compositions. Ordinarily, an aqueous aerosol is made by formulating an aqueous solution or suspension of a subject composition together with conventional pharmaceutically acceptable carriers and stabilizers. The carriers and stabilizers vary with the requirements of the particular subject composition, but typically include non-ionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Pharmaceutical compositions suitable for parenteral administration comprise a subject composition in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and non-aqueous carriers which may be employed in the pharmaceutical compositions include water, ethanol, polyols (such as glycerol, propylene glycol, polyethylene glycol, and the like), and suitable mixtures thereof, vegetable oils, such as olive oil, and injectable organic esters, such as ethyl oleate and cyclodextrins. Proper fluidity may be maintained, for example, by the use of coating materials, such as lecithin, by the maintenance of the required particle size in the case of dispersions, and by the use of surfactants Also contemplated are enteral pharmaceutical formulations including a disclosed compound and an enteric material; and a pharmaceutically acceptable carrier or excipient thereof. Enteric materials refer to polymers that are substantially insoluble in the acidic environment of the stomach, and that are predominantly soluble in intestinal fluids at specific pHs. The small intestine is the part of the gastrointestinal tract (gut) between the stomach and the large intestine, and includes the duodenum, jejunum, and ileum. The pH of the duodenum is about 5.5, the pH of the jejunum is about 6.5 and the pH of the distal ileum is about 7.5. Accordingly, enteric materials are not soluble, for example, until a pH of about 5.0, of about 5.2, of about 5.4, of about 5.6, of about 5.8, of about 6.0, of about 6.2, of about 6.4, of about 6.6, of about 6.8, of about 7.0, of about 7.2, of about 7.4, of about 7.6, of about 7.8, of about 8.0, of about 8.2, of about 8.4, of about 8.6, of about 8.8, of about 9.0, of about 9.2, of about 9.4, of about 9.6, of about 9.8, or of about 10.0. Exemplary enteric materials include cellulose acetate phthalate (CAP), hydroxypropyl methylcellulose phthalate (HPMCP), polyvinyl acetate phthalate (PVAP), hydroxypropyl methylcellulose acetate succinate (HPMCAS), cellulose acetate trimellitate, hydroxypropyl methylcellulose succinate, cellulose acetate succinate, cellulose acetate hexahydrophthalate, cellulose propionate phthalate, cellulose acetate maleate, cellulose acetate butyrate, cellulose acetate propionate, copolymer of methylmethacrylic acid and methyl methacrylate, copolymer of methyl acrylate, methylmethacrylate and methacrylic acid, copolymer of methylvinyl ether and maleic anhydride (Gantrez ES series), ethyl methyacrylate-methylmethacrylate-chlorotrimethylammonium ethyl acrylate copolymer, natural resins such as zein, shellac and copal collophorium, and several commercially available enteric dispersion systems (e.g., Eudragit L30D55, Eudragit FS30D, Eudragit L100, Eudragit S100, Kollicoat EMM30D, Estacryl 30D, Coateric, and Aquateric). The solubility of each of the above materials is either known or is readily determinable in vitro. The foregoing is a list of possible materials, but one of skill in the art with the benefit of the disclosure would recognize that it is not comprehensive and that there are other enteric materials that would meet the objectives of the present disclosure

EXAMPLES

The compounds described herein can be prepared in a number of ways based on the teachings contained herein and synthetic procedures known in the art. In the description of the synthetic methods described below, it is to be understood that all proposed reaction conditions, including choice of solvent, reaction atmosphere, reaction temperature, duration of the experiment and workup procedures, can be chosen to be the conditions standard for that reaction, unless otherwise indicated. It is understood by one skilled in the art of organic synthesis that the functionality present on various portions of the molecule should be compatible with the reagents and reactions proposed. Substituents not compatible with the reaction conditions will be apparent to one skilled in the art, and alternate methods are therefore indicated. The starting materials for the examples are either commercially available or are readily prepared by standard methods from known materials.

All commercially available chemicals were obtained from Aldrich, Acros, Fisher, Fluka, Maybridge or the like and were used without further purification, except where noted. Dry solvents are obtained, for example, by passing these through activated alumina columns. All reactions are typically carried out under an inert nitrogen atmosphere using oven-baked glassware unless otherwise noted. Flash chromatography is performed using 230-400 mesh silica gel 60. NMR spectra were generated on either Varian 400 MHz Bruker 300, Bruker 400, Bruker 500 or Bruker 600 MHz instruments or the like. Chemical shifts are typically recorded in ppm relative to tetramethylsilane (TMS) with multiplicities given as s (singlet), bs (broad singlet), d (doublet), t (triplet), dt (double of triplets), q (quadruplet), qd (quadruplet of doublets), m (multiplet).

Procedure A: Synthesis of NHS-Carbamates

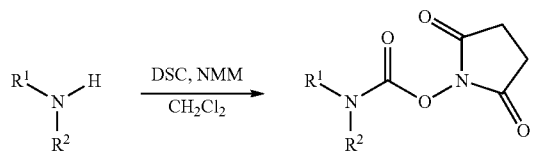

To a stirring solution of N,N'-disuccinimidyl carbonate (130 mg, 0.50 mmol, 1.0 equiv) and N-methylmorpholine (0.16 mL, 1.5 mmol, 3.0 equiv) in dry CH$_2$Cl$_2$ (5.0 mL) was added 1° or 2° amines (0.50 mmol, 1.0 equiv). The reaction mixture was stirred at room temperature for 12 h. A stream of nitrogen was passed over the reaction mixture to remove the solvent and to the remaining residue was added EtOAc (20 mL). The resulting precipitate was filtered off and the filtrate was concentrated and purified by SiO$_2$ flash chromatography (EtOAc/hexanes) to give the pure NHS carbamate.

Procedure B. Synthesis of Substituted O—(N-Hydroxyimide)Carbamates

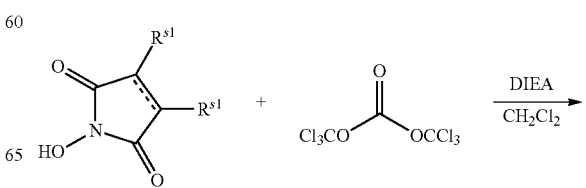

-continued

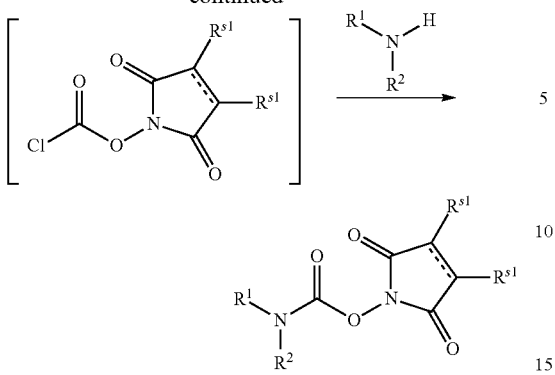

To a stirring solution of triphosgene (148 mg, 0.50 mmol, 0.3 equiv) in CH$_2$Cl$_2$ (50 mL) was added N-hydroxyimide (0.90 mmol, 1.0 equiv) followed by N,N-diisopropylethylamine (0.47 mL, 2.7 mmol, 3.0 equiv). After 2 h, the secondary amine (0.90 mmol, 1.0 equiv) was added as a solution in CH$_2$Cl$_2$ (2 mL) and stirred for another 2 h. The mixture was concentrated under reduced pressure and purified directly by SiO$_2$ flash chromatography (EtOAc/hexanes) to provide compound.

Example 1

2,5-Dioxopyrrolidin-1-yl 4-(bis(benzo[d][1,3]dioxol-5 yl)(hydroxy)methyl)piperidine-1-carboxylate

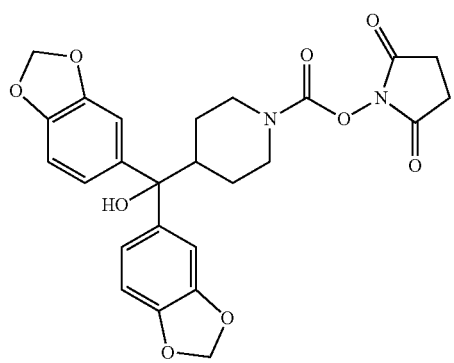

The title compound was synthesized according to Procedure A from bis(benzo[d][1,3]dioxol-5-yl)(piperidin-4-yl)methanol (27 mg, 0.075 mmol), DSC (19 mg, 0.075 mmol) and NMM (0.025 mL, 0.23 mmol). Purification of the crude product by flash chromatography (6:3:1 EtOAc:hexanes:MeOH) provided the title compound (31 mg, 84%) as a white solid: $^1$H NMR (400 MHz, CDCl$_3$) δ 6.92 (s, 2H), 6.90 (d, J=8.30 Hz, 2H), 6.74 (d, J=8.34 Hz, 2H), 5.92 (s, 4H), 4.27-4.09 (m, 2H), 3.02 (t, J=12.13 Hz, 1H), 2.89 (t, J=12.29 Hz, 1H), 2.80 (s, 4H), 2.44 (t, J=11.60 Hz, 1H), 2.19 (s, 1H), 1.66-1.56 (m, 2H), 1.56-1.36 (m, 2H); $^{13}$C NMR (101 MHz, CDCl$_3$) δ 170.25, 150.65, 148.13, 146.66, 139.94, 119.15, 108.26, 107.06, 101.45, 79.62, 46.06, 45.24, 44.40, 26.65, 26.40, 25.86; HRMS (ESI-TOF+) m/z calcd for C$_{25}$H$_{24}$N$_2$O$_9$ [M+Na]$^+$: 519.1374. found 519.1384.

Example 2

2,5-Dioxopyrrolidin-1-yl 4-[bis(4-chlorophenyl)methyl]piperazine-1-carboxylate

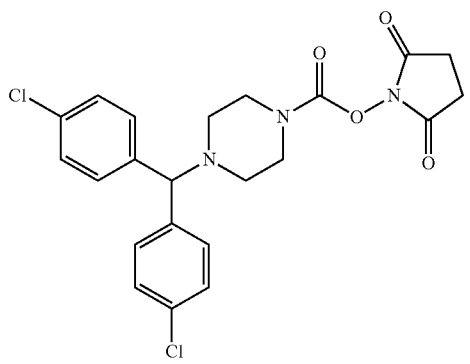

The title compound was synthesized according to Procedure A from 1-(bis(4-chlorophenyl)methyl)piperazine (160 mg, 0.50 mmol), DSC (130 mg, 0.50 mmol) and NMM (0.16 mL, 1.5 mmol). Purification of the crude product by flash chromatography (50% EtOAc/hexanes) provided the title compound (180 mg, 78%) as a colorless oil: $^1$H NMR (500 MHz, CDCl$_3$) δ 7.33-7.29 (m, 4H), 7.28-7.25 (m, 4H), 4.24 (s, 1H), 3.63 (bs, 2H), 3.51 (bs, 2H), 2.79 (s, 4H), 2.42 (d, J=4.8 Hz, 3H); $^{13}$C NMR (126 MHz, CDCl$_3$) δ 170.14, 150.70, 140.44, 133.60, 129.42, 74.76, 51.45, 51.38, 45.54, 45.04, 25.89; HRMS (ESI-TOF+) m/z calcd for C$_{22}$H$_{21}$Cl$_2$N$_3$O$_4$ [M+H]$^+$: 462.0987. found 462.0979.

Example 3

2,5-Dioxopyrrolidin-1-yl 4-[bis(4-bromophenyl)methyl]piperazine-1-carboxylate

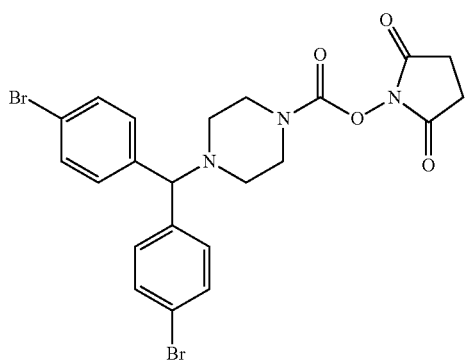

The title compound was synthesized according to Procedure A from 1-(bis(4-bromophenyl)methyl)piperazine (45 mg, 0.11 mmol), DSC (28 mg, 0.11 mmol) and NMM (0.036 mL, 0.33 mmol). Purification of the crude product by flash chromatography (50% EtOAc/hexanes) provided the title compound (50 mg, 83%) as an off-white crystalline solid: $^1$H NMR (600 MHz, CDCl$_3$) δ 7.42 (d, J=8.32 Hz, 4H), 7.25 (d, J=8.30 Hz, 4H), 4.21 (s, 1H), 3.64 (bs, 2H), 3.52 (bs, 2H), 2.81 (s, 4H), 2.44 (bs, 4H); $^{13}$C NMR (151 MHz, CDCl$_3$) δ

169.71, 150.26, 140.45, 131.98, 129.32, 121.32, 74.50, 51.04, 50.97, 45.11, 44.60, 25.46; HRMS (ESI-TOF+) m/z calcd for $C_{22}H_{21}Br_2N_3O_4$ [M+H]$^+$: 549.9977. found 549.9963.

Example 4

1-tert-Butyl 4-(2,5-dioxopyrrolidin-1-yl) piperazine-1,4-dicarboxylate

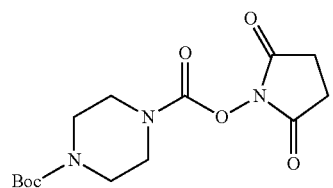

4

The title compound was synthesized according to Procedure A from tert-butyl piperazine-1-carboxylate (1.35 g, 7.25 mmol), DSC (1.86 g, 7.25 mmol) and NMM (2.39 mL, 21.7 mmol). Purification of the crude product by flash chromatography (50% EtOAc/hexanes) provided the title compound (1.70 g, 72%) as a white solid: $^1$H NMR (600 MHz, CDCl$_3$) δ 3.60 (s, 1H), 3.50 (d, J=10.0 Hz, 3H), 2.82 (s, 2H), 1.46 (d, J=1.5 Hz, 5H); $^{13}$C NMR (150 MHz, CDCl$_3$) δ 170.46, 155.23, 151.28, 81.39, 45.65, 45.34, 44.37, 43.30, 29.20, 26.34; HRMS (ESI-TOF+) m/z calcd for $C_{14}H_{21}N_3O_6$ [M+Na]$^+$: 350.1322. found 350.1315.

Example 5

2,5-Dioxopyrrolidin-1-yl 4-(4-methoxyphenyl)piperazine-1-carboxylate

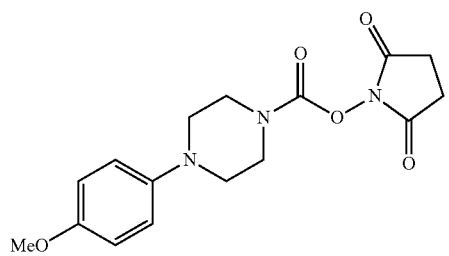

5

The title compound was synthesized according to Procedure A from 1-(4-methoxyphenyl)piperazine (100 mg, 0.52 mmol), DSC (130 mg, 0.52 mmol) and NMM (0.17 mL, 1.6 mmol). Purification of the crude product by flash chromatography (70% EtOAc/hexanes) provided the title compound (150 mg, 87%) as a colorless oil: $^1$H NMR (600 MHz, CDCl$_3$) δ 6.90 (d, J=8.5 Hz, 2H), 6.84 (d, J=8.6 Hz, 2H), 3.78 (bm, 2H), 3.76 (s, 3H), 3.67 (bm, 2H), 3.10 (bm, 4H), 2.81 (bm, 4H); $^{13}$C NMR (150 MHz, CDCl$_3$) δ 170.60, 155.43, 151.19, 145.96, 120.09, 115.37, 56.39, 51.50, 46.01, 45.57, 26.36; HRMS (ESI-TOF+) m/z calcd for $C_{16}H_{19}N_3O_5$ [M+H]$^+$: 334.1403. found 334.1388.

Example 6

2,5-Dioxopyrrolidin-1-yl N-[2-(4-phenoxyphenyl)ethyl]carbamate

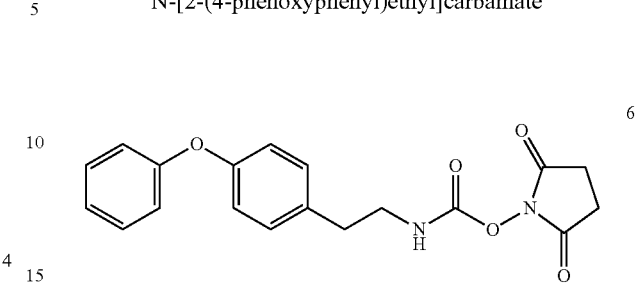

6

The title compound was synthesized according to Procedure A from 4-phenoxyphenylethylamine (122 mg, 0.57 mmol), DSC (147 mg, 0.57 mmol) and NMM (0.19 mL, 1.7 mmol). Purification of the crude product by flash chromatography (60% EtOAc/hexanes) provided the title compound (150 mg, 74%) as a colorless oil: $^1$H NMR (600 MHz, CDCl$_3$) δ 7.32 (t, J=7.7 Hz, 2H), 7.16 (d, J=8.0 Hz, 2H), 7.09 (t, J=7.3 Hz, 1H), 6.99 (d, J=8.1 Hz, 2H), 6.95 (d, J=8.1 Hz, 2H), 5.64 (t, J=5.9 Hz, 1H), 3.47 (q, J=6.8 Hz, 2H), 2.84 (t, J=7.2 Hz, 2H), 2.80 (bm, 4H); $^{13}$C NMR (150 MHz, CDCl$_3$) δ 170.85, 158.07, 156.91, 152.23, 133.52, 130.94, 130.60, 124.08, 120.04, 119.88, 119.65, 119.55, 44.10, 35.58, 26.32; HRMS (ESI-TOF+) m/z calcd for $C_{19}H_{18}N_2O_5$ [M+H]$^+$: 355.1294. found 355.1285.

Example 7

2,5-Dioxopyrrolidin-1-yl 4-[(3-phenoxyphenyl)methyl]piperazine-1-carboxylate

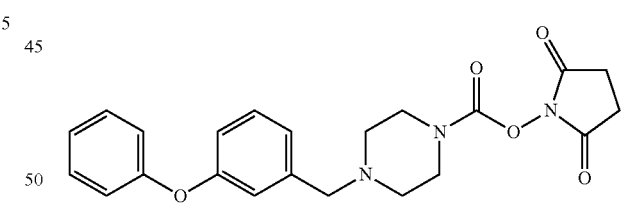

7

The title compound was synthesized according to Procedure A from 1-(3-phenoxybenzyl)piperazine (112 mg, 0.42 mmol), DSC (110 mg, 0.42 mmol) and NMM (0.14 mL, 1.3 mmol). Purification of the crude product by flash chromatography (50% EtOAc/hexanes) provided the title compound (140 mg, 82%) as a colorless oil: $^1$H NMR (600 MHz, CDCl$_3$) δ 7.31 (t, J=7.87 Hz, 2H), 7.24 (d, J=7.60 Hz, 1H), 7.08 (t, J=7.39 Hz, 1H), 7.02 (d, J=7.56 Hz, 1H), 6.99-6.97 (m, 3H), 6.87 (dd, J=2.41, 8.24 Hz, 1H), 3.61 (bs, 2H), 3.49 (s, 4H), 2.78 (s, 4H), 2.47 (bs, 4H); $^{13}$C NMR (150 MHz, CDCl$_3$) δ 170.64, 158.24, 157.96, 151.16, 140.60, 130.61, 130.47, 124.61, 124.15, 120.10, 119.73, 118.49, 63.22, 53.08, 53.01, 45.95, 45.44, 26.35; HRMS (ESI-TOF+) m/z calcd for $C_{22}H_{23}N_3O_5$ [M+H]$^+$: 410.1716. found 410.1720.

Example 8

2,5-Dioxopyrrolidin-1-yl 4-[2-(4-chlorophenyl)ethyl]piperidine-1-carboxylate

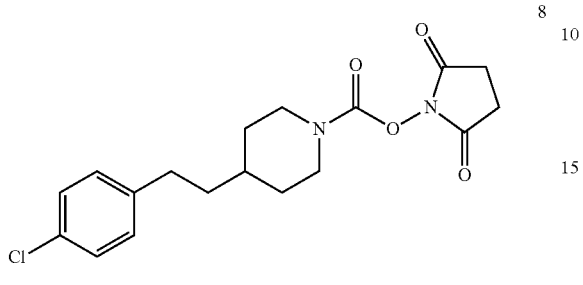

The title compound was synthesized according to Procedure A from 4-[2-(chloro-phenyl)-ethyl-piperidine (130 mg, 0.51 mmol), DSC (130 mg, 0.51 mmol) and NMM (0.17 mL, 1.5 mmol). Purification of the crude product by flash chromatography (30% EtOAc/hexanes) provided the title compound (130 mg, 70%) as a colorless oil: $^1$H NMR (600 MHz, CDCl$_3$) δ 7.23 (d, 151 7.6 Hz, 2H), 7.08 (d, J=7.6 Hz, 2H), 4.18 (d, J=13.2 Hz, 1H), 4.07 (d, J=13.0 Hz, 1H), 2.97 (t, J=13.1 Hz, 1H), 2.85 (d, J=13.1 Hz, 1H), 2.79 (s, 4H), 2.59 (t, J=8.4 Hz, 2H), 1.76 (d, J=12.9 Hz, 2H), 1.56 (dd, J=7.4 Hz, 2H), 1.47 (t, J=9.7 Hz, 1H), 1.35-1.22 (m, 2H); $^{13}$C NMR (150 MHz, CDCl$_3$) δ 170.78, 151.19, 141.41, 132.35, 130.48, 129.33, 46.49, 45.68, 38.66, 35.76, 33.01, 32.56, 32.23, 26.36; HRMS (ESI-TOF+) m/z calcd for C$_{18}$H$_{21}$ClN$_2$O$_4$ [M+H]$^+$: 365.1268. found 365.1264.

Example 9

2,5-Dioxopyrrolidin-1-yl N-benzyl-N-ethylcarbamate

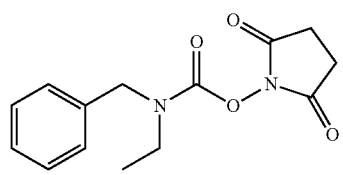

The title compound was synthesized according to Procedure A from N-ethylbenzylamine (110 mg, 0.81 mmol), DSC (210 mg, 0.81 mmol) and NMM (0.27 mL, 2.4 mmol). Purification of the crude product by flash chromatography (50% EtOAc/hexanes) provided the title compound (210 mg, 94%) as a colorless oil: 1H NMR (600 MHz, CDCl$_3$) δ 7.41-7.26 (m, 10H), 4.60 (s, 2H), 4.51 (s, 2H), 3.38 (q, J=7.1 Hz, 2H), 3.31 (q, J=7.2 Hz, 2H), 2.80 (s, 8H), 1.21 (t, J=7.1 Hz, 3H), 1.11 (t, J=7.2 Hz, 3H); $^{13}$C NMR (150 MHz, CDCl$_3$) δ 170.72, 152.98, 151.92, 137.00, 136.94, 129.62, 128.73, 128.70, 128.52, 52.51, 51.05, 44.05, 42.77, 26.37, 14.10, 13.27; HRMS (ESI-TOF+) m/z calcd for C$_{14}$H$_{16}$N$_2$O$_4$ [M+Na]$^+$: 299.1002. found 299.1006.

Example 10

2,5-Dioxopyrrolidin-1-yl 2-methylpiperidine-1-carboxylate

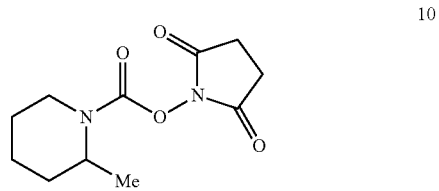 [SMILES: CC1CCCCN1C(=O)ON1C(=O)CCC1=O]

The title compound was synthesized according to Procedure A from 2-methylpiperidine (700 mg, 7.1 mmol), DSC (1.8 g, 7.1 mmol) and NMM (2.3 mL, 21 mmol). Purification of the crude product by flash chromatography (50% EtOAc/hexanes) provided the title compound (1.5 g, 88%) as a white solid: $^1$H NMR (600 MHz, CDCl$_3$) δ 4.44 (bs, 1H), 3.96 (bs, 1H), 3.07 (bs, 1H), 2.81 (s, 4H), 1.83-1.73 (m, 1H), 1.69 (d, J=13.1 Hz, 1H), 1.65-1.52 (m, 4H), 1.28 (bs, 3H); $^{13}$C NMR (150 MHz, CDCl$_3$) δ 170.82, 151.42, 49.00, 41.04, 30.55, 26.35, 25.98, 19.00, 16.78; HRMS (ESI-TOF+) m/z calcd for C$_{11}$H$_{16}$N$_2$O$_4$ [M+H]$^+$: 241.1188. found 241.1186.

Example 11

2,5-Dioxopyrrolidin-1-yl 2-(hydroxymethyl)piperidine-1-carboxylate

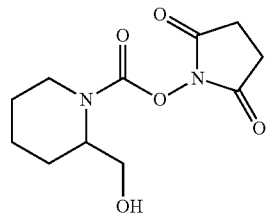

The title compound was synthesized according to Procedure A from 2-piperidinemethanol (120 mg, 1.1 mmol), DSC (270 mg, 1.1 mmol) and NMM (0.35 mL, 3.2 mmol). Purification of the crude product by flash chromatography (100% EtOAc) provided the title compound (140 mg, 51%) as a colorless oil: $^1$H NMR (600 MHz, CDCl$_3$) δ 4.47-4.13 (m, 1H), 4.01-3.78 (m, 2H), 3.62 (dd, J=11.6, 5.9 Hz, 1H), 3.18-2.94 (m, 1H), 2.78 (s, 4H), 1.79-1.44 (m, 6H); $^{13}$C NMR (150 MHz, CDCl$_3$) δ 171.26, 152.52, 61.49, 55.47, 54.59, 41.93, 26.36, 25.77, 25.59, 19.77; HRMS (ESI-TOF+) m/z calcd for C$_{11}$H$_{16}$N$_2$O$_5$ [M+H]$^+$: 257.1137. found 257.1134.

Example 12

2,5-Dioxopyrrolidin-1-yl N-methyl-N-{[3-(pyridin-4-yl)phenyl]methyl}carbamate

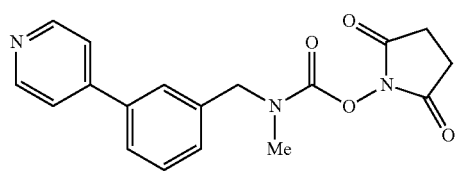

The title compound was synthesized according to Procedure A from N-methyl-N-(3-pyridin-4-ylbenzyl)amine (110 mg, 0.55 mmol), DSC (141 mg, 0.55 mmol) and NMM (0.18 mL, 1.7 mmol). Purification of the crude product by flash chromatography (100% EtOAc) provided the title compound (140 mg, 75%) as a colorless oil: $^1$H NMR (600 MHz, CDCl$_3$) δ 8.66 (s, 4H), 7.72 (s, 1H), 7.64-7.45 (m, 9H), 7.42 (d, J=7.7 Hz, 1H), 7.33 (d, J=7.6 Hz, 1H), 4.66 (s, 2H), 4.57 (s, 2H), 3.05 (s, 3H), 2.94 (s, 3H), 2.84 (s, 8H); $^{13}$C NMR (150 MHz, CDCl$_3$) δ 170.58, 153.08, 152.19, 151.16, 148.55, 148.47, 139.74, 139.67, 137.49, 137.43, 130.54, 130.49, 129.27, 127.50, 127.46, 127.09, 126.97, 122.54, 122.52, 54.73, 53.50, 36.22, 34.91, 26.38; HRMS (ESI-TOF+) m/z calcd for C$_{18}$H$_{17}$N$_3$O$_4$ [M+H]$^+$: 340.1297. found 340.1289.

Example 13

2,5-Dioxopyrrolidin-1-yl N-methyl-N-{[3-(pyridin-3-yl)phenyl]methyl}carbamate

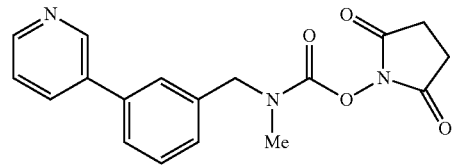

The title compound was synthesized according to Procedure A from N-methyl-N-(3-pyridin-3-ylbenzyl)amine (110 mg, 0.55 mmol), DSC (141 mg, 0.55 mmol) and NMM (0.18 mL, 1.7 mmol). Purification of the crude product by flash chromatography (100% EtOAc) provided the title compound (160 mg, 87%) as a colorless oil: $^1$H NMR (600 MHz, CDCl$_3$) δ 8.89 (bs, 1H), 8.84 (bs, 1H), 8.57 (bs, 2H), 7.97 (d, J=7.7 Hz, 1H), 7.88 (d, J=7.7 Hz, 1H), 7.65 (s, 1H), 7.56-7.42 (m, 5H), 7.39-7.34 (m, 3H), 7.28 (d, J=7.6 Hz, 1H), 4.64 (s, 2H), 4.55 (s, 2H), 3.03 (s, 3H), 2.93 (s, 3H), 2.81 (s, 8H); $^{13}$C NMR (150 MHz, CDCl$_3$) δ 170.62, 153.07, 152.20, 149.47, 149.13, 149.09, 139.39, 139.31, 137.42, 137.38, 136.92, 136.85, 135.42, 135.35, 130.50, 130.44, 128.31, 127.55, 127.26, 127.13, 124.49, 54.74, 53.51, 36.21, 34.89, 26.37; HRMS (ESI-TOF+) m/z calcd for C$_{18}$H$_{17}$N$_3$O$_4$ [M+H]$^+$: 340.1297. found 340.1294.

Example 14

2,5-Dioxopyrrolidin-1-yl N-methyl-N-{[3-(5-methyl-1,2,4-oxadiazol-3-yl)phenyl]methyl}carbamate

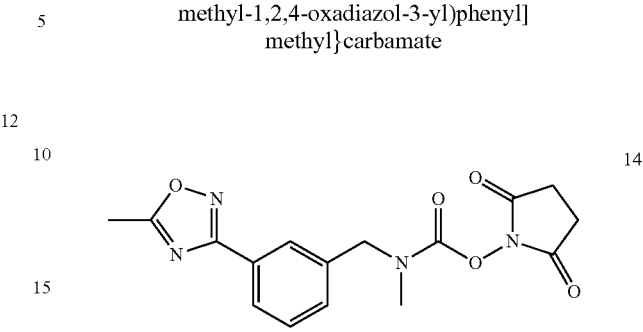

The title compound was synthesized according to Procedure A from N-methyl-N-[3-(5-methyl-1,2,4-oxadiazol-3-yl)benzyl]amine (70 mg, 0.34 mmol), DSC (88 mg, 0.34 mmol) and NMM (0.11 mL, 1.0 mmol). Purification of the crude product by flash chromatography (70% EtOAc/hexanes) provided the title compound (110 mg, 93%) as a colorless oil; $^1$H NMR (600 MHz, CDCl$_3$) δ 8.03-7.99 (m, 3H), 7.94 (s, 1H), 7.63 (d, J=7.6 Hz, 1H), 7.53 (t, J=7.7 Hz, 1H), 7.50 (t, J=7.7 Hz, 1H), 7.44 (d, J=7.7 Hz, 1H), 4.66 (s, 2H), 4.57 (s, 2H), 3.04 (s, 3H), 2.94 (s, 3H), 2.84 (s, 8H), 2.66 (s, 6H); $^{13}$C NMR (150 MHz, CDCl$_3$) δ 177.54, 177.53, 170.55, 170.53, 168.90, 168.89, 153.02, 152.18, 137.28, 137.26, 131.31, 131.23, 130.62, 130.57, 128.11, 127.92, 127.85, 127.82, 127.66, 54.59, 53.40, 36.17, 34.77, 26.37, 13.28; HRMS (ESI-TOF+) m/z calcd for C$_{16}$H$_{16}$N$_4$O$_5$ [M+H]$^+$: 345.1199. found 345.1186.

Example 15

2,5-Dioxopyrrolidin-1-yl N-methyl-N-(2-phenylethyl)carbamate

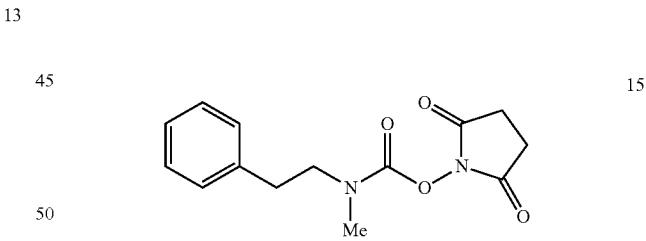

The title compound was synthesized according to Procedure A from N-methyl-phenethylamine (140 mg, 1.0 mmol), DSC (270 mg, 1.0 mmol) and NMM (0.34 mL, 3.1 mmol). Purification of the crude product by flash chromatography (50% EtOAc/hexanes) provided the title compound (260 mg, 90%) as a colorless oil; $^1$H NMR (600 MHz, CDCl$_3$) δ 7.33-7.26 (m, 4H), 7.26-7.19 (m, 6H), 3.58 (t, J=7.6 Hz, 1H), 3.50 (t, J=7.6 Hz, 1H), 3.01 (t, J=7.5 Hz, 2H), 2.96 (s, 3H), 2.88 (t, J=7.5 Hz, 2H), 2.81 (s, 3H), 2.78 (s, 4H), 2.77 (s, 4H); $^{13}$C NMR (150 MHz, CDCl$_3$) δ 170.80, 170.79, 152.20, 152.16, 139.08, 139.02, 129.71, 129.68, 129.54, 129.52, 127.48, 127.45, 53.47, 52.12, 37.68, 35.93, 35.25, 34.34, 26.37, 26.34; HRMS (ESI-TOF+) m/z calcd for C$_{14}$H$_{16}$N$_2$O$_4$ [M+H]$^+$: 277.1188. found 277.1184.

Example 16

2,5-Dioxopyrrolidin-1-yl 2-(morpholine-4-carbonyl)piperidine-1-carboxylate

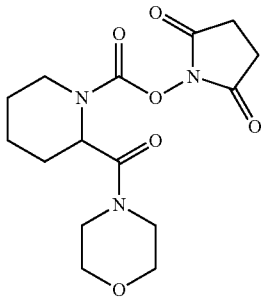

16

The title compound was synthesized according to Procedure A from morpholino(2-piperidinyl)methanone hydrochloride (63 mg, 0.27 mmol), DSC (69 mg, 0.27 mmol) and NMM (0.089 mL, 0.81 mmol). Purification of the crude product by flash chromatography (100% EtOAc) provided the title compound (42 mg, 46%) as a colorless oil (3:7 mixture of cis:trans carbamate isomers): $^1$H NMR (600 MHz, CDCl$_3$) δ 5.07 (s, 0.3H), 4.92 (d, J=5.9 Hz, 0.7H), 4.07 (d, J=12.7 Hz, 0.7H), 3.96 (d, J=12.1 Hz, 0.3H), 3.82-3.35 (m, 9H), 2.81 (s, 4H), 1.96-1.55 (m, 6H); $^{13}$C NMR (150 MHz, CDCl$_3$) δ 169.43, 168.86, 151.65, 150.58, 66.94, 66.74, 52.26, 51.46, 46.21, 43.79, 43.01, 42.54, 26.69, 26.39, 25.49, 24.77, 24.31, 19.37, 19.05; HRMS (ESI-TOF+) m/z calcd for C$_{15}$H$_{21}$N$_3$O$_6$ [M+H]$^+$: 340.1508. found 340.1514.

Example 17

2,5-Dioxopyrrolidin-1-yl piperidine-1-carboxylate

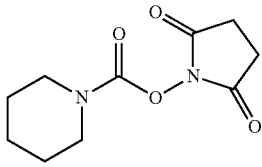

17

The title compound was synthesized according to Procedure A from piperidine (150 mg, 1.7 mmol), DSC (450 mg, 1.7 mmol) and NMM (0.57 mL, 5.2 mmol). Purification of the crude product by flash chromatography (50% EtOAc/hexanes) provided the title compound (310 mg, 79%) as a white solid; $^1$H NMR (600 MHz, CDCl$_3$) δ 3.56 (s, 2H), 3.44 (s, 2H), 2.79 (s, 4H), 1.62 (s, 6H); $^{13}$C NMR (150 MHz, CDCl$_3$) δ 170.78, 151.24, 47.18, 46.44, 26.35, 26.31, 26.02, 24.74; HRMS (ESI-TOF+) m/z calcd for C$_{10}$H$_{14}$N$_2$O$_4$ [M+H]$^+$: 227.1032. found 227.1028.

Example 18

2,5-Dioxopyrrolidin-1-yl 4-(2-methylquinolin-4-yl)piperazine-1-carboxylate

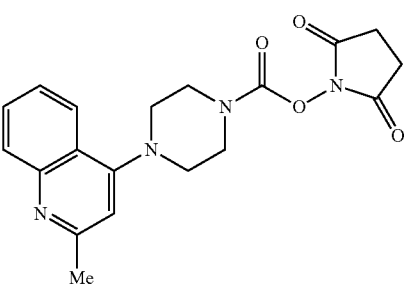

18

The title compound was synthesized according to Procedure A from 2-methyl-4-piperazinoquinoline (86 mg, 0.38 mmol), DSC (97 mg, 0.38 mmol) and NMM (0.13 mL, 1.1 mmol). Purification of the crude product by flash chromatography (50% EtOAc/hexanes) provided the title compound (110 mg, 79%) as a white solid; $^1$H NMR (600 MHz, CDCl$_3$) δ 7.97 (d, J=8.2 Hz, 1H), 7.91 (d, J=8.2 Hz, 1H), 7.62 (t, J=6.7 Hz, 1H), 7.43 (t, J=7.2 Hz, 1H), 6.74 (s, 1H), 3.91 (bs, 2H), 3.79 (bs, 2H), 3.24 (bs, 4H), 2.81 (s, 4H), 2.67 (s, 3H); $^{13}$C NMR (150 MHz, CDCl$_3$) δ 170.55, 160.37, 156.94, 151.33, 150.10, 130.21, 130.17, 125.89, 123.70, 122.47, 110.83, 52.41, 45.98, 45.58, 26.51, 26.35; HRMS (ESI-TOF+) m/z calcd for C$_{19}$H$_{20}$N$_4$O$_4$ [M+H]$^+$: 369.1563. found 369.1572.

Example 19

2,5-Dioxopyrrolidin-1-yl N-{[4-(piperidin-1-yl)phenyl]methyl}-N-propylcarbamate

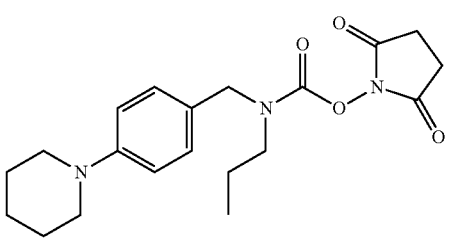

19

The title compound was synthesized according to Procedure A from N-(4-piperidin-1-ylbenzyl)-N-propylamine (23 mg, 0.10 mmol), DSC (25 mg, 0.10 mmol) and NMM (0.033 mL, 0.30 mmol). Purification of the crude product by flash chromatography (50% EtOAc/hexanes) provided the title compound (23 mg, 62%) as a colorless oil; $^1$H NMR (600 MHz, CDCl$_3$) δ 7.30-7.23 (m, 1H), 7.14 (d, J=7.9 Hz, 1H), 6.92 (d, J=8.1 Hz, 1H), 6.89 (d, J=7.9 Hz, 1H), 4.51 (s, 1H), 4.42 (s, 1H), 3.23 (s, 1H), 3.19-3.12 (m, 5H), 2.82 (s, 4H), 1.72-1.52 (m, 8H), 0.86 (dt, J=16.9, 7.5 Hz, 3H); $^{13}$C NMR (150 MHz, CDCl$_3$) δ 170.69, 170.67, 153.00, 152.68, 152.66, 152.22, 129.86, 129.61, 127.02, 126.88, 117.25, 52.37, 51.29, 51.27, 50.88, 50.26, 48.97, 26.62, 26.39, 25.13, 22.03, 21.27, 12.03, 11.97; HRMS (ESI-TOF+) m/z calcd for $C_{20}H_{27}N_3O_4$ [M+H]$^+$: 374.2080. found 374.2077.

Example 20

2,5-Dioxopyrrolidin-1-yl N-(1,2,3,4-tetrahydronaphthalen-1-yl)carbamate

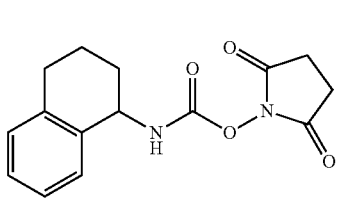

The title compound was synthesized according to Procedure A from 1,2,3,4-tetrahydro-1-naphthylamine (270 mg, 1.8 mmol), DSC (460 mg, 1.8 mmol) and NMM (0.59 mL, 5.4 mmol). Purification of the crude product by flash chromatography (50% EtOAc/hexanes) provided the title compound (230 mg, 44%) as a white solid: $^1$H NMR (600 MHz, CDCl$_3$) δ 7.36 (d, J=4.7 Hz, 1H), 7.23-7.20 (m, 2H), 7.12-7.10 (m, 1H), 5.37 (s, 1H), 4.91 (dd, J=13.9, 6.4 Hz, 1H), 2.86-2.71 (m, 6H), 2.14-2.06 (m, 1H), 1.97-1.83 (m, 3H); $^{13}$C NMR (150 MHz, CDCl$_3$) δ 170.69, 151.83, 138.33, 135.99, 130.08, 129.57, 128.61, 127.35, 51.57, 30.82, 29.91, 26.32, 20.63; HRMS (ESI-TOF+) m/z calcd for $C_{15}H_{16}N_2O_4$ [M+Na]$^+$: 311.1002. found 311.1002.

Example 21

2,5-Dioxopyrrolidin-1-yl 4-benzylpiperidine-1-carboxylate

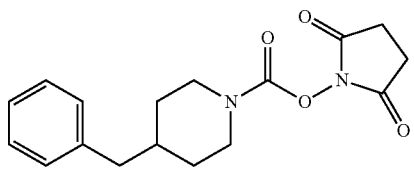

The title compound was synthesized according to Procedure A from 4-benzylpiperidine (690 mg, 3.9 mmol), DSC (1.0 g, 3.9 mmol) and NMM (1.3 mL, 12 mmol). Purification of the crude product by flash chromatography (60% EtOAc/hexanes) provided the title compound (1.1 g, 89%) as a white solid: $^1$H NMR (600 MHz, CDCl$_3$) δ 7.28 (t, J=7.4 Hz, 3H), 7.22-7.18 (m, 1H), 7.13 (d, J=7.5 Hz, 2H), 4.18 (d, J=13.1 Hz, 1H), 4.08 (d, J=13.1 Hz, 1H), 2.94 (t, J=12.9 Hz, 1H), 2.86-2.79 (m, 5H), 2.56 (d, J=6.9 Hz, 2H), 1.77-1.67 (m, 3H), 1.41-1.22 (m, 2H); $^{13}$C NMR (150 MHz, CDCl$_3$) δ 170.73, 151.17, 140.59, 129.92, 129.20, 126.97, 46.56, 45.73, 43.68, 38.56, 32.46, 32.21, 26.35; HRMS (ESI-TOF+) m/z calcd for $C_{17}H_{20}N_2O_4$ [M+Na]$^+$: 339.1315. found 339.1318.

Example 22

2,5-Dioxopyrrolidin-1-yl 2-benzylpiperidine-1-carboxylate

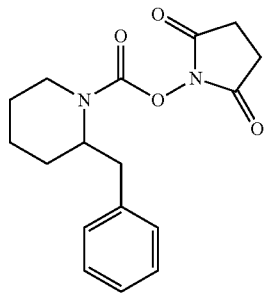

The title compound was synthesized according to Procedure A from 2-benzylpiperidine (180 mg, 1.0 mmol), DSC (260 mg, 1.0 mmol) and NMM (0.34 mL, 3.1 mmol). Purification of the crude product by flash chromatography (50% EtOAc/hexanes) provided the title compound (210 mg, 65%) as a colorless oil: $^1$H NMR (600 MHz, CDCl$_3$) δ 7.32-7.24 (m, 2H), 7.24-7.15 (m, 3H), 4.48-4.35 (m, 1H), 4.11-3.95 (m, 1H), 3.24-2.87 (m, 3H), 2.77 (s, 4H), 1.76-1.51 (m, 6H)$^{13}$C NMR (150 MHz, CDCl$_3$) δ 170.74, 151.65, 138.95, 130.03, 129.44, 127.35, 55.18, 54.82, 42.10, 41.55, 37.12, 36.60, 26.66, 26.37, 25.81, 19.09; HRMS (ESI-TOF+) m/z calcd for $C_{17}H_{20}N_2O_4$ [M+H]$^+$: 317.1501. found 317.1499.

Example 23

2,5-Dioxopyrrolidin-1-yl 2-phenylpiperidine-1-carboxylate

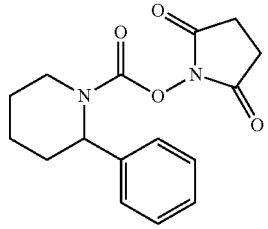

The title compound was synthesized according to Procedure A from 2-phenylpiperidine (117 mg, 0.73 mmol), DSC (190 mg, 0.73 mmol) and NMM (0.24 mL, 2.2 mmol). Purification of the crude product by flash chromatography (50% EtOAc/hexanes) provided the title compound (140 mg, 64%) as a colorless oil: $^1$H NMR (600 MHz, CDCl$_3$) δ 7.41-7.22 (m, 5H), 5.47 (bs, 1H), 4.05 (bs, 1H), 2.99 (bs, 1H), 2.78 (s, 4H), 2.41 (d, J=14.3 Hz, 1H), 2.06-1.97 (m, 1H), 1.72-1.57 (m, 3H), 1.57-1.45 (m, 1H); $^{13}$C NMR (150 MHz, CDCl$_3$) δ 170.76, 152.30, 138.66, 129.73, 127.90, 127.38, 55.72, 42.46, 28.30, 26.38, 26.00, 19.79; HRMS (ESI-TOF+) m/z calcd for $C_{16}H_{18}N_2O_4$ [M+Na]$^+$: 325.1159. found 325.1155.

Example 24

2,5-Dioxopyrrolidin-1-yl 2-(trifluoromethyl)piperidine-1-carboxylate

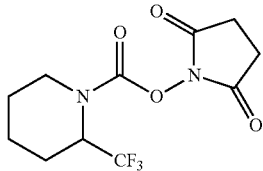

24

The title compound was synthesized according to Procedure A from 2-trifluoromethylpiperidine (170 mg, 1.1 mmol), DSC (280 mg, 1.1 mmol) and NMM (0.37 mL, 3.3 mmol). Purification of the crude product by flash chromatography (30% EtOAc/hexanes) provided the title compound (160 mg, 49%) as a colorless oil: $^1$H NMR (600 MHz, CDCl$_3$) δ 4.73-4.67 (m, 1H), 4.66-4.58 (m, 1H), 4.16 (d, J=13.6 Hz, 1H), 4.08 (d, J=13.2 Hz, 1H), 3.21 (t, J=13.3 Hz, 1H), 3.07 (t, J=13.4 Hz, 1H), 2.78 (s, 8H), 2.04 (d, J=14.7 Hz, 2H), 1.89-1.49 (m, 10H); $^{13}$C NMR (150 MHz, CDCl$_3$) δ 170.32, 152.44, 151.66, 126.56 (q, J=285 Hz), 126.37 (q, J=285 Hz), 53.04 (p, J=30.4 Hz), 43.25, 42.86, 26.29, 24.84, 24.64, 23.54, 23.23, 19.47; HRMS (ESI-TOF+) m/z calcd for $C_{11}H_{13}F_3N_2O_4$ [M+H]$^+$: 295.0905. found 295.0899.

Example 25

2,5-Dioxopyrrolidin-1-yl 2-(2-phenylethyl)piperidine-1-carboxylate

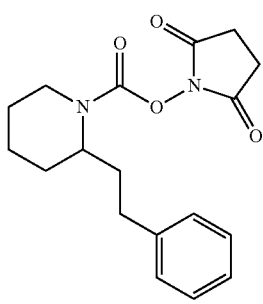

25

The title compound was synthesized according to Procedure A from 2-phenethylpiperidine (120 mg, 0.53 mmol), DSC (140 mg, 0.53 mmol) and NMM (0.18 mL, 1.6 mmol). Purification of the crude product by flash chromatography (50% EtOAc/hexanes) provided the title compound (130 mg, 74%) as a colorless oil: $^1$H NMR (600 MHz, CDCl$_3$) δ 7.30-7.14 (m, 5H), 4.37-4.26 (m, 1H), 4.10-3.94 (m, 1H), 3.11-2.96 (m, 1H), 2.79 (s, 4H), 2.75-2.56 (m, 2H), 2.14 (bs, 1H), 1.85-1.51 (m, 6H); $^{13}$C NMR (150 MHz, CDCl$_3$) δ 169.81, 150.82, 141.49, 128.30, 128.28, 125.82, 52.75, 52.20, 40.59, 40.12, 32.36, 31.61, 28.19, 25.44, 25.21, 24.97, 18.52, 18.47; HRMS (ESI-TOF+) m/z calcd for $C_{18}H_{22}N_2O_4$ [M+Na]$^+$: 353.1472. found 353.1472.

Example 26

2,5-Dioxopyrrolidin-1-yl 4-(pent-4-ynoyl)piperazine-1-carboxylate

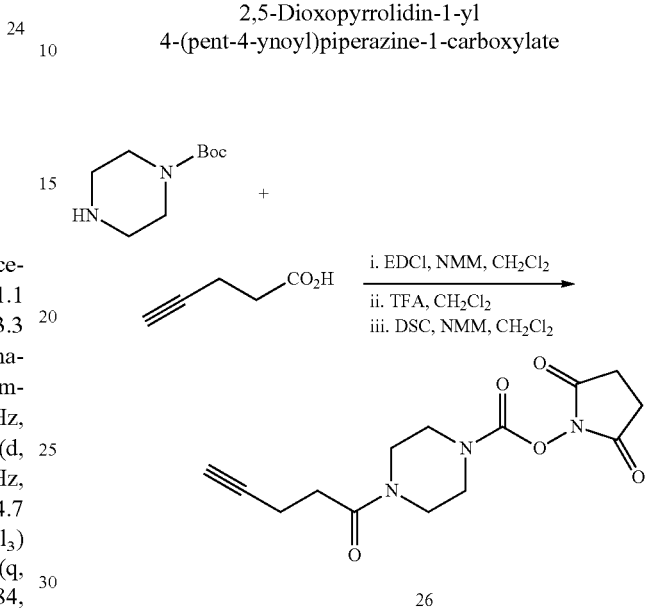

26

To a stirring solution of 4-pentynoic acid (75 mg, 0.76 mmol, 1.0 equiv), tert-butyl piperazine-1-carboxylate (156 mg, 0.84 mmol, 1.1 equiv) and NMM (0.097 mL, 0.84 mmol, 1.1 equiv) in dry CH$_2$Cl$_2$ (10 mL) was added EDCI (161 mg, 0.84 mmol, 1.1 equiv). After stirring at room temperature for 4 h, the reaction was quenched with a saturated solution of NH$_4$Cl (50 mL) and extracted with CH$_2$Cl$_2$ (50 mL, 3×). The combined organic layers were washed once with brine (50 mL), dried over anhydrous MgSO$_4$ and concentrated to provide tert-butyl 4-(pent-4-ynoyl)piperazine-1-carboxylate (187 mg, 92%), which was used without further purification. To a stirring solution of tert-butyl 4-(pent-4-ynoyl)piperazine-1-carboxylate (187 mg, 0.70 mmol) in CH$_2$Cl$_2$ (4.0 mL) was added TFA (1.0 mL). After 1 h, the reaction mixture was concentrated under a stream of N$_2$. The residue was redissolved in CH$_2$Cl$_2$ (5.0 mL) and concentrated under reduced pressure to remove residual TFA providing a crude colorless oil, which was used without further purification. The title compound was synthesized according to Procedure A from the deprotected piperazine (123 mg, 0.44 mmol), DSC (110 mg, 0.44 mmol) and NMM (0.15 mL, 1.3 mmol). Purification of the crude product by flash chromatography (50% EtOAc/hexanes) provided the title compound (82 mg, 61%) as a white solid: $^1$H NMR (600 MHz, CDCl$_3$) δ 3.77-3.48 (m, 8H), 2.82 (s, 4H), 2.56 (dd, J=13.8, 5.9 Hz, 4H), 1.98 (s, 1H); $^{13}$C NMR (150 MHz, CDCl$_3$) δ 170.43, 151.29, 151.12, 83.99, 69.89, 45.66, 45.57, 41.80, 32.92, 26.34, 15.32; HRMS (ESI-TOF+) m/z calcd for $C_{14}H_{12}N_3O_5$ [M+H]$^+$: 308.1246. found 308.1239.

Example 27

2,5-Dioxopyrrolidin-1-yl N-[2-(naphthalen-2-yl)ethyl]carbamate

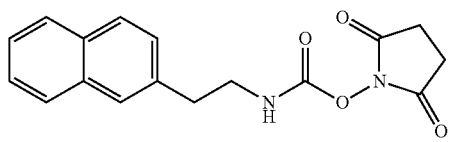

The title compound was synthesized according to Procedure A from 2-(2-naphthyl)-ethylamine (160 mg, 0.93 mmol), DSC (240 mg, 0.93 mmol) and NMM (0.31 mL, 2.8 mmol). Purification of the crude product by flash chromatography (100% EtOAc) provided the title compound (130 mg, 45%) as a white solid: $^1$H NMR (600 MHz, CDCl$_3$) δ (d, J=7.8 Hz, 3H), 7.67 (s, 1H), 7.46 (t, J=8.3 Hz, 2H), 7.33 (d, J=8.3 Hz, 1H), 5.54 (t, J=6.2 Hz, 1H), 3.57 (d, J=7.1 Hz, 2H), 3.05-3.00 (m, 2H), 2.75 (s, 4H); $^{13}$C NMR (150 MHz, CDCl$_3$) δ 170.76, 152.24, 136.14, 134.39, 133.18, 129.36, 128.50, 128.45, 128.27, 127.85, 127.09, 126.54, 43.85, 36.33, 26.27; HRMS (ESI-TOF+) m/z calcd for $C_{12}H_{16}N_2O_4$ [M+H]$^+$: 313.1188. found 313.1183.

Example 28

2,5-Dioxopyrrolidin-1-yl N-(hex-5-yn-1-yl)carbamate

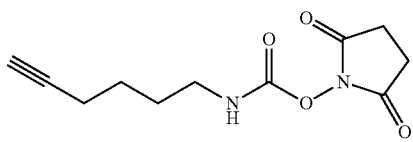

The title compound was synthesized according to Procedure A from 1-amino-5-hexyne (80 mg, 0.82 mmol), DSC (210 mg, 0.82 mmol) and NMM (0.27 mL, 2.5 mmol). Purification of the crude product by flash chromatography (80% EtOAc) provided the title compound (98 mg, 50%) as a white solid: $^1$H NMR (600 MHz, CDCl$_3$) δ 5.67-5.63 (m, 1H), 3.27 (q, J=6.6 Hz, 2H), 2.81 (s, 4H), 2.22 (td, J=6.8, 2.6 Hz, 2H), 1.95 (t, J=2.6 Hz, 1H), 1.71-1.66 (m, 2H), 1.60-1.53 (m, 2H); $^{13}$C NMR (150 MHz, CDCl$_3$) δ 170.90, 152.27, 84.59, 69.79, 42.36, 29.29, 26.31, 26.13, 18.83; HRMS (ESI-TOF+) m/z calcd for $C_{11}H_{14}N_2O_4$ [M+H]$^+$: 239.1032. found 239.1024.

Example 29

2,5-Dioxopyrrolidin-1-yl pyrrolidine-1-carboxylate

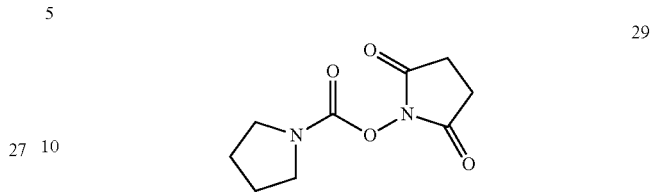

The title compound was synthesized according to Procedure A from pyrrolidine (330 mg, 4.7 mmol), DSC (1.2 g, 4.7 mmol) and NMM (1.5 mL, 14 mmol). Purification of the crude product by flash chromatography (50% EtOAc/hexanes) provided the title compound (720 mg, 72%) as a white solid: $^1$H NMR (600 MHz, CDCl$_3$) δ 3.56 (t, J=6.8 Hz, 2H), 3.45 (t, J=6.8 Hz, 2H), 2.81 (s, 4H), 1.96 (p, J=6.6 Hz, 2H), 1.90 (p, J=6.6 Hz, 2H); $^{13}$C NMR (150 MHz, CDCl$_3$) δ 170.85, 150.41, 48.33, 46.91, 26.67, 26.34, 25.48; HRMS (ESI-TOF+) m/z calcd for $C_9H_{12}N_2O_4$ [M+H]$^+$: 213.0875. found 213.0868.

Example 30

2,5-Dioxopyrrolidin-1-yl azetidine-1-carboxylate

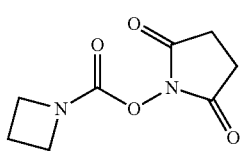

The title compound was synthesized according to Procedure A from azetidine (150 mg, 2.6 mmol), DSC (670 mg, 2.6 mmol) and NMM (0.87 mL, 7.9 mmol). Purification of the crude product by flash chromatography (50% EtOAc/hexanes) provided the title compound (340 mg, 65%) as a white solid: $^1$H NMR (600 MHz, CDCl$_3$) δ 4.30-4.26 (m, 2H), 4.15-4.10 (m, 2H), 2.79 (s, 4H), 2.36 (p, J=7.8 Hz, 2H); $^{13}$C NMR (150 MHz, CDCl$_3$) δ 170.70, 150.99, 51.43, 50.83, 26.32, 17.26; HRMS (ESI-TOF+) m/z calcd for $C_8H_{10}N_2O_4$ [M+H]$^+$: 199.0719. found 199.0710.

Example 31

2,5-Dioxopyrrolidin-1-yl N-[(9Z)-octadec-9-en-1-yl]carbamate

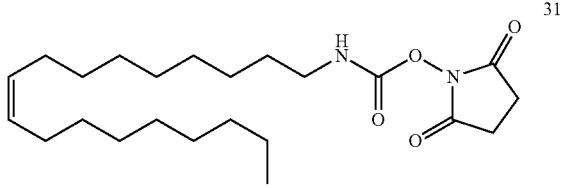 [SMILES: CCCCCCCC/C=C\CCCCCCCCNC(=O)ON1C(=O)CCC1=O]

The title compound was synthesized according to Procedure A from oleylamine (250 mg, 0.93 mmol), DSC (240 mg, 0.93 mmol) and NMM (0.31 mL, 2.8 mmol). Purification of the crude product by flash chromatography (50% EtOAc/hexanes) provided the title compound (150 mg, 39%) as a white solid: $^1$H NMR (600 MHz, CDCl$_3$) δ 5.64 (t, J=5.6 Hz, 1H), 5.40-5.30 (m, 2H), 3.22 (q, J=6.8 Hz, 2H), 2.81 (s, 4H), 2.05-1.92 (m, 4H), 1.54 (p, J=7.1 Hz, 2H), 1.32-1.23 (m, 22H), 0.87 (t, J=6.9 Hz, 3H); $^{13}$C NMR (150 MHz, CDCl$_3$) δ 170.96, 152.20, 130.80, 130.61, 42.93, 32.75, 30.61, 30.58, 30.37, 30.34, 30.29, 30.25, 30.16, 30.07, 30.01, 28.06, 28.04, 27.45, 26.31, 23.53, 14.97; HRMS (ESI-TOF+) m/z calcd for C$_{23}$H$_{40}$N$_2$O$_4$ [M+H]$^+$: 409.3066. found 409.3062.

Example 32

1,3-Dioxo-2,3-dihydro-1H-isoindol-2-yl 4-[2-(4-chlorophenyl)ethyl]piperidine-1-carboxylate

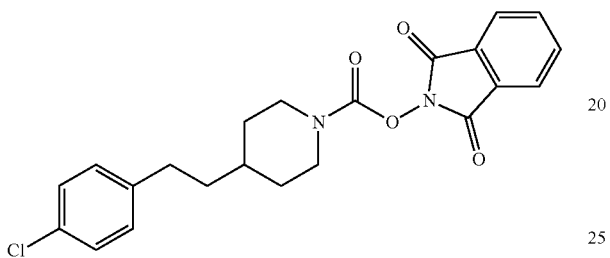

32

The title compound was synthesized according to Procedure B from 4-[2-(chloro-phenyl)-ethyl-piperidine (110 mg, 0.50 mmol), triphosgene (45 mg, 0.15 mmol), N-hydroxyphthalimide (82 mg, 0.50 mmol) and DIEA (0.26 mL, 1.5 mmol). Purification of the crude product by flash chromatography (40% EtOAc/hexanes) provided the title compound (120 mg, 58%) as a white solid: $^1$H NMR (600 MHz, CDCl$_3$) δ 7.89-7.85 (m, 2H), 7.78-7.75 (m, 2H), 7.25 (d, J=8.2 Hz, 2H), 7.10 (d, J=8.2 Hz, 2H), 4.30 (d, J=13.1 Hz, 1H), 4.11 (d, J=13.0 Hz, 1H), 3.03 (t, J=12.5 Hz, 1H), 2.88 (t, J=12.3 Hz, 1H), 2.62 (dd, J=6.5, 9.21 Hz, 2H), 1.80 (t, J=11.8 Hz, 2H), 1.60 (dd, J=7.2, 15.4 Hz, 2H), 1.55-1.47 (m, 1H), 1.43-1.26 (m, 2H); $^{13}$C NMR (150 MHz, CDCl$_3$) δ163.54, 152.09, 141.42, 135.47, 132.38, 130.48, 129.88, 129.35, 124.70, 46.57, 45.77, 38.72, 35.82, 33.03, 21.48; HRMS (ESI-TOF+) m/z calcd for C$_{22}$H$_{21}$ClN$_2$O$_4$ [M+H]$^+$: 413.1268. found 413.1262.

Example 33

1,3-Dioxo-2,3-dihydro-1H-isoindol-2-yl 4-[bis(4-chlorophenyl)methyl]piperazine-1-carboxylate

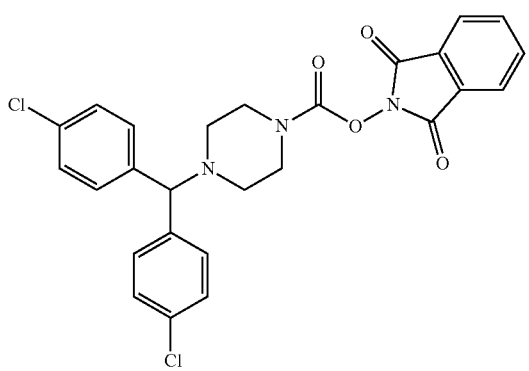

33

The title compound was synthesized according to Procedure B from 1-(4,4'-dichlorobenzhydryl)piperazine (137 mg, 0.43 mmol), triphosgene (38 mg, 0.13 mmol), N-hydroxyphthalimide (70 mg, 0.43 mmol) and DIEA (0.22 mL, 1.3 mmol). Purification of the crude product by flash chromatography (40% EtOAc/hexanes) provided the title compound (135 mg, 62%) as a colorless oil: $^1$H NMR (600 MHz, CDCl$_3$) δ 7.87 (dd, J=3.1, 5.4 Hz, 2H), 7.77 (dd, J=3.1, 5.5 Hz, 2H), 7.34-7.32 (m, 4H), 7.29-7.26 (m, 4H), 4.26 (s, 1H), 3.72 (bs, 2H), 3.54 (bs, 2H), 2.46 (d, J=20.2 Hz, 4H); $^{13}$C NMR (150 MHz, CDCl$_3$) δ 163.42, 152.04, 140.90, 135.53, 134.05, 129.93, 129.88, 129.86, 129.81, 129.71, 124.75, 75.26, 51.98, 51.89, 46.04, 45.55; HRMS (ESI-TOF+) m/z calcd for C$_{26}$H$_{21}$Cl$_2$N$_3$O$_4$ [M+H]$^+$: 510.0987. found 510.0989.

Example 34

1,3-Dioxo-2,3-dihydro-1H-isoindol-2-yl 4-(4-methoxyphenyl)piperazine-1-carboxylate

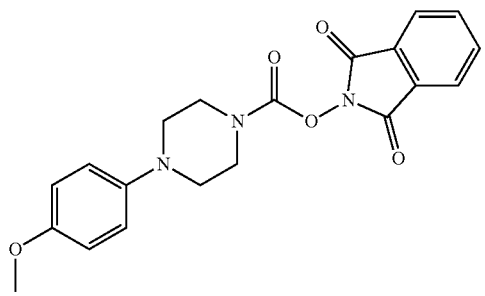

34

The title compound was synthesized according to Procedure B from 1-(4-methoxyphenyl)piperazine (303 mg, 1.6 mmol), triphosgene (140 mg, 0.47 mmol), N-hydroxyphthalimide (260 mg, 1.6 mmol) and DIEA (0.82 mL, 4.7 mmol). Purification of the crude product by flash chromatography (40% EtOAc/hexanes) provided the title compound (370 mg, 61%) as a white solid: $^1$H NMR (600 MHz, CDCl$_3$) δ 7.90-7.86 (m, 2H), 7.79-7.76 (m, 2H), 6.94-6.91 (m, 2H), 6.87-6.84 (m, 2H), 3.87 (bs, 2H), 3.77 (s, 3H), 3.70 (bs, 2H), 3.17-3.10 (m, 4H); $^{13}$C NMR (150 MHz, CDCl$_3$) δ 163.39, 155.42, 152.08, 146.01, 135.56, 129.82, 124.77, 120.08, 115.38, 56.40, 51.56, 46.07, 45.64; HRMS (ESI-TOF+) m/z calcd for C$_{20}$H$_{19}$N$_3$O$_5$ [M+H]$^+$: 382.1403. found 382.1400.

Example 35

2,5-Dioxopyrrolidin-1-yl 4-[(2-phenoxyphenyl)methyl]piperazine-1-carboxylate

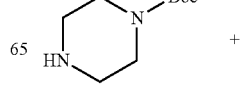

-continued

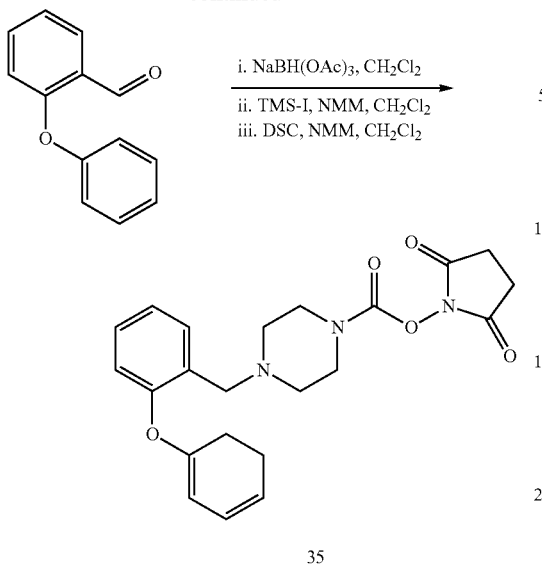

Example 36

2,5-Dioxopyrrolidin-1-yl 4-(2-((2-chloro-5-(trifluoromethyl)phenyl)amino)-2-oxoethyl)piperazine-1-carboxylate

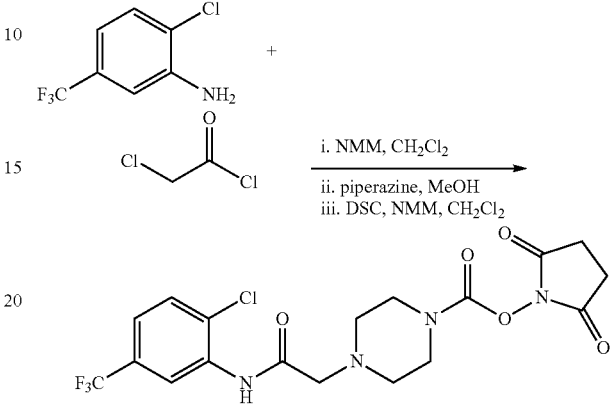

To a stirring solution of 2-phenoxybenzaldehyde (297 mg, 1.50 mmol, 1.0 equiv) and tert-butyl piperazine-1-carboxylate (307 mg, 1.65 mmol, 1.1 equiv) in CH$_2$Cl$_2$ (10 mL) was added NaBH(OAc)$_3$ (477 mg, 2.25 mmol, 1.5 equiv). The reaction was stirred for 2 h at room temperature and subsequently quenched upon addition of aqueous NaOH (10 mL, 1.0 M). The biphasic mixture was vigorously stirred for 30 min and poured into a separatory funnel containing brine (50 mL). The product was extracted with CH$_2$Cl$_2$ (50 mL, 3×), and the combined organic layers were dried over anhydrous MgSO$_4$ and concentrated under reduced pressure to provide a crude colorless oil, which was used in subsequent steps without further purification.

To a stirring solution of tert-butyl 4-(2-phenoxybenzyl)piperazine-1-carboxylate (192 mg, 0.52 mmol) and NMM (0.34 mL, 3.1 mmol) in CH$_2$Cl$_2$ (5.0 mL) at 0° C. was added TMS-I (0.22 mL, 1.6 mmol) dropwise. After 1 h, the reaction mixture was quenched with MeOH (1.0 mL) concentrated under a stream of N$_2$. The residue was redissolved in CH$_2$Cl$_2$ (5.0 mL) and concentrated under reduced pressure providing a crude oil, which was used without further purification.

The title compound was synthesized according to Procedure A from the deprotected amine (0.52 mmol [theoretical yield from previous step]), DSC (133 mg, 0.52 mmol) and NMM (0.29 mL, 2.6 mmol). Purification of the crude product by flash chromatography (70% EtOAc/hexanes, 1% TEA) provided the title compound (123 mg, 58%) as a colorless oil: $^1$H NMR (600 MHz, CDCl$_3$) δ 7.45 (dd, J=1.7, 7.7 Hz, 1H), 7.30 (t, J=7.9 Hz, 2H), 7.25 (dd, J=1.8, 7.8 Hz, 1H), 7.14 (t, J=7.5 Hz, 1H), 7.06 (t, J=7.4 Hz, 1H), 6.94 (d, J=8.1 Hz, 1H), 6.90 (d, J=8.7 Hz, 2H), 3.59 (s, 2H), 3.57 (bs, 2H), 3.45 (bs, 2H), 2.80 (s, 4H), 2.52 (d, J=6.4 Hz, 4H); $^{13}$C NMR (150 MHz, CDCl$_3$) δ 170.62, 158.85, 155.66, 151.10, 131.97, 130.50, 130.07, 129.53, 124.80, 123.46, 120.94, 118.31, 57.06, 52.97, 52.87, 45.95, 45.42, 26.33; HRMS (ESI-TOF+) m/z calcd for C$_{22}$H$_{23}$N$_3$O$_5$ [M+H]$^+$: 410.1716. found 410.1711.

To a stirring solution of 2-chloro-5-(trifluoromethyl)aniline (50 mg, 0.25 mmol, 1.0 equiv) and NMM (0.055 mL, 0.50 mmol, 2.0 equiv) in dry CH$_2$Cl$_2$ (3.0 mL) at 0° C. was added chloroacetylchloride (21 mg, 0.25 mmol, 1.0 equiv) dropwise. The reaction mixture was allowed to warm to room temperature and stirred for 2 h at which point TLC revealed complete consumption of the aniline. The reaction poured into a separatory funnel containing brine (10 mL) and the product was extracted with CH$_2$Cl$_2$ (10 mL, 3×). The combined organic layers were dried over anhydrous MgSO$_4$ and concentrated under reduced pressure. The resulting residue was redissolved in MeOH (1.0 mL) and to this solution was added piperazine (0.5 g, 5.8 mmol). After stirring for 12 h at room temperature, the reaction was poured into a separatory funnel containing a saturated solution of NaHCO$_3$ (10 mL) and the product was extracted with Et$_2$O (10 mL, 3×). The combined organic layers were washed with brine (10 mL, 2×), dried over anhydrous Na$_2$SO$_4$ and concentrated under reduced pressure to provide an orange oil, which was used without further purification. The title compound was synthesized according to Procedure A from the crude piperazine (0.25 mmol [theoretical yield from previous steps]), DSC (64 mg, 0.25 mmol) and NMM (0.082 mL, 0.75 mmol). Purification of the crude product by flash chromatography (50% EtOAc/hexanes) provided the title compound (49 mg, 42%) as a yellow solid: $^1$H NMR (600 MHz, CDCl$_3$) δ 9.95 (s, 1H), 8.83 (d, J=2.2 Hz, 1H), 7.52 (d, J=8.3 Hz, 1H), 7.32 (dd, J=2.1, 8.5 Hz, 1H), 3.78 (bs, 2H), 3.66 (bs, 2H), 3.28 (s, 2H), 2.84 (bs, 4H), 2.75 (bs, 4H); $^{13}$C NMR (150 MHz, CDCl$_3$) δ170.46, 168.73, 151.17, 135.68, 131.25 (q, J=33.1 Hz), 130.37, 126.63, 124.31 (q, J=273 Hz), 122.01 (q, J=3.7 Hz), 118.46 (q, J=3.9 Hz), 62.72, 53.44, 46.04, 45.57, 26.34; HRMS (ESI-TOF+) m/z calcd for C$_{18}$H$_{18}$ClF$_3$N$_4$O$_5$ [M+H]$^+$: 463.0996. found 463.0989.

Example 37

2,5-Dioxopyrrolidin-1-yl 4-[(4-bromo-2-phenoxyphenyl)methyl]piperazine-1-carboxylate

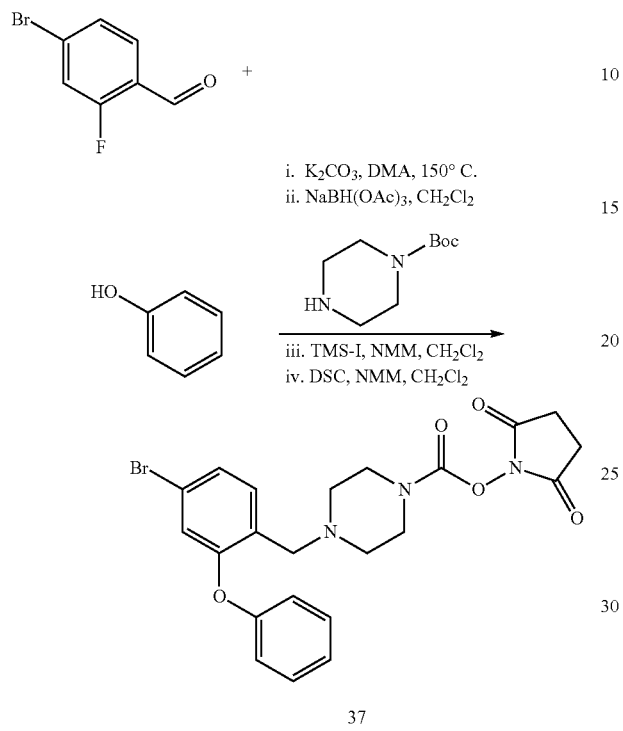

37

To a sealed tube was added 4-bromo-2-fluorobenzaldehyde (1.0 g, 5.0 mmol, 1.0 equiv), phenol (470 mg, 5.0 mmol, 1.0 equiv), K$_2$CO$_3$ (691 mg, 5.0 mmol, 1.0 equiv) and DMA (10 mL). The reaction was heated to 150° C. and stirred for 4 h. Upon cooling to room temperature, the reaction mixture was poured into a separatory funnel containing brine (250 mL) and the product was extracted with Et$_2$O (250 mL, 3×). The combined organic layers were dried over anhydrous MgSO$_4$ and concentrated under reduced pressure. The remaining residue was used in subsequent steps without further purification. To a stirring solution of the crude aldehyde (610 mg, 2.2 mmol, 1.0 equiv) and tert-butyl piperazine-1-carboxylate (451 mg, 2.42 mmol, 1.1 equiv) in CH$_2$Cl$_2$ (20 mL) was added NaBH(OAc)$_3$ (699 mg, 3.30 mmol, 1.5 equiv). The reaction was stirred for 2 h at room temperature and subsequently quenched upon addition of aqueous NaOH (20 mL, 1.0 M). The biphasic mixture was vigorously stirred for 30 min and poured into a separatory funnel containing brine (100 mL). The product was extracted with CH$_2$Cl$_2$ (100 mL, 3×) and the combined organic layers were dried over anhydrous MgSO$_4$ and concentrated under reduce pressure to provide a crude colorless oil which was used in subsequent steps without further purification. To a stirring solution of the crude piperazine (290 mg, 0.65 mmol, 1.0 equiv) and NMM (0.42 mL, 3.9 mmol, 6.0 equiv) in CH$_2$Cl$_2$ (10 mL) at 0° C. was added TMS-I (0.28 mL, 1.95 mmol, 3.0 equiv) dropwise. After 1 h, the reaction mixture was quenched with MeOH (1.0 mL) and concentrated under a stream of N$_2$. The residue was redissolved in CH$_2$Cl$_2$ (10 mL) and concentrated under reduced pressure providing a crude oil, which was used without further purification. The title compound was synthesized according to Procedure A from the deprotected amine (0.65 mmol [theoretical yield from previous step]), DSC (183 mg, 0.72 mmol) and NMM (0.24 mL, 2.2 mmol, 3.0 equiv). Purification of the crude product by flash chromatography (50% EtOAc/hexanes, 1% TEA) provided the title compound (143 mg, 45%) as a colorless oil: $^1$H NMR (600 MHz, CDCl$_3$) δ 7.34-7.30 (m, 3H), 7.24 (dd, J=1.9, 8.1 Hz, 1H), 7.10 (t, J=7.4 Hz, 1H), 7.01 (d, J=1.9 Hz, 1H), 6.91 (d, J=7.8 Hz, 2H), 3.57 (bs, 2H), 3.55 (s, 2H), 3.45 (s, 2H), 2.79 (s, 4H), 2.51 (d, J=5.5 Hz, 4H); $^{13}$C NMR (150 MHz, CDCl$_3$) δ 170.64, 157.85, 156.69, 151.11, 133.03, 130.75, 128.82, 127.61, 124.34, 123.19, 122.18, 118.97, 56.52, 52.96, 52.88, 45.92, 45.41, 26.34; HRMS (ESI-TOF+) m/z calcd for C$_{22}$H$_{22}$BrN$_3$O$_5$ [M+H]$^+$: 488.0821. found 488.0820.

Example 38

2,5-Dioxopyrrolidin-1-yl morpholine-4-carboxylate

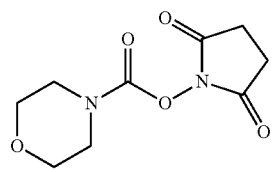

38

The title compound was synthesized according to Procedure A from morpholine (200 mg, 2.2 mmol), DSC (570 mg, 2.2 mmol) and NMM (0.74 mL, 6.7 mmol). Purification of the crude product by flash chromatography (60% EtOAc/hexanes) provided the title compound (400 mg, 78%) as a white solid: $^1$H NMR (600 MHz, CDCl$_3$) δ 3.73 (t, J=4.9 Hz, 4H), 3.63 (bs, 2H), 3.50 (bs, 2H), 2.81 (s, 4H); $^{13}$C NMR (150 MHz, CDCl$_3$) δ 170.51, 151.25, 67.10, 66.89, 45.81, 45.69, 26.33; HRMS (ESI-TOF+) m/z calcd for C$_9$H$_{12}$N$_2$O$_5$ [M+H]$^+$: 229.0824. found 229.0819.

Example 39

2,5-Dioxopyrrolidin-1-yl (3R)-3-(benzyloxy)pyrrolidine-1-carboxylate

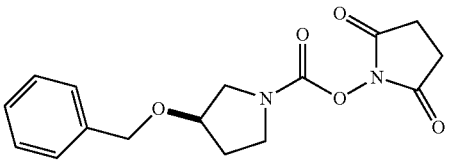 [SMILES: O=C(ON1C(=O)CCC1=O)N1CC[C@@H](OCc2ccccc2)C1]

The title compound was synthesized according to Procedure A from (R)-3-benzyloxy-pyrrolidine (76 mg, 0.36 mmol), DSC (91 mg, 0.36 mmol) and NMM (0.12 mL, 1.1 mmol). Purification of the crude product by flash chromatography (40% EtOAc/hexanes) provided the title compound (95 mg, 84%) as a colorless oil: $^1$H NMR (600 MHz, CDCl$_3$) δ 7.37-7.27 (m, 5H), 4.55-4.47 (m, 2H), 4.23-4.15 (m, 1H), 3.73-3.52 (m, 4H), 2.79 (s, 4H), 2.18-2.08 (m, 1H), 2.00 (m, 1H); $^{13}$C NMR (150 MHz, CDCl$_3$) δ 170.72, 150.55, 150.48, 138.47, 129.37, 128.72, 128.71, 128.52, 78.36, 77.07, 71.91, 71.85, 53.34, 52.14, 46.48, 45.26, 32.41, 31.24, 26.34; HRMS (ESI-TOF+) m/z calcd for C₁₆H₁₈N₂O₅ [M+H]⁺: 319.1294. found 319.1288.

Example 40

2,5-Dioxopyrrolidin-1-yl (3S)-3-(benzyloxy)pyrrolidine-1-carboxylate

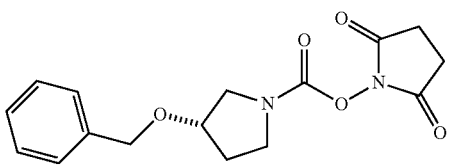 [SMILES: O=C(ON1C(=O)CCC1=O)N1CC[C@H](OCc2ccccc2)C1]

The title compound was synthesized according to Procedure A from (S)-3-benzyloxy-pyrrolidine (120 mg, 0.56 mmol), DSC (140 mg, 0.56 mmol) and NMM (0.19 mL, 1.7 mmol). Purification of the crude product by flash chromatography (40% EtOAc/hexanes) provided the title compound (160 mg, 90%) as a colorless oil. NMR for (S)-39 was identical to that of (R)-39; HRMS (ESI-TOF+) m/z calcd for C₁₆H₁₈N₂O₅ [M+H]⁺: 319.1294. found 319.1288.

Example 41

3-Methyl-2,5-dioxopyrrolidin-1-yl 4-(bis(4-chlorophenyl)methyl)piperazine-1-carboxylate

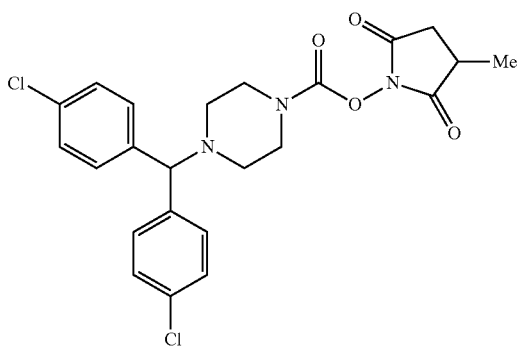 [SMILES: CC1CC(=O)N(OC(=O)N2CCN(C(c3ccc(Cl)cc3)c3ccc(Cl)cc3)CC2)C1=O]

Step 1: Preparation of 1-(benzyloxy)-3-methylpyrrolidine-2,5-dione

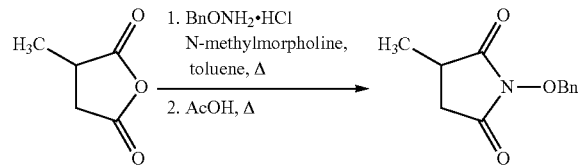

To a stirring solution of 3-methyldihydrofuran-2,5-dione (1.09 g, 9.55 mmol, 1.0 equiv) and N-methylmorpholine (1.93 g, 19.1 mmol, 2.0 equiv) in anhydrous toluene (50 mL) was added O-benzylhydroxylamine hydrochloride (1.52 g, 9.55 mmol, 1.0 equiv). The mixture was stirred for 30 min at room temperature and then heated to reflux with azeotropic removal of water. After 2 h, glacial acetic acid (1.0 mL) was added to the reaction mixture. After refluxing for 6 h, the reaction was cooled to room temperature, and the product was extracted from saturated NaHCO₃ (200 mL) with EtOAc (3×200 mL). The combined organic layers were dried over anhydrous Na₂SO₄ and concentrated under vacuum. The crude product was purified by SiO₂ chromatography (40% EtOAc/Hexanes) to yield the title compound as a white solid (1.44 g, 6.56 mmol, 69%): ¹H NMR (500 MHz, Chloroform-d) δ 7.46 (t, J=4.81 Hz, 2H), 7.41-7.32 (m, 3H), 5.11 (s, 2H), 2.82 (dd, J=8.96, 17.69 Hz, 1H), 2.78-2.69 (m, 1H), 2.19 (dd, J=3.93, 17.74 Hz, 1H), 1.24 (d, J=7.29 Hz, 3H); ¹³C NMR (126 MHz, Chloroform-d) δ 175.05, 170.97, 133.64, 130.44, 129.84, 128.89, 78.84, 34.15, 32.35, 17.10.

Step 2: Preparation of 1-hydroxy-3-methylpyrrolidine-2,5-dione

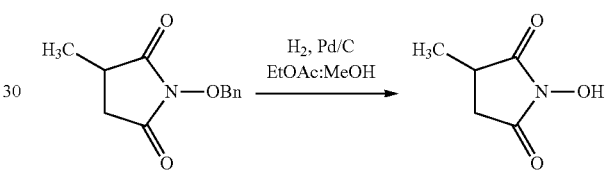

In a vial fitted with a rubber septum, 1-(benzyloxy)-3-methylpyrrolidine-2,5-dione (0.456 mmol, 1.0 equiv) was dissolved in a 1:1 mixture of EtOAc:MeOH (5.0 mL) under N₂. To this solution was added 10% Pd/C (20 mg), and the vial was purged with H₂ (g). The reaction mixture was stirred for 2 h under H₂ (1 atm, balloon). The reaction vial was then purged with N₂, and the reaction mixture was filtered through Celite, eluting with EtOAc:MeOH (1:1). The filtrate was concentrated under reduced pressure to provide the title compound (100 mg, 0.46 mmol) as a white solid, which was used in subsequent steps without purification.

Step 3: Preparation of 4-(bis(4-chlorophenyl)methyl)piperazine-1-carbonyl chloride

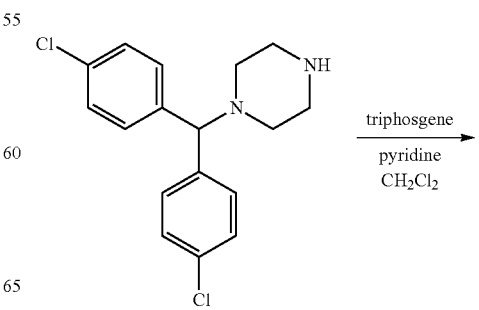

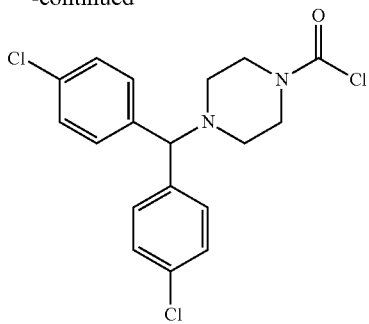

To a stirring solution of triphosgene (460 mg, 1.56 mmol, 0.5 equiv) in anhydrous CH₂Cl₂ (25 mL) at 0° C. under N₂ was added pyridine (0.25 mL, 3.11 mmol, 1.0 equiv). After stirring for 5 min, 1-(bis(4-chlorophenyl)methyl)piperazine (3.11 mmol, 1.0 equiv) was added in small portions over 15 min. The reaction mixture was stirred for 1 h and then allowed to warm to room temperature. After stirring for an additional 4 h, the reaction mixture was quenched with cold HCl (10 mL, 1.0 N), and the product was extracted with CH₂Cl₂ (3×20 mL). The combined organic layers were washed with saturated NaHCO₃ (2×20 mL), dried over anhydrous Na₂SO₄, and concentrated under reduced pressure. The crude 4-(bis(4-chlorophenyl)methyl)piperazine-1-carbonyl chloride was used without further purification.

Step 4: Preparation of 3-methyl-2,5-dioxopyrrolidin-1-yl 4-(bis(4-chlorophenyl)methyl)piperazine-1-carboxylate

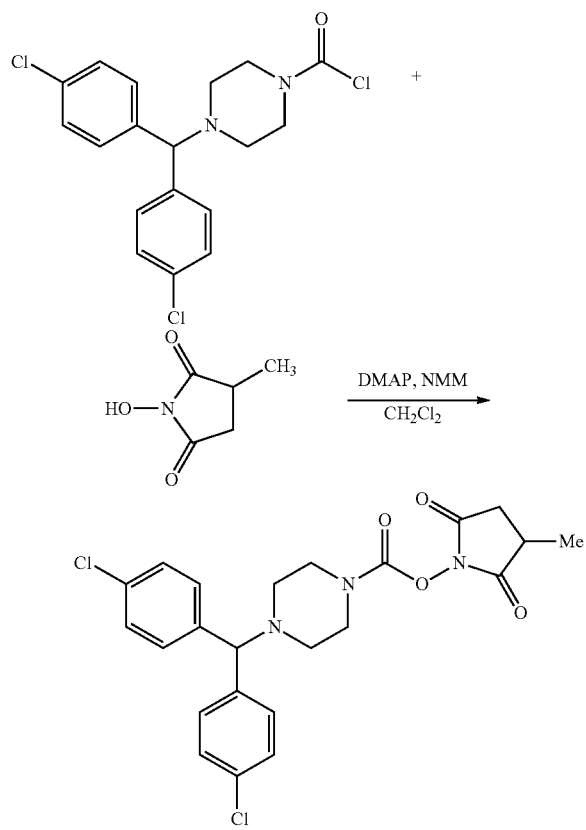

To a stirring solution of 4-(bis(4-chlorophenyl)methyl)piperazine-1-carbonyl chloride (50 mg, 0.13 mmol, 1.0 equiv) and 1-hydroxy-3-methylpyrrolidine-2,5-dione (34 mg, 0.26 mmol, 2.0 equiv) in anhydrous CH₂Cl₂ (5.0 mL) was added N-methylmorpholine (29 μL, 0.26 mmol, 2.0 equiv) and catalytic DMAP (~2 mg). The reaction mixture was stirred overnight at room temperature and then concentrated under a stream of N₂. Purification of the crude product by SiO₂ preparative TLC (50% EtOAc/hexanes) provided the title compound (57 mg, 0.12 mmol, 92%) as a white solid: ¹H NMR (600 MHz, Chloroform-d) δ 7.31 (d, J=8.46 Hz, 4H), 7.26 (d, J=8.39 Hz, 4H), 4.23 (s, 1H), 3.63 (bs, 2H), 3.51 (bs, 2H), 3.04-2.91 (m, 2H), 2.49-2.36 (m, 5H), 1.40 (d, J=7.02 Hz, 3H); ¹³C NMR (151 MHz, Chloroform-d) δ 173.33, 169.25, 150.30, 139.98, 133.13, 128.97, 128.94, 74.32, 51.00, 50.92, 45.06, 44.55, 33.73, 32.18, 16.72; HRMS (ESI) m/z calcd for [M+H]⁺ C₂₃H₂₃Cl₂N₃O₄: 476.1138. found 476.1140.

Example 42

3,3-Dimethyl-2,5-dioxopyrrolidin-1-yl 4-(bis(4-chlorophenyl)methyl)piperazine-1-carboxylate

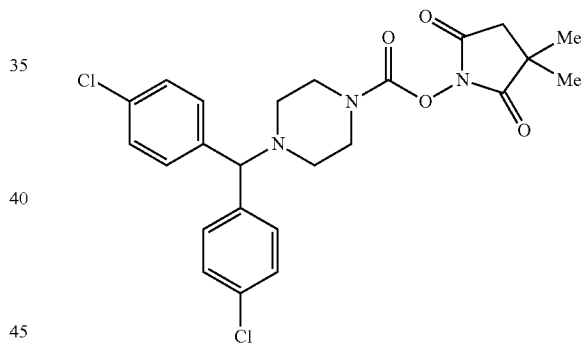

The title compound was synthesized directly from 1-hydroxy-3,3-dimethylpyrrolidine-2,5-dione, itself prepared from 3,3-dimethyldihydrofuran-2,5-dione, according to the representative procedure of Example 41, Steps 1 and 2, and 4-(bis(4-chlorophenyl)methyl)piperazine-1-carbonyl chloride according to the representative procedure of Example 41, Steps 3 and 4 to provide 3,3-dimethyl-2,5-dioxopyrrolidin-1-yl 4-(bis(4-chlorophenyl)methyl)piperazine-1-carboxylate as a white solid: ¹H NMR (500 MHz, Chloroform-d) δ 7.31 (d, J=8.49 Hz, 4H), 7.27 (d, J=8.36 Hz, 4H), 4.24 (s, 1H), 3.63 (bs, 2H), 3.51 (bs, 2H), 2.62 (s, 2H), 2.43 (bs, 4H), 1.39 (s, 6H); ¹³C NMR (126 MHz, Chloroform-d) δ 176.62, 169.29, 150.88, 140.44, 133.62, 129.43, 129.40, 74.80, 51.43, 45.52, 45.02, 41.44, 38.56, 26.00; HRMS (ESI) m/z calcd for [M+H]⁺ C₂₄H₂₅N₃O₄: 490.1295. found 490.1292.

Example 43

2,5-Dioxo-3-propylpyrrolidin-1-yl 4-(bis(4-chlorophenyl)methyl)piperazine-1-carboxylate

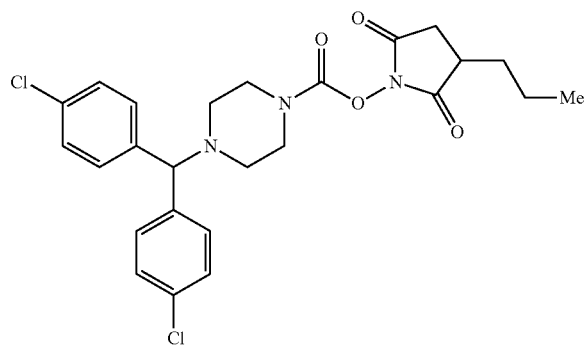 [SMILES: CCCC1CC(=O)N(OC(=O)N2CCN(C(c3ccc(Cl)cc3)c3ccc(Cl)cc3)CC2)C1=O]

The title compound was synthesized directly from 1-hydroxy-3-propylpyrrolidine-2,5-dione, itself prepared from 3-propyldihydrofuran-2,5-dione, according to the representative procedure of Example 41, Steps 1 and 2, and 4-(bis(4-chlorophenyl)methyl)piperazine-1-carbonyl chloride according to the representative procedure of Example 41, Steps 3 and 4 to provide 2,5-dioxo-3-propylpyrrolidin-1-yl 4-(bis(4-chlorophenyl)methyl)piperazine-1-carboxylate as a white solid: $^1$H NMR (600 MHz, Chloroform-d) δ 7.31 (d, J=8.51 Hz, 4H), 7.26 (d, J=8.41 Hz, 4H), 4.23 (s, 1H), 3.63 (bs, 2H), 3.51 (bs, 2H), 2.93-2.86 (m, 2H), 2.49-2.39 (m, 5H), 1.93-1.86 (m, 1H), 1.63-1.56 (m, 1H), 1.51-1.36 (m, 2H), 0.95 (t, J=7.31 Hz, 3H); $^{13}$C NMR (151 MHz, Chloroform-d) δ 172.79, 169.46, 150.29, 139.98, 133.12, 128.95, 128.93, 74.31, 50.99, 50.91, 45.04, 44.55, 36.98, 33.12, 31.58, 19.49, 13.65; HRMS (ESI) calcd for [M+H]$^+$ C$_{25}$H$_{27}$Cl$_2$N$_3$O$_4$: 504.1451. found 504.1455.

Example 44

2,5-Dioxo-3-phenylpyrrolidin-1-yl 4-(bis(4-chlorophenyl)methyl)piperazine-1-carboxylate

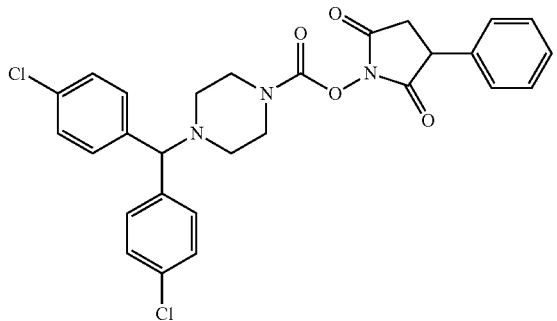 [SMILES: O=C(ON1C(=O)CC(c2ccccc2)C1=O)N1CCN(C(c2ccc(Cl)cc2)c2ccc(Cl)cc2)CC1]

The title compound was synthesized directly from 1-hydroxy-3-phenylpyrrolidine-2,5-dione, itself prepared from 3-phenyldihydrofuran-2,5-dione, according to the representative procedure of Example 41, Steps 1 and 2, and 4-(bis(4-chlorophenyl)methyl)piperazine-1-carbonyl chloride according to the representative procedure of Example 41, Steps 3 and 4 to provide 2,5-dioxo-3-phenylpyrrolidin-1-yl 4-(bis(4-chlorophenyl)methyl)piperazine-1-carboxylate as a white solid: $^1$H NMR (500 MHz, Chloroform-d) δ 7.41-7.34 (m, 2H), 7.34-7.24 (m, 11H), 4.23 (s, 1H), 4.14-4.04 (m, 1H), 3.65 (bs, 2H), 3.54 (bs, 2H), 3.28 (dd, J=9.52, 18.34 Hz, 1H), 2.85 (dd, J=4.18, 18.35 Hz, 1H), 2.43 (bs, 4H); $^{13}$C NMR (126 MHz, Chloroform-d) δ 171.18, 169.42, 150.75, 140.44, 133.63, 129.76, 129.44, 129.42, 128.67, 128.03, 74.79, 51.48, 51.41, 45.62, 45.11, 43.78, 35.52; HRMS (ESI) m/z calcd for [M+H]$^+$ C$_{28}$H$_{25}$Cl$_2$N$_3$O$_4$: 538.1295. found 538.1295.

Example 45

1,3-Dioxohexahydro-1H-isoindol-2(3H)-yl 4-(bis(4-chlorophenyl)methyl)piperazine-1-carboxylate

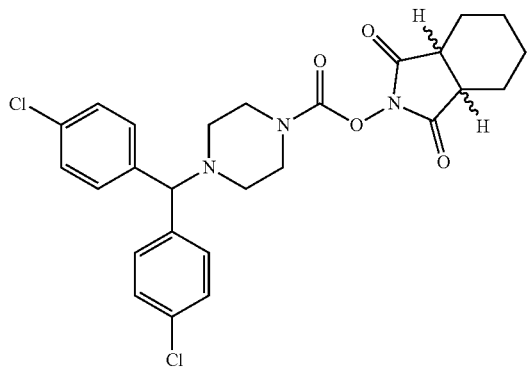

1:1 (cis:trans)

The title compound was synthesized directly from 2-hydroxyhexahydro-1H-isoindole-1,3(2H)-dione, itself prepared from hexahydroisobenzofuran-1,3-dione, according to the representative procedure of Example 41, Steps 1 and 2, and 4-(bis(4-chlorophenyl)methyl)piperazine-1-carbonyl chloride according to the representative procedure of Example 41, Steps 3 and 4 to provide 1,3-dioxohexahydro-1H-isoindol-2(3H)-yl 4-(bis(4-chlorophenyl)methyl)piperazine-1-carboxylate as a white solid: $^1$H NMR (500 MHz, Chloroform-d) δ 7.39 (d, J=7.79 Hz, 4H), 7.34 (d, J=7.42 Hz, 4H), 4.32 (s, 1H), 3.71 (bs, 2H), 3.59 (bs, 2H), 3.05 (bs, 1H), 2.58 (bs, 1H), 2.50 (bs, 4H), 2.34 (d, J=12.61 Hz, 1H), 2.09-1.90 (m, 3H), 1.61-1.50 (m, 3H), 1.45-1.36 (m, 1H); $^{13}$C NMR (126 MHz, Chloroform-d) δ 173.27, 170.80, 151.35, 151.14, 140.46, 133.60, 129.41, 74.79, 51.45, 45.47, 45.02, 37.96, 25.77, 24.93, 23.96, 21.75; FIRMS (ESI) m/z calcd for [M+H]$^+$ C$_{26}$H$_{27}$Cl$_2$N$_3$O$_4$: 516.1451. found 516.1453.

Example 46

2,5-Dioxoimidazolidin-1-yl 4-(bis(4-chlorophenyl)methyl)piperazine-1-carboxylate

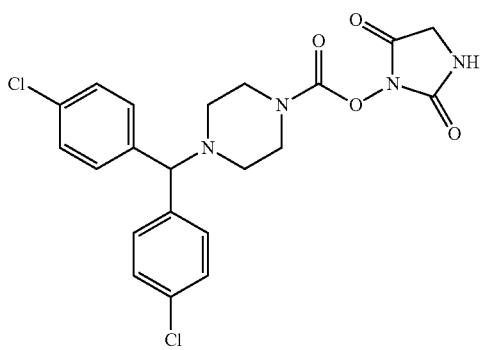 [SMILES: O=C(ON1C(=O)CNC1=O)N1CCN(C(c2ccc(Cl)cc2)c2ccc(Cl)cc2)CC1]

Step 1: Preparation of tert-butyl (2-((benzyloxy)amino)-2-oxoethyl)carbamate

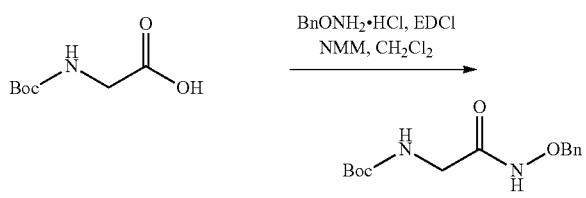

To a stirring solution of 2-((tert-butoxycarbonyl)amino)acetic acid (1.1 g, 6.3 mmol, 1.0 equiv), O-benzylhydroxylamine hydrochloride (1.1 g, 6.9 mmol, 1.1 equiv), and N-methylmorpholine (0.74 mL, 6.9 mmol, 1.0 equiv) in anhydrous CH$_2$Cl$_2$ (50 mL) under nitrogen was added EDCI (1.3 g, 6.9 mmol, 1.1 equiv) at 0° C. After stirring for 1 h, the reaction mixture was allowed to warm to room temperature and was stirred for an additional 4 h. The reaction was quenched with ice cold 5% aqueous HCl (100 mL), and the product was extracted with CH$_2$Cl$_2$ (3×100 mL). The combined organic layers were washed with brine (2×100 mL), dried over anhydrous Na$_2$SO$_4$, and concentrated under reduced pressure to provide crude, tert-butyl (2-((benzyloxy)amino)-2-oxoethyl)carbamate, which was used in subsequent steps without further purification.

Step 2: Preparation of 2-amino-N-(benzyloxy)acetamide

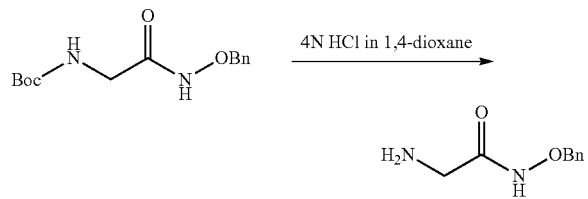

To a solution of HCl (5 mL, 4 N in 1,4-dioxane) was added tert-butyl (2-((benzyloxy)amino)-2-oxoethyl)carbamate from Step 1. The reaction mixture was stirred for 1 h at room temperature. The product was concentrated under a stream of N$_2$ and then under reduced pressure. The remaining residue, 2-amino-N-(benzyloxy)acetamide, was used in subsequent steps without further purification.

Step 3: Preparation of 3-(benzyloxy)imidazolidine-2,4-dione

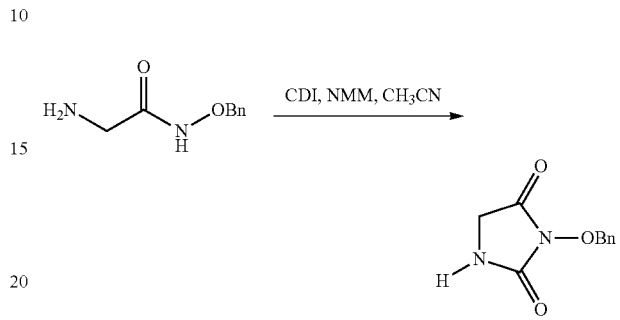

To a solution of crude 2-amino-N-(benzyloxy)acetamide (665 mg, 3.69 mmol, 1.0 equiv) and N-methylmorpholine (0.81 mL, 7.38 mmol, 2.0 equiv) in anhydrous CH$_2$Cl$_2$ (50 mL) was added 1,1'-carbonyldiimidazole (659 mg, 4.06 mmol, 1.1 equiv) at room temperature. After stirring overnight, the reaction mixture was poured into a separatory funnel containing ice cold 5% aqueous HCl (50 mL), and the product was extracted with CH$_2$Cl$_2$ (3×50 mL). The combined organic layers were dried over anhydrous Na$_2$SO$_4$ and concentrated under reduced pressure. The remaining residue was purified by SiO$_2$ flash chromatography (EtOAc/hexanes) to provide 3-(benzyloxy)imidazolidine-2,4-dione as a white solid: $^1$H NMR (600 MHz, Chloroform-d) δ 7.51-7.46 (m, 2H), 7.41-7.34 (m, 3H), 6.44 (s, 1H), 5.12 (s, 2H), 3.86 (s, 2H); $^{13}$C NMR (151 MHz, Chloroform-d) δ 166.48, 155.48, 134.10, 130.74, 130.32, 129.44, 80.33, 45.28.

Step 4: Preparation of 3-hydroxyimidazolidine-2,4-dione

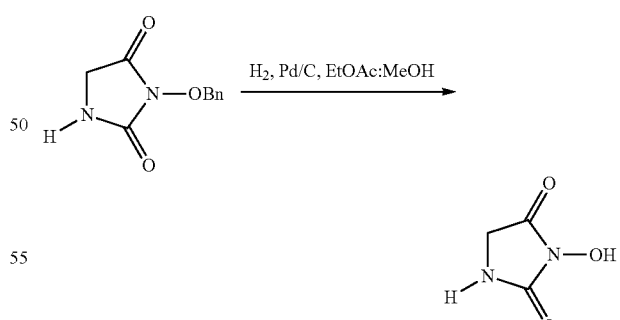

In a vial fitted with a rubber septum, 3-(benzyloxy)imidazolidine-2,4-dione (298 mg, 1.45 mmol, 1.0 equiv) was dissolved in a 1:4 mixture of EtOAc:MeOH (5.0 mL) under N$_2$. To this solution was added 10% Pd/C (50 mg), and the vial was purged with H$_2$ (g). The reaction mixture was stirred for 2 h under H$_2$ (1 atm, balloon) or until the starting material had been completely consumed as judged by TLC. The reaction vial was then purged with N$_2$, and the reaction mixture was filtered through Celite, eluting with MeOH. The filtrate was concentrated under reduced pressure to provide crude 3-hydroxyimidazolidine-2,4-dione, which was used in subsequent steps without further purification.

Step 5: Preparation of 2,5-dioxoimidazolidin-1-yl 4-(bis(4-chlorophenyl)methyl)piperazine-1-carboxylate The title compound was prepared according to the procedure of Example 41, Step 4 using 4-(bis(4-chlorophenyl)methyl)piperazine-1-carbonyl chloride (50 mg, 0.13 mmol) and 3-hydroxyimidazolidine-2,4-dione (30 mg, 0.26 mmol). Note: Anhydrous DMF was used as the reaction solvent instead of $CH_2Cl_2$. Purification of the crude product by $SiO_2$ preparative TLC (50% EtOAc/hexanes, 3% MeOH) provided 2,5-dioxoimidazolidin-1-yl 4-(bis(4-chlorophenyl)methyl)piperazine-1-carboxylate (44 mg, 73%) as a white solid: $^1$H NMR (600 MHz, Chloroform-d) δ 7.31 (d, J=8.41 Hz, 4H), 7.27 (d, J=8.19 Hz, 4H), 5.98 (s, 1H), 4.24 (s, 1H), 4.07 (bs, 2H), 3.65 (bs, 2H), 3.53 (bs, 2H), 2.43 (bs, 4H); $^{13}$C NMR (151 MHz, Chloroform-d) δ 165.69, 153.87, 151.62, 140.82, 134.07, 129.88, 129.83, 75.20, 51.87, 51.80, 46.05, 45.50, 45.45; HRMS (ESI) m/z calcd for [M+H]$^+$ $C_{21}H_{20}Cl_2N_4O_4$: 463.0934. found 463.0934.

Example 47

4-Isopropyl-2,5-dioxoimidazolidin-1-yl 4-(bis(4-chlorophenyl)methyl)piperazine-1-carboxylate

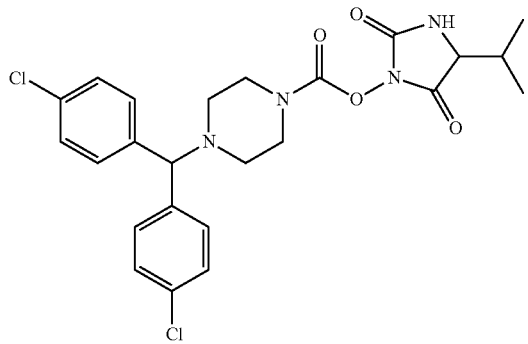 [SMILES: CC(C)C1NC(=O)N(OC(=O)N2CCN(C(c3ccc(Cl)cc3)c3ccc(Cl)cc3)CC2)C1=O]

The title compound was synthesized directly from 3-hydroxy-5-isopropylimidazolidine-2,4-dione, itself prepared from 2-((tert-butoxycarbonyl)amino)-3-methylbutanoic acid according to the representative procedure of Example 46, Steps 1, 2, 3 and 4, and 4-(bis(4-chlorophenyl)methyl)piperazine-1-carbonyl chloride according to the representative procedure of Example 41, Step 4 to provide 4-isopropyl-2,5-dioxoimidazolidin-1-yl 4-(bis(4-chlorophenyl)methyl)piperazine-1-carboxylate as a white solid (Note: Anhydrous DMF was used as the reaction solvent instead of $CH_2Cl_2$ in Step 5): $^1$H NMR (600 MHz, Chloroform-d) δ 7.30 (d, J=8.50 Hz, 4H), 7.26 (d, J=7.30 Hz, 4H), 5.86 (s, 1H), 4.22 (s, 1H), 4.02 (bs, 1H), 3.63 (bs, 2H), 3.51 (bs, 2H), 2.41 (bs, 4H), 2.31-2.23 (m, 1H), 1.06 (d, J=6.93 Hz, 3H), 1.00 (d, J=5.74 Hz, 3H); $^{13}$C NMR (151 MHz, Chloroform-d) δ 167.00, 152.84, 150.74, 139.98, 133.19, 129.00, 128.96, 74.36, 60.78, 51.04, 50.95, 45.14, 44.59, 30.19, 18.52, 16.19; HRMS (ESI) m/z calcd for [M+H]$^+$ $C_{24}H_{26}Cl_2N_4O_4$: 505.1404. found 505.1402.

Example 48

2,5-Dioxoimidazolidin-1-yl 4-(4-chlorophenethyl)piperidine-1-carboxylate

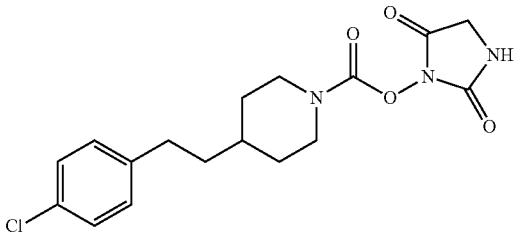 [SMILES: O=C(ON1C(=O)CNC1=O)N1CCC(CCc2ccc(Cl)cc2)CC1]

The title compound was synthesized directly from 3-hydroxyimidazolidine-2,4-dione, itself prepared as described in Example 46, Steps 1, 2, 3 and 4, and commercially available 4-(4-chlorophenethyl)piperidine according to the representative procedure of Example 41, Steps 3 and 4 to provide 2,5-dioxoimidazolidin-1-yl 4-(4-chlorophenethyl)piperidine-1-carboxylate as a white solid (Note: Anhydrous DMF was used as the reaction solvent instead of $CH_2Cl_2$ in Step 5): $^1$H NMR (600 MHz, Chloroform-d) δ 7.24 (d, J=8.29 Hz, 2H), 7.09 (d, J=8.25 Hz, 2H), 6.30 (s, 1H), 4.20 (d, J=12.91 Hz, 1H), 4.11-4.04 (m, 3H), 2.98 (t, J=12.42 Hz, 1H), 2.86 (t, J=12.26 Hz, 1H), 2.63-2.58 (m, 2H), 1.78 (d, J=12.73 Hz, 2H), 1.61-1.54 (m, 2H), 1.53-1.43 (m, 1H), 1.37-1.22 (m, 2H); $^{13}$C NMR (151 MHz, Chloroform-d) δ 165.97, 154.26, 151.75, 141.35, 132.38, 130.46, 129.35, 46.57, 45.66, 45.54, 38.64, 35.72, 33.01, 32.54, 32.23; HRMS (ESI) calcd for [M+H]$^+$ $C_{17}H_{20}ClN_3O_4$: 366.1215. found 366.1206.

Example 49

3-Methyl-2,5-dioxoimidazolidin-1-yl 4-(4-chlorophenethyl)piperidine-1-carboxylate

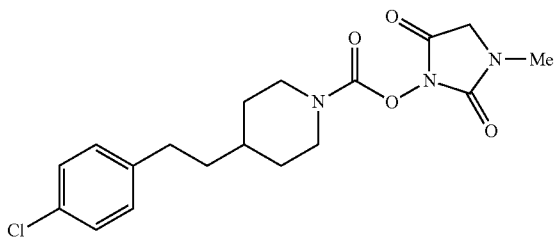 [SMILES: CN1CC(=O)N(OC(=O)N2CCC(CCc3ccc(Cl)cc3)CC2)C1=O]

To a stirring solution of 2,5-dioxoimidazolidin-1-yl 4-(4-chlorophenethyl)piperidine-1-carboxylate (Example 48, 6.5 mg, 0.02 mmol, 1.0 equiv) in $CH_3CN$ (2 mL) was added methyl iodide (5.6 μL, 0.09 mmol, 5.0 equiv) followed by $Cs_2CO_3$ (8.0 mg, 0.024 mmol, 1.2 equiv). After stirring for 4 h, the reaction mixture was poured into a separatory funnel containing brine (25 mL), and the product was extracted with $CH_2Cl_2$ (3×25 mL). The combined organic layers were dried over anhydrous $Na_2SO_4$ and concentrated under vacuum. Purification of the crude product by $SiO_2$ preparative TLC (25% EtOAc/hexanes) provided the title compound (4.0 mg, 59%) as an off-white solid: $^1$H NMR (600 MHz, Chloroform-d) δ 7.25 (d, J=8.33 Hz, 2H), 7.09 (d, J=8.25 Hz, 2H), 4.21 (d, J=14.06 Hz, 1H), 4.10 (d, J=12.53 Hz, 1H), 3.97 (s, 2H), 3.02 (s, 3H), 2.98 (t, J=12.70 Hz, 1H), 2.86 (t, J=12.38 Hz, 1H), 2.62-2.59 (m, 2H), 1.78 (d, J=12.95 Hz, 2H), 1.60-1.54 (m, 2H), 1.52-1.44 (m, 1H), 1.39-1.23 (m, 2H); $^{13}$C NMR (151 MHz, Chloroform-d) δ 164.85, 153.11, 151.82, 141.38, 132.39, 130.46, 129.35, 50.67, 46.55, 45.66, 38.67, 35.76, 33.02, 32.55, 32.24, 31.11; HRMS (ESI) m/z calcd for [M+H]$^+$ C$_{18}$H$_{22}$ClN$_3$O$_4$: 380.1372. found 380.1388

Example 50

3-Benzyl-2,5-dioxoimidazolidin-1-yl 4-(4-chlorophenethyl)piperidine-1-carboxylate

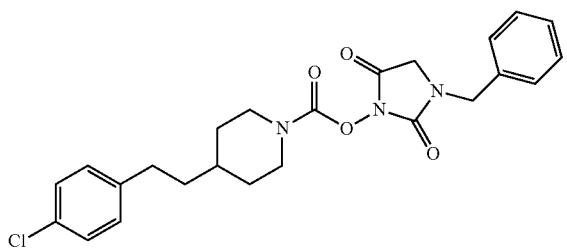 [SMILES: O=C(ON1C(=O)CN(Cc2ccccc2)C1=O)N1CCC(CCc2ccc(Cl)cc2)CC1]

To a stirring solution of 2,5-dioxoimidazolidin-1-yl 4-(4-chlorophenethyl)piperidine-1-carboxylate (Example 48, 9.5 mg, 0.026 mmol, 1.0 equiv) in CH$_3$CN (2 mL) was added benzyl bromide (9.0 mg, 0.052 mmol, 2.0 equiv) followed by Cs$_2$CO$_3$ (10 mg, 0.031 mmol, 1.2 equiv). After stirring for 12 h, the reaction mixture was poured into a separatory funnel containing brine (25 mL), and the product was extracted with CH$_2$Cl$_2$ (3×25 mL). The combined organic layers were dried over anhydrous Na$_2$SO$_4$ and concentrated under vacuum. Purification of the crude product by SiO$_2$ preparative TLC (20% EtOAc/hexanes) provided 3-benzyl-2,5-dioxoimidazolidin-1-yl 4-(4-chlorophenethyl)piperidine-1-carboxylate (8.7 mg, 74%) as a colorless oil: $^1$H NMR (600 MHz, Chloroform-d) δ 7.39-7.31 (m, 3H), 7.26 (t, J=8.76 Hz, 4H), 7.10 (d, J=8.27 Hz, 2H), 4.58 (s, 2H), 4.23 (d, J=12.62 Hz, 1H), 4.12 (d, J=13.27 Hz, 1H), 3.82 (s, 2H), 2.99 (t, J=12.76 Hz, 1H), 2.87 (t, J=12.39 Hz, 1H), 2.63-2.59 (m, 2H), 1.79 (d, J=12.92 Hz, 2H), 1.61-1.56 (m, 2H), 1.54-1.44 (m, 1H), 1.40-1.23 (m, 2H); $^{13}$C NMR (151 MHz, Chloroform-d) δ 164.08, 152.31, 150.95, 140.51, 134.49, 131.52, 129.60, 129.13, 128.48, 128.39, 128.08, 47.15, 47.10, 45.71, 44.82, 37.81, 34.91, 32.15, 31.71, 31.39; HRMS (ESI) in/z calcd for [M+H]$^+$ C$_{24}$H$_{26}$ClN$_3$O$_4$: 456.1685. found 456.1699.

Example 51

2,5-Dioxopyrrolidin-1-yl 4-acetylpiperazine-1-carboxylate

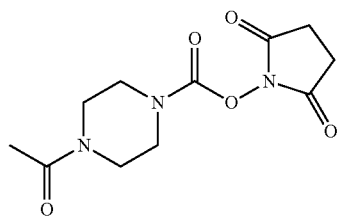 [SMILES: CC(=O)N1CCN(C(=O)ON2C(=O)CCC2=O)CC1]

A 50-mL round-bottom flask was charged with 1-(piperazin-1-yl)ethan-1-one (200 mg, 1.56 mmol, 1.00 equiv), bis(2,5-dioxopyrrolidin-1-yl) carbonate (799 mg, 3.12 mmol, 2.00 equiv), triethylamine (315 mg, 3.11 mmol, 2.00 equiv), and CH$_3$CN (15 mL). The resulting solution was stirred overnight at room temperature and concentrated under reduced pressure. The crude product (200 mg) was purified by preparative HPLC using the following gradient conditions: 20% CH$_3$CN/80% Phase A increasing to 80% CH$_3$CN over 10 min, then to 100% CH$_3$CN over 0.1 min, holding at 100% CH$_3$CN for 1.9 min, then reducing to 20% CH$_3$CN over 0.1 min, and holding at 20% for 1.9 min, on a Waters 2767-5 Chromatograph. Column: Xbridge Prep C$_{18}$, 19*150 mm, 5 um; Mobile phase: Phase A: water; Phase B: CH$_3$CN; Detector, UV 220 & 254 nm. Purification resulted in 139 mg (33% yield) of 2,5-dioxopyrrolidin-1-yl 4-acetylpiperazine-1-carboxylate as a white solid. $^1$H NMR (300 MHz, Chloroform-d) δ 3.57-3.69 (m, 8H), 2.84 (s, 4H), 2.13 (s, 3H). LCMS (ESI, m/z): 270 [M+H]$^+$.

Example 52

3,3-Dimethyl-2,5-dioxopyrrolidin-1-yl 4-(4-methoxyphenyl)piperazine-1-carboxylate

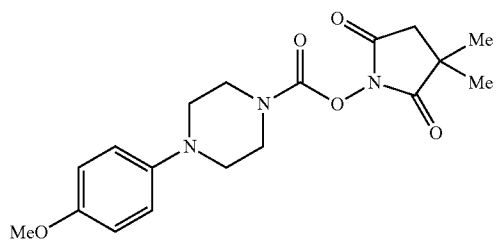 [SMILES: COc1ccc(N2CCN(C(=O)ON3C(=O)CC(C)(C)C3=O)CC2)cc1]

The title compound was synthesized directly from 1-hydroxy-3,3-dimethylpyrrolidine-2,5-dione, itself prepared from 3,3-dimethyldihydrofuran-2,5-dione according to Example 41, Steps 1 and 2, and commercially available 1-(4-methoxyphenyl)piperazine according to the representative procedure of Example 41, Steps 3 and 4 to provide 3,3-dimethyl-2,5-dioxopyrrolidin-1-yl 4-(4-methoxyphenyl)piperazine-1-carboxylate as a white solid: $^1$H NMR (500 MHz, Chloroform-d) δ 6.93-6.88 (m, 2H), 6.87-6.82 (m, 2H), 3.78 (bs, 2H), 3.77 (s, 3H), 3.67 (bs, 2H), 3.11 (bs, 4H), 2.64 (s, 2H), 1.41 (s, 6H); $^{13}$C NMR (126 MHz, Chloroform-d) δ 176.63, 169.30, 155.01, 150.93, 145.54, 119.65, 114.95, 55.95, 51.07, 45.55, 45.12, 41.45, 38.58, 26.01; HRMS (ESI) m/z calcd for [M+H]$^+$ C$_{18}$H$_{23}$N$_3$O$_5$: 362.1716. found 362.1726.

Example 53

1,3-Dioxohexahydro-1H-isoindol-2(3H)-yl 4-(4-methoxyphenyl)piperazine-1-carboxylate

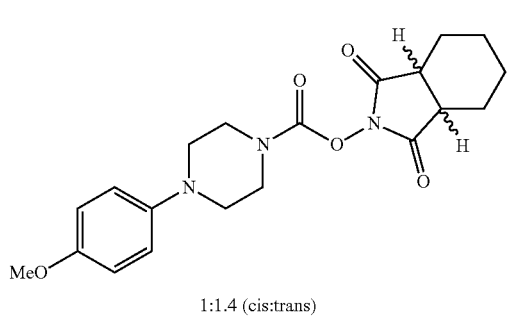 [SMILES: COc1ccc(N2CCN(C(=O)ON3C(=O)C4CCCCC4C3=O)CC2)cc1]

1:1.4 (cis:trans)

The title compound was synthesized directly from 2-hydroxyhexahydro-1H-isoindole-1,3(2H)-dione, itself prepared from hexahydroisobenzofuran-1,3-dione, according to the representative procedure of Example 41, Steps 1 and 2, and commercially available 1-(4-methoxyphenyl)piperazine according to the representative procedure of Example 41, Steps 3 and 4 to provide 1,3-dioxohexahydro-1H-isoindol-2(3H)-yl 4-(4-methoxyphenyl)piperazine-1-carboxylate as a white solid: $^1$H NMR (500 MHz, Chloroform-d) δ 6.90 (d, J=8.79 Hz, 2H), 6.87-6.83 (m, 2H), 3.78 (bs, 2H), 3.77 (s, 3H), 3.66 (bs, 2H), 3.10 (bs, 4H), 2.99 (p, J=7.47 Hz, 0.83H), 2.52 (bs, 1.17H), 2.27 (d, J=11.86 Hz, 1.17H), 1.99-1.86 (m, 3.17H), 1.57-1.43 (m, 2.83H), 1.34 (t, J=10.86 Hz, 1.17H); $^{13}$C NMR (126 MHz, Chloroform-d) δ 173.26, 170.79, 154.99, 151.40, 145.57, 119.64, 114.94, 55.95, 51.07, 45.50, 45.11, 37.98, 25.78, 24.94, 23.98, 21.77; HRMS (ESI) m/z calcd for [M+H]$^+$ C$_{20}$H$_{25}$N$_3$O$_5$: 388.1867. found 388.1883.

Example 54

2,5-Dioxo-3-phenylpyrrolidin-1-yl 4-(4-methoxyphenyl)piperazine-1-carboxylate

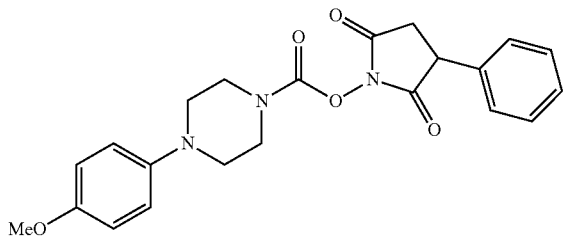 [SMILES: COc1ccc(N2CCN(C(=O)ON3C(=O)CC(c4ccccc4)C3=O)CC2)cc1]

The title compound was synthesized directly from 1-hydroxy-3-phenylpyrrolidine-2,5-dione, itself prepared from 3-phenyldihydrofuran-2,5-dione, according to the representative procedure of Example 41, Steps 1 and 2, and commercially available 1-(4-methoxyphenyl)piperazine according to the representative procedure of Example 41, Steps 3 and 4 to provide 2,5-dioxo-3-phenylpyrrolidin-1-yl 4-(4-methoxyphenyl)piperazine-1-carboxylate as a white solid: $^1$H NMR (500 MHz, Chloroform-d) δ 7.42-7.37 (m, 2H), 7.36-7.29 (m, 3H), 6.93-6.89 (m, 2H), 6.87-6.84 (m, 2H), 4.12 (bs, 1H), 3.82 (bs, 2H), 3.77 (s, 3H), 3.70 (bs, 2H), 3.31 (dd, J=9.54, 18.35 Hz, 1H), 3.12 (bs, 4H), 2.88 (dd, J=4.30, 18.35 Hz, 1H); $^{13}$C NMR (126 MHz, Chloroform-d) δ 169.43, 155.04, 150.81, 145.53, 129.76, 128.68, 128.05, 119.68, 114.96, 55.95, 51.09, 45.65, 45.19, 43.79, 35.53; HRMS (ESI) m/z calcd for [M+H]$^+$ C$_{22}$H$_{23}$N$_3$O$_5$: 410.1716. found 410.125.

Example 55

4-Isopropyl-2,5-dioxoimidazolidin-1-yl 4-(4-methoxyphenyl)piperazine-1-carboxylate

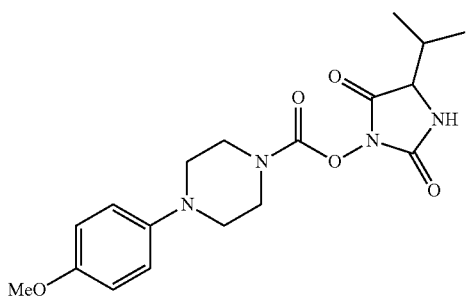 [SMILES: COc1ccc(N2CCN(C(=O)ON3C(=O)NC(C(C)C)C3=O)CC2)cc1]

The title compound was synthesized directly from 3-hydroxy-5-isopropylimidazolidine-2,4-dione, itself prepared from 2-((tert-butoxycarbonyl)amino)-3-methylbutanoic acid according to the representative procedure of Example 46, Steps 1, 2, 3 and 4, and commercially available 1-(4-methoxyphenyl)piperazine according to the representative procedure of Example 41, Steps 3 and 4 to provide 4-isopropyl-2,5-dioxoimidazolidin-1-yl 4-(4-methoxyphenyl)piperazine-1-carboxylate as a white solid: $^1$H NMR (600 MHz, Chloroform-d) δ 6.91-6.88 (m, 2H), 6.86-6.83 (m, 2H), 6.58 (s, 1H), 4.06-4.03 (m, 1H), 3.79 (bs, 2H), 3.77 (s, 3H), 3.67 (bs, 2H), 3.10 (bs, 4H), 2.28 (s, 1H), 1.08 (d, J=6.95 Hz, 3H), 1.02 (d, J=5.37 Hz, 3H); $^{13}$C NMR (151 MHz, Chloroform-d) δ 168.05, 155.42, 154.15, 151.71, 145.94, 120.06, 115.38, 61.70, 56.39, 51.49, 46.03, 45.56, 31.09, 17.08; HRMS (ESI) m/z calcd for [M+H]$^+$ C$_{18}$H$_{24}$N$_4$O$_5$: 377.1819. found 377.1838.

Example 56

3-Methyl-2,5-dioxoimidazolidin-1-yl 4-(bis(4-chlorophenyl)methyl)piperazine-1-carboxylate

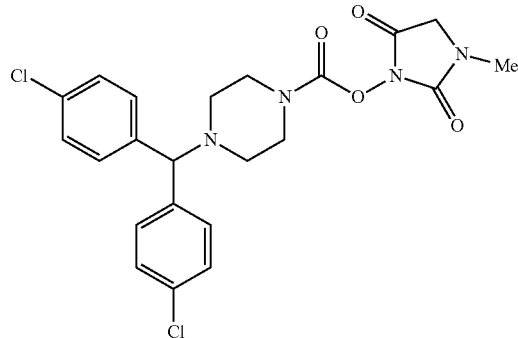 [SMILES: CN1CC(=O)N(OC(=O)N2CCN(C(c3ccc(Cl)cc3)c3ccc(Cl)cc3)CC2)C1=O]

To a stirring solution of 2,5-dioxoimidazolidin-1-yl 4-(bis(4-chlorophenyl)methyl)piperazine-1-carboxylate (Example 46, 20 mg, 0.043 mmol, 1.0 equiv) in CH$_3$CN (2 mL) was added methyl iodide (13 μL, 0.22 mmol, 5.0 equiv) followed by Cs$_2$CO$_3$ (17 mg, 0.052 mmol, 1.2 equiv). After stirring for 4 h, the reaction mixture was poured into a separatory funnel containing brine (25 mL), and the product was extracted with CH$_2$Cl$_2$ (3×25 mL). The combined organic layers were dried over anhydrous Na$_2$SO$_4$ and concentrated under vacuum. Purification of the crude product by SiO$_2$ preparative TLC (25% EtOAc/hexanes) provided 3-methyl-2,5-dioxo imidazolidin-1-yl 4-(bis(4-chlorophenyl)methyl)piperazine-1-carboxylate (17 mg, 83%) as an off-white solid: $^1$H NMR (600 MHz, Chloroform-d) δ 7.31 (d, J=8.43 Hz, 4H), 7.26 (d, J=8.44 Hz, 4H), 4.23 (s, 1H), 3.96 (s, 2H), 3.63 (bs, 2H), 3.52 (bs, 2H), 3.01 (s, 3H), 2.42 (bs, 4H); $^{13}$C NMR (151 MHz, Chloroform-d) δ 164.75, 152.96, 151.75, 140.87, 134.03, 129.86, 129.84, 75.22, 51.89, 51.82, 50.64, 46.01, 45.43, 31.11; HRMS (ESI) m/z calcd for [M+H]$^+$ C$_{22}$H$_{22}$Cl$_2$N$_4$O$_4$: 477.1091. found 477.1108.

Example 57

2,5-Dioxopyrrolidin-1-yl dimethylcarbamate

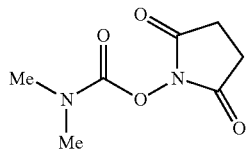 [SMILES: CN(C)C(=O)ON1C(=O)CCC1=O]

The title compound was prepared from commercially available dimethylcarbamoyl chloride and commercially available 1-hydroxypyrrolidine-2,5-dione according to the representative procedure of Example 41, Step 4, as a white solid: $^1$H NMR (600 MHz, Chloroform-d) δ 3.07 (s, 3H), 2.97 (s, 3H), 2.79 (s, 4H); $^{13}$C NMR (151 MHz, Chloroform-d) δ 170.77, 152.31, 38.57, 37.01, 26.32; HRMS (ESI) m/z calcd for [M+H]$^+$ C$_7$H$_{10}$N$_2$O$_4$: 187.0713. found 187.0721.

Example 58

2,5-Dioxoimidazolidin-1-yl dimethylcarbamate

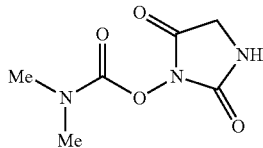 [SMILES: CN(C)C(=O)ON1C(=O)CNC1=O]

The title compound was prepared from commercially available dimethylcarbamoyl chloride and 3-hydroxyimidazolidine-2,4-dione, itself prepared as described in Example 46, Steps 1, 2, 3 and 4, according to the representative procedure of Example 41, Step 4 (Note: Anhydrous DMF was used as the reaction solvent instead of CH$_2$Cl$_2$) to provide 2,5-dioxoimidazolidin-1-yl dimethylcarbamate as a white solid: $^1$H NMR (600 MHz, Chloroform-d) δ 6.26 (s, 1H), 4.08 (s, 2H), 3.10 (s, 3H), 3.01 (s, 3H); $^{13}$C NMR (151 MHz, Chloroform-d) δ 165.92, 154.20, 152.89, 45.53, 38.68, 37.04; HRMS (ESI) m/z calcd for [M+H]$^+$ C$_6$H$_9$N$_3$O$_4$: 188.0666. found 188.0663.

Example 59

2,5-Dioxo-3-phenylpyrrolidin-1-yl dimethylcarbamate

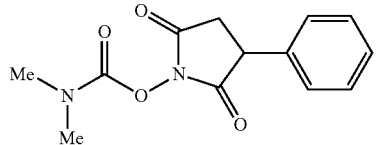 [SMILES: CN(C)C(=O)ON1C(=O)CC(c2ccccc2)C1=O]

The title compound was prepared from commercially available dimethylcarbamoyl chloride and 1-hydroxy-3-phenylpyrrolidine-2,5-dione, itself prepared from 3-phenyl-dihydrofuran-2,5-dione (Example 44), according to the representative procedure of Example 41, Step 4, as a white solid: $^1$H NMR (600 MHz, Chloroform-d) δ 7.37 (t, J=7.40 Hz, 2H), 7.34-7.26 (m, 3H), 4.13-4.07 (m, 1H), 3.29 (dd, J=9.55, 18.36 Hz, 1H), 3.09 (s, 3H), 3.00 (s, 3H), 2.84 (dd, J=3.88, 18.37 Hz, 1H); $^{13}$C NMR (151 MHz, Chloroform-d) δ 171.77, 170.06, 152.38, 137.56, 130.17, 129.06, 128.52, 44.20, 38.63, 37.06, 35.89; FIRMS (ESI) m/z calcd for [M+H]$^+$ C$_{13}$H$_{14}$N$_2$O$_4$: 263.1026. found 263.1017.

Example 60

2,5-Dioxo-3-phenylpyrrolidin-1-yl piperidine-1-carboxylate

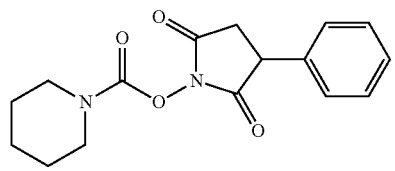 [SMILES: O=C(ON1C(=O)CC(c2ccccc2)C1=O)N1CCCCC1]

The title compound was prepared from 1-hydroxy-3-phenylpyrrolidine-2,5-dione, itself prepared from 3-phenyl-dihydrofuran-2,5-dione (Example 44), and commercially available piperidine according to the representative procedure of Example 41, Steps 3 and 4, to provide 2,5-dioxo-3-phenylpyrrolidin-1-yl piperidine-1-carboxylate as a white solid: $^1$H NMR (600 MHz, Chloroform-d) δ 7.40-7.34 (m, 2H), 7.34-7.28 (m, 3H), 4.11-4.07 (m, 1H), 3.59 (bs, 2H), 3.47 (bs, 2H), 3.29 (dd, J=9.54, 18.34 Hz, 1H), 2.84 (dd, J=3.97, 18.32 Hz, 1H), 1.63 (bs, 6H); $^{13}$C NMR (151 MHz, Chloroform-d) δ 171.84, 170.09, 151.29, 137.59, 130.16, 129.03, 128.52, 47.26, 46.51, 44.22, 35.94, 26.34, 26.04, 24.75; HRMS (ESI) % calcd for [M+H]$^+$ C$_{16}$H$_{18}$N$_2$O$_4$: 303.1339. found 303.1349.

Example 61

2,5-Dioxoimidazolidin-1-yl piperidine-1-carboxylate

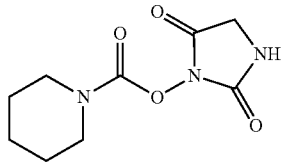 [SMILES: O=C(ON1C(=O)CNC1=O)N1CCCCC1]

The title compound was synthesized directly from 3-hydroxyimidazolidine-2,4-dione, itself prepared as described in Example 46, Steps 1, 2, 3 and 4, and piperidine according to the representative procedure of Example 41, Steps 3 and 4 to provide 2,5-dioxoimidazolidin-1-yl piperidine-1-carboxylate as a white solid (Note: Anhydrous DMF was used as the reaction solvent instead of CH$_2$Cl$_2$ in Step 5): $^1$H NMR (600 MHz, Chloroform-d) δ 6.30 (s, 1H), 4.07 (s, 2H), 3.58 (bs, 2H), 3.46 (bs, 2H), 1.64 (bs, 6H); $^{13}$C NMR (151 MHz, Chloroform-d) δ 166.00, 154.33, 151.81, 47.26, 46.42, 45.54, 26.30, 26.02, 24.70; HRMS (ESI) m/z calcd for [M+H]$^+$ C$_9$H$_{13}$N$_3$O$_4$: 228.0979. found 228.0990.

Example 62

2,5-Dioxopyrrolidin-1-yl 4-(2-fluoro-4-morpholinobenzyl)-piperazine-1-carboxylate

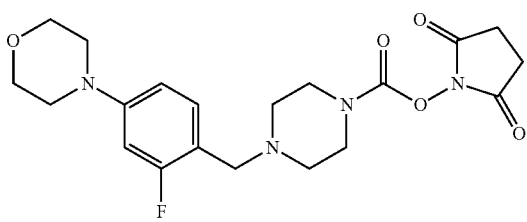 [SMILES: O=C(ON1C(=O)CCC1=O)N1CCN(Cc2ccc(N3CCOCC3)cc2F)CC1]

Step 1: Preparation of tert-butyl 4-(2-fluoro-4-morpholinobenzyl)piperazine-1-carboxylate

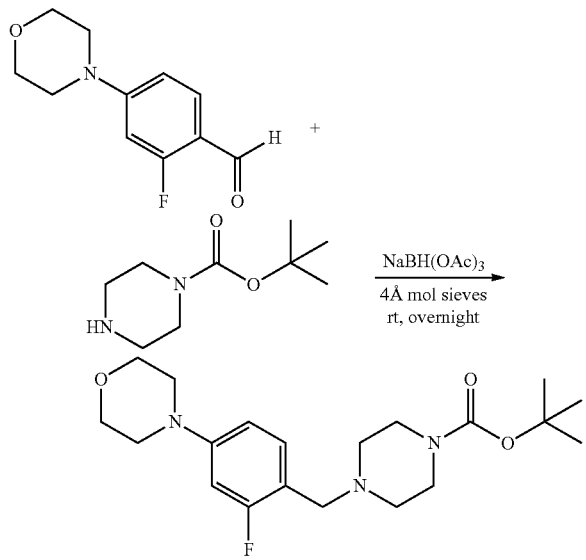

A 50-mL round-bottom flask, equipped with a magnetic stir bar, was charged with tert-butyl piperazine-1-carboxylate (445 mg, 2.39 mmol) under $N_2$. The solid was dissolved in 10 mL of anhydrous dichloromethane (DCM) and stirred at room temperature (rt). 2-Fluoro-4-morpholinobenzaldehyde (500 mg, 2.39 mmol) was added followed by 4 Å molecular sieves (440 mg, 8-12 mesh beads). The reaction was allowed to continue to stir at rt for 1 h. At that point, NaBH(OAc)$_3$ (557 mg, 2.63 mmol, 1.10 equiv) was added. The reaction was monitored for disappearance of aldehyde by thin layer chromatography. After 15 h, the reaction was quenched with saturated NaHCO$_3$ (15 mL). After the addition of DCM (15 mL), the mixture was partitioned into two phases. The aqueous phase was extracted twice with DCM (15 mL). The combined organic layers were dried over anhydrous Na$_2$SO$_4$, filtered, and concentrated. The crude mixture was applied to a chromatography column containing 24 g silica and DCM. A gradient solvent was used from 100% DCM to 10% MeOH in DCM to provide 833 mg (92%) of tert-butyl 4-(2-fluoro-4-morpholinobenzyl)piperazine-1-carboxylate as a pale yellow solid. $^1$H NMR (400 MHz, Chloroform-d) δ 7.22 (t, J=8.4 Hz, 1H), 6.66 (d, J=8.4 Hz, 1H), 6.57 (d, J=13.0 Hz, 1H), 3.90-3.85 (m, 4H), 3.53 (s, 2H), 3.43 (bs, 4H), 3.20-3.15 (m, 4H), 2.41 (bs, 4H), 1.46 (s, 9H).

Step 2: Preparation of 4-(3-fluoro-4-(piperazin-1-ylmethyl)phenyl)morpholine

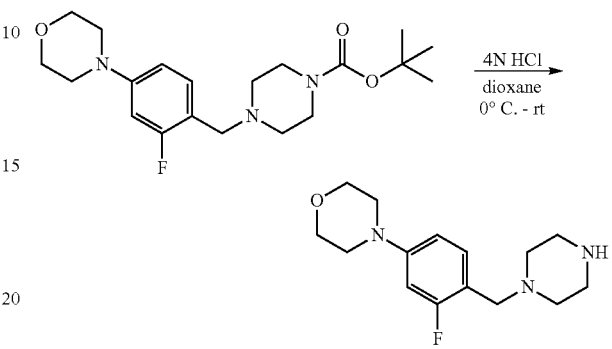

A 100-mL round-bottom flask, equipped with a magnetic stir bar, was charged with tert-butyl 4-(2-fluoro-4-morpholinobenzyl)piperazine-1-carboxylate (819 mg, 2.16 mmol) and DCM (14 mL). The resulting solution was cooled to 0° C. Hydrochloric acid (3.2 mL, 4 N in dioxane) was added via syringe. The ice bath was removed, and the resulting cloudy suspension was allowed to stir at rt overnight. After 20 h, the white suspension was transferred to a 250-mL Erlenmeyer flask and stirred with saturated aqueous Na$_2$CO$_3$ (30 mL), H$_2$O (20 mL), and DCM (30 mL) for 30 min. The layers were separated, and the aqueous layer was extracted twice with DCM (30 mL). The organic layers were washed with saturated aqueous NaHCO$_3$ (30 mL), combined, dried over anhydrous Na$_2$SO$_4$, and concentrated. The resulting yellow oil was chromatographed on a 24 g silica column with a gradient (100% DCM to 90% DCM/10% MeOH containing 2M NH$_3$) to provide 4-(3-fluoro-4-(piperazin-1-ylmethyl)phenyl)morpholine as a yellow oil (580 mg, 96%). $^1$H NMR (400 MHz, Chloroform-d) δ 7.22 (t, J=8.5 Hz, 1H), 6.65 (d, J=8.5 Hz, 1H), 6.56 (d, J=13 Hz, 1H) 3.90-3.80 (m, 4H), 3.49 (d, J=14.5 Hz, 2H), 3.20-3.10 (m, 4H), 2.92-2.88 (m, 4H), 2.44 (bs, 4H), 1.64 (s, 1H).

Step 3: Preparation of 2,5-dioxopyrrolidin-1-yl 4-(2-fluoro-4-morpholinobenzyl)-piperazine-1-carboxylate

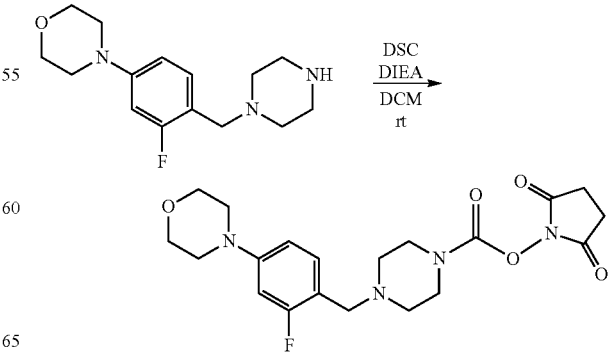

A 10-mL round-bottom flask, equipped with a magnetic stir bar, was charged with 4-(3-fluoro-4-(piperazin-1-ylmethyl)phenyl)morpholine (26 mg, 0.095 mmol) and DCM (1.5 mL) under nitrogen. The resulting suspension was cooled to 0° C., and N,N-diisopropylethylamine (DIEA, 33 uL, 2.0 equiv) was added via syringe, followed by N,N-disuccinimidyl carbonate (DSC, 36 mg, 0.14 mmol, 85% pure). The ice bath was removed, and the suspension was stirred at rt overnight. The solvent was removed by rotary evaporation, and the resulting oil was applied to a chromatography column containing 12 g silica and DCM. A gradient solvent was used from 100% DCM to 10% MeOH in DCM to provide 38 mg (96%) of 2,5-dioxopyrrolidin-1-yl 4-(2-fluoro-4-morpholinobenzyl)piperazine-1-carboxylate as an amorphous white powder. $^1$H NMR (400 MHz, Chloroform-d) δ 7.11 (t, J=8.5 Hz, 1H), 6.58 (dd, J=8.5, 2.4 Hz, 1H), 6.49 (dd, J=13.0, 2.4 Hz, 1H), 3.78 (t, J=4.8 Hz, 4H), 3.61-3.53 (m, 2H), 3.57-3.42 (m, 4H), 3.45 (s, 2H), 3.09 (t, J=4.8 Hz, 4H), 2.75 (s, 4H), 2.45 (s, 4H). LCMS (ESI, m/z): 443.1 [M+Na]$^+$.

Example 63

2,5-Dioxopyrrolidin-1-yl 4-(2-methyl-4-morpholinobenzyl)piperazine-1-carboxylate

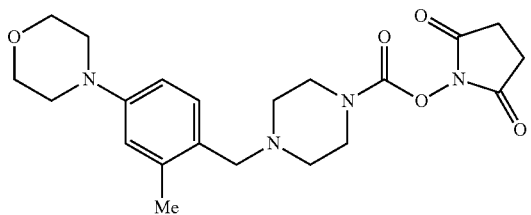 [SMILES: Cc1cc(N2CCOCC2)ccc1CN1CCN(C(=O)ON2C(=O)CCC2=O)CC1]

The title compound was synthesized directly from commercially available 2-methyl-4-morpholinobenzaldehyde according to the representative procedure of Example 35, Steps i, ii, and iii to provide 2,5-dioxopyrrolidin-1-yl 4-(2-methyl-4-morpholinobenzyl)-piperazine-1-carboxylate as a white solid. $^1$H NMR (400 MHz, Chloroform-d) δ 7.11 (d, J=8.3 Hz, 1H), 6.74 (d, J=2.4 Hz, 1H), 6.69 (dd, J=8.3, 2.5 Hz, 1H), 3.90-3.79 (m, 4H), 3.68-3.46 (m, 4H), 3.43 (s, 2H), 3.20-3.10 (m, 4H), 2.81 (s, 4H), 2.55-2.41 (m, 4H), 2.34 (s, 3H). LCMS (ESI, m/z): 417.1 [C$_{21}$H$_{28}$N$_4$O$_5$]$^+$.

Example 64

2,5-Dioxopyrrolidin-1-yl 4-(4-chlorobenzyl)piperazine-1-carboxylate

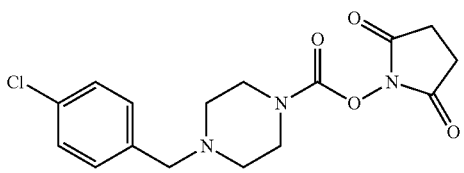 [SMILES: O=C(ON1C(=O)CCC1=O)N1CCN(Cc2ccc(Cl)cc2)CC1]

The title compound was synthesized directly from commercially available 4-chlorobenz-aldehyde according to the representative procedure of Example 35, Steps i, ii, and iii to provide 2,5-dioxopyrrolidin-1-yl 4-(4-chlorobenzyl)piperazine-1-carboxylate as a white solid. $^1$H NMR (400 MHz, Chloroform-d) δ 7.34-7.22 (m, 4H), 3.64 (s, 2H), 3.51 (s, 4H), 2.81 (s, 4H), 2.50 (s, 4H). LCMS (ESI, m/z): 352.1 [C$_{16}$H$_{18}$ClN$_3$O$_4$]$^+$.

Example 65

2,5-Dioxopyrrolidin-1-yl 4-(4-bromo-2-(piperidin-1-yl)benzyl)piperazine-1-carboxylate

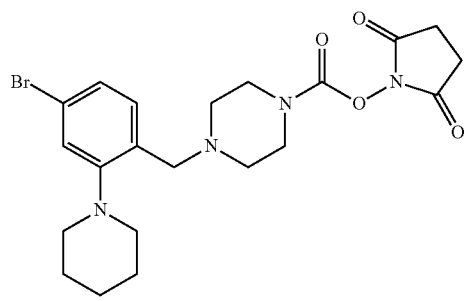

Step 1: Preparation of 4-bromo-2-(piperidin-1-yl)benzaldehyde

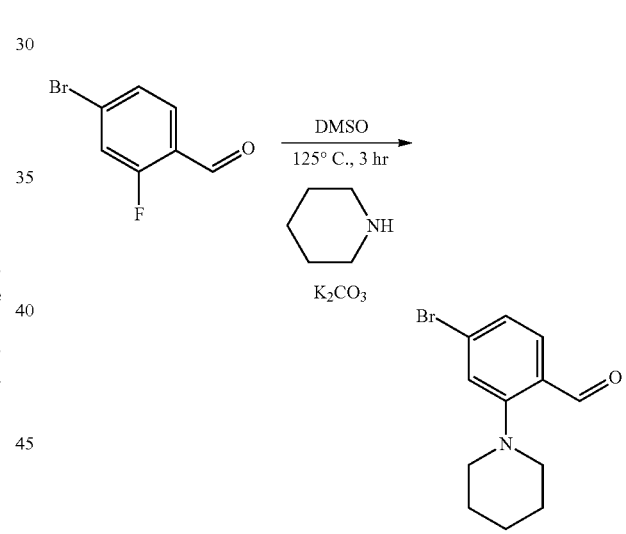

A 50-mL round-bottom flask, equipped with a magnetic stir bar, was charged with 4-bromo-2-fluorobenzaldehyde (200 mg, 0.939 mmol). The solid was dissolved in 10 mL DMSO. Piperidine (116 μL, 1.56 mmol) and K$_2$CO$_3$ (204 mg, 2.20 mmol) were added, and the reaction mixture was stirred vigorously and heated to 120° C. After 3 h, the reaction mixture was diluted with CH$_2$Cl$_2$ (100 mL) and washed with brine (3×). The organics were dried over anhydrous Na$_2$SO$_4$, filtered, and concentrated. The crude mixture was applied to a chromatography column containing 24 g silica. A gradient solvent was used from 100% hexanes to 20% EtOAC in hexanes to provide 4-bromo-2-(piperidin-1-yl)benzaldehyde (264 mg, 92%). $^1$H NMR (400 MHz, Chloroform-d) δ 10.24-10.18 (m, 1H), 7.66 (dd, J=8.3, 2.4 Hz, 1H), 7.31-7.17 (m, 2H), 3.11-3.03 (m, 4H), 1.84-1.72 (m, 4H), 1.71-1.60 (m, 2H). LCMS (ESI, m/z): 268.0 [C$_{12}$H$_{14}$BrNO]$^+$.

Step 2: Preparation of tert-butyl 4-(4-bromo-2-(piperidin-1-yl)benzyl)piperazine-1-carboxylate

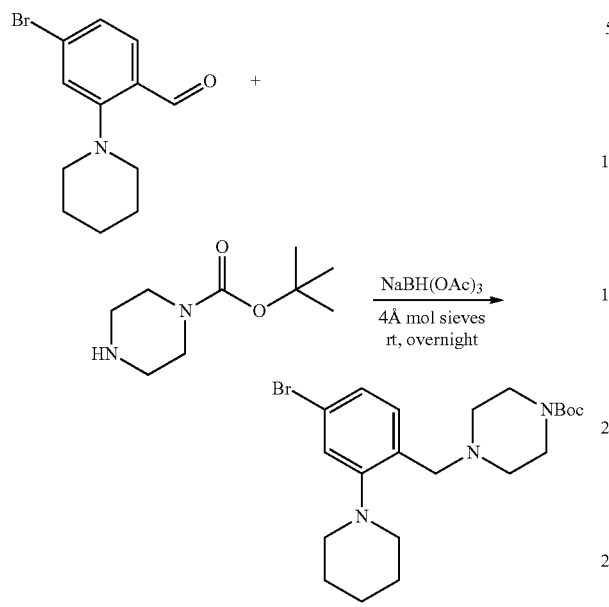

The title compound was synthesized directly from 4-bromo-2-(piperidin-1-yl)benzaldehyde according to the representative procedure of Example 62, Step 1 to provide tert-butyl 4-(4-bromo-2-(piperidin-1-yl)benzyl)piperazine-1-carboxylate as an orange foam. $^{1}$H NMR (400 MHz, Chloroform-d) δ 7.33 (d, J=8.7 Hz, 1H), 7.20-7.13 (m, 2H), 3.50 (s, 2H), 3.46-3.38 (m, 4H), 2.93-2.81 (m, 4H), 2.46-2.38 (m, 4H), 1.78-1.63 (m, 4H), 1.66-1.52 (m, 2H), 1.48 (s, 9H). LCMS (ESI, m/z): 438.1 $[C_{21}H_{32}BrN_3O_2]^{+}$.

Step 3: Preparation of 1-(4-bromo-2-(piperidin-1-yl)benzyl)piperazine

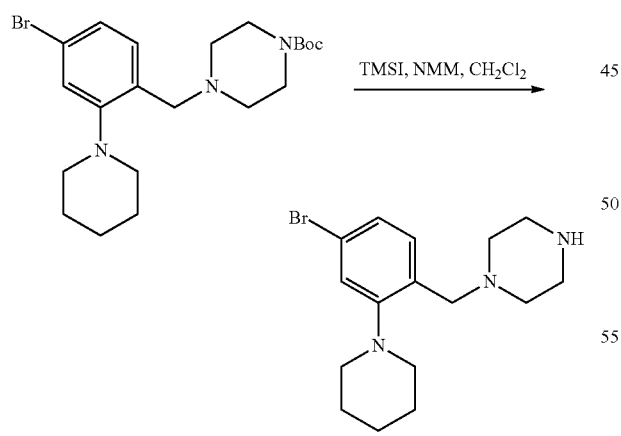

A 50-mL round-bottom flask, equipped with a magnetic stir bar, was charged with tert-butyl 4-(4-bromo-2-(piperidin-1-yl)benzyl)piperazine-1-carboxylate (300 mg, 0.685 mmol). The solid was dissolved in 10 mL of anhydrous dichloromethane (DCM), and N-methylmorpholine (207 mg, 2.01 mmol) was added. The reaction mixture was cooled to 0° C., and iodotrimethylsilane (164 mg, 0.822 mmol) was added dropwise over 1 min. After 15 min at 0° C., the reaction mixture was diluted in DCM (100 mL) and washed with saturated $Na_2CO_3$ (3×). The organics were dried over anhydrous $Na_2SO_4$, filtered and concentrated to provide 1-(4-bromo-2-(piperidin-1-yl)benzyl)piperazine, which was used without further purification. $^{1}$H NMR (400 MHz, Chloroform-d) δ 7.17 (dt, J=7.0, 3.1 Hz, 1H), 7.10-7.02 (m, 2H), 3.74-3.66 (m, 4H), 3.37-3.31 (m, 2H), 2.89-2.81 (m, 4H), 2.74-2.67 (m, 4H), 2.33-2.14 (m, 6H). LCMS (ESI, m/z): 338.1 $[C_{16}H_{24}BrN_3]^{+}$.

Step 4: Preparation of 2,5-dioxopyrrolidin-1-yl 4-(4-bromo-2-(piperidin-1-yl)benzyl)piperazine-1-carboxylate

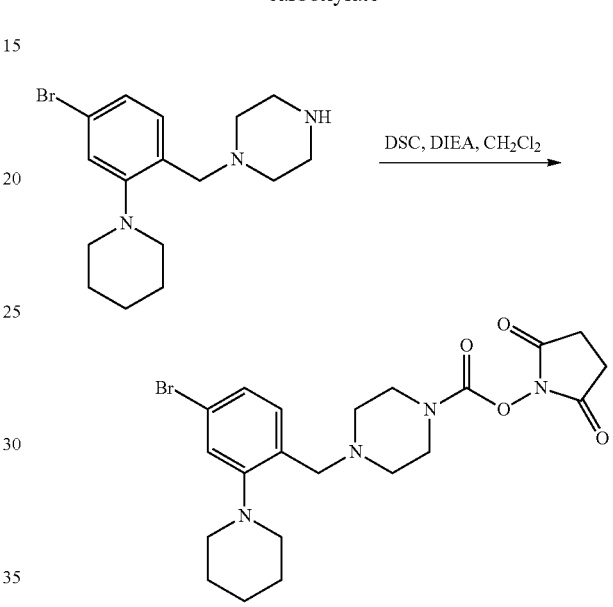

The title compound was synthesized directly from 1-(4-bromo-2-(piperidin-1-yl)benzyl)piperazine according to the representative procedure of Example 62, Step 3 to provide tert-butyl 4-(4-bromo-2-(piperidin-1-yl)benzyl)piperazine-1-carboxylate as a white solid. $^{1}$H NMR (400 MHz, Chloroform-d) δ 7.36-7.29 (m, 1H), 7.21-7.14 (m, 2H), 3.68-3.56 (m, 2H), 3.56-3.48 (m, 4H), 2.88-2.75 (m, 8H), 2.53 (t, J=5.1 Hz, 4H), 1.76-1.65 (m, 4H), 1.63-1.52 (m, 2H). LCMS (ESI, m/z): 479.1 $[C_{21}H_{22}BrN_4O_4]^{+}$.

Example 66

2,5-Dioxopyrrolidin-1-yl 4-(4-bromo-2-morpholinobenzyl)piperazine-1-carboxylate

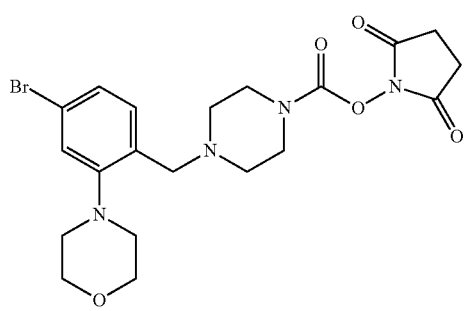

The title compound was synthesized directly from commercially available 4-chloro-2-fluorobenzaldehyde and morpholine according to the representative procedure of Example 65, Steps 1, 2, 3 and 4 to provide 2,5-dioxopyrrolidin-1-yl 4-(4-bromo-2-morpholinobenzyl)piperazine-1-carboxylate as a white solid. $^1$H NMR (400 MHz, Chloroform-d) δ 7.31 (d, J=8.4 Hz, 1H), 7.24-7.17 (m, 2H), 3.89-3.78 (m, 4H), 3.62 (d, J=12.3 Hz, 4H), 3.52 (s, 2H), 2.94-2.85 (m, 4H), 2.81 (s, 4H), 2.59 (s, 4H). LCMS (ESI, m/z): 481.1 $[C_{20}H_{25}BrN_4O_5]^+$.

Example 67

2,5-Dioxopyrrolidin-1-yl 4-(2-methoxy-4-morpholinobenzyl)piperazine-1-carboxylate

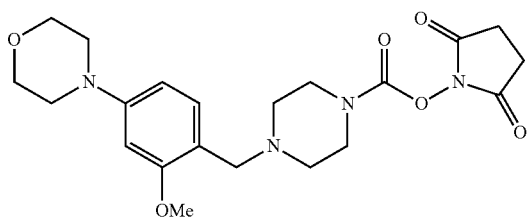 [SMILES: COc1cc(N2CCOCC2)ccc1CN1CCN(C(=O)ON2C(=O)CCC2=O)CC1]

The title compound was synthesized directly from commercially available 2-methoxy-4-morpholinobenzaldehyde and tert-butyl piperazine-1-carboxylate according to the representative procedure of Example 62, Steps 1, 2 and 3 to provide 2,5-dioxopyrrolidin-1-yl 4-(2-methoxy-4-morpholinobenzyl)piperazine-1-carboxylate as a white solid: $^1$H NMR (400 MHz, Chloroform-d) δ 7.15 (d, J=8.3 Hz, 1H), 6.51-6.39 (m, 2H), 3.89-3.83 (m, 4H), 3.81 (s, 3H), 3.74-3.69 (m, 2H), 3.66 (s, 2H), 3.63-3.57 (m, 2H), 3.21-3.13 (m, 4H), 2.81 (s, 4H), 2.70-2.61 (m, 4H). LCMS (ESI, m/z): 206.1 $[C_{12}H_{16}NO_2]^+$.

Example 68

2,5-Dioxopyrrolidin-1-yl 4-(2-methyl-4-(pyrrolidin-1-yl)benzyl)piperazine-1-carboxylate

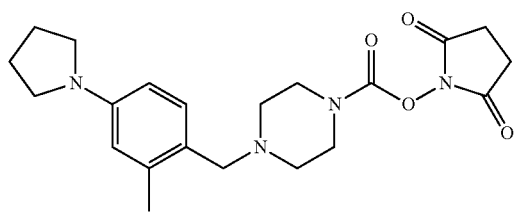 [SMILES: Cc1cc(N2CCCC2)ccc1CN1CCN(C(=O)ON2C(=O)CCC2=O)CC1]

The title compound was synthesized directly from commercially available 2-methyl-4-(pyrrolidin-1-yl)benzaldehyde and tert-butyl piperazine-1-carboxylate according to the representative procedure of Example 62, Steps 1, 2 and 3 to provide 2,5-dioxopyrrolidin-1-yl 4-(2-methyl-4-(pyrrolidin-1-yl)benzyl)piperazine-1-carboxylate as a white solid: $^1$H NMR (400 MHz, Chloroform-d) δ 7.02 (d, J=8.2 Hz, 1H), 6.44-6.27 (m, 2H), 3.63-3.56 (m, 2H), 3.52-3.46 (m, 2H), 3.40 (s, 2H), 3.31-3.24 (m, 4H), 2.81 (s, 4H), 2.53-2.43 (m, 4H), 2.33 (s, 3H), 2.03-1.92 (m, 4H). LCMS (ESI, m/z): 423.2 [M+Na]$^+$.

Example 69

2,5-Dioxopyrrolidin-1-yl 4-(4-chloro-2-morpholinobenzyl)piperazine-1-carboxylate

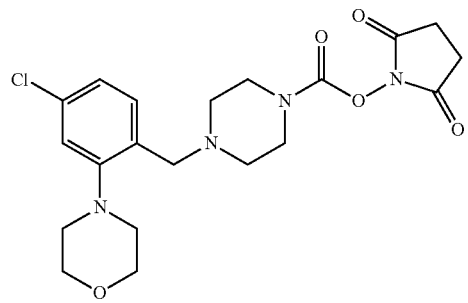 [SMILES: O=C(ON1C(=O)CCC1=O)N1CCN(Cc2ccc(Cl)cc2N2CCOCC2)CC1]

The title compound was synthesized directly from commercially available 4-chloro-2-fluorobenzaldehyde and morpholine according to the representative procedure of Example 65, Steps 1, 2, 3 and 4 to provide 2,5-dioxopyrrolidin-1-yl 4-(4-chloro-2-morpholinobenzyl)piperazine-1-carboxylate as a white solid. $^1$H NMR (400 MHz, Chloroform-d) δ 7.40 (d, J=8.0 Hz, 1H), 7.13-7.05 (m, 2H), 3.90-3.82 (m, 4H), 3.64 (d, J=5.8 Hz, 2H), 3.60-3.48 (m, 4H), 2.96 (t, J=4.5 Hz, 4H), 2.85 (s, 4H), 2.55 (t, J=5.0 Hz, 4H). LCMS (ESI, m/z): 437.1 $[C_{20}H_{25}ClN_4O_5]^+$.

Example 70

2,5-Dioxopyrrolidin-1-yl 4-(4-methoxybenzyl)piperazine-1-carboxylate

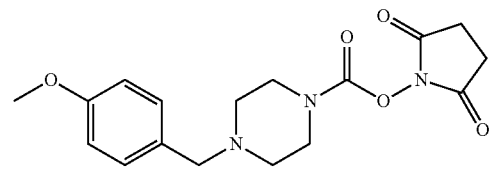 [SMILES: COc1ccc(CN2CCN(C(=O)ON3C(=O)CCC3=O)CC2)cc1]

The title compound was synthesized directly from commercially available 4 and tert-butyl piperazine-1-carboxylate according to the representative procedure of Example 62, Steps 1, 2 and 3 to provide 2,5-dioxopyrrolidin-1-yl 4-(4-methoxybenzyl)piperazine-1-carboxylate as a white solid: $^1$H NMR (400 MHz, Chloroform-d) δ 7.22 (d, J=8.6 Hz, 2H), 6.89-6.82 (m, 2H), 3.80 (s, 3H), 3.67-3.61 (m, 2H), 3.55-3.46 (m, 4H), 2.82 (s, 4H), 2.55-2.42 (m, 4H). LCMS (ESI, m/z): 348.1 [M+H]$^+$.

Example 71

2,5-Dioxopyrrolidin-1-yl 4-(4-methylbenzyl)piperazine-1-carboxylate

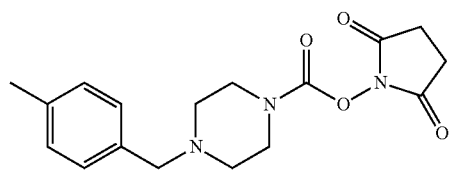 [SMILES: Cc1ccc(CN2CCN(C(=O)ON3C(=O)CCC3=O)CC2)cc1]

The title compound was synthesized directly from commercially available 4 and tert-butyl piperazine-1-carboxylate according to the representative procedure of Example 62, Steps 1, 2 and 3 to provide 2,5-dioxopyrrolidin-1-yl 4-(4-methylbenzyl)piperazine-1-carboxylate as a white solid: $^1$H NMR (400 MHz, Chloroform-d) δ 7.22-7.18 (m, 2H), 7.15-7.12 (m, 2H), 3.67-3.61 (m, 2H), 3.55-3.48 (m, 4H), 2.82 (s, 4H), 2.56-2.43 (m, 4H), 2.34 (s, 3H). LCMS (ESI, m/z): 332.1 [M+H]+.

Example 72

2,5-Dioxopyrrolidin-1-yl 4-(4-bromo-2-(pyrrolidin-1-yl)benzyl)piperazine-1-carboxylate

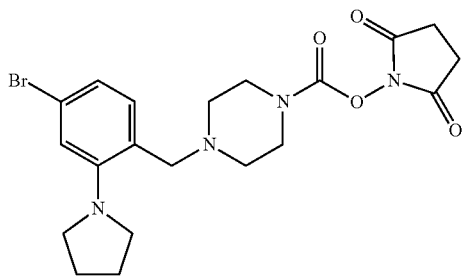

The title compound was synthesized directly from commercially available 4-bromo-2-fluorobenzaldehyde and pyrrolidine according to the representative procedure of Example 65, Steps 1, 2, 3 and 4 to provide 2,5-dioxopyrrolidin-1-yl 4-(4-bromo-2-(pyrrolidin-1-yl)benzyl)piperazine-1-carboxylate as a white solid. $^1$H NMR (400 MHz, Chloroform-d) δ 7.30-7.20 (m, 1H), 7.03-6.93 (m, 2H), 3.64 (s, 2H), 3.50 (s, 4H), 3.25-3.16 (m, 4H), 2.82 (s, 4H), 2.50 (s, 4H), 1.99-1.87 (m, 4H). LCMS (ESI, m/z): 465.1 [$C_{20}H_{25}BrN_4O_4$]+.

Example 73

2,5-Dioxopyrrolidin-1-yl 4-(2-morpholinobenzyl)piperazine-1-carboxylate

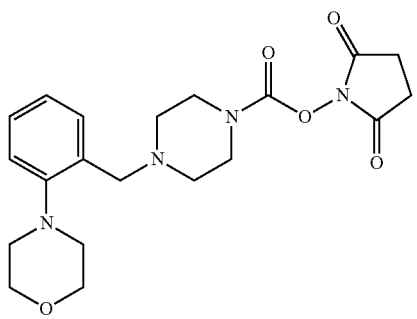 [SMILES: O=C(ON1C(=O)CCC1=O)N1CCN(Cc2ccccc2N2CCOCC2)CC1]

The title compound was synthesized directly from commercially available 2-morpholinobenzaldehyde and tert-butyl piperazine-1-carboxylate according to the representative procedure of Example 62, Steps 1, 2 and 3 to provide 2,5-dioxopyrrolidin-1-yl 4-(2-morpholinobenzyl)piperazine-1-carboxylate as a white solid: $^1$H NMR (400 MHz, Chloroform-d) δ 7.44-7.40 (m, 1H), 7.30-7.25 (m, 2H), 7.14-7.07 (m, 2H), 3.87-3.81 (m, 4H), 3.65-3.59 (m, 4H), 3.54-3.47 (m, 2H), 3.02-2.90 (m, 4H), 2.83 (s, 4H), 2.59-2.52 (m, 4H). LCMS (ESI, m/z): 403.2 [M+H]+.

Example 74

2,5-Dioxopyrrolidin-1-yl 4-(4-chloro-2-(pyrrolidin-1-yl)benzyl)piperazine-1-carboxylate

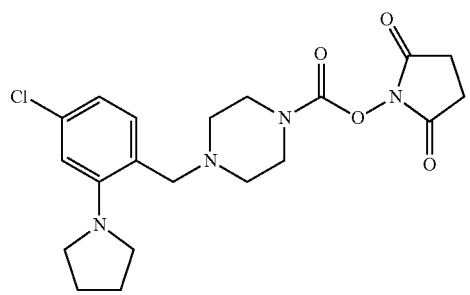 [SMILES: O=C(ON1C(=O)CCC1=O)N1CCN(Cc2ccc(Cl)cc2N2CCCC2)CC1]

The title compound was synthesized directly from commercially available 4-chloro-2-fluorobenzaldehyde and pyrrolidine according to the representative procedure of Example 65, Steps 1, 2, 3 and 4 to provide 2,5-dioxopyrrolidin-1-yl 4-(4-chloro-2-(pyrrolidin-1-yl)benzyl)piperazine-1-carboxylate as a white solid. $^1$H NMR (400 MHz, Chloroform-d) δ 7.28 (d, J=8.0 Hz, 1H), 6.85-6.76 (m, 2H), 3.66-3.59 (m, 2H), 3.50 (s, 4H), 3.24-3.16 (m, 4H), 2.80 (s, 4H), 2.48 (t, J=5.1 Hz, 4H), 1.98-1.88 (m, 4H). LCMS (ESI, m/z): 420.1 [$C_{20}H_{25}ClN_4O_4$]+.

Example 75

2,5-Dioxopyrrolidin-1-yl 4-(3-fluoro-4-(pyrrolidin-1-yl)benzyl)piperazine-1-carboxylate

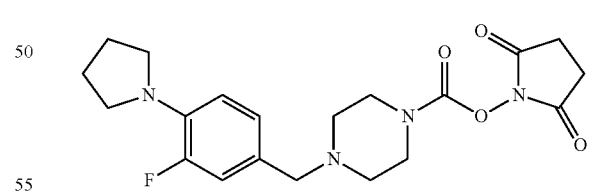

The title compound was synthesized directly from commercially available 3-fluoro-4-(pyrrolidin-1-yl)benzaldehyde and tert-butyl piperazine-1-carboxylate according to the representative procedure of Example 62, Steps 1, 2 and 3 to provide 2,5-dioxopyrrolidin-1-yl 4-(3-fluoro-4-(pyrrolidin-1-yl)benzyl)piperazine-1-carboxylate as a white solid: $^1$H NMR (400 MHz, Chloroform-d) δ 7.04-6.84 (m, 2H), 6.60 (t, J=8.7 Hz, 1H), 3.67-3.60 (m, 2H), 3.56-3.49 (s, 2H), 3.47-3.30 (m, 6H), 2.82 (s, 4H), 2.51-2.44 (m, 4H), 2.05-1.84 (m, 4H). LCMS (ESI, m/z): 405.2 [M+H]+.

Example 76

2,5-Dioxopyrrolidin-1-yl 4-{[4-(morpholin-4-yl)-2-(trifluoromethyl)phenyl]methyl}piperazine-1-carboxylate

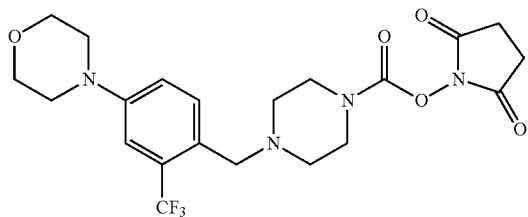 [SMILES: O=C(ON1C(=O)CCC1=O)N1CCN(Cc2ccc(N3CCOCC3)cc2C(F)(F)F)CC1]

Step 1: Preparation of 4-(morpholin-4-yl)-2-(trifluoromethyl)benzaldehyde

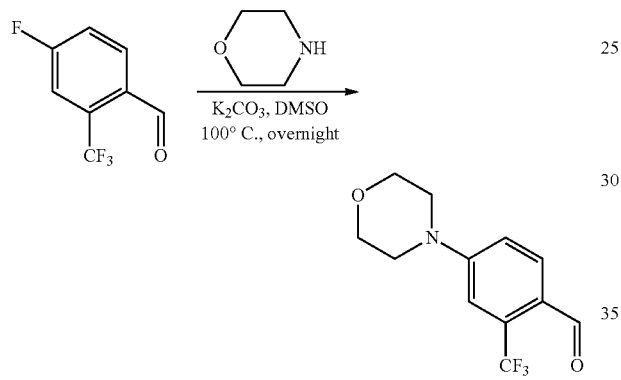

A 100-mL round-bottom flask was charged with 4-fluoro-2-(trifluoromethyl)benzaldehyde (1.00 g, 5.21 mmol, 1.00 equiv), morpholine (0.500 g, 5.74 mmol, 1.10 equiv), potassium carbonate (1.40 g, 10.1 mmol, 2.00 equiv), and DMSO (15 mL). The resulting solution was stirred overnight at 100° C., diluted with H$_2$O (10 mL), and extracted with ethyl acetate (3×10 mL). The organic layers were combined and washed with brine (1×50 mL), dried over anhydrous sodium sulfate, and concentrated under reduced pressure. The residue was chromatographed on a silica gel column with ethyl acetate/petroleum ether (25/75) to provide 1.00 g (74% yield) of 4-(morpholin-4-yl)-2-(trifluoromethyl)benzaldehyde as a yellow solid. LCMS (ESI, m/z): 260 [M+H]$^+$.

Step 2: Preparation of tert-butyl 4-[[4-(morpholin-4-yl)-2(trifluoromethyl)phenyl]methyl]piperazine-1-carboxylate

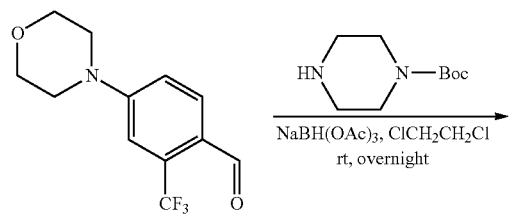

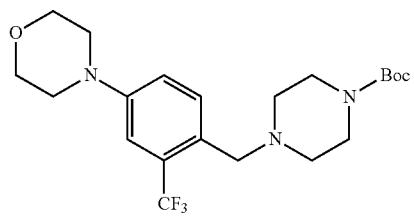

A 100-mL round-bottom flask was charged with 4-(morpholin-4-yl)-2-(trifluoromethyl)benzaldehyde (1.00 g, 3.86 mmol, 1.00 equiv), tert-butyl piperazine-1-carboxylate (0.720 g, 3.86 mmol, 1.00 equiv), and 1,2-dichloroethane (15 mL). The mixture was stirred for 30 min at room temperature. Sodium triacetoxyborohydride (2.40 g, 11.3 mmol, 3.00 equiv) was added. The resulting solution was stirred overnight at room temperature, diluted with H$_2$O (10 mL), and extracted with dichloromethane (3×10 mL). The organic layers were combined and washed with brine (50 mL), dried over anhydrous sodium sulfate, and concentrated under reduced pressure. The residue was chromatographed on a silica gel column with ethyl acetate/petroleum ether (25/75) to provide 1.60 g (97% yield) of tert-butyl 4-[[4-(morpholin-4-yl)-2(trifluoromethyl)phenyl]methyl]piperazine-1-carboxylate as a yellow oil. LCMS (ESI, m/z): 430 [M+H]$^+$.

Step 3: Preparation of 4-[4-(piperazin-1-ylmethyl)-3-(trifluoromethyl)phenyl]morpholine

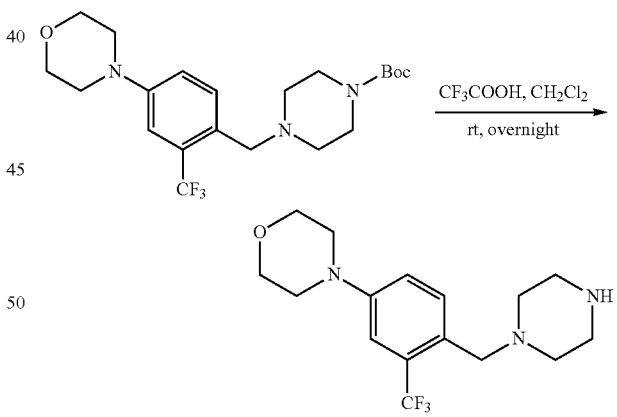

A 100-mL round-bottom flask was charged with tert-butyl 4-[[4-(morpholin-4-yl)-2-(trifluoromethyl)phenyl]methyl]piperazine-1-carboxylate (1.60 g, 3.73 mmol, 1.00 equiv) and dichloromethane (10 mL). Trifluoroacetic acid (3.10 g, 27.2 mmol, 7.30 equiv) was added at 0° C. The resulting solution was stirred overnight at room temperature and concentrated under reduced pressure to yield 1.00 g (81% yield) of 4-[4-(piperazin-1-ylmethyl)-3-(trifluoromethyl)phenyl]morpholine as a yellow oil. LCMS (ESI, m/z): 330 [M+H]$^+$.

Step 4: Preparation of 2,5-dioxopyrrolidin-1-yl 4-{[4-(morpholin-4-yl)-2-(trifluoromethyl)phenyl]methyl}piperazine-1-carboxylate

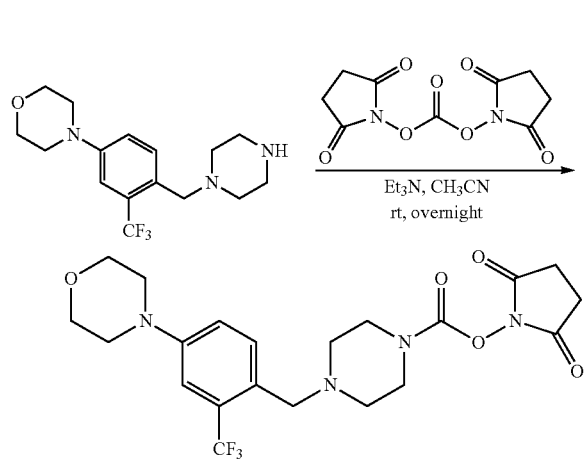

A 100-mL round-bottom flask was charged with 4-[4-(piperazin-1-ylmethyl)-3-(trifluoromethyl)phenyl]morpholine (210 mg, 0.640 mmol, 1.00 equiv), bis(2,5-dioxopyrrolidin-1-yl) carbonate (327 mg, 1.28 mmol, 2.00 equiv), triethylamine (645 mg, 6.40 mmol, 10.00 equiv), and CH₃CN (15 mL). The resulting solution was stirred overnight at room temperature and concentrated under reduced pressure. The crude product (500 mg) was purified by preparative HPLC using the following gradient conditions: 20% CH₃CN/80% Phase A increasing to 70% CH₃CN over 10 min, then to 100% CH₃CN over 0.1 min, holding at 100% CH₃CN for 1.9 min, then reducing to 20% CH₃CN over 0.1 min, and holding at 20% for 1.9 min, on a Waters 2767-5 Chromatograph. Column: Xbridge Prep C18, 19*150 mm, 5um; Mobile phase: Phase A: H₂O; Phase B: CH₃CN; Detector, UV 220 & 254 nm. Purification resulted in 286 mg (95% yield) of 2,5-dioxopyrrolidin-1-yl 4-{[4-(morpholin-4-yl)-2-(trifluoromethyl)phenyl]methyl}piperazine-1-carboxylate as a yellow semi-solid. $^1$H NMR (400 MHz, Chloroform-d) δ 7.59 (d, J=8.4 Hz, 1H), 7.15 (s, 1H), 7.05 (d, J=8.8 Hz, 1H), 3.89 (t, J=4.8 Hz, 4H), 3.54-3.66 (m, 6H), 3.21 (t, J=4.6 Hz, 4H), 2.84 (s, 4H), 2.53 (s, 4H). LCMS (ESI, m/z): 471 [M+H]$^+$.

Example 77

2,5-Dioxopyrrolidin-1-yl (2S)-2-methyl-4-{[4-(morpholin-4-yl)-2-(trifluoromethyl)phenyl]methyl}piperazine-1-carboxylate

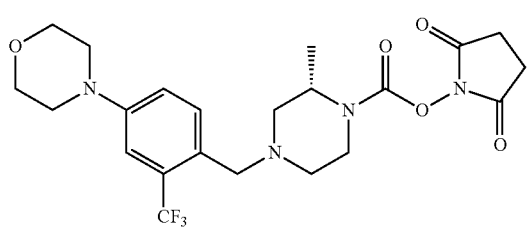 [SMILES: C[C@H]1CN(Cc2ccc(N3CCOCC3)cc2C(F)(F)F)CCN1C(=O)ON1C(=O)CCC1=O]

Step 1: Preparation of tert-butyl (2S)-2-methyl-4-[[4-(morpholin-4-yl)-2-(trifluoromethyl)phenyl]methyl]piperazine-1-carboxylate

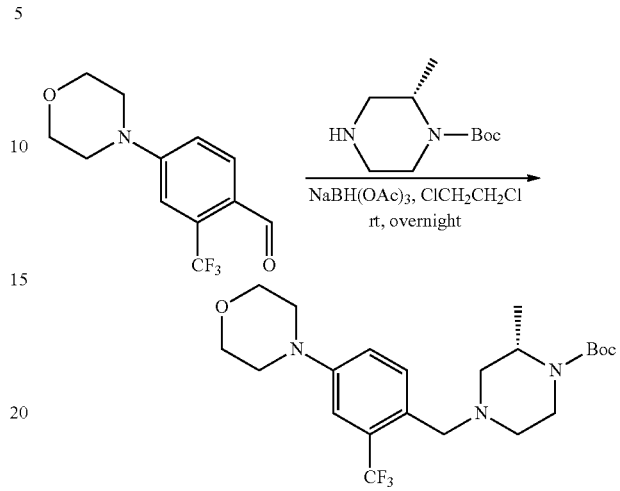

A 100-mL round-bottom flask was charged with 4-(morpholin-4-yl)-2-(trifluoromethyl)benzaldehyde (1.00 g, 3.86 mmol, 1.00 equiv), tert-butyl (2S)-2-methylpiperazine-1-carboxylate (0.850 g, 4.24 mmol, 1.10 equiv), and 1,2-dichloroethane (20 mL). The mixture was stirred for 30 min at room temperature. Sodium triacetoxyborohydride (2.40 g, 11.3 mmol, 3.00 equiv) was added. The resulting solution was stirred overnight at room temperature, diluted with H₂O (20 mL), and extracted with dichloromethane (3×15 mL). The organic layers were combined and washed with brine (50 mL), dried over anhydrous sodium sulfate, and concentrated under reduced pressure. The residue was chromatographed on a silica gel column with ethyl acetate/petroleum ether (20/80) to provide 1.70 g (99% yield) of tert-butyl (2S)-2-methyl-4-[[4-(morpholin-4-yl)-2-(trifluoromethyl)phenyl]methyl]piperazine-1-carboxylate as a yellow oil. LCMS (ESI, m/z): 444 [M+H]$^+$.

Step 2: Preparation of 4-(4-[[(3S)-3-methylpiperazin-1-yl]methyl]-3-(trifluoromethyl)phenyl)morpholine

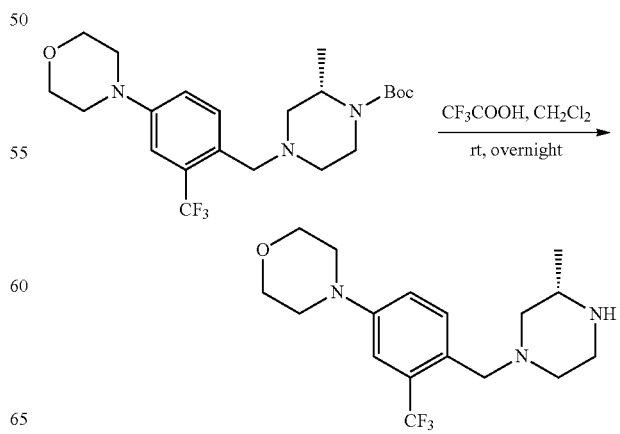

A 100-mL round-bottom flask was charged with tert-butyl (2S)-2-methyl-4-[[4-(morpholin-4-yl)-2-(trifluoromethyl)phenyl]methyl]piperazine-1-carboxylate (1.70 g, 3.83 mmol, 1.00 equiv) and dichloromethane (15 mL). Trifluoroacetic acid (3.80 g, 33.3 mmol, 8.70 equiv) was added at 0° C. The resulting solution was stirred overnight at room temperature and concentrated under reduced pressure to yield 1.00 g (crude) of 4-(4-[[(3S)-3-methylpiperazin-1-yl]methyl]-3-(trifluoromethyl)phenyl)morpholine as a brown oil. LCMS (ESI, m/z): 344 [M+H]+.

Step 3: Preparation of 2,5-dioxopyrrolidin-1-yl (2S)-2-methyl-4-{[4-(morpholin-4-yl)-2-(trifluoromethyl)phenyl]methyl}piperazine-1-carboxylate

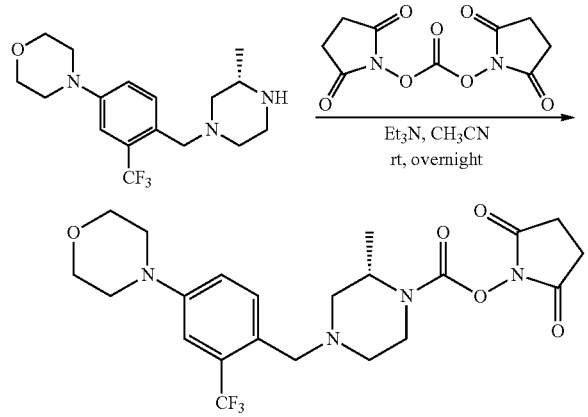

A 100-mL round-bottom flask was charged with 4-(4-[[(3S)-3-methylpiperazin-1-yl]methyl]-3-(trifluoromethyl)phenyl)morpholine (210 mg, 0.610 mmol, 1.00 equiv), bis(2,5-dioxopyrrolidin-1-yl) carbonate (298 mg, 1.16 mmol, 2.00 equiv), triethylamine (589 mg, 5.91 mmol, 10.00 equiv), and CH₃CN (15 mL). The resulting solution was stirred overnight at room temperature and concentrated under reduced pressure. The crude product (500 mg) was purified by preparative HPLC using the following gradient conditions: 20% CH₃CN/80% Phase A increasing to 70% CH₃CN over 10 min, then to 100% CH₃CN over 0.1 min, holding at 100% CH₃CN for 1.9 min, then reducing to 20% CH₃CN over 0.1 min, and holding at 20% for 1.9 min, on a Waters 2767-5 Chromatograph. Column: Xbridge Prep C18, 19*150 mm, 5um; Mobile phase: Phase A: H₂O; Phase B: CH₃CN; Detector, UV 220 & 254 nm. Purification resulted in 285 mg (96% yield) of 2,5-dioxopyrrolidin-1-yl (2S)-2-methyl-4-{[4-(morpholin-4-yl)-2-(trifluoromethyl)phenyl]methyl}piperazine-1-carboxylate as a light yellow oil. $^1$H NMR (400 MHz, Chloroform-d) δ 7.57 (d, J=8.8 Hz, 1H), 7.13 (s, 1H), 7.01-7.04 (m, 1H), 4.26 (br, 1H), 3.85 (t, J=4.8 Hz, 5H), 3.54 (s, 2H), 3.32-3.34 (m, 1H), 3.16-3.22 (m, 4H), 2.75-2.79 (m, 5H), 2.61 (d, J=11.6 Hz, 1H), 2.34 (t, J=5.8 Hz, 1H), 2.18 (t, J=10.8 Hz, 1H), 1.38 (s, 3H). LCMS (ESI, m/z): 485 [M+H]+.

Example 78

2,5-Dioxopyrrolidin-1-yl 4-(2-chloro-4-(pyrrolidin-1-yl)benzyl)piperazine-1-carboxylate

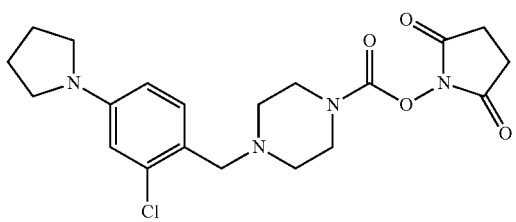 [SMILES: O=C(ON1C(=O)CCC1=O)N1CCN(Cc2ccc(N3CCCC3)cc2Cl)CC1]

The title compound was synthesized directly from commercially available 2-chloro-4-(pyrrolidin-1-yl)benzaldehyde and tert-butyl piperazine-1-carboxylate according to the representative procedure of Example 62, Steps 1, 2 and 3 to provide 2,5-dioxopyrrolidin-1-yl 4-(2-chloro-4-(pyrrolidin-1-yl)benzyl)piperazine-1-carboxylate as a white solid: $^1$H NMR (400 MHz, Chloroform-d) δ 7.20 (d, J=8.4 Hz, 1H), 6.56 (d, J=2.5 Hz, 1H), 6.44 (dd, J=8.5, 2.5 Hz, 1H), 3.68-3.61 (m, 2H), 3.58 (s, 2H), 3.56-3.50 (m, 2H), 3.35-3.24 (m, 4H), 2.84 (s, 4H), 2.60-2.52 (m, 4H), 2.09-1.96 (m, 4H). LCMS (ESI, m/z): 443.1 [M+Na]+.

Example 79

2,5-Dioxopyrrolidin-1-yl (2R)-4-{[2-fluoro-4-(morpholin-4-yl)phenyl]methyl}-2-methylpiperazine-1-carboxylate

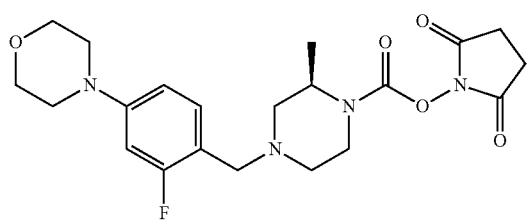 [SMILES: C[C@@H]1CN(Cc2ccc(N3CCOCC3)cc2F)CCN1C(=O)ON1C(=O)CCC1=O]

Step 1: Preparation of tert-butyl (2R)-4-[[2-fluoro-4-(morpholin-4-yl)phenyl]methyl]-2-methylpiperazine-1-carboxylate

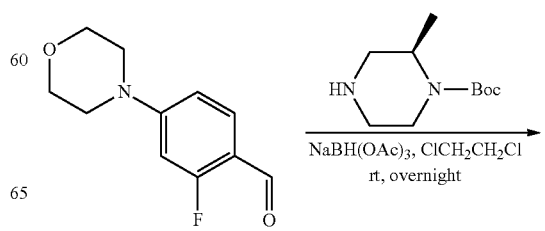

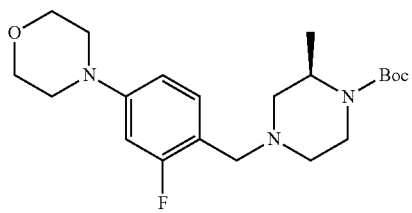

A 100-mL round-bottom flask was charged with 2-fluoro-4-(morpholin-4-yl)benzaldehyde (0.800 g, 3.82 mmol, 1.00 equiv), tert-butyl (2R)-2-methylpiperazine-1-carboxylate (0.840 g, 4.20 mmol, 1.10 equiv), and 1,2-dichloroethane (20 mL). The mixture was stirred for 30 min at room temperature. Sodium triacetoxyborohydride (2.40 g, 11.3 mmol, 3.00 equiv) was added. The resulting solution was stirred overnight at room temperature, diluted with H₂O (10 mL), and extracted with dichloromethane (3×10 mL). The organic layers were combined and washed with brine (50 mL), dried over anhydrous sodium sulfate, and concentrated under reduced pressure. The residue was chromatographed on a silica gel column with ethyl acetate/petroleum ether (20/80) to provide 1.40 g (93% yield) of tert-butyl (2R)-4-[[2-fluoro-4-(morpholin-4-yl)phenyl]methyl]-2-methylpiperazine-1-carboxylate as a white solid. LCMS (ESI, m/z): 394 [M+H]⁺.

Step 2: Preparation of 4-(3-fluoro-4-[[(3R)-3-methylpiperazin-1-yl]methyl]phenyl)morpholine

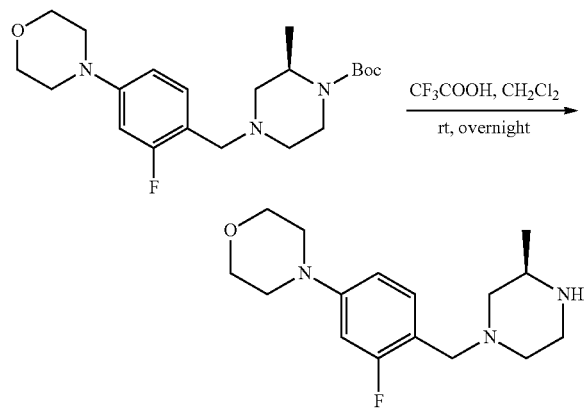

A 100-mL round-bottom flask was charged with tert-butyl (2R)-4-[[2-fluoro-4-(morpholin-4-yl)phenyl]methyl]-2-methylpiperazine-1-carboxylate (1.40 g, 3.56 mmol, 1.00 equiv), and dichloromethane (15 mL). Trifluoroacetic acid (3.80 g, 33.3 mmol, 9.40 equiv) was added at 0° C. The resulting solution was stirred overnight at room temperature and concentrated under reduced pressure to yield 0.90 g (86% yield) of 4-(3-fluoro-4-[[(3R)-3-methylpiperazin-1-yl]methyl]phenyl)morpholine as a yellow oil. LCMS (ESI, m/z): 294 [M+H]⁺.

Step 3: Preparation of 2,5-dioxopyrrolidin-1-yl (2R)-4-{[2-fluoro-4-(morpholin-4-yl)phenyl]methyl}-2-methylpiperazine-1-carboxylate

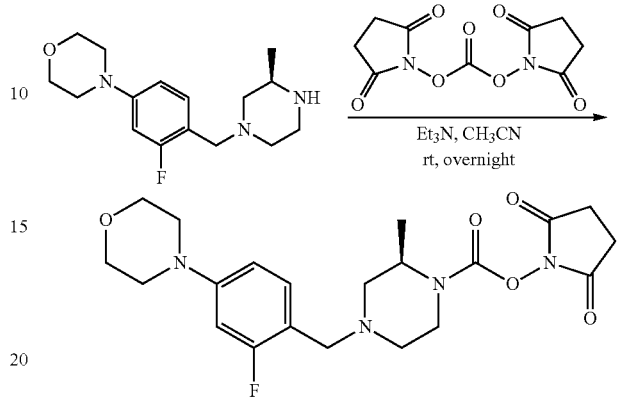

A 100-mL round-bottom flask was charged with 4-(3-fluoro-4-[[(3R)-3-methylpiperazin-1-yl]methyl]phenyl)morpholine (200 mg, 0.680 mmol, 1.00 equiv), bis(2,5-dioxopyrrolidin-1-yl) carbonate (262 mg, 1.02 mmol, 1.50 equiv), triethylamine (345 mg, 3.41 mmol, 5.00 equiv), and CH₃CN (15 mL). The resulting solution was stirred overnight at room temperature and concentrated under reduced pressure. The crude product (500 mg) was purified by preparative HPLC using the following gradient conditions: 20% CH₃CN/80% Phase A increasing to 70% CH₃CN over 10 min, then to 100% CH₃CN over 0.1 min, holding at 100% CH₃CN for 1.9 min, then reducing to 20% CH₃CN over 0.1 min, and holding at 20% for 1.9 min, on a Waters 2767-5 Chromatograph. Column: Xbridge Prep C18, 19*150 mm, 5um; Mobile phase: Phase A: H₂O; Phase B: CH₃CN; Detector, UV 220 & 254 nm. Purification resulted in 191 mg (65% yield) of 2,5-dioxopyrrolidin-1-yl (2R)-4-{[2-fluoro-4-(morpholin-4-yl)phenyl]methyl}-2-methylpiperazine-1-carboxylate as a brown oil. ¹H NMR (300 MHz, Chloroform-d) δ 7.23 (t, J=8.6 Hz, 1H), 6.63-6.67 (m, 1H), 6.53-6.58 (m, 1H), 4.27 (br, 1H), 3.84 (t, J=4.8 Hz, 5H), 3.51 (s, 2H), 3.29-3.38 (m, 1H), 3.11-3.17 (m, 4H), 2.79-2.84 (m, 5H), 2.65 (d, J=11.4 Hz, 1H), 2.29-2.35 (m, 1H), 2.14-2.22 (m, 1H), 1.37 (d, J=6.3 Hz, 3H). LCMS (ESI, m/z): 435 [M+H]⁺.

Example 80

2,5-Dioxopyrrolidin-1-yl (2R)-2-methyl-4-{[4-(morpholin-4-yl)-2-(trifluoromethyl)phenyl]methyl}piperazine-1-carboxylate

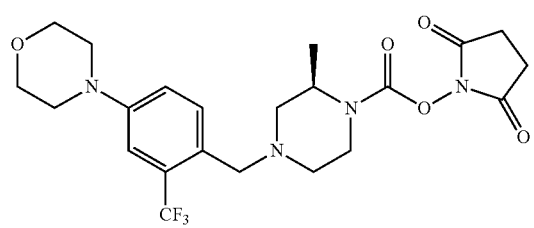 [SMILES: C[C@@H]1CN(Cc2ccc(N3CCOCC3)cc2C(F)(F)F)CCN1C(=O)ON1C(=O)CCC1=O]

Step 1: Preparation of tert-butyl (2R)-2-methyl-4-[[4-(morpholin-4-yl)-2-(trifluoromethyl)phenyl]methyl]piperazine-1-carboxylate

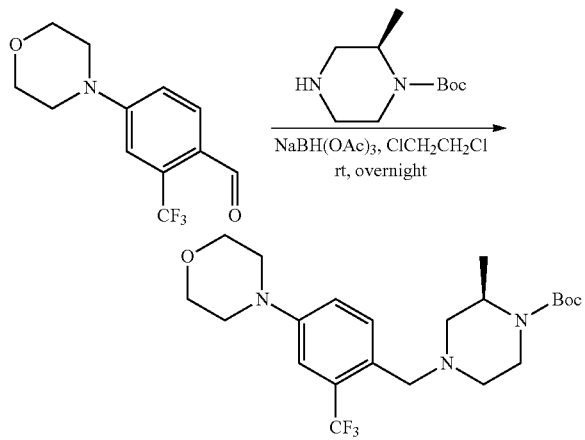

A 100-mL round-bottom flask was charged with 4-(morpholin-4-yl)-2-(trifluoromethyl)benzaldehyde (1.00 g, 3.86 mmol, 1.00 equiv), tert-butyl (2R)-2-methylpiperazine-1-carboxylate (0.850 g, 4.24 mmol, 1.10 equiv), and 1,2-dichloroethane (20 mL). The mixture was stirred for 30 min at room temperature. Sodium triacetoxyborohydride (2.40 g, 11.3 mmol, 3.00 equiv) was added. The resulting solution was stirred overnight at room temperature, diluted with H$_2$O (10 mL), and extracted with dichloromethane (3×10 mL). The organic layers were combined and washed with brine (50 mL), dried over anhydrous sodium sulfate, and concentrated under reduced pressure. The residue was chromatographed on a silica gel column with ethyl acetate/petroleum ether (20/80) to provide 1.70 g (99% yield) of tert-butyl (2R)-2-methyl-4-[[4-(morpholin-4-yl)-2-(trifluoromethyl)phenyl]methyl]piperazine-1-carboxylate as a yellow oil. LCMS (ESI, m/z): 444 [M+H]$^+$.

Step 2: Preparation of 4-(4-[[(3R)-3-methylpiperazin-1-yl]methyl]-3-(trifluoromethyl)phenyl)morpholine

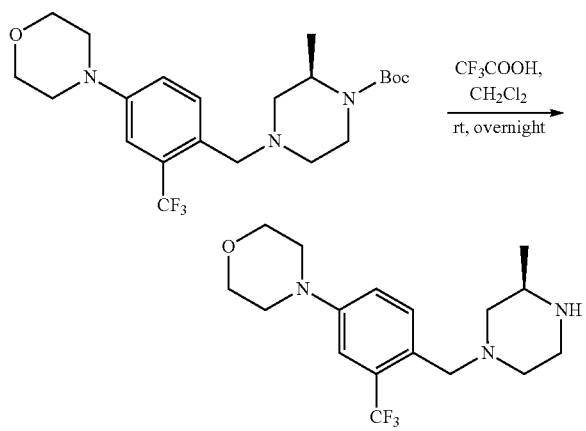

A 100-mL round-bottom flask was charged with tert-butyl (2R)-2-methyl-4-[[4-(morpholin-4-yl)-2-(trifluoromethyl)phenyl]methyl]piperazine-1-carboxylate (1.70 g, 3.83 mmol, 1.00 equiv), and dichloromethane (15 mL). Trifluoroacetic acid (3.80 g, 33.3 mmol, 8.70 equiv) was added at 0° C. The resulting solution was stirred overnight at room temperature and concentrated under reduced pressure to yield 1.00 g (crude) of 4-(4-[[(3R)-3-methylpiperazin-1-yl]methyl]-3-(trifluoromethyl)phenyl)morpholine as a yellow oil. LCMS (ESI, m/z): 344 [M+H]$^+$.

Step 3: Preparation of 2,5-Dioxopyrrolidin-1-yl (2R)-2-methyl-4-{[4-(morpholin-4-yl)-2-(trifluoromethyl)phenyl]methyl}piperazine-1-carboxylate

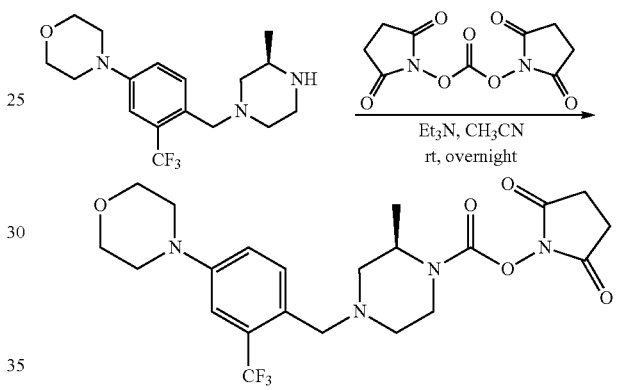

A 100-mL round-bottom flask was charged with 4-(4-[[(3R)-3-methylpiperazin-1-yl]methyl]-3-(trifluoromethyl)phenyl)morpholine (200 mg, 0.580 mmol, 1.00 equiv), bis(2,5-dioxopyrrolidin-1-yl) carbonate (224 mg, 0.870 mmol, 1.50 equiv), triethylamine (294 mg, 2.91 mmol, 5.00 equiv), and CH$_3$CN (15 mL). The resulting solution was stirred overnight at room temperature and concentrated under reduced pressure. The crude product (400 mg) was purified by preparative HPLC using the following gradient conditions: 20% CH$_3$CN/80% Phase A increasing to 70% CH$_3$CN over 10 min, then to 100% CH$_3$CN over 0.1 min, holding at 100% CH$_3$CN for 1.9 min, then reducing to 20% CH$_3$CN over 0.1 min, and holding at 20% for 1.9 min, on a Waters 2767-5 Chromatograph. Column: Xbridge Prep C18, 19*150 mm, 5 um; Mobile phase: Phase A: H$_2$O; Phase B: CH$_3$CN; Detector, UV 220 & 254 nm. Purification resulted in 240 mg (85% yield) of 2,5-dioxopyrrolidin-1-yl (2R)-2-methyl-4-{[4-(morpholin-4-yl)-2-(trifluoromethyl)phenyl]methyl}piperazine-1-carboxylate as a yellow oil. $^1$H NMR (300 MHz, Chloroform-d) δ 7.59 (d, J=8.4 Hz, 1H), 7.13 (s, 1H), 7.01-7.05 (m, 1H), 4.28 (br, 1H), 3.87 (t, J=4.8 Hz, 5H), 3.57 (s, 2H), 3.35 (br, 1H), 3.20 (t, J=4.8 Hz, 4H), 2.81 (s, 5H), 2.63 (d, J=11.7 Hz, 1H), 2.33-2.38 (m, 1H), 2.21 (t, J=10.4 Hz, 1H), 1.39 (d, J=5.1 Hz, 3H). LCMS (ESI, m/z): 485 [M+H]$^+$.

Example 81

2,5-Dioxopyrrolidin-1-yl 4-{[2-chloro-6-(morpholin-4-yl)phenyl]methyl}piperazine-1-carboxylate

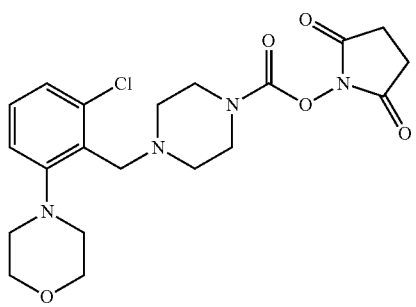 [SMILES: O=C(ON1C(=O)CCC1=O)N1CCN(Cc2c(Cl)cccc2N2CCOCC2)CC1]

Step 1: Preparation of 2-chloro-6-(morpholin-4-yl)benzaldehyde

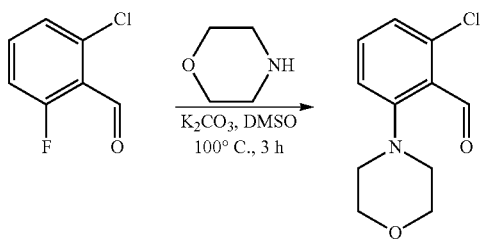 [SMILES: O=Cc1c(F)cccc1Cl ; C1COCCN1 ; O=Cc1c(Cl)cccc1N1CCOCC1]

A 100-mL round-bottom flask was charged with 2-chloro-6-fluorobenzaldehyde (8.00 g, 50.5 mmol, 1.00 equiv), morpholine (6.60 g, 75.8 mmol, 1.50 equiv), potassium carbonate (17.4 g, 126 mmol, 2.50 equiv), and dimethyl sulfoxide (50 mL). The resulting solution was stirred for 3 h at 100° C. (oil bath) and then diluted with $H_2O$ (50 mL). The resulting mixture was extracted with ethyl acetate (3×100 mL), and the organic layers were combined, washed with $H_2O$ (2×50 mL), dried over anhydrous sodium sulfate, filtered, and concentrated under reduced pressure. The residue was chromatographed on a silica gel column with ethyl acetate/petroleum ether (1/9) to yield 5.00 g (44%) of 2-chloro-6-(morpholin-4-yl)benzaldehyde as a yellow solid. LCMS (ESI, m/z): 226 [M+H]$^+$.

Step 2: Preparation of tert-butyl 4-[[2-chloro-6-(morpholin-4-yl)phenyl]methyl]piperazine-1-carboxylate

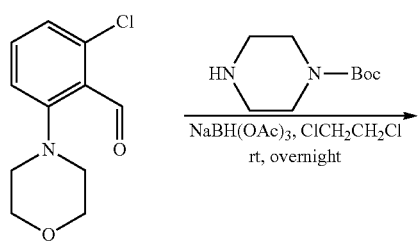

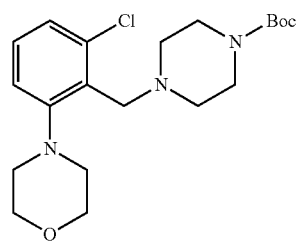

A 100-mL round-bottom flask was charged with 2-chloro-6-(morpholin-4-yl)benzaldehyde (1.34 g, 5.92 mmol, 1.00 equiv), tert-butyl piperazine-1-carboxylate (1.00 g, 5.37 mmol, 0.910 equiv), and 1,2-dichloroethane (30 mL). The mixture was stirred at room temperature for 0.5 h. Sodium triacetoxyborohydride (3.42 g, 16.1 mmol, 2.72 equiv) was added. The resulting solution was stirred overnight at room temperature and diluted with 1,2-dichloroethane (20 mL). The resulting mixture was washed with $H_2O$ (2×30 mL), dried over anhydrous sodium sulfate, filtered, and concentrated under reduced pressure. The residue was chromatographed on a silica gel column with ethyl acetate/petroleum ether (1/2) to yield 1.80 g (77% yield) of tert-butyl 4-[[2-chloro-6-(morpholin-4-yl)phenyl]methyl]piperazine-1-carboxylate as a colorless oil. LCMS (ESI, m/z): 396 [M+H]$^+$.

Step 3: Preparation of 4-[3-chloro-2-(piperazin-1-ylmethyl)phenyl]morpholine

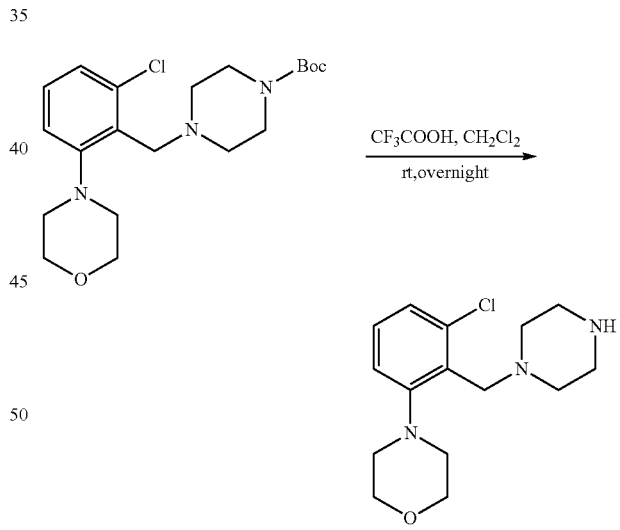

A 50-mL round-bottom flask was charged with tert-butyl 4-[[2-chloro-6-(morpholin-4-yl)phenyl]methyl]piperazine-1-carboxylate (1.80 g, 4.55 mmol, 1.00 equiv) and dichloromethane (30 mL). The mixture was cooled to 0° C., and then trifluoroacetic acid (5 mL) was added dropwise at 0° C. The resulting solution was stirred overnight at room temperature and concentrated under reduced pressure to provide 0.990 g (crude) of 4-[3-chloro-2-(piperazin-1-ylmethyl)phenyl]morpholine as a light yellow oil. LCMS (ESI, m/z): 296 [M+H]$^+$.

Step 4: Preparation of 2,5-dioxopyrrolidin-1-yl 4-{[2-chloro-6-(morpholin-4-yl)phenyl]methyl}piperazine-1-carboxylate

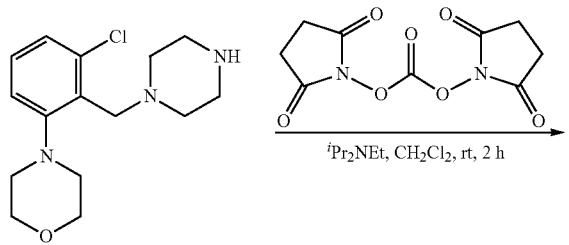

A 50-mL round-bottom flask was charged with 4-[3-chloro-2-(piperazin-1-ylmethyl)phenyl]morpholine (300 mg, 1.01 mmol, 1.00 equiv), bis(2,5-dioxopyrrolidin-1-yl) carbonate (256 mg, 1.00 mmol, 0.99 equiv), and dichloromethane (10 mL). N,N-Diisopropylethylamine (314 mg, 2.43 mmol, 2.40 equiv) was added dropwise. The resulting solution was stirred for 2 h at room temperature and diluted with H$_2$O (30 mL). The resulting solution was extracted with dichloromethane (3×10 mL), and the organic layers were combined, washed with H$_2$O (3×5 mL), dried over anhydrous sodium sulfate, filtered, and concentrated under reduced pressure. The residue was chromatographed on a silica gel column with ethyl acetate/petroleum ether (20/1). The crude product (301 mg) was purified by preparative HPLC using the following gradient conditions: 20% CH$_3$CN/80% Phase A increasing to 80% CH$_3$CN over 10 min, then to 100% CH$_3$CN over 0.1 min, holding at 100% CH$_3$CN for 1.9 min, then reducing to 20% CH$_3$CN over 0.1 min, and holding at 20% for 1.9 min, on a Waters 2767-5 Chromatograph. Column: Xbridge Prep C18, 19*150 mm, 5 um; Mobile phase: Phase A: water; Phase B: CH$_3$CN; Detector, UV 220 & 254 nm. Purification resulted in 108 mg (24% yield) of 2,5-dioxopyrrolidin-1-yl 4-{[2-chloro-6-(morpholin-4-yl)phenyl]methyl}piperazine-1-carboxylate as a white solid. $^1$H NMR (300 MHz, Chloroform-d) δ 7.18-7.24 (m, 2H), 7.08-7.11 (m, 1H), 3.79-3.85 (m, 6H), 3.45-3.57 (m, 4H), 2.99 (br, 4H), 2.82 (br, 4H), 2.64 (br, 4H). LCMS (ESI, m/z): 437 [M+H]$^+$.

Example 82

2,5-Dioxopyrrolidin-1-yl 4-{[3-chloro-2-(morpholin-4-yl)phenyl]methyl}piperazine-1-carboxylate

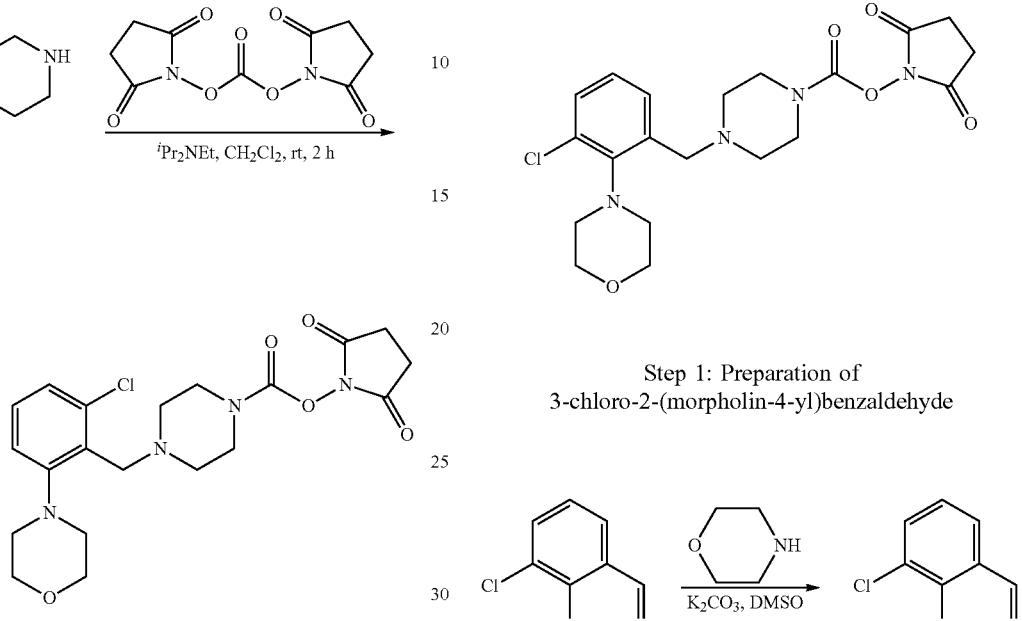

Step 1: Preparation of 3-chloro-2-(morpholin-4-yl)benzaldehyde

A 100-mL round-bottom flask was charged with 3-chloro-2-fluorobenzaldehyde (3.00 g, 18.9 mmol, 1.00 equiv), morpholine (2.50 g, 28.7 mmol, 1.52 equiv), potassium carbonate (6.50 g, 47.0 mmol, 2.49 equiv), and dimethyl sulfoxide (30 mL). The resulting solution was stirred for 3 h at 100° C. in an oil bath and diluted with H$_2$O (30 mL). The resulting solution was extracted with dichloromethane (3×20 mL), and the organic layers were combined and washed with H$_2$O (2×50 mL), dried over anhydrous sodium sulfate, filtered, and concentrated under reduced pressure. The residue was chromatographed on a silica gel column with ethyl acetate/petroleum ether (1/20) to provide 1.40 g (33% yield) of 3-chloro-2-(morpholin-4-yl)benzaldehyde as a yellow solid. LCMS (ESI, m/z): 226 [M+H]$^+$.

Step 2: Preparation of tert-butyl 4-[[3-chloro-2-(morpholin-4-yl)phenyl]methyl]piperazine-1-carboxylate

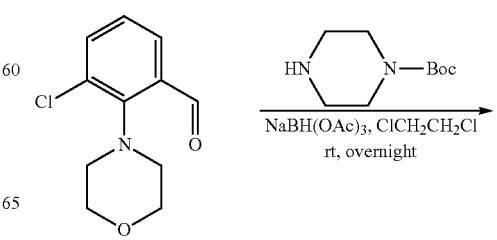

-continued

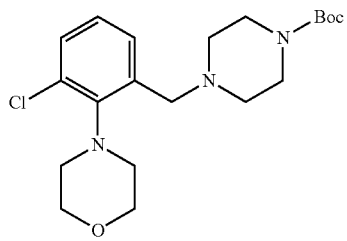

A 100-mL round-bottom flask was charged with 3-chloro-2-(morpholin-4-yl)benzaldehyde (1.34 g, 5.94 mmol, 1.10 equiv), tert-butyl piperazine-1-carboxylate (1.00 g, 5.37 mmol, 1.00 equiv), and 1,2-dichloroethane (30 mL). The mixture was stirred at room temperature for 0.5 h. Sodium triacetoxyborohydride (3.42 g, 16.1 mmol, 3.00 equiv) was added. The resulting solution was stirred for 2 h at room temperature and diluted with water (30 mL). The resulting solution was extracted with dichloromethane (3×30 mL), and the organic layers were combined, washed with H₂O (3×20 mL), dried over anhydrous sodium sulfate, filtered, and concentrated under reduced pressure. The residue was chromatographed on a silica gel column with ethyl acetate/petroleum ether (1/3) to provide 0.800 g (34% yield) of tert-butyl 4-[[3-chloro-2-(morpholin-4-yl)phenyl]methyl]piperazine-1-carboxylate as a light red oil. LCMS (ESI, m/z): 396 [M+H]⁺.

Step 3: Preparation of 4-[2-chloro-6-(piperazin-1-ylmethyl)phenyl]morpholine

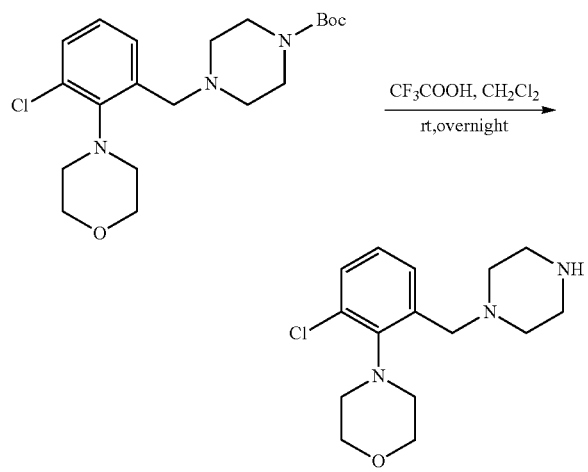

A 50-mL round-bottom flask was charged with tert-butyl 4-[[3-chloro-2-(morpholin-4-yl)phenyl]methyl]piperazine-1-carboxylate (800 mg, 2.02 mmol, 1.00 equiv) and dichloromethane (15 mL). The mixture was cooled to 0° C. Trifluoroacetic acid (2.5 mL) was added dropwise at 0° C. The resulting solution was stirred overnight at room temperature and concentrated under reduced pressure to yield 580 mg (crude) of 4-[2-chloro-6-(piperazin-1-ylmethyl)phenyl]morpholine as colorless oil. LCMS (ESI, m/z): 296 [M+H]⁺.

Step 4: Preparation of 2,5-dioxopyrrolidin-1-yl 4-{[3-chloro-2-(morpholin-4-yl)phenyl]methyl}piperazine-1-carboxylate

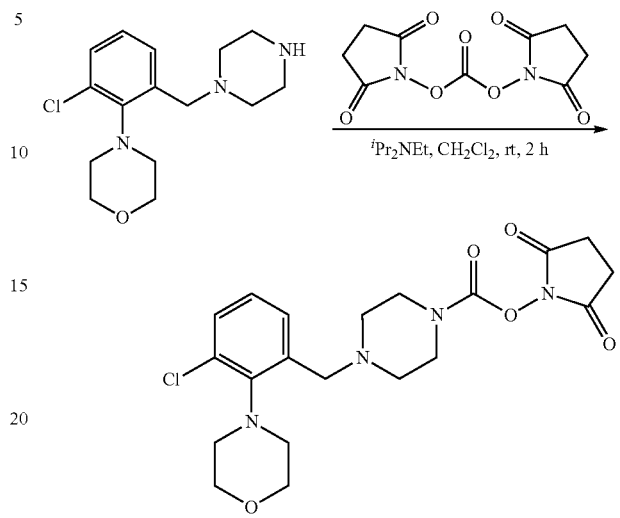

A 50-mL round-bottom flask was charged with 4-[2-chloro-6-(piperazin-1-ylmethyl)phenyl]morpholine (290 mg, 0.980 mmol, 1.00 equiv), bis(2,5-dioxopyrrolidin-1-yl) carbonate (256 mg, 1.00 mmol, 1.02 equiv), and dichloromethane (10 mL). N,N-Diisopropylethylamine (314 mg, 2.43 mmol, 2.40 equiv) was added dropwise. The resulting solution was stirred for 2 h at room temperature and diluted with H₂O (30 mL). The resulting solution was extracted with dichloromethane (3×10 mL), and the organic layers were combined, washed with H₂O (3×5 mL), dried over anhydrous sodium sulfate, filtered, and concentrated under reduced pressure. The residue was chromatographed on a silica gel column with ethyl acetate/petroleum ether (9/1). The crude product (312 mg) was purified by preparative HPLC using the following gradient conditions: 20% CH₃CN/80% Phase A increasing to 80% CH₃CN over 10 min, then to 100% CH₃CN over 0.1 min, holding at 100% CH₃CN for 1.9 min, then reducing to 20% CH₃CN over 0.1 min, and holding at 20% for 1.9 min, on a Waters 2767-5 Chromatograph. Column: Xbridge Prep C18, 19*150 mm, 5um; Mobile phase: Phase A: water; Phase B: CH₃CN; Detector, UV 220 & 254 nm. Purification resulted in 118 mg (27% yield) of 2,5-dioxopyrrolidin-1-yl 4-{[3-chloro-2-(morpholin-4-yl)phenyl]methyl}piperazine-1-carboxylate as yellow oil. ¹H NMR (300 MHz, Chloroform-d) δ 7.26-7.30 (m, 2H), 7.08 (t, J=7.8 Hz, 1H), 3.81-3.90 (m, 2H), 3.50-3.81 (m, 10H), 2.71-2.82 (m, 6H), 2.53 (br, 4H). LCMS (ESI, m/z): 437 [M+H]⁺.

Example 83

2,5-Dioxopyrrolidin-1-yl 4-(3-morpholinobenzyl)piperazine-1-carboxylate

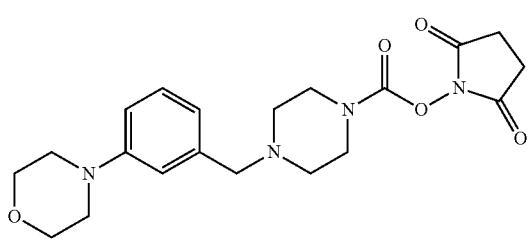 [SMILES: O=C(ON1C(=O)CCC1=O)N1CCN(Cc2cccc(N3CCOCC3)c2)CC1]

The title compound was synthesized directly from commercially available 3-morpholinobenzaldehyde and tert-butyl piperazine-1-carboxylate according to the representative procedure of Example 62, Steps 1, 2 and 3 to provide 2,5-dioxopyrrolidin-1-yl 4-(3-morpholinobenzyl)piperazine-1-carboxylate as a white solid: $^1$H NMR (400 MHz, Chloroform-d) δ 7.16 (t, J=7.8 Hz, 1H), 6.88-6.71 (m, 3H), 3.87-3.73 (m, 4H), 3.61-3.54 (m, 2H), 3.50-3.44 (m, 2H), 3.43 (s, 2H), 3.18-3.02 (m, 4H), 2.75 (s, 4H), 2.53-2.34 (m, 4H). LCMS (ESI, m/z): 403.1 [M+H]$^+$.

Example 84

2,5-Dioxopyrrolidin-1-yl 4-(4-chloro-2-(1H-pyrazol-1-yl)benzyl)piperazine-1-carboxylate

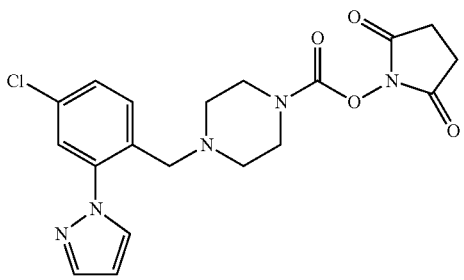 [SMILES: O=C(ON1C(=O)CCC1=O)N1CCN(Cc2ccc(Cl)cc2-n2cccn2)CC1]

The title compound was synthesized directly from commercially available 4-chloro-2-fluorobenzaldehyde and 1H-pyrazole according to the representative procedure of Example 65, Steps 1, 2, 3 and 4 to provide 2,5-dioxopyrrolidin-1-yl 4-(4-chloro-2-(1H-pyrazol-1-yl)benzyl)piperazine-1-carboxylate as an opaque oil. $^1$H NMR (400 MHz, Chloroform-d) δ 7.88 (d, J=2.4 Hz, 1H), 7.76-7.70 (m, 1H), 7.49-7.44 (m, 2H), 7.37 (ddd, J=8.2, 2.3, 1.0 Hz, 1H), 6.48-6.44 (m, 1H), 3.62-3.55 (m, 2H), 3.49-3.44 (m, 4H), 2.82 (s, 4H), 2.47-2.39 (m, 4H). LCMS (ESI, m/z): 418.1 [C$_{19}$H$_{20}$ClN$_5$O$_4$]$^+$.

Example 85

2,5-Dioxopyrrolidin-1-yl 4-(2-(3-acetamidopyrrolidin-1-yl)-4-chlorobenzyl)piperazine-1-carboxylate

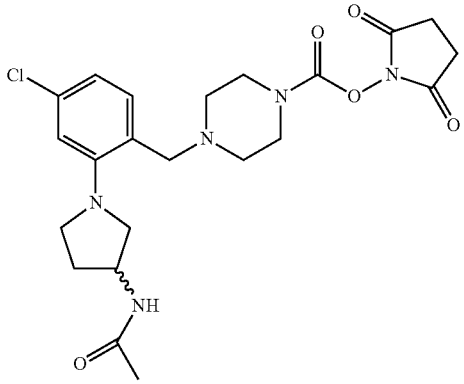 [SMILES: CC(=O)NC1CCN(c2cc(Cl)ccc2CN2CCN(C(=O)ON3C(=O)CCC3=O)CC2)C1]

The title compound was synthesized directly from commercially available 4-chloro-2-fluorobenzaldehyde and N-(pyrrolidin-3-yl)acetamide according to the representative procedure of Example 65, Steps 1, 2, 3 and 4 to provide 2,5-dioxopyrrolidin-1-yl 4-(2-(3-acetamidopyrrolidin-1-yl)-4-chlorobenzyl)piperazine-1-carboxylate as a clear oil. $^1$H NMR (400 MHz, Chloroform-d) δ 7.34-7.26 (m, 1H), 6.93-6.81 (m, 2H), 6.13 (d, J=6.6 Hz, 1H), 4.60-4.49 (m, 1H), 3.65 (s, 2H), 3.51 (s, 4H), 3.47-3.32 (m, 2H), 3.19-3.06 (m, 2H), 2.82 (s, 4H), 2.57-2.44 (m, 4H), 2.31 (dq, J=13.2, 7.1, 6.4 Hz, 1H), 2.18 (d, J=2.3 Hz, 3H), 1.93-1.80 (m, 1H). LCMS (ESI, m/z): 478.2 [C$_{22}$H$_{28}$ClN$_5$O$_5$]$^+$.

Example 86

2,5-Dioxopyrrolidin-1-yl 2,2-dimethyl-4-{[4-(morpholin-4-yl)-2-(trifluoromethyl)phenyl]methyl}piperazine-1-carboxylate

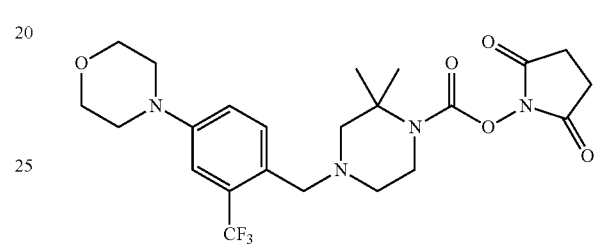

Step 1: Preparation of tert-butyl 2,2-dimethyl-4-[[4-(morpholin-4-yl)-2-(trifluoromethyl)phenyl]methyl]piperazine-1-carboxylate

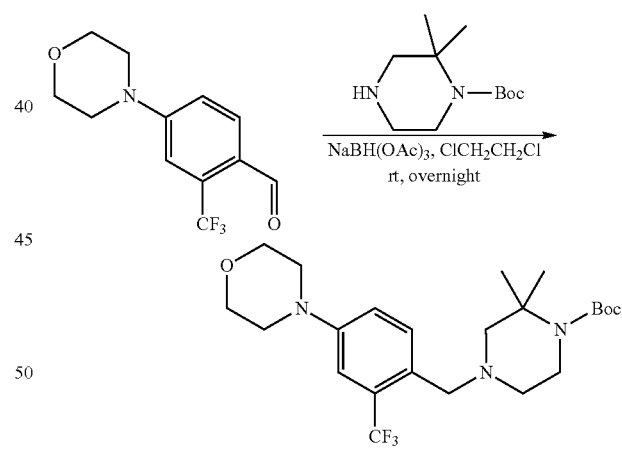

A 100-mL round-bottom flask was charged with 4-(morpholin-4-yl)-2-(trifluoromethyl)benzaldehyde (1.00 g, 3.86 mmol, 1.00 equiv), tert-butyl 2,2-dimethylpiperazine-1-carboxylate (0.909 g, 4.24 mmol, 1.10 equiv), and 1,2-dichloroethane (20 mL). The mixture was stirred for 30 min at room temperature. Sodium triacetoxyborohydride (2.40 g, 11.32 mmol, 3.00 equiv) was added. The resulting solution was stirred overnight at room temperature and then diluted with H$_2$O (10 mL). The resulting mixture was extracted with dichloromethane (3×10 mL). The organic layers were combined, washed with brine (1×50 mL), dried over anhydrous sodium sulfate, filtered, and concentrated under reduced pressure. The residue was chromatographed on a silica gel column with ethyl acetate/petroleum ether (25/75) to provide 1.50 g (85% yield) of tert-butyl 2,2-dimethyl-4-[[4-(morpholin-4-yl)-2-(trifluoromethyl)phenyl]methyl]piperazine-1-carboxylate as a yellow oil. LCMS (ESI, m/z): 458 [M+H]$^+$.

Step 2: Preparation of 4-[4-[(3,3-dimethylpiperazin-1-yl)methyl]-3-(trifluoromethyl)phenyl]morpholine

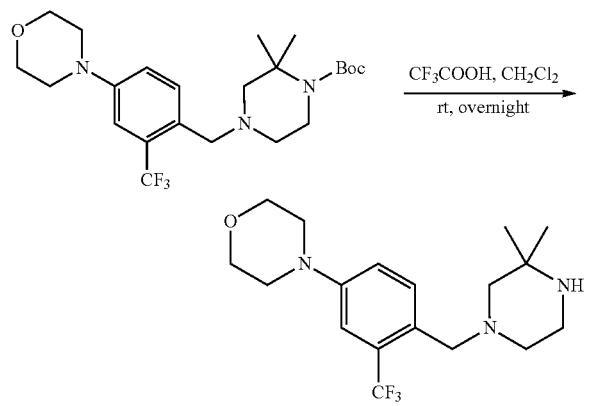

A 100-mL round-bottom flask was charged with tert-butyl 2,2-dimethyl-4-[[4-(morpholin-4-yl)-2-(trifluoromethyl)phenyl]methyl]piperazine-1-carboxylate (1.50 g, 3.28 mmol, 1.00 equiv) and dichloromethane (15 mL). Trifluoroacetic acid (2 mL) was added at 0° C. The resulting solution was stirred overnight at room temperature and concentrated under reduced pressure to yield 1.00 g (85% yield) of 4-[4-[(3,3-dimethylpiperazin-1-yl)methyl]-3-(trifluoromethyl)phenyl]morpholine as a yellow oil. LCMS (ESI, m/z): 358 [M+H]$^+$.

Step 3: Preparation of 2,5-dioxopyrrolidin-1-yl 2,2-dimethyl-4-{[4-(morpholin-4-yl)-2-(trifluoromethyl)phenyl]methyl}piperazine-1-carboxylate

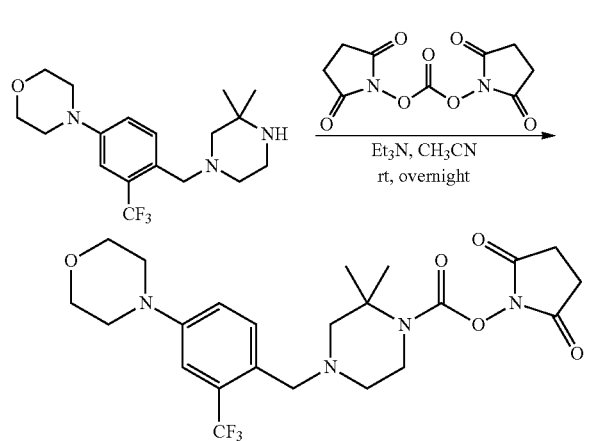

A 100-mL round-bottom flask was charged with bis(2,5-dioxopyrrolidin-1-yl) carbonate (215 mg, 0.840 mmol, 1.50 equiv), 4-[4-[(3,3-dimethylpiperazin-1-yl)methyl]-3-(trifluoromethyl)phenyl]morpholine (200 mg, 0.560 mmol, 1.00 equiv), triethylamine (339 mg, 3.35 mmol, 6.00 equiv), and CH$_3$CN (15 mL). The resulting solution was stirred overnight at room temperature and concentrated under reduced pressure. The crude product (380 mg) was purified by preparative HPLC using the following gradient conditions: 20% CH$_3$CN/80% Phase A increasing to 70% CH$_3$CN over 10 min, then to 100% CH$_3$CN over 0.1 min, holding at 100% CH$_3$CN for 1.9 min, then reducing to 20% CH$_3$CN over 0.1 min, and holding at 20% for 1.9 min, on a Waters 2767-5 Chromatograph. Column: Xbridge Prep C18, 19*150 mm, 5 um; Mobile phase: Phase A: H$_2$O; Phase B: CH$_3$CN; Detector, UV 220 & 254 nm. Purification resulted in 170 mg (41% yield) of 2,5-dioxopyrrolidin-1-yl 2,2-dimethyl-4-{[4-(morpholin-4-yl)-2-(trifluoromethyl)phenyl]methyl}piperazine-1-carboxylate as a white solid. $^1$H NMR (300 MHz, Chloroform-d) δ 7.60 (d, J=8.1 Hz, 1H), 7.13 (s, 1H), 7.01-7.05 (m, 1H), 3.85-3.89 (m, 4H), 3.69 (br, 2H), 3.55 (s, 2H), 3.18-3.22 (m, 4H), 2.81 (s, 4H), 2.51 (br, 2H), 2.29 (s, 2H), 1.45 (s, 6H). LCMS (ESI, m/z): 499 [M+H]$^+$.

Example 87

2,5-Dioxopyrrolidin-1-yl 2,2-dimethyl-4-{[4-(morpholin-4-yl)-2-(trifluoromethoxy)phenyl]methyl}piperazine-1-carboxylate

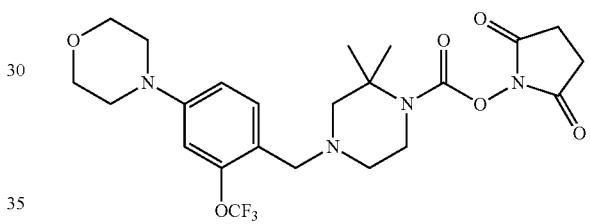

Step 1: Preparation of tert-butyl 2,2-dimethyl-4-[[4-(morpholin-4-yl)-2-(trifluoromethoxy)phenyl]methyl]piperazine-1-carboxylate

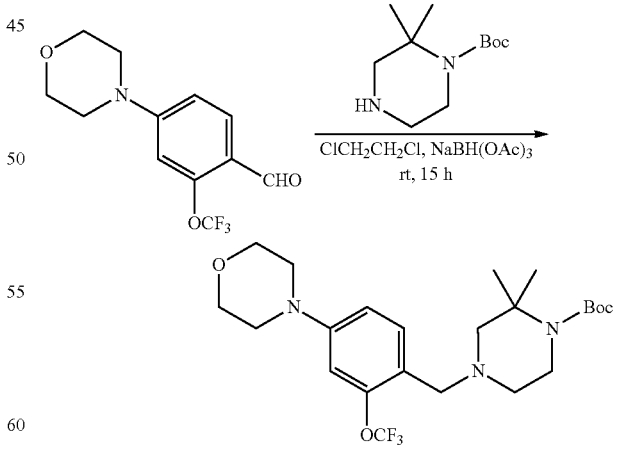

A 100-mL round-bottom flask was charged with 4-(morpholin-4-yl)-2-(trifluoromethoxy)benzaldehyde (340 mg, 1.24 mmol, 1.00 equiv), tert-butyl 2,2-dimethylpiperazine-1-carboxylate (264 mg, 1.23 mmol, 1.00 equiv), and 1,2-dichloroethane (15 mL). The resulting solution was stirred for 1 h at room temperature. Sodium triacetoxyhydroborate (789 mg, 3.72 mmol, 3.01 equiv) was added. The resulting solution was stirred for 15 h at room temperature. Reaction progress was monitored by LCMS. The reaction mixture was diluted with H₂O (15 mL). The resulting solution was extracted with dichloromethane (3×15 mL), and the organic layers were combined, dried over anhydrous sodium sulfate, filtered, and concentrated under reduced pressure. The residue was chromatographed on a silica gel column with ethyl acetate/petroleum ether (1/4) to provide 575 mg (98% yield) of tert-butyl 2,2-dimethyl-4-[[4-(morpholin-4-yl)-2-(trifluoromethoxy)phenyl]methyl]piperazine-1-carboxylate as a light yellow oil. LCMS (ESI, m/z): 474 [M+H]⁺.

Step 2: Preparation of 4-[4-[(3,3-dimethylpiperazin-1-yl)methyl]-3-(trifluoromethoxy)phenyl]morpholine

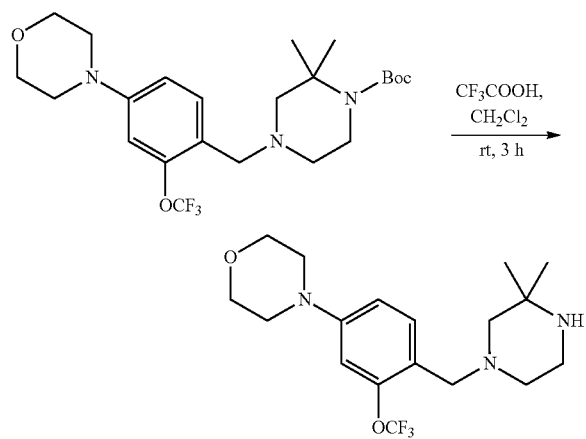

A 50-mL round-bottom flask was charged with a solution of tert-butyl 2,2-dimethyl-4-[[4-(morpholin-4-yl)-2-(trifluoromethoxy)phenyl]methyl]piperazine-1-carboxylate (550 mg, 1.16 mmol, 1.00 equiv) in dichloromethane (15 mL). Trifluoroacetic acid (2 mL) was added dropwise at 0° C. The resulting solution was stirred for 3 h at room temperature. Reaction progress was monitored by LCMS. The resulting mixture was concentrated under reduced pressure to provide 430 mg (crude) of 4-[4-[(3,3-dimethylpiperazin-1-yl)methyl]-3-(trifluoromethoxy)phenyl]morpholine as a light yellow oil. LCMS (ESI, m/z): 374 [M+H]⁺.

Step 3: Preparation of 2,5-dioxopyrrolidin-1-yl 2,2-dimethyl-4-{[4-(morpholin-4-yl)-2-(trifluoromethoxy)phenyl]methyl}piperazine-1-carboxylate

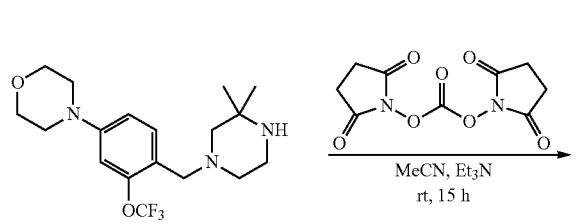

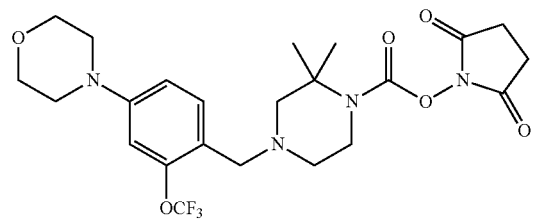 [SMILES: CC1(C)CN(Cc2ccc(N3CCOCC3)cc2OC(F)(F)F)CCN1C(=O)ON1C(=O)CCC1=O]

A 50-mL round-bottom flask was purged and maintained with an inert atmosphere of nitrogen and was charged with 4-[4-[(3,3-dimethylpiperazin-1-yl)methyl]-3-(trifluoromethoxy)phenyl]morpholine (190 mg, 0.510 mmol, 1.00 equiv), bis(2,5-dioxopyrrolidin-1-yl) carbonate (261 mg, 1.02 mmol, 2.00 equiv), acetonitrile (15 mL), and triethylamine (257 mg, 2.54 mmol, 4.99 equiv). The resulting solution was stirred for 15 h at room temperature. Reaction progress was monitored by LCMS. The resulting mixture was concentrated under reduced pressure. The crude product (283 mg) was purified by preparative HPLC using the following gradient conditions: 20% CH₃CN/80% Phase A increasing to 80% CH₃CN over 10 min, then to 100% CH₃CN over 0.1 min, holding at 100% CH₃CN for 1.9 min, then reducing to 20% CH₃CN over 0.1 min, and holding at 20% for 1.9 min, on a Waters 2767-5 Chromatograph. Column: Xbridge Prep C18, 19*150 mm, 5um; Mobile phase: Phase A: water; Phase B: CH₃CN; Detector, UV 220 & 254 nm. Purification resulted in 105 mg (40% yield) of 2,5-dioxopyrrolidin-1-yl 2,2-dimethyl-4-{[4-(morpholin-4-yl)-2-(trifluoromethoxy)phenyl]methyl}piperazine-1-carboxylate as a light yellow oil. ¹H NMR (300 MHz, Chloroform-d) δ 7.41 (d, J=8.4 Hz, 1H), 6.80-6.84 (m, 1H), 6.73 (s, 1H), 3.86 (t, J=4.8 Hz, 4H), 3.69 (t, J=4.8 Hz, 2H), 3.49 (s, 2H), 3.17 (t, J=4.8 Hz, 4H), 2.80 (s, 4H), 2.52 (s, 2H), 2.29 (s, 2H), 1.45 (s, 6H). LCMS (ESI, m/z): 537 [M+Na]⁺.

Example 88

2,5-Dioxopyrrolidin-1-yl (2S)-4-{[2-fluoro-4-(morpholin-4-yl)phenyl]methyl}-2-methylpiperazine-1-carboxylate

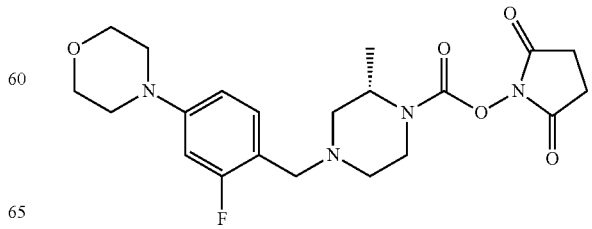

Step 1: Preparation of tert-butyl (2S)-4-[[2-fluoro-4-(morpholin-4-yl)phenyl]methyl]-2-methylpiperazine-1-carboxylate

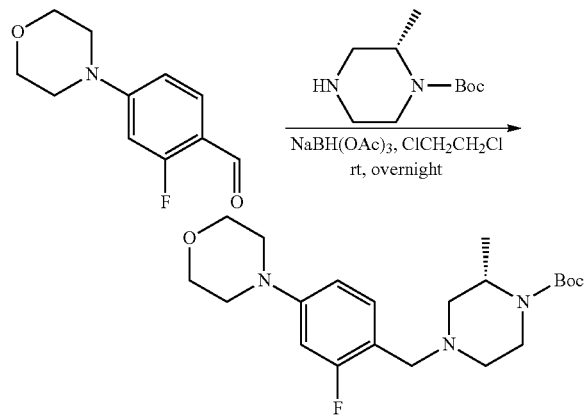

A 100-mL round-bottom flask was charged with 2-fluoro-4-(morpholin-4-yl)benzaldehyde (0.800 g, 3.82 mmol, 1.00 equiv), tert-butyl (2S)-2-methylpiperazine-1-carboxylate (0.840 g, 4.20 mmol, 1.10 equiv), and 1,2-dichloroethane (20 mL). The mixture was stirred for 30 min at room temperature. Sodium triacetoxyborohydride (2.40 g, 11.3 mmol, 3.00 equiv) was added. The resulting solution was stirred overnight at room temperature, diluted with H$_2$O (10 mL), and extracted with dichloromethane (3×10 mL). The organic layers were combined and washed with brine (50 mL), dried over anhydrous sodium sulfate, and concentrated under reduced pressure. The residue was chromatographed on a silica gel column with ethyl acetate/petroleum ether (25/75) to provide 1.40 g (93% yield) of tert-butyl (2S)-4-[[2-fluoro-4-(morpholin-4-yl)phenyl]methyl]-2-methylpiperazine-1-carboxylate as a white solid. LCMS (ESI, m/z): 394 [M+H]$^+$.

Step 2: Preparation of 4-(4-[[(3S)-3-methylpiperazin-1-yl]methyl]-3-(trifluoromethyl)phenyl)morpholine

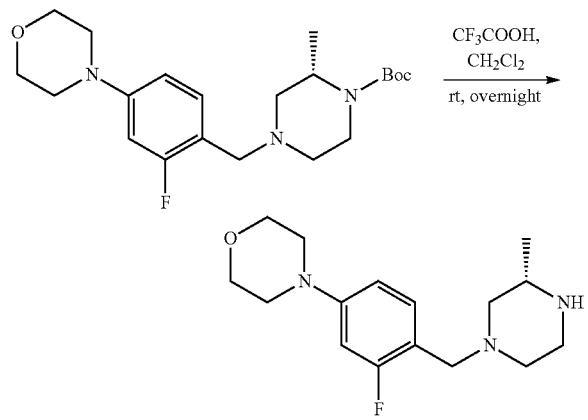

A 100-mL round-bottom flask was charged with tert-butyl (2S)-4-[[2-fluoro-4-(morpholin-4-yl)phenyl]methyl]-2-methylpiperazine-1-carboxylate (1.40 g, 3.56 mmol), dichloromethane (15 mL). Trifluoroacetic acid (2 mL) was added at 0° C. The resulting solution was stirred overnight at room temperature and concentrated under reduced pressure to yield 0.900 g (86% yield) of 4-(3-fluoro-4-[[(3S)-3-methylpiperazin-1-yl]methyl]phenyl)morpholine as colorless oil. LCMS (ESI, m/z): 294 [M+H]$^+$.

Step 3: Preparation of 2,5-dioxopyrrolidin-1-yl (2S)-4-{[2-fluoro-4-(morpholin-4-yl)phenyl]methyl}-2-methylpiperazine-1-carboxylate

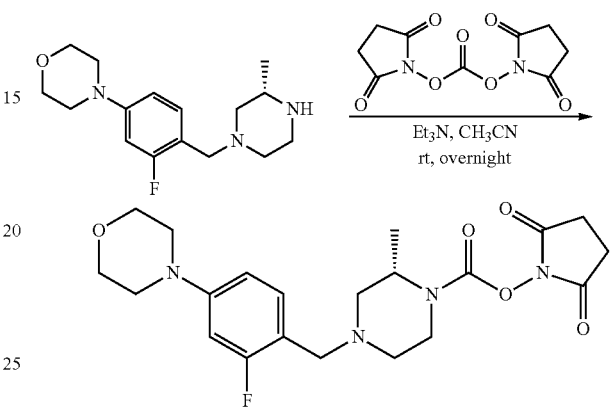

A 100-mL round-bottom flask was charged with 4-(3-fluoro-4-[[(3S)-3-methylpiperazin-1-yl]methyl]phenyl)morpholine (200 mg, 0.680 mmol, 1.00 equiv), bis(2,5-dioxopyrrolidin-1-yl) carbonate (262 mg, 1.02 mmol, 1.50 equiv), triethylamine (345 mg, 3.41 mmol, 6.00 equiv), and CH$_3$CN (15 mL). The resulting solution was stirred overnight at room temperature and concentrated under reduced pressure. The crude product (400 mg) was purified by preparative HPLC using the following gradient conditions: 20% CH$_3$CN/80% Phase A increasing to 70% CH$_3$CN over 10 min, then to 100% CH$_3$CN over 0.1 min, holding at 100% CH$_3$CN for 1.9 min, then reducing to 20% CH$_3$CN over 0.1 min, and holding at 20% for 1.9 min, on a Waters 2767-5 Chromatograph. Column: Xbridge Prep C18, 19*150 mm, 5 um; Mobile phase: Phase A: H$_2$O; Phase B: CH$_3$CN; Detector, UV 220 & 254 nm. Purification resulted in 200.4 mg (68% yield) of 2,5-dioxopyrrolidin-1-yl (2S)-4-{[2-fluoro-4-(morpholin-4-yl)phenyl]methyl}-2-methylpiperazine-1-carboxylate as a white solid. $^1$H NMR (300 MHz, Chloroform-d) δ 7.22 (t, J=8.6 Hz, 1H), 6.63-6.67 (m, 1H), 6.53-6.58 (m, 1H), 4.27 (br, 1H), 3.83-3.87 (m, 5H), 3.51 (s, 2H), 3.34 (br, 1H), 3.16 (t, J=4.8 Hz, 4H), 2.81 (s, 5H), 2.64 (d, J=11.4 Hz, 1H), 2.14-2.34 (m, 2H), 1.37 (d, J=5.4 Hz, 3H). LCMS (ESI, m/z): 435 [M+H]$^+$.

Example 89

2,5-Dioxopyrrolidin-1-yl (2S)-4-{[2-chloro-4-(morpholin-4-yl)phenyl]methyl}-2-methylpiperazine-1-carboxylate

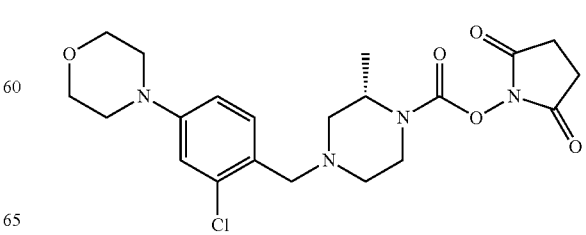

Step 1: Preparation of tert-butyl (2S)-4-[[2-chloro-4-(morpholin-4-yl)phenyl]methyl]-2-methylpiperazine-1-carboxylate

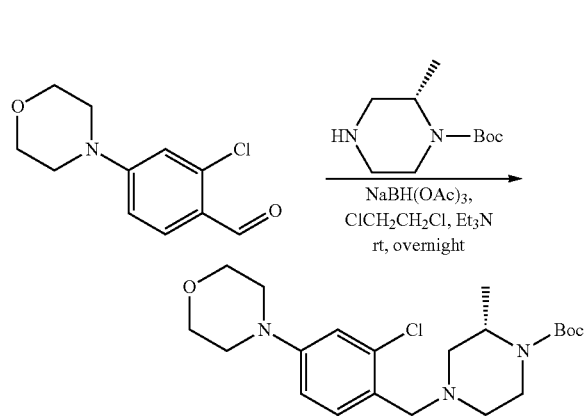

A 100-mL round-bottom flask was charged with 2-chloro-4-(morpholin-4-yl)benzaldehyde (0.800 g, 3.54 mmol, 1.00 equiv), tert-butyl (2S)-2-methylpiperazine-1-carboxylate (0.783 g, 3.91 mmol, 1.10 equiv), and 1,2-dichloroethane (20 mL). The mixture was stirred for 30 min at room temperature. Sodium triacetoxyborohydride (2.26 g, 10.7 mmol, 3.00 equiv) was added. The resulting solution was stirred overnight at room temperature, diluted with H$_2$O (30 mL), extracted with dichloromethane (3×30 mL), and the organic layers were combined, dried over Na$_2$SO$_4$, filtered, and concentrated under reduced pressure. The residue was chromatographed on a silia gel column with ethyl acetate/petroleum ether (25/75) to provide 1.20 g (74% yield) of tert-butyl (2S)-4-[[2-chloro-4-(morpholin-4-yl)phenyl]methyl]-2-methylpiperazine-1-carboxylate as a white solid. LCMS (ESI, m/z): 410 [M+H]$^+$.

Step 2: Preparation of 4-(3-chloro-4-[[(3S)-3-methylpiperazin-1-yl]methyl]phenyl)morpholine

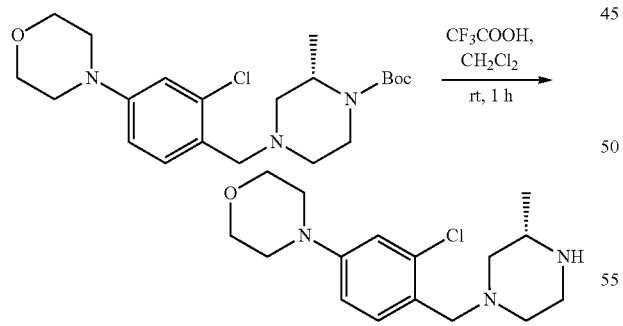

A 100-mL round-bottom flask was charged with tert-butyl (2S)-4-[[2-chloro-4-(morpholin-4-yl)phenyl]methyl]-2-methylpiperazine-1-carboxylate (1.20 g, 2.93 mmol, 1.00 equiv), trifluoroacetic acid (4 mL), and dichloromethane (20 mL). The resulting solution was stirred for 1 h at room temperature and concentrated under reduced pressure to yield 0.910 g (crude) of 4-(3-chloro-4-[[(3S)-3-methylpiperazin-1-yl]methyl]phenyl)morpholine as a light yellow oil. LCMS (ESI, m/z): 310 [M+H]$^+$.

Step 3: Preparation of 2,5-dioxopyrrolidin-1-yl (2S)-4-{[2-chloro-4-(morpholin-4-yl)phenyl]methyl}-2-methylpiperazine-1-carboxylate

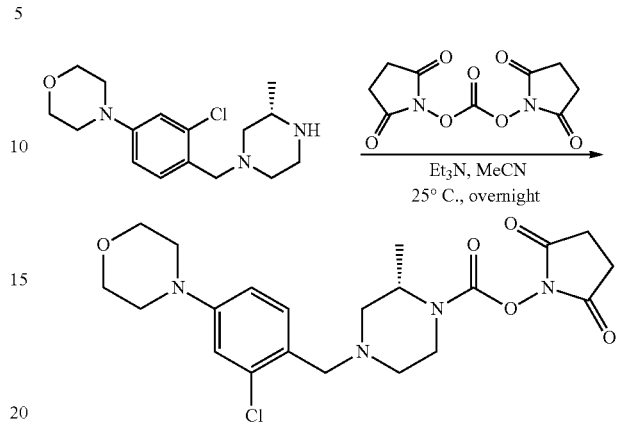

A 50-mL round-bottom flask was charged with 4-(3-chloro-4-[[(3S)-3-methylpiperazin-1-yl]methyl]phenyl)morpholine (300 mg, 0.970 mmol, 1.00 equiv), MeCN (8 mL), and bis(2,5-dioxopyrrolidin-1-yl)carbonate (497 mg, 1.94 mmol, 2.00 equiv). Triethylamine (490 mg, 4.84 mmol, 5.00 equiv) was added. The resulting solution was stirred overnight at room temperature and diluted with 5% citric acid solution (20 mL). The resulting solution was extracted with dichloromethane (3×15 mL), and the organic layers were combined, dried over anhydrous sodium sulfate, filtered, and concentrated under reduced pressure. The crude product (140 mg) was purified by preparative HPLC using the following gradient conditions: 20% CH$_3$CN/80% Phase A increasing to 80% CH$_3$CN over 10 min, then to 100% CH$_3$CN over 0.1 min, holding at 100% CH$_3$CN for 1.9 min, then reducing to 20% CH$_3$CN over 0.1 min, and holding at 20% for 1.9 min, on a Waters 2767-5 Chromatograph. Column: Xbridge Prep C18, 19*150 mm, 5 um; Mobile phase: Phase A: H$_2$O; Phase B: CH$_3$CN; Detector, UV 220 & 254 nm. Purification resulted in 84.4 mg (19%) of 2,5-dioxopyrrolidin-1-yl (2S)-4-{[2-chloro-4-(morpholin-4-yl)phenyl]methyl}-2-methylpiperazine-1-carboxylate as a white solid. $^1$H NMR (400 MHz, Chloroform-d) δ 7.29-7.33 (m, 1H), 6.90 (d, J=2.0 Hz, 1H), 6.80-6.82 (m, 1H), 4.31 (br, 1H), 3.87 (t, J=4.4 Hz, 5H), 3.56 (br, 2H), 3.35-3.36 (m, 1H), 3.18 (t, J=4.8 Hz, 4H), 2.84 (s, 5H), 2.68-2.75 (m, 1H), 2.41 (br, 1H), 2.25 (br, 1H), 1.32-1.42 (m, 3H). LCMS (ESI, m/z): 452 [M+H]$^+$.

Example 90

2,5-Dioxopyrrolidin-1-yl (2S)-2-methyl-4-{[4-(morpholin-4-yl)-2-(trifluoromethoxy)phenyl]methyl}piperazine-1-carboxylate

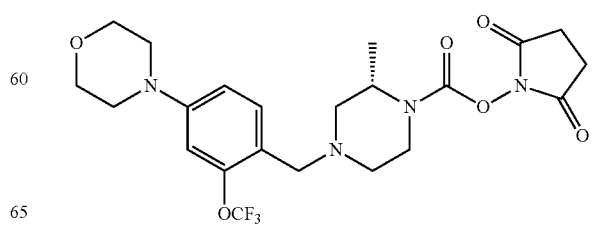

127

Step 1: Preparation of (S)-test-butyl 2-methyl-4-(4-morpholino-2-(trifluoromethoxy)benzyl)piperazine-1-carboxylate

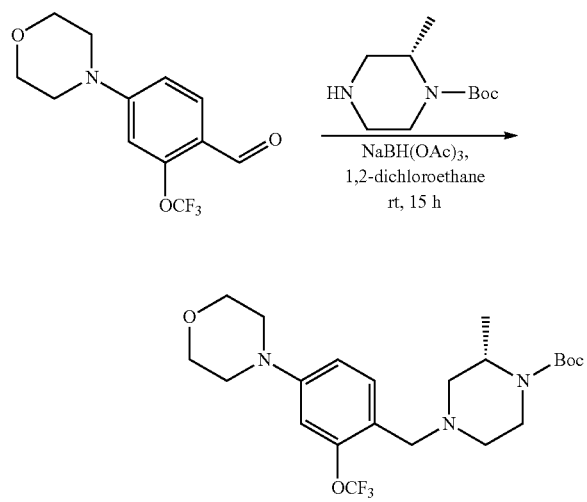

The title compound was synthesized according to the representative procedure of Example 88, Step 1 using 4-morpholino-2-(trifluoromethoxy)benzaldehyde: LCMS (ESI, m/z): 459 [M+H]⁺.

Step 2: Preparation of (S)-4-(4-((3-methylpiperazin-1-yl)methyl)-3-(trifluoromethoxy)phenyl)morpholine

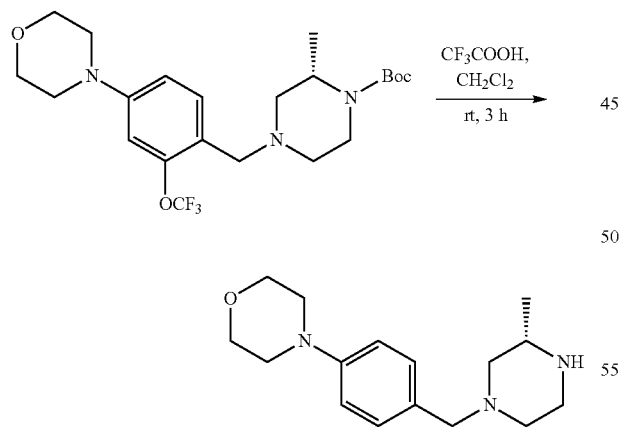

The title compound was synthesized according to the representative procedure of Example 88, Step 2 using (5)-tert-butyl 2-methyl-4-(4-morpholino-2-(trifluoromethoxy)benzyl)piperazine-1-carboxylate: LCMS (ESI, m/z): 359 [M+H]⁺.

128

Step 3: Preparation of 2,5-dioxopyrrolidin-1-yl (2S)-2-methyl-4-{[4-(morpholin-4-yl)-2-(trifluoromethoxy)phenyl]methyl}piperazine-1-carboxylate

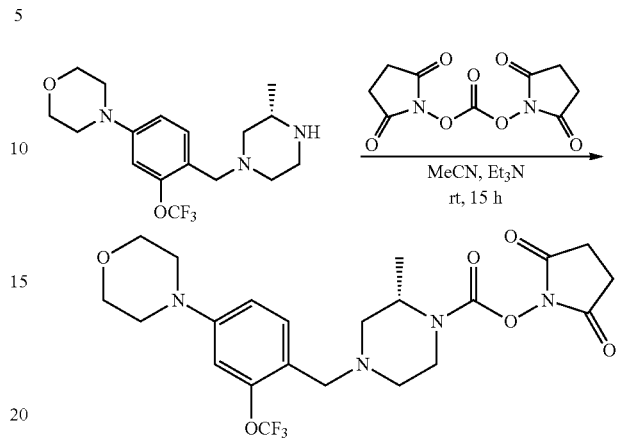

A 50-mL round-bottom flask was purged and maintained with an inert atmosphere of nitrogen and was charged with (S)-4-(4-((3-methylpiperazin-1-yl)methyl)-3-(trifluoromethoxy)phenyl)morpholine (200 mg, 0.560 mmol, 1.00 equiv), bis(2,5-dioxopyrrolidin-1-yl) carbonate (284 mg, 1.11 mmol, 1.99 equiv), acetonitrile (15 mL), triethylamine (280 mg, 2.77 mmol, 4.97 equiv). The resulting solution was stirred for 15 h at room temperature. Reaction progress was monitored by LCMS. The resulting mixture was concentrated under reduced pressure. The crude product (343 mg) was purified by preparative HPLC using the following gradient conditions: 20% CH₃CN/80% Phase A increasing to 80% CH₃CN over 10 min, then to 100% CH₃CN over 0.1 min, holding at 100% CH₃CN for 1.9 min, then reducing to 20% CH₃CN over 0.1 min, and holding at 20% for 1.9 min, on a Waters 2767-5 Chromatograph. Column: Xbridge Prep C18, 19*150 mm, 5 um; Mobile phase: Phase A: water; Phase B: CH₃CN; Detector, UV 220 & 254 nm. Purification resulted in 129 mg (46% yield) of 2,5-dioxopyrrolidin-1-yl (2S)-2-methyl-4-{[4-(morpholin-4-yl)-2-(trifluoromethoxy)phenyl]methyl}piperazine-1-carboxylate as a off-white solid. $^1$H NMR (300 MHz, Chloroform-d) δ 7.39 (s, 1H), 6.80-6.84 (m, 1H), 6.73 (s, 1H), 4.36 (br, 1H), 3.86 (t, J=4.9 Hz, 5H), 3.66 (br, 3H), 3.10-3.29 (m, 4H), 2.95 (s, 5H), 2.68 (br, 1H), 2.09-2.35 (m, 2H), 1.43 (s, 3H). LCMS (ESI, m/z): 523 [M+Na]⁺.

Example 91

2,5-Dioxopyrrolidin-1-yl 4-{[2-(morpholin-4-yl)-4-(trifluoromethyl)phenyl]methyl}piperazine-1-carboxylate

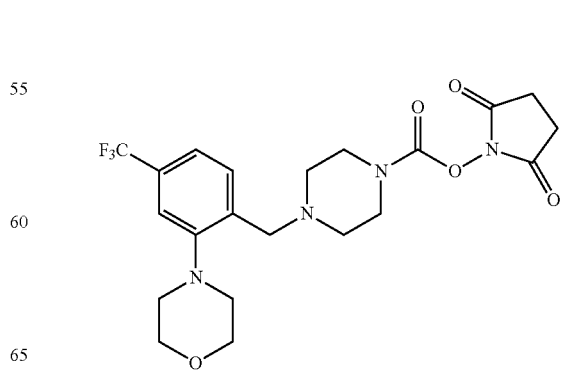

Step 1: Preparation of 2-(morpholin-4-yl)-4-(trifluoromethyl)benzaldehyde

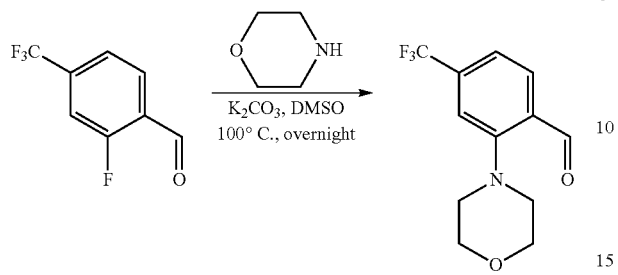

A 100-mL round-bottom flask was charged with 2-fluoro-4-(trifluoromethyl)benzaldehyde (1.90 g, 9.89 mmol, 1.00 equiv), morpholine (1.30 g, 14.9 mmol, 1.51 equiv), potassium carbonate (3.45 g, 25.0 mmol, 2.52 equiv), and dimethyl sulfoxide (20 mL). The resulting solution was stirred overnight at 100° C. in an oil bath and diluted with H$_2$O (30 mL). The resulting solution was extracted with dichloromethane (2×20 mL), and the organic layers were combined, washed with H$_2$O (3×20 mL), dried over anhydrous sodium sulfate, filtered, and concentrated under reduced pressure. The residue was chromatographed on a silica gel column with ethyl acetate/petroleum ether (1/5) to yield 1.06 g (41% yield) of 2-(morpholin-4-yl)-4-(trifluoromethyl)benzaldehyde as yellow oil. LCMS (ESI, m/z): 260 [M+H]$^+$.

Step 2: Preparation of tert-butyl 4-[[2-(morpholin-4-yl)-4-(trifluoromethyl)phenyl]methyl]piperazine-1-carboxylate

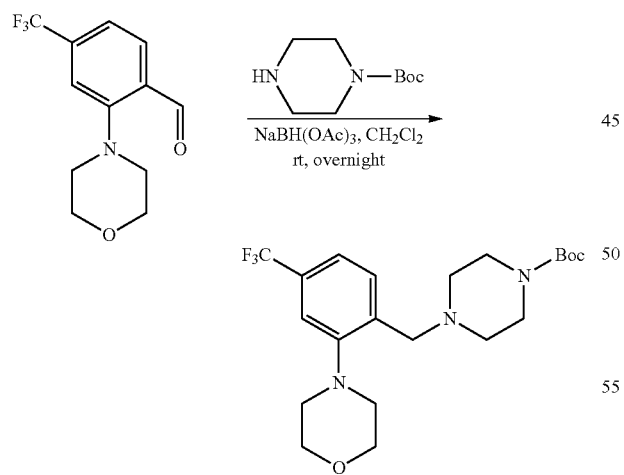

A 100-mL round-bottom flask was charged with 2-(morpholin-4-yl)-4-(trifluoromethyl)benzaldehyde (1.00 g, 3.86 mmol, 1.00 equiv), tert-butyl piperazine-1-carboxylate (0.650 g, 3.51 mmol, 0.91 equiv), and dichloromethane (15 mL). The mixture was stirred at room temperature for 0.5 h. Sodium triacetoxyborohydride (2.23 g, 10.5 mmol, 2.73 equiv) was added. The resulting solution was stirred overnight at room temperature and diluted with dichloromethane (15 mL). The organic layers were washed with H$_2$O (2×10 mL), dried over anhydrous sodium sulfate, filtered, and concentrated under reduced pressure. The residue was chromatographed on a silica gel column with ethyl acetate/petroleum ether (1/4) to yield 1.30 g (78% yield) of tert-butyl 4-[[2-(morpholin-4-yl)-4-(trifluoromethyl)phenyl]methyl]piperazine-1-carboxylate as a light yellow oil. LCMS (ESI, m/z): 430 [M+H]$^+$.

Step 3: Preparation of 4-[2-(piperazin-1-ylmethyl)-5-(trifluoromethyl)phenyl]morpholine

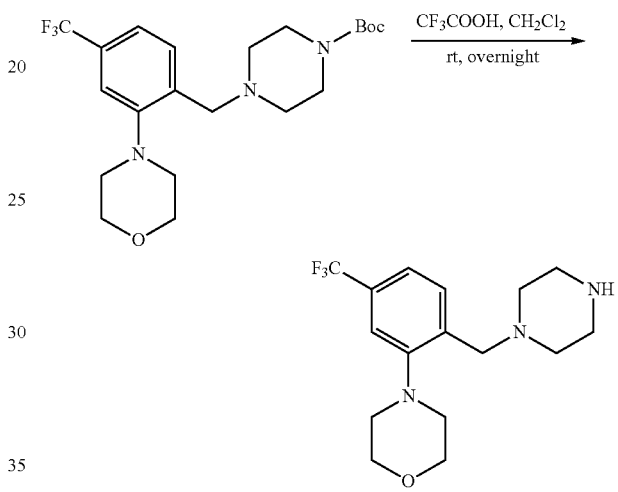

A 100-mL round-bottom flask was charged with tert-butyl 4-[[2-(morpholin-4-yl)-4-(trifluoromethyl)phenyl]methyl]piperazine-1-carboxylate (1.30 g, 3.03 mmol, 1.00 equiv) and dichloromethane (20 mL). The mixture was cooled to 0° C. Trifluoroacetic acid (3 mL) was added dropwise. The resulting solution was stirred overnight at room temperature and concentrated under pressure to yield 0.800 g (crude) of 4-[2-(piperazin-1-ylmethyl)-5-(trifluoromethyl)phenyl]morpholine as a light yellow solid. LCMS (ESI, m/z): 330 [M+H]$^+$.

Step 4: Preparation of 2,5-dioxopyrrolidin-1-yl 4-{[2-(morpholin-4-yl)-4-(trifluoromethyl)phenyl]methyl}piperazine-1-carboxylate

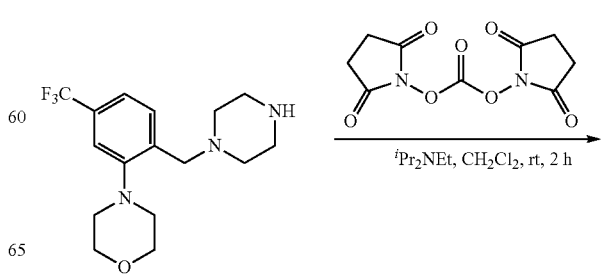

-continued

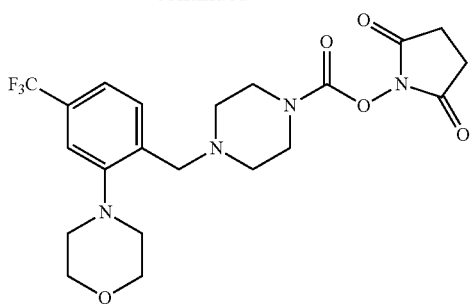 [SMILES: O=C(ON1C(=O)CCC1=O)N1CCN(Cc2ccc(C(F)(F)F)cc2N2CCOCC2)CC1]

A 50-mL round-bottom flask was charged with 4-[2-(piperazin-1-ylmethyl)-5-(trifluoromethyl)phenyl]morpholine (329 mg, 1.00 mmol, 1.00 equiv), bis(2,5-dioxopyrrolidin-1-yl) carbonate (256 mg, 1.00 mmol, 1.00 equiv), and dichloromethane (10 mL). N,N-Diisopropylethylamine (256 mg, 1.98 mmol, 1.98 equiv) was added dropwise. The resulting solution was stirred for 2 h at room temperature and then diluted with H$_2$O (10 mL). The resulting mixture was extracted with dichloromethane (3×10 mL), and the organic layers were combined, dried over anhydrous sodium sulfate, filtered, and concentrated under reduced pressure. The residue was chromatographed on a silica gel column with dichloromethane/MeOH (95/5). The crude product (303 mg) was purified by preparative HPLC using the following gradient conditions: 20% CH$_3$CN/80% Phase A increasing to 80% CH$_3$CN over 10 min, then to 100% CH$_3$CN over 0.1 min, holding at 100% CH$_3$CN for 1.9 min, then reducing to 20% CH$_3$CN over 0.1 min, and holding at 20% for 1.9 min, on a Waters 2767-5 Chromatograph. Column: Xbridge Prep C18, 19*150 mm, 5 um; Mobile phase: Phase A: water; Phase B: CH$_3$CN; Detector, UV 220 & 254 nm. Purification resulted in 132 mg (28% yield) of 2,5-dioxopyrrolidin-1-yl 4-{[2-(morpholin-4-yl)-4-(trifluoromethyl)phenyl]methyl}piperazine-1-carboxylate as a white solid. $^1$H NMR (300 MHz, Chloroform-d) δ 7.61 (d, J=9.0 Hz, 1H), 7.31-7.36 (m, 2H), 3.84-3.87 (m, 4H), 3.53-3.64 (m, 6H), 2.95-2.98 (m, 4H), 2.83 (br, 4H), 2.55 (br, 4H). LCMS (ESI, m/z): 471 [M+H]$^+$.

Example 92

2,5-Dioxopyrrolidin-1-yl 4-{[5-chloro-2-(morpholin-4-yl)phenyl]methyl}piperazine-1-carboxylate

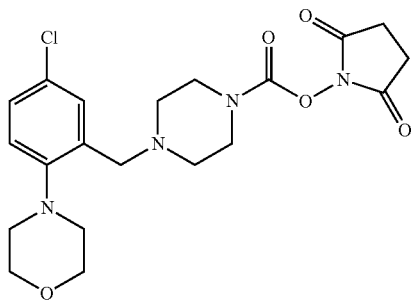

Step 1: Preparation of 5-chloro-2-(morpholin-4-yl)benzaldehyde

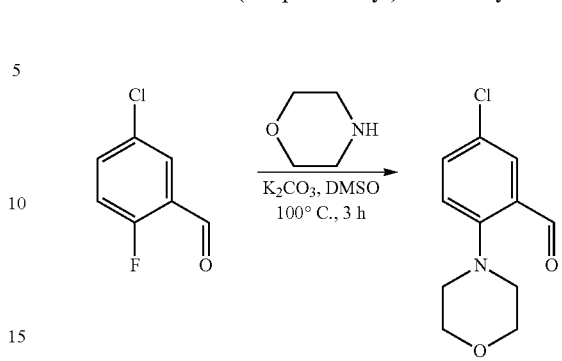

A 50-mL round-bottom flask was charged with 5-chloro-2-fluorobenzaldehyde (3.00 g, 18.9 mmol, 1.00 equiv), morpholine (2.50 g, 28.7 mmol, 1.52 equiv), potassium carbonate (6.50 g, 47.0 mmol, 2.49 equiv), and DMSO (20 mL). The resulting solution was stirred overnight at 100° C. (oil bath) and diluted with H$_2$O (50 mL). The resulting solution was extracted with dichloromethane (3×20 mL), and the organic layers were combined, washed with H$_2$O (2×50 mL), dried over anhydrous sodium sulfate, filtered, and concentrated under reduced pressure. The residue was chromatographed on a silica gel column with ethyl acetate/petroleum ether (1/9) to provide 3.24 g (76% yield) of 5-chloro-2-(morpholin-4-yl)benzaldehyde as a brown oil. LCMS (ESI, m/z): 226 [M+H]$^+$.

Step 2: Preparation of tert-butyl 4-[[5-chloro-2-(morpholin-4-yl)phenyl]methyl]piperazine-1-carboxylate

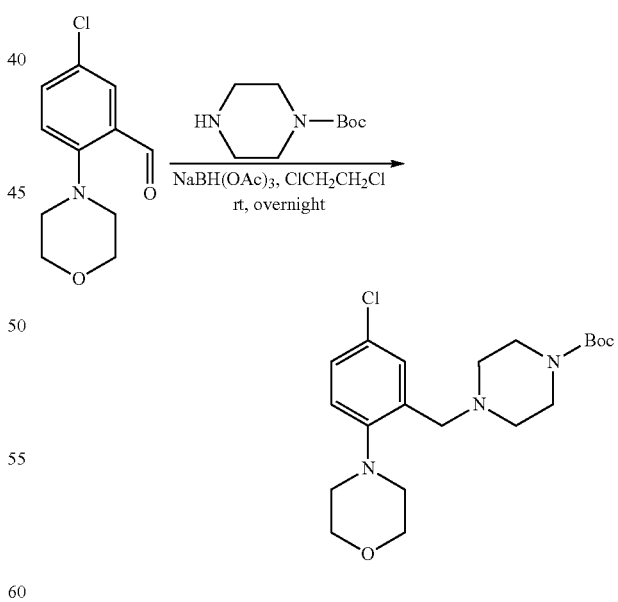

A round-bottom flask was charged with 5-chloro-2-(morpholin-4-yl)benzaldehyde (1.60 g, 7.09 mmol, 1.00 equiv), tert-butyl piperazine-1-carboxylate (1.20 g, 6.43 mmol, 0.910 equiv), and 1,2-dichloromethane (20 mL). The mixture was stirred at room temperature for 0.5 h. Sodium triacetoxyborohydride (4.09 g, 19.3 mmol, 2.72 equiv) was added. The resulting solution was stirred overnight at room temperature and diluted with H₂O (50 mL). The resulting solution was extracted with dichloromethane (2×20 mL), and the organic layers were combined, dried over anhydrous sodium sulfate, filtered, and concentrated under reduced pressure. The residue was chromatographed on a silica gel column with ethyl acetate/petroleum ether (1/4) to yield 2.90 g (crude) of tert-butyl 4-[[5-chloro-2-(morpholin-4-yl)phenyl]methyl]piperazine-1-carboxylate as a yellow oil. LCMS (ESI, m/z): 396 [M+H]⁺.

Step 3: Preparation of 4-[4-chloro-2-(piperazin-1-ylmethyl)phenyl]morpholine

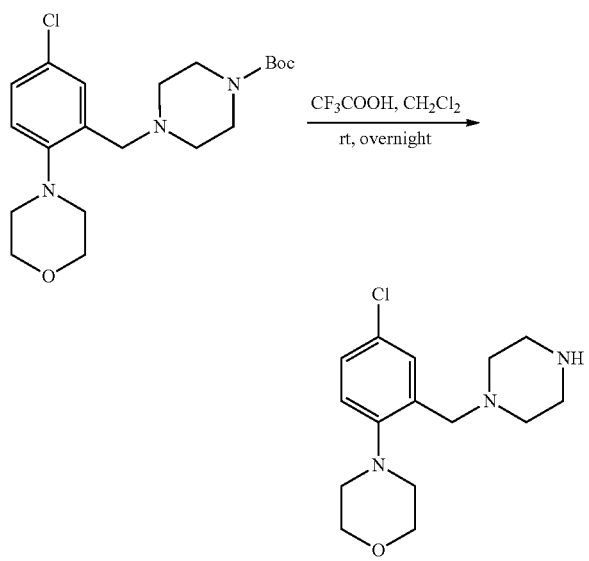

A 100 mL round-bottom flask was charged with tert-butyl 4-[[5-chloro-2-(morpholin-4-yl)phenyl]methyl]piperazine-1-carboxylate (2.90 g, 7.32 mmol, 1.00 equiv) and dichloromethane (35 mL). The mixture was cooled to 0° C., and trifluoroacetic acid (7 mL) was added dropwise. The resulting solution was stirred overnight at room temperature. The resulting solution was concentrated under reduced pressure to yield 2.60 g (crude) of 4-[4-chloro-2-(piperazin-1-ylmethyl)phenyl]morpholine as a light yellow oil. LCMS (ESI, m/z): 296 [M+H]⁺.

Step 4: Preparation of 2,5-dioxopyrrolidin-1-yl 4-{[5-chloro-2-(morpholin-4-yl)phenyl]methyl}piperazine-1-carboxylate

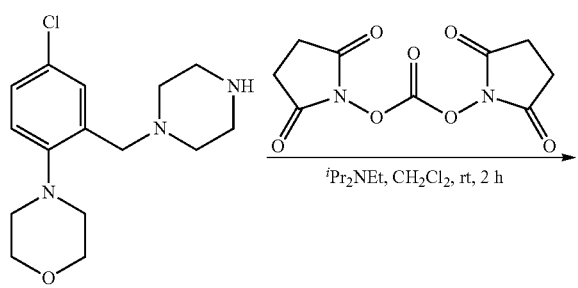

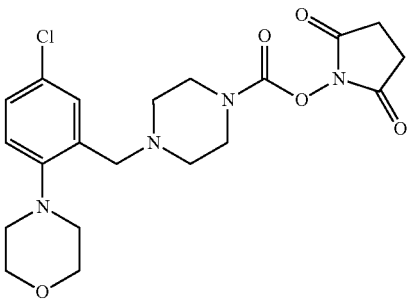 [SMILES: O=C(ON1C(=O)CCC1=O)N1CCN(Cc2cc(Cl)ccc2N2CCOCC2)CC1]

A 50-mL round-bottom flask was charged with 4-[4-chloro-2-(piperazin-1-ylmethyl)phenyl]morpholine (300 mg, 1.01 mmol, 1.00 equiv), bis(2,5-dioxopyrrolidin-1-yl) carbonate (256 mg, 1.00 mmol, 0.99 equiv), and dichloromethane (10 mL). N,N-Diisopropylethylamine (314 mg, 2.43 mmol, 2.40 equiv) was added dropwise. The resulting solution was stirred for 2 h at room temperature and diluted with H₂O (30 mL). The resulting solution was extracted with dichloromethane (3×10 mL), and the organic layers were combined, washed with H₂O (3×5 mL), dried over anhydrous sodium sulfate, filtered, and concentrated under reduced pressure. The residue was chromatographed on a silica gel column with ethyl acetate/petroleum ether (12/1). The crude product (354 mg) was purified by preparative HPLC using the following gradient conditions: 20% CH₃CN/80% Phase A increasing to 80% CH₃CN over 10 min, then to 100% CH₃CN over 0.1 min, holding at 100% CH₃CN for 1.9 min, then reducing to 20% CH₃CN over 0.1 min, and holding at 20% for 1.9 min, on a Waters 2767-5 Chromatograph. Column: Xbridge Prep C18, 19*150 mm, 5 um; Mobile phase: Phase A: water; Phase B: CH₃CN; Detector, UV 220 & 254 nm. Purification resulted in 176 mg (40% yield) of 2,5-dioxopyrrolidin-1-yl 4-{[5-chloro-2-(morpholin-4-yl)phenyl]methyl}piperazine-1-carboxylate as a light yellow oil. ¹H NMR (300 MHz, Chloroform-d) δ 7.45 (d, J=2.4 Hz, 1H), 7.20-7.23 (m, 1H), 7.04 (d, J=8.4 Hz, 1H), 3.83 (br, 4H), 3.52-3.75 (m, 6H), 2.82-3.02 (m, 8H), 2.54 (br, 4H). LCMS (ESI, m/z): 437 [M+H]⁺.

Example 93

2,5-Dioxopyrrolidin-1-yl 4-{[3-fluoro-2-(morpholin-4-yl)phenyl]methyl}piperazine-1-carboxylate

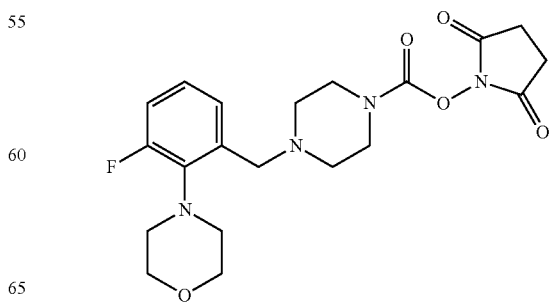

Step 1: Preparation of 3-fluoro-2-(morpholin-4-yl)benzaldehyde

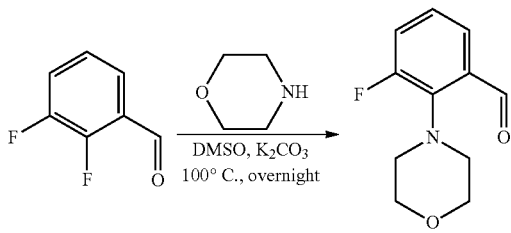 [SMILES: O=Cc1cccc(F)c1F ; C1COCCN1 ; O=Cc1cccc(F)c1N1CCOCC1]

A 100-mL round-bottom flask was charged with 2,3-difluorobenzaldehyde (2.00 g, 14.1 mmol, 1.00 equiv), morpholine (1.84 g, 21.1 mmol, 1.50 equiv), potassium carbonate (4.90 g, 35.4 mmol, 2.52 equiv), and dimethyl sulfoxide (20 mL). The resulting solution was stirred overnight at 100° C. (oil bath) and diluted with $H_2O$ (50 mL). The resulting solution was extracted with dichloromethane (3×20 mL), and the organic layers were combined, washed with $H_2O$ (3×50 mL), dried over anhydrous sodium sulfate, filtered, and concentrated under reduced pressure. The residue was chromatographed on a silica gel column with ethyl acetate/petroleum ether (1/20) to yield 0.840 g (28% yield) of 3-fluoro-2-(morpholin-4-yl)benzaldehyde as a yellow solid. $^1$H NMR 300 MHz, ($CDCl_3$) δ 10.54 (s, 1H), 7.63 (d, J=7.5 Hz, 1H), 7.18-7.34 (m, 2H), 3.85 (br, 4H), 3.23 (br, 4H). LCMS (ESI, m/z): 210 $[M+H]^+$.

Step 2: Preparation of tert-butyl 4-[[3-fluoro-2-(morpholin-4-yl)phenyl]methyl]piperazine-1-carboxylate

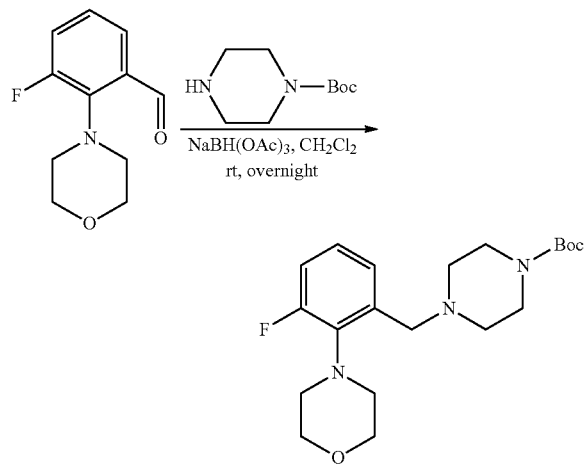

A 50-mL round-bottom flask was charged with 3-fluoro-2-(morpholin-4-yl)benzaldehyde (0.500 g, 2.39 mmol, 1.00 equiv), tert-butyl piperazine-1-carboxylate (404 mg, 2.17 mmol, 0.91 equiv), and dichloromethane (10 mL). The mixture was stirred at room temperature for 0.5 h. Sodium triacetoxyborohydride (1.38 g, 6.51 mmol, 2.72 equiv) was added. The resulting solution was stirred overnight at room temperature and diluted with dichloromethane. The resulting mixture was washed with $H_2O$ (3×10 mL), dried over anhydrous sodium sulfate, filtered, and concentrated under reduced pressure. The residue was chromatographed on a silica gel column with ethyl acetate/petroleum ether (1/3) to yield 1.00 g (crude) of tert-butyl 4-[[3-fluoro-2-(morpholin-4-yl)phenyl]methyl]piperazine-1-carboxylate as a colorless oil. LCMS (ESI, m/z): 380 $[M+H]^+$.

Step 3: Preparation of 4-[2-fluoro-6-(piperazin-1-ylmethyl)phenyl]morpholine

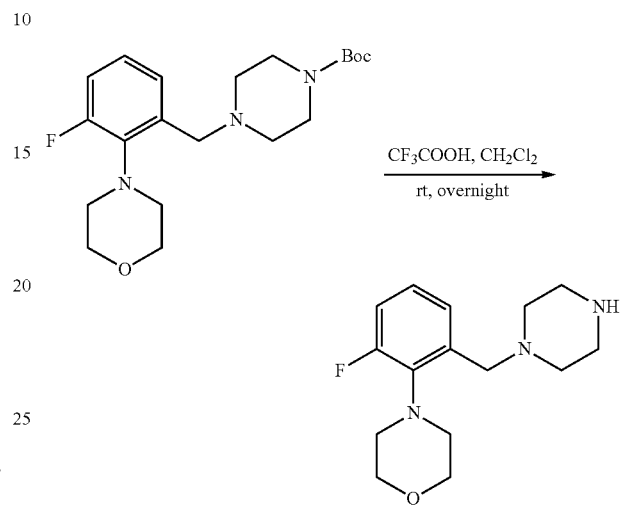

A 100-mL round-bottom flask was charged with tert-butyl 4-[[3-fluoro-2-(morpholin-4-yl)phenyl]methyl]piperazine-1-carboxylate (1.00 g, 2.64 mmol, 1.00 equiv) and dichloromethane (20 mL). The mixture was cooled to 0° C. Trifluoroacetic acid (2 mL) was added dropwise at 0° C. The resulting solution was stirred overnight at room temperature and concentrated under reduced pressure to yield 0.600 g (crude) of 4-[2-fluoro-6-(piperazin-1-ylmethyl)phenyl]morpholine as a light yellow oil. LCMS (ESI, m/z): 280 $[M+H]^+$.

Step 4: Preparation of 2,5-dioxopyrrolidin-1-yl 4-{[3-fluoro-2-(morpholin-4-yl)phenyl]methyl}piperazine-1-carboxylate

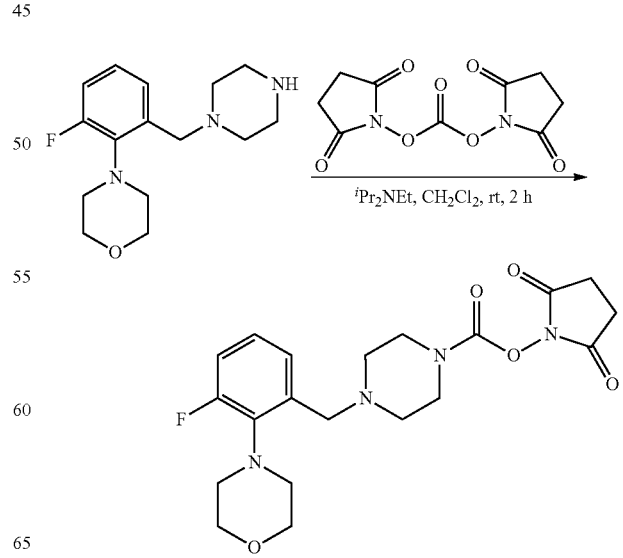

A 50-mL round-bottom flask was charged with 4-[2-fluoro-6-(piperazin-1-ylmethyl)phenyl]morpholine (200 mg, 0.717 mmol, 1.00 equiv), bis(2,5-dioxopyrrolidin-1-yl) carbonate (183 mg, 0.715 mmol, 1.00 equiv), and dichloromethane (10 mL). N,N-Diisopropylethylamine (225 mg, 1.74 mmol, 2.43 equiv) was added dropwise. The resulting solution was stirred for 2 h at room temperature and diluted with H$_2$O (30 mL). The resulting solution was extracted with dichloromethane (3×10 mL), and the organic layers were combined, washed with H$_2$O (3×5 mL), dried over anhydrous sodium sulfate, filtered, and concentrated under reduced pressure. The residue was chromatographed on a silica gel column with ethyl acetate/petroleum ether (7/1). The crude product (205 mg) was purified by preparative HPLC using the following gradient conditions: 20% CH$_3$CN/80% Phase A increasing to 80% CH$_3$CN over 10 min, then to 100% CH$_3$CN over 0.1 min, holding at 100% CH$_3$CN for 1.9 min, then reducing to 20% CH$_3$CN over 0.1 min, and holding at 20% for 1.9 min, on a Waters 2767-5 Chromatograph. Column: Xbridge Prep C18, 19*150 mm, 5 um; Mobile phase: Phase A: water; Phase B: CH$_3$CN; Detector, UV 220 & 254 nm. Purification resulted in 94.0 mg (31% yield) of 2,5-dioxopyrrolidin-1-yl 4-{[3-fluoro-2-(morpholin-4-yl)phenyl]methyl}piperazine-1-carboxylate as a white solid. $^1$H NMR (300 MHz, Chloroform-d) δ 7.08-7.17 (m, 2H), 6.97 (t, J=9.0 Hz, 1H), 3.80 (br, 4H), 3.50-3.67 (m, 6H), 3.10 (br, 4H), 2.83 (br, 4H), 2.54 (br, 4H). LCMS (ESI, m/z): 420 [M+H]$^+$.

Example 94

2,5-Dioxopyrrolidin-1-yl 4-(2-chloro-4-morpholinobenzyl)piperazine-1-carboxylate

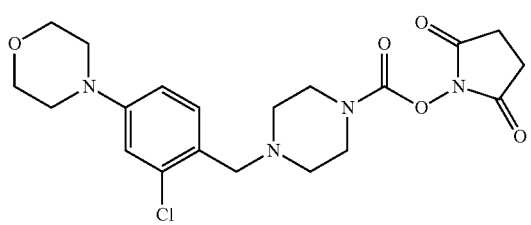 [SMILES: O=C(ON1C(=O)CCC1=O)N1CCN(Cc2ccc(N3CCOCC3)cc2Cl)CC1]

The title compound was synthesized directly from commercially available 2-chloro-4-morpholinobenzaldehyde and tert-butyl piperazine-1-carboxylate according to the representative procedure of Example 62, Steps 1, 2 and 3 to provide 2,5-dioxopyrrolidin-1-yl 4-(2-chloro-4-morpholinobenzyl)piperazine-1-carboxylate as a white solid: $^1$H NMR (400 MHz, Chloroform-d) δ 7.29-7.25 (m, 1H), 6.88 (d, J=2.5 Hz, 1H), 6.81-6.76 (m, 1H), 3.88-3.82 (m, 4H), 3.67-3.50 (m, 6H), 3.18-3.12 (m, 4H), 2.82 (s, 4H), 2.58-2.51 (m, 4H). LCMS (ESI, m/z): 459.1 [M+Na]$^+$.

Example 95

2,5-Dioxopyrrolidin-1-yl 4-(4-chloro-2-(4-chloro-1H-pyrazol-1-yl)benzyl)piperazine-1-carboxylate

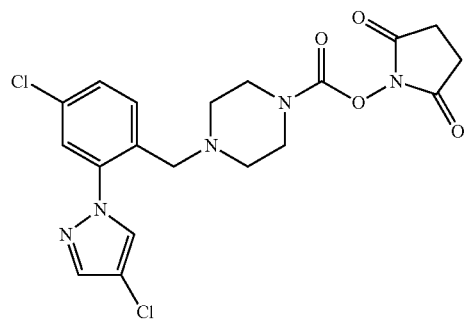 [SMILES: O=C(ON1C(=O)CCC1=O)N1CCN(Cc2ccc(Cl)cc2-n2cc(Cl)cn2)CC1]

The title compound was synthesized directly from commercially available 4-chloro-2-fluorobenzaldehyde and 4-chloro-1H-pyrazole according to the representative procedure of Example 65, Steps 1, 2, 3 and 4 to provide 2,5-dioxopyrrolidin-1-yl 4-(4-chloro-2-(4-chloro-1H-pyrazol-1-yl)benzyl)piperazine-1-carboxylate as a yellow oil. $^1$H NMR (400 MHz, Chloroform-d) δ 8.00 (s, 1H), 7.69-7.66 (m, 1H), 7.49-7.43 (m, 2H), 7.40 (dd, J=8.3, 2.1 Hz, 1H), 3.69-3.56 (m, 2H), 3.55-3.43 (m, 4H), 2.84 (s, 4H), 2.55-2.39 (m, 5H). LCMS (ESI, m/z): 452.0 [C$_{19}$H$_{19}$Cl$_2$N$_5$O$_4$]$^+$.

Example 96

2,5-Dioxopyrrolidin-1-yl (2R)-4-{[2-chloro-4-(morpholin-4-yl)phenyl]methyl}-2-methylpiperazine-1-carboxylate

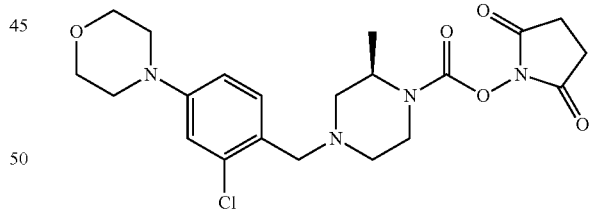

The title compound was synthesized directly from commercially available 2-chloro-4-morpholinobenzaldehyde and tert-butyl (2R)-2-methylpiperazine-1-carboxylate according to the representative procedure of Example 79, Steps 1, 2 and 3, to provide 2,5-dioxopyrrolidin-1-yl (2R)-4-{[2-chloro-4-(morpholin-4-yl)phenyl]methyl}-2-methylpiperazine-1-carboxylate as a white solid. $^1$H NMR (300 MHz, Chloroform-d) δ 7.26-7.35 (m, 1H), 6.88 (d, J=1.2 Hz, 1H), 6.78-6.81 (m, 1H), 4.31 (br, 1H), 3.85 (t, J=4.8 Hz, 5H), 3.22-3.60 (m, 3H), 3.16 (t, J=4.8 Hz, 4H), 2.82-2.95 (m, 1H), 2.74 (s, 4H), 2.57-2.69 (m, 1H), 2.29-2.53 (m, 2H), 1.30-1.69 (m, 3H). LCMS (ESI, m/z): 473 [M+Na]$^+$.

Example 97

2,5-Dioxopyrrolidin-1-yl 4-{[2-chloro-6-(pyrrolidin-1-yl)phenyl]methyl}piperazine-1-carboxylate

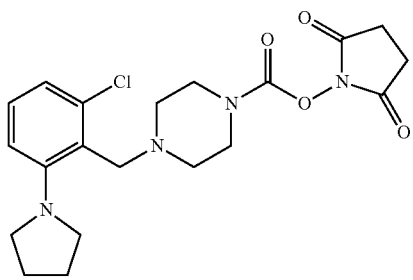 [SMILES: O=C(ON1C(=O)CCC1=O)N1CCN(Cc2c(Cl)cccc2N2CCCC2)CC1]

Step 1: Preparation of 2-chloro-6-(pyrrolidin-1-yl)benzaldehyde

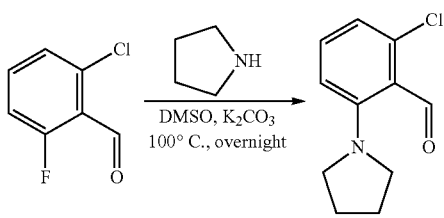

A 100-mL round-bottom flask was charged with 2-chloro-6-fluorobenzaldehyde (2.00 g, 12.6 mmol, 1.00 equiv), pyrrolidine (1.34 g, 18.8 mmol, 1.49 equiv), potassium carbonate (4.34 g, 31.4 mmol, 2.49 equiv), and dimethyl sulfoxide (20 mL). The resulting solution was stirred overnight at 100° C. in an oil bath, then diluted with H$_2$O (20 mL). The resulting solution was extracted with dichloromethane (3×20 mL), and the organic layers were combined, washed with H$_2$O (3×10 mL), dried over anhydrous sodium sulfate, filtered, and concentrated under reduced pressure. The residue was chromatographed on a silica gel column with ethyl acetate/petroleum ether (1/15) to yield 1.40 g (53% yield) of 2-chloro-6-(pyrrolidin-1-yl)benzaldehyde as a yellow solid. $^1$H NMR 300 MHz (CDCl$_3$) δ 10.49 (s, 1H), 7.20-7.25 (m, 1H), 6.73-6.78 (m, 2H), 3.14-3.19 (m, 4H), 1.94-2.02 (m, 4H). LCMS (ESI, m/z): 210 [M+H]$^+$.

Step 2: Preparation of tert-butyl 4-[[2-chloro-6-(pyrrolidin-1-yl)phenyl]methyl]piperazine-1-carboxylate

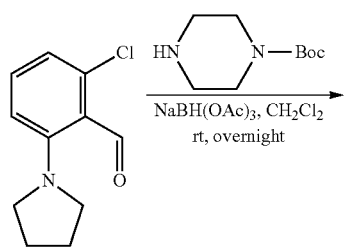

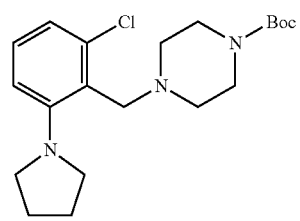

A 100-mL round-bottom flask was charged with 2-chloro-6-(pyrrolidin-1-yl)benzaldehyde (1.40 g, 6.68 mmol, 1.10 equiv), tert-butyl piperazine-1-carboxylate (1.13 g, 6.07 mmol, 1.00 equiv), and dichloromethane (20 mL). The mixture was stirred 30 min at room temperature. Sodium triacetoxyborohydride (3.85 g, 18.2 mmol, 2.99 equiv) was added. The resulting solution was stirred overnight at room temperature and diluted with 1,2-dichloroethane (20 mL). The resulting solution was washed with H$_2$O (2×20 mL), dried over anhydrous sodium sulfate, filtered, and concentrated under reduced pressure. The residue was chromatographed on a silica gel column with ethyl acetate/petroleum ether (3/7) to yield 1.95 g (77% yield) of tert-butyl 4-[[2-chloro-6-(pyrrolidin-1-yl)phenyl]methyl]piperazine-1-carboxylate as a yellow oil. LCMS (ESI, m/z): 380 [M+H]$^+$.

Step 3: Preparation of 1-[[2-chloro-6-(pyrrolidin-1-yl)phenyl]methyl]piperazine

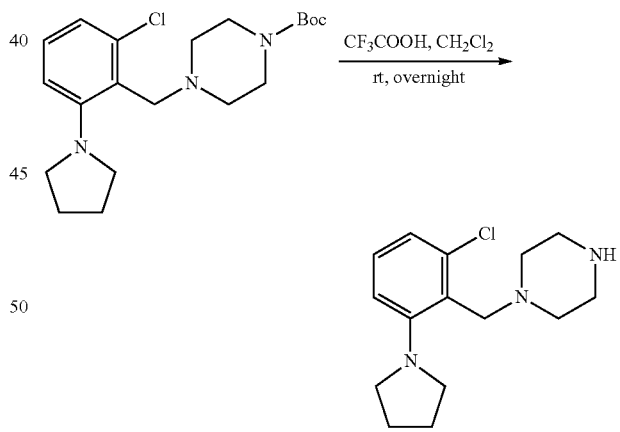

A 100 mL round-bottom flask was charged with tert-butyl 4-[[2-chloro-6-(pyrrolidin-1-yl)phenyl]methyl]piperazine-1-carboxylate (500 mg, 1.32 mmol, 1.00 equiv), dichloromethane (10 mL). The mixture was cooled to 0° C. Trifluoroacetic acid (1 mL) was added dropwise at 0° C. The resulting solution was stirred overnight at room temperature and concentrated under reduced pressure to yield 490 mg (crude) of 1-[[2-chloro-6-(pyrrolidin-1-yl)phenyl]methyl]piperazine as a yellow oil. LCMS (ESI, m/z): 280 [M+H]$^+$.

Step 3: Preparation of 2,5-dioxopyrrolidin-1-yl 4-{[2-chloro-6-(pyrrolidin-1-yl)phenyl]methyl}piperazine-1-carboxylate

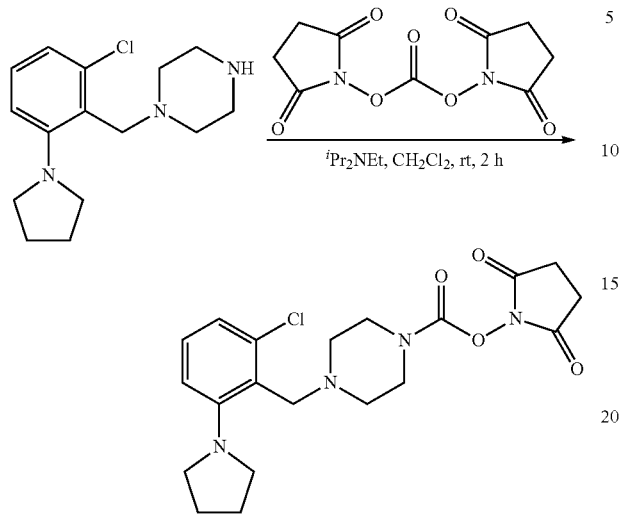

A 50-mL round-bottom flask was charged with 1-[[2-chloro-6-(pyrrolidin-1-yl)phenyl]methyl]piperazine (280 mg, 1.00 mmol, 1.00 equiv), bis(2,5-dioxopyrrolidin-1-yl) carbonate (256 mg, 1.00 mmol, 1.00 equiv), and dichloromethane (10 mL). N,N-Diisopropylethylamine (258 mg, 2.00 mmol, 1.99 equiv) was added dropwise. The resulting solution was stirred for 2 h at room temperature and diluted with H$_2$O (30 mL). The resulting solution was extracted with dichloromethane (3×10 mL), and the organic layers were combined, washed with H$_2$O (3×5 mL), dried over anhydrous sodium sulfate, filtered, and concentrated under reduced pressure. The residue was chromatographed on a silica gel column with ethyl acetate/petroleum ether (15/1). The crude product (453 mg) was purified by preparative HPLC using the following gradient conditions: 20% CH$_3$CN/80% Phase A increasing to 80% CH$_3$CN over 10 min, then to 100% CH$_3$CN over 0.1 min, holding at 100% CH$_3$CN for 1.9 min, then reducing to 20% CH$_3$CN over 0.1 min, and holding at 20% for 1.9 min, on a Waters 2767-5 Chromatograph. Column: Xbridge Prep C18, 19*150 mm, 5 um; Mobile phase: Phase A: water; Phase B: CH$_3$CN; Detector, UV 220 & 254 nm. Purification resulted in 269 mg (64% yield) of 2,5-dioxopyrrolidin-1-yl 4-{[2-chloro-6-(pyrrolidin-1-yl)phenyl]methyl}piperazine-1-carboxylate as a yellow oil. $^1$H NMR (300 MHz, Chloroform-d) δ 7.08-7.14 (m, 1H), 6.93-7.01 (m, 2H), 3.77 (br, 2H), 3.44-3.57 (m, 4H), 3.16-3.20 (m, 4H), 2.79 (br, 4H), 2.58 (br, 4H), 1.86-1.95 (m, 4H). LCMS (ESI, m/z): 421 [M+H]$^+$.

Example 98

2,5-Dioxopyrrolidin-1-yl 4-{[5-chloro-2-(pyrrolidin-1-yl)phenyl]methyl}piperazine-1-carboxylate

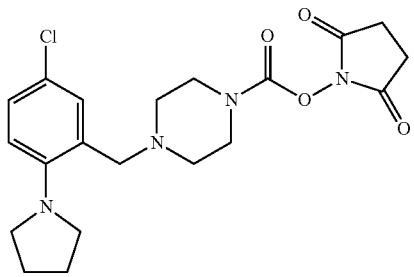 [SMILES: O=C(ON1C(=O)CCC1=O)N1CCN(Cc2cc(Cl)ccc2N2CCCC2)CC1]

Step 1: Preparation of 5-chloro-2-(pyrrolidin-1-yl)benzaldehyde

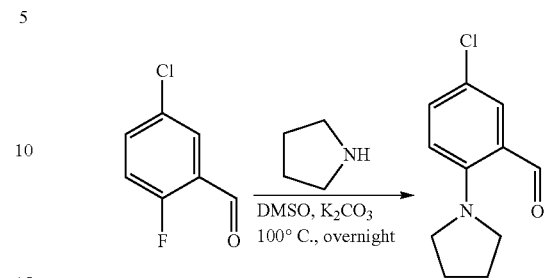

A 100-mL round-bottom flask was charged with 5-chloro-2-fluorobenzaldehyde (2.00 g, 12.6 mmol, 1.00 equiv), pyrrolidine (1.34 g, 18.8 mmol, 1.49 equiv), potassium carbonate (4.34 g, 31.4 mmol, 1.92 equiv), and dimethyl sulfoxide (10 mL). The resulting solution was stirred overnight at 100° C. (oil bath) and diluted with H$_2$O (20 mL). The resulting solution was extracted with dichloromethane (3×20 mL), and the organic layers were combined, washed with H$_2$O (3×10 mL), dried over anhydrous sodium sulfate, filtered, and concentrated under reduced pressure. The residue was chromatographed on a silica gel column with ethyl acetate/petroleum ether (1/10) to yield 1.80 g (68% yield) of 5-chloro-2-(pyrrolidin-1-yl)benzaldehyde as a brown oil. $^1$H NMR 300 MHz (CDCl$_3$) δ 10.05 (s, 1H), 7.66 (d, J=2.4 Hz, 1H), 7.267-7.31 (m, 1H), 6.76 (d, J=9.0 Hz, 1H), 3.29-3.37 (m, 4H), 1.95-2.04 (m, 4H). LCMS (ESI, m/z): 210 [M+H]$^+$.

Step 2: Preparation of tert-butyl 4-[[5-chloro-2-(pyrrolidin-1-yl)phenyl]methyl]piperazine-1-carboxylate

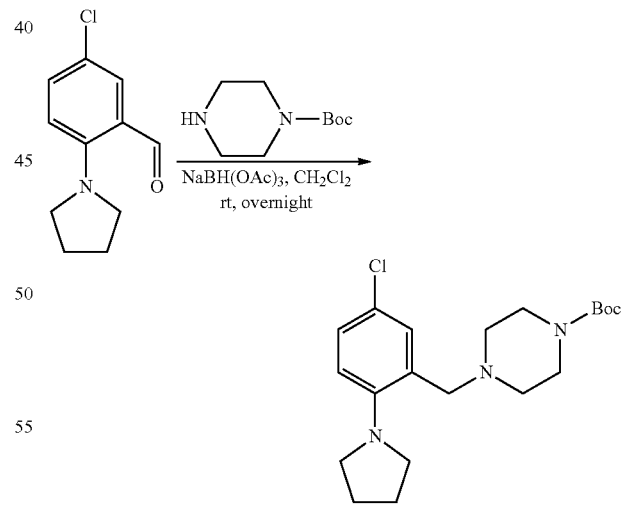

A 100-mL round-bottom flask was charged with 5-chloro-2-(pyrrolidin-1-yl)benzaldehyde (1.80 g, 8.58 mmol, 1.10 equiv), tert-butyl piperazine-1-carboxylate (1.45 g, 7.79 mmol, 1.00 equiv), and dichloromethane (20 mL). The mixture was stirred 30 min at room temperature. Sodium triacetoxyborohydride (4.96 g, 23.4 mmol, 3.01 equiv) was added. The resulting solution was stirred overnight at room temperature. The resulting mixture was washed with H$_2$O (2×20 mL), dried over anhydrous sodium sulfate, filtered, and concentrated under reduced pressure. The residue was chromatographed on a silica gel column with ethyl acetate/petroleum ether (1/4) to yield 2.50 g (77% yield) of tert-butyl 4-[[5-chloro-2-(pyrrolidin-1-yl)phenyl]methyl]piperazine-1-carboxylate as a yellow oil. LCMS (ESI, m/z): 380 [M+H]$^+$.

Step 3: Preparation of 1-[[5-chloro-2-(pyrrolidin-1-yl)phenyl]methyl]piperazine

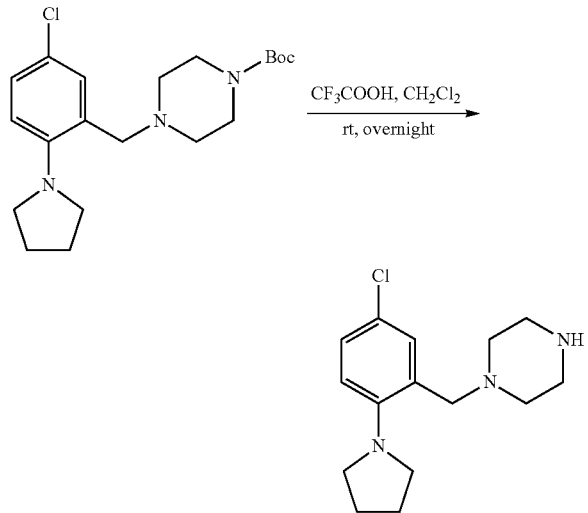

A 100-mL round-bottom flask was charged with tert-butyl 4-[[5-chloro-2-(pyrrolidin-1-yl)phenyl]methyl]piperazine-1-carboxylate (500 mg, 1.32 mmol, 1.00 equiv) and dichloromethane (10 mL). The mixture was cooled to 0° C. Trifluoroacetic acid (1 mL) was added dropwise at 0° C. The resulting solution was stirred overnight at room temperature. The resulting mixture was concentrated under reduced pressure to yield 490 mg (crude) of 1-[[5-chloro-2-(pyrrolidin-1-yl)phenyl]methyl]piperazine as a brown solid. LCMS (ESI, m/z): 280 [M+H]$^+$.

Step 4: Preparation of 2,5-dioxopyrrolidin-1-yl 4-{[5-chloro-2-(pyrrolidin-1-yl)phenyl]methyl}piperazine-1-carboxylate

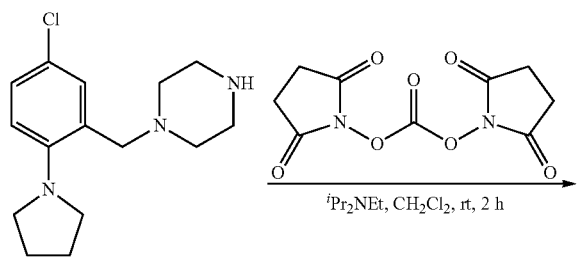

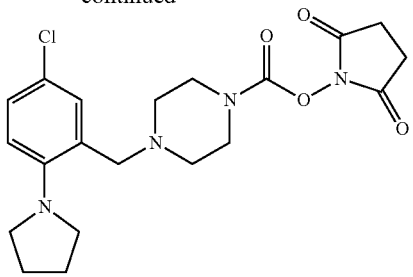

A 50-mL round-bottom flask was charged with 1-[[5-chloro-2-(pyrrolidin-1-yl)phenyl]methyl]piperazine (280 mg, 1.00 mmol, 1.00 equiv), bis(2,5-dioxopyrrolidin-1-yl) carbonate (256 mg, 1.00 mmol, 1.00 equiv), and dichloromethane (10 mL). N,N-Diisopropylethylamine (258 mg, 2.00 mmol, 1.99 equiv) was added dropwise. The resulting solution was stirred for 2 h at room temperature and diluted with H$_2$O (30 mL). The resulting solution was extracted with dichloromethane (3×10 mL), and the organic layers were combined, washed with H$_2$O (3×5 mL), dried over anhydrous sodium sulfate, filtered, and concentrated under reduced pressure. The residue was chromatographed on a silica gel column with ethyl acetate/petroleum ether (3/1). The crude product (304 mg) was purified by preparative HPLC using the following gradient conditions: 20% CH$_3$CN/80% Phase A increasing to 80% CH$_3$CN over 10 min, then to 100% CH$_3$CN over 0.1 min, holding at 100% CH$_3$CN for 1.9 min, then reducing to 20% CH$_3$CN over 0.1 min, and holding at 20% for 1.9 min, on a Waters 2767-5 Chromatograph. Column: Xbridge Prep C18, 19*150 mm, 5 um; Mobile phase: Phase A: water; Phase B: CH$_3$CN; Detector, UV 220 & 254 nm. Purification resulted in 119 mg (28% yield) of 2,5-dioxopyrrolidin-1-yl 4-{[5-chloro-2-(pyrrolidin-1-yl)phenyl]methyl}piperazine-1-carboxylate as a white solid. $^1$H NMR (300 MHz, Chloroform-d) δ 7.42-7.43 (m, 1H), 7.10-7.13 (m, 1H), 6.86 (d, J=8.4 Hz, 1H), 3.54-3.67 (m, 6H), 3.10-3.14 (m, 4H), 2.82 (br, 4H), 2.53 (br, 4H), 1.90-1.97 (m, 4H). LCMS (ESI, m/z): 421 [M+H]$^+$.

Example 99

2,5-Dioxopyrrolidin-1-yl 4-(4-(pyrrolidin-1-yl)benzyl)piperazine-1-carboxylate

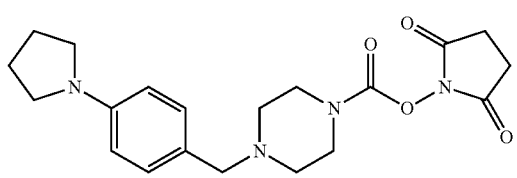 [SMILES: O=C(ON1C(=O)CCC1=O)N1CCN(Cc2ccc(N3CCCC3)cc2)CC1]

The title compound was synthesized directly from commercially available 4-(pyrrolidin-1-yl)benzaldehyde and tert-butyl piperazine-1-carboxylate according to the representative procedure of Example 62, Steps 1, 2 and 3 to provide 2,5-dioxopyrrolidin-1-yl 4-(4-(pyrrolidin-1-yl)benzyl)piperazine-1-carboxylate as an amorphous white solid. $^1$H NMR (400 MHz, Chloroform-d) δ 7.07 (d, J=8.3 Hz, 2H), 6.45 (d, J=8.2 Hz, 2H), 3.66-3.50 (m, 2H), 3.50-3.40 (m, 2H), 3.38 (s, 2H), 3.26-3.09 (m, 4H), 2.81-2.67 (m, 4H), 2.47-2.30 (m, 4H), 1.98-1.80 (m, 4H). LCMS (ESI, m/z): 386.1 [M+H]$^+$.

Example 100

2,5-Dioxopyrrolidin-1-yl 4-(4-morpholinobenzyl)piperazine-1-carboxylate

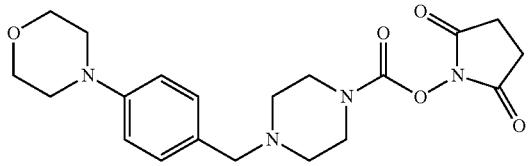 [SMILES: O=C(ON1C(=O)CCC1=O)N1CCN(Cc2ccc(N3CCOCC3)cc2)CC1]

The title compound was synthesized directly from commercially available 4-morpholinobenzaldehyde and tert-butyl piperazine-1-carboxylate according to the representative procedure of Example 62, Steps 1, 2 and 3 to provide 2,5-dioxopyrrolidin-1-yl 4-(4-morpholinobenzyl)piperazine-1-carboxylate as an amorphous white solid. $^1$H NMR (400 MHz, Chloroform-d) δ 7.14 (d, J=8.1 Hz, 2H), 6.81 (d, J=8.4 Hz, 2H), 3.84-3.73 (m, 4H), 3.56 (s, 2H), 3.45 (s, 2H), 3.40 (s, 2H), 3.14-3.03 (m, 4H), 2.75 (s, 4H), 2.46-2.32 (m, 4H). LCMS (ESI, m/z): 425.0 [M+Na]$^+$.

Example 101

2,5-dioxopyrrolidin-1-yl 4-(3-chloro-4-morpholinobenzyl)piperazine-1-carboxylate

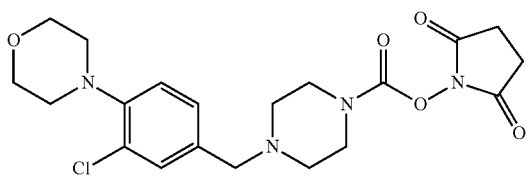 [SMILES: O=C(ON1C(=O)CCC1=O)N1CCN(Cc2ccc(N3CCOCC3)c(Cl)c2)CC1]

The title compound was synthesized directly from commercially available 3-chloro-4-morpholinobenzaldehyde and tert-butyl piperazine-1-carboxylate according to the representative procedure of Example 62, Steps 1, 2 and 3 to provide 2,5-dioxopyrrolidin-1-yl 4-(3-chloro-4-morpholinobenzyl)piperazine-1-carboxylate as a white solid: $^1$H NMR (400 MHz, Chloroform-d) δ 7.36 (d, J=1.9 Hz, 1H), 7.17 (dd, J=8.2, 2.0 Hz, 1H), 7.00 (d, J=8.1 Hz, 1H), 3.92-3.86 (m, 4H), 3.66-3.62 (m, 2H), 3.58-3.52 (m, 2H), 3.46 (s, 2H), 3.13-2.99 (m, 4H), 2.83 (s, 4H), 2.53-2.47 (m, 4H). LCMS (ESI, m/z): 437.1 [M+H]$^+$.

Example 102

2,5-Dioxopyrrolidin-1-yl 4-{[4-(morpholin-4-yl)-2-(trifluoromethoxy)phenyl]methyl}piperazine-1-carboxylate

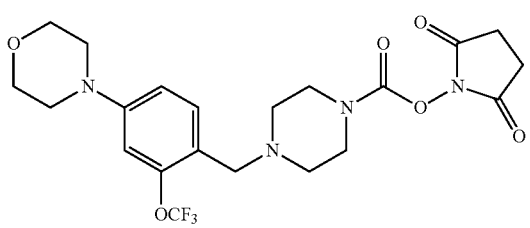

Step 1: Preparation of 4-(morpholin-4-yl)-2-(trifluoromethoxy)benzaldehyde

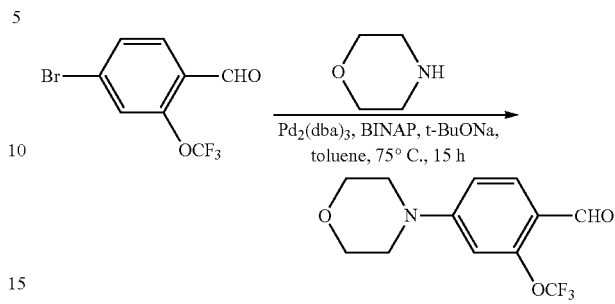

A 500-mL round-bottom flask was purged with and maintained under an inert atmosphere of nitrogen then charged with 4-bromo-2-(trifluoromethoxy)benzaldehyde (8.00 g, 29.7 mmol, 1.00 equiv), morpholine (2.59 g, 29.7 mmol, 1.00 equiv), t-BuONa (4.28 g, 44.5 mmol, 1.50 equiv), Pd$_2$(dba)$_3$ (1.36 g, 1.49 mmol, 0.05 equiv), BINAP (1.85 g, 2.97 mmol, 0.10 equiv), and toluene (150 mL). The resulting solution was stirred for 15 h at 75° C. in an oil bath. The reaction progress was monitored by LCMS. The resulting solution was diluted with 50 mL of water and extracted with ethyl acetate (3×30 mL). The organic layers were combined, dried over anhydrous sodium sulfate, filtered, and concentrated under reduced pressure. The residue was chromatographed on a silica gel column with ethyl acetate/petroleum ether (1/4) to provide 0.800 g (10% yield) of 4-(morpholin-4-yl)-2-(trifluoromethoxy)benzaldehyde as a yellow solid. LCMS (ESI, m/z): 276 [M+H]$^+$.

Step 2: Preparation of tert-butyl 4-[[4-(morpholin-4-yl)-2-(trifluoromethoxy)phenyl]methyl]piperazine-1-carboxylate

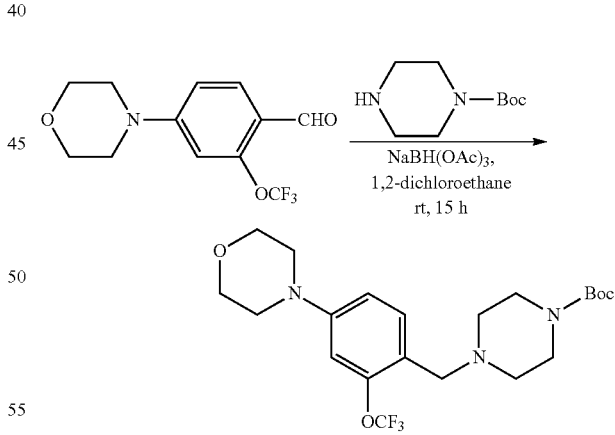

A 40-mL vial was charged with 4-(morpholin-4-yl)-2-(trifluoromethoxy)benzaldehyde (400 mg, 1.45 mmol, 1.00 equiv), tert-butyl piperazine-1-carboxylate (270 mg, 1.45 mmol, 1.00 equiv), and 1,2-dichloroethane (15 mL). The resulting solution was stirred for 1 h at room temperature. Sodium triacetoxyhydroborate (925 mg, 4.36 mmol, 3.00 equiv) was added. The resulting solution was stirred for 15 h at room temperature. Reaction progress was monitored by LCMS. The resulting solution was diluted with 15 mL of water. The resulting solution was extracted with dichloromethane (3×15 mL), and the organic layers were combined, dried over anhydrous sodium sulfate, filtered, and concentrated under reduced pressure. The residue was chromatographed on a silica gel column with ethyl acetate/petroleum ether (1/3) to provide 590 mg (91% yield) of tert-butyl 4-[[4-(morpholin-4-yl)-2-(trifluoromethoxy)phenyl]methyl]piperazine-1-carboxylate as a yellow oil. LCMS (ESI, m/z): 446 [M+H]$^+$.

Step 3: Preparation of 4-[4-(piperazin-1-ylmethyl)-3-(trifluoromethoxy)phenyl]morpholine

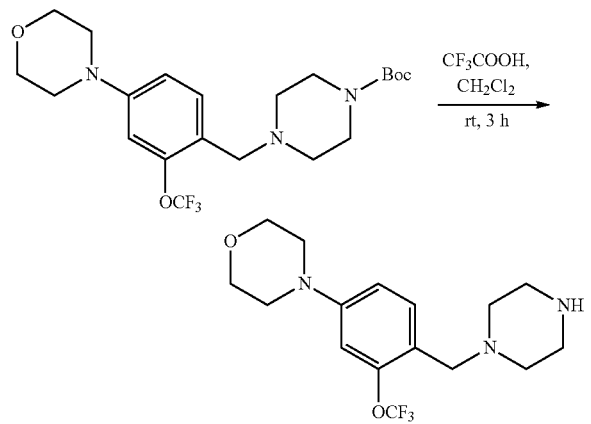

A 50-mL round-bottom flask was charged with a solution of tert-butyl 4-[[4-(morpholin-4-yl)-2-(trifluoromethoxy)phenyl]methyl]piperazine-1-carboxylate (590 mg, 1.32 mmol, 1.00 equiv) in dichloromethane (15 mL). Trifluoroacetic acid (262 mg, 2.30 mmol, 1.74 equiv) was added dropwise at 0° C. The resulting solution was stirred for 3 h at room temperature. Reaction progress was monitored by LCMS. The resulting mixture was concentrated under reduced pressure to provide 445 mg (crude) of 4-[4-(piperazin-1-ylmethyl)-3-(trifluoromethoxy)phenyl]morpholine as a light yellow oil. LCMS (ESI, m/z): 346 [M+H]$^+$.

Step 4: Preparation of 2,5-dioxopyrrolidin-1-yl 4-{[4-(morpholin-4-yl)-2-(trifluoromethoxy)phenyl]methyl}piperazine-1-carboxylate

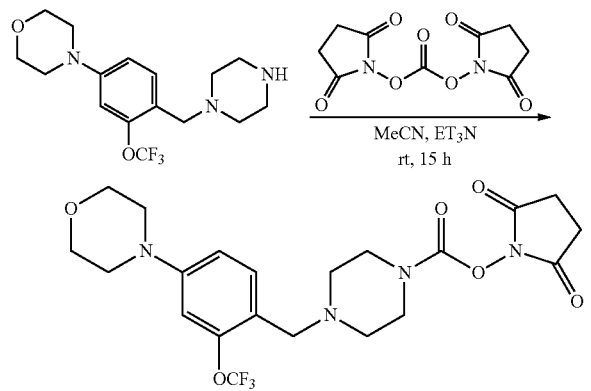

A 50-mL round-bottom flask was purged and maintained with an inert atmosphere of nitrogen and charged with 4-[4-(piperazin-1-ylmethyl)-3-(trifluoromethoxy)phenyl]morpholine (200 mg, 0.580 mmol, 1.00 equiv), bis(2,5-dioxopyrrolidin-1-yl) carbonate (297 mg, 1.16 mmol, 2.00 equiv), acetonitrile (15 mL), and triethylamine (293 mg, 2.90 mmol, 5.00 equiv). The resulting solution was stirred for 15 h at room temperature. Reaction progress was monitored by LCMS. The resulting mixture was concentrated under reduced pressure. The crude product (393 mg) was purified by preparative HPLC using the following gradient conditions: 20% CH$_3$CN/80% Phase A increasing to 80% CH$_3$CN over 10 min, then to 100% CH$_3$CN over 0.1 min, holding at 100% CH$_3$CN for 1.9 min, then reducing to 20% CH$_3$CN over 0.1 min, and holding at 20% for 1.9 min, on a Waters 2767-5 Chromatograph. Column: Xbridge Prep C18, 19*150 mm, 5 um; Mobile phase: Phase A: water; Phase B: CH$_3$CN; Detector, UV 220 & 254 nm. Purification resulted in 106 mg (38% yield) of 2,5-dioxopyrrolidin-1-yl 4-{[4-(morpholin-4-yl)-2-(trifluoromethoxy)phenyl]methyl}piperazine-1-carboxylate as a white solid. $^1$H NMR (300 MHz, Chloroform-d) δ 7.36 (d, J=7.8 Hz, 1H), 6.82-6.86 (m, 1H), 6.76 (s, 1H), 3.84-3.90 (m, 4H), 3.66 (s, 2H), 3.56 (s, 4H), 3.18-3.21 (m, 4H), 2.85 (s, 4H), 2.54 (s, 4H). LCMS (ESI, m/z): 509 [M+Na]$^+$.

Example 103

2,5-Dioxopyrrolidin-1-yl (2R)-2-methyl-4-{[4-(morpholin-4-yl)-2-(trifluoromethoxy)phenyl]methyl}piperazine-1-carboxylate

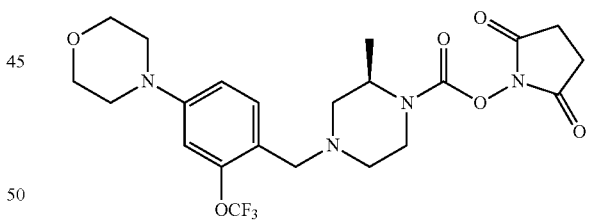

4-(Morpholin-4-yl)-2-(trifluoromethoxy)benzaldehyde was prepared according to Example 102, Step 1. The title compound was synthesized from this aldehyde and tert-butyl (2R)-2-methylpiperazine-1-carboxylate according to the representative procedure of Example 79, Steps 1, 2 and 3 to provide 2,5-dioxopyrrolidin-1-yl (2R)-2-methyl-4-{[4-(morpholin-4-yl)-2-(trifluoromethoxy)phenyl]methyl}piperazine-1-carboxylate as a white solid. $^1$H NMR (300 MHz, Chloroform-d) δ 7.36 (d, J=8.4 Hz, 1H), 6.80-6.83 (m, 1H), 6.73 (s, 1H), 4.28 (br, 1H), 3.86 (t, J=4.8 Hz, 5H), 3.48 (s, 2H), 3.33 (s, 1H), 3.17 (t, J=4.6 Hz, 4H), 2.81 (s, 5H), 2.63 (d, J=11.1 Hz, 1H), 2.33 (d, J=10.8 Hz, 1H), 2.18 (t, J=10.0 Hz, 1H), 1.39 (s, 3H). LCMS (ESI, m/z): 523 [M+Na]$^+$.

Example 104

2,5-Dioxopyrrolidin-1-yl 4-{[4-(pyrrolidin-1-yl)-2-(trifluoromethoxy)phenyl]methyl}piperazine-1-carboxylate

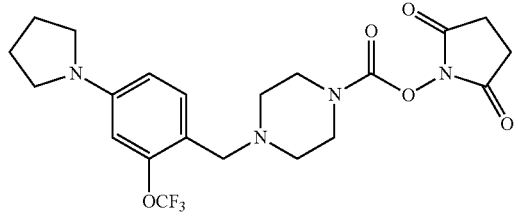 [SMILES: O=C(ON1C(=O)CCC1=O)N1CCN(Cc2ccc(N3CCCC3)cc2OC(F)(F)F)CC1]

4-Pyrrolidino-2-(trifluoromethoxy)benzaldehyde was prepared according to the representative procedure of Example 102, Step 1 using pyrrolidine. The title compound was synthesized directly from this aldehyde and tert-butyl piperazine-1-carboxylate according to the representative procedure of Example 65, Steps 2, 3 and 4, to provide 2,5-dioxopyrrolidin-1-yl 4-{[4-(pyrrolidin-1-yl)-2-(trifluoromethoxy)phenyl]methyl}piperazine-1-carboxylate as a light yellow oil. $^1$H NMR (300 MHz, Chloroform-d) δ 7.25 (s, 1H), 6.46-6.50 (m, 1H), 6.40 (s, 1H), 3.54-3.66 (m, 6H), 3.23-3.33 (m, 4H), 2.84 (s, 4H), 2.53 (s, 4H), 2.02-2.07 (m, 4H). LCMS (ESI, m/z): 493 [M+Na]$^+$.

Example 105

2,5-Dioxopyrrolidin-1-yl 4-{[2-(pyrrolidin-1-yl)-4-(trifluoromethyl)phenyl]methyl}piperazine-1-carboxylate

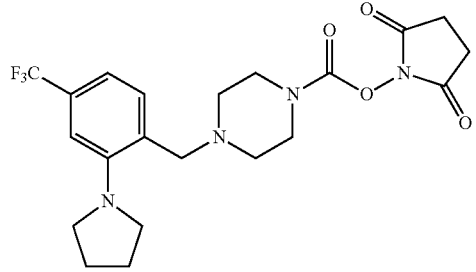 [SMILES: O=C(ON1C(=O)CCC1=O)N1CCN(Cc2ccc(C(F)(F)F)cc2N2CCCC2)CC1]

The title compound was synthesized directly from 2-fluoro-4-(trifluoromethyl)benzaldehyde and pyrrolidine according to the representative procedure of Example 76, Steps 1, 2, 3 and 4 to provide 2,5-dioxopyrrolidin-1-yl 4-{[2-(pyrrolidin-1-yl)-4-(trifluoromethyl)phenyl]methyl}piperazine-1-carboxylate as a light yellow oil. $^1$H NMR (300 MHz, Chloroform-d) δ 7.52 (d, J=8.4 Hz, 1H), 7.08-7.10 (m, 2H), 3.53-3.65 (m, 6H), 3.22-3.26 (m, 4H), 2.80 (br, 4H), 2.49-2.52 (m, 4H), 1.93-1.97 (m, 4H). LCMS (ESI, m/z): 455 [M+H]$^+$.

Example 106

2,5-Dioxopyrrolidin-1-yl 4-{[3-chloro-2-(pyrrolidin-1-yl)phenyl]methyl}piperazine-1-carboxylate

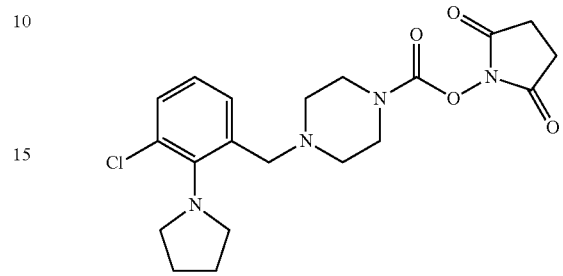

The title compound was synthesized directly from 3-chloro-2-fluorobenzaldehyde and pyrrolidine according to the representative procedure of Example 76, Steps 1, 2, 3 and 4 to provide 2,5-dioxopyrrolidin-1-yl 4-{[3-chloro-2-(pyrrolidin-1-yl)phenyl]methyl}piperazine-1-carboxylate as an orange solid. $^1$H NMR (300 MHz, Chloroform-d) δ 7.35-7.37 (m, 1H), 7.30 (s, 1H), 7.06-7.12 (m, 1H), 3.54-3.62 (m, 6H), 3.19-3.23 (m, 4H), 2.82 (br, 4H), 2.52 (br, 4H), 1.95-2.04 (m, 4H). LCMS (ESI, m/z): 421 [M+H]$^+$.

Example 107

2,5-Dioxopyrrolidin-1-yl 4-{[3-fluoro-2-(pyrrolidin-1-yl)phenyl]methyl}piperazine-1-carboxylate

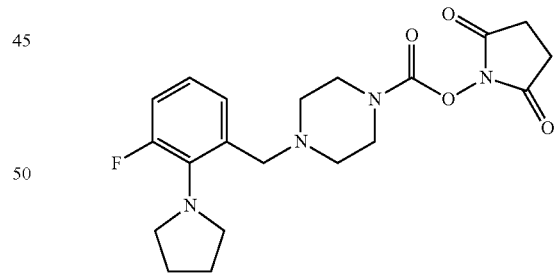

The title compound was synthesized directly from 2,3-difluorobenzaldehyde and pyrrolidine according to the representative procedure of Example 76, Steps 1, 2, 3 and 4 to provide 2,5-dioxopyrrolidin-1-yl 4-{[3-fluoro-2-(pyrrolidin-1-yl)phenyl]methyl}piperazine-1-carboxylate as an orange syrup. $^1$H NMR (300 MHz, Chloroform-d) δ 7.18-7.20 (m, 1H), 7.03-7.10 (m, 1H), 6.90-6.98 (m, 1H), 3.51-3.63 (m, 6H), 3.11-3.15 (m, 4H), 2.80 (br, 4H), 2.52 (br, 4H), 1.89-1.98 (m, 4H). LCMS (ESI, m/z): 405 [M+H]$^+$.

Example 108

2,5-Dioxopyrrolidin-1-yl 4-(3-fluoro-4-(1H-pyrazol-1-yl)benzyl)piperazine-1-carboxylate

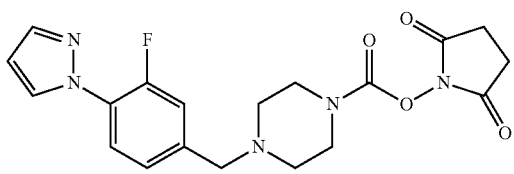 [SMILES: O=C(ON1C(=O)CCC1=O)N1CCN(Cc2ccc(-n3cccn3)c(F)c2)CC1]

The title compound was synthesized directly from commercially available 3-fluoro-4-(1H-pyrazol-1-yl)benzaldehyde and tert-butyl piperazine-1-carboxylate according to the representative procedure of Example 62, Steps 1, 2 and 3 to provide 2,5-dioxopyrrolidin-1-yl 4-(3-fluoro-4-(1H-pyrazol-1-yl)benzyl)piperazine-1-carboxylate as an amorphous white solid. $^1$H NMR (400 MHz, Chloroform-d) δ 7.93 (s, 1H), 7.82-7.72 (m, 1H), 7.67 (s, 1H), 7.18-7.08 (m, 2H), 6.42 (s, 1H), 3.61 (s, 2H), 3.49 (s, 4H), 2.76 (s, 4H), 2.53-2.39 (m, 4H). LCMS (ESI, m/z): 402.1 [M+H]$^+$.

Example 109

2,5-Dioxopyrrolidin-1-yl 4-[(4-chloro-2-{8-oxa-2-azaspiro[4.5]decan-2-yl}phenyl)methyl]piperazine-1-carboxylate

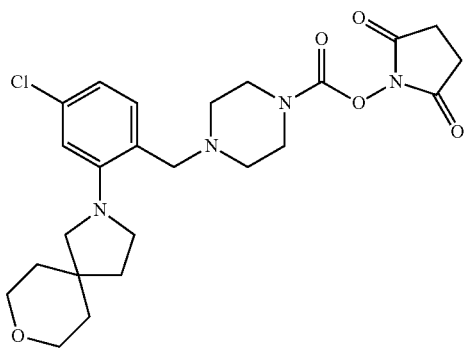 [SMILES: O=C(ON1C(=O)CCC1=O)N1CCN(Cc2ccc(Cl)cc2N2CCC3(CCOCC3)C2)CC1]

The title compound was synthesized directly from 4-chloro-2-fluorobenzaldehyde and 8-oxa-2-azaspiro[4.5]decane according to the representative procedure of Example 76, Steps 1, 2, 3 and 4 to provide 2,5-dioxopyrrolidin-1-yl 4-[(4-chloro-2-{8-oxa-2-azaspiro[4.5]decan-2-yl}phenyl)methyl]piperazine-1-carboxylate as a white solid. $^1$H NMR (300 MHz, Chloroform-d) δ: 7.23-7.26 (m, 1H), 6.82 (s, 2H), 3.63-3.78 (m, 6H), 3.50 (br, 4H), 3.31 (t, J=6.8 Hz, 2H), 3.15 (s, 2H), 2.82 (s, 4H), 2.48 (br, 4H), 1.82-1.91 (m, 2H), 1.60-1.71 (m, 4H). LCMS (ESI, m/z): 491 [M+H]$^+$.

Example 110

2,5-Dioxopyrrolidin-1-yl 4-{[4-chloro-2-(4-methanesulfonylpiperazin-1-yl)phenyl]methyl}piperazine-1-carboxylate

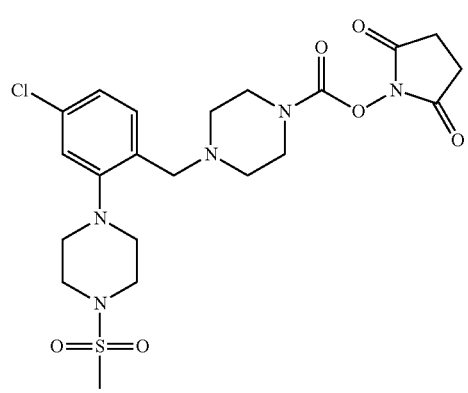 [SMILES: CS(=O)(=O)N1CCN(c2cc(Cl)ccc2CN2CCN(C(=O)ON3C(=O)CCC3=O)CC2)CC1]

The title compound was synthesized directly from 4-chloro-2-fluorobenzaldehyde and 1-(methylsulfonyl)piperazine according to the representative procedure of Example 76, Steps 1, 2, 3 and 4 to provide 2,5-dioxopyrrolidin-1-yl 4-{[4-chloro-2-(4-methanesulfonylpiperazin-1-yl)phenyl]methyl}piperazine-1-carboxylate as a white solid. 1H NMR (300 MHz, Chloroform-d): δ 7.40 (d, J=8.1 Hz, 1H), 7.06-7.11 (m, 2H), 3.54-3.62 (m, 6H), 3.38 (br, 4H), 3.05 (br, 4H), 2.82-2.88 (m, 7H), 2.52 (br, 4H). LCMS (ESI, m/z): 514 [M+H]$^+$.

Example 111

2,5-Dioxopyrrolidin-1-yl 4-[(4-chloro-2-{1-oxo-2,8-diazaspiro[4.51]decan-8-yl}phenyl)methyl]piperazine-1-carboxylate

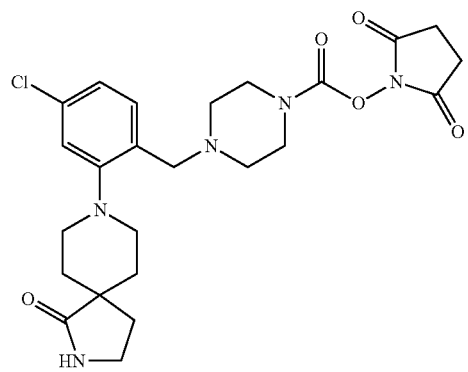 [SMILES: O=C(ON1C(=O)CCC1=O)N1CCN(Cc2ccc(Cl)cc2N2CCC3(CCNC3=O)CC2)CC1]

The title compound was synthesized directly from 4-chloro-2-fluorobenzaldehyde and 2,8-diazaspiro[4.5]decan-1-one according to the representative procedure of Example 76, Steps 1, 2, 3 and 4 to provide 2,5-dioxopyrrolidin-1-yl 4-[(4-chloro-2-{1-oxo-2,8-diazaspiro[4.5]decan-8-yl}phenyl)methyl]piperazine-1-carboxylate as a pink solid. $^1$H NMR (300 MHz, Chloroform-d): δ 7.32-7.34 (m, 1H), 7.03-7.07 (m, 2H), 6.08 (s, 1H), 3.50-3.61 (m, 6H), 3.36-3.41 (m, 2H), 3.23-3.27 (m, 2H), 2.82 (br, 4H), 2.68-

2.76 (m, 2H), 2.54 (br, 4H), 2.06-2.16 (m, 4H), 1.54-1.58 (m, 2H). LCMS (ESI, m/z): 504 [M+H]⁺.

Example 112

2,5-Dioxopyrrolidin-1-yl 4-{[2-(azetidin-1-yl)-4-chlorophenyl]methyl}piperazine-1-carboxylate

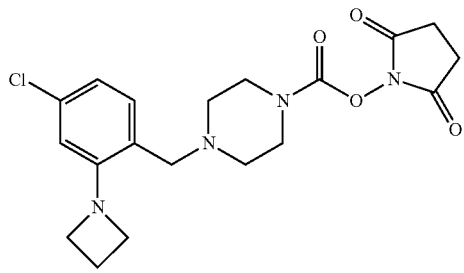 [SMILES: O=C(ON1C(=O)CCC1=O)N1CCN(Cc2ccc(Cl)cc2N2CCC2)CC1]

Step 1: Preparation of tert-butyl 4-[(2-bromo-4-chlorophenyl)methyl]piperazine-1-carboxylate

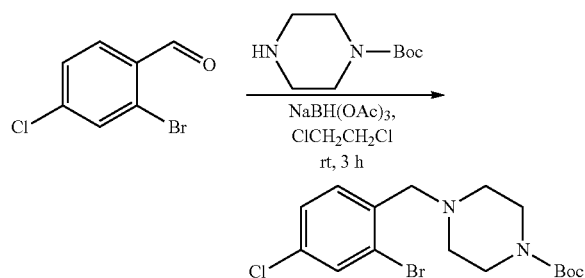

A 500-mL round-bottom flask was charged with 2-bromo-4-chlorobenzaldehyde (30.0 g, 137 mmol, 1.00 equiv), tert-butyl piperazine-1-carboxylate (23.2 g, 124 mmol, 0.910 equiv), and 1,2-dichloroethane (300 mL). The mixture was stirred at room temperature for 30 min. Sodium triacetoxyborohydride (52.8 g, 249 mmol, 1.82 equiv) was added. The resulting solution was stirred for 3 h at room temperature and washed with H₂O (3×100 mL), dried over anhydrous sodium sulfate, filtered, and concentrated under reduced pressure. The residue was chromatographed on a silica gel column with ethyl acetate/petroleum ether (1/20) to provide 40.0 g (75% yield) of tert-butyl 4[(2-bromo-4-chlorophenyl)methyl]piperazine-1-carboxylate as a light yellow solid. ¹H NMR (300 MHz, CDCl₃): δ 7.56-7.57 (m, 1H), 7.43-7.46 (m, 1H), 7.29-7.30 (m, 1H), 3.61 (br, 2H), 3.46 (br, 4H), 2.49 (br, 4H), 1.46 (s, 9H). LCMS (ESI, m/z): 390 [M+H]⁺.

Step 2: Preparation of tert-butyl 4-[[2-(azetidin-1-yl)-4-chlorophenyl]methyl]piperazine-1-carboxylate

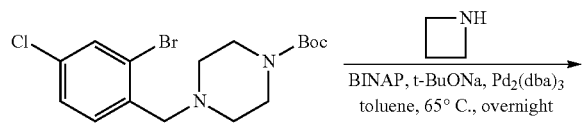

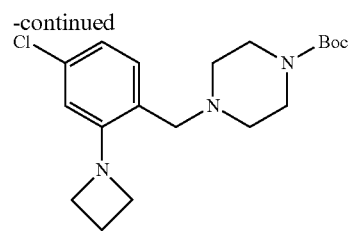

A 100-mL round-bottom flask was purged and maintained with an inert atmosphere of nitrogen and charged with tert-butyl 4-[(2-bromo-4-chlorophenyl)methyl]piperazine-1-carboxylate (800 mg, 2.05 mmol, 1.00 equiv), azetidine (234 mg, 4.10 mmol, 2.00 equiv), t-BuONa (276 mg, 2.87 mmol, 1.40 equiv), BINAP (191 mg, 0.310 mmol, 0.150 equiv), Pd₂(dba)₃ (94.0 mg, 0.100 mmol, 0.05 equiv), and toluene (10 mL). The resulting solution was stirred overnight at 65° C. in an oil bath. The resulting mixture was concentrated under reduced pressure and diluted with H₂O (20 mL). The resulting solution was extracted with ethyl acetate (3×10 mL), and the organic layers were combined, dried over anhydrous sodium sulfate, filtered, and concentrated under reduced pressure. The residue was chromatographed on a silica gel column with ethyl acetate/petroleum ether (1/3) to provide 670 mg (89% yield) of tert-butyl 4-[[2-(azetidin-1-yl)-4-chlorophenyl]methyl]piperazine-1-carboxylate as a yellow oil. LCMS (ESI, m/z): 366 [M+H]⁺.

Step 3: Preparation of 1-[[2-(azetidin-1-yl)-4-chlorophenyl]methyl]piperazine

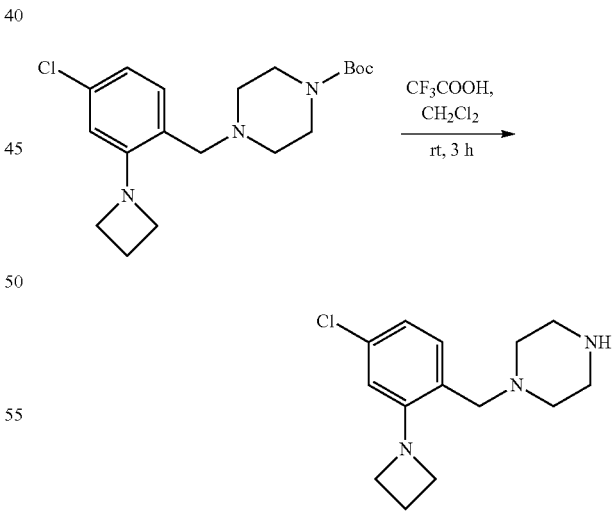

A 100-mL round-bottom flask was charged with tert-butyl 4-[[2-(azetidin-1-yl)-4-chlorophenyl]methyl]piperazine-1-carboxylate (670 mg, 1.83 mmol, 1.00 equiv) and dichloromethane (15 mL). The mixture was cooled to 0° C. Trifluoroacetic acid (3 mL) was added dropwise with stirring. The resulting solution was stirred overnight at room temperature. The resulting mixture was concentrated under reduced pressure to provide 600 mg (crude) of 1-[[2-(azetidin-1-yl)-4-chlorophenyl]methyl]piperazine as a yellow solid. LCMS (ESI, m/z): 266 [M+H]$^+$.

Step 4: Preparation of 2,5-dioxopyrrolidin-1-yl 4-{[2-(azetidin-1-yl)-4-chlorophenyl]methyl}piperazine-1-carboxylate

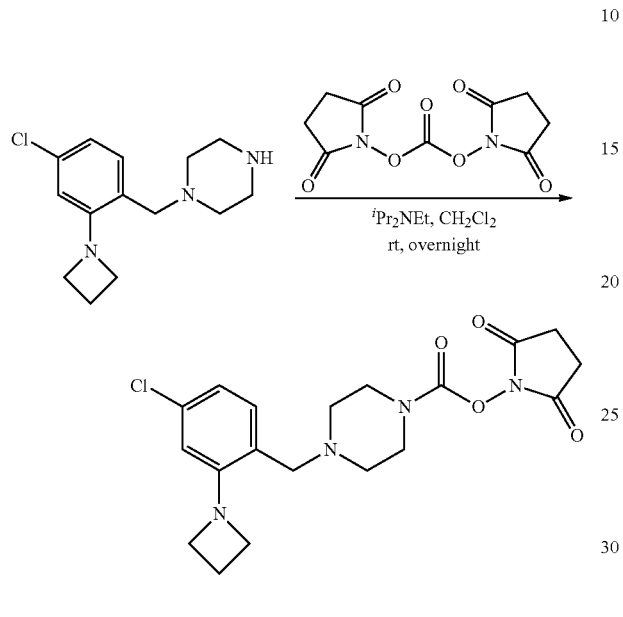

A 50-mL round-bottom flask was charged with 1-[[2-(azetidin-1-yl)-4-chlorophenyl]methyl]piperazine (266 mg, 1.00 mmol, 1.00 equiv), bis(2,5-dioxopyrrolidin-1-yl) carbonate (256 mg, 1.00 mmol, 1.00 equiv), and dichloromethane (10 mL). N,N-Diisopropylethylamine (258 mg, 2.00 mmol, 1.99 equiv) was added dropwise. The resulting solution was stirred for 2 h at room temperature and diluted with H$_2$O (30 mL). The resulting solution was extracted with dichloromethane (3×10 mL), and the organic layers were combined, washed with H$_2$O (3×5 mL), dried over anhydrous sodium sulfate, filtered, and concentrated under reduced pressure. The residue was chromatographed on a silica gel column with ethyl acetate/petroleum ether (9/1). The crude product (263 mg) was purified by preparative HPLC using the following gradient conditions: 20% CH$_3$CN/80% Phase A increasing to 80% CH$_3$CN over 10 min, then to 100% CH$_3$CN over 0.1 min, holding at 100% CH$_3$CN for 1.9 min, then reducing to 20% CH$_3$CN over 0.1 min, and holding at 20% for 1.9 min, on a Waters 2767-5 Chromatograph. Column: Xbridge Prep C18, 19*150 mm, 5 um; Mobile phase: Phase A: water; Phase B: CH$_3$CN; Detector, UV 220 & 254 nm. Purification resulted in 105 mg (26% yield) of 2,5-dioxopyrrolidin-1-yl 4-{[2-(azetidin-1-yl)-4-chlorophenyl]methyl}piperazine-1-carboxylate as a brown syrup. $^1$H NMR (300 MHz, Chloroform-d): δ 7.06 (d, J=6.0 Hz, 1H), 6.66-6.69 (m, 1H), 6.38 (s, 1H), 3.95-4.01 (m, 4H), 3.62 (br, 2H), 3.50 (br, 2H), 3.37 (br, 2H), 2.78 (br, 4H), 2.46 (br, 4H), 2.24-2.31 (m, 2H). LCMS (ESI, m/z): 407 [M+H]$^+$.

Example 113

2,5-Dioxopyrrolidin-1-yl 4-{[4-(2,6-dimethylpyridin-4-yl)-2-methylphenyl]methyl}piperazine-1-carboxylate

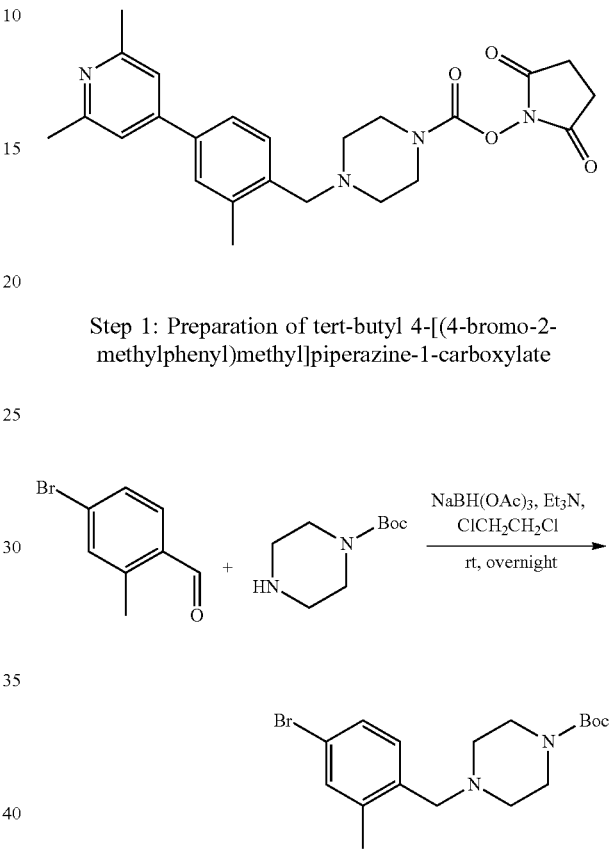

Step 1: Preparation of tert-butyl 4-[(4-bromo-2-methylphenyl)methyl]piperazine-1-carboxylate A 500-mL round-bottom flask was charged with 4-bromo-2-methylbenzaldehyde (8.00 g, 40.2 mmol, 1.00 equiv), tert-butyl piperazine-1-carboxylate (9.40 g, 50.5 mmol, 1.26 equiv), triethylamine (6.50 g, 64.2 mmol, 1.60 equiv), and 1,2-dichloroethane (200 mL). The resulting solution was stirred for 30 min at room temperature. Solid sodium triacetoxyborohydride (27.0 g, 127 mmol, 3.17 equiv) was added. The resulting solution was stirred overnight at room temperature. Reaction progress was monitored by LCMS. The reaction was then quenched by the addition of water (100 mL). The resulting solution was extracted with dichloromethane (3×200 mL), and the organic layers were combined, washed with brine (2×200 mL), dried over anhydrous sodium sulfate, and concentrated under reduced pressure. The residue was chromatographed on a silica gel column with ethyl acetate/petroleum ether (2/3) to yield 10.0 g (67% yield) of tert-butyl 4-[(4-bromo-2-methylphenyl)methyl]piperazine-1-carboxylate as a white solid. LCMS (ESI, m/z): 369 [M+H]$^+$.

Step 2: Preparation of tert-butyl 4-[[4-(2,6-dimethylpyridin-4-yl)-2-methylphenyl]methyl]piperazine-1-carboxylate

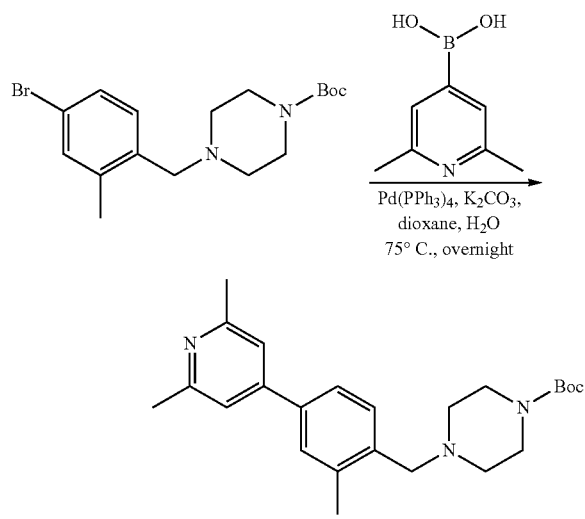

A 25-mL round-bottom flask maintained with an inert atmosphere of nitrogen was charged with tert-butyl 4-[(4-bromo-2-methylphenyl)methyl]piperazine-1-carboxylate (368 mg, 1.00 mmol, 1.00 equiv), (2,6-dimethylpyridin-4-yl)boronic acid (300 mg, 1.99 mmol, 1.99 equiv), Pd(PPh$_3$)$_4$ (116 mg, 0.100 mmol, 0.10 equiv), potassium carbonate (414 mg, 3.00 mmol, 3.01 equiv), dioxane (6 mL), and water (1 mL). The resulting solution was stirred overnight at 75° C. Reaction progress was monitored by LCMS. The reaction was then quenched by the addition of water (10 mL). The resulting solution was extracted with ethyl acetate (3×10 mL), and the organic layers were combined, washed with brine (2×10 mL), dried over anhydrous sodium sulfate, and concentrated under reduced pressure. The residue was chromatographed on a silica gel column with ethyl acetate/petroleum ether (1/1) to yield 350 mg (89% yield) of tert-butyl 4-[[4-(2,6-dimethylpyridin-4-yl)-2-methylphenyl]methyl]piperazine-1-carboxylate as a yellow oil. LCMS (ESI, m/z): 396 [M+H]$^+$.

Step 3: Preparation of 1-[[4-(2,6-dimethylpyridin-4-yl)-2-methylphenyl]methyl]piperazine

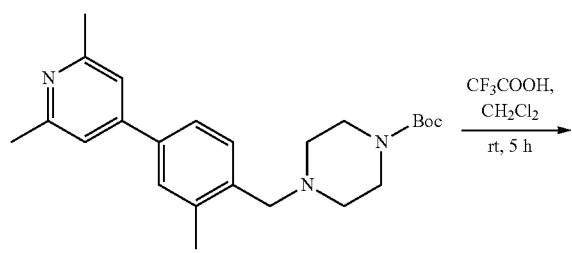

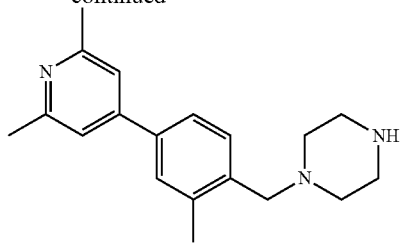

A 50-mL round-bottom flask maintained with an inert atmosphere of nitrogen was charged with tert-butyl 4-[[4-(2,6-dimethylpyridin-4-yl)-2-methylphenyl]methyl]piperazine-1-carboxylate (350 mg, 0.880 mmol, 1.00 equiv) and dichloromethane (5 mL). Trifluoroacetic acid (0.5 mL) was added dropwise at 0° C. The resulting solution was stirred for 5 h at room temperature. Reaction progress was monitored by LCMS. The reaction was then quenched by the addition of water (10 mL). The resulting solution was extracted with dichloromethane (3×10 mL), and the organic layers were combined, washed with brine (2×10 mL), dried over anhydrous sodium sulfate, and concentrated under reduced pressure to yield 270 mg (crude) of 1-[[4-(2,6-dimethylpyridin-4-yl)-2-methylphenyl]methyl]piperazine as a yellow oil. LCMS (ESI, m/z): 296 [M+H]$^+$.

Step 4: Preparation of 2,5-dioxopyrrolidin-1-yl 4-{[4-(2,6-dimethylpyridin-4-yl)-2-methylphenyl]methyl}piperazine-1-carboxylate

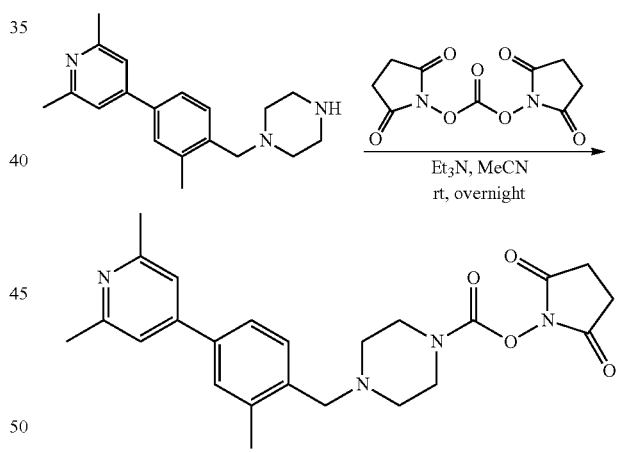

A 25-mL round-bottom flask was purged and maintained with an inert atmosphere of nitrogen and charged with 1-[[4-(2,6-dimethylpyridin-4-yl)-2-methylphenyl]methyl]piperazine (130 mg, 0.440 mmol, 1.00 equiv), bis(2,5-dioxopyrrolidin-1-yl) carbonate (677 mg, 2.64 mmol, 6.01 equiv), triethylamine (133 mg, 1.31 mmol, 2.99 equiv), and MeCN (5 mL). The resulting solution was stirred overnight at room temperature. Reaction progress was monitored by LCMS. The resulting mixture was concentrated under reduced pressure. The crude product (360 mg) was purified by preparative HPLC using the following gradient conditions: 30% CH$_3$CN/60% Phase A increasing to 60% CH$_3$CN over 10 min, then to 100% CH$_3$CN over 0.1 min, holding at 100% CH$_3$CN for 1.9 min, then reducing to 30% CH$_3$CN over 0.1 min, and holding at 30% for 1.9 min, on a Waters 2767-5 Chromatograph. Column: Xbridge Prep C18, 19*150 mm, 5 um; Mobile phase: Phase A: water; Phase B: CH₃CN; Detector, UV 220 & 254 nm. Purification resulted in 78.2 mg (41% yield) of 2,5-dioxopyrrolidin-1-yl 4-{[4-(2,6-dimethylpyridin-4-yl)-2-methylphenyl]methyl}piperazine-1-carboxylate as a light yellow semi-solid. $^1$H NMR (400 MHz, Chloroform-d) δ 7.35-7.50 (m, 3H), 7.24-7.26 (m, 2H), 3.65 (br, 4H), 3.55 (s, 2H), 2.83 (s, 4H), 2.64 (s, 6H), 2.52-2.56 (m, 4H), 2.44 (s, 3H). LCMS (ESI, m/z): 437 [M+H]$^+$.

Example 114

2,5-Dioxopyrrolidin-1-yl 4-[(4-chloro-2-{5H,6H,7H-pyrrolo[3,4-b]pyridin-6-yl}phenyl)methyl]piperazine-1-carboxylate

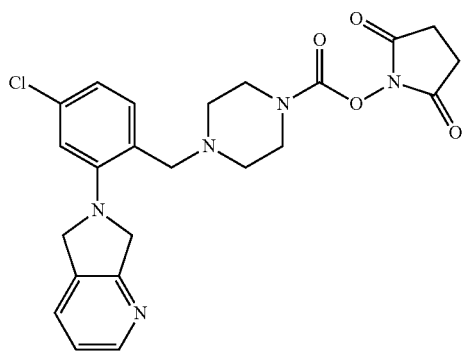 [SMILES: O=C(ON1C(=O)CCC1=O)N1CCN(Cc2ccc(Cl)cc2N2Cc3cccnc3C2)CC1]

Step 1: Preparation of 4-chloro-2-[5H,6H,7H-pyrrolo[3,4-b]pyridin-6-yl]benzaldehyde

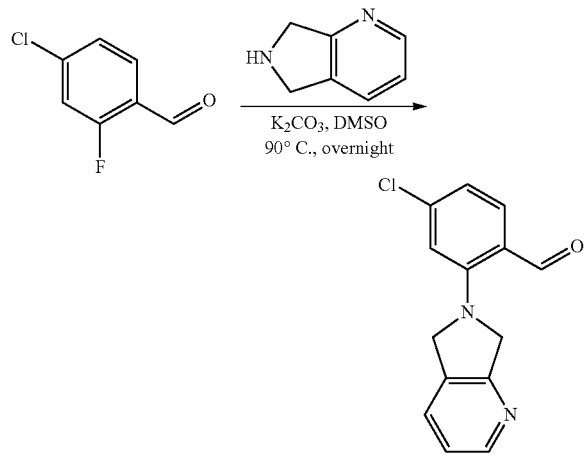

A 100-mL round-bottom flask was purged with and maintained an inert atmosphere of nitrogen and was then charged with 4-chloro-2-fluorobenzaldehyde (1.00 g, 6.31 mmol, 1.00 equiv), 5H,6H,7H-pyrrolo[3,4-b]pyridine (1.20 g, 10.00 mmol, 1.58 equiv), potassium carbonate (3.06 g, 22.1 mmol, 3.51 equiv), and DMSO (20 mL). The resulting solution was stirred overnight at 90° C. and was then diluted with water (10 mL) and extracted with dichloromethane (3×10 mL). The organic layers were combined, dried over anhydrous sodium sulfate, filtered, and concentrated under reduced pressure. The residue was chromatographed on a silica gel column with ethyl acetate/petroleum ether (1/1) to provide 0.400 g (25% yield) of 4-chloro-2-[5H,6H,7H-pyrrolo[3,4-b]pyridin-6-yl]benzaldehyde as a brown solid. LCMS (ESI, m/z): 259 [M+H]$^+$.

Step 2: Preparation of tert-butyl 4-[(4-chloro-2-[5H,6H,7H-pyrrolo[3,4-b]pyridin-6-yl]phenyl)methyl]piperazine-1-carboxylate

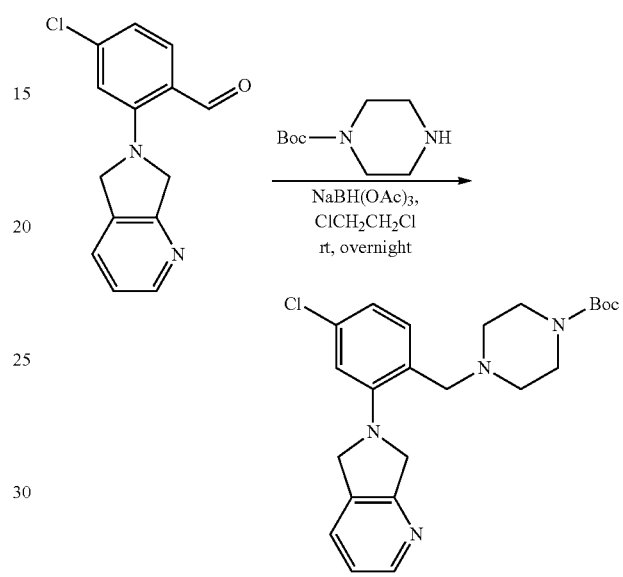

A 100-mL round-bottom flask was charged with 4-chloro-2-[5H,6H,7H-pyrrolo[3,4-b]pyridin-6-yl]benzaldehyde (230 mg, 0.890 mmol, 1.00 equiv), tert-butyl piperazine-1-carboxylate (199 mg, 1.07 mmol, 1.20 equiv), and dichloromethane (10 mL). The mixture was stirred for 30 min at room temperature. Sodium triacetoxyborohydride (567 mg, 2.68 mmol, 3.01 equiv) was added. The resulting solution was stirred overnight at room temperature and then diluted with water (10 mL). The resulting mixture was extracted with dichloromethane (3×10 mL), and the organic layers were combined, dried over anhydrous sodium sulfate, filtered, and concentrated under reduced pressure. The residue was chromatographed on a silica gel column with ethyl acetate/petroleum ether (3/2) to provide 300 mg (79% yield) of tert-butyl 4-[(4-chloro-2-[5H,6H,7H-pyrrolo[3,4-b]pyridin-6-yl]phenyl)methyl]piperazine-1-carboxylate as a yellow oil. LCMS (ESI, m/z): 429 [M+1-1]$^+$.

Step 3: Preparation of 1-[(4-chloro-2-[5H,6H,7H-pyrrolo[3,4-b]pyridin-6-yl]phenyl)methyl]piperazine

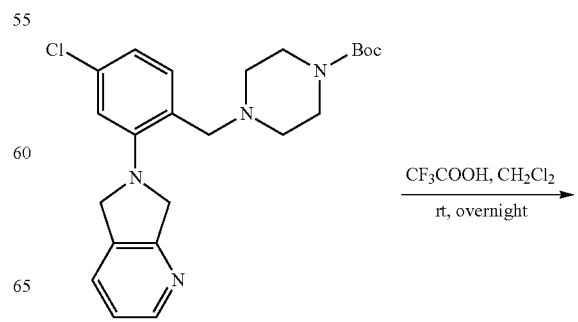

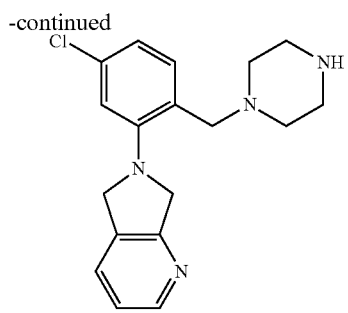

A 100-mL round-bottom flask was charged with tert-butyl 4-[(4-chloro-2-[5H,6H,7H-pyrrolo[3,4-b]pyridin-6-yl]phenyl)methyl]piperazine-1-carboxylate (300 mg, 0.700 mmol, 1.00 equiv), dichloromethane (5 mL), and trifluoroacetic acid (2 mL). The resulting solution was stirred overnight at room temperature. The resulting mixture was concentrated under reduced pressure to provide 230 mg (crude) of 1-[(4-chloro-2-[5H,6H,7H-pyrrolo[3,4-b]pyridin-6-yl]phenyl)methyl]piperazine as a yellow oil. LCMS (ESI, m/z): 329 $[M+H]^+$.

Step 4: Preparation of 2,5-dioxopyrrolidin-1-yl 4-[(4-chloro-2-{5H,6H,7H-pyrrolo[3,4-b]pyridin-6-yl}phenyl)methyl]piperazine-1-carboxylate

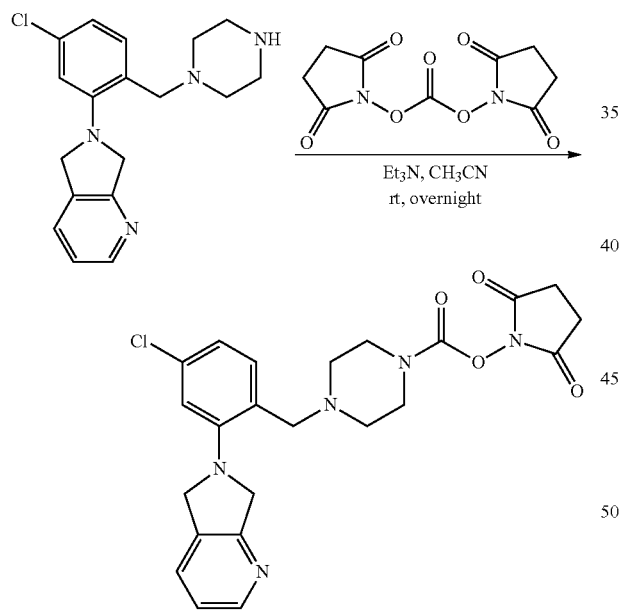

A 100-mL round-bottom flask was charged with 1-[(4-chloro-2-[5H,6H,7H-pyrrolo[3,4-b]pyridin-6-yl]phenyl)methyl]piperazine (130 mg, 0.400 mmol, 1.00 equiv), bis (2,5-dioxopyrrolidin-1-yl) carbonate (205 mg, 0.800 mmol, 2.02 equiv), CH₃CN (10 mL), and triethylamine (81.0 mg, 0.800 mmol, 2.02 equiv). The resulting solution was stirred overnight at room temperature. The resulting mixture was concentrated under reduced pressure. The crude product (200 mg) was purified by preparative HPLC using the following gradient conditions: 20% CH₃CN/80% Phase A increasing to 80% CH₃CN over 10 min, then to 100% CH₃CN over 0.1 min, holding at 100% CH₃CN for 1.9 min, then reducing to 20% CH₃CN over 0.1 min, and holding at 20% for 1.9 min, on a Waters 2767-5 Chromatograph. Column: Xbridge Prep C18, 19*150 mm, 5 um; Mobile phase: Phase A: water; Phase B: CH₃CN; Detector, UV 220 & 254 nm. Purification resulted in 78.5 mg (42% yield) of 2,5-dioxopyrrolidin-1-yl 4-[(4-chloro-2-{5H,6H,7H-pyrrolo[3,4-b]pyridin-6-yl}phenyl)methyl]piperazine-1-carboxylate as a yellow solid. $^1$H NMR (300 MHz, Chloroform-d) δ: 8.50 (d, J=5.1 Hz, 1H), 7.62 (d, J=7.5 Hz, 1H), 7.20-7.26 (m, 2H), 6.87-6.98 (m, 2H), 4.70-4.78 (m, 4H), 3.51-3.65 (m, 6H), 2.81 (s, 4H), 2.51 (br, 4H). LCMS (ESI, m/z): 470 $[M+H]^+$.

Example 115

2,5-Dioxopyrrolidin-1-yl 4-{[2-(4-acetylpiperazin-1-yl)-4-chlorophenyl]methyl}piperazine-1-carboxylate

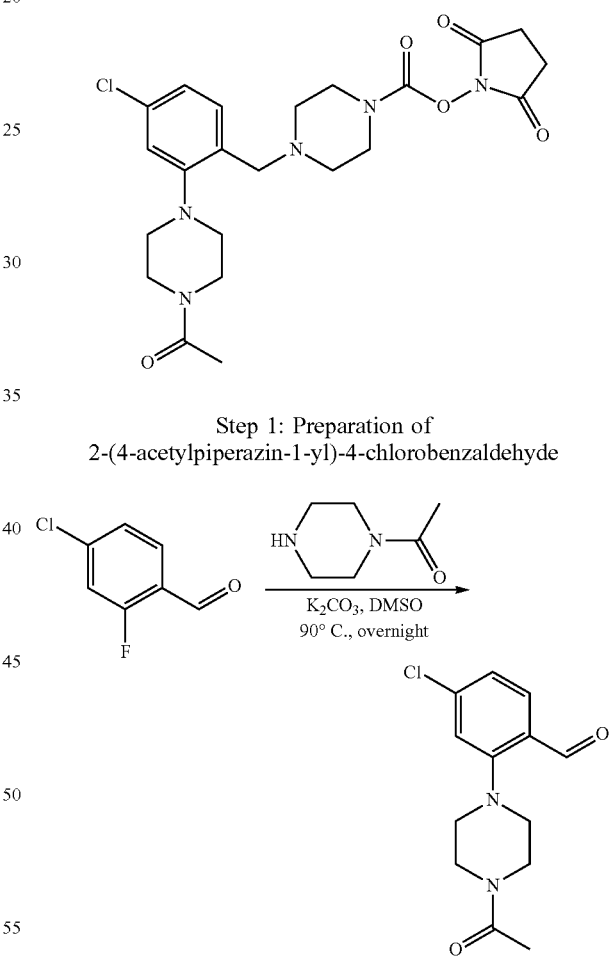

Step 1: Preparation of 2-(4-acetylpiperazin-1-yl)-4-chlorobenzaldehyde

A 100-mL round-bottom flask was purged with and maintained an inert atmosphere of nitrogen and was then charged with 4-chloro-2-fluorobenzaldehyde (1.00 g, 6.31 mmol, 1.00 equiv), 1-(piperazin-1-yl)ethan-1-one (0.970 g, 7.57 mmol, 1.20 equiv), potassium carbonate (2.20 g, 16.0 mmol, 2.52 equiv), and DMSO (15 mL). The resulting solution was stirred overnight at 90° C. and was then diluted with water (10 mL) and extracted with dichloromethane (3×10 mL). The organic layers were combined, dried over anhydrous sodium sulfate, filtered, and concentrated under reduced pressure. The residue was chromatographed on a silica gel column with ethyl acetate/petroleum ether (60/40). This resulted in 1.20 g (71% yield) of 2-(4-acetylpiperazin-1-yl)-4-chlorobenzaldehyde as a yellow oil. LCMS (ESI, m/z): 267 [M+H]+.

Step 2: Preparation of tert-butyl 4-[[2-(4-acetylpiperazin-1-yl)-4-chlorophenyl]methyl]piperazine-1-carboxylate

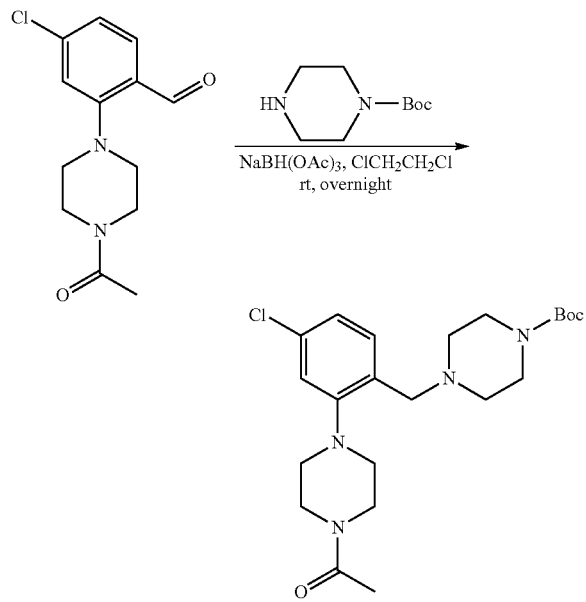

A 100-mL round-bottom flask was charged with 2-(4-acetylpiperazin-1-yl)-4-chlorobenzaldehyde (0.500 g, 1.87 mmol, 1.00 equiv), tert-butyl piperazine-1-carboxylate (0.420 g, 2.26 mmol, 1.20 equiv), and dichloromethane (10 mL). The mixture was stirred for 30 min at room temperature. Sodium triacetoxyborohydride (1.20 g, 5.66 mmol, 3.02 equiv) was added. The resulting solution was stirred overnight at room temperature and then diluted with water (10 mL). The resulting mixture was extracted with dichloromethane (3×10 mL), and the organic layers were combined, dried over anhydrous sodium sulfate, filtered, and concentrated under reduced pressure. The residue was chromatographed on a silica gel column with dichloromethane/methanol (15/1) to provide 0.700 g (85% yield) of tert-butyl 4-[[2-(4-acetylpiperazin-1-yl)-4-chlorophenyl]methyl]piperazine-1-carboxylate as yellow oil. LCMS (ESI, m/z): 437 [M+H]+.

Step 3: Preparation of 1-[4-[5-methyl-2-(piperazin-1-ylmethyl)phenyl]piperazin-1-yl]ethan-1-one

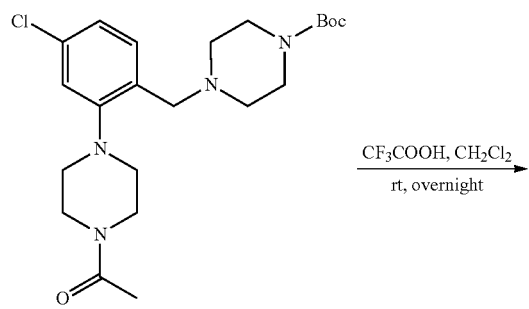

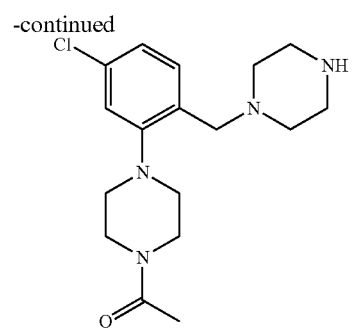

A 100-mL round-bottom flask was charged with tert-butyl 4-[[2-(4-acetylpiperazin-1-yl)-4-chlorophenyl]methyl]piperazine-1-carboxylate (700 mg, 1.60 mmol, 1.00 equiv), dichloromethane (10 mL), trifluoroacetic acid (2 mL). The resulting solution was stirred overnight at room temperature. The resulting mixture was concentrated under reduced pressure to provide 530 mg (crude) of 1-[4-[5-chloro-2-(piperazin-1-ylmethyl)phenyl]piperazin-1-yl]ethan-1-one as yellow oil. LCMS (ESI, m/z): 337 [M+H]+.

Step 4: Preparation of 2,5-dioxopyrrolidin-1-yl 4-{[2-(4-acetylpiperazin-1-yl)-4-chlorophenyl]methyl}piperazine-1-carboxylate

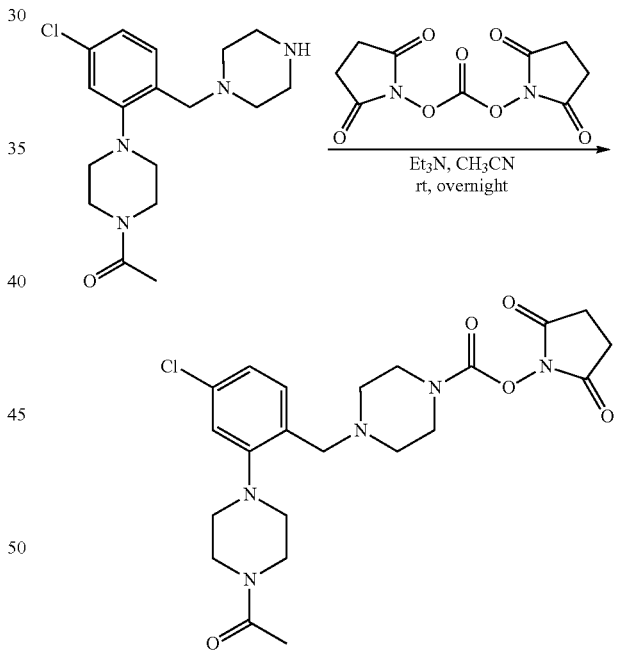

A 100-mL round-bottom flask was charged with 1-[4-[5-chloro-2-(piperazin-1-ylmethyl)phenyl]piperazin-1-yl]ethan-1-one (150 mg, 0.450 mmol, 1.00 equiv), bis(2,5-dioxopyrrolidin-1-yl) carbonate (225 mg, 0.880 mmol, 1.97 equiv), CH₃CN (10 mL), and triethylamine (89.0 mg, 0.880 mmol, 1.98 equiv). The resulting solution was stirred overnight at room temperature. The resulting mixture was concentrated under reduced pressure. The crude product (230 mg) was purified by preparative HPLC using the following gradient conditions: 20% CH₃CN/80% Phase A increasing to 80% CH₃CN over 10 min, then to 100% CH₃CN over 0.1 min, holding at 100% CH₃CN for 1.9 min, then reducing to 20% CH₃CN over 0.1 min, and holding at 20% for 1.9 min, on a Waters 2767-5 Chromatograph. Column: Xbridge Prep C18, 19*150 mm, 5 um; Mobile phase: Phase A: water; Phase B: CH₃CN; Detector, UV 220 & 254 nm. Purification resulted in 89.6 mg (42% yield) of 2,5-dioxopyrrolidin-1-yl 4-{[2-(4-acetylpiperazin-1-yl)-4-chlorophenyl]methyl}piperazine-1-carboxylate as a white solid. ¹H NMR (300 MHz, Chloroform-d) δ: 7.36 (d, J=8.1 Hz, 1H), 7.03-7.10 (m, 2H), 3.75 (br, 4H), 3.52-3.62 (m, 6H), 2.89-2.97 (m, 4H), 2.82 (s, 4H), 2.54 (br, 4H), 2.15 (s, 3H). LCMS (ESI, m/z): 478 [M+H]⁺.

Example 116

2,5-Dioxopyrrolidin-1-yl 4-({4-chloro-2-[4-(pyrrolidine-1-carbonyl)piperidin-1-yl]phenyl}methyl)piperazine-1-carboxylate

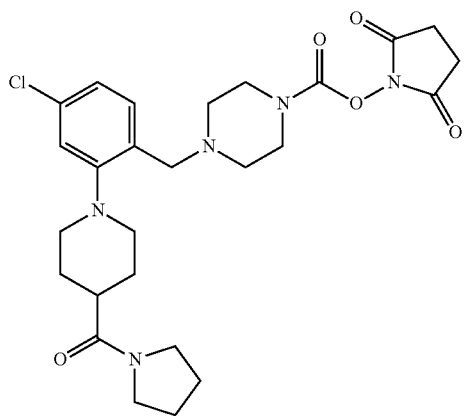 [SMILES: O=C(ON1C(=O)CCC1=O)N1CCN(Cc2ccc(Cl)cc2N2CCC(C(=O)N3CCCC3)CC2)CC1]

Step 1: Preparation of 4-chloro-2-[4-[(pyrrolidin-1-yl)carbonyl]piperidin-1-yl]benzaldehyde

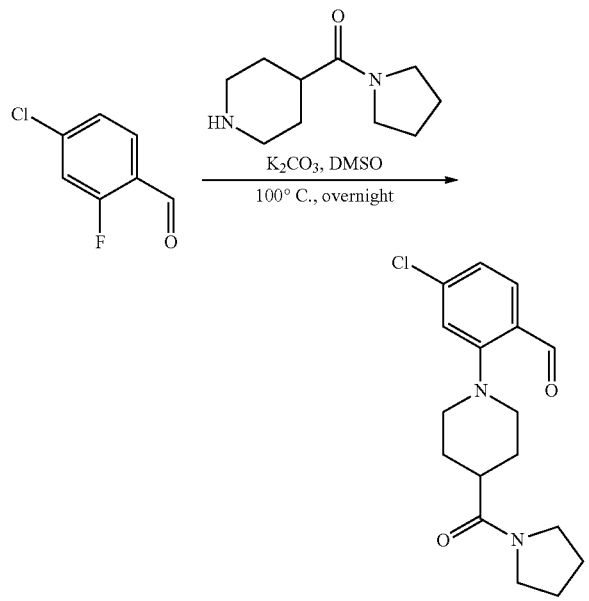

A 20-mL round-bottom flask was charged with 4-chloro-2-fluorobenzaldehyde (1.00 g, 6.31 mmol, 1.00 equiv), 4-[(pyrrolidin-1-yl)carbonyl]piperidine hydrochloride (1.65 g, 7.54 mmol, 1.20 equiv), potassium carbonate (3.47 g, 25.1 mmol, 3.98 equiv), and DMSO (10 mL). The resulting solution was stirred overnight at 100° C. and then diluted with H₂O (10 mL). The resulting solution was extracted with ethyl acetate (3×20 mL), and the organic layers were combined, washed with H₂O (3×5 mL), dried over anhydrous sodium sulfate, filtered, and concentrated under reduced pressure. The residue was chromatographed on a silica gel column with ethyl acetate/petroleum ether (1/3) to provide 1.50 g (74% yield) of 4-chloro-2-[4-[(pyrrolidin-1-yl)carbonyl]piperidin-1-yl]benzaldehyde as a yellow solid. ¹H NMR (300 MHz, Chloroform-d): δ 10.26 (s, 1H), 7.70-7.75 (m, 1H), 7.05-7.08 (m, 2H), 3.38-3.53 (m, 6H), 2.90-2.99 (m, 2H), 1.86-2.16 (m, 8H). LCMS (ESI, m/z): 321 [M+H]⁺.

Step 2: Preparation of tert-butyl 4-[(4-chloro-2-[4-[(pyrrolidin-1-yl)carbonyl]piperidin-1-yl]phenyl)methyl]piperazine-1-carboxylate

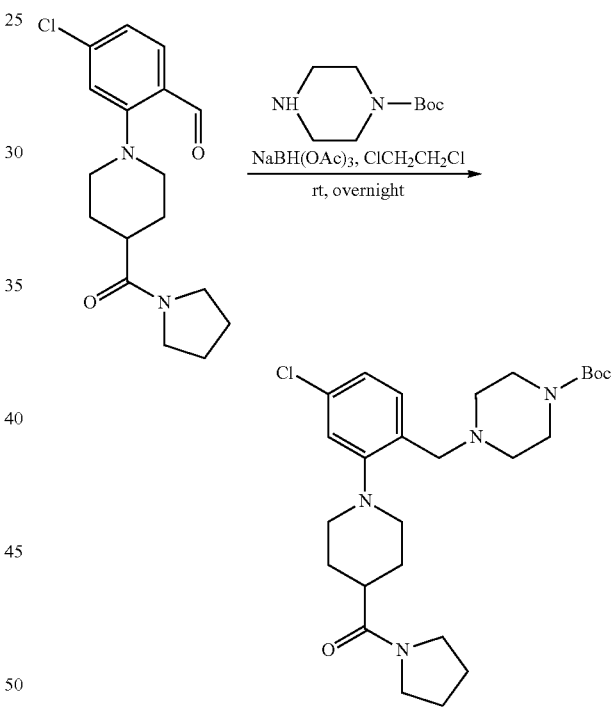

A 20-mL round-bottom flask was charged with 4-chloro-2-[4-[(pyrrolidin-1-yl)carbonyl]piperidin-1-yl]benzaldehyde (321 mg, 1.00 mmol, 1.10 equiv), tert-butyl piperazine-1-carboxylate (169 mg, 0.909 mmol, 1.00 equiv), 1,2-dichloroethane (10 mL). The mixture was stirred at room temperature for 30 min. Sodium triacetoxyborohydride (385 mg, 1.82 mmol, 2.00 equiv) was added. The resulting solution was stirred overnight at room temperature and then diluted with 1,2-dichloroethane (10 mL). The resulting mixture was washed with H₂O (3×5 mL), dried over anhydrous sodium sulfate, filtered, and concentrated under reduced pressure. The residue was chromatographed on a silica gel column with ethyl acetate/petroleum ether (1/4) to provide 400 mg (81% yield) of tert-butyl 4-[(4-chloro-2-[4-[(pyrrolidin-1-yl)carbonyl]piperidin-1-yl]phenyl)methyl]

piperazine-1-carboxylate as light yellow oil. $^1$H NMR (300 MHz, Chloroform-d): δ 7.37 (d, J=8.4 Hz, 1H), 7.01-7.03 (m, 2H), 3.73 (m, 2H), 3.52-3.73 (m, 6H), 3.38-3.49 (m, 4H), 3.26-3.29 (m, 2H), 2.43-2.50 (m, 5H), 1.82-2.04 (m, 8H), 1.45 (s, 9H). LCMS (ESI, m/z): 532 [M+H]$^+$.

Step 3: Preparation 1-[(4-chloro-2-[4-[(pyrrolidin-1-yl)carbonyl]piperidin-1-yl]phenyl)methyl]piperazine

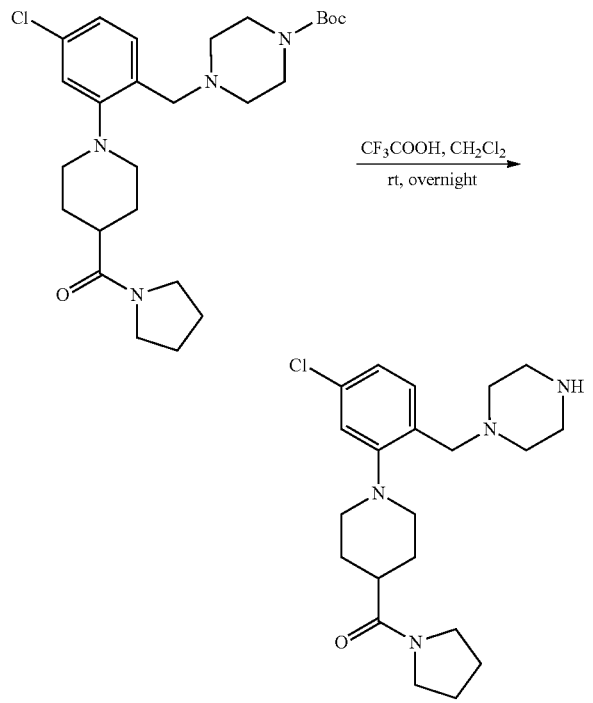

A 20-mL round-bottom flask was charged with tert-butyl 4-[(4-chloro-2-[4-[(pyrrolidin-1-yl)carbonyl]piperidin-1-yl]phenyl)methyl]piperazine-1-carboxylate (400 mg, 0.81 mmol, 1.00 equiv), dichloromethane (5 mL). Trifluoroacetic acid (1 mL) was added dropwise. The resulting solution was stirred overnight at room temperature. The resulting solution was concentrated under reduced pressure to provide 1000 mg (crude) of 1-[(4-chloro-2-[4-[(pyrrolidin-1-yl)carbonyl]piperidin-1-yl]phenyl)methyl]piperazine as yellow oil. LCMS (ESI, m/z): 391 [M+H]$^+$.

Step 4: Preparation of 2,5-dioxopyrrolidin-1-yl 4-({4-chloro-2-[4-(pyrrolidine-1-carbonyl)piperidin-1-yl]phenyl}methyl)piperazine-1-carboxylate

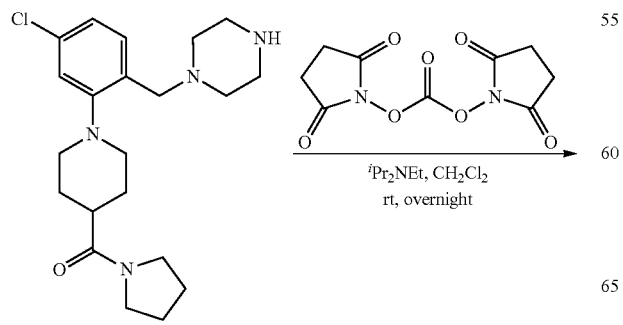

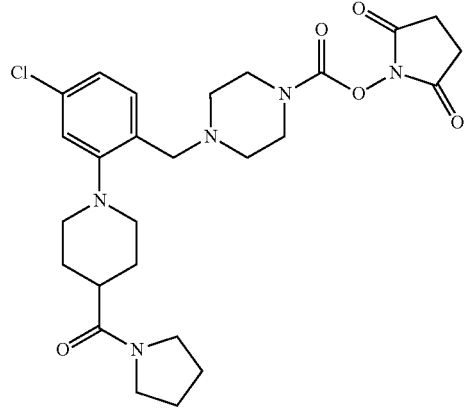

A 20-mL round-bottom flask was charged with 1-[(4-chloro-2-[4-[(pyrrolidin-1-yl)carbonyl]piperidin-1-yl]phenyl)methyl]piperazine (500 mg, 1.28 mmol, 1.00 equiv), bis(2,5-dioxopyrrolidin-1-yl) carbonate (327 mg, 1.28 mmol, 1.00 equiv), and dichloromethane (10 ml). N,N-Diisopropylethylamine (330 mg, 2.55 mmol, 2.00 equiv) was added dropwise. The resulting solution was stirred for 2 h at room temperature and diluted with H$_2$O (30 mL). The resulting solution was extracted with dichloromethane (3×10 mL), and the organic layers were combined, washed with H$_2$O (3×5 mL), dried over anhydrous sodium sulfate, filtered, and concentrated under reduced pressure. The residue was chromatographed on a silica gel column with ethyl acetate/petroleum ether (9/1). The crude product (304 mg) was purified by preparative HPLC using the following gradient conditions: 20% CH$_3$CN/80% Phase A increasing to 80% CH$_3$CN over 10 min, then to 100% CH$_3$CN over 0.1 min, holding at 100% CH$_3$CN for 1.9 min, then reducing to 20% CH$_3$CN over 0.1 min, and holding at 20% for 1.9 min, on a Waters 2767-5 Chromatograph. Column: Xbridge Prep C18, 19*150 mm, 5 um; Mobile phase: Phase A: water; Phase B: CH$_3$CN; Detector, UV 220 & 254 nm. Purification resulted in 138 mg (20% yield) of 2,5-dioxopyrrolidin-1-yl 4-({4-chloro-2-[4-(pyrrolidine-1-carbonyl)piperidin-1-yl]phenyl}methyl)piperazine-1-carboxylate as a off-white solid. $^1$H NMR (300 MHz, Chloroform-d): δ 7.30-7.32 (m, 1H), 7.02-7.04 (m, 2H), 3.47-3.60 (m, 9H), 3.30-3.33 (m, 2H), 2.82 (br, 4H), 2.44-2.76 (m, 7H), 1.85-2.07 (m, 9H). LCMS (ESI, m/z): 532 [M+H]$^+$.

Example 117

2,5-Dioxopyrrolidin-1-yl 4-[(4-chloro-2-{5H,6H,7H,8H-[1,2,4]triazolo[1,5-a]pyrazin-7-yl}phenyl)methyl]piperazine-1-carboxylate

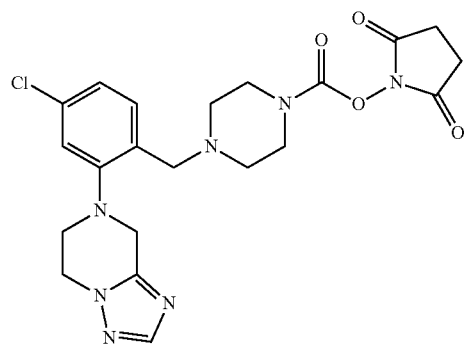 [SMILES: O=C(ON1C(=O)CCC1=O)N1CCN(Cc2ccc(Cl)cc2N2CCn3ncnc3C2)CC1]

Step 1: Preparation of tert-butyl 4-[(4-chloro-2-[5H,6H,7H,8H-[1,2,4]triazolo[1,5-a]pyrazin-7-yl]phenyl)methyl]piperazine-1-carboxylate

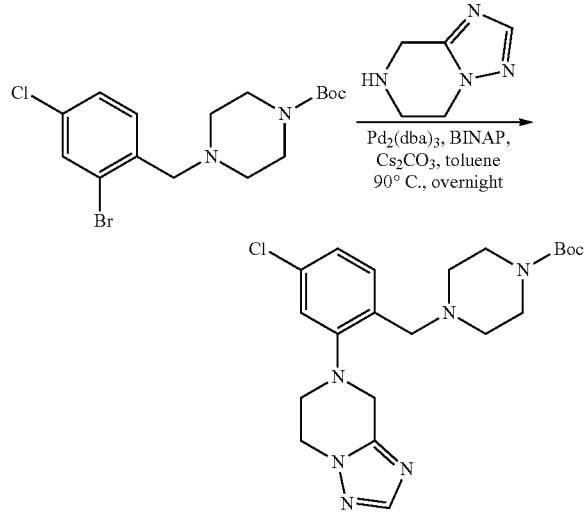

A 40-mL vial was purged with and maintained an inert atmosphere of nitrogen then was charged with tert-butyl 4[(2-bromo-4-chlorophenyl)methyl]piperazine-1-carboxylate (600 mg, 1.54 mmol, 1.00 equiv), 5H,6H,7H,8H-[1,2,4]triazolo[1,5-a]pyrazine (229 mg, 1.84 mmol, 1.20 equiv), Cs₂CO₃ (1.00 g, 3.10 mmol, 2.00 equiv), 2,2'-bis(diphenylphosphino)-1,1'-binaphthyl (144 mg, 0.230 mmol, 0.15 equiv), Pd₂(dba)₃ (70.0 mg, 0.080 mmol, 0.05 equiv), and toluene (15 mL). The resulting solution was stirred overnight at 90° C. and then was diluted with water (20 mL) and extracted with dichloromethane (3×10 mL). The organic layers were combined, dried over anhydrous sodium sulfate, filtered, and concentrated under reduced pressure. The residue was chromatographed on a silica gel column with ethyl acetate/petroleum ether (20/80) to provide 500 mg (75% yield) of tert-butyl 4-[(4-chloro-2-[5H,6H,7H,8H-[1,2,4]triazolo[1,5-a]pyrazin-7-yl]phenyl)methyl]piperazine-1-carboxylate as a yellow solid. LCMS (ESI, m/z): 433 [M+H]⁺.

Step 2: Preparation of 1-[(4-chloro-2-[5H,6H,7H,8H-[1,2,4]triazolo[1,5-a]pyrazin-7-yl]phenyl)methyl]piperazine

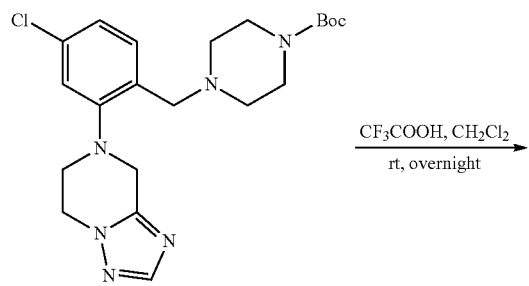

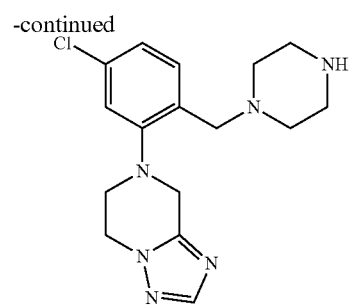

A 50-mL round-bottom flask was charged with tert-butyl 4-[(4-chloro-2-[5H,6H,7H,8H-[1,2,4]triazolo[1,5-a]pyrazin-7-yl]phenyl)methyl]piperazine-1-carboxylate (500 mg, 1.15 mmol, 1.00 equiv), dichloromethane (10 mL), and trifluoroacetic acid (2 mL). The resulting solution was stirred overnight at room temperature. The resulting mixture was concentrated under vacuum. This resulted in 350 mg (crude) of 1-[(4-chloro-2-[5H,6H,7H,8H-[1,2,4]triazolo[1,5-a]pyrazin-7-yl]phenyl)methyl]piperazine as a yellow oil. LCMS (ESI, m/z): 333 [M+H]⁺.

Step 3: Preparation of 2,5-dioxopyrrolidin-1-yl 4-[(4-chloro-2-{5H,6H,7H,8H-[1,2,4]triazolo[1,5-a]pyrazin-7-yl}phenyl)methyl]piperazine-1-carboxylate

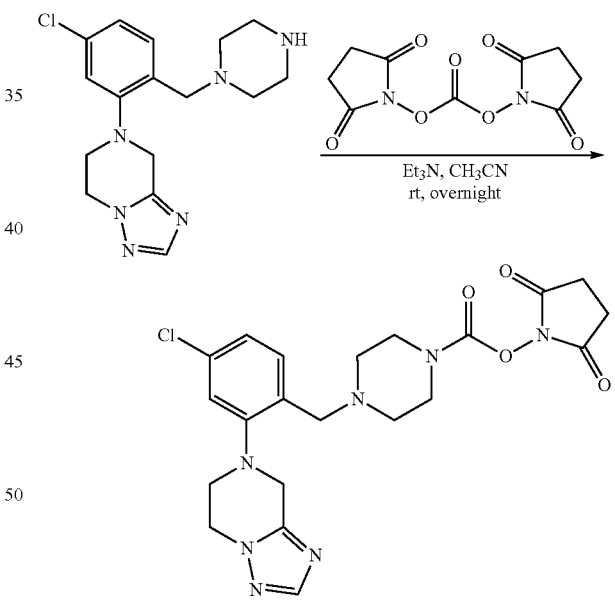

A 100-mL round-bottom flask was charged with 1-[(4-chloro-2-[5H,6H,7H,8H-[1,2,4]triazolo[1,5-a]pyrazin-7-yl]phenyl)methyl]piperazine (150 mg, 0.450 mmol, 1.00 equiv), bis(2,5-dioxopyrrolidin-1-yl) carbonate (230 mg, 0.900 mmol, 2.00 equiv), CH₃CN (10 mL), and triethylamine (91.0 mg, 0.900 mmol, 2.00 equiv). The resulting solution was stirred overnight at room temperature. The resulting mixture was concentrated under reduced pressure. The crude product (230 mg) was purified by preparative HPLC using the following gradient conditions: 20% CH₃CN/80% Phase A increasing to 80% CH₃CN over 10 min, then to 100% CH₃CN over 0.1 min, holding at 100%

CH₃CN for 1.9 min, then reducing to 20% CH₃CN over 0.1 min, and holding at 20% for 1.9 min, on a Waters 2767-5 Chromatograph. Column: Xbridge Prep C18, 19*150 mm, 5 um; Mobile phase: Phase A: water; Phase B: CH₃CN; Detector, UV 220 & 254 nm. Purification resulted in 87.2 mg (41% yield) of 2,5-dioxopyrrolidin-1-yl 4-[(4-chloro-2-{5H,6H,7H,8H-[1,2,4]triazolo[1,5-a]pyrazin-7-yl}phenyl)methyl]piperazine-1-carboxylate as a white solid. ¹H NMR (300 MHz, Chloroform-d) δ: 7.94 (s, 1H), 7.35-7.37 (m, 1H), 7.14-7.18 (m, 2H), 4.30-4.38 (m, 4H), 3.56-3.63 (m, 8H), 2.82 (s, 4H), 2.52 (br, 4H). LCMS (ESI, m/z): 474 [M+H]⁺.

Example 118

2,5-Dioxopyrrolidin-1-yl 4-(3-(methoxycarbonyl)-4-morpholinobenzyl)piperazine-1-carboxylate

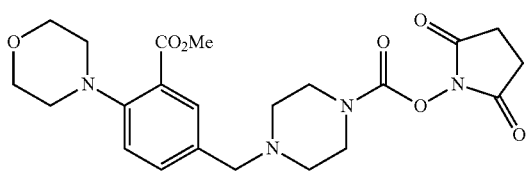 [SMILES: COC(=O)c1cc(CN2CCN(C(=O)ON3C(=O)CCC3=O)CC2)ccc1N1CCOCC1]

The title compound was synthesized directly from commercially available methyl 5-formyl-2-morpholinobenzoate and tert-butyl piperazine-1-carboxylate according to the representative procedure of Example 62, Steps 1, 2 and 3 to provide 2,5-dioxopyrrolidin-1-yl 4-(3-(methoxycarbonyl)-4-morpholinobenzyl)piperazine-1-carboxylate as an amorphous white solid. ¹H NMR (400 MHz, Chloroform-d) δ 7.61-7.57 (m, 1H), 7.32-7.26 (m, 1H), 6.91 (d, J=8.5 Hz, 1H), 3.80 (s, 3H), 3.79-3.75 (m, 4H), 3.55 (s, 2H), 3.44 (s, 2H), 3.39 (s, 2H), 2.99-2.91 (m, 4H), 2.73 (s, 4H), 2.44-2.35 (m, 4H). LCMS (ESI, m/z): 461.1 [M+H]⁺.

Example 119

2,5-Dioxopyrrolidin-1-yl 4-{[2-(morpholin-4-yl)-5-(trifluoromethyl)phenyl]methyl}piperazine-1-carboxylate

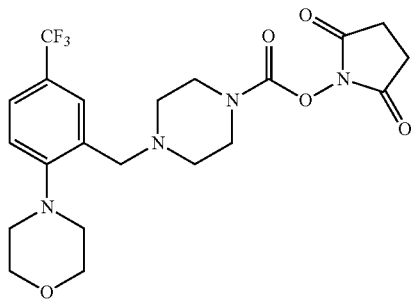 [SMILES: O=C(ON1C(=O)CCC1=O)N1CCN(Cc2cc(C(F)(F)F)ccc2N2CCOCC2)CC1]

Step 1: Preparation of 2-(morpholin-4-yl)-5-(trifluoromethyl)benzaldehyde

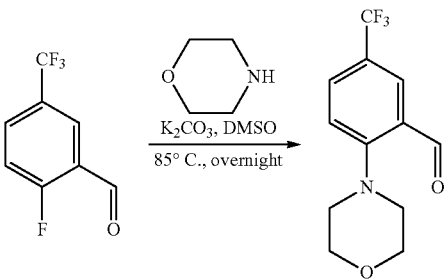 [SMILES: O=Cc1cc(C(F)(F)F)ccc1F ; C1COCCN1 ; O=Cc1cc(C(F)(F)F)ccc1N1CCOCC1]

A 25-mL round-bottom flask was charged with 2-fluoro-5-(trifluoromethyl)benzaldehyde (1.00 g, 5.21 mmol, 1.00 equiv), morpholine (0.680 g, 7.81 mmol, 1.50 equiv), potassium carbonate (1.80 g, 13.0 mmol, 2.50 equiv), and DMSO (10 mL). The resulting solution was stirred overnight at 85° C. and then diluted with H₂O (10 mL). The resulting solution was extracted with ethyl acetate (3×20 mL), and the organic layers were combined, washed with H₂O (3×5 mL), dried over anhydrous sodium sulfate, filtered, and concentrated under reduced pressure. The residue was chromatographed on a silica gel column with ethyl acetate/petroleum ether (1/4) to provide 1.10 g (79% yield) of 2-(morpholin-4-yl)-5-(trifluoromethyl)benzaldehyde as a yellow oil. ¹H NMR (300 MHz, DMSO-d₆): δ 10.13 (s, 1H), 7.98 (s, 1H), 7.90 (d, J=8.7 Hz, 1H), 7.35 (d, J=8.7 Hz, 1H), 3.78-3.82 (m, 4H), 3.16-3.18 (m, 4H). LCMS (ESI, m/z): 260 [M+H]⁺.

Step 2: Preparation of tert-butyl 4-[[2-(morpholin-4-yl)-5-(trifluoromethyl)phenyl]methyl]piperazine-1-carboxylate

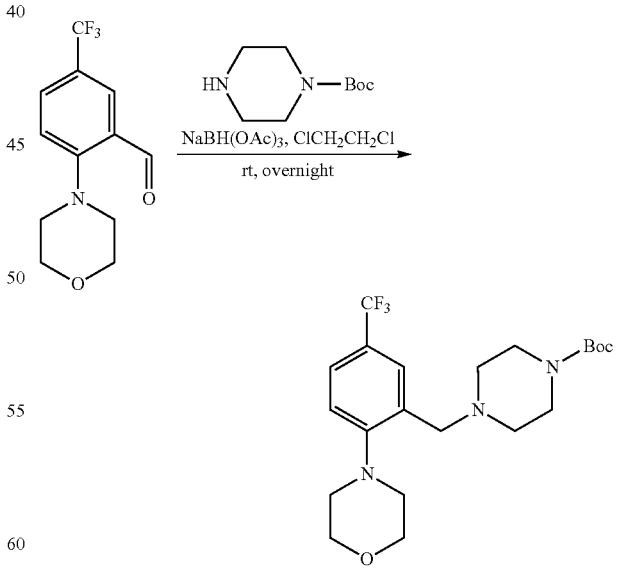

A 50-mL round-bottom flask was charged with 2-(morpholin-4-yl)-5-(trifluoromethyl)benzaldehyde (1.10 g, 4.24 mmol, 1.00 equiv), tert-butyl piperazine-1-carboxylate (0.720 g, 3.87 mmol, 0.91 equiv), 1,2-dichloroethane (10 mL), and sodium triacetoxyborohydride (1.64 g, 7.74 mmol, 1.82 equiv). The resulting solution was stirred overnight at room temperature and then diluted with dichloromethane (10 mL). The resulting mixture was washed with H₂O (3×5 mL), dried over anhydrous sodium sulfate, filtered, and concentrated under reduced pressure. The residue was chromatographed on a silica gel column with ethyl acetate/petroleum ether (3/7) to provide 1.39 g (73% yield) of tert-butyl 4-[[2-(morpholin-4-yl)-5-(trifluoromethyl)phenyl]methyl]piperazine-1-carboxylate as a colorless oil. ¹H NMR (300 MHz, DMSO-d₆): δ 7.72 (s, 1H), 7.57-7.60 (m, 1H), 7.24 (s, 1H), 3.73-3.76 (m, 4H), 3.56 (br, 2H), 2.95-2.98 (m, 4H), 2.50-2.51 (m, 4H), 1.39 (s, 9H), 1.25-1.30 (m, 4H). LCMS (ESI, m/z): 430 [M+H]⁺.

Step 3: Preparation of 4-[2-(piperazin-1-ylmethyl)-4-(trifluoromethyl)phenyl]morpholine

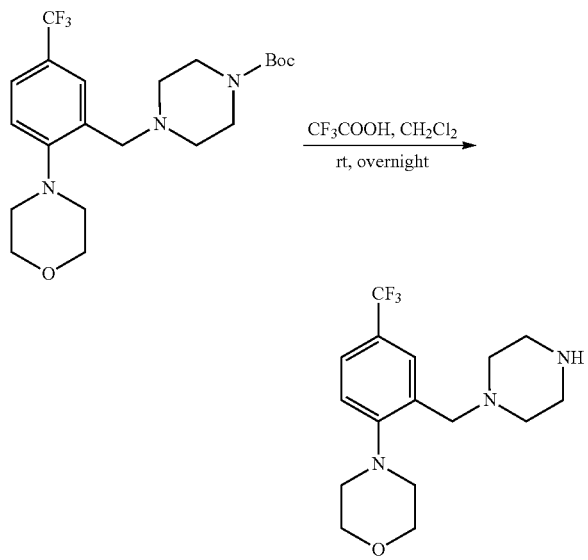

A 20-mL round-bottom flask was charged with tert-butyl 4-[[2-(morpholin-4-yl)-5-(trifluoromethyl)phenyl]methyl]piperazine-1-carboxylate (1.39 g, 3.23 mmol, 1.00 equiv), and dichloromethane (20 mL). Trifluoroacetic acid (4 mL) was added dropwise. The resulting solution was stirred overnight at room temperature. The resulting solution was concentrated under reduced pressure to provide 1.47 g (crude) of 4-[2-(piperazin-1-ylmethyl)-4-(trifluoromethyl)phenyl]morpholine as an off-white solid. LCMS (ESI, m/z): 330 [M+H]⁺.

Step 4: Preparation of 2,5-dioxopyrrolidin-1-yl 4-{[2-(morpholin-4-yl)-5-(trifluoromethyl)phenyl]methyl}piperazine-1-carboxylate

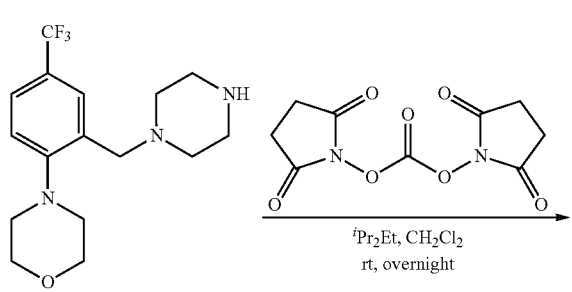

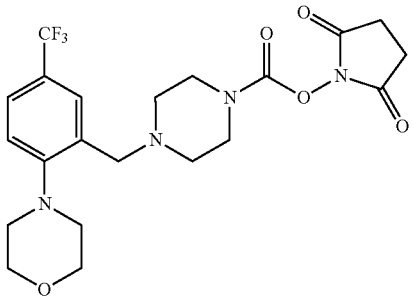

A 20-mL round-bottom flask was charged with 4-[2-(piperazin-1-ylmethyl)-4-(trifluoromethyl)phenyl]morpholine (330 mg, 1.00 mmol, 1.00 equiv), bis(2,5-dioxopyrrolidin-1-yl) carbonate (256 mg, 1.00 mmol, 1.00 equiv), and dichloromethane (5 mL). N,N-Diisopropylethylamine (258 mg, 2.00 mmol, 1.99 equiv) was added dropwise. The resulting solution was stirred for 2 h at room temperature and diluted with H₂O (30 mL). The resulting solution was extracted with dichloromethane (3×10 mL), and the organic layers were combined, washed with H₂O (3×5 mL), dried over anhydrous sodium sulfate, filtered, and concentrated under reduced pressure. The residue was chromatographed on a silica gel column with ethyl acetate/petroleum ether (2/3). The crude product (203 mg) was purified by preparative HPLC using the following gradient conditions: 20% CH₃CN/80% Phase A increasing to 80% CH₃CN over 10 min, then to 100% CH₃CN over 0.1 min, holding at 100% CH₃CN for 1.9 min, then reducing to 20% CH₃CN over 0.1 min, and holding at 20% for 1.9 min, on a Waters 2767-5 Chromatograph. Column: Xbridge Prep C18, 19*150 mm, 5 um; Mobile phase: Phase A: water; Phase B: CH₃CN; Detector, UV 220 & 254 nm. Purification resulted in 83.5 mg (18% yield) of 2,5-dioxopyrrolidin-1-yl 4-{[2-(morpholin-4-yl)-5-(trifluoromethyl)phenyl]methyl}piperazine-1-carboxylate as a white solid. ¹H NMR (300 MHz, Chloroform-d): δ 7.76 (s, 1H), 7.52 (d, J=7.5 Hz, 1H), 7.15 (d, J=7.5 Hz, 1H), 3.85-3.88 (m, 4H), 3.55-3.62 (m, 6H), 2.97-3.00 (m, 4H), 2.82 (br, 4H), 2.56-2.65 (m, 4H). LCMS (ESI, m/z): 471 [M+H]⁺.

Example 120

2,5-Dioxopyrrolidin-1-yl 4-{[2-(pyrrolidin-1-yl)-5-(trifluoromethyl)phenyl]methyl}piperazine-1-carboxylate

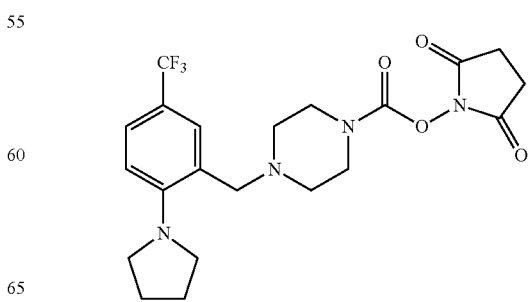

Step 1: Preparation of 2-(pyrrolidin-1-yl)-5-(trifluoromethyl)benzaldehyde

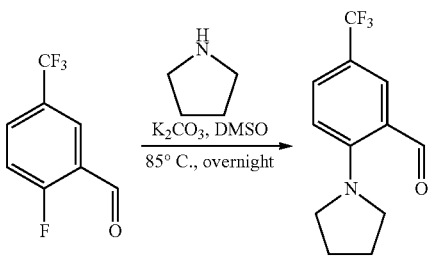 [SMILES: O=Cc1cc(C(F)(F)F)ccc1F ; C1CCNC1 ; O=Cc1cc(C(F)(F)F)ccc1N1CCCC1]

A 25-mL round-bottom flask was charged with 2-fluoro-5-(trifluoromethyl)benzaldehyde (1.00 g, 5.21 mmol, 1.00 equiv), pyrrolidine (0.550 g, 7.73 mmol, 1.49 equiv), potassium carbonate (1.80 g, 13.0 mmol, 2.50 equiv), and DMSO (10 mL). The resulting solution was stirred overnight at 85° C. and diluted with H$_2$O (30 mL). The resulting solution was extracted with dichloromethane (3×10 mL), and the organic layers were combined, washed with H$_2$O (3×5 mL), dried over anhydrous sodium sulfate, filtered, and concentrated under reduced pressure. The residue was chromatographed on a silica gel column with ethyl acetate/petroleum ether (1/4) to provide 0.970 g (75% yield) of 2-(pyrrolidin-1-yl)-5-(trifluoromethyl)benzaldehyde as orange oil. $^1$H NMR (300 MHz, DMSO-d$_6$): δ 10.12 (s, 1H), 7.99 (s, 1H), 7.63-7.66 (m, 1H), 7.01 (d, J=9.0 Hz, 1H), 3.36-3.40 (m, 4H), 1.92-1.96 (m, 4H). LCMS (ESI, m/z): 414 [M+H]$^+$.

Step 2: Preparation of tert-butyl 4-[[2-(pyrrolidin-1-yl)-5-(trifluoromethyl)phenyl]methyl]piperazine-1-carboxylate

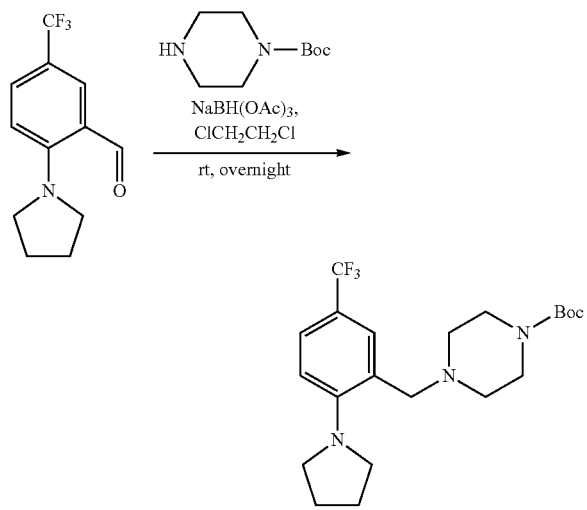

A 50-mL round-bottom flask was charged with 2-(pyrrolidin-1-yl)-5-(trifluoromethyl)benzaldehyde (970 mg, 3.99 mmol, 1.00 equiv), tert-butyl piperazine-1-carboxylate (675 mg, 3.62 mmol, 0.91 equiv), 1,2-dichloroethane (10 mL), and sodium triacetoxyborohydride (1.54 g, 7.27 mmol, 1.82 equiv). The resulting solution was stirred overnight at room temperature and diluted with H$_2$O (30 mL). The resulting solution was extracted with dichloromethane (3×10 mL), and the organic layers were combined, washed with H$_2$O (3×5 mL), dried over anhydrous sodium sulfate, filtered, and concentrated under reduced pressure. The residue was chromatographed on a silica gel column with ethyl acetate/petroleum ether (3/7) to provide 1.55 g (90% yield) of tert-butyl 4-[[2-(pyrrolidin-1-yl)-5-(trifluoromethyl)phenyl]methyl]piperazine-1-carboxylate as an off-white solid. $^1$H NMR (300 MHz, DMSO-d$_6$): δ 7.52 (s, 1H), 7.36-7.40 (m, 1H), 6.84 (d, J=8.7 Hz, 1H), 3.53 (br, 2H), 3.29-3.39 (m, 8H), 2.28-2.31 (m, 4H), 1.85-1.89 (m, 4H), 1.38 (s, 9H). LCMS (ESI, m/z): 414 [M+H]$^+$.

Step 3: Preparation of 1-[[2-(pyrrolidin-1-yl)-5-(trifluoromethyl)phenyl]methyl]piperazine

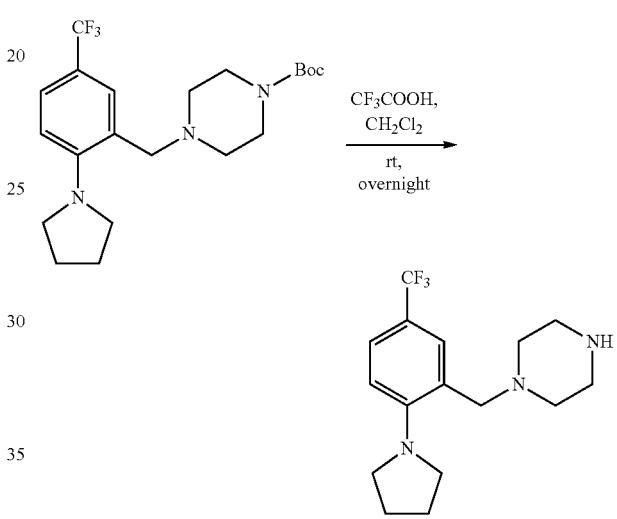

A 20-mL round-bottom flask was charged with tert-butyl 4-[[2-(pyrrolidin-1-yl)-5-(trifluoromethyl)phenyl]methyl]piperazine-1-carboxylate (1.55 g, 3.75 mmol, 1.00 equiv), and dichloromethane (20 mL). Trifluoroacetic acid (4 mL) was added dropwise. The resulting solution was stirred overnight at room temperature. The resulting mixture was concentrated under reduced pressure to provide 1.73 g (crude) of 1-[[2-(pyrrolidin-1-yl)-5-(trifluoromethyl)phenyl]methyl]piperazine as a brown oil. LCMS (ESI, m/z): 314 [M+H]$^+$.

Step 4: Preparation of 2,5-dioxopyrrolidin-1-yl 4-{[2-(pyrrolidin-1-yl)-5-(trifluoromethyl)phenyl]methyl}piperazine-1-carboxylate

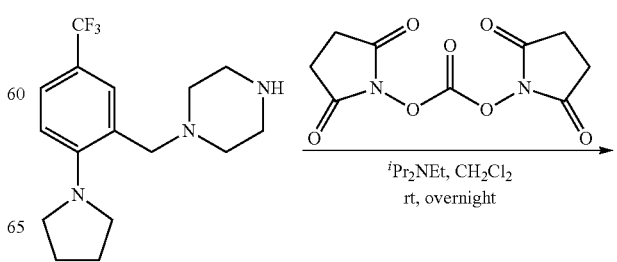

-continued

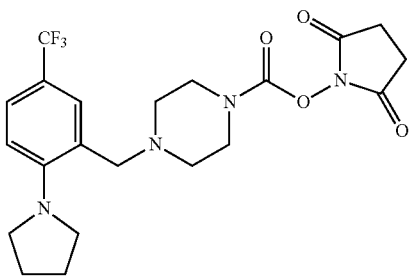

A 20-mL round-bottom flask was charged with 1-[[2-(pyrrolidin-1-yl)-5-(trifluoromethyl)phenyl]methyl]piperazine (313 mg, 1.00 mmol, 1.00 equiv), bis(2,5-dioxopyrrolidin-1-yl) carbonate (256 mg, 1.00 mmol, 1.00 equiv), and dichloromethane (5 mL). N,N-Diisopropylethylamine (258 mg, 2.00 mmol, 2.00 equiv) was added dropwise. The resulting solution was stirred for 2 h at room temperature and diluted with H$_2$O (30 mL). The resulting solution was extracted with dichloromethane (3×10 mL), and the organic layers were combined, washed with H$_2$O (3×5 mL), dried over anhydrous sodium sulfate, filtered, and concentrated under reduced pressure. The residue was chromatographed on a silica gel column with dichloromethane/methanol (5/1). The crude product (219 mg) was purified by preparative HPLC using the following gradient conditions: 20% CH$_3$CN/80% Phase A increasing to 80% CH$_3$CN over 10 min, then to 100% CH$_3$CN over 0.1 min, holding at 100% CH$_3$CN for 1.9 min, then reducing to 20% CH$_3$CN over 0.1 min, and holding at 20% for 1.9 min, on a Waters 2767-5 Chromatograph. Column: Xbridge Prep C18, 19*150 mm, 5um; Mobile phase: Phase A: water; Phase B: CH$_3$CN; Detector, UV 220 & 254 nm. Purification resulted in 99.1 mg (22% yield) of 2,5-dioxopyrrolidin-1-yl 4-{[2-(pyrrolidin-1-yl)-5-(trifluoromethyl)phenyl]methyl}piperazine-1-carboxylate as a white solid. $^1$H NMR (300 MHz, Chloroform-d): δ 7.59 (s, 1H), 7.38 (d, J=8.1 Hz, 1H), 6.83 (d, J=8.7 Hz, 1H), 3.47-3.65 (m, 6H), 3.32-3.36 (m, 4H), 2.82 (br, 4H), 2.50 (br, 4H), 1.96 (br, 4H). LCMS (ESI, m/z): 455 [M+H]$^+$.

Example 121

2,5-Dioxopyrrolidin-1-yl 4-(2-methyl-3-morpholinobenzyl)piperazine-1-carboxylate

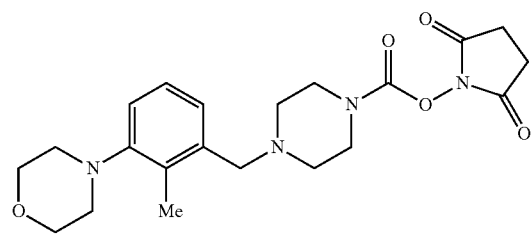 [SMILES: Cc1c(CN2CCN(C(=O)ON3C(=O)CCC3=O)CC2)cccc1N1CCOCC1]

Preparation of tert-butyl 4-(2-methyl-3-morpholinobenzyl)piperazine-1-carboxylate (Buchwald coupling)

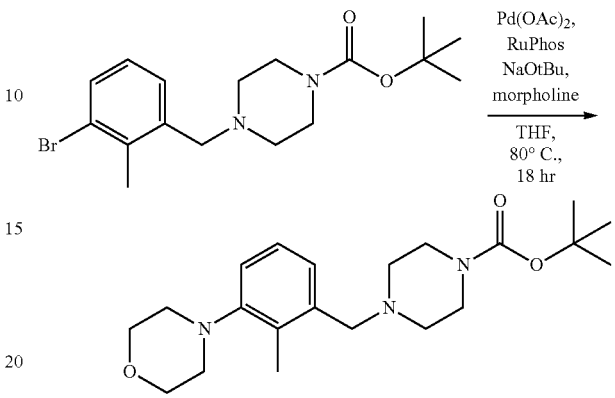

tert-Butyl 4-(3-bromo-2-methylbenzyl)piperazine-1-carboxylate, prepared from commercially available 3-bromo-2-methylbenzaldehyde and tert-butyl piperazine-1-carboxylate according to the reductive-amination procedure of Example 62, Step 1, (185 mg, 0.5 mmol) was transferred to a silica septum-sealed vial equipped with a magnetic stir bar. To this vial was added Pd(OAc)$_2$ (2.22 mg, 0.01 mmol, 2 mol %), RuPhos (18.7 mg, 0.04 mmol, 4 mol %), and tBuONa (72 mg, 0.75 mmol). The vial was connected to a high vacuum, and the contents were dried for at least 1 h. The vial was then back-filled with nitrogen, and then put under vacuum, for 3 cycles. After the third fill of nitrogen, morpholine (53 mg, 0.6 mmol) was added to the vial via syringe, followed by anhydrous THF (3 mL) via syringe. The resulting mixture was stirred and heated to 80° C. for 18 h. The reaction was quenched with saturated H$_2$O (15 mL). The aqueous phase was extracted with EtOAc (15 mL*3). The combined organic layers were washed with brine (15 mL) and dried over anhydrous Na$_2$SO$_4$, filtered, and concentrated. The crude mixture was applied to a chromatography column containing 24 g silica and DCM. A gradient solvent was used from 0% to 100% Ethyl acetate in hexanes to provide 188 mg (89%) of tert-butyl 4-(2-methyl-3-morpholinobenzyl)piperazine-1-carboxylate. $^1$H NMR (400 MHz, CDCl$_3$): δ 1.46 (s, 9H), 2.34 (s, 3H), 2.38-2.40 (m, 4H), 2.89-2.91 (m, 4H), 3.90-3.42 (m, 4H), 3.46 (s, 2H), 3.86-3.88 (m, 4H), 6.98-7.04 (m, 2H), 7.14 (t, J=8.0 Hz, 1H). $^{13}$C NMR (100 MHz, CDCl3): δ 13.20, 28.41, 52.62, 52.96, 61.47, 67.42, 79.48, 118.00, 125.36, 125.63, 132.32, 137.56, 151.64, 154.79.

Preparation of 2,5-Dioxopyrrolidin-1-yl 4-(2-methyl-3-morpholinobenzyl)piperazine-1-carboxylate The title compound was synthesized from the tert-butyl 4-(2-methyl-3-morpholinobenzyl)piperazine-1-carboxylate intermediate according to the representative procedure of Example 62, Steps 2 and 3, which provided 2,5-dioxopyrrolidin-1-yl 4-(2-methyl-3-morpholinobenzyl)piperazine-1-carboxylate as a white solid: $^1$H NMR (400 MHz, CDCl$_3$): δ 2.33 (s, 3H), 2.49 (m, 4H), 2.79 (s, 4H), 2.86-2.89 (m, 4H), 3.48 (m, 4H), 3.60 (s, 2H), 3.83-3.85 (m, 4H), 6.97-7.01 (m, 2H), 7.12 (t, J=7.6 Hz, 1H). $^{13}$C NMR (100 MHz, CDCl$_3$):

δ 13.12, 25.36, 44.56, 45.08, 52.17, 52.49 61.16, 67.27, 118.10, 125.27, 125.62, 132.26, 136.97, 150.18, 151.63, 169.73. LCMS (ESI, m/z): 417.1 [M+H]⁺.

Example 122

2,5-Dioxopyrrolidin-1-yl 4-(2-methyl-3-(piperidin-1-yl)benzyl)piperazine-1-carboxylate

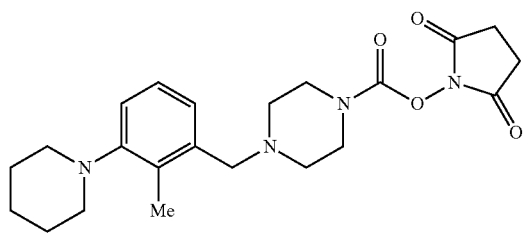 [SMILES: Cc1c(CN2CCN(C(=O)ON3C(=O)CCC3=O)CC2)cccc1N1CCCCC1]

Using the representative procedure of Example 121, tert-butyl 4-(2-methyl-3-(piperidin-1-yl)benzyl)piperazine-1-carboxylate was synthesized from piperidine and tert-butyl 4-(3-bromo-2-methylbenzyl)piperazine-1-carboxylate (itself prepared from commercially available 3-bromo-2-methylbenzaldehyde and tert-butyl piperazine-1-carboxylate according to the reductive-amination procedure of Example 62, Step 1). The intermediate was afforded as a colorless oil.

The title compound was synthesized from the tert-butyl 4-(2-methyl-3-(piperidin-1-yl)benzyl)piperazine-1-carboxylate intermediate according to the representative procedure of Example 62, Steps 2 and 3, which provided 2,5-dioxopyrrolidin-1-yl 4-(2-methyl-3-(piperidin-1-yl)benzyl)piperazine-1-carboxylate as a white solid. ¹H NMR (400 MHz, CDCl₃): δ 1.58 (m, 2H), 1.70-1.75 (m, 4H), 2.33 (s, 3H), 2.52 (m, 4H), 2.83 (m, 8H), 3.49 (m, 4H), 3.63 (m, 2H), 6.96-6.99 (m, 2H), 7.12 (t, J=8.0 Hz, 1H). ¹³C NMR (100 MHz, CDCl₃): δ 13.19, 24.36, 25.46, 26.56, 44.68, 45.21, 52.28, 53.73, 61.32, 109.93, 118.18, 124.58, 125.45, 132.38, 136.72, 150.27, 153.37, 169.77. LCMS (ESI, m/z): 415.2 [M+H]⁺.

Example 123

2,5-Dioxopyrrolidin-1-yl 4-(2-methyl-3-(pyrrolidin-1-yl)benzyl)piperazine-1-carboxylate

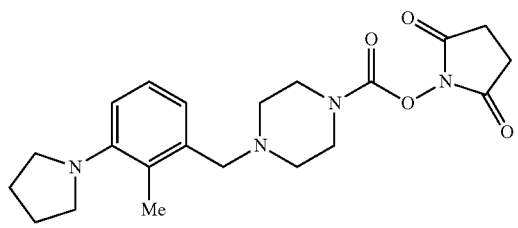 [SMILES: Cc1c(CN2CCN(C(=O)ON3C(=O)CCC3=O)CC2)cccc1N1CCCC1]

Using the representative procedure of Example 121, tert-butyl 4-(2-methyl-3-(pyrrolidin-1-yl)benzyl)piperazine-1-carboxylate was synthesized from pyrrolidine and ten-butyl 4-(3-bromo-2-methylbenzyl)piperazine-1-carboxylate (itself prepared from commercially available 3-bromo-2-methylbenzaldehyde and tert-butyl piperazine-1-carboxylate according to the reductive-amination procedure of Example 62, Step 1). The intermediate was afforded as a colorless oil.

The title compound was synthesized from the tert-butyl 4-(2-methyl-3-(pyrrolidin-1-yl)benzyl)piperazine-1-carboxylate intermediate according to the representative procedure of Example 62, Steps 2 and 3, which provided 2,5-dioxopyrrolidin-1-yl 4-(2-methyl-3-(pyrrolidin-1-yl)benzyl)piperazine-1-carboxylate as a white solid. ¹H NMR (400 MHz, CDCl₃): δ 1.91-1.95 (m, 4H), 2.31 (s, 3H), 2.51 (m, 4H), 2.81 (m, 4H), 3.09-3.12 (m, 4H), 3.50 (s, 4H), 6.89 (d, J=7.6 Hz, 1H), 6.94 (d, J=7.6 Hz, 1H), 7.07 (t, J=7.6 Hz, 1H). ¹³C NMR (100 MHz, CDCl₃): δ 14.89, 24.53, 25.40, 44.63, 45.16, 51.47, 52.17, 61.41, 115.88, 123.30, 125.21, 129.90, 136.77, 149.93, 150.23, 169.75. LCMS (ESI, m/z): 401.1 [M+H]⁺.

Example 124

2,5-Dioxopyrrolidin-1-yl 4-(4-fluoro-3-(pyrrolidin-1-yl)benzyl)piperazine-1-carboxylate

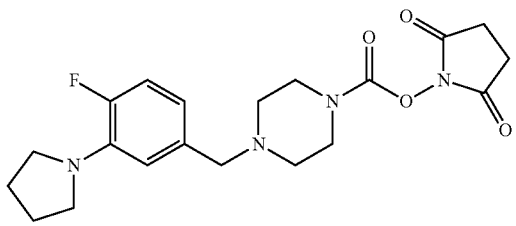 [SMILES: O=C(ON1C(=O)CCC1=O)N1CCN(Cc2ccc(F)c(N3CCCC3)c2)CC1]

The title compound was synthesized directly from commercially available 4-fluoro-3-(pyrrolidin-1-yl)benzaldehyde and tert-butyl piperazine-1-carboxylate according to the representative procedure of Example 62, Steps 1, 2 and 3 to provide 2,5-dioxopyrrolidin-1-yl 4-(4-fluoro-3-(pyrrolidin-1-yl)benzyl)piperazine-1-carboxylate as an amorphous white solid. ¹H NMR (400 MHz, Chloroform-d) δ 6.98-6.89 (m, 1H), 6.66-6.61 (m, 1H), 6.61-6.56 (m, 1H), 3.66 (s, 2H), 3.55 (s, 2H), 3.46 (s, 2H), 3.44-3.36 (m, 4H), 2.93-2.76 (m, 4H), 2.58-2.44 (m, 4H), 2.06-1.86 (m, 4H). LCMS (ESI, m/z): 405.1 [M+H]⁺.

Example 125

2,5-Dioxopyrrolidin-1-yl 4-({2-[(8aR)-octahydropyrrolo[1,2-a]piperazin-2-yl]-4-chlorophenyl}methyl)piperazine-1-carboxylate

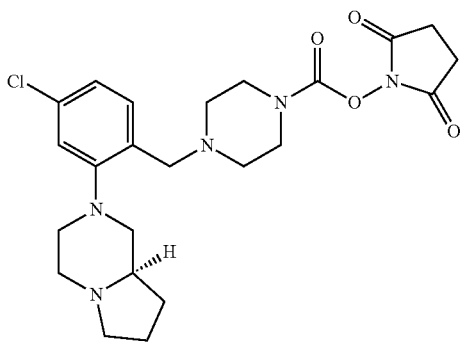 [SMILES: O=C(ON1C(=O)CCC1=O)N1CCN(Cc2ccc(Cl)cc2N2CCN3CCC[C@@H]3C2)CC1]

Step 1: Preparation of 2-[(8aR)-octahydropyrrolo[1,2-a]piperazin-2-yl]-4-chlorobenzaldehyde

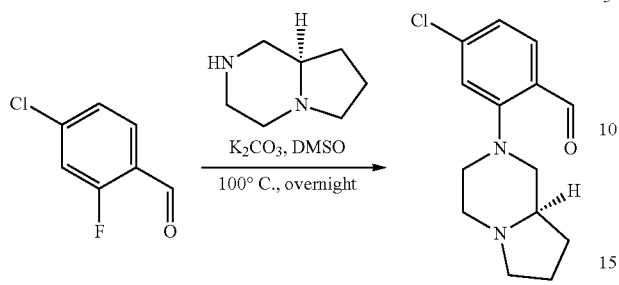

A 100-mL round-bottom flask was purged and maintained with an inert atmosphere of nitrogen and charged with 4-chloro-2-fluorobenzaldehyde (1.00 g, 6.31 mmol, 1.00 equiv), (8aR)-octahydropyrrolo[1,2-a]piperazine (0.950 mg, 7.53 mmol, 1.19 equiv), potassium carbonate (2.17 g, 15.7 mmol, 2.49 equiv), and DMSO (20 mL). The resulting solution was stirred overnight at 100° C. and diluted with H$_2$O (15 mL). The resulting solution was extracted with ethyl acetate (3×20 mL), and the organic layers were combined, washed with H$_2$O (3×10 mL), dried over anhydrous sodium sulfate, filtered, and concentrated under reduced pressure. The residue was chromatographed on a silica gel column with ethyl acetate/petroleum ether (1/4) to provide 0.700 g (42% yield) of 2-[(8aR)-octahydropyrrolo[1,2-a]piperazin-2-yl]-4-chlorobenzaldehyde as a light yellow oil. $^1$H NMR (300 MHz, Chloroform-d): δ 10.21 (s, 1H), 7.73 (d, J=8.1 Hz, 1H), 7.02-7.09 (m, 2H), 3.34-3.38 (m, 1H), 3.13-3.26 (m, 4H), 2.71-2.84 (m, 1H), 2.52 (br, 1H), 2.18-2.29 (m, 2H), 1.68-1.97 (m, 3H), 1.41-1.50 (m, 1H). LCMS (ESI, m/z): 265 [M+H]$^+$.

Step 2: Preparation of tert-butyl 4-([2-[(8aR)-octahydropyrrolo[1,2-a]piperazin-2-yl]-4-chlorophenyl]methyl)piperazine-1-carboxylate

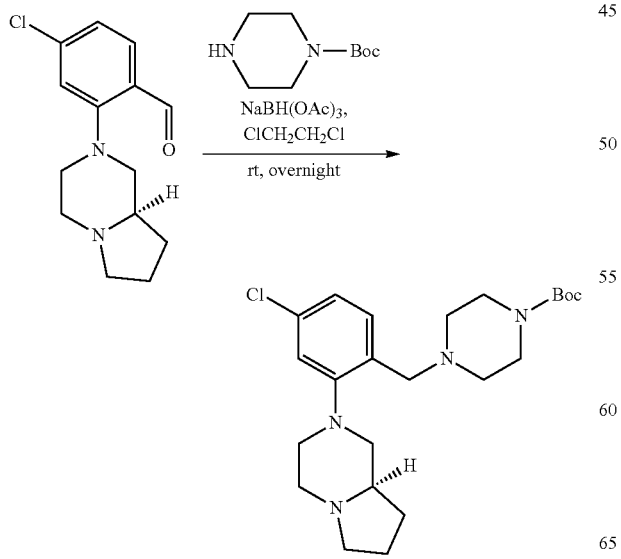

A 20-mL round-bottom flask was charged with 2-[(8aR)-octahydropyrrolo[1,2-a]piperazin-2-yl]-4-chlorobenzaldehyde (265 mg, 1.00 mmol, 1.00 equiv), tert-butyl piperazine-1-carboxylate (186 mg, 1.00 mmol, 1.00 equiv), and 1,2-dichloroethane (5 mL). The mixture was stirred at room temperature for 30 min. Sodium triacetoxyborohydride (414 mg, 1.95 mmol, 1.95 equiv) was added. The resulting solution was stirred overnight at room temperature and diluted with H$_2$O (15 mL). The resulting solution was extracted with dichloromethane (3×10 mL), and the organic layers were combined, washed with H$_2$O (3×5 mL), dried over anhydrous sodium sulfate, filtered, and concentrated under reduced pressure. The residue was chromatographed on a silica gel column with ethyl acetate/petroleum ether (3/1) to provide 200 mg (43% yield) of tert-butyl 4-([2-[(8aR)-octahydropyrrolo[1,2-a]piperazin-2-yl]-4-chlorophenyl]methyl)piperazine-1-carboxylate as a yellow oil. LCMS (ESI, m/z): 435 [M+H]$^+$.

Step 3: Preparation of 1-([2-[(8aR)-octahydropyrrolo[1,2-a]piperazin-2-yl]-4-chlorophenyl]methyl)piperazine

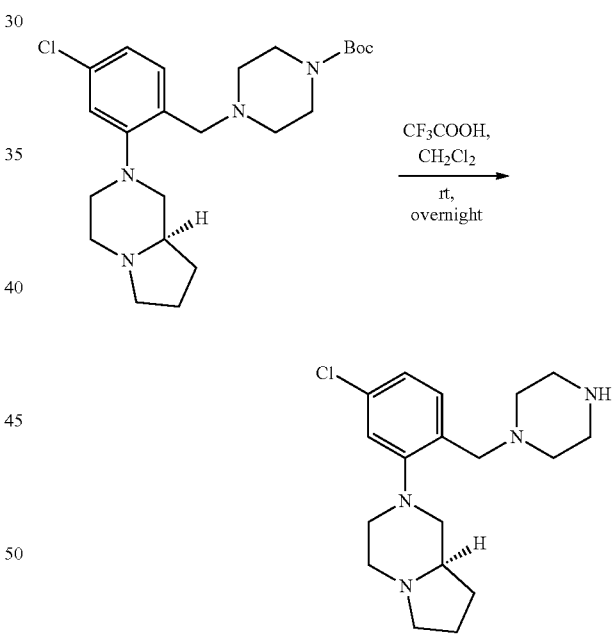

A 50-mL round-bottom flask was charged with tert-butyl 4-([2-[(8aR)-octahydropyrrolo[1,2-a]piperazin-2-yl]-4-chlorophenyl]methyl)piperazine-1-carboxylate (200 mg, 0.460 mmol, 1.00 equiv) and dichloromethane (5 mL). Trifluoroacetic acid (1 mL) was added dropwise. The resulting solution was stirred overnight at room temperature. The resulting mixture was concentrated under reduced pressure to provide 402 mg (crude) of 1-([2-[(8aR)-octahydropyrrolo[1,2-a]piperazin-2-yl]-4-chlorophenyl]methyl)piperazine as a brown oil. LCMS (ESI, m/z): 335 [M+H]$^+$.

183

Step 4: Preparation of 2,5-dioxopyrrolidin-1-yl 4-({2-[(8aR)-octahydropyrrolo[1,2-a]piperazin-2-yl]-4-chlorophenyl}methyl)piperazine-1-carboxylate

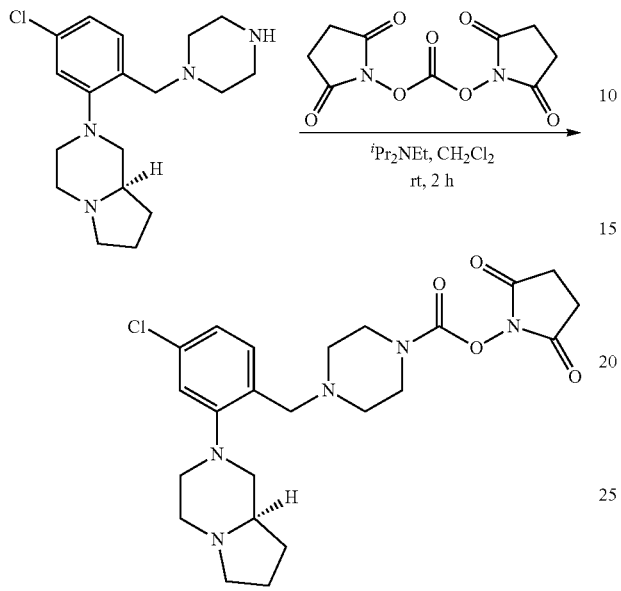

A 25-mL round-bottom flask was charged with 1-([2-[(8aR)-octahydropyrrolo[1,2-a]piperazin-2-yl]-4-chlorophenyl]methyl)piperazine (335 mg, 1.00 mmol, 1.00 equiv), bis(2,5-dioxopyrrolidin-1-yl) carbonate (256 mg, 1.00 mmol, 1.00 equiv), and dichloromethane (5 mL). N,N-Diisopropylethylamine (258 mg, 2.00 mmol, 2.00 equiv) was added dropwise. The resulting solution was stirred for 2 h at room temperature and diluted with $H_2O$ (30 mL). The resulting solution was extracted with dichloromethane (3×10 mL), and the organic layers were combined, washed with $H_2O$ (3×5 mL), dried over anhydrous sodium sulfate, filtered, and concentrated under reduced pressure. The residue was chromatographed on a silica gel column with ethyl acetate/petroleum ether (100/1). The crude product (231 mg) was purified by preparative HPLC using the following gradient conditions: 20% $CH_3CN$/80% Phase A increasing to 80% $CH_3CN$ over 10 min, then to 100% $CH_3CN$ over 0.1 min, holding at 100% $CH_3CN$ for 1.9 min, then reducing to 20% $CH_3CN$ over 0.1 min, and holding at 20% for 1.9 min, on a Waters 2767-5 Chromatograph. Column: Xbridge Prep C18, 19*150 mm, 5 um; Mobile phase: Phase A: water; Phase B: $CH_3CN$; Detector, UV 220 & 254 nm. Purification resulted in 97.2 mg (20% yield) of 2,5-dioxopyrrolidin-1-yl 4-({2-[(8aR)-octahydropyrrolo[1,2-a]piperazin-2-yl]-4-chlorophenyl}methyl)piperazine-1-carboxylate as a yellow solid. $^1$H NMR (300 MHz, Chloroform-d) δ 7.35 (d, J=8.1 Hz, 1H), 7.02-7.08 (m, 2H), 3.35-3.62 (m, 6H), 3.09-3.28 (m, 4H), 2.88-2.95 (m, 1H), 2.82 (br, 4H), 2.41-2.63 (m, 6H), 2.24-2.32 (m, 2H), 1.83-1.93 (m, 3H), 1.45-1.55 (m, 1H). LCMS (ESI, m/z): 476 [M+H]$^+$.

184

Example 126

2,5-Dioxopyrrolidin-1-yl 4-methanesulfonylpiperazine-1-carboxylate

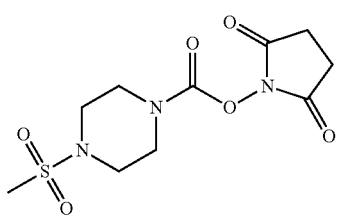 [SMILES: CS(=O)(=O)N1CCN(C(=O)ON2C(=O)CCC2=O)CC1]

The title compound was prepared directly from commercially available 1-methanesulfonylpiperazine and bis(2,5-dioxopyrrolidin-1-yl) carbonate according to the representative procedure of Example 51 to provide 2,5-dioxopyrrolidin-1-yl 4-methanesulfonylpiperazine-1-carboxylate as a white solid: $^1$H NMR (300 MHz, Chloroform-d) δ 3.57-3.69 (m, 8H), 2.84 (s, 4H), 2.13 (s, 3H). LCMS (ESI, m/z): 306 [M+H]$^+$.

Example 127

2,5-Dioxopyrrolidin-1-yl 4-{[5-methyl-2-(morpholin-4-yl)phenyl]methyl}piperazine-1-carboxylate

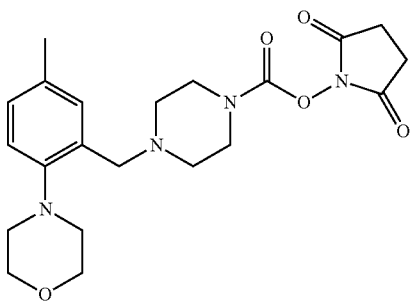 [SMILES: Cc1ccc(N2CCOCC2)c(CN2CCN(C(=O)ON3C(=O)CCC3=O)CC2)c1]

Step 1: Preparation of tert-butyl 4-[(2-bromo-5-methylphenyl)methyl]piperazine-1-carboxylate

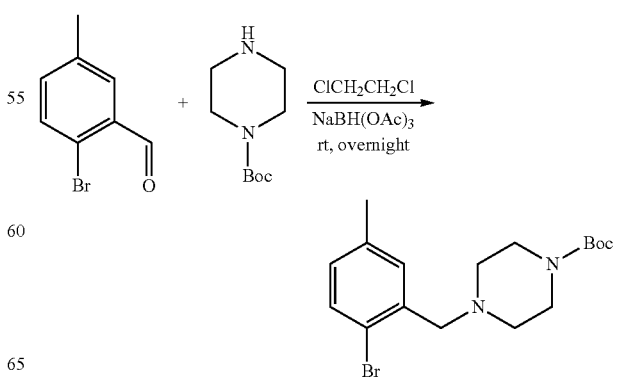

A 25-mL round-bottom flask was charged with 2-bromo-5-methylbenzaldehyde (1.00 g, 5.05 mmol, 1.00 equiv), tert-butyl piperazine-1-carboxylate (1.03 g, 5.56 mmol, 1.10 equiv), and 1,2-dichloroethane (15 mL). The mixture was stirred at room temperature for 1 h. Sodium triacetoxyborohydride (3.22 g, 15.2 mmol, 3.00 equiv) was added. The resulting solution was stirred overnight at room temperature, diluted with water (100 mL), and extracted with dichloromethane (2×150 mL). The organic layers were combined, dried over anhydrous sodium sulfate, filtered, and concentrated under reduced pressure. The residue was chromatographed on a silica gel column with ethyl acetate/petroleum ether (1/5) to provide 1.50 g (81% yield) of tert-butyl 4-[2-bromo-5-methylphenyl)methyl]piperazine-1-carboxylate as a light yellow oil. LCMS (ESI, m/z): 369 [M+H]$^+$.

Step 2: Preparation of tert-butyl 4-[[5-methyl-2-(morpholin-4-yl)phenyl]methyl]piperazine-1-carboxylate

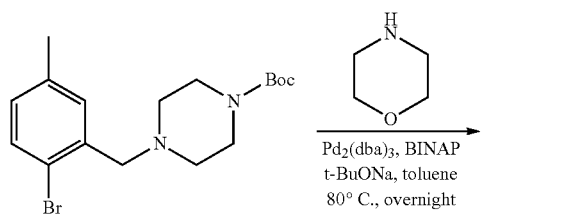

A 40-mL round-bottom flask was charged with tert-butyl 4-[(2-bromo-5-methylphenyl)methyl]piperazine-1-carboxylate (600 mg, 1.62 mmol, 1.00 equiv), morpholine (213 mg, 2.44 mmol, 1.50 equiv), Pd$_2$(dba)$_3$ (73 mg, 0.08 mmol, 0.05 equiv), BINAP (149 mg, 0.24 mmol, 0.15 equiv), t-BuONa (235 mg, 2.45 mmol, 1.50 equiv), and toluene (10 mL). The resulting solution was stirred overnight at 80° C. and diluted with water (100 mL). The resulting solution was extracted with ethyl acetate (2×150 mL), and the organic layers were combined, dried over anhydrous sodium sulfate, and concentrated under reduced pressure. The residue was chromatographed on a silica gel column with ethyl acetate/petroleum ether (1/5) to provide 500 mg (74% yield) of tert-butyl 4-[[5-methyl-2-(morpholin-4-yl)phenyl]methyl]piperazine-1-carboxylate as a yellow oil. LCMS (ESI, m/z): 376 [M+H]$^+$.

Step 3: Preparation of 4-[4-methyl-2-(piperazin-1-ylmethyl)phenyl]morpholine

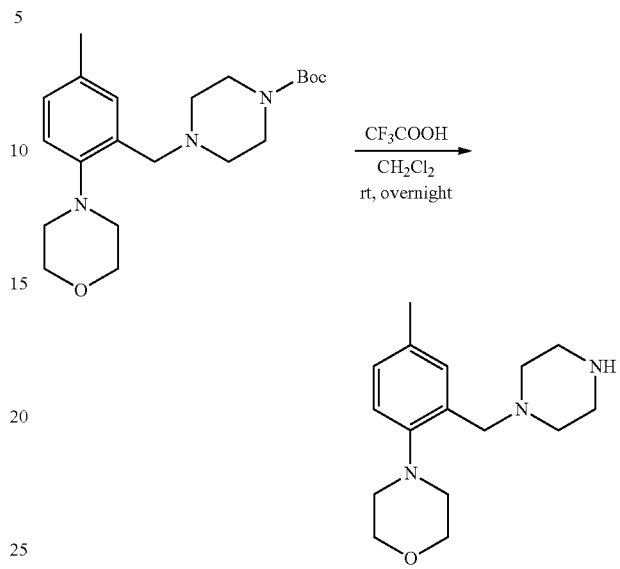

A 100-mL round-bottom flask was charged with tert-butyl 4-[[5-methyl-2-(morpholin-4-yl)phenyl]methyl]piperazine-1-carboxylate (500 mg, 1.33 mmol, 1.00 equiv), dichloromethane (15 mL), and trifluoroacetic acid (2.0 mL). The resulting solution was stirred overnight at room temperature and concentrated under reduced pressure to provide 365 mg (crude) of 4-[4-methyl-2-(piperazin-1-ylmethyl)phenyl]morpholine as a brown oil. LCMS (ESI, m/z): 276 [M+H]$^+$.

Step 4: Preparation of 2,5-dioxopyrrolidin-1-yl 4-{[5-methyl-2-(morpholin-4-yl)phenyl]methyl}piperazine-1-carboxylate

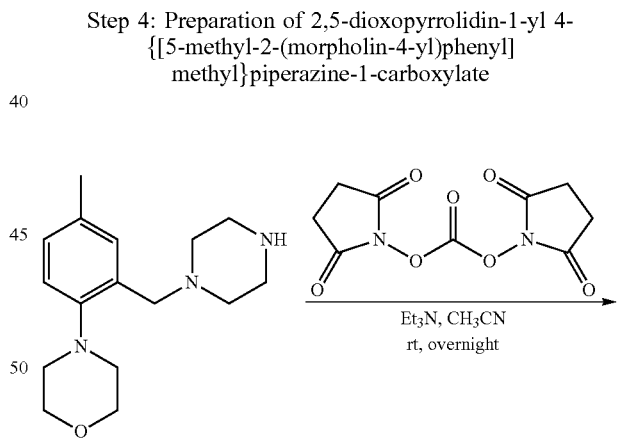

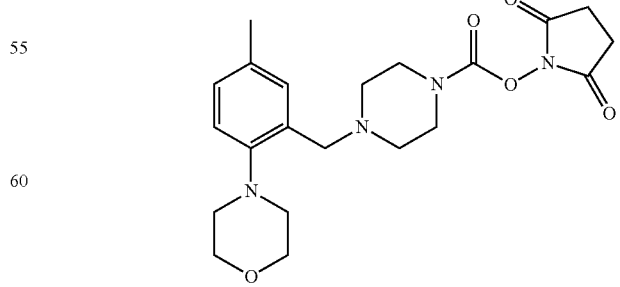

A 50-mL round-bottom flask was charged with 4-[4-methyl-2-(piperazin-1-ylmethyl)phenyl]morpholine (165 mg, 0.60 mmol, 1.00 equiv), bis(2,5-dioxopyrrolidin-1-yl) carbonate (307 mg, 1.20 mmol, 2.00 equiv), acetonitrile (15 mL), and triethylamine (182 mg, 1.80 mmol, 3.00 equiv). The resulting solution was stirred overnight at room temperature and concentrated under reduced pressure. The crude product (200 mg) was purified by preparative HPLC using the following gradient conditions: 20% CH$_3$CN/80% Phase A increasing to 80% CH$_3$CN over 10 min, then to 100% CH$_3$CN over 0.1 min, holding at 100% CH$_3$CN for 1.9 min, then reducing to 20% CH$_3$CN over 0.1 min, and holding at 20% for 1.9 min, on a Waters 2767-5 Chromatograph. Column: Xbridge Prep C18, 19*150 mm, 5um; Mobile phase: Phase A: water; Phase B: CH$_3$CN; Detector, UV 220 & 254 nm. Purification resulted in 112 mg (45% yield) of 2,5-dioxopyrrolidin-1-yl 4-{[5-methyl-2-(morpholin-4-yl)phenyl]methyl}piperazine-1-carboxylate as a white solid. $^1$H NMR (300 MHz, chloroform-d) δ 7.21 (s, 1H), 7.02-7.10 (m, 2H), 3.81-3.84 (m, 4H), 3.51-3.59 (m, 6H), 2.90-2.93 (m, 4H), 2.82 (s, 4H), 2.55 (br, 4H), 2.32 (s, 3H). LCMS (ESI, m/z): 439 [M+Na]$^+$.

Example 128

2,5-Dioxopyrrolidin-1-yl 4-{[5-methyl-2-(pyrrolidin-1-yl)phenyl]methyl}piperazine-1-carboxylate

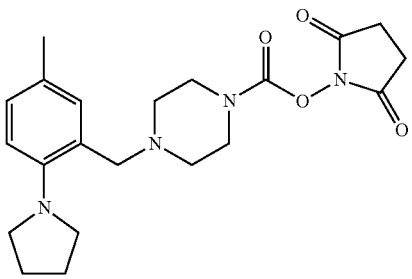 [SMILES: Cc1ccc(N2CCCC2)c(CN2CCN(C(=O)ON3C(=O)CCC3=O)CC2)c1]

Step 1: Preparation of tert-butyl 4-[[5-methyl-2-(pyrrolidin-1-yl)phenyl]methyl]piperazine-1-carboxylate

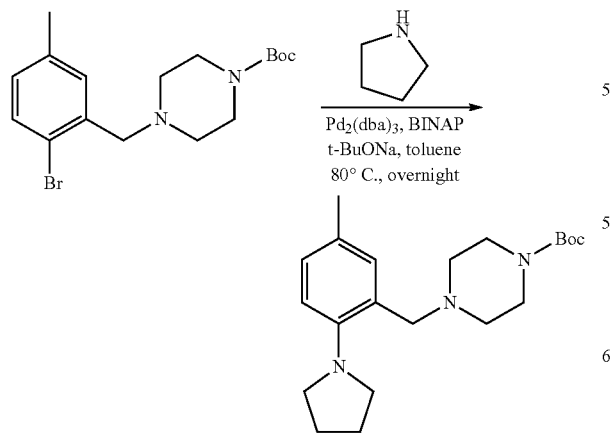

A 40-mL round-bottom flask was charged with tert-butyl 4-[(2-bromo-5-methylphenyl)methyl]piperazine-1-carboxylate (700 mg, 1.90 mmol, 1.00 equiv), pyrrolidine (202 mg, 2.84 mmol, 1.50 equiv), Pd$_2$(dba)$_3$ (92 mg, 0.10 mmol, 0.05 equiv), BINAP (180 mg, 0.29 mmol, 0.15 equiv), t-BuONa (274 mg, 2.85 mmol, 1.50 equiv), and toluene (10 mL). The resulting solution was stirred overnight at 80° C. and diluted with water (100 mL). The resulting solution was extracted with ethyl acetate (2×150 mL), and the organic layers were combined, dried over anhydrous sodium sulfate, and concentrated under reduced pressure. The residue was chromatographed on a silica gel column with ethyl acetate/ petroleum ether (1/5) to provide 450 mg (59% yield) of tert-butyl 4-[[5-methyl-2-(pyrrolidin-1-yl)phenyl]methyl] piperazine-1-carboxylate as a yellow oil. LCMS (ESI, m/z): 360 [M+H]$^+$.

Step 2: Preparation of 1-[[5-methyl-2-(pyrrolidin-1-yl)phenyl]methyl]piperazine

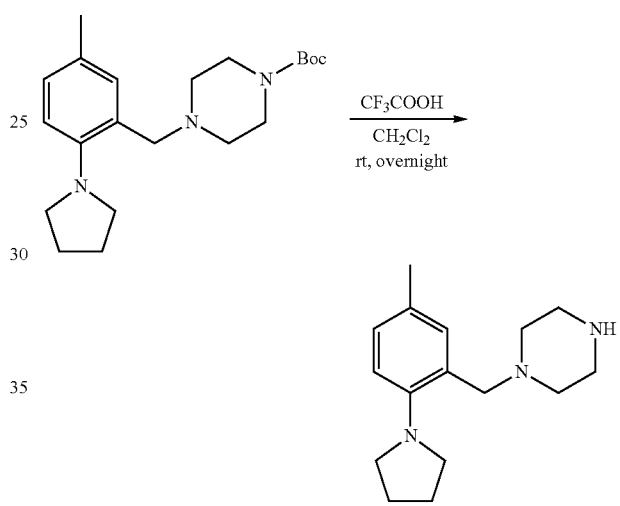

A 100-mL round-bottom flask was charged with tert-butyl 4-[[5-methyl-2-(pyrrolidin-1-yl)phenyl]methyl]piperazine-1-carboxylate (450 mg, 1.25 mmol, 1.00 equiv), dichloromethane (15 mL), and trifluoroacetic acid (2.0 mL). The resulting solution was stirred overnight at room temperature and concentrated under reduced pressure to provide 323 mg (crude) of 1-[[5-methyl-2-(pyrrolidin-1-yl)phenyl]methyl] piperazine as a brown oil. LCMS (ESI, m/z): 260 [M+H]$^+$.

Step 3: Preparation of 2,5-dioxopyrrolidin-1-yl 4-{[5-methyl-2-(pyrrolidin-1-yl)phenyl] methyl}piperazine-1-carboxylate

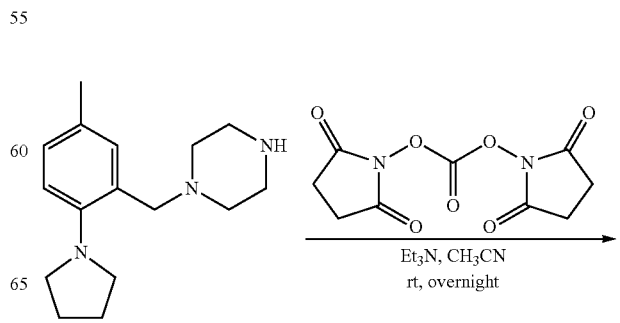

-continued

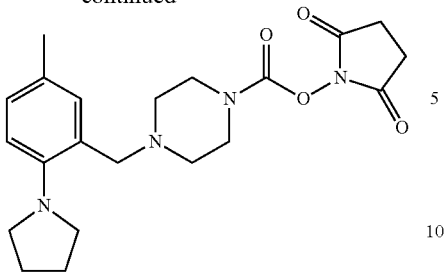

A 50-mL round-bottom flask was charged with 1-[[5-methyl-2-(pyrrolidin-1-yl)phenyl]methyl]piperazine (123 mg, 0.47 mmol, 1.00 equiv), bis(2,5-dioxopyrrolidin-1-yl) carbonate (241 mg, 0.940 mmol, 2.00 equiv), acetonitrile (15 mL), and triethylamine (142 mg, 1.40 mmol, 3.00 equiv). The resulting solution was stirred overnight at room temperature and concentrated under reduced pressure. The crude product (300 mg) was purified by preparative HPLC using the following gradient conditions: 20% CH$_3$CN/80% Phase A increasing to 80% CH$_3$CN over 10 min, then to 100% CH$_3$CN over 0.1 min, holding at 100% CH$_3$CN for 1.9 min, then reducing to 20% CH$_3$CN over 0.1 min, and holding at 20% for 1.9 min, on a Waters 2767-5 Chromatograph. Column: Xbridge Prep C18, 19*150 mm, 5um; Mobile phase: Phase A: water; Phase B: CH$_3$CN; Detector, UV 220 & 254 nm. Purification resulted in 124 mg (65% yield) of 2,5-dioxopyrrolidin-1-yl 4-{[5-methyl-2-(pyrrolidin-1-yl)phenyl]methyl}piperazine-1-carboxylate as a white solid. $^1$H NMR (300 MHz, chloroform-d) δ 7.21 (s, 1H), 6.82-7.01 (m, 1H), 6.88-6.91 (m, 1H), 3.55-3.64 (m, 6H), 3.10 (br, 4H), 2.82 (br, 4H), 2.53 (br, 4H), 2.23 (s, 3H), 1.90 (br, 4H). LCMS (ESI, m/z): 401 [M+H]$^+$.

Example 129

2,5-Dioxopyrrolidin-1-yl 4-(4-chloro-2-(piperidin-1-yl)benzyl)piperazine-1-carboxylate

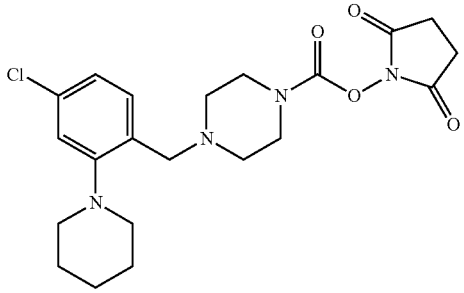 [SMILES: O=C(ON1C(=O)CCC1=O)N1CCN(Cc2ccc(Cl)cc2N2CCCCC2)CC1]

The title compound was synthesized directly from commercially available 4-chloro-2-fluorobenzaldehyde and piperidine according to the representative procedure of Example 65, Steps 1, 2, 3 and 4 to provide 2,5-dioxopyrrolidin-1-yl 4-(4-chloro-2-(piperidin-1-yl)benzyl)piperazine-1-carboxylate as a light yellow solid. $^1$H NMR (400 MHz, Chloroform-d) δ 7.37 (d, J=7.9 Hz, 1H), 7.03 (s, 1H), 7.00 (d, J=2.1 Hz, 1H), 3.63 (s, 2H), 3.56-3.49 (m, 4H), 2.87-2.77 (m, 8H), 2.57-2.49 (m, 4H), 1.75-1.65 (m, 4H), 1.64-1.48 (m, 2H). LCMS (ESI, m/z): 435.1 [C$_{21}$H$_{27}$ClN$_4$O$_4$]$^+$.

Example 130

2,5-Dioxopyrrolidin-1-yl 4-(2-(8-oxa-3-azabicyclo[3.2.1]octan-3-yl)-4-chlorobenzyl)piperazine-1-carboxylate

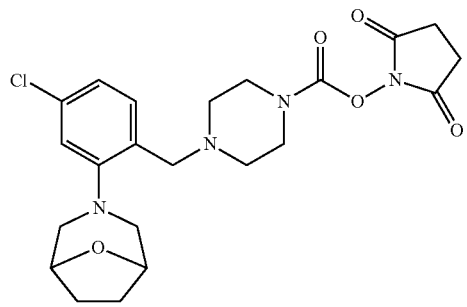 [SMILES: O=C(ON1C(=O)CCC1=O)N1CCN(Cc2ccc(Cl)cc2N2CC3CCC(C2)O3)CC1]

The title compound was synthesized directly from commercially available 4-chloro-2-fluorobenzaldehyde and 8-oxa-3-azabicyclo[3.2.1]octane according to the representative procedure of Example 65, Steps 1, 2, 3 and 4 to provide 2,5-dioxopyrrolidin-1-yl 4-(2-(8-oxa-3-azabicyclo[3.2.1]octan-3-yl)-4-chlorobenzyl)-piperazine-1-carboxylate as a clear oil. $^1$H NMR (400 MHz, Chloroform-d) δ 7.36 (d, J=8.1 Hz, 1H), 7.11-7.02 (m, 2H), 4.38 (s, 2H), 3.62 (s, 2H), 3.56 (s, 2H), 3.50 (s, 2H), 3.02 (d, J=11.2 Hz, 2H), 2.84-2.73 (m, 6H), 2.49 (s, 4H), 2.13-1.91 (m, 4H). LCMS (ESI, m/z): 463.1 [C$_{22}$H$_{27}$ClN$_4$O$_5$]$^+$.

Example 131

2,5-Dioxopyrrolidin-1-yl 4-(4-chloro-2-(hexahydrocyclopenta[b][1,4]oxazin-4(4aH)-yl)benzyl)piperazine-1-carboxylate

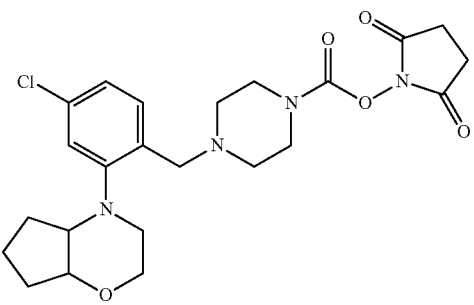 [SMILES: O=C(ON1C(=O)CCC1=O)N1CCN(Cc2ccc(Cl)cc2N2CCOC3CCCC32)CC1]

The title compound was synthesized directly from commercially available 4-chloro-2-fluorobenzaldehyde and octahydrocyclopenta[b][1,4]oxazine according to the representative procedure of Example 65, Steps 1, 2, 3 and 4 to provide 2,5-dioxopyrrolidin-1-yl 4-(4-chloro-2-(hexahydrocyclopenta[b][1,4]oxazin-4(4aH)-yl)benzyl)piperazine-1-carboxylate as a clear oil. $^1$H NMR (400 MHz, Chloroform-d) δ 7.42-7.35 (m, 1H), 7.13-7.07 (m, 2H), 3.97 (dd, J=11.4, 2.4 Hz, 1H), 3.91 (s, 1H), 3.85 (td, J=11.5, 2.5 Hz, 1H), 3.72-3.42 (m, 6H), 3.00 (d, J=11.8 Hz, 1H), 2.87-2.62 (m, 6H), 2.52 (s, 4H), 2.06-1.92 (m, 1H), 1.82-1.65 (m, 4H), 1.15-1.02 (m, 1H). LCMS (ESI, m/z): 477.1 [C$_{23}$H$_{29}$ClN$_4$O$_5$]$^+$.

Example 132

2,5-Dioxopyrrolidin-1-yl 4-(3-chloro-5-(piperidin-1-yl)benzyl)piperazine-1-carboxylate

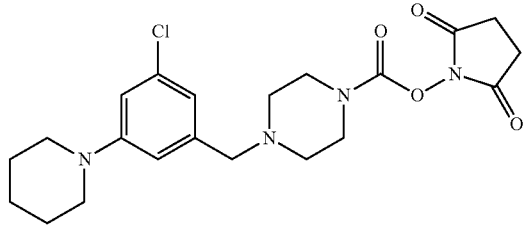 [SMILES: O=C(ON1C(=O)CCC1=O)N1CCN(Cc2cc(Cl)cc(N3CCCCC3)c2)CC1]

Step 1: Preparation of tert-butyl 4-(3-bromo-5-chlorobenzyl)piperazine-1-carboxylate

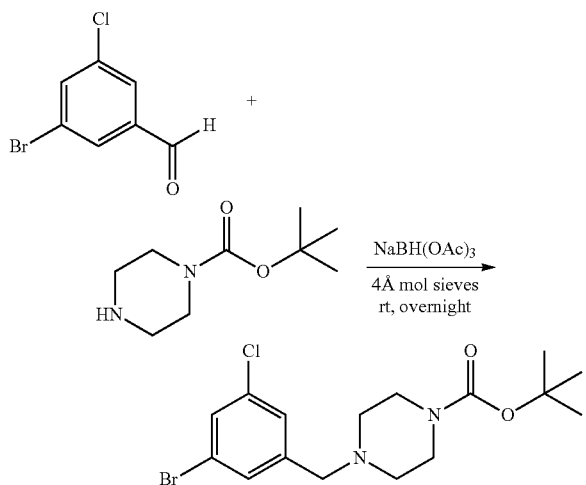

The title compound was synthesized directly from commercially available 3-bromo-5-chlorobenzaldehyde and tert-butyl piperazine-1-carboxylate according to the representative procedure from Example 62, Step 1 to provide tert-butyl 4-(3-bromo-5-chlorobenzyl)piperazine-1-carboxylate as an amorphous white solid (1.2 g, 56% yield). $^1$H NMR (400 MHz, Chloroform-d) δ 7.44-7.38 (m, 2H), 7.29 (s, 1H), 3.50-3.42 (m, 6H), 2.47-2.29 (m, 4H), 1.54-1.42 (m, 9H).

Step 2: Preparation of tert-butyl 4-(3-chloro-5-(piperidin-1-yl)benzyl)piperazine-1-carboxylate

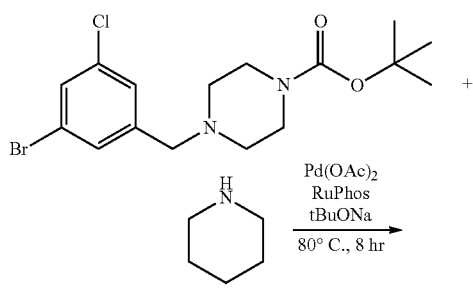

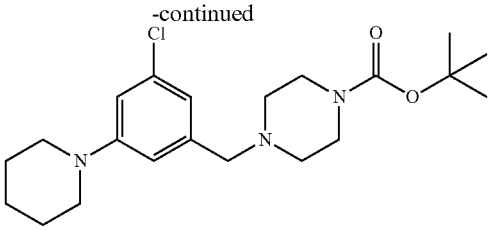

A 12-mL vial equipped with a magnetic stir bar was charged with tert-butyl 4-(3-bromo-5-chlorobenzyl)piperazine-1-carboxylate (257 mg, 0.659 mmol). To this vial was added Pd(OAc)$_2$ (4.44 mg, 0.0200 mmol), RuPhos (36.9 mg, 0.0790 mmol), and tBuONa (95.0 mg, 0.988 mmol). The contents of the vial were dried in vacuo for 1 h. The vial was then flushed with nitrogen and evacuated 3 times. Piperidine (61.7 mg, 0.725 mmol) was then added to the vial, followed by anhydrous THF (3 mL). The resulting stirred mixture was heated at 80° C. for 8 h. The reaction mixture was then cooled to rt whereupon 5 mL H$_2$O was added. The reaction mixture was extracted with EtOAc (3×10 mL), and the combined organic layers were dried over Na$_2$SO4, filtered, and concentrated under reduced pressure to yield a brown oil. The oil was purified using a 12 g ISCO SiO$_2$ column eluting with 0-20% of EtOAc/Hexanes over 30 min. The desired fractions were combined and concentrated under reduced pressure to yield tert-butyl 4-(3-chloro-5-(piperidin-1-yl)benzyl)piperazine-1-carboxylate as a clear oil (169 mg, 65% yield). $^1$H NMR (400 MHz, Chloroform-d) δ 6.72-6.40 (m, 3H), 3.36-3.17 (m, 6H), 3.09-2.92 (m, 4H), 2.32-2.13 (m, 4H), 2.02 (s, 1H), 1.62-1.37 (m, 7H), 1.33-1.22 (m, 9H).

Step 3: Preparation of 2,5-dioxopyrrolidin-1-yl 4-(3-chloro-5-(piperidin-1-yl)benzyl)piperazine-1-carboxylate

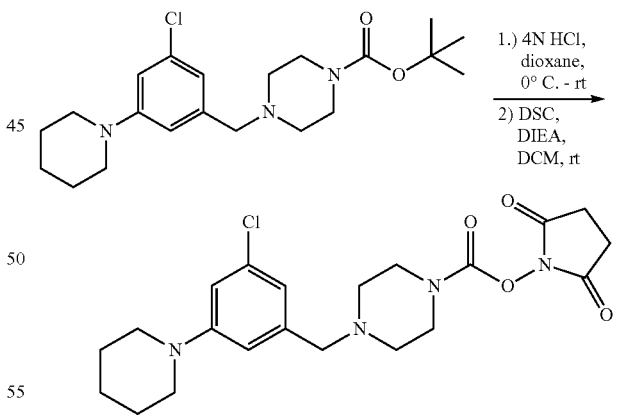

The title compound was synthesized directly from tert-butyl 4-(3-chloro-5-(piperidin-1-yl)benzyl)piperazine-1-carboxylate according to the representative procedure of Example 62, Steps 2 and 3 to provide 2,5-dioxopyrrolidin-1-yl 4-(3-chloro-5-(piperidin-1-yl)benzyl)piperazine-1-carboxylate as an amorphous white solid. $^1$H NMR (400 MHz, Chloroform-d) δ 6.86-6.72 (m, 3H), 3.79-3.62 (m, 2H), 3.62-3.51 (m, 2H), 3.46 (s, 2H), 3.26-3.10 (m, 4H), 2.93-2.73 (m, 4H), 2.60-2.43 (m, 4H), 1.76-1.67 (m, 4H), 1.65-1.60 (m, 2H). LCMS (ESI, m/z): 435.1 [M+H]$^+$.

Example 133

2,5-Dioxopyrrolidin-1-yl 4-(3-(piperidin-1-yl)benzyl)piperazine-1-carboxylate

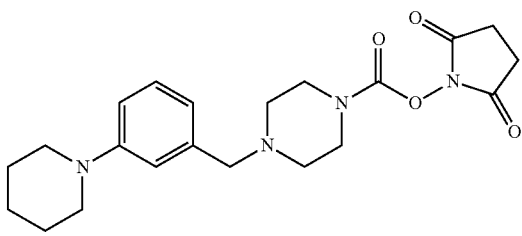 [SMILES: O=C(ON1C(=O)CCC1=O)N1CCN(Cc2cccc(N3CCCCC3)c2)CC1]

The title compound was synthesized directly from commercially available 3-(piperidin-1-yl)benzaldehyde and tert-butyl piperazine-1-carboxylate according to the representative procedure of Example 62, Steps 1, 2 and 3 to provide 2,5-dioxopyrrolidin-1-yl 4-(3-(piperidin-1-yl)benzyl)piperazine-1-carboxylate as an amorphous white solid. $^1$H NMR (400 MHz, Chloroform-d) δ 7.26-7.18 (m, 1H), 6.95 (s, 1H), 6.91-6.84 (m, 1H), 6.83-6.75 (m, 1H), 3.75-3.62 (m, 2H), 3.63-3.54 (m, 2H), 3.52 (s, 2H), 3.25-3.12 (m, 4H), 2.90-2.77 (m, 4H), 2.63-2.43 (m, 4H), 1.79-1.67 (m, 4H), 1.65-1.53 (m, 2H). LCMS (ESI, m/z): 401.2 [M+H]$^+$.

Example 134

2,5-Dioxopyrrolidin-1-yl 4-((3-oxo-3,4-dihydro-2H-benzo[b][1,4]oxazin-6-yl)methyl)piperazine-1-carboxylate

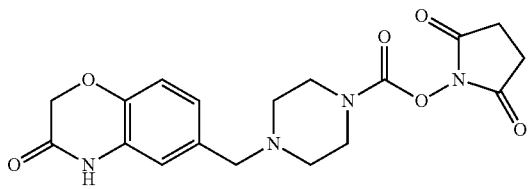 [SMILES: O=C1COc2ccc(CN3CCN(C(=O)ON4C(=O)CCC4=O)CC3)cc2N1]

The title compound was synthesized directly from commercially available 3-oxo-3,4-dihydro-2H-benzo[b][1,4]oxazine-6-carbaldehyde and tert-butyl piperazine-1-carboxylate according to the representative procedure of Example 62, Steps 1, 2 and 3 to provide 2,5-dioxopyrrolidin-1-yl 4-((3-oxo-3,4-dihydro-2H-benzo[b][1,4]oxazin-6-yl)methyl)piperazine-1-carboxylate as an amorphous white solid. $^1$H NMR (400 MHz, Chloroform-d) δ 7.79 (d, J=8.0 Hz, 2H), 7.40 (t, J=8.0 Hz, 2H), 7.30 (t, J=8.0, 1H), 6.47 (s, 1H), 3.95 (s, 3H), 3.67 (bs, 2H), 3.59 (s, 2H), 3.56 (bs, 2H), 2.84 (s, 4H), 2.57 (t, J=4.5 Hz, 4H). LCMS (ESI, m/z): 398.2 [M+H]$^+$.

Example 135

2,5-Dioxopyrrolidin-1-yl 4-((4-bromo-1-methyl-1H-pyrazol-5-yl)methyl)piperazine-1-carboxylate

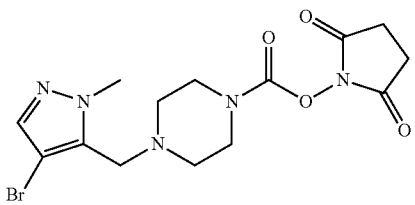 [SMILES: Cn1ncc(Br)c1CN1CCN(C(=O)ON2C(=O)CCC2=O)CC1]

The title compound was synthesized directly from commercially available 4-bromo-1-methyl-1H-pyrazole-5-carbaldehyde and tert-butyl piperazine-1-carboxylate according to the representative procedure of Example 35, Steps i, ii, and iii to provide 2,5-dioxopyrrolidin-1-yl 4-((4-bromo-1-methyl-1H-pyrazol-5-yl)methyl)piperazine-1-carboxylate as a white solid. $^1$H NMR (400 MHz, Chloroform-d) δ 7.41 (s, 1H), 3.92 (s, 3H), 3.72-3.44 (m, 6H), 2.83 (s, 4H), 2.68-2.39 (m, 4H). LCMS (ESI, m/z): 400.1 [C$_{14}$H$_{18}$BrN$_5$O$_4$]$^+$.

Example 136

2,5-Dioxopyrrolidin-1-yl 4-((5-(4-methoxyphenyl)isoxazol-3-yl)methyl)piperazine-1-carboxylate

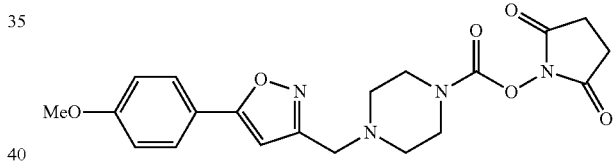

The title compound was synthesized directly from commercially available 5-(4-methoxyphenyl)isoxazole-3-carbaldehyde and tert-butyl piperazine-1-carboxylate according to the representative procedure of Example 35, Steps i, ii, and iii to provide 2,5-dioxopyrrolidin-1-yl 4-((5-(4-methoxyphenyl)isoxazol-3-yl)methyl)piperazine-1-carboxylate as a white solid. $^1$H NMR (400 MHz, Chloroform-d) δ 7.74-7.65 (m, 2H), 7.06-6.87 (m, 2H), 6.41 (s, 1H), 3.83 (s, 3H), 3.64 (s, 4H), 3.53 (s, 2H), 2.80 (d, J=8.4 Hz, 4H), 2.58 (s, 4H). LCMS (ESI, m/z): 415.1 [C$_{20}$H$_{22}$N$_4$O$_6$]$^+$.

Example 137

2,5-Dioxopyrrolidin-1-yl 4-((5-phenylisoxazol-3-yl)methyl)piperazine-1-carboxylate

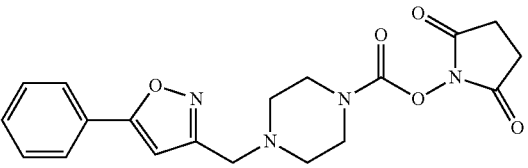 [SMILES: O=C(ON1C(=O)CCC1=O)N1CCN(Cc2cc(-c3ccccc3)on2)CC1]

The title compound was synthesized directly from commercially available 5-phenyl-isoxazole-3-carbaldehyde and tert-butyl piperazine-1-carboxylate according to the representative procedure of Example 35, Steps i, ii, and iii to provide 2,5-dioxopyrrolidin-1-yl 4-((5-phenylisoxazol-3-yl)methyl)piperazine-1-carboxylate as a white solid. $^1$H NMR (400 MHz, Chloroform-d) δ 7.82-7.73 (m, 2H), 7.52-7.39 (m, 3H), 6.57 (d, J=2.8 Hz, 1H), 3.68 (d, J=2.5 Hz, 4H), 3.55 (s, 2H), 2.89-2.77 (m, 4H), 2.60 (s, 4H). LCMS (ESI, m/z): 385.1 $[C_{19}H_{20}N_4O_5]^+$.

Example 138

2,5-Dioxopyrrolidin-1-yl 4-((3-methyl-1-phenyl-1H-pyrazol-4-yl)methyl)piperazine-1-carboxylate

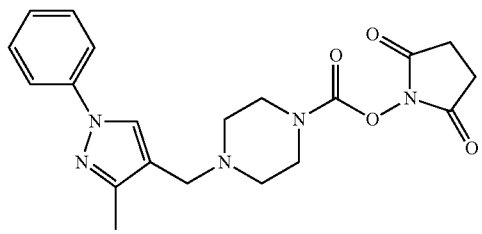 [SMILES: Cc1nn(-c2ccccc2)cc1CN1CCN(C(=O)ON2C(=O)CCC2=O)CC1]

The title compound was synthesized directly from commercially available 3-methyl-1-phenyl-1H-pyrazole-4-carbaldehyde and tert-butyl piperazine-1-carboxylate according to the representative procedure of Example 62, Steps 1, 2 and 3 to provide 2,5-dioxopyrrolidin-1-yl 4-((3-methyl-1-phenyl-1H-pyrazol-4-yl)methyl)piperazine-1-carboxylate as an amorphous white solid. $^1$H NMR (400 MHz, Chloroform-d) δ 7.79 (s, 1H), 7.65 (d, J=8.4, 2H), 7.43 (t, J=8.4, 2H), 7.23 (t, J=8.4, 1H), 3.45-3.40 (m, 6H), 2.42-2.38 (m, 4H), 2.34 (s, 3H), 1.47 (s, 9H). LCMS (ESI, m/z): 398.2 [M+H]$^+$.

Example 139

2,5-dioxopyrrolidin-1-yl 4-((1-methyl-3-phenyl-1H-pyrazol-5-yl)methyl)piperazine-1-carboxylate

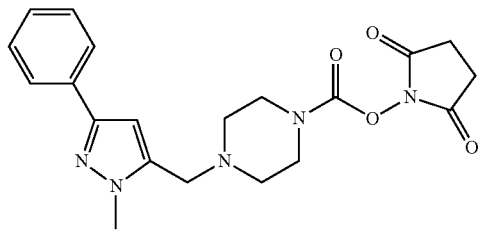 [SMILES: Cn1nc(-c2ccccc2)cc1CN1CCN(C(=O)ON2C(=O)CCC2=O)CC1]

The title compound was synthesized directly from commercially available 1-methyl-3-phenyl-1H-pyrazole-5-carboxaldehyde and tert-butyl piperazine-1-carboxylate according to the representative procedure of Example 62, Steps 1, 2 and 3 to provide 2,5-dioxopyrrolidin-1-yl 4-((1-methyl-3-phenyl-1H-pyrazol-5-yl)methyl)piperazine-1-carboxylate as an amorphous white solid. $^1$H NMR (400 MHz, Chloroform-d) δ 7.79 (d, J=8.0 Hz, 2H), 7.40 (t, J=8.0 Hz, 2H), 7.30 (t, J=8.0 Hz, 1H), 6.47 (s, 1H), 3.95 (s, 3H), 3.67 (bs, 2H), 3.59 (s, 2H), 3.56 (bs, 2H), 2.84 (s, 4H), 2.57 (t, J=4.5 Hz, 4H). LCMS (ESI, m/z): 398.2 [M+H]$^+$.

Example 140

2,5-Dioxopyrrolidin-1-yl 4-{[3-(2-chlorophenyl)-1-methyl-1H-pyrazol-4-yl]methyl}piperazine-1-carboxylate

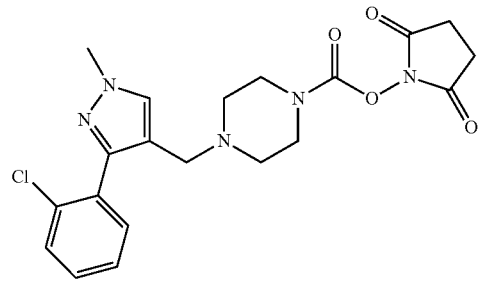 [SMILES: Cn1cc(CN2CCN(C(=O)ON3C(=O)CCC3=O)CC2)c(-c2ccccc2Cl)n1]

Step 1: Preparation of (Z)-1-[1-(2-chlorophenyl)ethylidene]-2-methylhydrazine

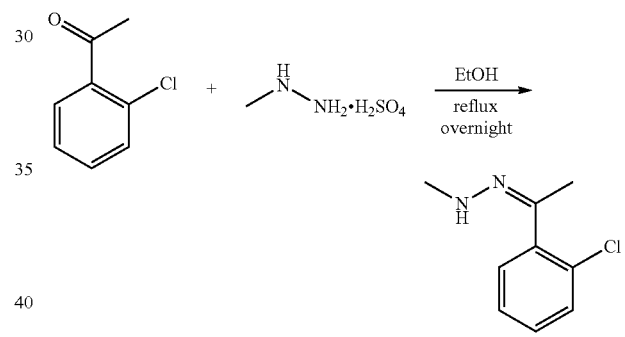

A 100-mL round-bottom flask was purged and maintained with an inert atmosphere of nitrogen and charged with 1-(2-chlorophenyl)ethan-1-one (3.80 g, 24.6 mmol, 1.20 equiv), methylhydrazine sulfate (3.00 g, 20.8 mmol, 1.00 equiv), and ethanol (30 mL). The resulting solution was heated to reflux overnight. Reaction progress was monitored by LCMS. The resulting mixture was concentrated under reduced pressure to provide 7.0 g (crude) of (Z)-1-[1-(2-chlorophenyl)ethylidene]-2-methylhydrazine as a yellow oil. LCMS (ESI, m/z): 183 [M+H]$^+$.

Step 2: Preparation of 3-(2-chlorophenyl)-1-methyl-1H-pyrazole-4-carbaldehyde

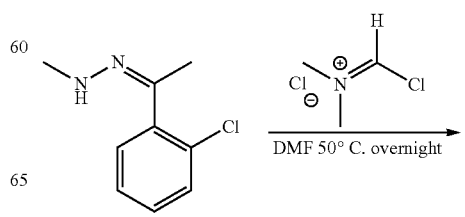

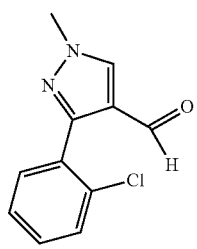

A 100-mL round-bottom flask was purged and maintained with an inert atmosphere of nitrogen and charged with (Z)-1-[1-(2-chlorophenyl)ethylidene]-2-methylhydrazine (2.00 g, 10.9 mmol, 1.00 equiv), (chloromethylidene)dimethylazanium chloride (12.7 g, 99.2 mmol, 9.06 equiv), and N,N-dimethylformamide (40 mL). The resulting solution was stirred overnight at 50° C. Reaction progress was monitored by LCMS. The reaction was then quenched by the addition of saturated sodium carbonate solution (100 mL). The resulting solution was extracted with ethyl acetate (3×100 mL), and the organic layers were combined, washed with brine (2×100 mL), dried over sodium sulfate, and concentrated under reduced pressure. The residue was chromatographed on a silica gel column with ethyl acetate/petroleum ether (1/1) to provide 1.00 g (41% yield) of 3-(2-chlorophenyl)-1-methyl-1H-pyrazole-4-carbaldehyde as a yellow solid. LCMS (ESI, m/z): 221 [M+H]⁺.

Step 3: Preparation of tert-butyl 4-[[3-(2-chlorophenyl)-1-methyl-1H-pyrazol-4-yl]methyl]piperazine-1-carboxylate

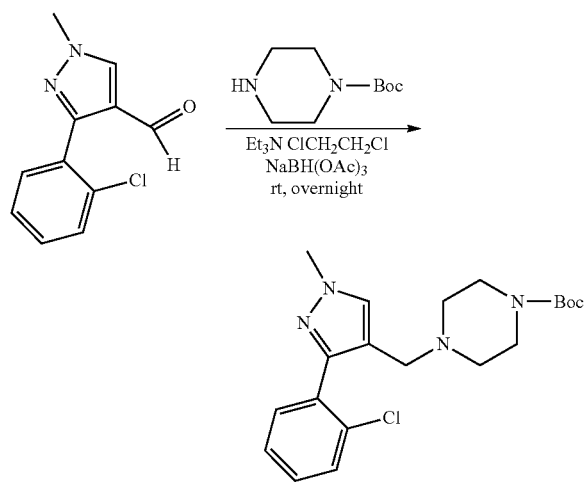

A 25-mL round-bottom flask was purged and maintained with an inert atmosphere of nitrogen and charged with 3-(2-chlorophenyl)-1-methyl-1H-pyrazole-4-carbaldehyde (500 mg, 2.27 mmol, 1.00 equiv), tert-butyl piperazine-1-carboxylate (465 mg, 2.50 mmol, 1.10 equiv), triethylamine (344 mg, 3.40 mmol, 1.50 equiv), and 1,2-dichloroethane (5 mL). The resulting solution was stirred 30 min at room temperature. Solid sodium triacetoxyborohydride (1.40 g, 6.61 mmol, 2.92 equiv) was added. The resulting solution was stirred overnight at room temperature. Reaction progress was monitored by LCMS. The reaction was then quenched by water (20 mL). The resulting solution was extracted with dichloromethane (3×30 mL), and the organic layers were combined, washed with brine (2×30 mL), dried over anhydrous sodium sulfate, and concentrated under reduced pressure. The residue was chromatographed on a gel column with ethyl acetate/petroleum ether (1/1) to yield 750 mg (85% yield) of tert-butyl 4-[[3-(2-chlorophenyl)-1-methyl-1H-pyrazol-4-yl]methyl]piperazine-1-carboxylate as a yellow oil. LCMS (ESI, m/z): 391 [M+H]⁺.

Step 4: Preparation of 1-[[3-(2-chlorophenyl)-1-methyl-1H-pyrazol-4-yl]methyl]piperazine

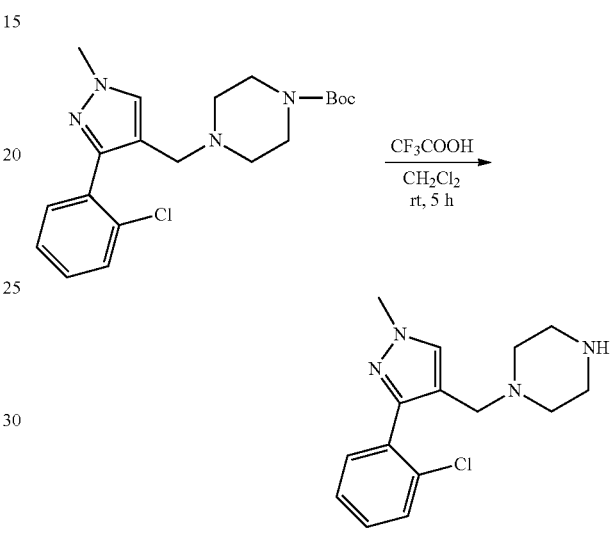

A 100-mL round-bottom flask was purged and maintained with an inert atmosphere of nitrogen and charged with tert-butyl 4-[[3-(2-chlorophenyl)-1-methyl-1H-pyrazol-4-yl]methyl]piperazine-1-carboxylate (750 mg, 1.92 mmol, 1.00 equiv) in dichloromethane (10 mL). Trifluoroacetic acid (2.5 mL) was added dropwise at 0° C. The resulting solution was stirred for 5 h at room temperature. Reaction progress was monitored by LCMS. The resulting mixture was concentrated under reduced pressure to provide 520 mg (crude) of 1-[[3-(2-chlorophenyl)-1-methyl-1H-pyrazol-4-yl]methyl]piperazine as a yellow oil. LCMS (ESI, m/z): 291 [M+H]⁺.

Step 5: Preparation of 2,5-dioxopyrrolidin-1-yl 4-{[3-(2-chlorophenyl)-1-methyl-1H-pyrazol-4-yl]methyl}piperazine-1-carboxylate

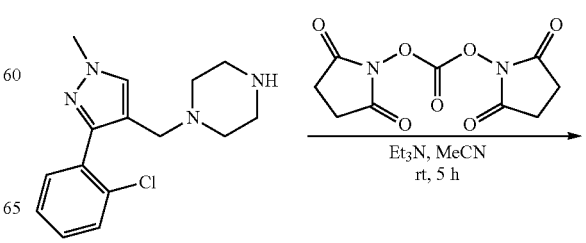

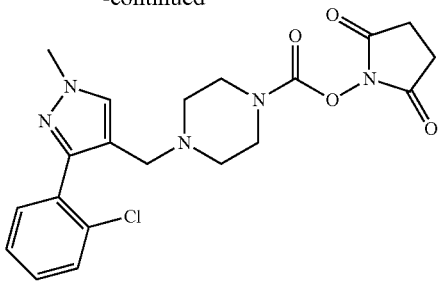

A 100-mL round-bottom flask was purged and maintained with an inert atmosphere of nitrogen and charged with 1-[[3-(2-chlorophenyl)-1-methyl-1H-pyrazol-4-yl]methyl] piperazine (260 mg, 0.89 mmol, 1.00 equiv), bis(2,5-dioxopyrrolidin-1-yl) carbonate (1.38 g, 5.39 mmol, 6.03 equiv), triethylamine (273 mg, 2.70 mmol, 3.00 equiv), and MeCN (10 mL). The resulting solution was stirred overnight at room temperature. Reaction progress was monitored by LCMS. The resulting mixture was concentrated under reduced pressure. Crude product (420 mg) was purified by preparative HPLC using the following gradient conditions: 30% CH$_3$CN/60% Phase A increasing to 60% CH$_3$CN over 10 min, then to 100% CH$_3$CN over 0.1 min, holding at 100% CH$_3$CN for 1.9 min, then reducing to 30% CH$_3$CN over 0.1 min, and holding at 30% for 1.9 min, on a Waters 2767-5 Chromatograph. Column: Xbridge Prep C18, 19*150 mm, 5 um; Mobile phase: Phase A: water; Phase B: CH$_3$CN; Detector, UV 220 & 254 nm. Purification resulted in 180 mg (47% yield) of 2,5-dioxopyrrolidin-1-yl 4-{[3-(2-chlorophenyl)-1-methyl-1H-pyrazol-4-yl]methyl}piperazine-1-carboxylate as a white solid. $^1$H NMR (300 MHz, Chloroform-d) δ 7.26-7.46 (m, 5H), 3.95 (s, 3H), 3.38-3.50 (m, 6H), 2.80 (s, 4H), 2.37 (br, 4H). LCMS (ESI, m/z): 432 [M+H]$^+$.

Example 141

2,5-Dioxopyrrolidin-1-yl 4-{[3-phenyl-1-(propan-2-yl)-1H-pyrazol-4-yl]methyl}piperazine-1-carboxylate

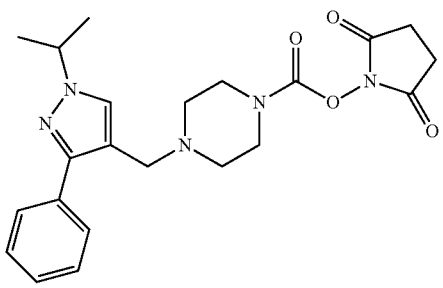 [SMILES: CC(C)n1cc(CN2CCN(C(=O)ON3C(=O)CCC3=O)CC2)c(-c2ccccc2)n1]

The title compound was prepared from commercially available acetophenone and isopropylhydrazine hydrochloride according to the representative procedure of Example 140, Steps 1, 2, 3, 4 and 5 to provide 2,5-dioxopyrrolidin-1-yl 4-{[3-phenyl-1-(propan-2-yl)-1H-pyrazol-4-yl] methyl}piperazine-1-carboxylate as a white solid. $^1$H NMR (300 MHz, Chloroform-d) δ 7.72-7.8 (m, 2H), 7.32-7.43 (m, 4H), 4.51-4.57 (m, 1H), 3.49-3.73 (m, 6H), 2.82 (s, 4H), 2.52 (br, 4H), 1.55 (d, J=6.6 Hz, 6H). LCMS (ESI, m/z): 448 [M+Na]$^+$.

Example 142

2,5-Dioxopyrrolidin-1-yl 4-{[3-(2-chlorophenyl)-1-(propan-2-yl)-1H-pyrazol-4-yl]methyl}piperazine-1-carboxylate

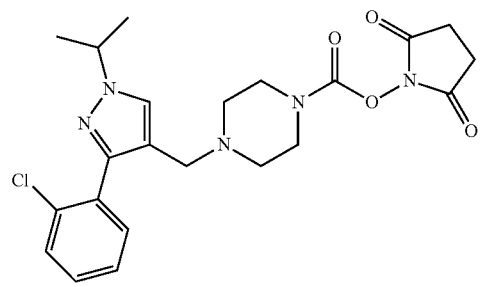 [SMILES: CC(C)n1cc(CN2CCN(C(=O)ON3C(=O)CCC3=O)CC2)c(-c2ccccc2Cl)n1]

The title compound was prepared from commercially available 1-(2-chlorophenyl)ethan-1-one and isopropylhydrazine hydrochloride according to the representative procedure of Example 140, Steps 1, 2, 3, 4 and 5 to provide 2,5-dioxopyrrolidin-1-yl 4-{[3-(2-chlorophenyl)-1-(propan-2-yl)-1H-pyrazol-4-yl]methyl}piperazine-1-carboxylate as a white solid. $^1$H NMR (300 MHz, Chloroform-d) δ: 7.26-7.44 (m, 5H), 4.48-4.57 (m, 1H), 3.42-3.50 (m, 6H), 2.80 (s, 4H), 2.36 (br, 4H), 1.57 (s, 3H), 1.54 (s, 3H). LCMS (ESI, m/z): 460 [M+H]$^+$.

Example 143

2,5-Dioxopyrrolidin-1-yl 4-((4-methyl-2-phenyloxazol-5-yl)methyl)piperazine-1-carboxylate

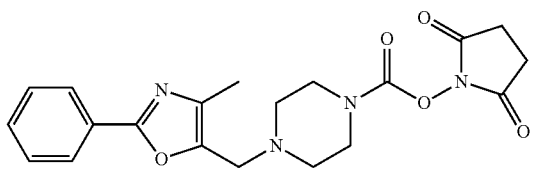 [SMILES: Cc1nc(-c2ccccc2)oc1CN1CCN(C(=O)ON2C(=O)CCC2=O)CC1]

The title compound was synthesized directly from commercially available 4-methyl-2-phenyloxazole-5-carbaldehyde and tert-butyl piperazine-1-carboxylate according to the representative procedure of Example 35, Steps i, ii, and iii to provide 2,5-dioxopyrrolidin-1-yl 4-((4-methyl-2-phenyloxazol-5-yl)methyl)piperazine-1-carboxylate as an orange solid. $^1$H NMR (400 MHz, Chloroform-d) δ 7.99 (dd, J=5.8, 2.2 Hz, 2H), 7.40 (dd, J=7.2, 3.1 Hz, 3H), 3.66 (s, 2H), 3.55 (s, 2H), 3.46 (s, 2H), 2.79 (s, 4H), 2.56 (s, 4H), 2.35 (s, 3H). LCMS (ESI, m/z): 399.1 [C$_{20}$H$_{22}$N$_4$O$_5$]$^+$.

Example 144

2,5-Dioxopyrrolidin-1-yl 4-(((6-chloro-2-methylimidazo[1,2-a]pyridin-3-yl)methyl)piperazine-1-carboxylate

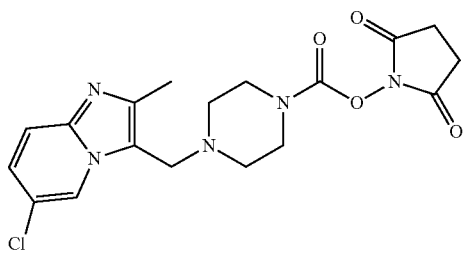 [SMILES: Cc1nc2ccc(Cl)cn2c1CN1CCN(C(=O)ON2C(=O)CCC2=O)CC1]

The title compound was synthesized directly from commercially available 6-chloro-2-methylimidazo[1,2-c]pyridine-3-carbaldehyde and tert-butyl piperazine-1-carboxylate according to the representative procedure of Example 35, Steps i, ii, and iii to provide 2,5-dioxopyrrolidin-1-yl 4-((6-chloro-2-methylimidazo[1,2-a]pyridin-3-yl)methyl)piperazine-1-carboxylate as a white solid. $^1$H NMR (400 MHz, Chloroform-d) δ 8.23 (s, 1H), 7.48 (dd, J=9.5, 2.2 Hz, 1H), 7.15 (dt, J=9.5, 2.5 Hz, 2H), 3.78 (d, J=2.4 Hz, 2H), 3.72-3.37 (m, 4H), 2.83 (s, 4H), 2.60-2.47 (m, 4H), 2.43 (s, 3H). LCMS (ESI, m/z): 406.1 $[C_{18}H_{20}ClN_5O_4]^+$.

Example 145

2,5-Dioxopyrrolidin-1-yl 4-((6-chloroimidazo[1,2-a]pyridin-3-yl)methyl)piperazine-1-carboxylate

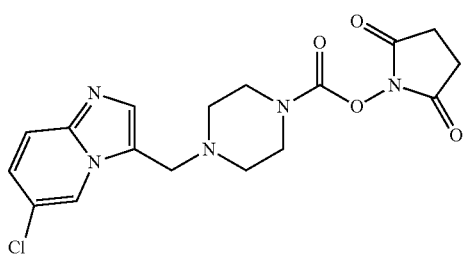 [SMILES: O=C(ON1C(=O)CCC1=O)N1CCN(Cc2cnc3ccc(Cl)cn23)CC1]

The title compound was synthesized directly from commercially available 6-chloroimidazo[1,2-a]pyridine-3-carbaldehyde and tert-butyl piperazine-1-carboxylate according to the representative procedure of Example 35, Steps i, ii, and iii to provide 2,5-dioxopyrrolidin-1-yl 4-((6-chloroimidazo[1,2-a]pyridin-3-yl)methyl)piperazine-1-carboxylate as a white solid. $^1$H NMR (400 MHz, Chloroform-d) δ 8.34 (s, 1H), 7.59-7.48 (m, 2H), 7.17 (dd, J=9.6, 2.0 Hz, 1H), 3.82 (s, 2H), 3.63 (s, 2H), 3.52 (s, 2H), 2.81 (s, 4H), 2.55-2.47 (m, 4H). LCMS (ESI, m/z): 392.1 $[C_{17}H_{18}ClN_5O_4]^+$.

Example 146

2,5-Dioxopyrrolidin-1-yl 4-{[3-methyl-1-(propan-2-yl)-1H-pyrazol-5-yl]methyl}piperazine-1-carboxylate

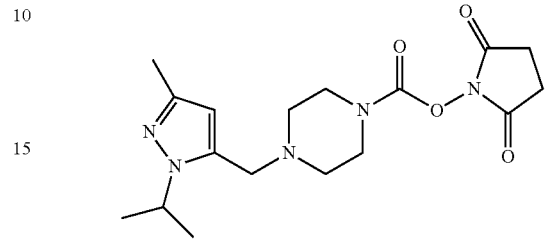

Step 1: Preparation of ethyl (2E)-2-(methoxyimino)-4-oxopentanoate

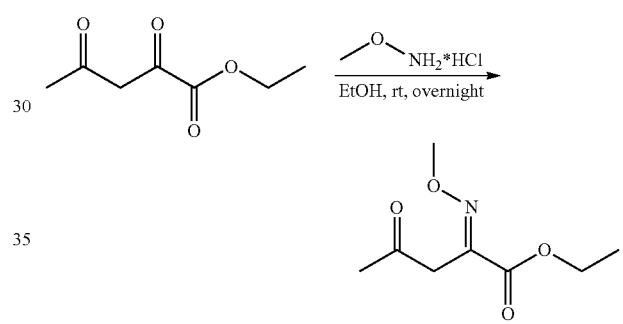

A 100-mL round-bottom flask was purged and maintained with an inert atmosphere of nitrogen and charged with ethyl 2,4-dioxopentanoate (15.0 g, 94.8 mmol, 1.00 equiv), methoxylamine hydrochloride (7.90 g, 95.2 mmol, 1.05 equiv), and ethanol (100 mL). The resulting solution was stirred overnight at room temperature. Reaction progress was monitored by LCMS. The resulting mixture was concentrated under reduced pressure. The residue was chromatographed on a gel column with ethyl acetate/petroleum ether (1/5) to yield 6.50 g (37% yield) of ethyl (2E)-2-(methoxyimino)-4-oxopentanoate as a colorless oil. LCMS (ESI, m/z): 188 [M+H]$^+$.

Step 2: Preparation of ethyl 3-methyl-1-(propan-2-yl)-1H-pyrazole-5-carboxylate

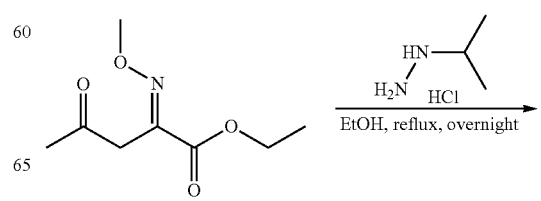

-continued

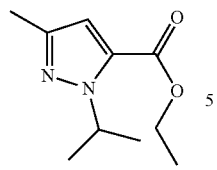

A 100-mL round-bottom flask was purged and maintained with an inert atmosphere of nitrogen and charged with ethyl (2E)-2-(methoxyimino)-4-oxopentanoate (2.50 g, 13.4 mmol, 1.00 equiv), propan-2-ylhydrazine hydrochloride (2.90 g, 26.2 mmol, 1.99 equiv), and ethanol (50 mL). The resulting solution was heated at reflux overnight. Reaction progress was monitored by LCMS. The resulting mixture was concentrated under reduced pressure. The residue was chromatographed on a gel column with ethyl acetate/petroleum ether (1/10) to provide 2.10 g (80% yield) of ethyl 3-methyl-1-(propan-2-yl)-1H-pyrazole-5-carboxylate as a colorless oil. LCMS (ESI, m/z): 197 [M+H]$^+$.

Step 3: Preparation of [3-methyl-1-(propan-2-yl)-1H-pyrazol-5-yl]methanol

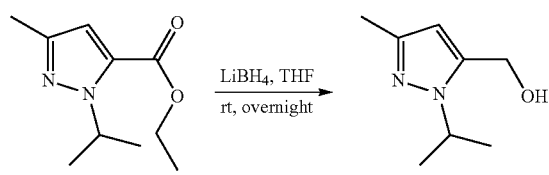

A 100-mL round-bottom flask was purged and maintained with an inert atmosphere of nitrogen and charged with ethyl 3-methyl-1-(propan-2-yl)-1H-pyrazole-5-carboxylate (2.10 g, 10.7 mmol, 1.00 equiv) in tetrahydrofuran (20 mL) and LiBH$_4$ (1.18 g, 53.6 mmol, 5.01 equiv). The resulting solution was stirred overnight at room temperature. Reaction progress was monitored by LCMS. The reaction was then quenched by water (30 mL). The resulting solution was extracted with ethyl acetate (3×30 mL), and the organic layers were combined, washed with brine (2×30 mL), dried over anhydrous sodium sulfate, filtered, and concentrated under reduced pressure to provide 1.80 g (crude) of [3-methyl-1-(propan-2-yl)-1H-pyrazol-5-yl]methanol as a colorless oil. LCMS (ESI, m/z): 155 [M+H]$^+$.

Step 4: Preparation of 3-methyl-1-(propan-2-yl)-1H-pyrazole-5-carbaldehyde

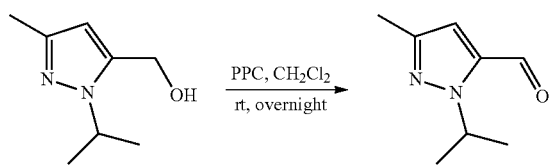

A 100-mL round-bottom flask was purged and maintained with an inert atmosphere of nitrogen and charged with [3-methyl-1-(propan-2-yl)-1H-pyrazol-5-yl]methanol (1.80 g, 10.0 mmol, 1.00 equiv), pyridinium chlorochromate (4.30 g, 19.9 mmol, 1.99 equiv), and dichloromethane (25 mL). The resulting solution was stirred overnight at room temperature. Reaction progress was monitored by LCMS. The reaction was quenched by water (50 mL). The resulting solution was extracted with dichloromethane (3×50 mL), and the organic layers were combined, washed with brine (2×50 mL), dried over anhydrous sodium sulfate, filtered, and concentrated under reduced pressure. The residue was chromatographed on a gel column with ethyl acetate/petroleum ether (1/3) to provide 0.900 g (59% yield) of 3-methyl-1-(propan-2-yl)-1H-pyrazole-5-carbaldehyde as a light yellow oil. LCMS (ESI, m/z): 153 [M+H]$^+$.

Step 5: Preparation of tert-butyl 4-[[3-methyl-1-(propan-2-yl)-1H-pyrazol-5-yl]methyl]piperazine-1-carboxylate

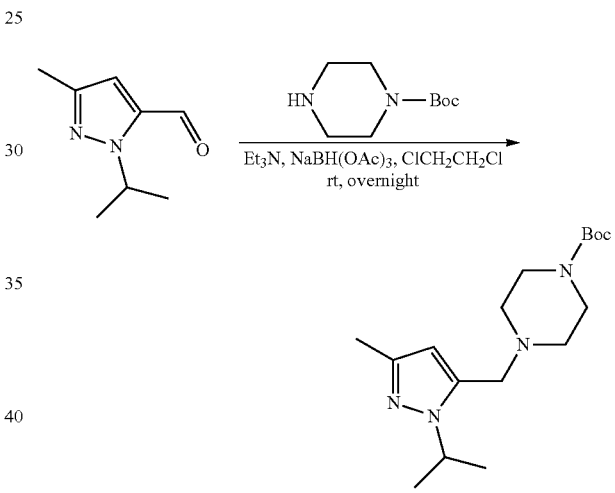

A 50-mL round-bottom flask was purged and maintained with an inert atmosphere of nitrogen and charged with 3-methyl-1-(propan-2-yl)-1H-pyrazole-5-carbaldehyde (450 mg, 2.96 mmol, 1.00 equiv), tert-butyl piperazine-1-carboxylate (606 mg, 3.25 mmol, 1.10 equiv), triethylamine (448 mg, 4.43 mmol, 1.50 equiv), and 1,2-dichloroethane (10 mL). The resulting solution was stirred 1 h at room temperature. Solid sodium triacetoxyborohydride (1.88 g, 8.87 mmol, 3.00 equiv) was added. The resulting solution was stirred overnight at room temperature. Reaction progress was monitored by LCMS. The reaction was then quenched by water (20 mL). The resulting solution was extracted with dichloromethane (3×30 mL), and the organic layers were combined, washed with brine (2×30 mL), dried over anhydrous sodium sulfate, filtered, and concentrated under reduced pressure. The residue was chromatographed on a gel column with ethyl acetate/petroleum ether (1/4) to yield 400 mg (42% yield) of tert-butyl 4-[[3-methyl-1-(propan-2-yl)-1H-pyrazol-5-yl]methyl]piperazine-1-carboxylate as a colorless oil. LCMS (ESI, m/z): 323 [M+H]$^+$.

Step 6: Preparation of 1-1-[[3-methyl-1-(propan-2-yl)-1H-pyrazol-5-yl]methyl]piperazine

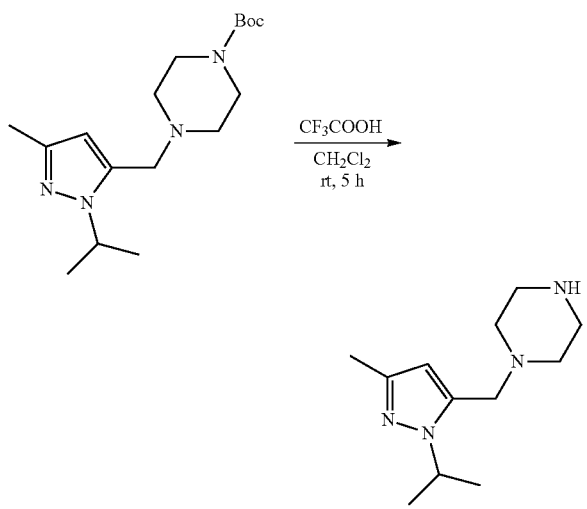

A 100-mL round-bottom flask was purged and maintained with an inert atmosphere of nitrogen and charged with tert-butyl 4-[[3-methyl-1-(propan-2-yl)-1H-pyrazol-5-yl]methyl]piperazine-1-carboxylate (400 mg, 1.24 mmol, 1.00 equiv), trifluoroacetic acid (2.5 mL), and dichloromethane (10 mL). The resulting solution was stirred for 5 h at room temperature. Reaction progress was monitored by LCMS. The resulting mixture was concentrated under reduced pressure to provide 400 mg (crude) of 1-[[3-methyl-1-(propan-2-yl)-1H-pyrazol-5-yl]methyl]piperazine as a colorless oil. LCMS (ESI, m/z): 223 [M+H]$^+$.

Step 7: Preparation of 2,5-dioxopyrrolidin-1-yl 4-{[3-methyl-1-(propan-2-yl)-1H-pyrazol-5-yl]methyl}piperazine-1-carboxylate

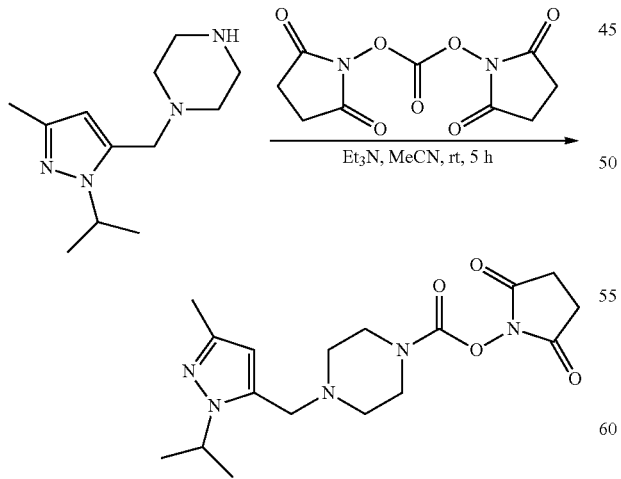

A 50-mL round-bottom flask was purged and maintained with an inert atmosphere of nitrogen and charged with 1-[[3-methyl-1-(propan-2-yl)-1H-pyrazol-5-yl]methyl]piperazine (133 mg, 0.600 mmol, 1.00 equiv), bis(2,5-dioxopyrrolidin-1-yl) carbonate (922 mg, 3.60 mmol, 6.02 equiv), triethylamine (182 mg, 1.80 mmol, 3.01 equiv), and MeCN (10 mL). The resulting solution was stirred for 5 h at room temperature. Reaction progress was monitored by LCMS. The resulting mixture was concentrated under reduced pressure. The crude product (330 mg) was purified by preparative HPLC using the following gradient conditions: 30% CH$_3$CN/60% Phase A increasing to 60% CH$_3$CN over 10 min, then to 100% CH$_3$CN over 0.1 min, holding at 100% CH$_3$CN for 1.9 min, then reducing to 30% CH$_3$CN over 0.1 min, and holding at 30% for 1.9 min, on a Waters 2767-5 Chromatograph. Column: Xbridge Prep C18, 19*150 mm, 5 um; Mobile phase: Phase A: water; Phase B: CH$_3$CN; Detector, UV 220 & 254 nm. Purification resulted in 142 mg (66% yield) of 2,5-dioxopyrrolidin-1-yl 4-{[3-methyl-1-(propan-2-yl)-1H-pyrazol-5-yl]methyl}piperazine-1-carboxylate as a white solid. $^1$H NMR (300 MHz, Chloroform-d) δ 5.87 (s, 1H), 4.54-4.63 (m, 1H), 3.49-3.63 (m, 6H), 2.82 (s, 4H), 2.49 (br, 4H), 2.25 (s, 3H), 1.45 (d, J=6.6 Hz, 6H). LCMS (ESI, m/z): 458 [M+H]$^+$.

Example 147

2,5-Dioxopyrrolidin-1-yl 4-(imidazo[1,2-a]pyridin-3-ylmethyl)piperazine-1-carboxylate

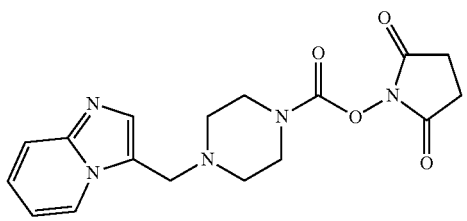 [SMILES: O=C(ON1C(=O)CCC1=O)N1CCN(Cc2cnc3ccccn23)CC1]

The title compound was synthesized directly from commercially available imidazo[1,2-c]pyridine-3-carbaldehyde and tert-butyl piperazine-1-carboxylate according to the representative procedure of Example 35, Steps i, ii, and iii to provide 2,5-dioxopyrrolidin-1-yl 4-(imidazo[1,2-a]pyridin-3-ylmethyl)piperazine-1-carboxylate as a white solid. $^1$H NMR (400 MHz, Chloroform-d) δ 8.31 (dt, J=6.9, 1.1 Hz, 1H), 7.68-7.61 (m, 1H), 7.53 (s, 1H), 7.27-7.19 (m, 1H), 6.86 (td, J=6.8, 1.1 Hz, 1H), 3.85 (s, 2H), 3.64-3.48 (m, 4H), 2.82 (s, 4H), 2.56-2.48 (m, 4H), 1.48-1.41 (m, 4H). LCMS (ESI, m/z): 358.0 [C$_{17}$H$_{19}$N$_5$O$_4$]$^+$.

Example 148

2,5-Dioxopyrrolidin-1-yl 4-((4-methyl-2-(piperidin-1-yl)thiazol-5-yl)methyl)piperazine-1-carboxylate

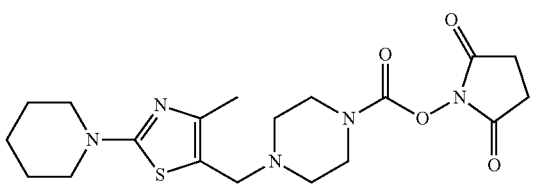 [SMILES: Cc1nc(N2CCCCC2)sc1CN1CCN(C(=O)ON2C(=O)CCC2=O)CC1]

The title compound was synthesized directly from commercially available 4-methyl-2-(piperidin-1-yl)thiazole-5- carbaldehyde and tert-butyl piperazine-1-carboxylate according to the representative procedure of Example 35, Steps i, ii, and iii to provide 2,5-dioxopyrrolidin-1-yl 4-((4-methyl-2-(piperidin-1-yl)thiazol-5-yl)methyl)piperazine-1-carboxylate as a orange oil. $^1$H NMR (400 MHz, Chloroform-d) δ 5.33-5.21 (m, 1H), 3.62 (s, 1H), 3.45 (s, 2H), 3.43-3.30 (m, 8H), 2.45-2.26 (m, 4H), 2.14 (s, 3H), 1.70-1.53 (m, 4H), 1.43 (s, 9H). LCMS (ESI, m/z): 422.1 $[C_{19}H_{27}N_5O_4S]^+$.

Example 149

2,5-Dioxopyrrolidin-1-yl 4-((1-methyl-3-phenyl-1H-pyrazol-4-yl)methyl)piperazine-1-carboxylate

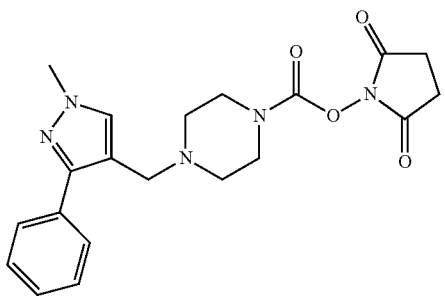 [SMILES: Cn1cc(CN2CCN(C(=O)ON3C(=O)CCC3=O)CC2)c(-c2ccccc2)n1]

The title compound was synthesized directly from commercially available 1-methyl-3-phenyl-1H-pyrazole-4-carbaldehyde and tert-butyl piperazine-1-carboxylate according to the representative procedure of Example 62, Steps 1, 2 and 3 to provide 2,5-dioxopyrrolidin-1-yl 4-((1-methyl-3-phenyl-1H-pyrazol-4-yl)methyl)piperazine-1-carboxylate as an amorphous white solid. $^1$H NMR (400 MHz, Chloroform-d) δ 7.65-7.61 (m, 2H), 7.55 (s, 1H), 7.46-7.39 (m, 2H), 7.39-7.32 (m, 1H), 3.95 (s, 3H), 3.73 (s, 2H), 3.73-3.66 (m, 2H), 3.60-3.53 (m, 2H), 2.81 (s, 4H), 2.69-2.60 (m, 4H). LCMS (ESI, m/z): 398.1 [M+H]$^+$.

Example 150

2,5-Dioxopyrrolidin-1-yl 4-[bis(2,2-difluoro-2H-1,3-benzodioxol-5-yl)methyl]piperazine-1-carboxylate

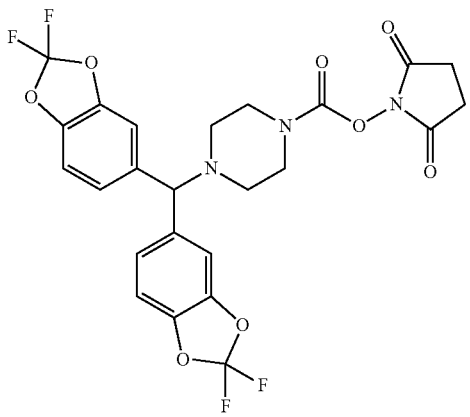 [SMILES: O=C(ON1C(=O)CCC1=O)N1CCN(C(c2ccc3c(c2)OC(F)(F)O3)c2ccc3c(c2)OC(F)(F)O3)CC1]

Step 1: Preparation of bis(2,2-difluorobenzo[d][1,3]dioxol-5-yl)methanol

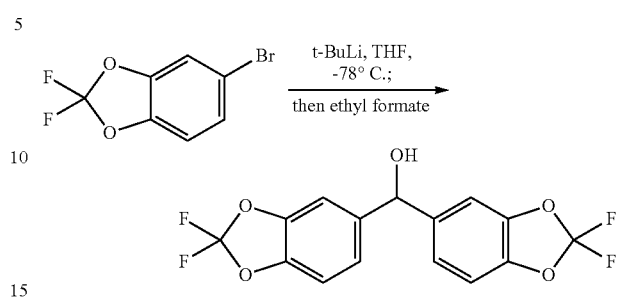

To a stirring solution of tert-butyllithium (1.76 mL, 3.0 mmol, 2.0 equiv, 1.7 M in pentane) at −78° C. was added dropwise a solution of 5-bromo-2,2-difluorobenzo-[1,3]-dioxole (355 mg, 1.5 mmol, 1.0 equiv) in THF (5 mL). After 30 min, ethyl formate (44 mg, 0.5 mmol, 0.33 equiv) in THF (1 mL) was added. The mixture was stirred at −78° C. for 1 h and subsequently warmed to room temperature and stirred for an additional 4 h. The reaction mixture was quenched by the addition of a saturated solution of NH$_4$Cl and extracted with EtOAc (3×). The organic layers were combined, dried over Na$_2$SO$_4$, and concentrated under reduced pressure. Purification of the crude oil by flash chromatography (15% EtOAc/hexanes) provided bis(2,2-difluorobenzo[d][1,3]dioxol-5-yl)methanol as an off-white solid (196 mg, 92%): $^1$H NMR (400 MHz, CDCl$_3$) δ 7.09 (d, J=1.61 Hz, 2H), 7.07 (dd, J=1.74, 8.18 Hz, 2H), 7.02 (d, J=8.15 Hz, 2H), 5.81 (d, J=3.03 Hz, 1H), 2.28 (d, J=3.27 Hz, 1H).

Step 2: Preparation of tert-butyl 4-(bis(2,2-difluorobenzo[d][1,3]dioxol-5-yl)methyl)piperazine-1-carboxylate

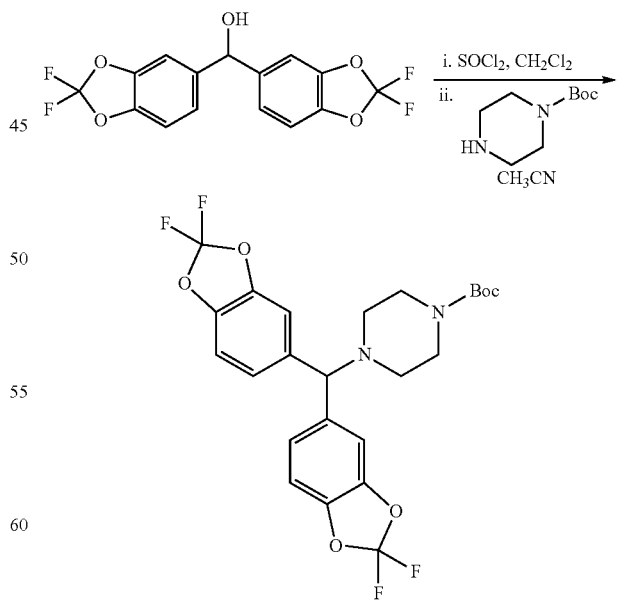

To a stirring solution of bis(2,2-difluorobenzo[d][1,3]dioxol-5-yl)methanol (21 mg, 0.060 mmol, 1.0 equiv) in CH$_2$Cl$_2$ (0.3 mL) was added thionyl chloride (40 μL, 0.60 mmol, 10 equiv), and the mixture was stirred for 48 h. The reaction mixture was evaporated to dryness under a stream of N$_2$, and the crude product redissolved in acetonitrile (1.0 mL). tert-Butyl piperazine-1-carboxylate (22.3 mg, 0.12 mmol, 2.0 equiv) was added, and the mixture was refluxed for 4 h. The reaction mixture was concentrated under reduced pressure, redissolved in CH$_2$Cl$_2$ and passed through a short pad of SiO2, providing the tert-butyl 4-(bis(2,2-difluorobenzo[d][1,3]dioxol-5-yl)methyl)piperazine-1-carboxylate.

Step 3: Preparation of 2,5-dioxopyrrolidin-1-yl 4-[bis(2,2-difluoro-2H-1,3-benzodioxol-5-yl)methyl]piperazine-1-carboxylate

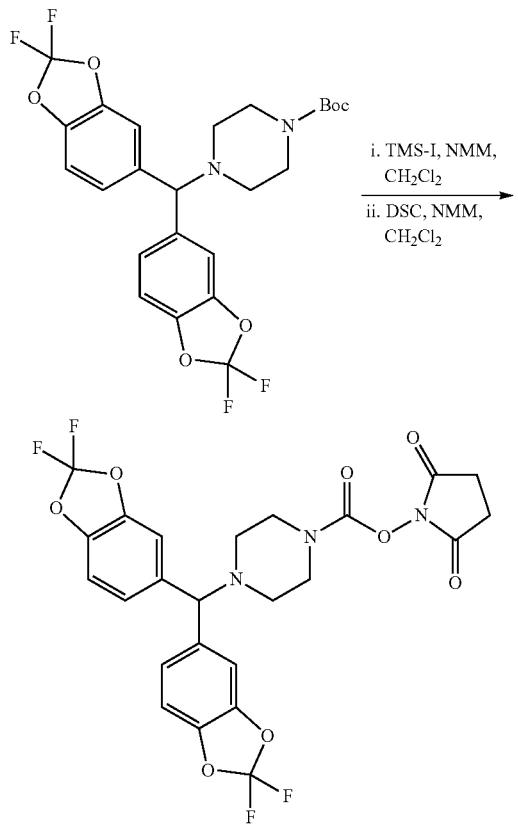

To a solution of tert-butyl 4-(bis(2,2-difluorobenzo[d][1,3]dioxol-5-yl)methyl)piperazine-1-carboxylate (26 mg, 0.05 mmol, 1.0 equiv) in dry CH$_2$Cl$_2$ (3 mL) was added N-methylmorpholine (27 µL, 0.25 mmol, 5.0 equiv) and iodotrimethylsilane (27 µL, 0.20 mmol, 4.0 equiv). After TLC indicated complete consumption of the starting material, the mixture was poured into a saturated solution of NaHCO$_3$, and the product was extracted with CH$_2$Cl$_2$ (3×). The combined organic layers were dried over Na$_2$SO$_4$ and concentrated under reduced pressure to provide the secondary amine, which was used without further purification. 2,5-Dioxopyrrolidin-1-yl 4-[bis(2,2-difluoro-2H-1,3-benzodioxol-5-yl)methyl]piperazine-1-carboxylate was synthesized according to Procedure A from this crude, deprotected amine (0.05 mmol), DSC (13 mg, 0.05 mmol), and NMM (0.016 mL, 0.15 mmol). Purification of the crude product by flash chromatography (35% EtOAc/hexanes) provided the title compound (20 mg, 73%) as an off-white solid: $^1$H NMR (600 MHz, CDCl$_3$) δ 7.12 (s, 2H), 7.06 (d, J=8.24 Hz, 2H), 6.97 (d, J=8.22 Hz, 2H), 4.25 (s, 1H), 3.65 (bs, 2H), 3.53 (bs, 2H), 2.81 (s, 4H), 2.44 (bs, 4H); $^{13}$C NMR (151 MHz, CDCl$_3$) δ 170.56, 151.11, 145.10, 143.89, 138.58, 132.44 (t, J=256 Hz), 123.67, 110.45, 109.26, 75.63, 51.93, 51.86, 45.94, 45.45, 26.33; HRMS (ESI+) m/z calcd for [M+H]$^+$ C$_{24}$H$_{19}$F$_4$N$_3$O$_8$: 554.1181. found 554.1188.

Example 151

2,5-Dioxopyrrolidin-1-yl 4-[bis(4-chlorophenyl)methyl]-3-methylpiperazine-1-carboxylate

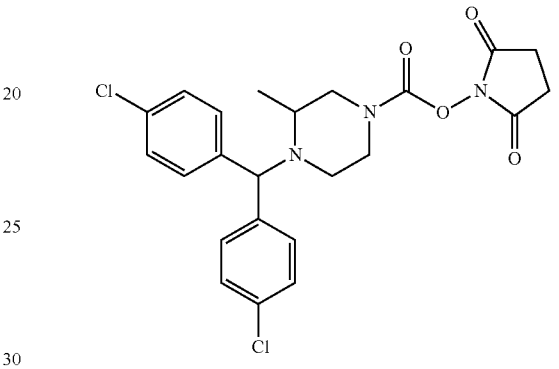

Step 1: Preparation of tert-butyl 4-(bis(4-chlorophenyl)methyl)-3-methylpiperazine-1-carboxylate

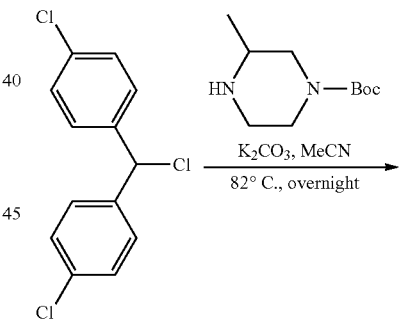

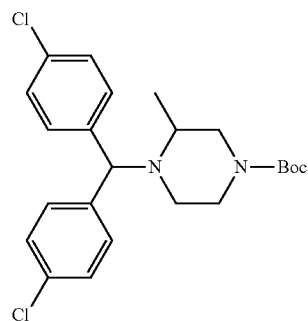

A 100-mL round-bottom flask was charged with tert-butyl 3-methylpiperazine-1-carboxylate (2.00 g, 9.99 mmol, 1.00 equiv), 1-chloro-4-[chloro(4-chlorophenyl)methyl]benzene (5.46 g, 20.1 mmol, 2.01 equiv), potassium carbonate (6.90 g, 49.9 mmol, 5.00 equiv), and acetonitrile (30 mL). The resulting solution was stirred overnight at 82° C. and then diluted with H₂O (50 mL). The resulting solution was extracted with dichloromethane (3×20 mL), and the organic layers were combined, washed with H₂O (3×10 mL), dried over anhydrous sodium sulfate, and concentrated under reduced pressure. The residue was chromatographed on a silica gel column with ethyl acetate/petroleum ether (1/4) to yield 1.70 g (53% yield) of tert-butyl 4-[bis(4-chlorophenyl) methyl]-3-methylpiperazine-1-carboxylate as a light yellow solid. LCMS (ESI, m/z): 435 [M+H]⁺.

Preparation of 2,5-dioxopyrrolidin-1-yl 4-[bis(4-chlorophenyl)methyl]-3-methylpiperazine-1-carboxylate The title compound was prepared according to the representative procedure of Example 77, Steps 2 and 3 to provide 2,5-dioxopyrrolidin-1-yl 4-[bis(4-chlorophenyl)methyl]-3-methylpiperazine-1-carboxylate as a white solid. ¹H NMR (300 MHz, Chloroform-d): δ 7.25-7.38 (m, 8H), 4.62-4.63 (m, 1H), 3.64-3.94 (m, 2H), 3.16-3.49 (m, 2H), 3.00 (br, 1H), 2.82 (s, 4H), 2.56-2.69 (m, 1H), 2.44-2.48 (m, 1H), 1.01-1.09 (m, 3H). LCMS (ESI, m/z): 476 [M+H]⁺.

Example 152

2,5-Dioxopyrrolidin-1-yl 4-(bis(oxazol-4-yl)methyl)piperazine-1-carboxylate

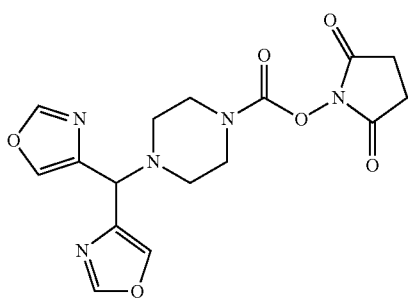 [SMILES: O=C(ON1C(=O)CCC1=O)N1CCN(C(c2cocn2)c2cocn2)CC1]

Step 1: Preparation of bis(oxazol-4-yl)methanol

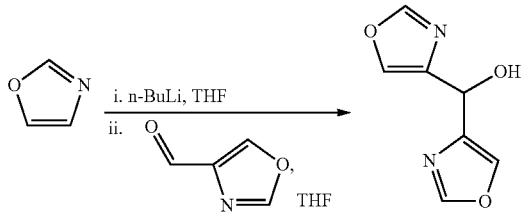 [SMILES: c1cocn1 ; O=Cc1cocn1 ; OC(c1cocn1)c1cocn1 ; "THF"]

A round bottom flask was charged with oxazole (476 μL, 7.2 mmol) and THF (100 mL). The solution was cooled to −78° C. A solution of n-butyllithium (2.3 M in hexanes, 3.5 mL, 8.05 mmol) was added dropwise. After stirring at −78° C. for 40 min, a solution of oxazole-4-carbaldehyde (773 mg, 7.96 mmol, in 8 mL THF) was added dropwise. The reaction was allowed to warm to room temperature. After 30 min, the reaction was quenched with saturated NH₄Cl and extracted with CH₂Cl₂ (3×). The organics were dried (Na₂SO₄), filtered, and concentrated under reduced pressure. The residue was chromatographed on a silica gel column (100% CH₂Cl₂ to 10% MeOH in CH₂Cl₂) and yielded bis(oxazol-4-yl)methanol (354 mg, 29%) as a light brown solid. ¹H NMR 400 MHz (CDCl₃) δ 7.93 (s, 2H), 7.73 (s, 2H), 5.87 (s, 1H), 3.52 (s, 1H). LCMS (ESI, m/z): 167.0 [M+H]⁺.

Step 2: Preparation of tert-butyl 4-(bis(oxazol-4-yl)methyl)piperazine-1-carboxylate

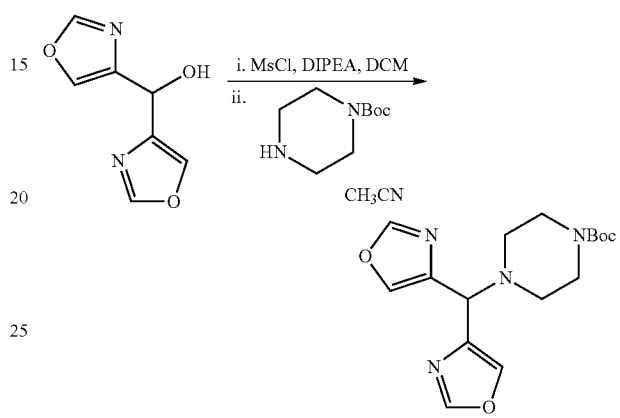

A round bottom flask was charged with bis(oxazol-4-yl)methanol (200 mg, 1.20 mmol), CH₂Cl₂ (3 mL), and DIPEA (412 μL, 2.41 mmol). The solution was cooled to 0° C. and MsCl (112 μL, 1.45 mmol) was added dropwise. After stirring 0° C. for 30 min, more MsCl (100 μL, 1.29 mmol) was added. After an additional 30 min at 0° C., the reaction was quenched with brine, and the mixture was extracted with CH₂Cl₂ (3×). The organics were dried (Na₂SO₄), filtered, and concentrated under reduced pressure yielding the crude alkyl chloride. The crude intermediate was dissolved in CH₂Cl₂ (3 mL) and treated with tert-butyl piperazine-1-carboxylate (224 mg, 1.20 mmol), and the solution was stirred at room temperature. After 48 h at room temperature, the reaction was quenched with brine, and the mixture was extracted with CH₂Cl₂ (3×). The organics were dried (Na₂SO₄), filtered, and concentrated under reduced pressure. The residue was chromatographed on a silica gel column (100% CH₂Cl₂ to 4% MeOH in CH₂Cl₂) yielding tert-butyl 4-(bis(oxazol-4-yl)methyl)piperazine-1-carboxylate (114 mg, 28%) as a light brown oil. ¹H NMR 400 MHz (CDC₃) δ 7.87 (s, 2H), 7.69 (s, 2H), 4.78 (s, 1H), 3.45-3.37 (m, 4H), 2.53-2.40 (m, 4H), 1.39 (s, 9H). LCMS (ESI, m/z): 335.0 [M+H]⁺.

Step 3: Preparation of 2,5-dioxopyrrolidin-1-yl 4-(bis(oxazol-4-yl)methyl)piperazine-1-carboxylate

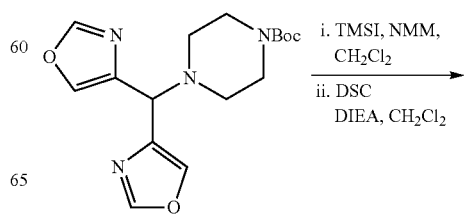

-continued

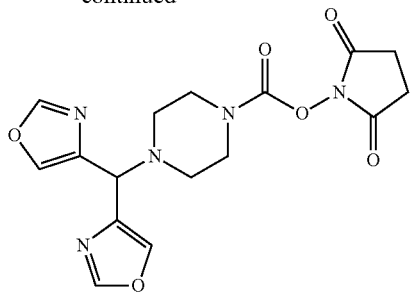

The title compound was synthesized directly from tert-butyl 4-(bis(oxazol-4-yl)methyl)piperazine-1-carboxylate according to the representative procedure of Example 65, Steps 3 and 4 to provide 2,5-dioxopyrrolidin-1-yl 4-(bis(oxazol-4-yl)methyl)piperazine-1-carboxylate as a white solid. $^1$H NMR (400 MHz, Chloroform-d) δ 7.92 (s, 2H), 7.75 (s, 2H), 4.87 (s, 1H), 3.67 (s, 2H), 3.55 (s, 2H), 2.81 (s, 4H), 2.63 (s, 4H). LCMS (ESI, m/z): 376.1 $[C_{16}H_{17}N_5O_6]^+$.

Example 153

2,5-Dioxopyrrolidin-1-yl 4-(bis(4-chloro-2-methylphenyl)methyl)piperazine-1-carboxylate

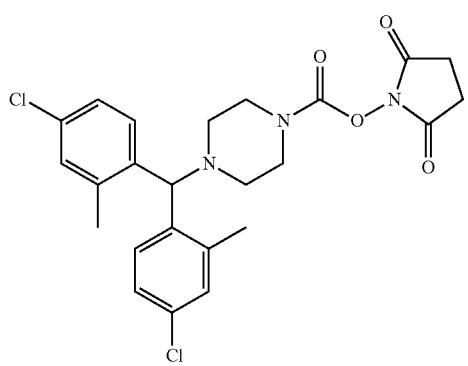 [SMILES: Cc1cc(Cl)ccc1C(c1ccc(Cl)cc1C)N1CCN(C(=O)ON2C(=O)CCC2=O)CC1]

Step 1: Preparation of bis(4-chloro-2-methylphenyl)methanol

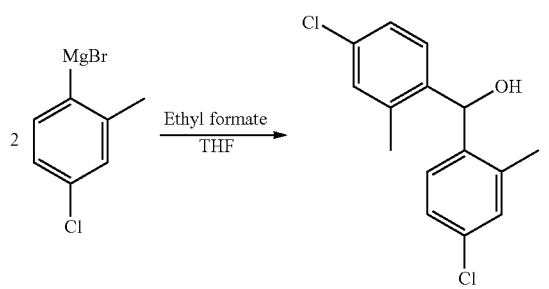

A round-bottom flask was charged with a 4-chloro-2-methylphenyl magnesium bromide solution (10 mL of a 0.5 M THF solution, 5 mmol) and THF (50 mL). The solution was cooled to −78° C., and an ethyl formate solution (200 μL, 2.50 mmol, in 10 mL THF) was added dropwise. The reaction mixture was allowed to stir at −78° C. for 15 min and then allowed to warm to room temperature slowly and stir for 18 h. The reaction mixture was diluted in EtOAc and washed with brine (3×). The organics were dried (Na$_2$SO$_4$), filtered, and concentrated under reduced pressure. The residue was chromatographed on a silica gel column (hexanes to 15% EtOAc in hexanes) and yielded bis(4-chloro-2-methylphenyl)methanol (643 mg, 46%) as a clear crystalline solid. $^1$H NMR 400 MHz (CDCl$_3$) δ 7.25-7.14 (m, 6H), 6.07 (s, 1H), 2.26 (s, 6H), 1.57 (s, 2H). LCMS (ESI, m/z): 263.0 $[M+H]^+$.

Step 2: Preparation of tert-butyl 4-(bis(4-chloro-2-methylphenyl)methyl)piperazine-1-carboxylate

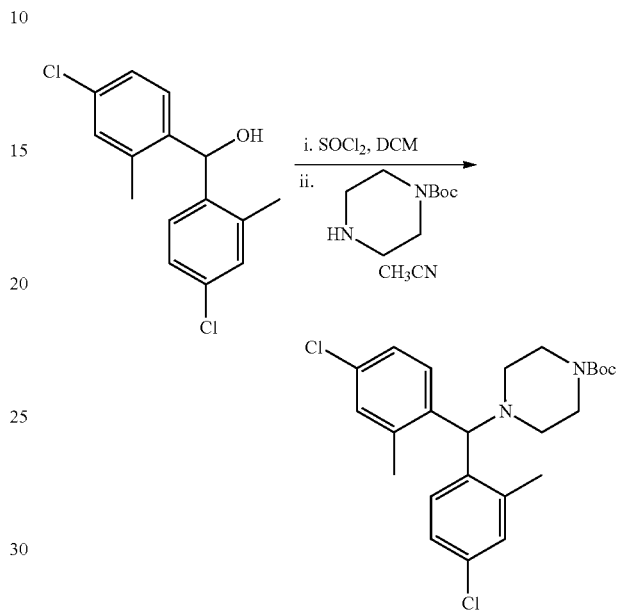

A round-bottom flask was charged with bis(4-chloro-2-methylphenyl)methanol (200 mg, 0.711 mmol) and CH$_2$Cl$_2$ (7 mL). Thionyl chloride (100 μL, 1.37 mmol) was added, and the reaction mixture was stirred at room temperature for 24 h. The reaction mixture was concentrated. Acetonitrile was added, and the reaction mixture was concentrated two times. Acetonitrile (6 mL), tert-butyl piperazine-1-carboxylate (200 mg, 1.07 mmol) and K$_2$CO$_3$ (200 mg, 1.42 mmol) were added, and the reaction mixture was heated to 80° C. for 4 h and 120° C. for 18 h. The reaction mixture was poured into brine and extracted with EtOAc (2×). The residue was chromatographed on a silica gel column (100% hexanes to 20% EtOAc) and yielded the title compound (184 mg, 57%) as a clear oil. $^1$H NMR 400 MHz (CDCl$_3$) δ 7.49 (d, J=8.4 Hz, 2H), 7.16 (d, J=8.4 Hz, 2H), 7.11 (s, 2H), 4.65 (s, 1H), 3.44-3.37 (m, 4H), 2.38 (s, 4H), 2.29 (s, 6H), 1.46 (s, 9H). LCMS (ESI, m/z): 471.0 $[M+H]^+$.

Step 3: Preparation of 1-(bis(4-chloro-2-methylphenyl)methyl)piperazine

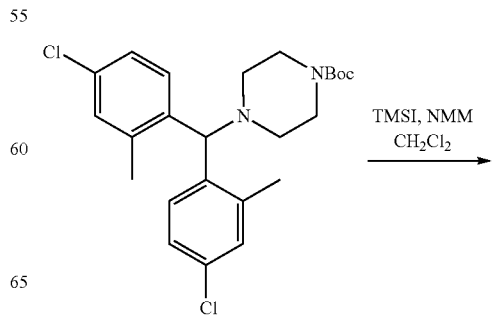

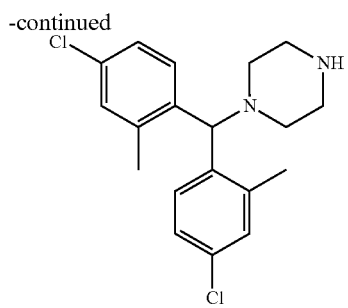

A round-bottom flask was charged with tert-butyl 4-(bis (4-chloro-2-methylphenyl)methyl)piperazine-1-carboxylate (184 mg, 409 mmol), CH₂Cl₂ (5 mL), and NMM (90 µL, 0.819 mmol). The reaction mixture was cooled to 0° C., and TMSI (70 µL, 0.491 mmol) was added dropwise. After 15 min at 4° C. the reaction mixture was quenched with saturated Na₂CO₃ and extracted with CH₂Cl₂ (3×). The organics were dried (Na₂SO₄), filtered, and concentrated. The residue was chromatographed on a silica gel column (100% CH₂Cl₂ to 6% 2M NH₃ in MeOH) and yielded 1-(bis(4-chloro-2-methylphenyl)methyl)-piperazine (143 mg, 70%). ¹H NMR 400 MHz (CDCl₃) δ 7.47 (dd, J=8.4, 1.1 Hz, 2H), 7.16-7.11 (m, 1H), 7.11-7.06 (m, 2H), 4.64 (s, 1H), 2.88-2.80 (m, 4H), 2.44-2.33 (m, 5H), 2.28 (s, 7H). LCMS (ESI, m/z): 349.0 [M+H]⁺.

Step 4: Preparation of 2,5-dioxopyrrolidin-1-yl 4-(bis(4-chloro-2-methylphenyl)methyl)piperazine-1-carboxylate

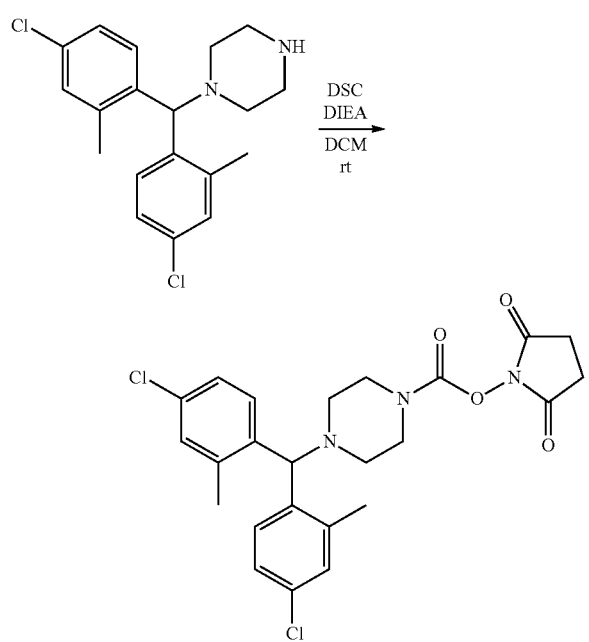

The title compound was synthesized directly from 1-(bis (4-chloro-2-methylphenyl)-methyl)piperazine according to the representative procedure of Example 65, Step 4 to provide 2,5-dioxopyrrolidin-1-yl 4-(bis(4-chloro-2-methylphenyl)methyl)piperazine-1-carboxylate as a clear oil. LCMS (ESI, m/z): 512.0 [C₂₄H₂₅Cl₂N₃O₄Na]⁺.

Example 154

Preparation of 2,5-dioxopyrrolidin-1-yl 4-(bis(1-methyl-1H-indazol-5-yl)methyl)piperazine-1-carboxylate Step 1: Preparation of bis(1-methyl-1H-indazol-5-yl)methanol

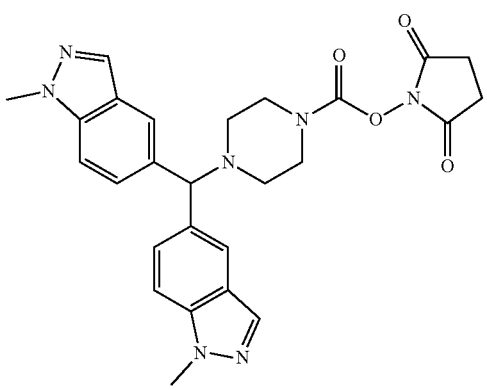 [SMILES: Cn1ncc2cc(C(c3ccc4c(cnn4C)c3)N3CCN(C(=O)ON4C(=O)CCC4=O)CC3)ccc21]

A round-bottom flask was charged with 5-bromo-1-methyl-1H-indazole (300 mg, 1.42 mmol) and THF (45 mL). The solution was cooled to −78° C., and an n-butyllithium solution (2.3 M in THF, 680 µL, 1.56 mmol) was added dropwise. After 30 min, a solution of ethyl formate (57 µL, 0.697 mmol, in 10 mL THF) was added dropwise, and the reaction mixture was stirred at −78° C. for 10 min and room temperature for 3 h. The reaction mixture was quenched with saturated NH₄CL and extracted with EtOAc (3×). The organics were dried (Na₂CO₃), filtered, and concentrated under reduced pressure. The residue was chromatographed on a silica gel column (100% CH₂Cl₂ to 10% MeOH in CH₂Cl₂) and yielded bis(1-methyl-1H-indazol-5-yl)methanol (134 mg, 32%) as a brown oil. ¹H NMR 400 MHz (CDCl₃) δ 7.90 (s, 2H), 7.77 (s, 2H), 7.39 (dd, J=8.7, 1.2 Hz, 2H), 7.31 (d, J=8.7 Hz, 2H), 6.07 (s, 1H), 4.02 (s, 7H). LCMS (ESI, m/z): 293 [M+H]⁺.

Step 2: Preparation of tert-butyl 4-(bis(1-methyl-1H-indazol-5-yl)methyl)piperazine-1-carboxylate

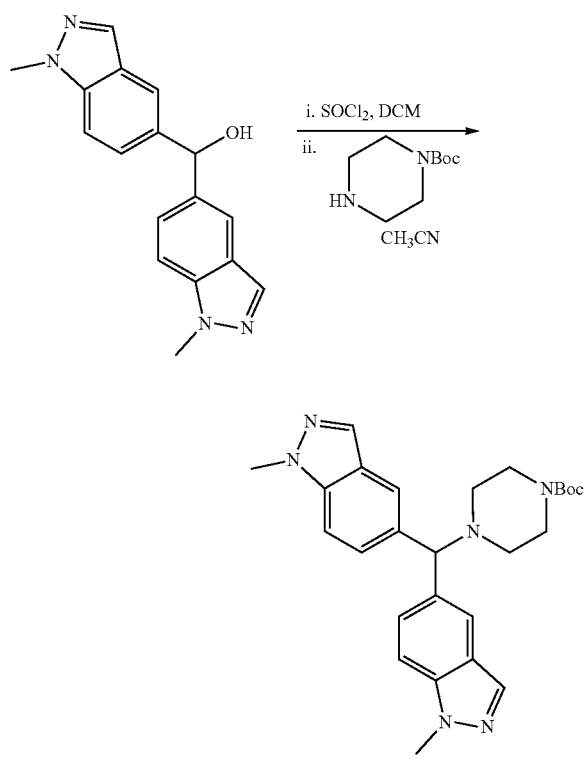

A round-bottom flask was charged with bis(1-methyl-1H-indazol-5-yl)methanol (50 mg, 0.17 mmol) and CH₂Cl₂ (5 mL). Thionyl chloride (25 μL, 342 mmol) was added, resulting in a cloudy solution. After 15 min the solution become a clear pink solution and was stirred at room temperature for 48 h. The solution was concentrated under reduced pressure. Acetonitrile was added, and the solution was concentrated two times. Acetonitrile (7 mL) and tert-butyl piperazine-1-carboxylate (60 mg, 0.32 mmol) was added, and the solution was stirred at room temperature overnight. The reaction mixture was concentrated under reduced pressure and purified by silica chromatography (100% CH₂Cl₂ to 3% MeOH in CH₂Cl₂) yielding tert-butyl 4-(bis(1-methyl-1H-indazol-5-yl)methyl)piperazine-1-carboxylate (53 mg, 56%) as a light brown oil. ¹H NMR 400 MHz (CDCl₃) δ 7.97-7.89 (m, 2H), 7.79 (s, 2H), 7.54 (dd, J=8.8, 1.5 Hz, 2H), 7.32 (d, J=8.7 Hz, 2H), 4.49 (s, 1H), 4.03 (s, 6H), 3.47 (s, 4H), 2.41 (s, 4H), 1.45 (s, 9H). LCMS (ESI, m/z): 483 [M+H]⁺.

Step 3: Preparation of 2,5-dioxopyrrolidin-1-yl 4-(bis(1-methyl-1H-indazol-5-yl)methyl)piperazine-1-carboxylate

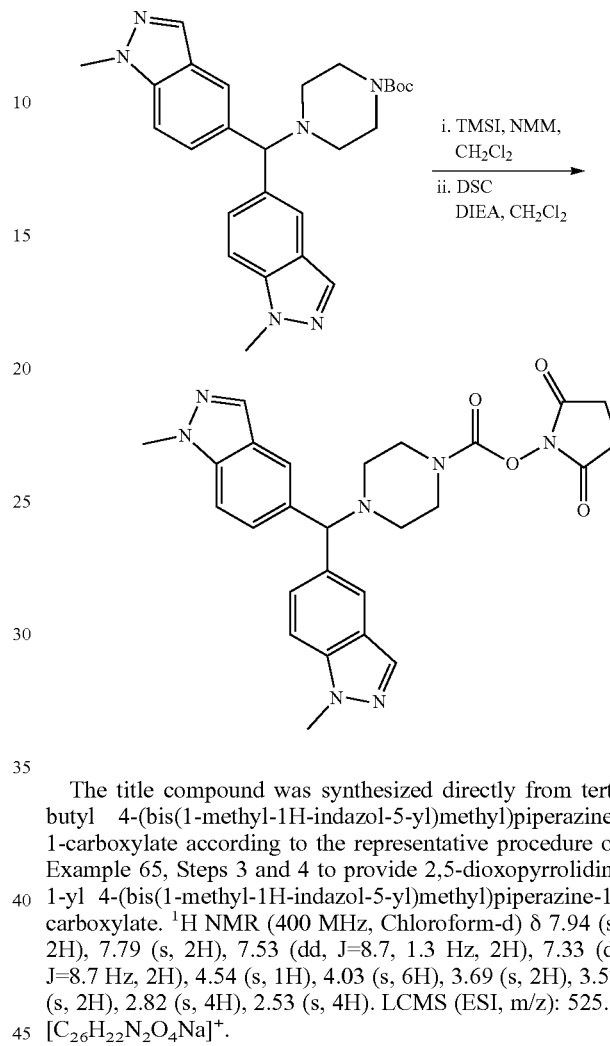

The title compound was synthesized directly from tert-butyl 4-(bis(1-methyl-1H-indazol-5-yl)methyl)piperazine-1-carboxylate according to the representative procedure of Example 65, Steps 3 and 4 to provide 2,5-dioxopyrrolidin-1-yl 4-(bis(1-methyl-1H-indazol-5-yl)methyl)piperazine-1-carboxylate. ¹H NMR (400 MHz, Chloroform-d) δ 7.94 (s, 2H), 7.79 (s, 2H), 7.53 (dd, J=8.7, 1.3 Hz, 2H), 7.33 (d, J=8.7 Hz, 2H), 4.54 (s, 1H), 4.03 (s, 6H), 3.69 (s, 2H), 3.57 (s, 2H), 2.82 (s, 4H), 2.53 (s, 4H). LCMS (ESI, m/z): 525.1 [C₂₆H₂₂N₂O₄Na]⁺.

Example 155

2,5-Dioxopyrrolidin-1-yl 4-(di(pyridin-3-yl)methyl)piperazine-1-carboxylate

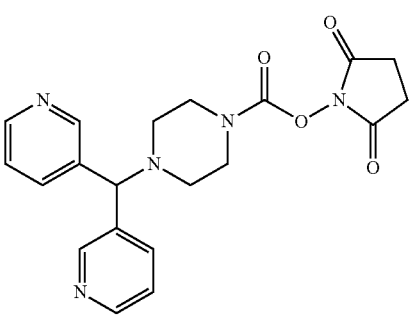 [SMILES: O=C(ON1C(=O)CCC1=O)N1CCN(C(c2cccnc2)c2cccnc2)CC1]

Step 1: Preparation of di(pyridin-3-yl)methanol

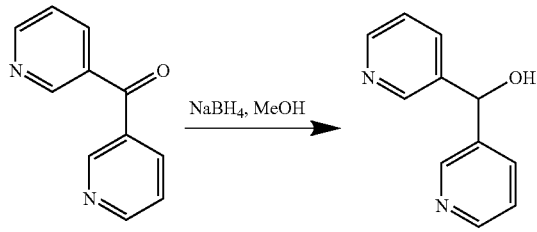 [SMILES: O=C(c1cccnc1)c1cccnc1 ; OC(c1cccnc1)c1cccnc1]

A round-bottom flask was charged with di(pyridin-3-yl) methanone (500 mg, 2.72 mmol), MeOH (30 mL), and $CH_2Cl_2$ (15 mL), and cooled to 0° C. $NaBH_4$ (51 mg, 1.35 mmol) was added in one portion. The solution was stirred for 1 h at 0° C. and quenched with 1N NaOH, and the reaction mixture was extracted with $CH_2Cl_2$ (3×). The organic layers were combined, dried over $Na_2SO_4$, and concentrated under reduced pressure. Crude di(pyridin-3-yl)methanol (505 mg, 100%) was used in the next step without further purification. $^1$H NMR 400 MHz ($CDCl_3$) δ 8.32 (s, 2H), 8.24 (d, J=4.8 Hz, 2H), 7.47 (d, J=7.9 Hz, 2H), 7.09-7.01 (m, 2H), 5.67 (s, 1H).

Step 2: Preparation of 3,3'-(chloromethylene)dipyridine

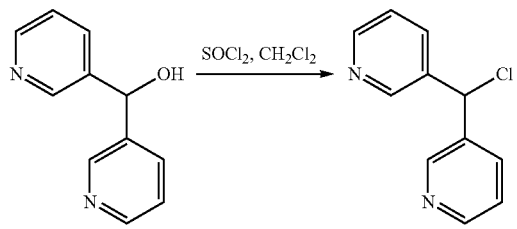 [SMILES: OC(c1cccnc1)c1cccnc1 ; ClC(c1cccnc1)c1cccnc1]

A round-bottom flask was charged with di(pyridin-3-yl) methanol (600 mg, 3.22 mmol) and $CH_2Cl_2$ (50 mL). Thionyl chloride (353 µl, 4.83 mmol) was added, and the reaction mixture was stirred for 18 h at room temperature. The solution was concentrated under reduced pressure. The residue was chromatographed on a silica gel column (100% $CH_2Cl_2$ to 5% 2 M $NH_3$ in MeOH) and yielded 3,3'-(chloromethylene)dipyridine (415 mg, 64%). $^1$H NMR 400 MHz ($CDCl_3$) δ 8.66 (d, J=2.4 Hz, 2H), 8.59 (dd, J=4.7, 1.6 Hz, 2H), 7.76 (m, 2H), 7.34 (m, 2H), 6.17 (s, 1H).

Step 3: Preparation of tert-butyl 4-(di(pyridin-3-yl)methyl)piperazine-1-carboxylate

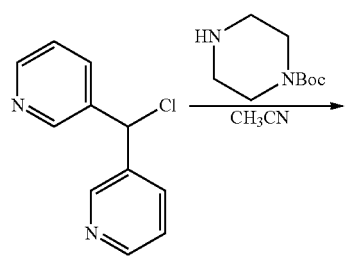

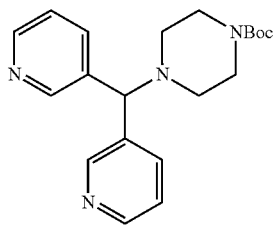

A round-bottom flask was charged with 3,3'-(chloromethylene)-dipyridine (415 mg, 2.03 mmol), tert-butyl piperazine-1-carboxylate (1.20 g, 6.45 mmol), and acetonitrile (50 mL). The reaction mixture was heated to 80° C. for 2 h, concentrated under reduced pressure, and purified by silica chromatography (100% $CH_2Cl_2$ to 5% 2 M $NH_3$ in MeOH), yielding tert-butyl 4-(di(pyridin-3-yl)methyl)piperazine-1-carboxylate (220 mg, 31%). $^1$H NMR 400 MHz ($CDCl_3$) δ 8.64 (d, J=2.0 Hz, 3H), 8.48 (dd, J=4.8, 1.7 Hz, 3H), 7.70 (dt, J=7.9, 1.9 Hz, 3H), 7.24 (ddd, J=7.9, 4.8, 0.7 Hz, 3H), 5.28 (s, 1H), 4.36 (s, 1H), 3.47-3.39 (m, 6H), 2.34 (s, 6H), 1.42 (s, 9H). LCMS (ESI, m/z): 355 [M+H]$^+$

Step 4: Preparation of 1-(di(pyridin-3-yl)methyl)piperazine

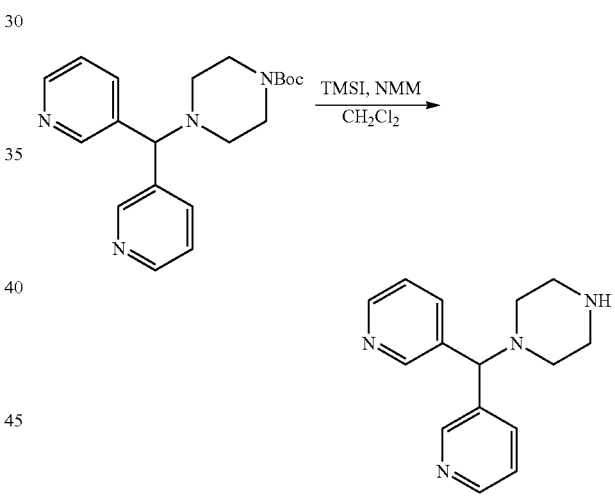

A round-bottom flask was charged with tert-butyl 4-(di(pyridin-3-yl)methyl)piperazine-1-carboxylate (220 mg, 0.621 mmol), $CH_2Cl_2$ (20 mL), and NMM (136 µL, 1.23 mmol). The reaction mixture was cooled to 0° C., and TMSI (106 µL, 0.745 mmol) was added dropwise. After 10 min at 0° C., additional TMSI (100 µL, 0.700 mmol) was added. After stirring 10 min at 0° C., the reaction mixture was allowed to warm to room temperature. After 15 min at room temperature, the reaction mixture was diluted in $CH_2Cl_2$ and washed (1×) with saturated $Na_2CO_3$. The organics were dried ($Na_2SO_4$), filtered, and concentrated, yielding 103 mg crude product (0.406 mmol, 65%) as a yellow oil, which was used without further purification in the next step. $^1$H NMR 400 MHz ($CDCl_3$) δ 8.64 (d, J=2.4 Hz, 2H), 8.47 (dd, J=4.8, 1.6 Hz, 2H), 7.70 (dt, J=8.0, 2.0 Hz, 2H), 7.23 (dd, J=7.9, 4.8 Hz, 2H), 4.36 (s, 1H), 2.91 (t, J=4.9 Hz, 4H), 2.38 (t, J=5.0 Hz, 5H). LCMS (ESI, m/z): 255 [M+H]$^+$.

Step 5: Preparation of 2,5-dioxopyrrolidin-1-yl 4-(di(pyridin-3-yl)methyl)piperazine-1-carboxylate

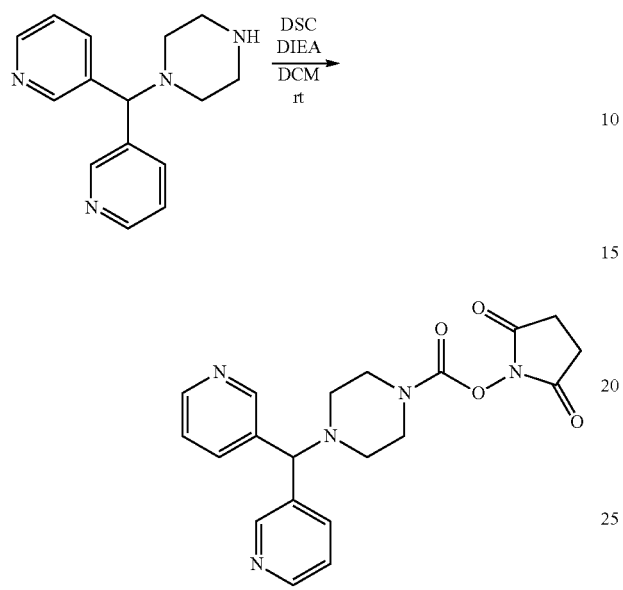

The title compound was synthesized directly from 1-(di(pyridin-3-yl)methyl)-piperazine according to the representative procedure of Example 65, Step 4 to provide 2,5-dioxopyrrolidin-1-yl 4-(di(pyridin-3-yl)methyl)piperazine-1-carboxylate as a yellow solid. $^1$H NMR (400 MHz, Chloroform-d) δ 8.66 (d, J=2.2 Hz, 2H), 8.51 (dd, J=4.8, 1.7 Hz, 2H), 7.73 (dt, J=8.0, 2.0 Hz, 2H), 7.33-7.24 (m, 2H), 4.43 (s, 1H), 3.71-3.59 (m, 2H), 3.59-3.51 (m, 2H), 2.81 (s, 4H), 2.51-2.44 (m, 4H). LCMS (ESI, m/z): 396.0 $[C_{20}H_{21}N_5O_4]^+$.

Example 156

2,5-Dioxopyrrolidin-1-yl 4-[bis(2H-1,3-benzodioxol-5-yl)methyl]piperazine-1-carboxylate

Step 1: Preparation of bis(2H-1,3-benzodioxol-5-yl)methanol

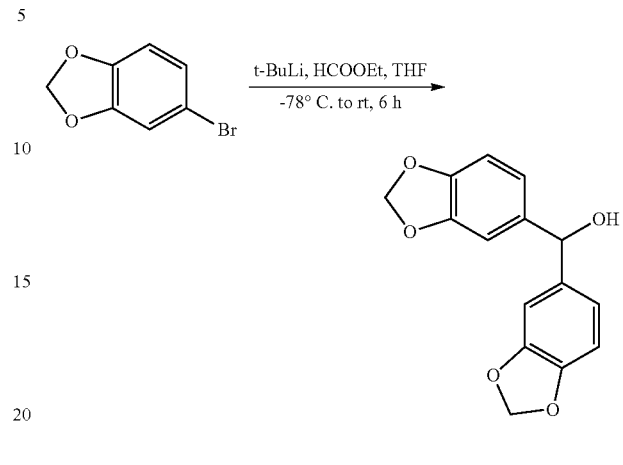

A 100-mL 3-necked round-bottom flask was charged with tert-butyllithium (12.5 mL, 19.9 mmol, 2.00 equiv) and tetrahydrofuran (25 mL) with an inert atmosphere of nitrogen. A solution of 5-bromo-2H-1,3-benzodioxole (2.00 g, 9.95 mmol, 1.00 equiv) in THF (3 mL) was added. The mixture was stirred for 0.5 h at −78° C. Ethyl formate (0.259 g, 3.50 mmol, 0.35 equiv) was added dropwise. The mixture was stirred for 1 h at −78° C. and then 4 h at room temperature. The mixture was quenched by saturated NH₄Cl solution (40 mL). The resulting solution was extracted with dichloromethane (3×30 mL), and the organic layers were combined, dried over anhydrous sodium sulfate, filtered, and concentrated under reduced pressure. The residue was chromatographed on a silica gel column with ethyl acetate/petroleum ether (20/80) to provide 850 mg (28% yield) of bis(2H-1,3-benzodioxol-5-yl)methanol as light yellow oil. $^1$H NMR (300 MHz, Chloroform-d) δ 6.88 (s, 2H), 6.80-6.82 (d, J=6.0 Hz, 4H), 6.00 (s, 4H), 5.77-5.78 (d, J=4.2 Hz, 1H), 5.54-5.55 (d, J=3.9 Hz, 1H). LCMS (ESI, m/z): 255 [M-OH]⁺.

Step 2: Preparation of tert-butyl 4-[bis(2H-1,3-benzodioxol-5-yl)methyl]piperazine-1-carboxylate

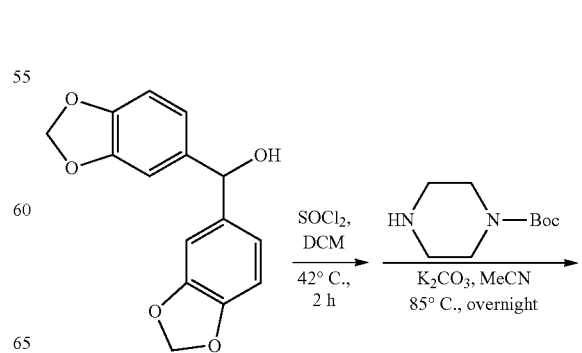

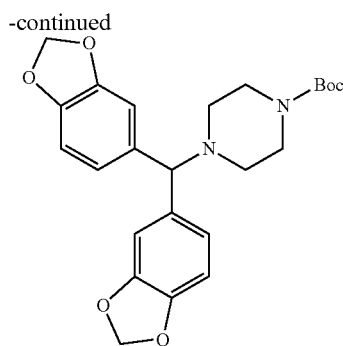

A 100-mL round-bottom flask was charged with bis(2H-1,3-benzodioxol-5-yl)methanol (850 mg, 3.12 mmol, 1.00 equiv), dichloromethane (15 mL), and thionyl chloride (2.21 mg, 18.8 mmol, 6.01 equiv). The mixture was stirred at 42° C. for 2 h and concentrated under reduced pressure. MeCN (10 mL), tert-butyl piperazine-1-carboxylate (0.738 g, 3.96 mmol, 1.27 equiv) and potassium carbonate (1.81 g, 13.1 mmol, 4.20 equiv) were added. The resulting solution was stirred overnight at 85° C. and diluted with water (25 mL). The resulting solution was extracted with ethyl acetate (3×14 mL), and the organic layers were combined, dried over anhydrous sodium sulfate, filtered, and concentrated under reduced pressure. The residue was chromatographed on a silica gel column with ethyl acetate/petroleum ether (15/85) to provide 1.20 g (74% yield) of tert-butyl 4-[bis(2H-1,3-benzodioxol-5-yl)methyl]piperazine-1-carboxylate as a light yellow oil. LCMS (ESI, m/z): 441 [M+H]+.

Preparation of 2,5-Dioxopyrrolidin-1-yl 4-[bis(2H-1,3-benzodioxol-5-yl)methyl]piperazine-1-carboxylate The title compound was prepared from tert-butyl 4-[bis(2H-1,3-benzodioxol-5-yl)methyl]piperazine-1-carboxylate according to the representative procedure of Example 77, Steps 2 and 3 to provide 2,5-dioxopyrrolidin-1-yl 4-[bis(2H-1,3-benzodioxol-5-yl)methyl]piperazine-1-carboxylate as a white solid. $^1$H NMR (300 MHz, Chloroform-d) δ 6.70-6.91 (m, 6H), 5.91-5.92 (d, J=4.5 Hz, 4H), 4.10 (s, 1H), 3.52-3.63 (m, 4H), 2.81 (s, 4H), 2.45 (br, 4H). LCMS (ESI, m/z): 255 $[C_{15}H_{11}O_4]^+$.

Example 157

2,5-Dioxopyrrolidin-1-yl 4-[bis(1,3-dihydro-2-benzofuran-5-yl)methyl]piperazine-1-carboxylate

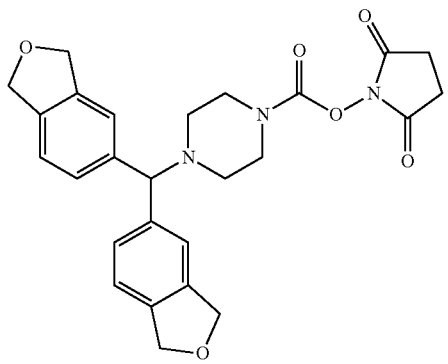 [SMILES: O=C(ON1C(=O)CCC1=O)N1CCN(C(c2ccc3c(c2)COC3)c2ccc3c(c2)COC3)CC1]

The title compound was prepared from commercially available 5-bromo-1,3-dihydro-2-benzofuran according to the representative procedure of Example 156, Steps 1 and 2, followed by the representative procedure of Example 77, Steps 2 and 3 to provide 2,5-dioxopyrrolidin-1-yl 4-[bis(1,3-dihydro-2-benzofuran-5-yl)methyl]piperazine-1-carboxylate as a light yellow solid. $^1$H NMR (300 MHz, Chloroform-d) δ 7.35-7.36 (d, J=3.6 Hz, 4H), 7.23-7.25 (d, J=6.0 Hz, 2H), 4.93-4.95 (d, J=6.0 Hz, 8H), 4.45 (s, 1H), 3.45-3.57 (m, 4H), 2.76 (s, 4H), 2.27-2.38 (m, 4H). LCMS (ESI, m/z): 478 [M+H]+.

Example 158

2,5-Dioxopyrrolidin-1-yl 4-[bis(1,3-dihydro-2-benzofuran-5-yl)(hydroxy)methyl]piperidine-1-carboxylate

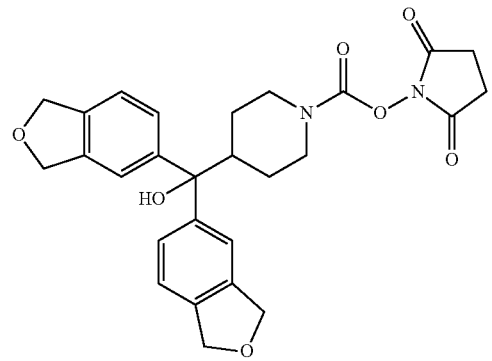 [SMILES: O=C(ON1C(=O)CCC1=O)N1CCC(C(O)(c2ccc3c(c2)COC3)c2ccc3c(c2)COC3)CC1]

Step 1: Preparation of tert-butyl 4-[bis(1,3-dihydro-2-benzofuran-5-yl)(hydroxy)methyl]piperidine-1-carboxylate

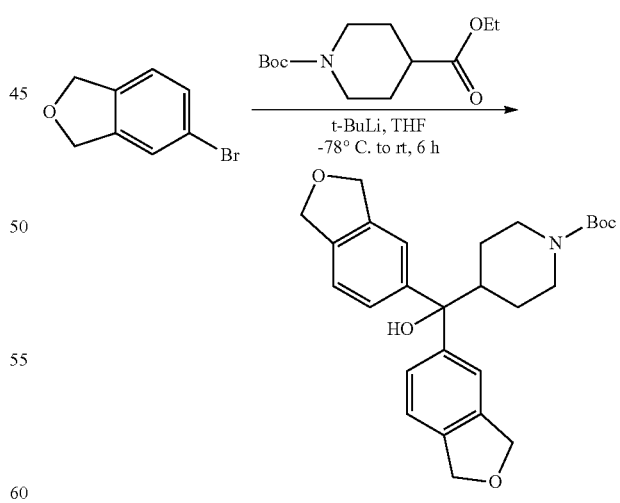

A 250-mL 3-necked round-bottom flask was charged with tetrahydrofuran (40 mL), t-BuLi (15.8 mL, 25.1 mmol, 2.00 equiv) with an inert atmosphere of nitrogen. A solution of 5-bromo-1,3-dihydro-2-benzofuran (2.50 g, 12.6 mmol, 1.00 equiv) in THF (3 mL) was added at −78° C. The mixture was stirred for 0.5 h at −78° C. 1-tert-Butyl 4-ethyl piperidine-1,4-dicarboxylate (1.62 g, 6.30 mmol, 0.50 equiv) was added dropwise at −78° C. The mixture was stirred for 1 h at −78° C. and then for 4 h at room temperature. The reaction was then quenched by saturated NH4Cl solution (60 mL). The resulting solution was extracted with dichloromethane (3×45 mL), and the organic layers were combined, dried over anhydrous sodium sulfate, filtered, and concentrated under reduced pressure. The residue was chromatographed on a silica gel column with ethyl acetate/petroleum ether (20/80) to provide 1.50 g (24% yield) of tert-butyl 4-[bis(1,3-dihydro-2-benzofuran-5-yl)(hydroxy)methyl]piperidine-1-carboxylate as a light yellow oil. LCMS (ESI, m/z): 434 [M−OH]+.

Preparation of 2,5-dioxopyrrolidin-1-yl 4-[bis(1,3-dihydro-2-benzofuran-5-yl)(hydroxy)methyl]piperidine-1-carboxylate The title compound was prepared from tert-butyl 4-[bis(1,3-dihydro-2-benzofuran-5-yl)(hydroxy)methyl]piperidine-1-carboxylate according to the representative procedure of Example 77, Steps 2 and 3 to provide 2,5-dioxopyrrolidin-1-yl 4-[bis(1,3-dihydro-2-benzofuran-5-yl)(hydroxy)methyl]piperidine-1-carboxylate as a light yellow solid. $^1$H NMR (300 MHz, Chloroform-d) δ 7.36 (d, J=6.0 Hz, 4H), 7.19 (d, J=8.4 Hz, 2H), 5.07 (s, 8H), 4.14-4.26 (m, 2H), 2.97-3.04 (m, 2H), 2.92 (s, 4H), 2.61-2.81 (m, 1H), 1.59 (br, 4H). LCMS (ESI, m/z): 475 [M-OH]+.

Example 159

2,5-Dioxopyrrolidin-1-yl 4-{[2-methyl-4-(2-methylpyridin-4-yl)phenyl]methyl}piperazine-1-carboxylate

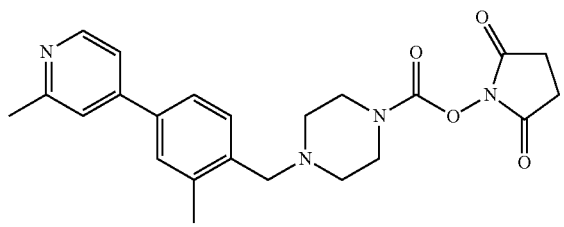 [SMILES: Cc1cc(-c2ccc(CN3CCN(C(=O)ON4C(=O)CCC4=O)CC3)c(C)c2)ccn1]

Step 1: Preparation of tert-butyl 4-[(4-bromo-2-methylphenyl)methyl]piperazine-1-carboxylate

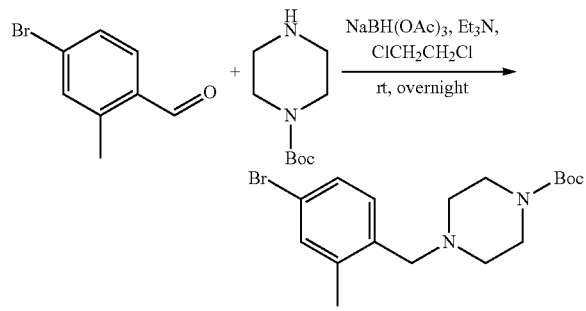

A 500-mL round-bottom flask was charged with 4-bromo-2-methylbenzaldehyde (8.00 g, 40.2 mmol, 1.00 equiv), tert-butyl piperazine-1-carboxylate (9.40 g, 50.5 mmol, 1.26 equiv), triethylamine (6.50 g, 64.2 mmol, 1.60 equiv), and dichloroethane (200 mL). The resulting solution was stirred for 30 min at room temperature. Solid sodium triacetoxyborohydride (27.0 g, 127 mmol, 3.17 equiv) was added. The resulting solution was stirred overnight at room temperature. Reaction progress was monitored by LCMS. The reaction was then quenched by the addition of water (100 mL). The resulting solution was extracted with dichloromethane (3×200 mL), and the organic layers were combined, washed with brine (2×200 mL), dried over anhydrous sodium sulfate, and concentrated under reduced pressure. The residue was chromatographed on a silica gel column with ethyl acetate/petroleum ether (2/3) to yield 10.0 g (67% yield) of tert-butyl 4-[(4-bromo-2-methylphenyl)methyl]piperazine-1-carboxylate as a white solid. LCMS (ESI, m/z): 396 [M+H]+.

Step 2: Preparation of tert-butyl 4-[[2-methyl-4-(2-methylpyridin-4-yl)phenyl]methyl]piperazine-1-carboxylate

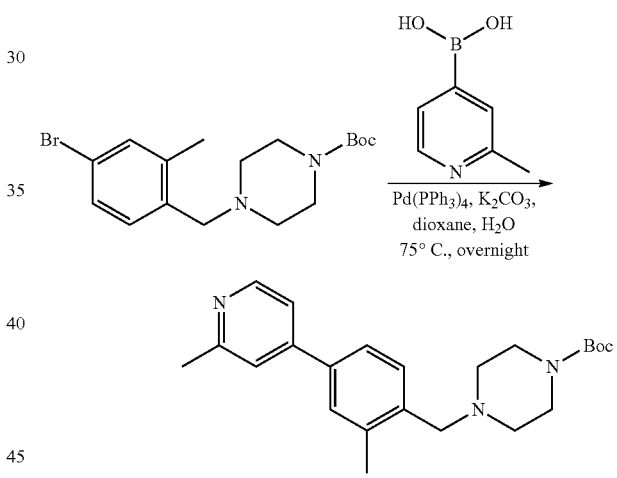

A 100-mL round-bottom flask was purged and maintained with an inert atmosphere of nitrogen then charged with tert-butyl 4-[(4-bromo-2-methylphenyl)methyl]piperazine-1-carboxylate (2.00 g, 5.42 mmol, 1.00 equiv), (2-methylpyridin-4-yl)boronic acid (1.50 g, 10.9 mmol, 2.02 equiv), Pd(PPh3)4 (0.624 g, 0.540 mmol, 0.10 equiv), potassium carbonate (2.25 g, 16.3 mmol, 3.01 equiv), dioxane (20 mL), and water (4 mL). The resulting solution was stirred overnight at 75° C. Reaction progress was monitored by LCMS. The reaction was then quenched by water (30 mL). The resulting solution was extracted with ethyl acetate (3×30 mL), and the organic layers were combined, washed with brine (2×30 mL), dried over anhydrous sodium sulfate, and concentrated under reduced pressure. The residue was chromatographed on a silica gel column with ethyl acetate/petroleum ether (1/1) to provide 1.70 g (82% yield) of tert-butyl 4-[[2-methyl-4-(2-methylpyridin-4-yl)phenyl]methyl]piperazine-1-carboxylate as a yellow oil. LCMS (ESI, m/z): 382 [M+H]+.

Step 3: Preparation of 1-[[2-methyl-4-(2-methyl-pyridin-4-yl)phenyl]methyl]piperazine

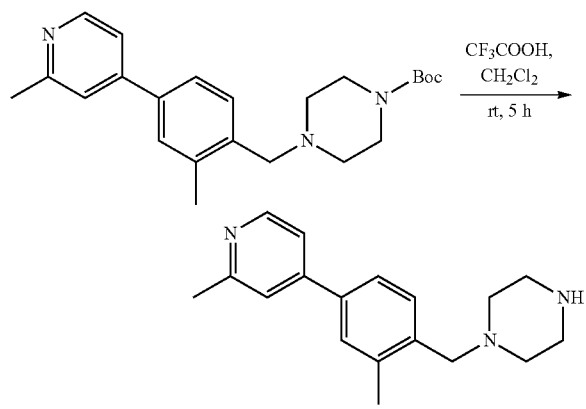

A 50-mL round-bottom flask maintained with an inert atmosphere of nitrogen was charged with tert-butyl 4-[[2-methyl-4-(2-methylpyridin-4-yl)phenyl]methyl]piperazine-1-carboxylate (600 mg, 1.57 mmol, 1.00 equiv) and dichloromethane (10 mL). Trifluoroacetic acid (1.0 mL) was added dropwise at 0° C. The resulting solution was stirred for 5 h at room temperature. Reaction progress was monitored by LCMS. The reaction was then quenched by the addition of water (20 mL). The resulting solution was extracted with dichloromethane (3×20 mL), and the organic layers were combined, washed with brine (2×20 mL), dried over anhydrous sodium sulfate, and concentrated under reduced pressure to yield 400 mg (crude) of 1-[[2-methyl-4-(2-methyl-pyridin-4-yl)phenyl]methyl]piperazine as a yellow oil. LCMS (ESI, m/z): 282 [M+H]$^+$.

Step 4: Preparation of 2,5-dioxopyrrolidin-1-yl 4-{[2-methyl-4-(2-methylpyridin-4-yl)phenyl]methyl}piperazine-1-carboxylate

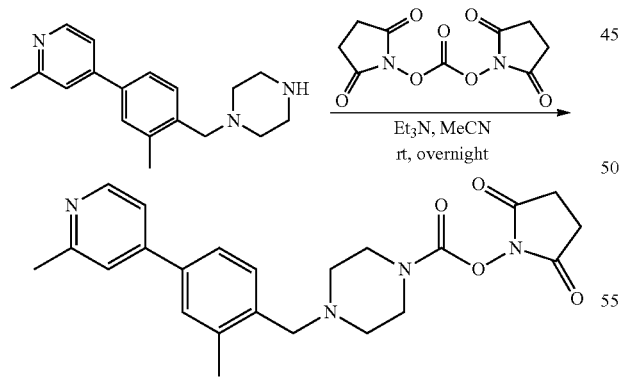

A 25-mL round-bottom flask was purged and maintained with an inert atmosphere of nitrogen and charged with 1-[[2-methyl-4-(2-methylpyridin-4-yl)phenyl]methyl]piperazine (200 mg, 0.710 mmol, 1.00 equiv), bis(2,5-dioxopyrrolidin-1-yl) carbonate (1.09 g, 4.26 mmol, 5.99 equiv), triethylamine (216 mg, 2.13 mmol, 3.00 equiv), and MeCN (6 mL). The resulting solution was stirred overnight at room temperature. Reaction progress was monitored by LCMS. The mixture was concentrated under reduced pressure. The crude product (350 mg) was purified by preparative HPLC using the following gradient conditions: 30% CH$_3$CN/60% Phase A increasing to 60% CH$_3$CN over 10 min, then to 100% CH$_3$CN over 0.1 min, holding at 100% CH$_3$CN for 1.9 min, then reducing to 30% CH$_3$CN over 0.1 min, and holding at 30% for 1.9 min, on a Waters 2767-5 Chromatograph. Column: Xbridge Prep C$_{18}$, 19*150 mm, 5 um; Mobile phase: Phase A: water; Phase B: CH$_3$CN; Detector, UV 220 & 254 nm. Purification resulted in 143 mg (48% yield) of 2,5-dioxopyrrolidin-1-yl 4-{[2-methyl-4-(2-methylpyridin-4-yl)phenyl]methyl}piperazine-1-carboxylate as a yellow oil. $^1$H NMR (300 MHz, Chloroform-d) δ 8.53 (d, J=5.1 Hz, 1H), 7.31-7.68 (m, 5H), 3.65 (br, 4H), 3.55 (s, 2H), 2.83 (s, 4H), 2.62 (s, 3H), 2.52-2.56 (m, 4H), 2.44 (s, 3H). LCMS (ESI, m/z): 423 [M+H]$^+$.

Example 160

2,5-Dioxopyrrolidin-1-yl 3-methyl-4-[(4-phenylphenyl)methyl]piperazine-1-carboxylate

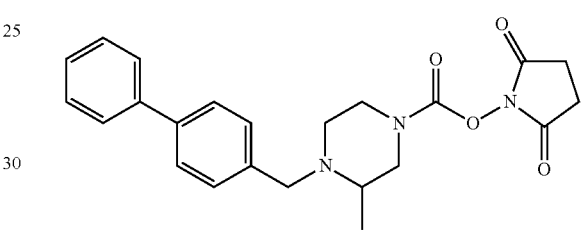

Step 1: Preparation of tert-butyl 3-methyl-4-[(4-phenylphenyl)methyl]piperazine-1-carboxylate

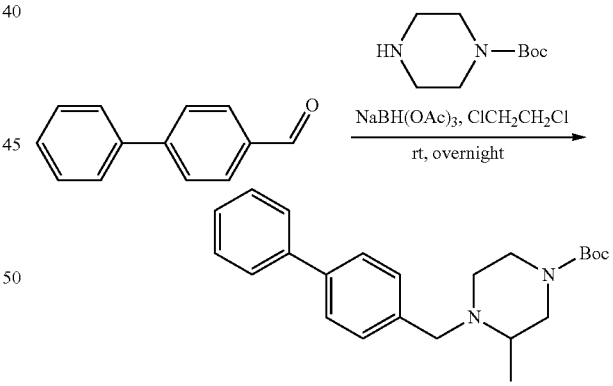

A 100-mL round-bottom flask was charged with tert-butyl 3-methylpiperazine-1-carboxylate (1.00 g, 4.99 mmol, 1.00 equiv), 4-phenylbenzaldehyde (1.00 g, 5.49 mmol, 1.10 equiv), sodium triacetoxyborohydride (3.18 g, 15.0 mmol, 3.01 equiv), and 1,2-dichloroethane (30 mL). The resulting solution was stirred overnight at room temperature and then diluted with dichloromethane (30 mL). The resulting mixture was washed with H$_2$O (3×20 mL), and the organic layer was dried over anhydrous sodium sulfate, filtered, and concentrated under reduced pressure. The residue was chromatographed on a silica gel column with ethyl acetate/petroleum ether to provide 1.71 g (93% yield) of tert-butyl 3-methyl-4-[(4-phenylphenyl)methyl]piperazine-1-carboxylate as a light yellow solid. LCMS (ESI, m/z): 367 [M+H]⁺.

Step 2: Preparation of
2-methyl-1-[(4-phenylphenyl)methyl]piperazine

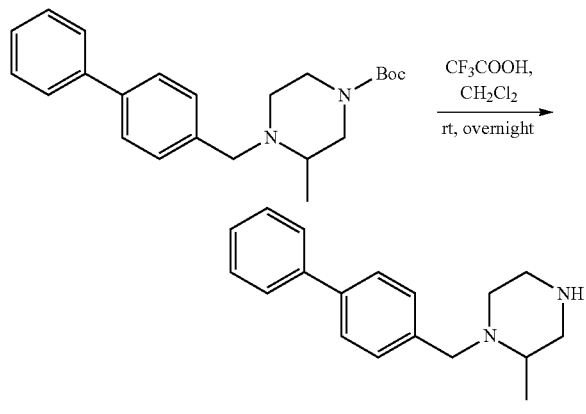

A 100-mL round-bottom flask was charged with tert-butyl 3-methyl-4-[(4-phenylphenyl)methyl]piperazine-1-carboxylate (600 mg, 1.64 mmol, 1.00 equiv) and dichloromethane (25 mL). Trifluoroacetic acid (1 mL) was added dropwise. The resulting solution was stirred overnight at room temperature. The resulting mixture was concentrated under reduced pressure to provide 532 mg (crude) of 2-methyl-1-[(4-phenylphenyl)methyl]piperazine as a brown oil. LCMS (ESI, m/z): 267 [M+H]⁺.

Step 3: Preparation of 2,5-dioxopyrrolidin-1-yl 3-methyl-4-[(4-phenylphenyl)methyl]piperazine-1-carboxylate

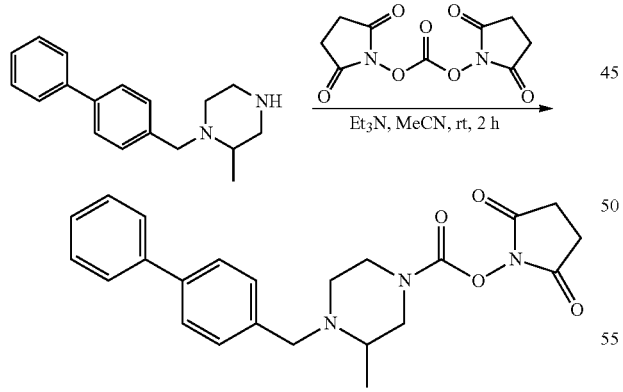

A 50-mL round-bottom flask was charged with 2-methyl-1-[(4-phenylphenyl)methyl]piperazine (266 mg, 1.00 mmol, 1.00 equiv), bis(2,5-dioxopyrrolidin-1-yl) carbonate (384 mg, 1.50 mmol, 1.50 equiv), and acetonitrile (10 mL). Triethylamine (202 mg, 2.00 mmol, 2.00 equiv) was added dropwise. The resulting solution was stirred for 2 h at room temperature and then diluted with H₂O (10 mL). The resulting mixture was extracted with dichloromethane (3×10 mL), and the organic layers were combined, washed with H₂O (3×5 mL), dried over anhydrous sodium sulfate, filtered, and concentrated under reduced pressure. The residue was chromatographed on a silica gel column with dichloromethane/MeOH (93/7). The crude product (315 mg) was purified by preparative HPLC using the following gradient conditions: 20% CH₃CN/80% Phase A increasing to 80% CH₃CN over 10 min, then to 100% CH₃CN over 0.1 min, holding at 100% CH₃CN for 1.9 min, then reducing to 20% CH₃CN over 0.1 min, and holding at 20% for 1.9 min, on a Waters 2767-5 Chromatograph. Column: Xbridge Prep C₁₈, 19*150 mm, 5 um; Mobile phase: Phase A: water; Phase B: CH₃CN; Detector, UV 220 & 254 nm. Purification resulted in 103 mg (25% yield) of 2,5-dioxopyrrolidin-1-yl 3-methyl-4[(4-phenylphenyl)methyl]piperazine-1-carboxylate as a white solid. ¹H NMR (300 MHz, Chloroform-d): δ 7.58 (t, J=8.6 Hz, 4H), 7.32-7.46 (m, 5H), 4.03-4.06 (m, 1H), 3.68-3.84 (m, 2H), 3.27-3.39 (m, 2H), 3.07 (br, 1H), 2.82 (s, 5H), 2.67 (br, 1H), 2.28 (br, 1H), 1.21-1.25 (m, 3H). LCMS (ESI, m/z): 462 [M+H]⁺.

Example 161

2,5-Dioxopyrrolidin-1-yl 4-((3-morpholino-[1,1'-biphenyl]-4-yl)methyl)piperazine-1-carboxylate

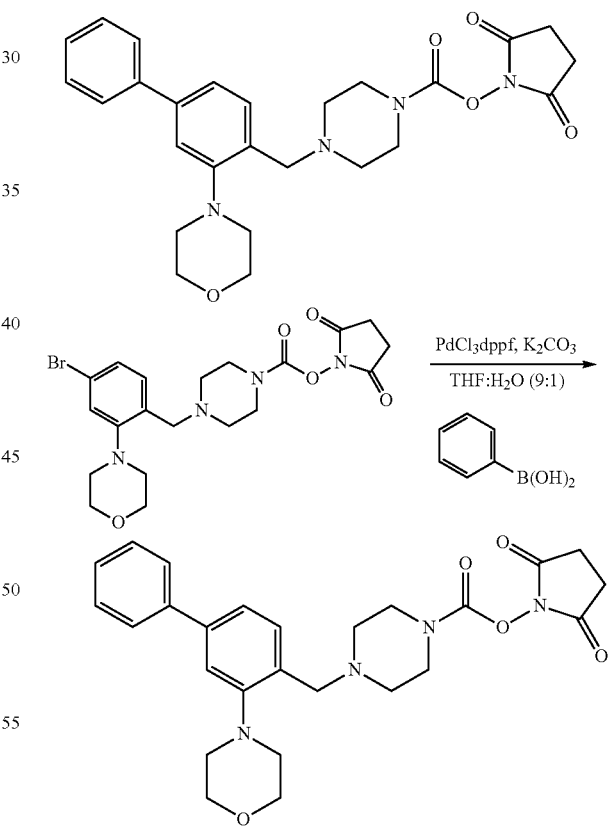

A round-bottom flask was charged with 2,5-dioxopyrrolidin-1-yl 4-(4-bromo-2-morpholinobenzyl)piperazine-1-carboxylate (Example 66, 30 mg, 0.0562 mmol), bis(diphenylphosphino)ferrocene-palladium(II)dichloride (5 mg, 6.13 μmol), phenylboronic acid (10 mg, 82.0 μmol), and K₂CO₃ (21 mg, 152 μmol). THF (4 mL) and H₂O (0.4 mL) were added, and the reaction mixture was heated to 70° C. for 2

1h. The reaction mixture was diluted in CH₂Cl₂ and washed with saturated Na₂CO₃ (2×) and brine (1×). The organics were dried (Na₂SO₄), filtered, and concentrated under reduced pressure. The residue was chromatographed on a silica gel column (100% to 80% hexanes in EtOAc) and yielded 2,5-dioxopyrrolidin-1-yl 4-((3-morpholino-[1,1'-biphenyl]-4-yl)methyl)piperazine-1-carboxylate (18 mg, 60%) $^1$H NMR (400 MHz, Chloroform-d) δ 7.63-7.57 (m, 2H), 7.53-7.43 (m, 3H), 7.41-7.31 (m, 3H), 3.94-3.82 (m, 4H), 3.67 (s, 4H), 3.61-3.45 (m, 2H), 3.12-3.00 (m, 4H), 2.84 (s, 4H), 2.61 (s, 4H). LCMS (ESI, m/z): 479.2 $[C_{26}H_{30}N_4O_5]^+$.

Example 162

2,5-Dioxopyrrolidin-1-yl 4-{[2-fluoro-4-(3-fluorophenyl)phenyl]methyl}piperazine-1-carboxylate

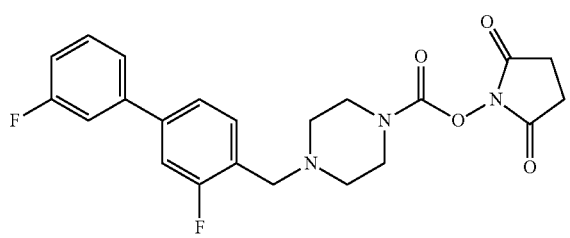 [SMILES: O=C(ON1C(=O)CCC1=O)N1CCN(Cc2ccc(-c3cccc(F)c3)cc2F)CC1]

The title compound was prepared directly from commercially available 4-bromo-2-fluorobenzaldehyde and (3-fluorophenyl)boronic acid according to the representative procedure of Example 159, Steps 1, 2, 3 and 4 to provide 2,5-dioxopyrrolidin-1-yl 4-{[2-fluoro-4-(3-fluorophenyl)phenyl]methyl}piperazine-1-carboxylate as a white solid. $^1$H NMR (300 MHz, Chloroform-d) δ 7.38-7.45 (m, 5H), 7.26-7.28 (m, 1H), 7.03-7.09 (m, 1H), 3.56-3.67 (m, 6H), 2.82 (s, 4H), 2.59 (s, 4H). LCMS (ESI, m/z): 430 [M+H]⁺.

Example 163

2,5-Dioxopyrrolidin-1-yl 4-{[2-methyl-4-(3-methylphenyl)phenyl]methyl}piperazine-1-carboxylate

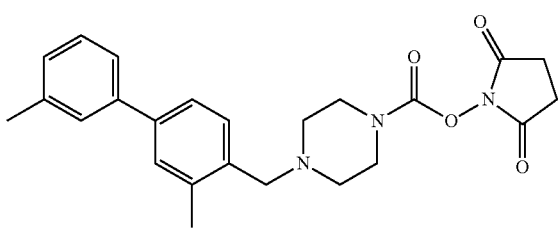 [SMILES: Cc1cccc(-c2ccc(CN3CCN(C(=O)ON4C(=O)CCC4=O)CC3)c(C)c2)c1]

The title compound was prepared directly from commercially available 4-bromo-2-methylbenzaldehyde and (3-methylphenyl)boronic acid according to the representative procedure of Example 159, Steps 1, 2, 3 and 4 to provide 2,5-dioxopyrrolidin-1-yl 4-{[2-methyl-4-(3-methylphenyl)phenyl]methyl}piperazine-1-carboxylate as a white solid. $^1$H NMR (300 MHz, Chloroform-d) δ 7.30-7.39 (m, 6H), 7.14-7.26 (m, 1H), 3.53-3.64 (m, 6H), 2.74-2.82 (m, 4H), 2.54-2.63 (m, 4H), 2.41-2.43 (m, 6H). LCMS (ESI, m/z): 422 [M+H]⁺.

Example 164

2,5-Dioxopyrrolidin-1-yl 4-[(2-fluoro-4-phenylphenyl)methyl]piperazine-1-carboxylate

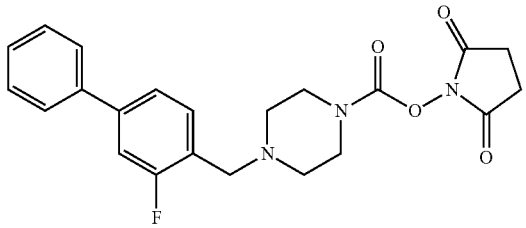 [SMILES: O=C(ON1C(=O)CCC1=O)N1CCN(Cc2ccc(-c3ccccc3)cc2F)CC1]

The title compound was prepared directly from commercially available 4-bromo-2-fluorobenzaldehyde and phenylboronic acid according to the representative procedure of Example 159, Steps 1, 2, 3 and 4 to provide 2,5-dioxopyrrolidin-1-yl 4-[(2-fluoro-4-phenylphenyl)methyl]piperazine-1-carboxylate as a white solid. $^1$H NMR (400 MHz, Chloroform-d) δ 7.60 (d, J=7.6 Hz, 2H), 7.38-7.49 (m, 5H), 7.28-7.33 (m, 1H), 3.59-3.70 (m, 6H), 2.84 (s, 4H), 2.62 (s, 4H). LCMS (ESI, m/z): 412 [M+H]⁺.

Example 165

2,5-Dioxopyrrolidin-1-yl 4-[(2-methyl-4-phenylphenyl)methyl]piperazine-1-carboxylate

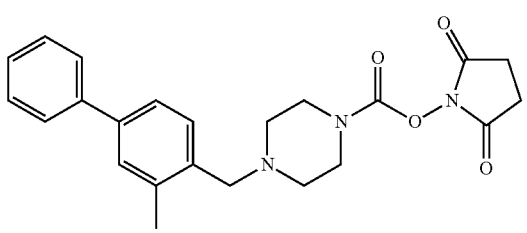 [SMILES: Cc1cc(-c2ccccc2)ccc1CN1CCN(C(=O)ON2C(=O)CCC2=O)CC1]

The title compound was prepared directly from commercially available 4-bromo-2-methylbenzaldehyde and phenylboronic acid according to the representative procedure of Example 159, Steps 1, 2, 3 and 4 to provide 2,5-dioxopyrrolidin-1-yl 4-[(2-methyl-4-phenylphenyl)methyl]piperazine-1-carboxylate as a white solid. $^1$H NMR (300 MHz, Chloroform-d) δ 7.60 (d, J=1.2 Hz, 1H), 7.57 (s, 1H), 7.26-7.46 (m, 6H), 3.64 (br, 2H), 3.54 (br, 4H), 2.82 (s, 4H), 2.55 (br, 4H), 2.43 (s, 3H). LCMS (ESI, m/z): 408 [M+H]⁺.

Example 166

2,5-Dioxopyrrolidin-1-yl 4-{[2-fluoro-4-(2-methylpyridin-4-yl)phenyl]methyl}piperazine-1-carboxylate

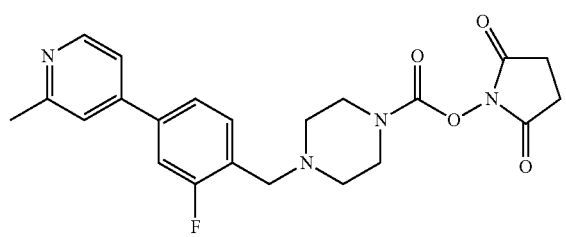 [SMILES: Cc1cc(-c2ccc(CN3CCN(C(=O)ON4C(=O)CCC4=O)CC3)c(F)c2)ccn1]

The title compound was prepared directly from commercially available 4-bromo-2-fluorobenzaldehyde and (2-methylpyridin-4-yl)boronic acid according to the representative procedure of Example 159, Steps 1, 2, 3 and 4 to provide 2,5-dioxopyrrolidin-1-yl 4-{[2-fluoro-4-(2-methylpyridin-4-yl)phenyl]methyl}piperazine-1-carboxylate as a white solid. ¹H NMR (400 MHz, Chloroform-d) δ 8.59 (d, J=5.2 Hz, 1H), 7.51-7.54 (m, 1H), 7.42-7.44 (m, 1H), 7.40 (s, 1H), 7.34-7.37 (m, 2H), 3.60-3.72 (m, 6H), 2.84 (s, 4H), 2.68 (s, 3H), 2.63 (br, 4H). LCMS (ESI, m/z): 427 [M+H]⁺.

Example 167

2,5-Dioxopyrrolidin-1-yl 4-[(2-methoxy-4-phenylphenyl)methyl]piperazine-1-carboxylate

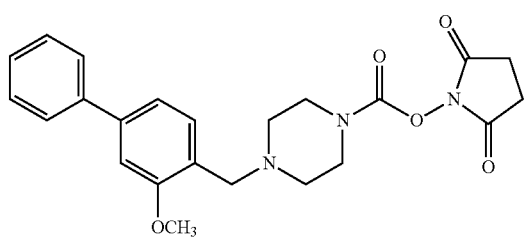 [SMILES: COc1cc(-c2ccccc2)ccc1CN1CCN(C(=O)ON2C(=O)CCC2=O)CC1]

The title compound was prepared directly from commercially available 4-bromo-2-methoxybenzaldehyde and phenylboronic acid according to the representative procedure of Example 159, Steps 1, 2, 3 and 4 to provide 2,5-dioxopyrrolidin-1-yl 4-[(2-methoxy-4-phenylphenyl)methyl]piperazine-1-carboxylate as a white solid. ¹H NMR (300 MHz, Chloroform-d) δ 7.60 (t, J=4.2 Hz, 2H), 7.33-7.47 (m, 4H), 7.71 (d, J=2.1 Hz, 1H), 7.08 (d, J=1.5 Hz, 1H), 3.90 (s, 3H), 3.58-3.67 (m, 6H), 2.82 (s, 4H), 2.61 (br, 4H). LCMS (ESI, m/z): 424 [M+H]⁺.

Example 168

2,5-Dioxopyrrolidin-1-yl 4-{[5-(3-fluorophenyl)pyridin-2-yl]methyl}piperazine-1-carboxylate

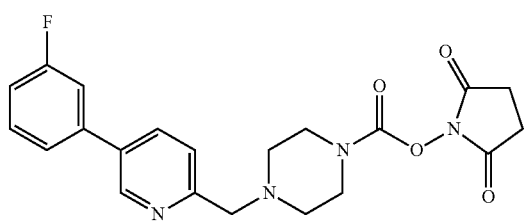 [SMILES: O=C(ON1C(=O)CCC1=O)N1CCN(Cc2ccc(-c3cccc(F)c3)cn2)CC1]

The title compound was prepared directly from commercially available 5-bromopicolinaldehyde and (3-fluorophenyl)boronic acid according to the representative procedure of Example 159, Steps 1, 2, 3 and 4 to provide 2,5-dioxopyrrolidin-1-yl 4-{[5-(3-fluorophenyl)pyridin-2-yl]methyl}piperazine-1-carboxylate as a white solid. ¹H NMR (300 MHz, Chloroform-d) δ 9.06 (s, 1H), 8.29-8.32 (m, 1H), 7.56-7.72 (m, 4H), 7.30-7.34 (m, 1H), 4.65 (s, 2H), 3.74-3.86 (m, 4H), 3.37 (br, 4H), 2.81 (s, 4H). LCMS (ESI, m/z): 413[M+H]⁺.

Example 169

2,5-Dioxopyrrolidin-1-yl 4-{[4-(3-methylphenyl)-2-phenoxyphenyl]methyl}piperazine-1-carboxylate

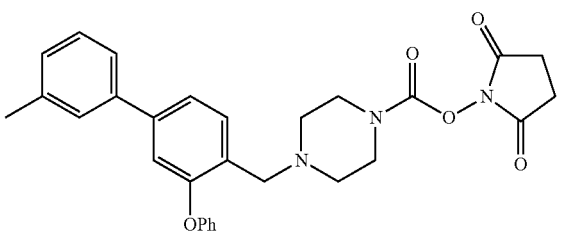 [SMILES: Cc1cccc(-c2ccc(CN3CCN(C(=O)ON4C(=O)CCC4=O)CC3)c(Oc3ccccc3)c2)c1]

Step 1: Preparation of 4-bromo-2-phenoxybenzaldehyde

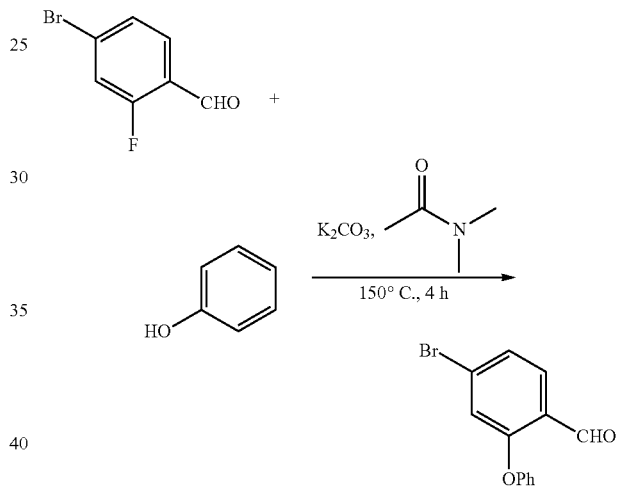

A 250-mL round-bottom flask was purged with and maintained under an inert atmosphere of nitrogen then charged with 4-bromo-2-fluorobenzaldehyde (2.00 g, 9.85 mmol, 1.00 equiv), phenol (0.926 g, 9.84 mmol, 1.00 equiv), potassium carbonate (1.35 g, 9.77 mmol, 0.99 equiv), and N,N-dimethylacetamide (30 mL). The resulting solution stirred for 4 h at 150° C. and then diluted with water (30 mL) and extracted with ethyl acetate (3×20 mL). The organic layers were combined, dried over anhydrous sodium sulfate, filtered, and concentrated under reduced pressure. The residue was chromatographed on a silica gel column with ethyl acetate/petroleum ether (1/99) to provide 2.40 g (88% yield) of 4-bromo-2-phenoxybenzaldehyde as a light yellow solid. ¹H NMR (300 MHz, Chloroform-d) δ 10.51 (s, 1H), 7.82 (d, J=8.4 Hz, 1H), 7.41-7.48 (m, 1H), 7.33 (d, J=8.4 Hz, 1H), 7.25-7.29 (m, 1H), 7.12 (d, J=7.6 Hz, 2H), 7.04 (s, 1H).

Preparation of 2,5-dioxopyrrolidin-1-yl 4-{[4-(3-methylphenyl)-2-phenoxyphenyl]methyl}piperazine-1-carboxylate The title compound was prepared directly from 4-bromo-2-phenoxybenzaldehyde (Step 1) and (3-methylphenyl)boronic acid according to the representative procedure of Example 159, Steps 1, 2, 3 and 4 to provide 2,5-dioxopyrrolidin-1-yl 4-{[4-(3-methylphenyl)-2-phenoxyphenyl]methyl}piperazine-1-carboxylate as a yellow oil. $^1$H NMR (300 MHz, Chloroform-d) δ 7.47-7.52 (m, 1H), 7.29-7.40 (m, 6H), 7.14-7.16 (m, 2H), 7.05-7.10 (m, 1H), 6.94 (t, J=8.4 Hz, 2H), 3.48-3.62 (m, 6H), 2.81 (s, 4H), 2.57 (br, 4H), 2.38 (s, 3H). LCMS (ESI, m/z): 500 [M+H]$^+$.

Example 170

2,5-Dioxopyrrolidin-1-yl 4-{[2-methyl-4-(2-methylpyridin-3-yl)phenyl]methyl}piperazine-1-carboxylate

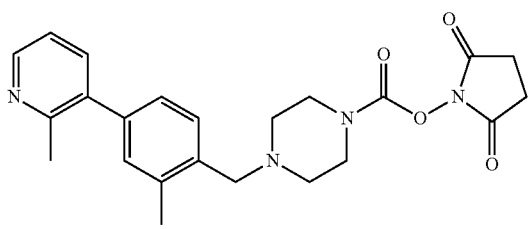 [SMILES: Cc1cc(-c2cccnc2C)ccc1CN1CCN(C(=O)ON2C(=O)CCC2=O)CC1]

The title compound was prepared directly from commercially available 4-bromo-2-methylbenzaldehyde and (2-methylpyridin-3-yl)boronic acid according to the representative procedure of Example 159, Steps 1, 2, 3 and 4 to provide 2,5-dioxopyrrolidin-1-yl 4-{[2-methyl-4-(2-methylpyridin-3-yl)phenyl]methyl}piperazine-1-carboxylate as a white semi-solid. $^1$H NMR (300 MHz, Chloroform-d) δ 8.50-8.52 (m, 1H), 7.55-7.58 (m, 1H), 7.34 (d, J=7.8 Hz, 1H), 7.21-7.25 (m, 1H), 7.11-7.13 (m, 2H), 3.57-3.68 (m, 6H), 2.83 (s, 4H), 2.55-2.58 (m, 7H), 2.42 (s, 3H). LCMS (ESI, m/z): 423 [M+H]$^+$.

Example 171

2,5-Dioxopyrrolidin-1-yl 4-{[2-methyl-4-(3-methylpyridin-4-yl)phenyl]methyl}piperazine-1-carboxylate

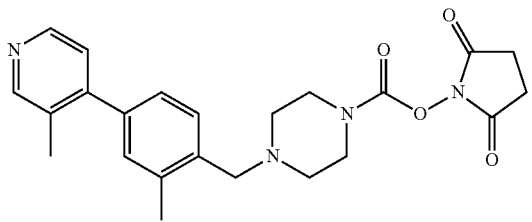 [SMILES: Cc1cc(-c2ccncc2C)ccc1CN1CCN(C(=O)ON2C(=O)CCC2=O)CC1]

The title compound was prepared directly from commercially available 4-bromo-2-methylbenzaldehyde and (3-methylpyridin-4-yl)boronic acid according to the representative procedure of Example 159, Steps 1, 2, 3 and 4 to provide 2,5-dioxopyrrolidin-1-yl 4-{[2-methyl-4-(3-methylpyridin-4-yl)phenyl]methyl}piperazine-1-carboxylate as a yellow oil. $^1$H NMR (300 MHz, Chloroform-d) δ 8.50 (s, 1H), 8.46 (d, J=5.1 Hz, 1H), 7.33-7.35 (m, 1H), 7.11-7.16 (m, 3H), 3.67 (br, 4H), 3.56 (s, 2H), 2.83 (s, 4H), 2.56 (br, 4H), 2.42 (s, 3H), 2.30 (s, 3H). LCMS (ESI, m/z): 423 [M+H]$^+$.

Example 172

2,5-Dioxopyrrolidin-1-yl 4-{[2-methyl-4-(pyridin-3-yl)phenyl]methyl}piperazine-1-carboxylate

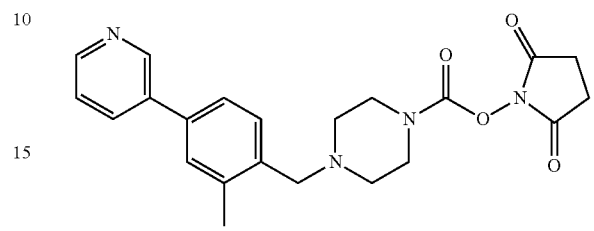

The title compound was prepared directly from commercially available 4-bromo-2-methylbenzaldehyde and pyridin-3-ylboronic acid according to the representative procedure of Example 159, Steps 1, 2, 3 and 4 to provide 2,5-dioxopyrrolidin-1-yl 4-{[2-methyl-4-(pyridin-3-yl)phenyl]methyl}piperazine-1-carboxylate as a white solid. $^1$H NMR (300 MHz, Chloroform-d) δ 8.84 (d, J=2.4 Hz, 1H), 8.57-8.59 (m, 1H), 7.86-7.90 (m, 1H), 7.35-7.38 (m, 4H), 3.59-3.68 (m, 6H), 2.83 (s, 4H), 2.53-2.71 (m, 4H), 2.45 (s, 3H). LCMS (ESI, m/z): 409 [M+H]$^+$.

Example 173

2,5-Dioxopyrrolidin-1-yl 4-{[2-methyl-4-(6-methylpyridin-2-yl)phenyl]methyl}piperazine-1-carboxylate

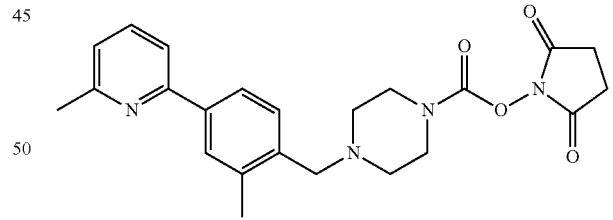

The title compound was prepared directly from commercially available 4-bromo-2-methylbenzaldehyde and (6-methylpyridin-2-yl)boronic acid according to the representative procedure of Example 159, Steps 1, 2, 3 and 4 to provide 2,5-dioxopyrrolidin-1-yl 4-{[2-methyl-4-(6-methylpyridin-2-yl)phenyl]methyl}piperazine-1-carboxylate as a white solid. $^1$H NMR (400 MHz, Chloroform-d) δ 7.83 (s, 1H), 7.74 (d, J=7.6 Hz, 1H), 7.63-7.67 (m, 1H), 7.52 (d, J=8.0 Hz, 1H), 7.30-7.36 (m, 1H), 7.11 (d, J=7.6 Hz, 1H), 3.57-3.65 (m, 6H), 2.85 (s, 4H), 2.65 (s, 3H), 2.55 (br, 4H), 2.47 (s, 3H). LCMS (ESI, m/z): 423 [M+H]$^+$.

Example 174

2,5-Dioxopyrrolidin-1-yl 4-{[2-fluoro-4-(2-methyl-pyridin-3-yl)phenyl]methyl}piperazine-1-carboxylate

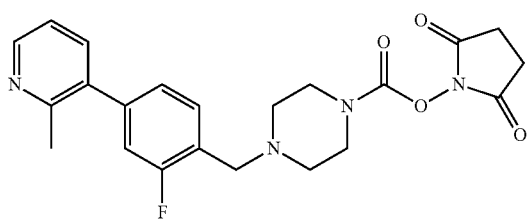 [SMILES: Cc1ncccc1-c1ccc(CN2CCN(C(=O)ON3C(=O)CCC3=O)CC2)c(F)c1]

The title compound was prepared directly from commercially available 4-bromo-2-fluorobenzaldehyde and (2-methylpyridin-3-yl)boronic acid according to the representative procedure of Example 159, Steps 1, 2, 3 and 4 to provide 2,5-dioxopyrrolidin-1-yl 4-{[2-fluoro-4-(2-methyl-pyridin-3-yl)phenyl]methyl}piperazine-1-carboxylate as a white solid. $^1$H NMR (300 MHz, Chloroform-d) δ 8.50-8.52 (m, 1H), 7.55-7.58 (m, 1H), 7.34 (d, J=7.8 Hz, 1H), 7.21-7.25 (m, 1H), 7.11-7.13 (m, 2H), 3.57-3.68 (m, 6H), 2.83 (s, 4H), 2.55-2.58 (m, 4H), 2.42 (s, 3H). LCMS (ESI, m/z): 4.27 [M+H]$^+$.

Example 175

2,5-Dioxopyrrolidin-1-yl 4-{[2-fluoro-4-(6-methyl-pyridin-2-yl)phenyl]methyl}piperazine-1-carboxylate

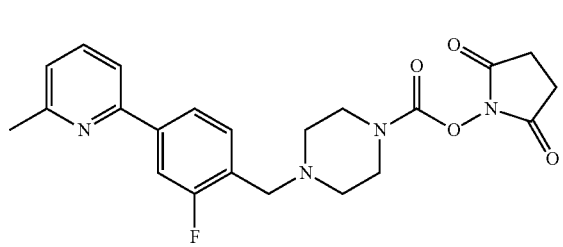 [SMILES: Cc1cccc(-c2ccc(CN3CCN(C(=O)ON4C(=O)CCC4=O)CC3)c(F)c2)n1]

The title compound was prepared directly from commercially available 4-bromo-2-fluorobenzaldehyde and (6-methylpyridin-2-yl)boronic acid according to the representative procedure of Example 159, Steps 1, 2, 3 and 4 to provide 2,5-dioxopyrrolidin-1-yl 4-{[2-fluoro-4-(6-methyl-pyridin-2-yl)phenyl]methyl}piperazine-1-carboxylate as a white solid. $^1$H NMR (400 MHz, Chloroform-d) δ 7.73-7.77 (m, 2H), 7.65-7.69 (m, 1H), 7.44-7.53 (m, 2H), 7.15 (d, J=7.6 Hz, 1H), 3.58-3.70 (m, 6H), 2.84 (s, 4H), 2.65 (s, 3H), 2.61 (br, 4H). LCMS (ESI, m/z): 427 [M+H]$^+$.

Example 176

2,5-Dioxopyrrolidin-1-yl 4-{[4-(2,6-dimethylpyridin-4-yl)-2-fluorophenyl]methyl}piperazine-1-carboxylate

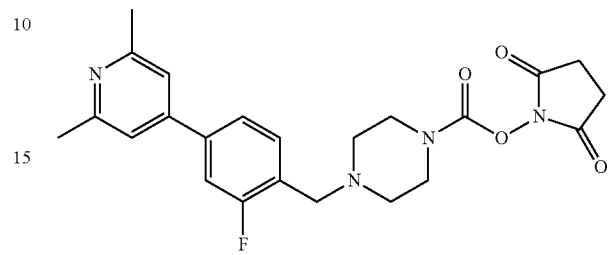

The title compound was prepared directly from commercially available 4-bromo-2-fluorobenzaldehyde and (2,6-dimethylpyridin-4-yl)boronic acid according to the representative procedure of Example 159, Steps 1, 2, 3 and 4 to provide 2,5-dioxopyrrolidin-1-yl 4-{[4-(2,6-dimethylpyridin-4-yl)-2-fluorophenyl]methyl}piperazine-1-carboxylate as a white solid. $^1$H NMR (400 MHz, Chloroform-d) δ 7.46-7.50 (m, 1H), 7.39-7.41 (m, 1H), 7.31-7.34 (m, 1H), 7.18 (s, 2H), 3.69 (s, 4H), 3.57 (br, 2H), 2.84 (s, 4H), 2.60-2.66 (m, 10H). LCMS (ESI, m/z): 441 [M+H]$^+$.

Example 177

2,5-Dioxopyrrolidin-1-yl 4-{[2-fluoro-4-(3-methyl-pyridin-4-yl)phenyl]methyl}piperazine-1-carboxylate

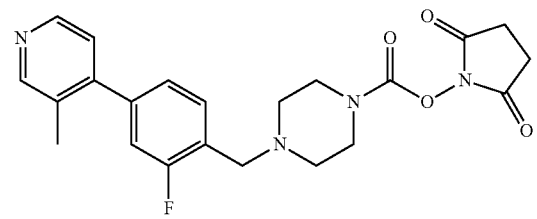 [SMILES: Cc1cnccc1-c1ccc(CN2CCN(C(=O)ON3C(=O)CCC3=O)CC2)c(F)c1]

The title compound was prepared directly from commercially available 4-bromo-2-fluorobenzaldehyde and (3-methylpyridin-4-yl)boronic acid according to the representative procedure of Example 159, Steps 1, 2, 3 and 4 to provide 2,5-dioxopyrrolidin-1-yl 4-{[2-fluoro-4-(3-methyl-pyridin-4-yl)phenyl]methyl}piperazine-1-carboxylate as a white solid. $^1$H NMR (400 MHz, Chloroform-d) δ 8.50-8.54 (m, 2H), 7.49 (t, J=15.2 Hz, 1H), 7.16-7.18 (m, 1H), 7.12-7.14 (m, 1H), 7.05-7.08 (m, 1H), 3.73 (br, 4H), 3.61 (br, 2H), 2.85 (s, 4H), 2.64 (br, 4H), 2.322 (s, 3H). LCMS (ESI, m/z): 427 [M+H]$^+$.

Example 178

2,5-Dioxopyrrolidin-1-yl 4-{[5-(2-fluorophenyl)-6-methylpyridin-2-yl]methyl}piperazine-1-carboxylate

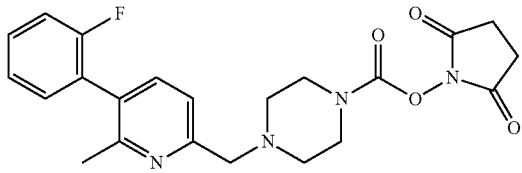

The title compound was prepared directly from commercially available 5-bromo-6-methylpicolinaldehyde and (2-fluorophenyl)boronic acid according to the representative procedure of Example 159, Steps 1, 2, 3 and 4 to provide 2,5-dioxopyrrolidin-1-yl 4-{[5-(2-fluorophenyl)-6-methylpyridin-2-yl]methyl}piperazine-1-carboxylate as a colorless semi-solid. $^1$H-NMR (300 MHz, Chloroform-d) δ 7.53 (d, J=7.8 Hz, 1H), 7.34-7.43 (m, 2H), 7.14-7.28 (m, 3H), 3.74-3.78 (m, 4H), 3.62 (br, 2H), 2.83 (s, 4H), 2.67 (br, 4H), 2.44 (s, 3H). LCMS (ESI, m/z): 427 [M+H]$^+$.

Example 179

2,5-Dioxopyrrolidin-1-yl 4-{[6-methyl-5-(2-methylphenyl)pyridin-2-yl]methyl}piperazine-1-carboxylate

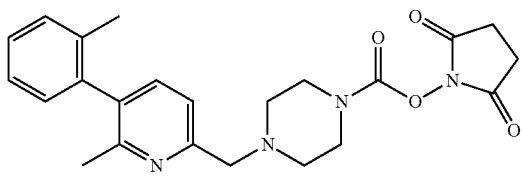 [SMILES: Cc1ccccc1-c1ccc(CN2CCN(C(=O)ON3C(=O)CCC3=O)CC2)nc1C]

The title compound was prepared directly from commercially available 5-bromo-6-methylpicolinaldehyde and (2-methylphenyl)boronic acid according to the representative procedure of Example 159, Steps 1, 2, 3 and 4 to provide 2,5-dioxopyrrolidin-1-yl 4-{[6-methyl-5-(2-methylphenyl)pyridin-2-yl]methyl}piperazine-1-carboxylate as a white solid. $^1$H NMR (300 MHz, Chloroform-d) δ 7.41-7.48 (m, 1H), 7.22-7.33 (m, 4H), 7.09 (d, J=6.9 Hz, 1H), 3.61-3.85 (m, 6H), 2.95 (s, 4H), 2.60-2.75 (m, 4H), 2.31 (s, 3H), 2.07 (s, 3H). LCMS (ESI, m/z): 423 [M+H]$^+$.

Example 180

2,5-Dioxopyrrolidin-1-yl 4-{[6-methyl-5-(3-methylphenyl)pyridin-2-yl]methyl}piperazine-1-carboxylate

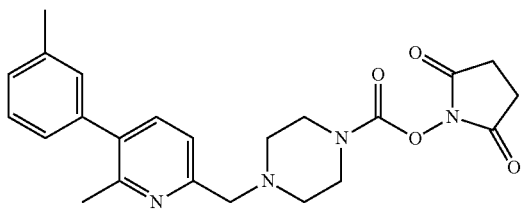 [SMILES: Cc1cccc(-c2ccc(CN3CCN(C(=O)ON4C(=O)CCC4=O)CC3)nc2C)c1]

The title compound was prepared directly from commercially available 5-bromo-6-methylpicolinaldehyde and (3-methylphenyl)boronic acid according to the representative procedure of Example 159, Steps 1, 2, 3 and 4 to provide 2,5-dioxopyrrolidin-1-yl 4-{[6-methyl-5-(3-methylphenyl)pyridin-2-yl]methyl}piperazine-1-carboxylate as a white solid. $^1$H NMR (300 MHz, Chloroform-d) δ 7.51 (d, J=7.5 Hz, 1H), 7.26-7.36 (m, 2H), 7.20 (d, J=7.8 Hz, 1H), 7.11-7.13 (m, 2H), 3.59-3.75 (m, 6H), 2.83 (s, 4H), 2.64 (br, 4H), 2.51 (s, 3H), 2.41 (s, 3H). LCMS (ESI, m/z): 423 [M+H]$^+$.

Example 181

2,5-Dioxopyrrolidin-1-yl 4-{[5-(3-fluorophenyl)-6-methylpyridin-2-yl]methyl}piperazine-1-carboxylate

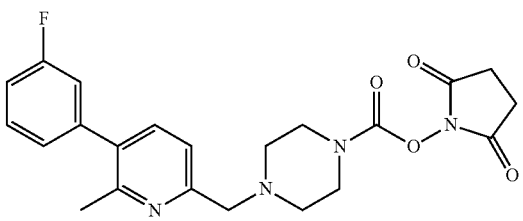 [SMILES: Cc1nc(CN2CCN(C(=O)ON3C(=O)CCC3=O)CC2)ccc1-c1cccc(F)c1]

The title compound was prepared directly from commercially available 5-bromo-6-methylpicolinaldehyde and (3-fluorophenyl)boronic acid according to the representative procedure of Example 159, Steps 1, 2, 3 and 4 to provide 2,5-dioxopyrrolidin-1-yl 4-{[5-(3-fluorophenyl)-6-methylpyridin-2-yl]methyl}piperazine-1-carboxylate as a white solid. $^1$H NMR (300 MHz, Chloroform-d) δ 7.51 (d, J=7.8 Hz, 1H), 7.32-7.45 (m, 2H), 7.02-7.12 (m, 3H), 3.60-3.75 (m, 6H), 2.83 (s, 4H), 2.65 (br, 4H), 2.51 (s, 3H). LCMS (ESI, m/z): 427 [M+H]$^+$.

Example 182

2,5-Dioxopyrrolidin-1-yl 4-{[2-methyl-6-(2-methylphenyl)pyridin-3-yl]methyl}piperazine-1-carboxylate

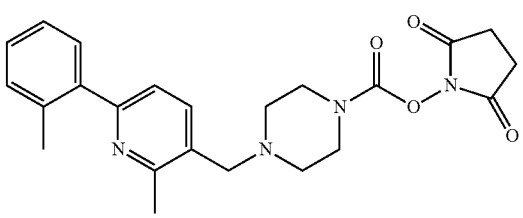

The title compound was prepared directly from commercially available 6-bromo-2-methylnicotinaldehyde and (2-methylphenyl)boronic acid according to the representative procedure of Example 159, Steps 1, 2, 3 and 4 to provide 2,5-dioxopyrrolidin-1-yl 4-{[2-methyl-6-(2-methylphenyl)pyridin-3-yl]methyl}piperazine-1-carboxylate as a white solid. $^1$H NMR (300 MHz, Chloroform-d) δ: 7.65 (d, J=7.8 Hz, 1H), 7.35-7.40 (m, 1H), 7.20-7.31 (m, 4H), 3.58-3.69 (m, 6H), 2.83 (s, 4H), 2.59-2.65 (m, 7H), 2.36 (s, 3H). LCMS (ESI, m/z): 423 [M+H]$^+$.

Example 183

2,5-Dioxopyrrolidin-1-yl 4-{[6-(2-fluorophenyl)-2-methylpyridin-3-yl]methyl}piperazine-1-carboxylate

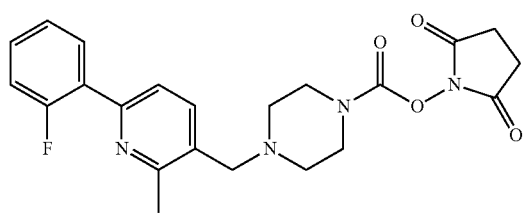 [SMILES: Cc1ccccc1-c1ccc(CN2CCN(C(=O)ON3C(=O)CCC3=O)CC2)c(C)n1]

The title compound was prepared directly from commercially available 6-bromo-2-methylnicotinaldehyde and (2-fluorophenyl)boronic acid according to the representative procedure of Example 159, Steps 1, 2, 3 and 4 to provide 2,5-dioxopyrrolidin-1-yl 4-{[6-(2-fluorophenyl)-2-methylpyridin-3-yl]methyl}piperazine-1-carboxylate as a white solid. $^1$H NMR (300 MHz, Chloroform-d) δ 7.96-8.02 (m, 1H), 7.57-7.65 (m, 2H), 7.32-7.39 (m, 1H), 7.23-7.28 (m, 1H), 7.11-7.18 (m, 1H), 3.56-3.67 (m, 6H), 2.82 (s, 4H), 2.66 (s, 3H), 2.55-2.58 (m, 4H). LCMS (ESI, m/z): 426 [M+H]$^+$.

Example 184

2,5-Dioxopyrrolidin-1-yl 4-{[2-methyl-6-(3-methylphenyl)pyridin-3-yl]methyl}piperazine-1-carboxylate

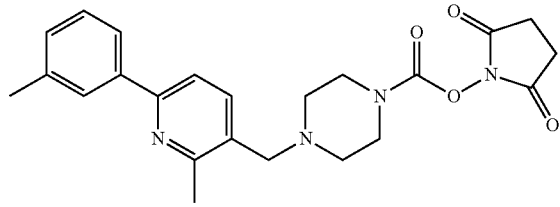 [SMILES: Cc1cccc(-c2ccc(CN3CCN(C(=O)ON4C(=O)CCC4=O)CC3)c(C)n2)c1]

The title compound was prepared directly from commercially available 6-bromo-2-methylnicotinaldehyde and (3-methylphenyl)boronic acid according to the representative procedure of Example 159, Steps 1, 2, 3 and 4 to provide 2,5-dioxopyrrolidin-1-yl 4-{[2-methyl-6-(3-methylphenyl)pyridin-3-yl]methyl}piperazine-1-carboxylate as light a yellow oil. $^1$H NMR (300 MHz, Chloroform-d) δ 7.83 (s, 1H), 7.75 (d, J=7.8 Hz, 1H), 7.57 (d, J=7.8 Hz, 1H), 7.49 (d, J=8.1 Hz, 1H), 7.328 (t, J=7.6 Hz, 1H), 7.19 (d, J=7.5 Hz, 1H), 3.50-3.63 (m, 6H), 2.75 (s, 4H), 2.70 (s, 3H), 2.59-2.64 (m, 4H), 2.42 (s, 3H). LCMS (ESI, m/z): 423 [M+H]$^+$.

Example 185

2,5-Dioxopyrrolidin-1-yl 4-{[6-(3-fluorophenyl)-2-methylpyridin-3-yl]methyl}piperazine-1-carboxylate

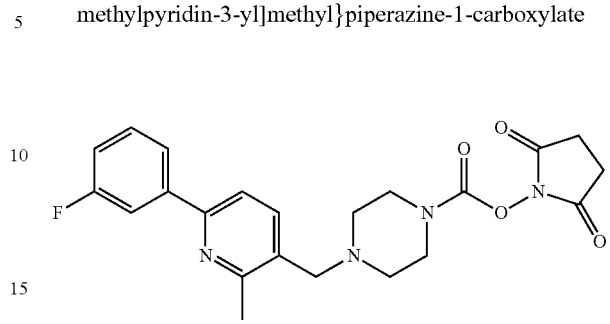

The title compound was prepared directly from commercially available 6-bromo-2-methylnicotinaldehyde and (3-fluorophenyl)boronic acid according to the representative procedure of Example 159, Steps 1, 2, 3 and 4 to provide 2,5-dioxopyrrolidin-1-yl 4-{[6-(3-fluorophenyl)-2-methylpyridin-3-yl]methyl}piperazine-1-carboxylate as a white solid. $^1$H NMR (300 MHz, Chloroform-d) δ 7.73-7.77 (m, 2H), 7.62-7.69 (m, 1H), 7.53 (d, J=7.5 Hz, 1H), 7.38-7.46 (m, 1H), 7.05-7.12 (m, 1H), 3.56-3.66 (m, 6H), 2.83 (s, 4H), 2.66 (s, 3H), 2.45-2.55 (m, 4H). LCMS (ESI, m/z): 427 [M+H]$^+$.

Example 186

2,5-Dioxopyrrolidin-1-yl 4-{[2-(propan-2-yl)-4-(pyrrolidin-1-yl)phenyl]methyl}piperazine-1-carboxylate

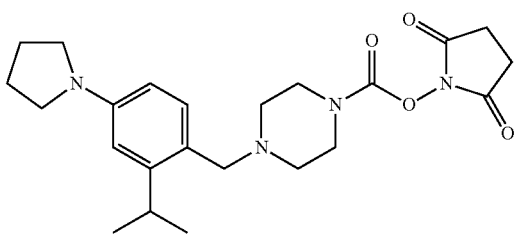 [SMILES: CC(C)c1cc(N2CCCC2)ccc1CN1CCN(C(=O)ON2C(=O)CCC2=O)CC1]

Step 1: Preparation of tert-butyl 4-[[2-(propan-2-yl)-4-(pyrrolidin-1-yl)phenyl]methyl]piperazine-1-carboxylate

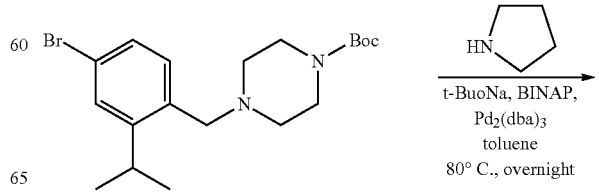

-continued

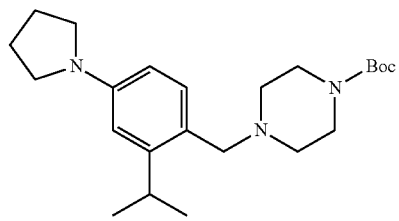

A 50-mL round-bottom flask was charged with tert-butyl 4-[[4-bromo-2-(propan-2-yl)phenyl]methyl]piperazine-1-carboxylate, itself prepared from commercially available 4-bromo-2-isopropylbenzaldehyde according to the representative procedure of Example 159, Step 1, (50.0 mg, 0.130 mmol, 1.00 equiv), pyrrolidine (11.0 mg, 0.150 mmol, 1.20 equiv), t-BuONa (17.5 mg, 0.180 mmol, 1.45 equiv), Pd$_2$(dba)$_3$ (6.00 mg, 0.010 mmol, 0.050 equiv), BINAP (12.0 mg, 0.020 mmol, 0.15 equiv), and toluene (2 mL). The resulting solution was stirred overnight at 80° C. with an inert atmosphere of nitrogen and then diluted with water (5 mL). The resulting solution was extracted with dichloromethane (3×5 mL), and the organic layers were combined, dried over anhydrous sodium sulfate, filtered, and concentrated under reduced pressure. The residue was chromatographed on a silica gel column with ethyl acetate/petroleum ether (20/80) to provide 31.0 mg (61% yield) of tert-butyl 4-[[2-(propan-2-yl)-4-(pyrrolidin-1-yl)phenyl]methyl]piperazine-1-carboxylate as a light yellow oil. LCMS (ESI, m/z): 388 [M+H]$^+$.

Preparation of 2,5-dioxopyrrolidin-1-yl 4-{[2-(propan-2-yl)-4-(pyrrolidin-1-yl)phenyl]methyl}piperazine-1-carboxylate

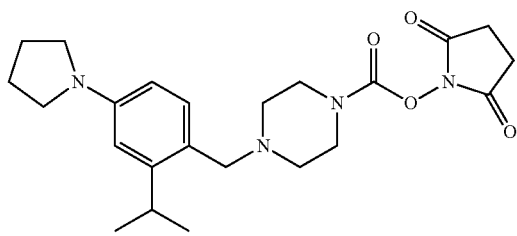 [SMILES: CC(C)c1cc(N2CCCC2)ccc1CN1CCN(C(=O)ON2C(=O)CCC2=O)CC1]

The title compound was prepared directly from tert-butyl 4-[[2-(propan-2-yl)-4-(pyrrolidin-1-yl)phenyl]methyl]piperazine-1-carboxylate (Step 1) according to the representative procedure of Example 159, Steps 3 and 4 to provide 2,5-dioxopyrrolidin-1-yl 4-{[2-(propan-2-yl)-4-(pyrrolidin-1-yl)phenyl]methyl}piperazine-1-carboxylate as a light yellow semi-solid. $^1$H NMR (400 MHz, Chloroform-d) δ 7.00-7.03 (m, 1H), 6.50 (d, J=2.4 Hz, 1H), 6.34-6.35 (m, 1H), 3.58 (br, 2H), 3.45 (br, 4H), 3.28-3.34 (m, 5H), 2.81 (s, 4H), 2.47 (m, 4H), 1.97-2.02 (m, 4H), 1.23 (d, J=6.8 Hz, 6H). LCMS (ESI, m/z): 451 [M+Na]$^+$.

Example 187

2,5-Dioxopyrrolidin-1-yl 4-{[4-(morpholin-4-yl)-2-(propan-2-yl)phenyl]methyl}piperazine-1-carboxylate

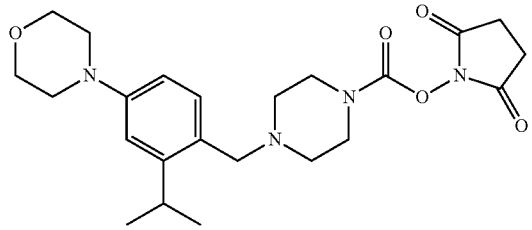 [SMILES: CC(C)c1cc(N2CCOCC2)ccc1CN1CCN(C(=O)ON2C(=O)CCC2=O)CC1]

The title compound was prepared directly from morpholine and tert-butyl 4-[[4-bromo-2-(propan-2-yl)phenyl]methyl]piperazine-1-carboxylate according to the representative procedure of Example 186, Step 1 followed by the representative procedure from Example 159, Steps 3 and 4 to provide 2,5-dioxopyrrolidin-1-yl 4-{[4-(morpholin-4-yl)-2-(propan-2-yl)phenyl]methyl}piperazine-1-carboxylate as a light yellow solid. $^1$H NMR (400 MHz, Chloroform-d) δ 7.80 (d, J=7.6 Hz, 1H), 6.86 (d, J=2.4 Hz, 1H), 6.66-6.68 (m, 1H), 3.87 (t, J=4.4 Hz, 4H), 3.48-3.60 (m, 6H), 3.28-3.33 (m, 1H), 3.16 (t, J=4.4 Hz, 4H), 2.82 (s, 4H), 2.48 (br, 4H), 1.22 (d, J=7.2 Hz, 6H). LCMS (ESI, m/z): 467 [M+Na]$^+$.

Example 188

2,5-Dioxopyrrolidin-1-yl 4-{[4-phenyl-2-(propan-2-yl)phenyl]methyl}piperazine-1-carboxylate The title compound was prepared directly from phenylboronic acid and tert-butyl 4-[[4-bromo-2-(propan-2-yl)phenyl]methyl]piperazine-1-carboxylate according to the representative procedure of Example 159, Steps 2, 3 and 4, to provide 2,5-dioxopyrrolidin-1-yl 4-{[4-phenyl-2-(propan-2-yl)phenyl]methyl}piperazine-1-carboxylate as a white solid. $^1$H NMR (300 MHz, Chloroform-d) δ 7.64 (d, J=1.5 Hz, 2H), 7.61-7.63 (m, 1H), 7.47-7.56 (m, 2H), 7.40-7.47 (m, 2H), 7.35-7.39 (m, 1H), 3.56-3.66 (m, 6H), 3.38-3.47 (m, 1H), 2.85 (s, 4H), 2.57 (t, J=4.8 Hz, 4H), 1.32 (d, J=6.6 Hz, 6H). LCMS (ESI, m/z): 436 [M+H]$^+$.

Example 189

2,5-Dioxopyrrolidin-1-yl 4-{[2-(dimethylcarbamoyl)-4-phenylphenyl]methyl}piperazine-1-carboxylate

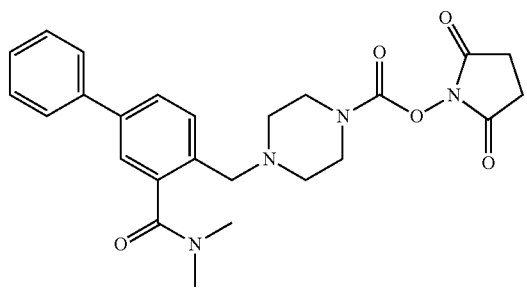 [SMILES: CN(C)C(=O)c1cc(-c2ccccc2)ccc1CN1CCN(C(=O)ON2C(=O)CCC2=O)CC1]

Step 1: Preparation of 5-bromo-2-formylbenzoic acid

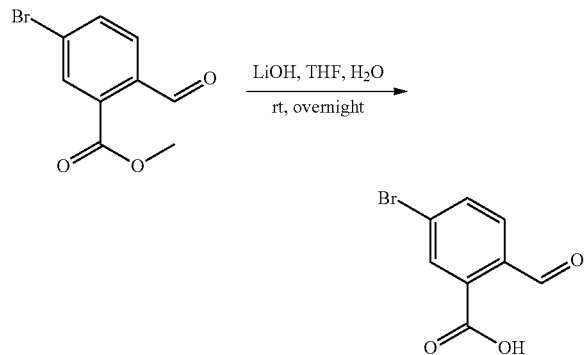

A 50-mL round-bottom flask was charged with methyl 5-bromo-2-formylbenzoate (1.00 g, 4.11 mmol, 1.00 equiv), lithium hydroxide (2.00 g, 83.5 mmol, 20.0 equiv), tetrahydrofuran (10 mL), and H$_2$O (10 mL). The resulting solution was stirred for 3 h at room temperature. The pH value of the solution was adjusted to 6 with hydrogen chloride solution (2 mol/L). The solids were collected by filtration to yield 0.700 g (crude) of 5-bromo-2-formylbenzoic acid as a light yellow solid. LCMS (ESI, m/z): 227 [M−H]$^-$.

Step 2: Preparation of 5-bromo-2-formyl-N,N-dimethylbenzamide

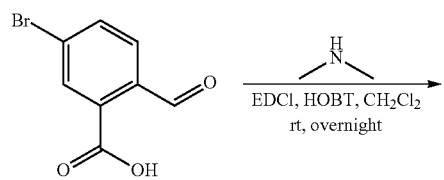

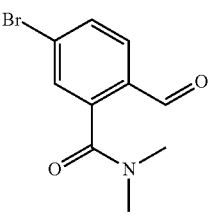

A 100-mL round-bottom flask was charged with 5-bromo-2-formylbenzoic acid (350 mg, 1.53 mmol, 1.00 equiv), N-(3-dimethylaminopropyl)-N'-ethylcarbodiimide hydrochloride (355 mg, 1.85 mmol, 1.20 equiv), 1-hydroxybenzotrizole (315 mg, 2.33 mmol, 1.50 equiv), and dichloromethane (10 mL). The resulting solution was stirred for 15 min at room temperature. Dimethylamine (208 mg, 4.61 mmol, 3.00 equiv) was added. The resulting solution was stirred overnight at room temperature, diluted with water (20 mL), extracted with dichloromethane (3×20 mL), and the organic layers were combined, dried over Na$_2$SO$_4$, filtered, and concentrated under reduced pressure. The residue was chromatographed on a silica gel column with ethyl acetate/petroleum ether (50/50) to provide 86.0 mg (22% yield) of 5-bromo-2-formyl-N,N-dimethylbenzamide as a light yellow oil. LCMS (ESI, m/z): 256 [M+H]$^+$.

Step 3: Preparation of tert-butyl 4-[[4-bromo-2-(dimethylcarbamoyl)phenyl]methyl]piperazine-1-carboxylate

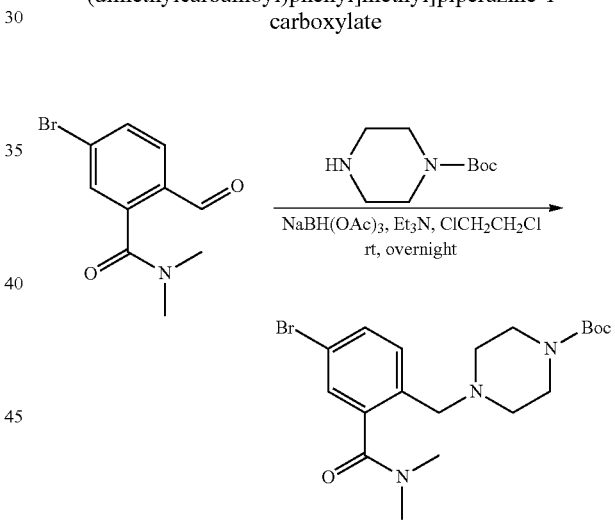

A 100-mL round-bottom flask was charged with tert-butyl piperazine-1-carboxylate (86.0 mg, 0.460 mmol, 1.00 equiv), 5-bromo-2-formyl-N,N-dimethylbenzamide (130 mg, 0.510 mmol, 1.10 equiv), and dichloromethane (10 mL). Triethylamine (139 mg, 1.37 mmol, 3.00 equiv) was added. The mixture was stirred for 30 min at room temperature. Sodium triacetoxyborohydride (293 mg, 1.38 mmol, 3.00 equiv) was added. The resulting solution was stirred overnight at room temperature, diluted with water (15 mL), and extracted with dichloromethane (3×15 mL), and the organic layers were combined, dried over Na$_2$SO$_4$, filtered, and concentrated under reduced pressure. The residue was chromatographed on a silia gel column with ethyl acetate/petroleum ether (50/50) to provide 170 mg (87% yield) of tert-butyl 4-[[4-bromo-2-(dimethylcarbamoyl)phenyl]methyl]piperazine-1-carboxylate as a light yellow oil. LCMS (ESI, m/z): 426 [M+H]$^+$.

Step 4: Preparation of tert-butyl 4-[[2-(dimethylcarbamoyl)-4-phenylphenyl]methyl]piperazine-1-carboxylate

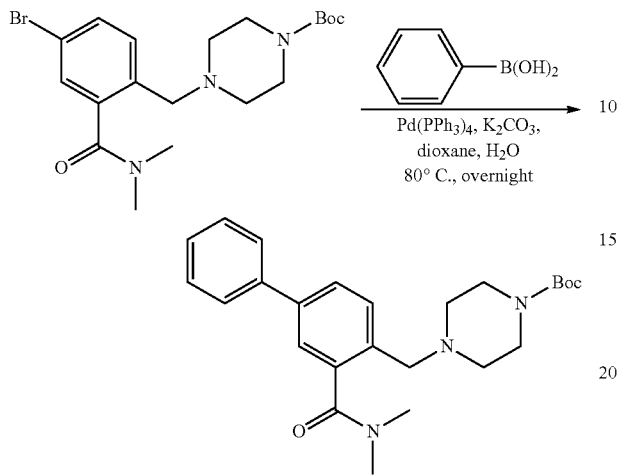

A 100-mL round-bottom flask was purged and maintained with an inert atmosphere of nitrogen, and was charged with tert-butyl 4-[[4-bromo-2-(dimethylcarbamoyl)phenyl]methyl]piperazine-1-carboxylate (130 mg, 0.300 mmol, 1.00 equiv), phenylboronic acid (113 mg, 0.930 mmol, 3.00 equiv), potassium carbonate (128 mg, 0.930 mmol, 3.00 equiv), tetrakis(triphenylphosphine)palladium (36.0 mg, 0.030 mmol, 0.10 equiv), and dioxane (4 mL), H$_2$O (0.4 mL). The resulting solution was stirred overnight at 80° C. and then concentrated under reduced pressure. The residue was chromatographed on a silia gel column with ethyl acetate/petroleum ether (25/75) to provide 100 mg (79% yield) of tert-butyl 4-[[2-(dimethylcarbamoyl)-4-phenylphenyl]methyl]piperazine-1-carboxylate as a light yellow oil. LCMS (ESI, m/z): 424 [M+H]$^+$.

Step 5: Preparation of N,N-dimethyl-5-phenyl-2-(piperazin-1-ylmethyl)benzamide

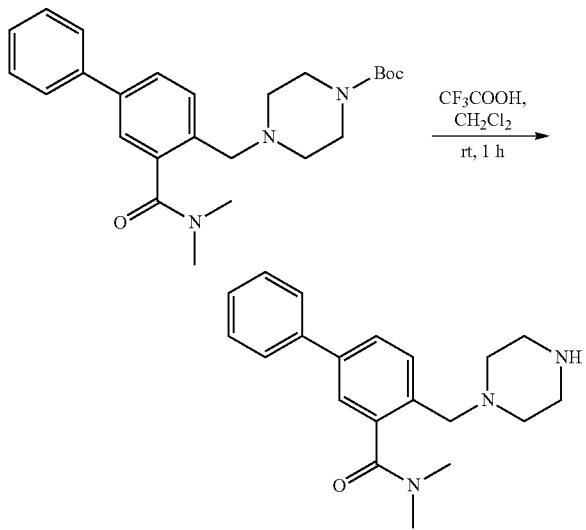

A 50-mL round-bottom flask was charged with tert-butyl 4-[[2-(dimethylcarbamoyl)-4-phenylphenyl]methyl]piperazine-1-carboxylate (300 mg, 0.710 mmol, 1.00 equiv), dichloromethane (5 mL), and trifluoroacetic acid (1 mL). The resulting solution was stirred for 1 h at room temperature, then concentrated under reduced pressure to yield 229 mg (crude) of N,N-dimethyl-5-phenyl-2-(piperazin-1-ylmethyl)benzamide as a light yellow oil. LCMS (ESI, m/z): 324 [M+H]$^+$.

Step 6: Preparation of 2,5-dioxopyrrolidin-1-yl 4-{[2-(dimethylcarbamoyl)-4-phenylphenyl]methyl}piperazine-1-carboxylate

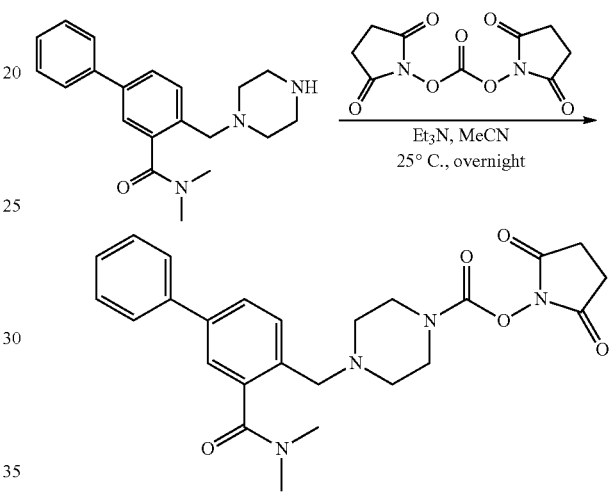

A 100-mL round-bottom flask was charged with N,N-dimethyl-5-phenyl-2-(piperazin-1-ylmethyl)benzamide (0.229 g, 0.710 mmol, 1.00 equiv), MeCN (5 mL), and bis(2,5-dioxopyrrolidin-1-yl) carbonate (1.09 g, 4.26 mmol, 6.00 equiv). Triethylamine (0.143 g, 1.41 mmol, 2.00 equiv) was added. The resulting solution was stirred overnight at room temperature and diluted with 5% citric acid solution (15 mL). The resulting solution was extracted with dichloromethane (3×10 mL), and the organic layers were combined, dried over anhydrous sodium sulfate, filtered, and concentrated under reduced pressure. The crude product (120 mg) was purified by preparative HPLC using the following gradient conditions: 20% CH$_3$CN/80% Phase A increasing to 80% CH$_3$CN over 10 min, then to 100% CH$_3$CN over 0.1 min, holding at 100% CH$_3$CN for 1.9 min, then reducing to 20% CH$_3$CN over 0.1 min, and holding at 20% for 1.9 min, on a Waters 2767-5 Chromatograph. Column: Xbridge Prep C$_{18}$, 19*150 mm, 5um; Mobile phase: Phase A: H$_2$O; Phase B: CH$_3$CN; Detector, UV 220 & 254 nm. Purification resulted in 51.6 mg (15% yield) of 2,5-dioxopyrrolidin-1-yl 4-{[2-(dimethylcarbamoyl)-4-phenylphenyl]methyl}piperazine-1-carboxylate as a white solid. $^1$H NMR (300 MHz, Chloroform-d) δ 7.54-7.61 (m, 3H), 7.43-7.47 (m, 5H), 3.50-3.93 (m, 6H), 3.15 (s, 3H), 2.90 (s, 3H), 2.62-2.83 (m, 4H), 2.54 (br, 4H). LCMS (ESI, m/z): 466 [M+H]$^+$.

Example 190

2,5-Dioxopyrrolidin-1-yl 4-{[3-chloro-2-(pyrrolidine-1-carbonyl)phenyl]methyl}piperazine-1-carboxylate Step 2: Preparation of tert-butyl 4-([3-chloro-2-[(pyrrolidin-1-yl)carbonyl]phenyl]methyl)piperazine-1-carboxylate

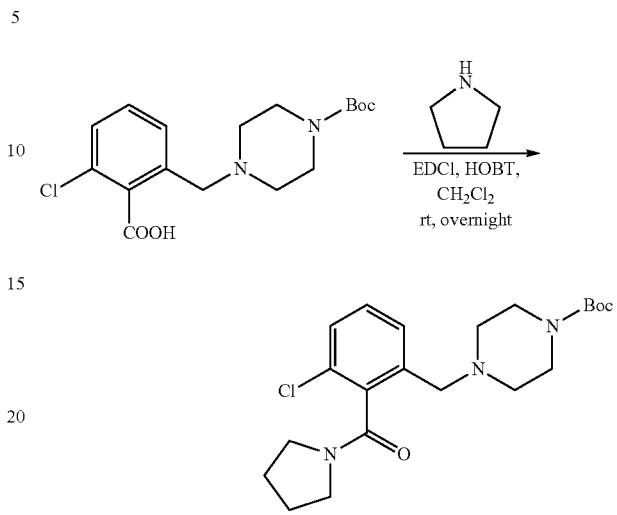

Step 1: Preparation of 2-((4-(tert-butoxycarbonyl)piperazin-1-yl)methyl)-6-chlorobenzoic acid

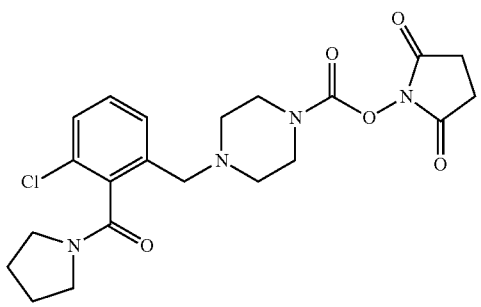 [SMILES: O=C(ON1C(=O)CCC1=O)N1CCN(Cc2cccc(Cl)c2C(=O)N2CCCC2)CC1]

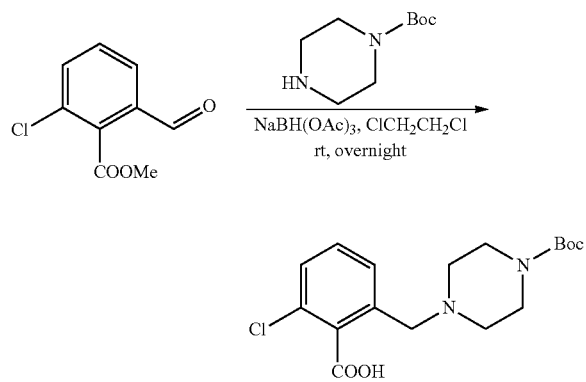

A 250-mL round-bottom flask was charged with methyl 2-chloro-6-formylbenzoate (2.00 g, 10.1 mmol, 1.00 equiv), tert-butyl piperazine-1-carboxylate (2.80 g, 15.0 mmol, 1.50 equiv), and 1,2-dichloroethane (80 mL). The mixture was stirred for 30 min at room temperature. Sodium triacetoxyborohydride (6.40 g, 30.2 mmol, 3.00 equiv) was added to the mixture, which was then diluted with H$_2$O (60 mL). The resulting mixture was extracted with dichloromethane (3×50 mL). The organic layers were combined, washed with brine (1×150 mL), dried over anhydrous sodium sulfate, filtered, and concentrated under reduced pressure. The residue was chromatographed on a silica gel column with methanol/dichloromethane (20/80) to provide 1.50 g (42% yield) of 2-((4-(tert-butoxycarbonyl)piperazin-1-yl)methyl)-6-chlorobenzoic acid as a yellow solid. $^1$H-NMR (300 MHz, DMSO-d$_6$) δ 7.34-7.40 (m, 3H), 3.53 (s, 2H), 3.30 (br, 4H), 2.30-2.34 (m, 4H), 1.39 (s, 9H). LCMS (ESI, m/z): 355 [M+H]$^+$.

A 100-mL round-bottom flask was charged with 2-((4-(tert-butoxycarbonyl)piperazin-1-yl)methyl)-6-chlorobenzoic acid (800 mg, 2.25 mmol, 1.00 equiv), pyrrolidine (321 mg, 4.51 mmol, 2.00 equiv), N-(3-dimethylaminopropyl)-N'-ethylcarbodiimide hydrochloride (651 mg, 3.40 mmol, 1.50 equiv), 1H-benzo[d][1,2,3]triazol-1-ol (458 mg, 3.39 mmol, 1.50 equiv), and dichloromethane (15 mL). The resulting solution was stirred overnight at room temperature and concentrated under reduced pressure. The residue was chromatographed on a silica gel column with ethyl acetate/petroleum ether (50/50) to provide 600 mg (65% yield) of tert-butyl 4-([3-chloro-2-[(pyrrolidin-1-yl)carbonyl]phenyl]methyl)piperazine-1-carboxylate as a yellow oil. LCMS (ESI, m/z): 408 [M+H]$^+$.

Step 3: Preparation of 1-([3-chloro-2-[(pyrrolidin-1-yl)carbonyl]phenyl]methyl)piperazine

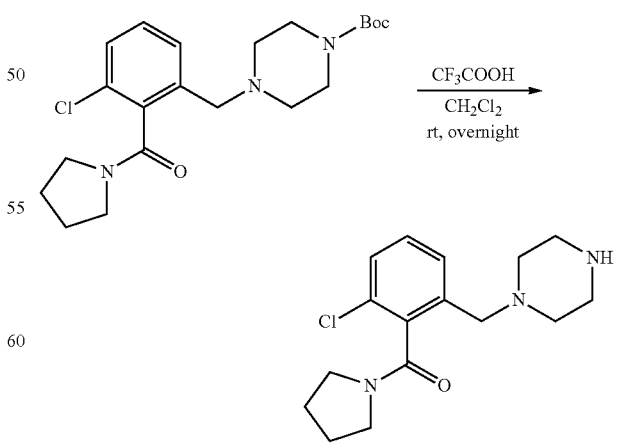

A 100-mL round-bottom flask was charged with tert-butyl 4-([3-chloro-2-[(pyrrolidin-1-yl)carbonyl]phenyl]methyl)

piperazine-1-carboxylate (600 mg, 1.47 mmol, 1.00 equiv) and dichloromethane (10 mL). Trifluoroacetic acid (2 mL) was added at 0° C. The resulting solution was stirred overnight at room temperature. The resulting mixture was concentrated under reduced pressure to yield 400 mg (88% yield) of 1-([3-chloro-2-[(pyrrolidin-1-yl)carbonyl]phenyl]methyl)piperazine as a yellow oil. LCMS (ESI, m/z): 308 [M+H]+.

Step 4: Preparation of 2,5-dioxopyrrolidin-1-yl 4-{[3-chloro-2-(pyrrolidine-1-carbonyl)phenyl]methyl}piperazine-1-carboxylate

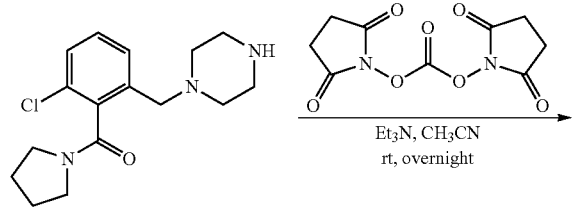

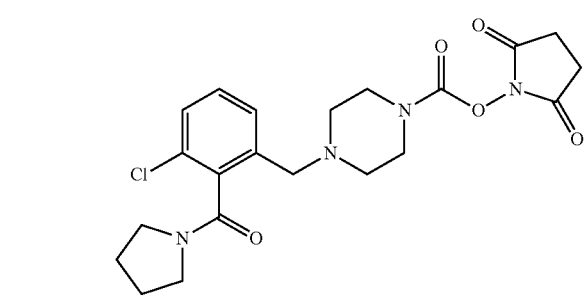

A 100-mL round-bottom flask was charged with 1-([3-chloro-2-[(pyrrolidin-1-yl)carbonyl]phenyl]methyl)piperazine (226 mg, 0.730 mmol, 1.00 equiv), bis(2,5-dioxopyrrolidin-1-yl) carbonate (283 mg, 1.10 mmol, 1.50 equiv), triethylamine (372 mg, 3.68 mmol, 5.00 equiv), and CH$_3$CN (15 mL). The resulting solution was stirred overnight at room temperature and concentrated under reduced pressure. The crude product (400 mg) was purified by preparative HPLC using the following gradient conditions: 20% CH$_3$CN/80% Phase A increasing to 70% CH$_3$CN over 10 min, then to 100% CH$_3$CN over 0.1 min, holding at 100% CH$_3$CN for 1.9 min, then reducing to 20% CH$_3$CN over 0.1 min, and holding at 20% for 1.9 min, on a Waters 2767-5 Chromatograph. Column: Xbridge Prep C$_{18}$, 19*150 mm, 5um; Mobile phase: Phase A: H$_2$O; Phase B: CH$_3$CN; Detector, UV 220 & 254 nm. Purification resulted in 218 mg (66% yield) of 2,5-dioxopyrrolidin-1-yl 4-{[3-chloro-2-(pyrrolidine-1-carbonyl)phenyl]methyl}piperazine-1-carboxylate as a yellow solid. $^1$H NMR (300 MHz, Chloroform-d) δ 7.23-7.33 (m, 3H), 3.71-3.78 (m, 2H), 3.48-3.69 (m, 5H), 3.24-3.35 (m, 2H), 3.03-3.11 (m, 1H), 2.82 (br, 4H), 2.52 (br, 4H), 1.94-2.05 (m, 4H). LCMS (ESI, m/z): 449 [M+H]+.

Example 191

2,5-Dioxopyrrolidin-1-yl 4-{[4-phenyl-2-(pyrrolidine-1-carbonyl)phenyl]methyl}piperazine-1-carboxylate

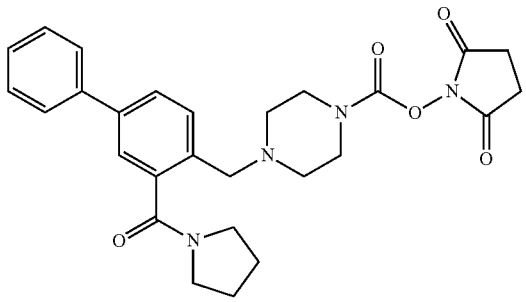 [SMILES: O=C(ON1C(=O)CCC1=O)N1CCN(Cc2ccc(-c3ccccc3)cc2C(=O)N2CCCC2)CC1]

The title compound was prepared directly from commercially available pyrrolidine and 5-bromo-2-formylbenzoic acid according to the representative procedure of Example 189, Steps 2, 3, 4, 5 and 6 to provide 2,5-dioxopyrrolidin-1-yl 4-{[4-phenyl-2-(pyrrolidine-1-carbonyl)phenyl]methyl}piperazine-1-carboxylate as a light yellow oil. $^1$H NMR (400 MHz, Chloroform-d) δ 8.05 (s, 2H), 7.60 (t, J=11.2 Hz, 3H), 7.42-7.52 (m, 3H), 4.45 (br, 2H), 3.90-3.99 (m, 4H), 3.72 (br, 2H), 3.35-3.55 (m, 6H), 2.85 (s, 4H), 1.95-2.05 (m, 4H). LCMS (ESI, m/z): 491 [M+H]+.

Example 192

2,5-Dioxopyrrolidin-1-yl 4-{[2-chloro-4-(morpholine-4-carbonyl)phenyl]methyl}piperazine-1-carboxylate

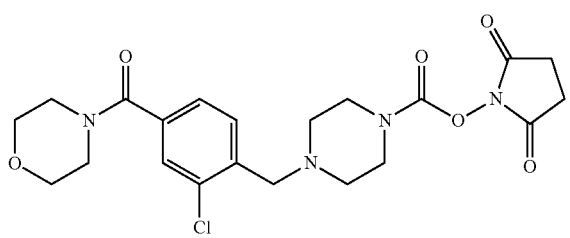 [SMILES: O=C(ON1C(=O)CCC1=O)N1CCN(Cc2ccc(C(=O)N3CCOCC3)cc2Cl)CC1]

Step 1: Preparation of tert-butyl 4-[[2-chloro-4-(methoxycarbonyl)phenyl]methyl]piperazine-1-carboxylate

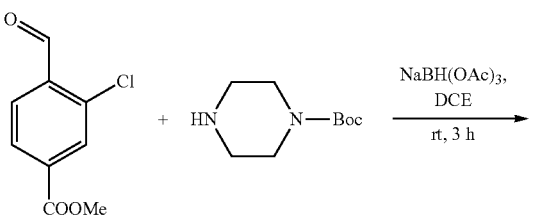

-continued

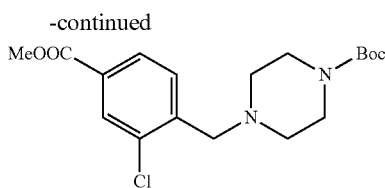

A 250-mL round-bottom flask was charged with methyl 3-chloro-4-formylbenzoate (2.00 g, 10.1 mmol, 1.00 equiv), tert-butyl piperazine-1-carboxylate (1.88 g, 10.1 mmol, 1.00 equiv), and 1,2-dichloroethane (50 mL). The resulting solution was stirred for 30 min at room temperature, and sodium triacetoxyborohydride (6.42 g, 30.3 mmol, 3.01 equiv) was added. The resulting solution was stirred for 3 h at room temperature and quenched by H$_2$O (15 mL). The resulting solution was extracted with dichloromethane (3×20 mL), and the organic layers were combined, washed with brine (20 mL), dried over anhydrous sodium sulfate, and concentrated under reduced pressure. The residue was chromatographed on a silica gel column with ethyl acetate/petroleum ether (18/82) to provide 3.54 g (95% yield) of tert-butyl 4-[[2-chloro-4-(methoxycarbonyl)phenyl]methyl]piperazine-1-carboxylate as a yellow oil. $^1$H NMR (300 MHz, Chloroform-d) δ 8.03 (s, 1H), 7.90-7.92 (m, 1H), 7.58-7.61 (m, 1H), 3.92 (s, 3H), 3.66 (br, 2H), 3.46 (br, 4H), 2.47 (br, 4H), 1.46 (s, 9H). LCMS (ESI, m/z): 369 [M+H]$^+$.

Step 2: Preparation of 4-([4-[(tert-butoxy)carbonyl]piperazin-1-yl]methyl)-3-chlorobenzoic acid

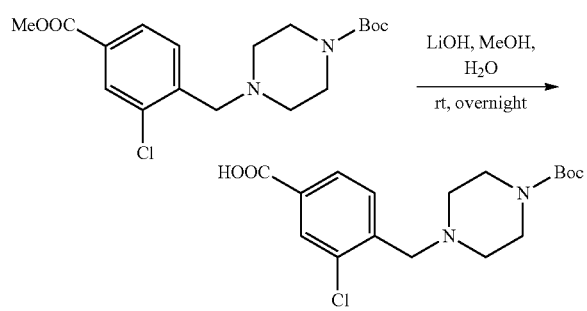

A 100-mL round-bottom flask was charged with tert-butyl 4-[[2-chloro-4-(methoxycarbonyl)phenyl]methyl]piperazine-1-carboxylate (3.54 g, 9.60 mmol, 1.00 equiv), methanol (20 mL), water (10 mL), and lithium hydroxide (690 mg, 28.8 mmol, 3.00 equiv). The resulting solution was stirred overnight at room temperature. The pH value of the solution was adjusted to 6 with hydrogen chloride solution (1 mol/L). The mixture was extracted with dichloromethane (3×20 mL) and the organic layers were combined, washed with brine (20 mL), dried over anhydrous sodium sulfate, and concentrated under reduced pressure to provide 2.90 g (crude) of 4-([4-[(tert-butoxy)carbonyl]piperazin-1-yl]methyl)-3-chlorobenzoic acid as a white solid. $^1$H NMR (300 MHz, Chloroform-d) δ 7.90-8.06 (m, 2H), 7.66 (d, J=9.0 Hz, 1H), 3.88 (br, 2H), 3.56 (br, 4H), 2.68 (br, 4H), 1.46 (s, 9H). LCMS (ESI, m/z): 369 [M+H]$^+$.

Step 3: Preparation of tert-butyl 4-([2-chloro-4-[(morpholin-4-yl)carbonyl]phenyl]methyl)piperazine-1-carboxylate

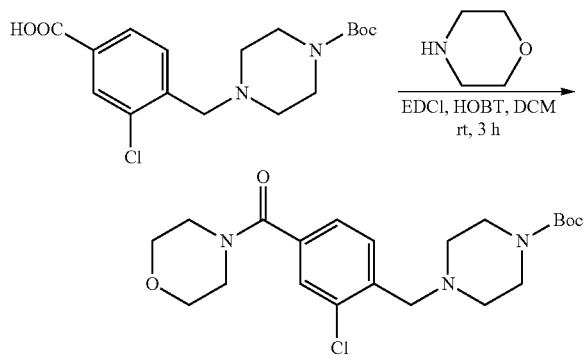

A 100-mL round-bottom flask was charged with 4-([4-[(tert-butoxy)carbonyl]piperazin-1-yl]methyl)-3-chlorobenzoic acid (600 mg, 1.69 mmol, 1.00 equiv), dichloromethane (15 mL), N-(3-dimethylaminopropyl)-N'-ethylcarbodiimide hydrochloride (487 mg, 2.54 mmol, 1.50 equiv), and 1-hydroxybenzotrizole (342 mg, 2.53 mmol, 1.50 equiv). The resulting solution was stirred for 30 min at room temperature, and morpholine (294 mg, 3.37 mmol, 2.00 equiv) was added. The resulting solution was stirred for 3 h at room temperature and diluted with H$_2$O (10 mL). The resulting solution was extracted with dichloromethane (3×15 mL), and the organic layers were combined, washed with brine (15 mL), dried over anhydrous sodium sulfate, and concentrated under reduced pressure. The residue was chromatographed on a silica gel column with ethyl acetate/petroleum ether (80/20) to provide 430 mg (60% yield) of tert-butyl 4-([2-chloro-4-[(morpholin-4-yl)carbonyl]phenyl]methyl)piperazine-1-carboxylate as a colorless oil. LCMS (ESI, m/z): 424 [M+H]$^+$.

Step 4: Preparation of 4-[[3-chloro-4-(piperazin-1-ylmethyl)phenyl]carbonyl]morpholine

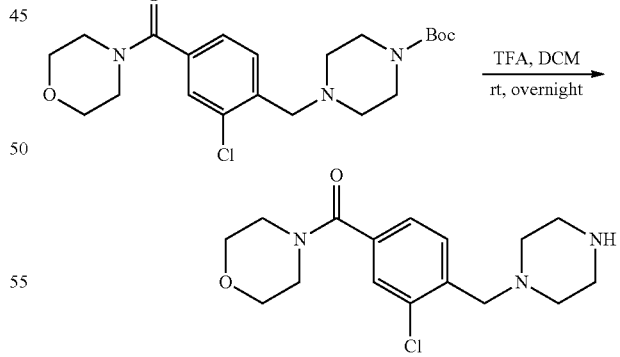

A 100-mL round-bottom flask was charged with tert-butyl 4-([2-chloro-4-[(morpholin-4-yl)carbonyl]phenyl]methyl)piperazine-1-carboxylate (168 mg, 0.400 mmol, 1.00 equiv), dichloromethane (6 mL), and trifluoroacetic acid (1.5 mL). The resulting solution was stirred for 3 h at room temperature and concentrated under reduced pressure to provide 300 mg (crude) of 4-[[3-chloro-4-(piperazin-1-ylmethyl)phenyl]carbonyl]morpholine as yellow oil. LCMS (ESI, m/z): 324 [M+H]$^+$.

Step 5: Preparation of 2,5-dioxopyrrolidin-1-yl 4-{[2-chloro-4-(morpholine-4-carbonyl)phenyl]methyl}piperazine-1-carboxylate

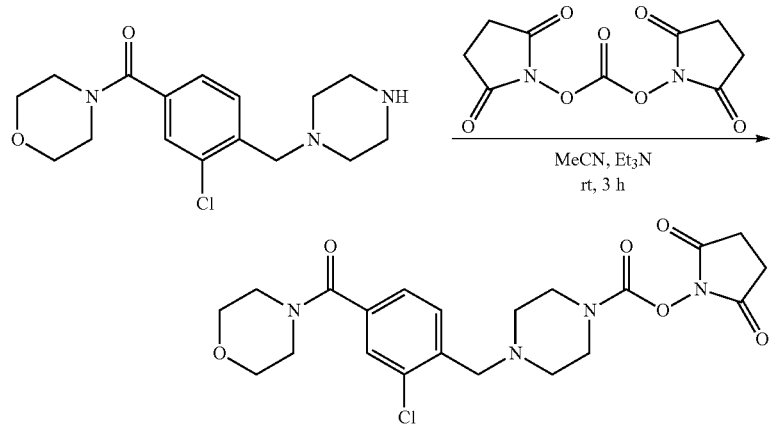

A 100-mL round-bottom flask was charged with 4-[[3-chloro-4-(piperazin-1-ylmethyl)phenyl]carbonyl]morpholine (128 mg, 0.400 mmol, 1.00 equiv), bis(2,5-dioxopyrrolidin-1-yl) carbonate (152 mg, 0.590 mmol, 1.50 equiv), acetonitrile (10 mL), and triethylamine (319 mg, 3.15 mmol, 7.98 equiv). The resulting solution was stirred for 3 h at room temperature and concentrated under reduced pressure. The crude product (150 mg) was purified by preparative HPLC using the following gradient conditions: 20% CH$_3$CN/80% Phase A increasing to 80% CH$_3$CN over 10 min, then to 100% CH$_3$CN over 0.1 min, holding at 100% CH$_3$CN for 1.9 min, then reducing to 20% CH$_3$CN over 0.1 min, and holding at 20% for 1.9 min, on a Waters 2767-5 Chromatograph. Column: Xbridge Prep C$_{18}$, 19*150 mm, 5 um; Mobile phase: Phase A: water; Phase B: CH$_3$CN; Detector, UV 220 & 254 nm. Purification resulted in 62.4 mg (34% yield) of 2,5-dioxopyrrolidin-1-yl 4-{[2-chloro-4-(morpholine-4-carbonyl)phenyl]methyl}piperazine-1-carboxylate as a colorless solid. $^1$H NMR (300 MHz, Chloroform-d) δ 7.52-7.54 (m, 1H), 7.44 (br, 1H), 7.29-7.31 (m, 1H), 3.56-3.68 (m, 14H), 2.83 (s, 4H), 2.59 (br, 4H). LCMS (ESI, m/z): 465 [M+H]$^+$.

Example 193

2,5-Dioxopyrrolidin-1-yl 4-{[2-chloro-4-(pyrrolidine-1-carbonyl)phenyl]methyl}piperazine-1-carboxylate

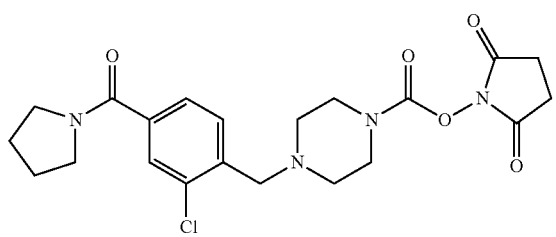 [SMILES: O=C(ON1C(=O)CCC1=O)N1CCN(Cc2ccc(C(=O)N3CCCC3)cc2Cl)CC1]

The title compound was prepared from pyrrolidine and 4-([4-[(tert-butoxy)carbonyl]piperazin-1-yl]methyl)-3-chlorobenzoic acid according to the representative procedure of Example 192, Steps, 3, 4 and 5. Purification as described in Example 192, Step 5, provided 2,5-dioxopyrrolidin-1-yl 4-{[2-chloro-4-(pyrrolidine-1-carbonyl)phenyl]methyl}piperazine-1-carboxylate as a white solid: $^1$H NMR (400 MHz, Chloroform-d) δ 7.51-7.54 (m, 2H), 7.40-7.42 (m, 1H), 3.56-3.68 (m, 8H), 3.42-3.46 (m, 2H), 2.83 (s, 4H), 2.59 (br, 4H), 1.86-2.01 (m, 4H). LCMS (ESI, m/z): 449 [M+H]$^+$.

Example 194

2,5-Dioxopyrrolidin-1-yl 4-{[4-(azetidine-1-carbonyl)-2-chlorophenyl]methyl}piperazine-1-carboxylate

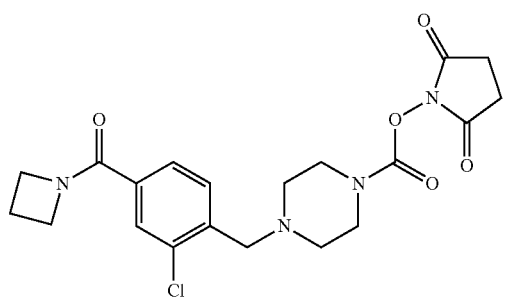 [SMILES: O=C(ON1C(=O)CCC1=O)N1CCN(Cc2ccc(C(=O)N3CCC3)cc2Cl)CC1]

The title compound was prepared from azetidine and 4-([4-[(tert-butoxy)carbonyl]piperazin-1-yl]methyl)-3-chlorobenzoic acid according to the representative procedure of Example 192, Steps, 3, 4 and 5. Purification as described in Example 192, Step 5, provided 2,5-dioxopyrrolidin-1-yl 4-{[4-(azetidine-1-carbonyl)-2-chlorophenyl]methyl}piperazine-1-carboxylate as a white solid. $^1$H NMR (300 MHz, Chloroform-d) δ 7.65 (br, 1H), 7.52 (br, 2H), 4.21-4.35 (m, 4H), 3.56-3.67 (m, 6H), 2.83 (s, 4H), 2.58 (br, 4H), 2.31-2.42 (m, 2H). LCMS (ESI, m/z): 435 [M+H]$^+$.

Example 195

2,5-Dioxopyrrolidin-1-yl 4-{[4-chloro-2-(morpholine-4-carbonyl)phenyl]methyl}piperazine-1-carboxylate

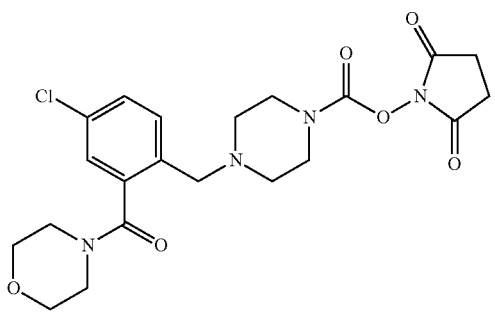 [SMILES: O=C(ON1C(=O)CCC1=O)N1CCN(Cc2ccc(Cl)cc2C(=O)N2CCOCC2)CC1]

Step 1: Preparation of methyl 5-chloro-2-formylbenzoate

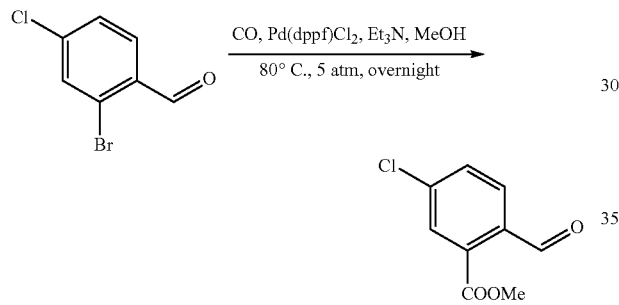

A 250-mL pressure tank reactor was charged with 2-bromo-4-chlorobenzaldehyde (20.0 g, 91.1 mmol, 1.00 equiv), methanol (120 mL), triethylamine (18.5 g, 183 mmol, 2.01 equiv), and Pd(dppf)Cl$_2$ (731 mg, 1.00 mmol, 0.01 equiv). To the above, CO (5 atm) was introduced. The resulting solution was stirred overnight at 80° C. and concentrated under reduced pressure. The residue was chromatographed on a silica gel column with ethyl acetate/petroleum ether (10/90) to provide 1.60 g (9% yield) of methyl 5-chloro-2-formylbenzoate as a yellow oil. $^1$H NMR (300 MHz, Chloroform-d) δ 10.47 (s, 1H), 7.78-7.88 (m, 2H), 7.50-7.52 (m, 1H), 3.90 (s, 3H). GCMS (EI, m/z): 198 M$^+$.

Step 2: Preparation of tert-butyl 4-[[4-chloro-2-(methoxycarbonyl)phenyl]methyl]piperazine-1-carboxylate

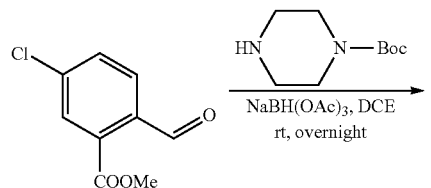

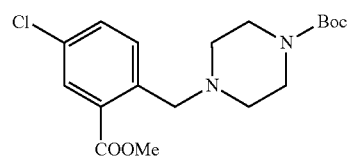

A 100-mL round-bottom flask was charged with methyl 5-chloro-2-formylbenzoate (1.58 g, 7.96 mmol, 1.00 equiv), tert-butyl piperazine-1-carboxylate (1.49 g, 8.01 mmol, 1.01 equiv), and 1,2-dichloroethane (20 mL). The resulting solution was stirred for 30 min at room temperature, and sodium triacetoxyborohydride (5.08 g, 24.0 mmol, 3.01 equiv) was added. The resulting solution was stirred overnight at room temperature and quenched by H$_2$O (15 mL). The resulting solution was extracted with dichloromethane (3×20 mL), and the organic layers were combined, washed with brine (20 mL), dried over anhydrous sodium sulfate, filtered, and concentrated under reduced pressure. The residue was chromatographed on a silica gel column with ethyl acetate/petroleum ether (15/85) to provide 1.50 g (51% yield) of tert-butyl 4-[[4-chloro-2-(methoxycarbonyl)phenyl]methyl]piperazine-1-carboxylate as a light yellow oil. $^1$H NMR (300 MHz, Chloroform-d) δ 8.14 (s, 1H), 7.41-7.44 (m, 1H), 7.15 (d, J=9.0 Hz, 1H), 3.81 (s, 3H), 3.50 (br, 4H), 2.68 (br, 4H), 2.09 (s, 2H), 1.46 (s, 9H). LCMS (ESI, m/z): 369 [M+H]$^+$.

Step 3: Preparation of 2-((4-(tert-butoxycarbonyl)piperazin-1-yl)methyl)-5-chlorobenzoic acid

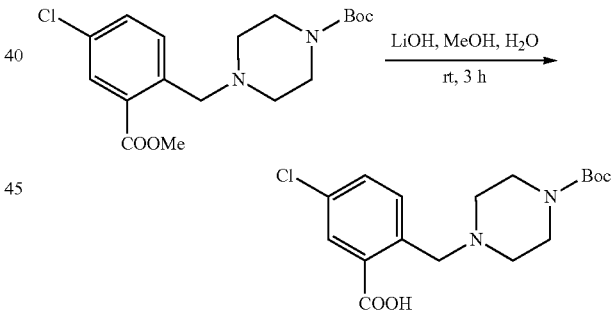

A 100-mL round-bottom flask was charged with tert-butyl 4-[[4-chloro-2-(methoxycarbonyl)phenyl]methyl]piperazine-1-carboxylate (720 mg, 1.95 mmol, 1.00 equiv), methanol (12 mL), water (6 mL), and lithium hydroxide (140 mg, 5.83 mmol, 3.00 equiv). The resulting solution was stirred for 3 h at room temperature. The pH value of the solution was adjusted to 6 with hydrogen chloride solution (1 mol/L). The resulting solution was extracted with dichloromethane (3×20 mL), and the organic layers were combined, washed with brine (10 mL), dried over anhydrous sodium sulfate, filtered, and concentrated under reduced pressure to provide 670 mg (crude) of 2-((4-(tert-butoxycarbonyl)piperazin-1-yl)methyl)-5-chlorobenzoic acid as a white solid. LCMS (ESI, m/z): 355 [M+H]$^+$.

Step 4: Preparation of tert-butyl 4-([4-chloro-2-[(morpholin-4-yl)carbonyl]phenyl]methyl)piperazine-1-carboxylate

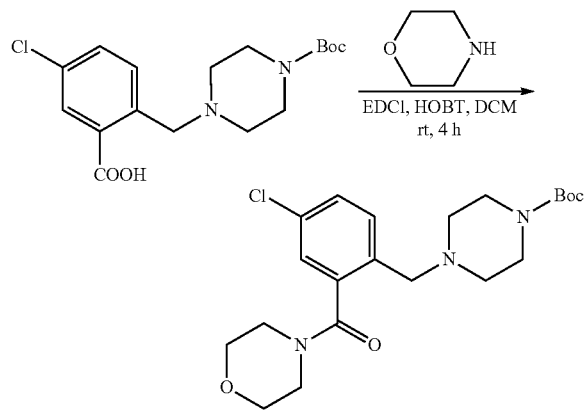

A 100-mL round-bottom flask was charged with 2-((4-(tert-butoxy carbonyl)piperazin-1-yl)methyl)-5-chlorobenzoic acid (500 mg, 1.41 mmol, 1.00 equiv), dichloromethane (15 mL), N-(3-dimethylaminopropyl)-N'-ethylcarbodiimide hydrochloride (406 mg, 2.12 mmol, 1.50 equiv), and 1-hydroxybenzotrizole (285 mg, 2.11 mmol, 1.50 equiv). The resulting solution was stirred for 1 h at room temperature, and morpholine (245 mg, 2.81 mmol, 2.00 equiv) was added. The resulting solution was stirred for 3 h at room temperature and diluted with $H_2O$ (10 mL). The resulting solution was extracted with dichloromethane (3×15 mL), and the organic layers were combined, washed with brine (15 mL), dried over anhydrous sodium sulfate, filtered, and concentrated under reduced pressure. The residue was chromatographed on a silica gel column with ethyl acetate/petroleum ether (52/48) to provide 230 mg (39% yield) of tert-butyl 4-([4-chloro-2-[(morpholin-4-yl)carbonyl]phenyl]methyl)piperazine-1-carboxylate as a white solid. $^1$H NMR (300 MHz, Chloroform-d) δ 7.29-7.34 (m, 2H), 7.20 (d, J=3.0 Hz, 1H), 3.61-3.82 (m, 7H), 3.20-3.41 (m, 7H), 2.38 (br, 4H), 1.47 (s, 9H). LCMS (ESI, m/z): 424 [M+H]$^+$.

Step 5: Preparation of (5-chloro-2-(piperazin-1-ylmethyl)phenyl)(morpholino)methanone

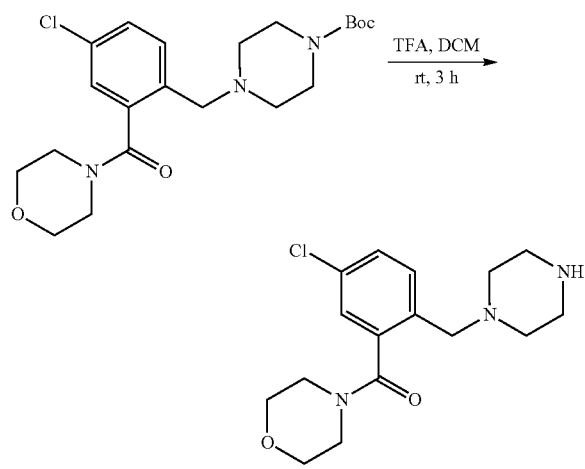

A 100-mL round-bottom flask was charged with tert-butyl 4-([4-chloro-2-[(morpholin-4-yl)carbonyl]phenyl]methyl) piperazine-1-carboxylate (230 mg, 0.540 mmol, 1.00 equiv), trifluoroacetic acid (1 mL), and dichloromethane (6 mL). The resulting solution was stirred for 3 h at room temperature and concentrated under reduced pressure to provide 400 mg (crude) of (5-chloro-2-(piperazin-1-ylmethyl)phenyl)(morpholino)methanone as a yellow oil. LCMS (ESI, m/z): 310 [M+H]$^+$.

Step 6: Preparation of 2,5-dioxopyrrolidin-1-yl 4-{[4-chloro-2-(morpholine-4-carbonyl)phenyl]methyl}piperazine-1-carboxylate

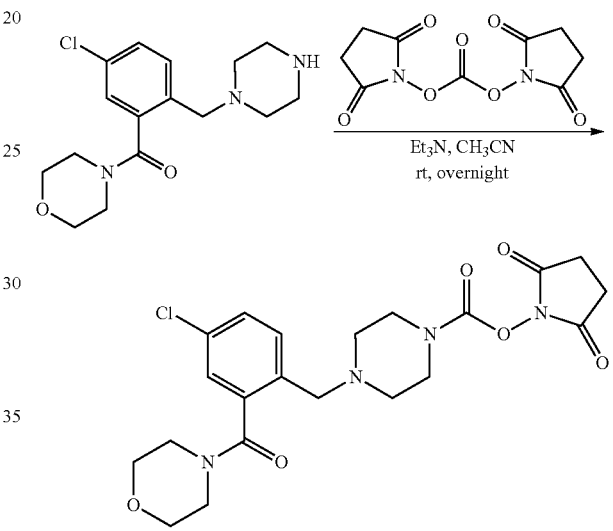

A 100-mL round-bottom flask was charged with (5-chloro-2-(piperazin-1-ylmethyl)phenyl)(morpholino) methanone (176 mg, 0.540 mmol, 1.00 equiv), bis(2,5-dioxopyrrolidin-1-yl) carbonate (209 mg, 0.820 mmol, 1.50 equiv), acetonitrile (10 mL), and triethylamine (439 mg, 4.34 mmol, 7.98 equiv). The resulting solution was stirred overnight at room temperature and concentrated under reduced pressure. The crude product (200 mg) was purified by preparative HPLC using the following gradient conditions: 20% $CH_3CN$/80% Phase A increasing to 80% $CH_3CN$ over 10 min, then to 100% $CH_3CN$ over 0.1 min, holding at 100% $CH_3CN$ for 1.9 min, then reducing to 20% $CH_3CN$ over 0.1 min, and holding at 20% for 1.9 min, on a Waters 2767-5 Chromatograph. Column: Xbridge Prep $C_{18}$, 19*150 mm, 5um; Mobile phase: Phase A: $H_2O$; Phase B: $CH_3CN$; Detector, UV 220 & 254 nm. Purification resulted in 74.0 mg (29% yield) of 2,5-dioxopyrrolidin-1-yl 4-{[4-chloro-2-(morpholine-4-carbonyl)phenyl]methyl}piperazine-1-carboxylate as a white solid. $^1$H NMR (300 MHz, Chloroform-d) δ 7.34 (br, 2H), 7.20 (s, 1H), 3.50-3.93 (m, 11H), 3.23-3.34 (m, 3H), 2.82 (s, 4H), 2.50 (br, 4H). LCMS (ESI, m/z): 451 [M+H]$^+$.

Example 196

2,5-Dioxopyrrolidin-1-yl 4-{[4-chloro-2-(pyrrolidine-1-carbonyl)phenyl]methyl}piperazine-1-carboxylate

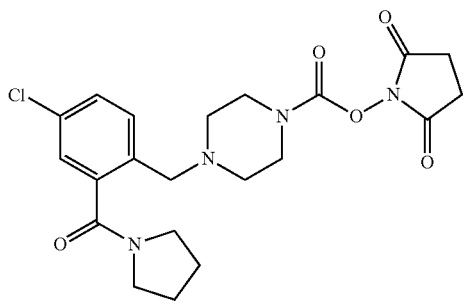 [SMILES: O=C(ON1C(=O)CCC1=O)N1CCN(Cc2ccc(Cl)cc2C(=O)N2CCCC2)CC1]

The title compound was prepared directly from commercially available pyrrolidine and 2-((4-(tert-butoxycarbonyl)piperazin-1-yl)methyl)-5-chlorobenzoic acid (Example 195, Step 3) according to the representative procedure of Example 195, Steps 4, 5 and 6 to provide 2,5-dioxopyrrolidin-1-yl 4-{[4-chloro-2-(pyrrolidine-1-carbonyl)phenyl]methyl}piperazine-1-carboxylate as a white solid. $^1$H NMR (300 MHz, Chloroform-d) δ 7.25-7.29 (m, 3H), 3.45-3.65 (m, 8H), 3.22 (t, J=7.5 Hz, 2H), 2.82 (s, 4H), 2.50 (br, 4H), 1.87-2.04 (m, 4H). LCMS (ESI, m/z): 449 [M+H]$^+$.

Example 197

2,5-Dioxopyrrolidin-1-yl 4-{[2-(azetidine-1-carbonyl)-4-chlorophenyl]methyl}piperazine-1-carboxylate

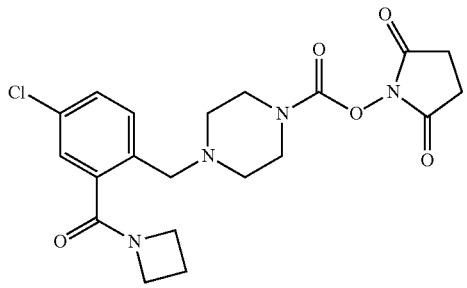 [SMILES: O=C(ON1C(=O)CCC1=O)N1CCN(Cc2ccc(Cl)cc2C(=O)N2CCC2)CC1]

The title compound was prepared directly from commercially available azetidine and 2-((4-(tert-butoxycarbonyl)piperazin-1-yl)methyl)-5-chlorobenzoic acid (Example 195, Step 3) according to the representative procedure of Example 195, Steps 4, 5 and 6 to provide 2,5-dioxopyrrolidin-1-yl 4-{[2-(azetidine-1-carbonyl)-4-chlorophenyl]methyl}piperazine-1-carboxylate as a white solid. $^1$H NMR (300 MHz, Chloroform-d) δ 7.29 (br, 2H), 7.25 (br, 1H), 4.18 (t, J=7.8 Hz, 2H), 3.92-3.96 (m, 2H), 3.50-3.64 (m, 6H), 2.82 (s, 4H), 2.53 (br, 4H), 2.32-2.38 (t, J=7.8 Hz, 2H). LCMS (ESI, m/z): 489 [M+H]$^+$.

Example 198

2,5-Dioxopyrrolidin-1-yl 4-{[3-chloro-2-(morpholine-4-carbonyl)phenyl]methyl}piperazine-1-carboxylate

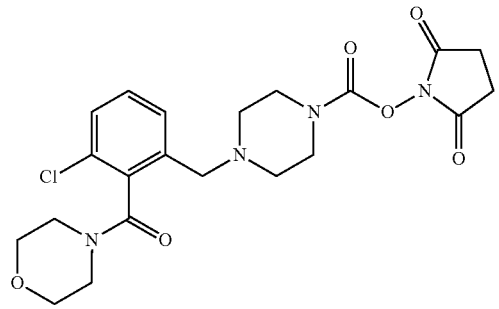 [SMILES: O=C(ON1C(=O)CCC1=O)N1CCN(Cc2cccc(Cl)c2C(=O)N2CCOCC2)CC1]

The title compound was prepared directly from commercially available morpholine and 2-bromo-3-chlorobenzaldehyde according to the representative procedure of Example 195, Steps 1, 2, 3, 4, 5 and 6 to provide 2,5-dioxopyrrolidin-1-yl 4-{[3-chloro-2-(morpholine-4-carbonyl)phenyl]methyl}piperazine-1-carboxylate as a yellow oil. $^1$H NMR (300 MHz, Chloroform-d) δ 7.28-7.38 (m, 3H), 4.04-4.11 (m, 1H), 3.52-3.87 (m, 10H), 3.34-3.38 (m, 1H), 3.14-3.27 (m, 2H), 2.82 (br, 4H), 2.52 (br, 4H). LCMS (ESI, m/z): 465 [M+H]$^+$.

Example 199

2,5-Dioxopyrrolidin-1-yl 4-{[5-chloro-2-(morpholine-4-carbonyl)phenyl]methyl}piperazine-1-carboxylate

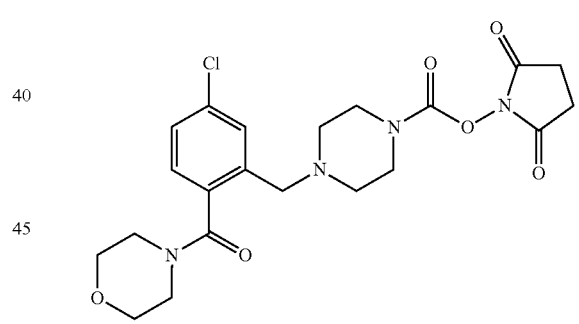

Step 1: Preparation of 5-chloro-2-(morpholine-4-carbonyl)benzaldehyde

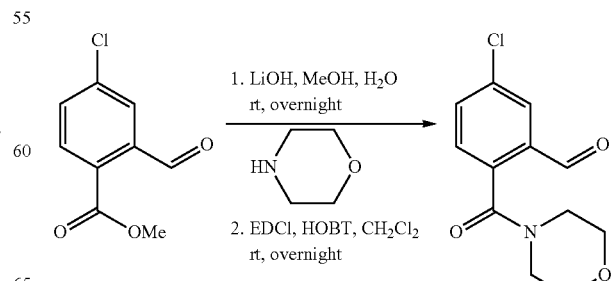

Part 1. A 100-mL round-bottom flask was charged with methyl 4-chloro-2-formylbenzoate (1.40 g, 7.05 mmol, 1.00 equiv), LiOH (339 mg, 14.15 mmol, 2.00 equiv), methanol (10 mL), and H$_2$O (1 mL). The resulting solution was stirred overnight at room temperature and adjusted to PH=4 with hydrogen chloride (1N). The solids were collected by filtration to provide 1.10 g (85% yield) of 4-chloro-2-formylbenzoic acid as a white solid. LCMS (ESI, m/z): 183 [M−H]$^-$.

Part 2. A 50-mL round-bottom flask was charged with 4-chloro-2-formylbenzoic acid (700 mg, 3.79 mmol, 1.00 equiv), N-(3-dimethylaminopropyl)-N'-ethylcarbodiimide hydrochloride (1.10 g, 5.74 mmol, 1.50 equiv), 1-hydroxybenzotrizole (770 mg, 5.70 mmol, 1.50 equiv), and dichloromethane (20 mL). The mixture was stirred for 20 min at room temperature. Morpholine (331 mg, 3.80 mmol, 1.00 equiv) was added. The resulting solution was stirred overnight at room temperature and concentrated under reduced pressure. The residue was chromatographed on a silica gel column with ethyl acetate/petroleum ether (30/70) to provide 250 mg (26% yield) of 5-chloro-2-(morpholine-4-carbonyl)benzaldehyde as a colorless oil. LCMS (ESI, m/z): 254 [M+H]$^+$.

Steps 2, 3 and 4: Preparation of 2,5-dioxopyrrolidin-1-yl 4-{[5-chloro-2-(morpholine-4-carbonyl)phenyl]methyl}piperazine-1-carboxylate

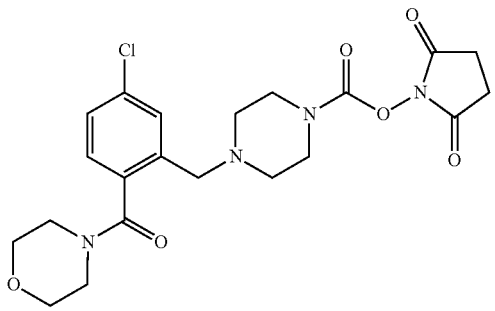 [SMILES: O=C(ON1C(=O)CCC1=O)N1CCN(Cc2cc(Cl)ccc2C(=O)N2CCOCC2)CC1]

The title compound was prepared from 5-chloro-2-(morpholine-4-carbonyl)benzaldehyde according to the representative procedure of Example 189, Steps 3, 5 and 6 to provide 2,5-dioxopyrrolidin-1-yl 4-{[5-chloro-2-(morpholine-4-carbonyl)phenyl]methyl}piperazine-1-carboxylate as a white solid. $^1$H NMR (300 MHz, Chloroform-d) δ 7.52 (s, 1H), 7.30-7.34 (m, 1H), 7.15 (d, J=8.1 Hz, 1H), 3.50-3.79 (m, 12H), 3.25 (br, 2H), 2.82 (br, 4H), 2.63 (br, 4H). LCMS (ESI, m/z): 465 [M+H]$^+$.

Example 200

2,5-Dioxopyrrolidin-1-yl 4-{[5-chloro-2-(pyrrolidine-1-carbonyl)phenyl]methyl}piperazine-1-carboxylate

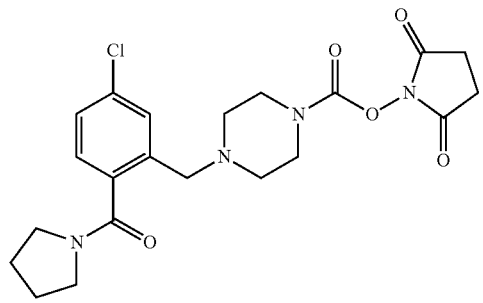 [SMILES: O=C(ON1C(=O)CCC1=O)N1CCN(Cc2cc(Cl)ccc2C(=O)N2CCCC2)CC1]

The title compound was prepared directly from commercially available pyrrolidine and methyl 4-chloro-2-formylbenzoate according to the representative procedure of Example 199, Steps 1, 2, 3 and 4 to provide 2,5-dioxopyrrolidin-1-yl 4-{[5-chloro-2-(pyrrolidine-1-carbonyl)phenyl]methyl}piperazine-1-carboxylate as a light yellow oil. $^1$H NMR (300 MHz, Chloroform-d) 67.38 (s, 1H), 7.29 (s, 1H), 7.18-7.21 (m, 1H), 3.46-3.64 (m, 8H), 3.17 (t, J=6.4 Hz, 2H), 2.82 (br, 4H), 2.52 (br, 4H), 1.85-2.04 (m, 4H). LCMS (ESI, m/z): 449 [M+H]$^+$.

Example 201

2,5-Dioxopyrrolidin-1-yl 4-{[5-methyl-2-(morpholine-4-carbonyl)phenyl]methyl}piperazine-1-carboxylate

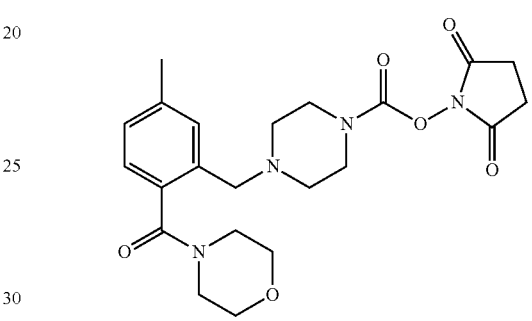

Step 1: Preparation of tert-butyl 4-[[2-(methoxycarbonyl)-5-methylphenyl]methyl]piperazine-1-carboxylate

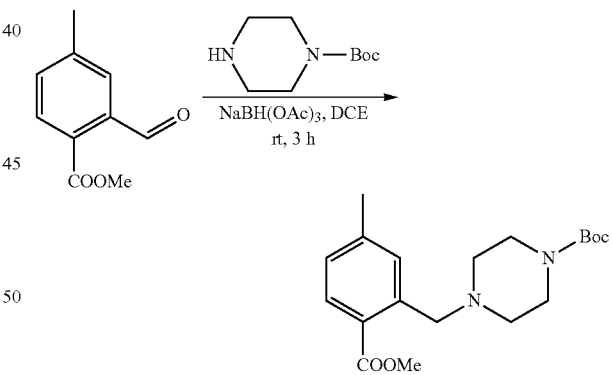

A 100-mL round-bottom flask was charged with methyl 2-formyl-4-methylbenzoate (300 mg, 1.68 mmol, 1.00 equiv), tert-butyl piperazine-1-carboxylate (300 mg, 1.61 mmol, 0.96 equiv), and 1,2-dichloroethane (15 mL). The resulting solution was stirred for 30 min at room temperature, and sodium triacetoxyborohydride (1.07 g, 5.05 mmol, 3.00 equiv) was added. The resulting solution was stirred for 3 h at room temperature and quenched by H$_2$O (10 mL). The resulting solution was extracted with dichloromethane (3×15 mL), and the organic layers were combined, washed with brine (15 mL), dried over anhydrous sodium sulfate, filtered, and concentrated under reduced pressure. The residue was chromatographed on a silica gel column with ethyl acetate/petroleum ether (19/81) to provide 500 mg (85% yield) of tert-butyl 4-[[2-(methoxycarbonyl)-5-methylphenyl]methyl]piperazine-1-carboxylate as a yellow oil. LCMS (ESI, m/z): 349 [M+H]+.

Step 2: Preparation of 2-((4-(tert-butoxycarbonyl)piperazin-1-yl)methyl)-4-methylbenzoic acid

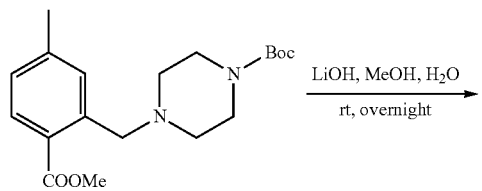

A 100-mL round-bottom flask was charged with tert-butyl 4-[[2-(methoxycarbonyl)-5-methylphenyl]methyl]piperazine-1-carboxylate (500 mg, 1.43 mmol, 1.00 equiv), methanol (6 mL), water (3 mL), and lithium hydroxide (172 mg, 7.18 mmol, 5.01 equiv). The resulting solution was stirred overnight at room temperature. The pH value of the solution was adjusted to 5 with hydrogen chloride solution (1 mol/L). The resulting mixture was concentrated under reduced pressure and extracted with dichloromethane (3×15 mL), and the organic layers were combined, dried over anhydrous sodium sulfate, filtered, and concentrated under reduced pressure to provide 450 mg (94% yield) of 2-((4-(tert-butoxycarbonyl)piperazin-1-yl)methyl)-4-methylbenzoic acid as a light yellow solid. LCMS (ESI, m/z): 335 [M+H]+.

Step 3: Preparation of tert-butyl 4-([5-methyl-2-[(morpholin-4-yl)carbonyl]phenyl]methyl)piperazine-1-carboxylate

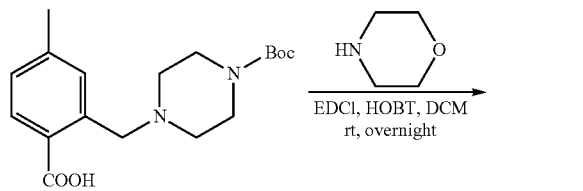

A 100-mL round-bottom flask was charged with 2-((4-(tert-butoxy carbonyl)piperazin-1-yl)methyl)-4-methylbenzoic acid (450 mg, 1.35 mmol, 1.00 equiv), dichloromethane (15 mL), N-(3-dimethylaminopropyl)-N'-ethylcarbodiimide hydrochloride (388 mg, 2.02 mmol, 1.50 equiv), and 1-hydroxybenzotrizole (273 mg, 2.02 mmol, 1.50 equiv). The resulting solution was stirred for 30 min at room temperature, and morpholine (234 mg, 2.69 mmol, 2.00 equiv) was added. The resulting solution was stirred overnight at room temperature and concentrated under reduced pressure. The residue was chromatographed on a silica gel column with ethyl acetate/petroleum ether (50/50) to provide 420 mg (77% yield) of tert-butyl 4-([5-methyl-2-[(morpholin-4-yl)carbonyl]phenyl]methyl)piperazine-1-carboxylate as a yellow oil. LCMS (ESI, m/z): 404 [M+H]+.

Step 4: Preparation of (4-methyl-2-(piperazin-1-ylmethyl)phenyl)(morpholino)methanone

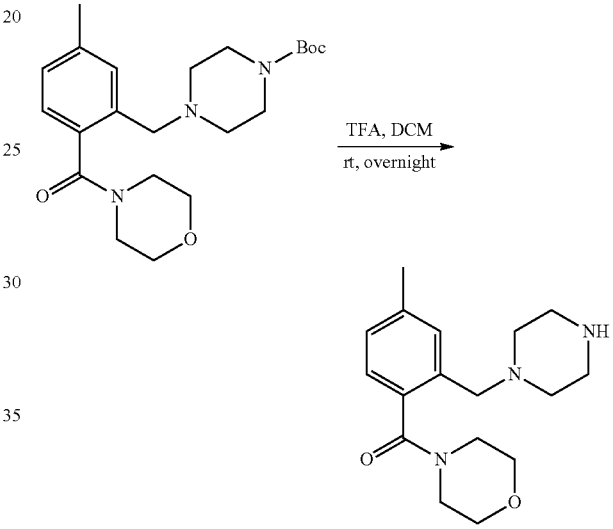

A 100-mL round-bottom flask was charged with tert-butyl 4-([5-methyl-2-[(morpholin-4-yl)carbonyl]phenyl]methyl)piperazine-1-carboxylate (420 mg, 1.04 mmol, 1.00 equiv) and dichloromethane (7.5 mL). Trifluoroacetic acid (1.5 mL) was added dropwise at 0° C. The resulting solution was stirred overnight at room temperature and concentrated under reduced pressure to provide 480 mg (crude) of (4-methyl-2-(piperazin-1-ylmethyl)phenyl)(morpholino)methanone as a yellow oil. LCMS (ESI, m/z): 304 [M+H]+.

Step 5: Preparation of 2,5-dioxopyrrolidin-1-yl 4-{[5-methyl-2-(morpholine-4-carbonyl)phenyl]methyl}piperazine-1-carboxylate

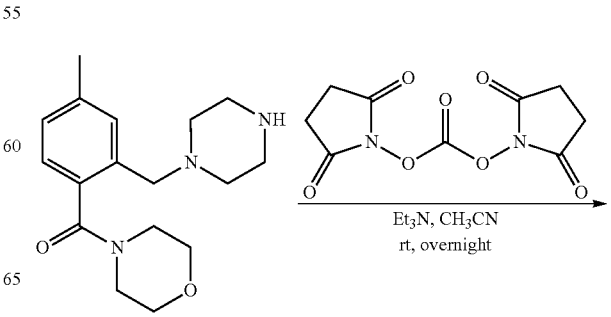

-continued

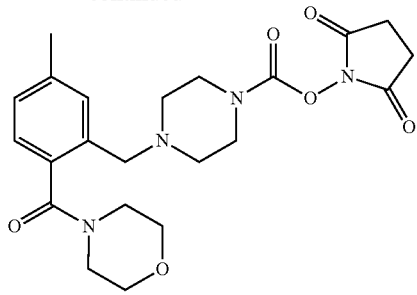

A 100-mL round-bottom flask was charged with (4-methyl-2-(piperazin-1-ylmethyl)phenyl)(morpholino) methanone (158 mg, 0.520 mmol, 1.00 equiv), bis(2,5-dioxopyrrolidin-1-yl) carbonate (200 mg, 0.780 mmol, 1.50 equiv), acetonitrile (10 mL), and triethylamine (421 mg, 4.16 mmol, 7.99 equiv). The resulting solution was stirred for 2 h at room temperature and concentrated under reduced pressure. The crude product (190 mg) was purified by preparative HPLC using the following gradient conditions: 20% CH$_3$CN/80% Phase A increasing to 80% CH$_3$CN over 10 min, then to 100% CH$_3$CN over 0.1 min, holding at 100% CH$_3$CN for 1.9 min, then reducing to 20% CH$_3$CN over 0.1 min, and holding at 20% for 1.9 min, on a Waters 2767-5 Chromatograph. Column: Xbridge Prep C$_{18}$, 19*150 mm, 5 um; Mobile phase: Phase A: H$_2$O; Phase B: CH$_3$CN; Detector, UV 220 & 254 nm. Purification resulted in 129 mg (56% yield) of 2,5-dioxopyrrolidin-1-yl 4-{[5-methyl-2-(morpholine-4-carbonyl)phenyl]methyl}piperazine-1-carboxylate as a white solid. $^1$H NMR (300 MHz, Chloroform-d) δ 7.19 (s, 1H), 7.09 (s, 2H), 3.61-3.94 (m, 9H), 3.24-3.50 (m, 5H), 2.82 (s, 4H), 2.50 (br, 4H), 3.20 (s, 3H). LCMS (ESI, m/z): 445 [M+H]$^+$.

Example 202

2,5-Dioxopyrrolidin-1-yl 4-{[5-methyl-2-(pyrrolidine-1-carbonyl)phenyl]methyl}piperazine-1-carboxylate

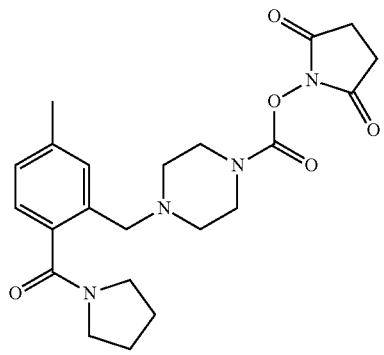 [SMILES: Cc1ccc(C(=O)N2CCCC2)c(CN2CCN(C(=O)ON3C(=O)CCC3=O)CC2)c1]

The title compound was prepared directly from commercially available pyrrolidine and 2-((4-(tert-butoxycarbonyl) piperazin-1-yl)methyl)-4-methylbenzoic acid (Example 201, Steps 1 and 2) according to the representative procedure of Example 201, Steps 3, 4 and 5 to provide 2,5-dioxopyrrolidin-1-yl 4-{[5-methyl-2-(pyrrolidine-1-carbo-nyl)phenyl]methyl}piperazine-1-carboxylate as a white solid. $^1$H NMR (300 MHz, Chloroform-d) δ 7.07-7.16 (m, 3H), 3.45-3.64 (m, 8H), 3.20 (t, J=7.5 Hz, 2H), 2.82 (s, 4H), 2.50 (br, 4H), 2.35 (s, 3H), 1.83-2.03 (m, 4H). LCMS (ESI, m/z): 429 [M+H]$^+$.

Example 203

2,5-Dioxopyrrolidin-1-yl 4-{[2-(morpholine-4-carbonyl)-5-(trifluoromethyl)phenyl]methyl}piperazine-1-carboxylate

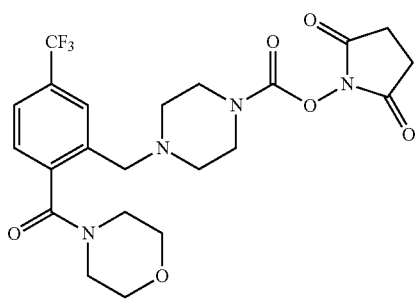 [SMILES: O=C(ON1C(=O)CCC1=O)N1CCN(Cc2cc(C(F)(F)F)ccc2C(=O)N2CCOCC2)CC1]

The title compound was prepared directly from commercially available methyl 2-formyl-4-(trifluoromethyl)benzoate according to the representative procedure of Example 201, Steps 1, 2, 3, 4 and 5 to provide 2,5-dioxopyrrolidin-1-yl 4-{[2-(morpholine-4-carbonyl)-5-(trifluoromethyl)phenyl]methyl}piperazine-1-carboxylate as a white solid. $^1$H NMR (300 MHz, chloroform-d) 7.71 (s, 1H), 7.59 (d, J=8.1 Hz, 1H), 7.33 (d, J=7.8 Hz, 1H), 3.41-4.00 (m, 12H), 3.21-3.26 (m, 2H), 2.82 (s, 4H), 2.54 (br, 4H). LCMS (ESI, m/z): 499 [M+H]$^+$.

Example 204

2,5-Dioxopyrrolidin-1-yl 4-{[2-(pyrrolidine-1-carbonyl)-5-(trifluoromethyl)phenyl]methyl}piperazine-1-carboxylate

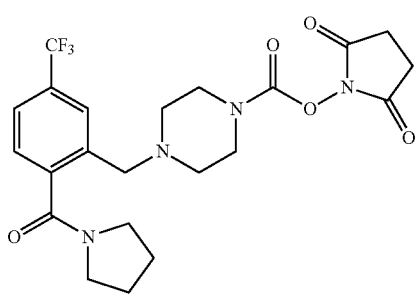 [SMILES: O=C(ON1C(=O)CCC1=O)N1CCN(Cc2cc(C(F)(F)F)ccc2C(=O)N2CCCC2)CC1]

The title compound was prepared directly from commercially available methyl 2-formyl-4-(trifluoromethyl)benzoate and pyrrolidine according to the representative procedure of Example 201, Steps 1, 2, 3, 4 and 5 to provide 2,5-dioxopyrrolidin-1-yl 4-{[2-(pyrrolidine-1-carbonyl)-5-(trifluoromethyl)phenyl]methyl}piperazine-1-carboxylate as a white solid. ¹H NMR (300 MHz, chloroform-d) δ 7.56-7.64 (m, 2H), 7.38 (d, J=7.8 Hz, 1H), 3.48-3.67 (m, 8H), 3.18 (t, J=6.6 Hz, 2H), 2.82 (s, 4H), 2.53 (br, 4H), 1.87-2.06 (m, 4H). LCMS (ESI, m/z): 483 [M+H]⁺.

Example 205

2,5-Dioxopyrrolidin-1-yl 4-{[2-methyl-3-(morpholine-4-carbonyl)phenyl]methyl}piperazine-1-carboxylate

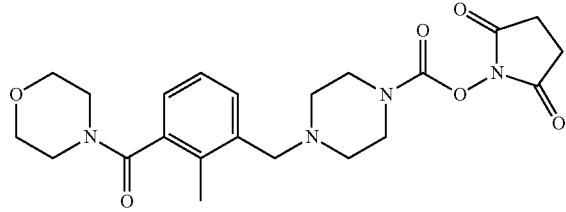 [SMILES: Cc1c(CN2CCN(C(=O)ON3C(=O)CCC3=O)CC2)cccc1C(=O)N1CCOCC1]

The title compound was prepared directly from commercially available methyl 3-formyl-2-methylbenzoate according to the representative procedure of Example 201, Steps 1, 2, 3, 4 and 5 to provide 2,5-dioxopyrrolidin-1-yl 4-{[2-methyl-3-(morpholine-4-carbonyl)phenyl]methyl}piperazine-1-carboxylate as a white solid. ¹H NMR (300 MHz, Chloroform-d) δ 7.27-7.31 (m, 1H), 7.19 (t, J=7.5 Hz, 1H), 7.09 (d, J=7.5 Hz, 1H), 3.78-3.89 (m, 4H), 3.43-3.62 (m, 8H), 3.21-3.26 (m 2H), 2.81 (s, 4H), 2.51 (br, 4H), 2.31 (s, 3H). LCMS (ESI, m/z): 445 [M+H]⁺.

Example 206

2,5-Dioxopyrrolidin-1-yl 4-{[2-methyl-3-(pyrrolidine-1-carbonyl)phenyl]methyl}piperazine-1-carboxylate

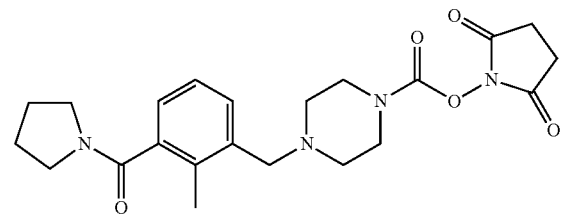 [SMILES: Cc1c(CN2CCN(C(=O)ON3C(=O)CCC3=O)CC2)cccc1C(=O)N1CCCC1]

The title compound was prepared directly from commercially available methyl 3-formyl-2-methylbenzoate and pyrrolidine according to the representative procedure of Example 201, Steps 1, 2, 3, 4 and 5 to provide 2,5-dioxopyrrolidin-1-yl 4-{[2-methyl-3-(pyrrolidine-1-carbonyl)phenyl]methyl}piperazine-1-carboxylate as a white solid. ¹H NMR (300 MHz, Chloroform-d) δ 7.15-7.26 (m, 3H), 3.51-3.70 (m, 8H), 3.10 (t, J=6.6 Hz, 2H), 2.82 (s, 4H), 2.51 (br, 4H), 2.32 (s, 3H), 1.83-2.02 (m, 4H). LCMS (ESI, m/z): 429 [M+H]⁺.

Example 207

2,5-Dioxopyrrolidin-1-yl 4-{[3-(azetidine-1-carbonyl)-2-methylphenyl]methyl}piperazine-1-carboxylate

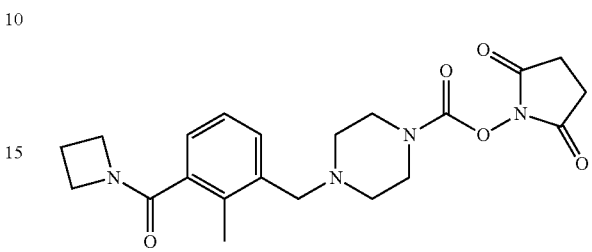

The title compound was prepared directly from commercially available methyl 3-formyl-2-methylbenzoate and azetidine according to the representative procedure of Example 201, Steps 1, 2, 3, 4 and 5 to provide 2,5-dioxopyrrolidin-1-yl 4-{[3-(azetidine-1-carbonyl)-2-methylphenyl]methyl}piperazine-1-carboxylate as a yellow solid. ¹H NMR (300 MHz, Chloroform-d) δ 7.34 (s, 1H), 7.27 (t, J=4.5 Hz, 1H), 7.15-7.19 (m, 1H), 4.21 (t, J=7.8 Hz, 2H), 3.88 (t, J=7.6 Hz, 2H), 3.51-3.62 (m, 6H), 2.81 (s, 4H), 2.59-2.68 (m, 4H), 2.50-2.52 (m, 3H), 2.25-2.42 (m, 2H). LCMS (ESI, m/z): 415 [M+H]⁺.

Example 208

2,5-Dioxopyrrolidin-1-yl 4-{[3-methyl-5-(morpholine-4-carbonyl)phenyl]methyl}piperazine-1-carboxylate

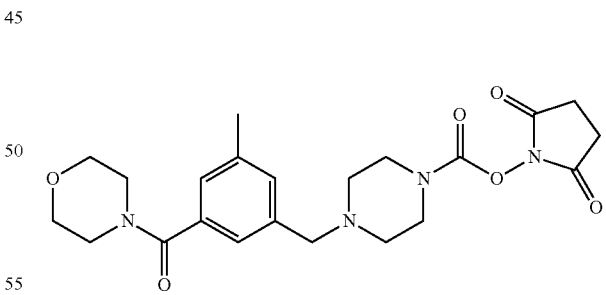

The title compound was prepared directly from commercially available methyl 3-formyl-5-methylbenzoate according to the representative procedure of Example 201, Steps 1, 2, 3, 4 and 5 to provide 2,5-dioxopyrrolidin-1-yl 4-{[3-methyl-5-(morpholine-4-carbonyl)phenyl]methyl}piperazine-1-carboxylate as a white solid. ¹H NMR (300 MHz, Chloroform-d) δ 7.20 (s, 1H), 7.14 (d, J=3.6 Hz, 2H), 3.53-3.66 (m, 14H), 2.82 (s, 4H), 2.58-2.68 (m, 4H), 2.37 (s, 3H). LCMS (ESI, m/z): 445 [M+H]⁺.

Example 209

2,5-Dioxopyrrolidin-1-yl 4-{[4-chloro-3-(morpholine-4-carbonyl)phenyl]methyl}piperazine-1-carboxylate

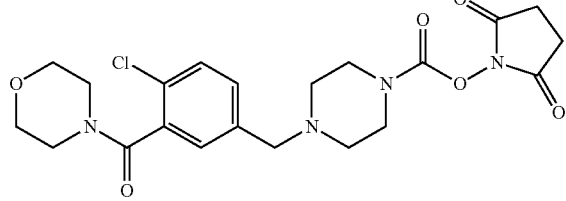

The title compound was prepared directly from commercially available methyl 2-chloro-5-formylbenzoate according to the representative procedure of Example 201, Steps 1, 2, 3, 4 and 5 to provide 2,5-dioxopyrrolidin-1-yl 4-{[4-chloro-3-(morpholine-4-carbonyl)phenyl]methyl}piperazine-1-carboxylate as a white solid. $^1$H NMR (300 MHz, Chloroform-d) δ 7.31-7.38 (m, 3H), 3.89-3.95 (m, 1H), 3.53-3.81 (m, 11H), 3.17-3.34 (m, 2H), 2.82 (s, 4H), 2.50 (br, 4H). LCMS (ESI, m/z): 465 [M+H]$^+$.

Example 210

2,5-Dioxopyrrolidin-1-yl 4-{[3-(azetidine-1-carbonyl)-4-chlorophenyl]methyl}piperazine-1-carboxylate

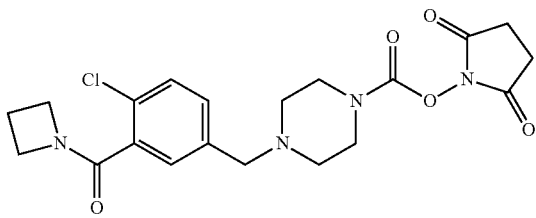 [SMILES: O=C(ON1C(=O)CCC1=O)N1CCN(Cc2ccc(Cl)c(C(=O)N3CCC3)c2)CC1]

The title compound was prepared directly from commercially available methyl 2-chloro-5-formylbenzoate and azetidine according to the representative procedure of Example 201, Steps 1, 2, 3, 4 and 5 to provide 2,5-dioxopyrrolidin-1-yl 4-{[3-(azetidine-1-carbonyl)-4-chlorophenyl]methyl}piperazine-1-carboxylate as an off-white solid. $^1$H NMR (300 MHz, Chloroform-d) δ 7.28-7.37 (m, 3H), 4.23 (t, J=3.9 Hz, 2H), 3.98 (t, J=3.9 Hz, 2H), 3.52-3.64 (m, 6H), 2.82 (s, 4H), 2.58-2.68 (m, 4H), 2.29-2.52 (m, 2H). LCMS (ESI, m/z): 435 [M+H]$^+$.

Example 211

2,5-Dioxopyrrolidin-1-yl 4-(3-chlorobenzoyl)piperazine-1-carboxylate

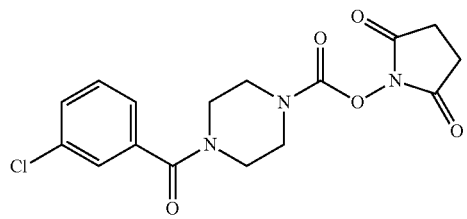 [SMILES: O=C(ON1C(=O)CCC1=O)N1CCN(C(=O)c2cccc(Cl)c2)CC1]

Step 1: Preparation of tert-butyl 4-[(3-chlorophenyl)carbonyl]piperazine-1-carboxylate

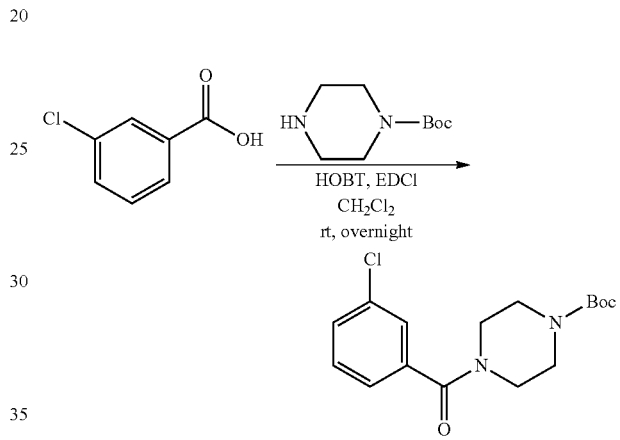

A 100-mL round-bottom flask was charged with 3-chlorobenzoic acid (600 mg, 3.83 mmol, 1.00 equiv), dichloromethane (20 mL), N-(3-dimethylaminopropyl)-N'-ethylcarbodiimide hydrochloride (1.11 g, 5.79 mmol, 1.51 equiv), and 1-hydroxybenzotrizole (780 mg, 5.77 mmol, 1.51 equiv). The mixture was stirred for 1 h at room temperature, and then tert-butyl piperazine-1-carboxylate (1.43 g, 7.68 mmol, 2.00 equiv) was added. The resulting solution was stirred overnight at room temperature and diluted with water (50 mL). The resulting mixture was extracted with dichloromethane (2×100 mL), and the organic layers were combined, dried over anhydrous sodium sulfate, filtered, and concentrated under reduced pressure. The residue was chromatographed on a silica gel column with ethyl acetate/petroleum ether (1/5) to provide 900 mg (89% yield) of tert-butyl 4-[(3-chlorophenyl)carbonyl]piperazine-1-carboxylate as a yellow oil. LCMS (ESI, m/z): 325 [M+H]$^+$.

Step 2: Preparation of 1-[(3-chlorophenyl)carbonyl]piperazine

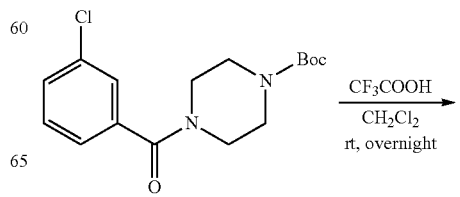

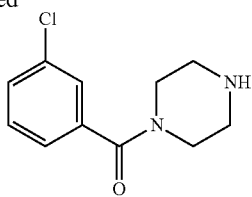

A 100-mL round-bottom flask was charged with tert-butyl 4-[(3-chlorophenyl)carbonyl]piperazine-1-carboxylate (900 mg, 2.77 mmol, 1.00 equiv), trifluoroacetic acid (2 mL), and dichloromethane (15 mL). The resulting solution was stirred overnight at room temperature and concentrated under reduced pressure to provide 622 mg (crude) of 1-[(3-chlorophenyl)carbonyl]piperazine as a yellow oil. LCMS (ESI, m/z): 225 [M+H]+.

Step 3: Preparation of 2,5-dioxopyrrolidin-1-yl 4-(3-chlorobenzoyl)piperazine-1-carboxylate The title compound was prepared from 1-[(3-chlorophenyl)carbonyl]piperazine and bis(2,5-dioxopyrrolidin-1-yl) carbonate according to the representative procedure of Example 51 to provide 2,5-dioxopyrrolidin-1-yl 4-(3-chlorobenzoyl)piperazine-1-carboxylate as a yellow solid. $^1$H NMR (300 MHz, Chloroform-d) δ 7.41-7.46 (m, 3H), 7.26-7.30 (m, 1H), 3.58-3.67 (m, 8H), 2.84 (s, 4H). LCMS (ESI, m/z): 388 [M+Na]+.

Example 212

2,5-Dioxopyrrolidin-1-yl 4-benzoylpiperazine-1-carboxylate

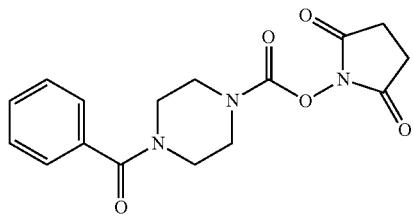 [SMILES: O=C(ON1C(=O)CCC1=O)N1CCN(C(=O)c2ccccc2)CC1]

The title compound was prepared directly from commercially available 1-benzoylpiperazine and bis(2,5-dioxopyrrolidin-1-yl) carbonate according to the representative procedure of Example 51 to provide 2,5-dioxopyrrolidin-1-yl 4-benzoylpiperazine-1-carboxylate as a white solid. $^1$H NMR (300 MHz, Chloroform-d) δ 7.42-7.48 (m, 5H), 3.58-3.67 (m, 8H), 2.83 (s, 4H). LCMS (ESI, m/z): 354 [M+Na]+.

Example 213

2,5-Dioxopyrrolidin-1-yl 4-[2-(piperidin-1-yl)acetyl]piperazine-1-carboxylate

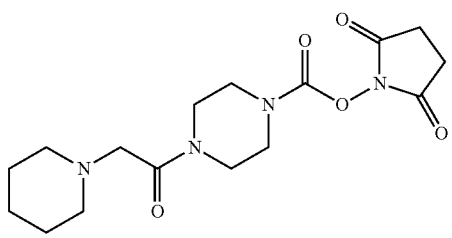 [SMILES: O=C(CN1CCCCC1)N1CCN(C(=O)ON2C(=O)CCC2=O)CC1]

The title compound was prepared from commercially available 2-(piperidin-1-yl)acetic acid according to the representative procedure of Example 211, Steps 1 and 2 followed by the representative procedure of Example 51 to provide 2,5-dioxopyrrolidin-1-yl 4-[2-(piperidin-1-yl)acetyl]piperazine-1-carboxylate. The crude product (200 mg) was purified by preparative HPLC using the following gradient conditions: 20% CH$_3$CN/80% Phase A increasing to 80% CH$_3$CN over 10 min, then to 100% CH$_3$CN over 0.1 min, holding at 100% CH$_3$CN for 1.9 min, then reducing to 20% CH$_3$CN over 0.1 min, and holding at 20% for 1.9 min, on a Waters 2767-5 Chromatograph. Column: Xbridge Prep C$_{18}$, 19*150 mm, 5 um; Mobile phase: Phase A: 0.05% formic acid in H$_2$O; Phase B: CH$_3$CN; Detector, UV 220 & 254 nm. Purification resulted in 69.7 mg (30% yield) of the formic acid salt of 2,5-dioxopyrrolidin-1-yl 4-[2-(piperidin-1-yl)acetyl]piperazine-1-carboxylate as a pink solid. $^1$H NMR (300 MHz, Chloroform-d) δ 10.08 (br, 1H), 8.18 (s, 1H), 3.96 (br, 2H), 3.54-3.70 (m, 8H), 3.32 (br, 4H), 2.84 (s, 4H), 1.89-1.92 (m, 4H), 1.64 (br, 2H). LCMS (ESI, m/z): 399 [M+H]+.

Example 214

2,5-Dioxopyrrolidin-1-yl 4-[2-(pyrrolidin-1-yl)acetyl]piperazine-1-carboxylate

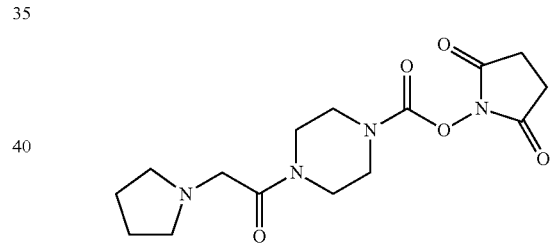

The title compound was prepared from commercially available 2-(pyrrolidin-1-yl)acetic acid according to the representative procedure of Example 211, Steps 1 and 2 followed by the representative procedure of Example 51 to provide 2,5-dioxopyrrolidin-1-yl 4-[2-(pyrrolidin-1-yl)acetyl]piperazine-1-carboxylate. The crude product (250 mg) was purified by preparative HPLC using the following gradient conditions: 20% CH$_3$CN/80% Phase A increasing to 80% CH$_3$CN over 10 min, then to 100% CH$_3$CN over 0.1 min, holding at 100% CH$_3$CN for 1.9 min, then reducing to 20% CH$_3$CN over 0.1 min, and holding at 20% for 1.9 min, on a Waters 2767-5 Chromatograph. Column: Xbridge Prep C18, 19*150 mm, 5 um; Mobile phase: Phase A: water; Phase B: CH$_3$CN; Detector, UV 220 & 254 nm. Purification resulted in 140 mg (40% yield) of the formic acid salt 2,5-dioxopyrrolidin-1-yl 4-[2-(pyrrolidin-1-yl)acetyl]piperazine-1-carboxylate as a white solid. $^1$H NMR (300 MHz, Chloroform-d) δ 11.47 (s, 1H), 8.37 (s, 1H), 3.64-3.68 (m, 10H), 2.94 (br, 4H), 2.84 (s, 4H), 1.92 (br, 4H). LCMS (ESI, m/z): 339 [M+HCOOH+H]+.

Example 215

2,5-Dioxopyrrolidin-1-yl 4-[2-(morpholin-4-yl)acetyl]piperazine-1-carboxylate

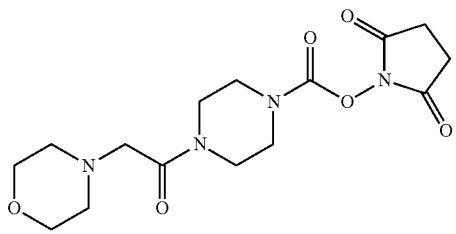 [SMILES: O=C(CN1CCOCC1)N1CCN(C(=O)ON2C(=O)CCC2=O)CC1]

The title compound was prepared from commercially available 2-morpholinoacetic acid according to the representative procedure of Example 211, Steps 1 and 2 followed by the representative procedure of Example 51 to provide 2,5-dioxopyrrolidin-1-yl 4-[2-(morpholin-4-yl)acetyl]piperazine-1-carboxylate. The crude product (200 mg) was purified by preparative HPLC using the following gradient conditions: 20% $CH_3CN$/80% Phase A increasing to 80% $CH_3CN$ over 10 min, then to 100% $CH_3CN$ over 0.1 min, holding at 100% $CH_3CN$ for 1.9 min, then reducing to 20% $CH_3CN$ over 0.1 min, and holding at 20% for 1.9 min, on a Waters 2767-5 Chromatograph. Column: Xbridge Prep C18, 19*150 mm, 5 um; Mobile phase: Phase A: water; Phase B: $CH_3CN$; Detector, UV 220 & 254 nm. Purification resulted in 102 mg (30% yield) of the formic acid salt of 2,5-dioxopyrrolidin-1-yl 4-[2-(morpholin-4-yl)acetyl]piperazine-1-carboxylate as a white solid. $^1$H NMR (300 MHz, Chloroform-d) δ 9.44 (s, 1H), 8.14 (s, 1H), 3.59-3.76 (m, 12H), 3.31 (s, 1H), 2.84 (s, 4H), 2.63 (br, 4H). LCMS (ESI, m/z): 355 $[M+HCOOH+H]^+$.

Example 216

2,5-Dioxopyrrolidin-1-yl 4-[2-(azetidin-1-yl)acetyl]piperazine-1-carboxylate

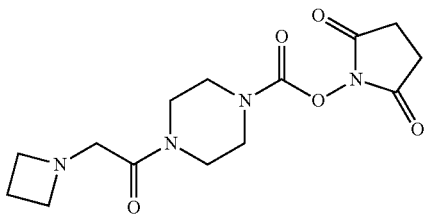 [SMILES: O=C(CN1CCC1)N1CCN(C(=O)ON2C(=O)CCC2=O)CC1]

Step 1: Preparation of tert-butyl 4-(2-chloroacetyl)piperazine-1-carboxylate

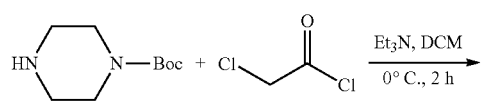

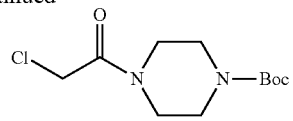

A 100-mL round-bottom flask was charged with tert-butyl piperazine-1-carboxylate (5.00 g, 26.8 mmol, 1.00 equiv), dichloromethane (30 mL), 2-chloroacetyl chloride (3.31 g, 29.3 mmol, 1.09 equiv), and triethylamine (4.07 g, 40.2 mmol, 1.50 equiv) at 0° C. The resulting solution was stirred for 2 h at 0° C. and quenched by water (15 mL). The resulting solution was extracted with dichloromethane (3×20 mL), and the organic layers were combined, washed with sodium bicarbonate solution (3×20 mL), dried over anhydrous sodium sulfate, filtered, and concentrated under reduced pressure. The residue was chromatographed on a silica gel column with ethyl acetate/petroleum ether (30/70) to provide 6.14 g (87% yield) of tert-butyl 4-(2-chloroacetyl)piperazine-1-carboxylate as a white solid. LCMS (ESI, m/z): 263 $[M+H]^+$.

Step 2: Preparation of tert-butyl 4-[2-(azetidin-1-yl)acetyl]piperazine-1-carboxylate

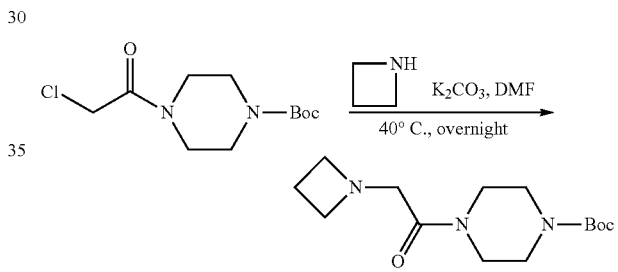

A 100-mL round-bottom flask was charged with azetidine (348 mg, 6.10 mmol, 2.00 equiv), potassium carbonate (1.26 g, 9.16 mmol, 3.01 equiv), N,N-dimethylformamide (20 mL), and tert-butyl 4-(2-chloroacetyl)piperazine-1-carboxylate (800 mg, 3.04 mmol, 1.00 equiv). The resulting solution was stirred overnight at 40° C. The resulting solution was diluted with $H_2O$ (10 mL) and extracted with ethyl acetate (3×20 mL), and the organic layers were combined, washed with brine (20 mL) dried over anhydrous sodium sulfate, filtered, and concentrated under reduced pressure. The residue was chromatographed on a silica gel column with $CH_3CN/H_2O$ (33/67) to provide 500 mg (58% yield) of tert-butyl 4-[2-(azetidin-1-yl)acetyl]piperazine-1-carboxylate as a brown oil. LCMS (ESI, m/z): 284 $[M+H]^+$.

Step 3: Preparation of 2,5-dioxopyrrolidin-1-yl 4-[2-(azetidin-1-yl)acetyl]piperazine-1-carboxylate The title compound was prepared according to the procedure of Example 211, Step 2 followed by the representative procedure of Example 51 using tert-butyl 4-[2-(azetidin-1-yl)acetyl]piperazine-1-carboxylate from Step 2 of this Example. Purification resulted in 118 mg (41% yield) of 2,5-dioxopyrrolidin-1-yl 4-[2-(azetidin-1-yl)acetyl]piperazine-1-carboxylate as a white solid: ¹H NMR (300 MHz, Chloroform-d) δ 4.11-4.47 (m, 6H), 3.47-3.70 (m, 8H), 2.84 (s, 4H), 2.49-2.76 (m, 2H). LCMS (ESI, m/z): 325 [M+H]⁺.

Example 217

2,5-Dioxopyrrolidin-1-yl 4-(pyrrolidin-1-yl)piperidine-1-carboxylate

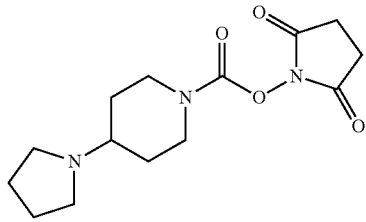 [SMILES: O=C(ON1C(=O)CCC1=O)N1CCC(N2CCCC2)CC1]

The title compound was prepared directly from commercially available 4-(pyrrolidin-1-yl)piperidine and bis(2,5-dioxopyrrolidin-1-yl) carbonate according to the representative procedure of Example 51 and the purification method of Example 215 to provide the formic acid salt of 2,5-dioxopyrrolidin-1-yl 4-(pyrrolidin-1-yl)piperidine-1-carboxylate as a white semi-solid. ¹H NMR (300 MHz, Chloroform-d) δ 12.56 (br, 1H), 8.44 (s, 1H), 4.23-4.27 (m, 2H), 2.97-3.23 (m, 7H), 2.82 (s, 4H), 2.04-2.15 (m, 6H), 1.86 (br, 2H). LCMS (ESI, m/z): 296 [M+HCOOH+H]⁺.

Example 218

2,5-Dioxopyrrolidin-1-yl 4-(piperidine-1-yl)piperidine-1-carboxylate

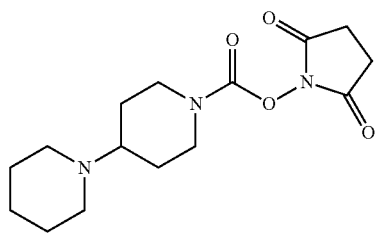 [SMILES: O=C(ON1C(=O)CCC1=O)N1CCC(N2CCCCC2)CC1]

The title compound was prepared directly from commercially available 1,4'-bipiperidine and bis(2,5-dioxopyrrolidin-1-yl) carbonate according to the representative procedure of Example 51 and the purification method of Example 215 to provide the formic acid salt of 2,5-dioxopyrrolidin-1-yl 4-(piperidine-1-yl)piperidine-1-carboxylate as a white semi-solid. ¹H NMR (400 MHz, Chloroform-d) δ 12.80 (br, 2H), 8.42 (s, 1H), 4.23-4.31 (m, 2H), 3.42 (br, 1H), 5.08 (br, 5H), 2.82 (s, 4H), 2.51-2.59 (m, 1H), 2.12 (br, 2H), 1.61-1.92 (m, 8H). LCMS (ESI, m/z): 310 [M+HCOOH+H]⁺.

Example 219

2,5-Dioxopyrrolidin-1-yl 4-(2-oxopyrrolidin-1-yl) piperidine-1-carboxylate

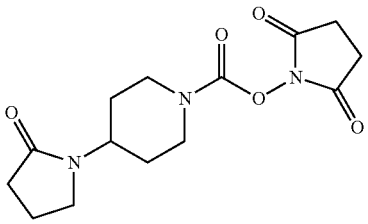 [SMILES: O=C(ON1C(=O)CCC1=O)N1CCC(N2CCCC2=O)CC1]

The title compound was prepared directly from commercially available 1-(piperidin-4-yl)pyrrolidin-2-one according to the representative procedure of Example 51 to provide 2,5-dioxopyrrolidin-1-yl 4-(2-oxopyrrolidin-1-yl)piperidine-1-carboxylate as a white solid: ¹H NMR (300 MHz, Chloroform-d) δ 4.16-4.32 (m, 3H), 3.33-3.38 (m, 2H), 2.99-3.11 (m, 2H), 2.83 (s, 4H), 2.38-2.44 (m, 2H), 1.98-2.08 (m, 2H), 1.75 (br, 4H). LCMS (ESI, m/z): 332 [M+Na]⁺.

Example 220

2,5-Dioxopyrrolidin-1-yl 4-(2-oxopiperidin-1-yl) piperidine-1-carboxylate

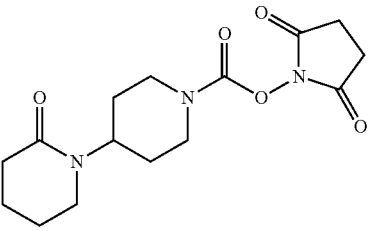 [SMILES: O=C(ON1C(=O)CCC1=O)N1CCC(N2CCCCC2=O)CC1]

Step 1: Preparation of N-(1-benzylpiperidin-4-yl)-5-bromopentanamide

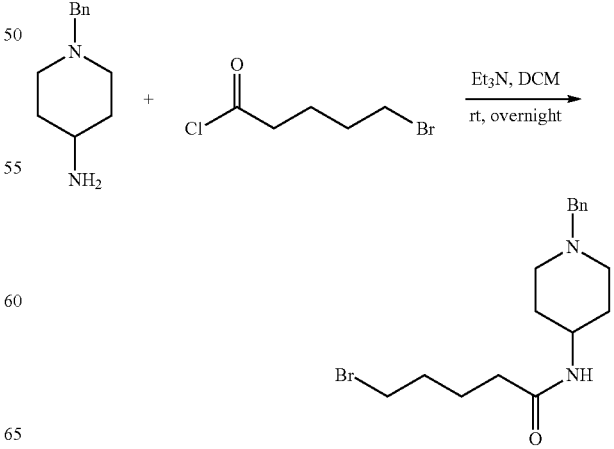

A 100-mL round-bottom flask was charged with 1-benzylpiperidin-4-amine (800 mg, 4.20 mmol, 1.00 equiv), dichloromethane (20 mL), triethylamine (637 mg, 6.30 mmol, 1.50 equiv), and 5-bromopentanoyl chloride (917 mg, 4.60 mmol, 1.09 equiv). The resulting solution was stirred overnight at room temperature and diluted with H$_2$O (10 mL). The resulting solution was extracted with dichloromethane (3×15 mL), and the organic layers were combined, washed with brine (15 mL), dried over anhydrous sodium sulfate, filtered, and concentrated under reduced pressure. The residue was chromatographed on a silica gel column with dichloromethane/methanol (93/7) to provide 910 mg (61% yield) of N-(1-benzylpiperidin-4-yl)-5-bromopentanamide as a white solid. LCMS (ESI, m/z): 353 [M+H]$^+$.

Step 2: Preparation of 1-(1-benzylpiperidin-4-yl)piperidin-2-one

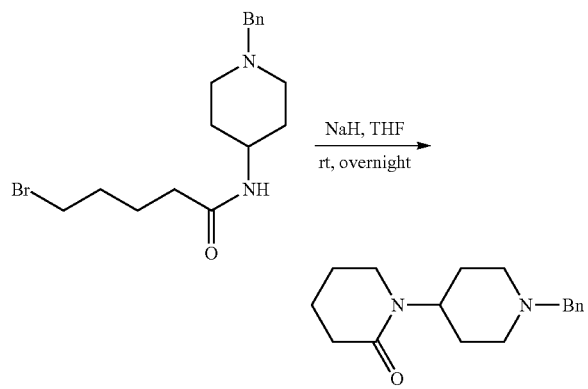

A 100-mL round-bottom flask was charged with N-(1-benzylpiperidin-4-yl)-5-bromopentanamide (910 mg, 2.58 mmol, 1.00 equiv), THF (15 mL), and sodium hydride (123 mg, 5.12 mmol, 1.99 equiv). The resulting solution was stirred overnight at room temperature and quenched with H$_2$O (10 mL). The resulting solution was extracted with ethyl acetate (3×20 mL), and the organic layers were combined, washed with brine (2×20 mL), dried over anhydrous sodium sulfate, filtered, and concentrated under reduced pressure. The residue was chromatographed on a silica gel column with ethyl acetate/petroleum ether (80/20) to provide 200 mg (29% yield) of 1-(1-benzylpiperidin-4-yl)piperidin-2-one as a yellow solid. $^1$H NMR (300 MHz, Chloroform-d) δ 7.23-7.35 (m, 5H), 4.60 (br, 1H), 3.56 (br, 2H), 3.22 (br, 3H), 3.09 (br, 2H), 2.39 (t, J=6.0 Hz, 3H), 2.18 (br, 2H), 1.70-1.79 (m, 6H). LCMS (ESI, m/z): 273 [M+H]$^+$.

Step 3: Preparation of 1-(piperidin-4-yl)piperidin-2-one

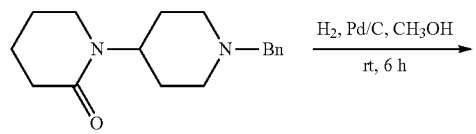

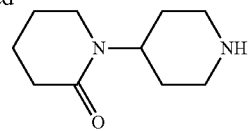

A 100-mL round-bottom flask was charged with 1-(1-benzylpiperidin-4-yl)piperidin-2-one (200 mg, 0.730 mmol, 1.00 equiv), palladium carbon (700 mg), and methanol (15 mL). To the above, H$_2$ was introduced. The resulting solution was stirred for 6 h at rt. The solids were filtered out and the filtrate concentrated under reduced pressure to provide 140 mg (crude) of 1-(piperidin-4-yl)piperidin-2-one as colorless oil. LCMS (ESI, m/z): 183 [M+H]$^+$.

Step 4: Preparation of 2,5-dioxopyrrolidin-1-yl 4-(2-oxopiperidin-1-yl)piperidine-1-carboxylate The title compound was prepared from 1-(piperidin-4-yl)piperidin-2-one according to the representative procedure of Example 51 to provide 2,5-dioxopyrrolidin-1-yl 4-(2-oxopiperidin-1-yl)piperidine-1-carboxylate as a white solid. $^1$H NMR (300 MHz, Chloroform) δ 4.73-4.83 (m, 1H), 4.18-4.31 (m, 2H), 3.00-3.20 (m, 4H), 2.826 (s, 4H), 2.42 (t, J=6.0 Hz, 2H), 1.71-1.80 (m, 8H). LCMS (ESI, m/z): 324 [M+H]$^+$.

Example 221

Compounds are tested to assess their MAGL and serine hydrolase activity using the following in vitro and in vivo assays.

In Vitro Competitive Activity-Based Protein Profiling.

Proteomes (mouse brain membrane fraction or cell lysates) (50 μL, 1.0 mg/ml total protein concentration) were preincubated with varying concentrations of inhibitors at 37° C. After 30 min, FP-Rh (1.0 μL, 50 μM in DMSO) was added and the mixture was incubated for another 30 min at 37° C. Reactions were quenched with SDS loading buffer (50 μL—4×) and run on SDS-PAGE. Following gel imaging, serine hydrolase activity was determined by measuring fluorescent intensity of gel bands corresponding to MAGL, ABHD6 and FAAH using ImageJ 1.43u software.

Preparation of Mouse Brain Proteomes from Inhibitor Treated Mice.

Inhibitors were administered to wild-type C57B1/6J by oral gavage in a vehicle of polyethylene glycol. Each animal was sacrificed 4 h following administration and brain proteomes were prepared and analyzed according to previously established methods (See Niphakis, M. J., et al. (2011) *ACS Chem. Neurosci.* and Long, J. Z., et al. *Nat. Chem. Biol.* 5:37-44)

Recombinant Expression of Human MAGL in HEK293T Cells.

hMAGL was expressed in HEK293T cells according to previously reported methods (see Niphakis, Long, and Blankman, J. L., et al. (2007) *Chem. Biol.* 14:1347-1356). Cell lysates were diluted with mock proteomes for use in competitive ABPP experiments.

Compounds demonstrated activity in the assays of this Example as indicated in the following table (Table 1).

TABLE 1

In vitro and in vivo serine hydrolase profiles for carbamate MAGL inhibitors.

| Example | Mouse (IC₅₀ value, nM) MAGL | FAAH | ABHD6 | Mouse brain MAGL (% inhibition at 20 mg/kg, p.o.) | Human MAGL (IC₅₀ value, nM) |
|---|---|---|---|---|---|
| 1 | *** | X | ** | 75% | *** |
| 2 | *** | X | ** | >95% | *** |
| 3 | *** | X | ** | >95% | *** |
| 4 | X | X | X | — | — |
| 5 | * | X | * | — | * |
| 6 | X | ** | X | — | — |
| 7 | *** | * | *** | — | *** |
| 8 | *** | ** | *** | — | *** |
| 9 | X | X | X | — | — |
| 10 | X | X | X | — | — |
| 11 | X | X | X | — | — |
| 12 | * | X | ** | — | — |
| 13 | X | X | X | — | — |
| 14 | * | X | ** | — | — |
| 15 | X | X | X | — | — |
| 16 | X | X | X | — | — |
| 17 | X | X | — | — | — |
| 18 | ** | X | * | — | — |
| 19 | X | X | x | — | — |
| 20 | X | X | X | — | — |
| 21 | ** | * | ** | — | — |
| 22 | X | X | X | — | — |
| 23 | X | X | X | — | — |
| 24 | X | X | X | — | — |
| 25 | X | X | X | — | — |
| 26 | X | X | X | — | — |
| 27 | X | — | X | — | — |
| 28 | X | * | * | — | — |
| 29 | X | X | X | — | — |
| 30 | X | X | X | — | — |
| 31 | * | * | * | — | — |
| 32 | * | *** | *** | — | — |
| 33 | X | X | ** | — | — |
| 34 | X | ** | *** | — | — |
| 35 | *** | * | *** | — | *** |
| 36 | *** | * | * | — | *** |
| 37 | *** | * | ** | — | *** |
| 38 | X | X | X | — | — |
| 39 | X | X | — | — | — |
| 40 | X | X | — | — | — |
| 41 | *** | X | ** | >95% | — |
| 42 | * | X | * | — | — |
| 43 | ** | X | ** | — | — |
| 44 | * | X | * | — | — |
| 45 | * | X | ** | — | — |
| 46 | *** | X | ** | >95% | — |
| 47 | ** | X | ** | — | — |
| 48 | *** | *** | *** | — | — |
| 49 | *** | ** | *** | — | — |
| 50 | ** | *** | *** | — | — |
| 52 | X | X | ** | — | — |
| 53 | X | X | *** | — | — |
| 54 | * | * | *** | — | — |
| 55 | X | * | *** | — | — |
| 56 | *** | X | ** | — | — |
| 57 | X | X | X | — | — |
| 58 | X | X | X | — | — |
| 59 | X | X | X | — | — |
| 60 | X | X | X | — | — |
| 61 | X | X | X | — | — |

*** is less than 100 nM;
** is between 100 and 1,000 nM;
* is between 1,000 and 10,000 nM;
X is greater than 10,000 nM

TABLE 2

In vitro and in vivo serine hydrolase profiles for carbamate MAGL inhibitors.

| Example | Mouse (IC₅₀ value, nM) MAGL | FAAH | ABHD6 | Mouse brain MAGL (% inhibition at 5 mg/kg, p.o.) |
|---|---|---|---|---|
| 62 | * | X | * | — |
| 63 | * | — | — | — |
| 64 | ** | — | — | — |
| 65 | *** | * | ** | — |
| 66 | *** | * | * | — |
| 67 | * | * | * | — |
| 68 | ** | * | ** | — |
| 69 | *** | * | ** | — |
| 70 | * | * | * | — |
| 71 | ** | * | * | — |
| 72 | *** | — | — | — |
| 74 | *** | X | ** | — |
| 75 | ** | X | * | — |
| 78 | *** | * | *** | — |
| 82 | ** | X | * | — |
| 83 | ** | X | ** | — |
| 84 | ** | X | * | — |
| 85 | *** | X | * | — |
| 91 | *** | X | ** | — |
| 92 | ** | X | * | — |
| 93 | ** | X | X | — |
| 94 | * | X | * | — |
| 95 | *** | X | ** | — |
| 97 | * | X | ** | — |
| 98 | *** | X | ** | — |
| 101 | * | X | ** | — |
| 104 | ** | X | ** | — |
| 105 | *** | X | * | 75% |
| 106 | *** | X | * | — |
| 107 | *** | X | ** | — |
| 108 | * | X | * | — |
| 109 | *** | X | * | — |
| 114 | *** | X | ** | — |
| 115 | ** | X | * | — |
| 118 | * | X | * | — |
| 121 | *** | X | ** | — |
| 122 | *** | X | ** | 100% |
| 123 | *** | X | ** | — |
| 124 | *** | X | ** | — |
| 129 | *** | X | ** | — |
| 130 | *** | X | * | — |
| 131 | *** | X | * | — |
| 132 | *** | X | ** | — |
| 133 | *** | X | *** | — |
| 134 | * | X | * | — |
| 138 | * | * | ** | — |
| 139 | ** | X | ** | — |
| 143 | ** | X | * | — |
| 144 | * | X | ** | — |
| 145 | * | X | * | — |
| 148 | * | X | * | — |
| 149 | * | X | * | — |
| 151 | ** | — | — | — |
| 152 | * | * | * | — |
| 153 | ** | X | * | — |
| 160 | ** | — | — | — |
| 161 | ** | — | — | — |
| 165 | ** | * | ** | — |
| 188 | ** | X | * | — |
| 189 | ** | X | * | — |
| 191 | ** | X | * | — |

*** is less than 100 nM;
** is between 100 and 1,000 nM;
* is between 1,000 and 10,000 nM;
X is greater than 10,000 nM

TABLE 3

In vitro serine hydrolase profiles for carbamate MAGL inhibitors.

| Example | % Inhibition at 1 uM | | |
|---|---|---|---|
| | MAGL | FAAH | ABHD6 |
| 76 | ** | * | ** |
| 77 | ** | * | ** |
| 79 | * | * | * |
| 80 | * | * | * |
| 81 | * | * | ** |
| 86 | * | * | * |
| 87 | * | * | * |
| 88 | ** | * | ** |
| 89 | ** | * | ** |
| 90 | ** | * | ** |
| 96 | * | * | * |
| 99 | ** | * | ** |
| 100 | * | * | * |
| 102 | *** | * | ** |
| 103 | * | * | * |
| 110 | ** | * | ** |
| 111 | ** | * | ** |
| 112 | *** | * | ** |
| 113 | ** | * | ** |
| 116 | ** | * | * |
| 117 | ** | * | * |
| 119 | ** | * | ** |
| 120 | *** | * | ** |
| 125 | *** | * | *** |
| 126 | ** | * | * |
| 127 | ** | * | ** |
| 128 | ** | * | * |
| 135 | ** | * | ** |
| 136 | ** | * | ** |
| 137 | ** | * | ** |
| 140 | ** | * | ** |
| 141 | ** | * | ** |
| 142 | ** | * | ** |
| 146 | ** | * | ** |
| 147 | * | * | * |
| 154 | ** | * | ** |
| 155 | ** | * | * |
| 156 | ** | * | ** |
| 157 | ** | * | ** |
| 158 | ** | * | * |
| 159 | ** | * | ** |
| 162 | *** | * | *** |
| 163 | ** | * | ** |
| 164 | *** | * | *** |
| 166 | ** | * | *** |
| 167 | *** | * | ** |
| 168 | ** | * | ** |
| 169 | ** | * | *** |
| 170 | ** | * | ** |
| 171 | ** | * | ** |
| 172 | ** | * | ** |
| 173 | ** | * | ** |
| 174 | ** | * | ** |
| 175 | ** | * | ** |
| 176 | ** | * | ** |
| 177 | ** | * | *** |
| 178 | ** | * | ** |
| 179 | ** | * | ** |
| 180 | *** | * | *** |
| 181 | ** | * | * |
| 182 | ** | * | *** |
| 183 | ** | * | *** |
| 184 | *** | * | ** |
| 185 | *** | * | *** |
| 186 | ** | * | ** |
| 187 | ** | * | ** |
| 190 | ** | * | * |
| 192 | ** | * | ** |
| 193 | ** | * | ** |
| 194 | ** | * | ** |
| 195 | * | * | * |
| 196 | ** | * | * |
| 197 | * | * | * |
| 198 | * | * | * |

TABLE 3-continued

In vitro serine hydrolase profiles for carbamate MAGL inhibitors.

| Example | % Inhibition at 1 uM | | |
|---|---|---|---|
| | MAGL | FAAH | ABHD6 |
| 199 | * | * | ** |
| 200 | * | * | * |
| 201 | * | * | * |
| 202 | * | * | * |
| 203 | * | * | * |
| 204 | * | * | * |
| 205 | * | * | *** |
| 206 | ** | * | *** |
| 207 | ** | * | *** |
| 208 | * | * | * |
| 209 | * | * | * |
| 210 | * | * | ** |

\*\*\* is >75%;
\*\* is between 25 and 75%;
\* is <25%

TABLE 4

In vitro serine hydrolase profiles for carbamate MAGL inhibitors.

| Compound | % Inhibition at 10 uM | | |
|---|---|---|---|
| | MAGL | FAAH | ABHD6 |
| 150 | *** | * | ** |
| 51 | * | * | * |
| 126 | * | * | * |
| 211 | ** | * | ** |
| 212 | ** | * | * |
| 213 | * | * | * |
| 214 | * | * | * |
| 215 | * | * | * |
| 216 | * | * | * |
| 217 | * | * | * |
| 218 | * | * | * |
| 219 | * | * | ** |
| 220 | * | * | ** |

\*\*\* is >75%;
\*\* is between 25 and 75%;
\* is <25%

INCORPORATION BY REFERENCE

All publications and patents mentioned herein, including those items listed below, are hereby incorporated by reference in their entirety for all purposes as if each individual publication or patent was specifically and individually incorporated by reference. In case of conflict, the present application, including any definitions herein, will control.

EQUIVALENTS

While specific embodiments of the disclosure have been discussed, the above specification is illustrative and not restrictive. Many variations will become apparent to those skilled in the art upon review of this specification. The full scope of the disclosure should be determined by reference to the claims, along with their full scope of equivalents, and the specification, along with such variations.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in this specification and attached claims are approximations that may vary depending upon the desired properties sought to be obtained by the present invention.

We claim:
1. A compound represented by:

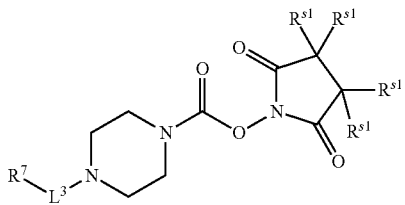

wherein
- R$^{s1}$ is independently selected for each occurrence from the group consisting of H, halogen, cyano, hydroxyl, phenyl, C$_{1-6}$alkyl (optionally substituted by one, two, or three halogens, cyano, phenyl, or hydroxyl), and C$_{1-6}$alkoxy (optionally substituted by one, two, or three halogens, cyano, or hydroxyl);
- L$^3$ is —CH$_2$—;
- R$^7$ is phenyl; wherein R$^7$ is substituted by R$^a$R$^b$N— and a moiety selected from the group consisting of: halogen, C$_{1-6}$alkyl (optionally substituted by one, two or three halogens), and C$_{1-6}$alkoxy (optionally substituted by one, two or three halogens);
- R$^a$ and R$^b$, together with the nitrogen to which they are attached, form a saturated 4-6 membered heterocyclic ring, which may have an additional heteroatom selected from O, S, or N; wherein the saturated 4-6 membered heterocyclic ring is optionally substituted by one or more substituents selected from the group consisting of halogen, cyano, oxo, C$_{1-6}$alkyl, —S(O)$_w$—C$_{1-6}$ alkyl (where w is 0, 1 or 2), hydroxyl, —C(O)—C$_{1-6}$alkyl, and —NH—C(O)—C$_{1-6}$ alkyl;

or a pharmaceutically acceptable salt or stereoisomer thereof.

2. The compound of claim 1, or a stereoisomer or pharmaceutically acceptable salt thereof, wherein R$^a$ and R$^b$, together with the nitrogen to which they are attached, form a saturated 4-6 membered heterocyclic ring selected from azetidine, pyrrolidine, piperidine, piperazine, and morpholine, and the saturated 4-6 membered heterocyclic ring is optionally substituted by one or more substituents selected from the group consisting of halogen, cyano, oxo, C$_{1-6}$alkyl, —S(O)$_w$—C$_{1-6}$alkyl (where w is 0, 1 or 2), hydroxyl, —C(O)—C$_{1-6}$alkyl, —NH$_2$, and —NH—C(O)—C$_{1-6}$alkyl.

3. The compound of claim 2, or a stereoisomer or pharmaceutically acceptable salt thereof, wherein the saturated 4-6 membered heterocyclic ring is pyrrolidine.

4. The compound of claim 2, or a stereoisomer or pharmaceutically acceptable salt thereof, wherein the saturated 4-6 membered heterocyclic ring is morpholine.

5. The compound of claim 2, or a stereoisomer or pharmaceutically acceptable salt thereof, wherein the saturated 4-6 membered heterocyclic ring is piperidine.

6. A compound selected from the group represented by: 2,5-dioxopyrrolidin-1-yl 4-(2-fluoro-4-morpholinobenzyl)piperazine-1-carboxylate; 2,5-dioxopyrrolidin-1-yl 4-(2-methyl-4-morpholinobenzyl)piperazine-1-carboxylate; 2,5-dioxopyrrolidin-1-yl 4-(4-bromo-2-(piperidin-1-yl)benzyl)piperazine-1-carboxylate; 2,5-dioxopyrrolidin-1-yl 4-(4-bromo-2-morpholinobenzyl)piperazine-1-carboxylate; 2,5-dioxopyrrolidin-1-yl 4-(2-methoxy-4-morpholinobenzyl)piperazine-1-carboxylate; 2,5-dioxopyrrolidin-1-yl 4-(2-methyl-4-(pyrrolidin-1-yl)benzyl)piperazine-1-carboxylate; 2,5-dioxopyrrolidin-1-yl 4-(4-chloro-2-morpholinobenzyl)piperazine-1-carboxylate; 2,5-dioxopyrrolidin-1-yl 4-(4-bromo-2-(pyrrolidin-1-yl)benzyl)piperazine-1-carboxylate; 2,5-dioxopyrrolidin-1-yl 4-(4-chloro-2-(pyrrolidin-1-yl)benzyl)piperazine-1-carboxylate; 2,5-dioxopyrrolidin-1-yl 4-(3-fluoro-4-(pyrrolidin-1-yl)benzyl)piperazine-1-carboxylate; 2,5-dioxopyrrolidin-1-yl 4-{[4-(morpholin-4-yl)-2-(trifluoromethyl)phenyl]methyl}piperazine-1-carboxylate; 2,5-dioxopyrrolidin-1-yl 4-(2-chloro-4-(pyrrolidin-1-yl)benzyl)piperazine-1-carboxylate; 2,5-dioxopyrrolidin-1-yl 4-{[2-chloro-6-(morpholin-4-yl)phenyl]methyl}piperazine-1-carboxylate; 2,5-dioxopyrrolidin-1-yl 4-{[3-chloro-2-(morpholin-4-yl)phenyl]methyl}piperazine-1-carboxylate; 2,5-dioxopyrrolidin-1-yl 4-(2-(3-acetamidopyrrolidin-1-yl)-4-chlorobenzyl)piperazine-1-carboxylate; 2,5-dioxopyrrolidin-1-yl 4-{[2-(morpholin-4-yl)-4-(trifluoromethyl)phenyl]methyl}piperazine-1-carboxylate; 2,5-dioxopyrrolidin-1-yl 4-{[5-chloro-2-(morpholin-4-yl)phenyl]methyl}piperazine-1-carboxylate; 2,5-dioxopyrrolidin-1-yl 4-{[3-fluoro-2-(morpholin-4-yl)phenyl]methyl}piperazine-1-carboxylate; 2,5-dioxopyrrolidin-1-yl 4-(2-chloro-4-morpholinobenzyl)piperazine-1-carboxylate; 2,5-dioxopyrrolidin-1-yl 4-{[2-chloro-6-(pyrrolidin-1-yl)phenyl]methyl}piperazine-1-carboxylate; 2,5-dioxopyrrolidin-1-yl 4-{[5-chloro-2-(pyrrolidin-1-yl)phenyl]methyl}piperazine-1-carboxylate; 2,5-dioxopyrrolidin-1-yl 4-(3-chloro-4-morpholinobenzyl)piperazine-1-carboxylate; 2,5-dioxopyrrolidin-1-yl 4-{[4-(morpholin-4-yl)-2-(trifluoromethoxy)phenyl]methyl}piperazine-1-carboxylate; 2,5-dioxopyrrolidin-1-yl 4-{[4-(pyrrolidin-1-yl)-2-(trifluoromethoxy)phenyl]methyl}piperazine-1-carboxylate; 2,5-dioxopyrrolidin-1-yl 4-{[2-(pyrrolidin-1-yl)-4-(trifluoromethyl)phenyl]methyl}piperazine-1-carboxylate; 2,5-dioxopyrrolidin-1-yl 4-{[3-chloro-2-(pyrrolidin-1-yl)phenyl]methyl}piperazine-1-carboxylate; 2,5-dioxopyrrolidin-1-yl 4-{[3-fluoro-2-(pyrrolidin-1-yl)phenyl]methyl}piperazine-1-carboxylate; 2,5-dioxopyrrolidin-1-yl 4-{[4-chloro-2-(4-methanesulfonylpiperazin-1-yl)phenyl]methyl}piperazine-1-carboxylate; 2,5-dioxopyrrolidin-1-yl 4-{[2-(azetidin-1-yl)-4-chlorophenyl]methyl}piperazine-1-carboxylate; 2,5-dioxopyrrolidin-1-yl 4-{[2-(4-acetylpiperazin-1-yl)-4-chlorophenyl]methyl}piperazine-1-carboxylate; 2,5-dioxopyrrolidin-1-yl 4-{[2-(morpholin-4-yl)-5-(trifluoromethyl)phenyl]methyl}piperazine-1-carboxylate; 2,5-dioxopyrrolidin-1-yl 4-{[2-(pyrrolidin-1-yl)-5-(trifluoromethyl)phenyl]methyl}piperazine-1-carboxylate; 2,5-dioxopyrrolidin-1-yl 4-(2-methyl-3-morpholinobenzyl)piperazine-1-carboxylate; 2,5-dioxopyrrolidin-1-yl 4-(2-methyl-3-(piperidin-1-yl)benzyl)piperazine-1-carboxylate; 2,5-dioxopyrrolidin-1-yl 4-(2-methyl-3-(pyrrolidin-1-yl)benzyl)piperazine-1-carboxylate; 2,5-dioxopyrrolidin-1-yl 4-(4-fluoro-3-(pyrrolidin-1-yl)benzyl)piperazine-1-carboxylate; 2,5-dioxopyrrolidin-1-yl 4-{[5-methyl-2-(morpholin-4-yl)phenyl]methyl}piperazine-1-carboxylate; 2,5-dioxopyrrolidin-1-yl 4-{[5-methyl-2-(pyrrolidin-1-yl)phenyl]methyl}piperazine-1-carboxylate; 2,5-dioxopyrrolidin-1-yl 4-(4-chloro-2-(piperidin-1-yl)benzyl)piperazine-1-carboxylate; 2,5-dioxopyrrolidin-1-yl 4-(3-chloro-5-(piperidin-1-yl)benzyl)piperazine-1-carboxylate; 2,5-dioxopyrrolidin-1-yl 4-{[2-(propan-2-yl)-4-(pyrrolidin-1-yl)phenyl]methyl}piperazine-1-carboxylate; and 2,5-dioxopyrrolidin-1-yl 4-{[4-(morpholin-4-yl)-2-(propan-2-yl)phenyl]methyl}piperazine-1-carboxylate;

or a pharmaceutically acceptable salt or stereoisomer thereof.

7. A pharmaceutically acceptable composition comprising a compound of claim 1, or a pharmaceutically acceptable salt or stereoisomer thereof, and a pharmaceutically acceptable excipient.

8. A pharmaceutically acceptable composition comprising a compound of claim 6, or a pharmaceutically acceptable salt or stereoisomer thereof, and a pharmaceutically acceptable excipient.

9. A method of treating pain in a patient in need thereof, comprising administering to a patient in need thereof an effective amount of a compound of claim 1, or a pharmaceutically acceptable salt or stereoisomer thereof.

10. A method of treating pain in a patient in need thereof, comprising administering to a patient in need thereof an effective amount of a compound of claim 6, or a pharmaceutically acceptable salt or stereoisomer thereof.

* * * * *